US008568732B2

(12) United States Patent
Grandi et al.

(10) Patent No.: US 8,568,732 B2
(45) Date of Patent: Oct. 29, 2013

(54) CHLAMYDIA ANTIGENS

(75) Inventors: Guido Grandi, Segrate (IT); Oretta Finco, Siena (IT); Renata Maria Grifantini, Siena (IT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/255,002

(22) PCT Filed: Mar. 8, 2010

(86) PCT No.: PCT/IB2010/050988

§ 371 (c)(1), (2), (4) Date: Nov. 21, 2011

(87) PCT Pub. No.: WO2010/100632

PCT Pub. Date: Sep. 10, 2010

(65) Prior Publication Data

US 2012/0093851 A1 Apr. 19, 2012

Related U.S. Application Data

(60) Provisional application No. 61/157,921, filed on Mar. 6, 2009.

(51) Int. Cl.

*A61K 39/118* (2006.01)
*A61K 39/02* (2006.01)
*C07K 14/195* (2006.01)
*C07K 7/06* (2006.01)
*C07K 7/08* (2006.01)

(52) U.S. Cl.

USPC ..................... 424/190.1; 424/263.1; 530/300; 530/350

(58) Field of Classification Search

None

See application file for complete search history.

(56) References Cited

U.S. PATENT DOCUMENTS 6,248,329 B1 * 6/2001 Chandrashekar et al. . 424/191.1

FOREIGN PATENT DOCUMENTS

| | | |
|---|---|---|
| WO | WO 99/27105 | 6/1999 |
| WO | WO 99/28475 | 6/1999 |
| WO | WO 00/27994 | 5/2000 |
| WO | WO 00/34483 | 6/2000 |
| WO | WO 00/37494 | 6/2000 |
| WO | WO 00/46359 | 8/2000 |
| WO | WO 00/66739 | 11/2000 |
| WO | WO 01/21804 | 3/2001 |
| WO | WO 01/21811 | 3/2001 |
| WO | WO 01/40474 | 6/2001 |
| WO | WO 01/46224 | 6/2001 |
| WO | WO 01/81379 | 11/2001 |
| WO | WO 01/85972 | 11/2001 |
| WO | WO 02/02646 | 1/2002 |
| WO | WO 02/08267 | 1/2002 |
| WO | WO 2007/110700 | 10/2007 |
| WO | WO 2009/109860 | 9/2009 |

OTHER PUBLICATIONS

Brunham, R. R C. in Chlamydia: Intracellular Biology, Pathogenesis, and Immunity ed. Stephens, 211-238 American Society for Microbiology Press, Washington DC, 1999.*
Read et al 2000 Nucleic Acids Res. 28, 1397-1406.*
Caldwell et al 2003. J. Clin. Invest. 111, 1757-1769.*
Lederman et al (Molecular Immunology 28:1171-1181, 1991).*
Li et al (Proc. Natl. Acad. Sci. USA 77:3211-3214, 1980.*
Goodall et al., "Identification of *Chlamydia trachomatis* Antigens Recongnized by Human CD4+ T Lymphocytes by Screening an Expression Library," Eur. J. Immunol. 31(5):1513-1522 (2001).
Goodall et al., "Recognition of the 60 Kilodalton Cysteine-Rich Outer Membrane Protein OMP2 by CD4+ T Cells From Humans Infected With *Chlamydia trachomatis*," Clin. Exp. Immunol. , 126(3):488-493 (2001).
Hassell et al., "Identification of T-Call Stimulatory Antigens of *Chlamydia trachomatis* Using Synovial Fluid-Derived T-Cell Clones," Immunology, 79(4):513-519 (1993).
Kalman et al., "Comparative Genomes of *Chlamydia pneumoniae* and *C. trachomatis*," Nature Genetics, vol. 21, pp. 385-389 (1999).
Stephens et al., "Genome Sequence of an Obligate Intracellular Pathogen of Humans: *Chlamydia trachomatis*," Science, American Association for the Advancement of Science, 282(5389):754-759 (1998).
"Putative Uncharacterized Protein", XP002585081, Database Accession No. 084738, Nov. 11, 1998.

* cited by examiner

*Primary Examiner* — Padma V Baskar
(74) *Attorney, Agent, or Firm* — Robins Law Group; Roberta L. Robins

(57) ABSTRACT

The invention provides *Chlamydia* antigens for use in the treatment, prevention and/or diagnosis of *Chlamydia* infection. In particular, the invention provides antigens CT733, CT153, CT601, CT279, CT443, CT372, CT456, CT381, CT255, CT341, CT716, CT745, CT387, CT812, CT869, CT166, CT175, CT163, CT214, CT721, CT127, CT043, CT823 and/or CT600 from *C. trachomatis* for the treatment, prevention or diagnosis of *Chlamydia* infection.

4 Claims, 12 Drawing Sheets

FIGURE 1
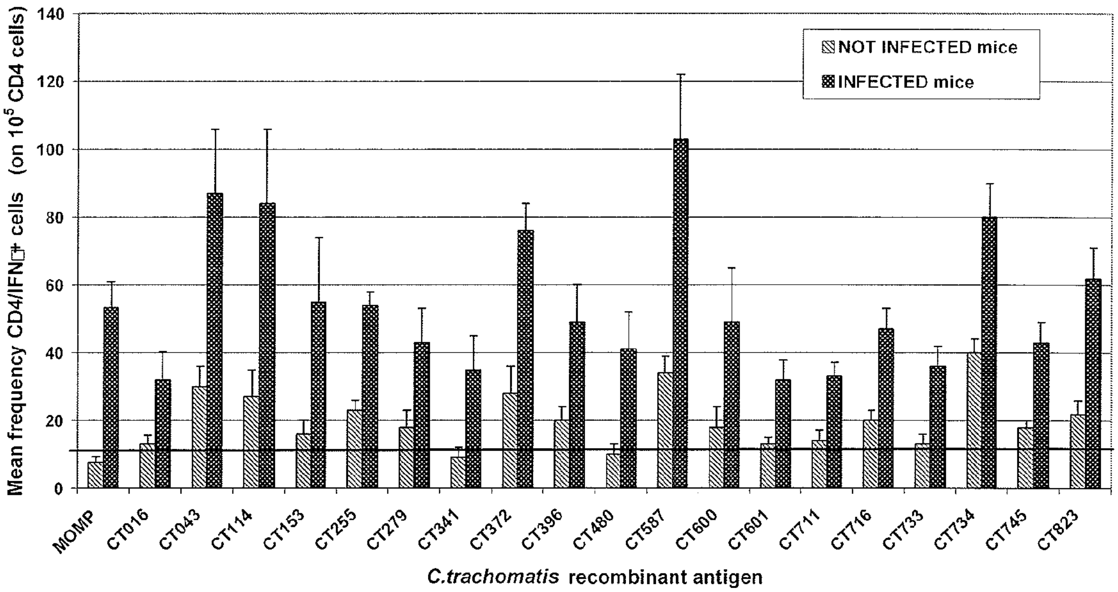
FIGURE 2
FIGURE 2A
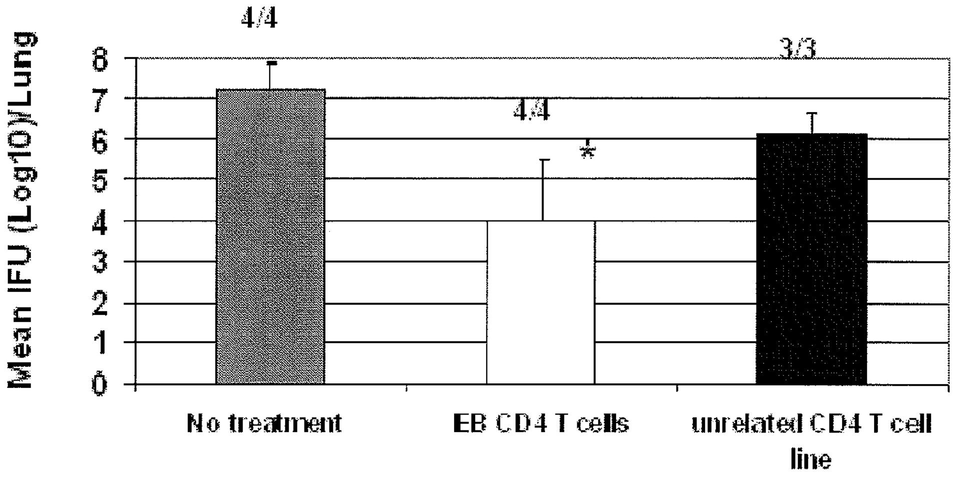

FIGURE 10
FIGURE 10A
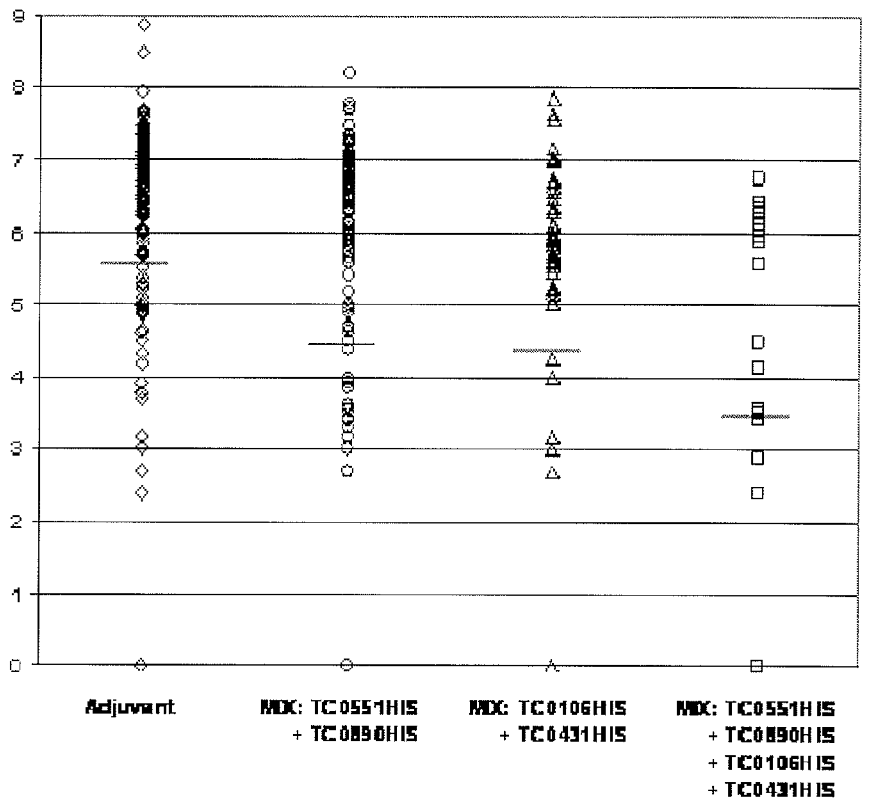
FIGURE 10B
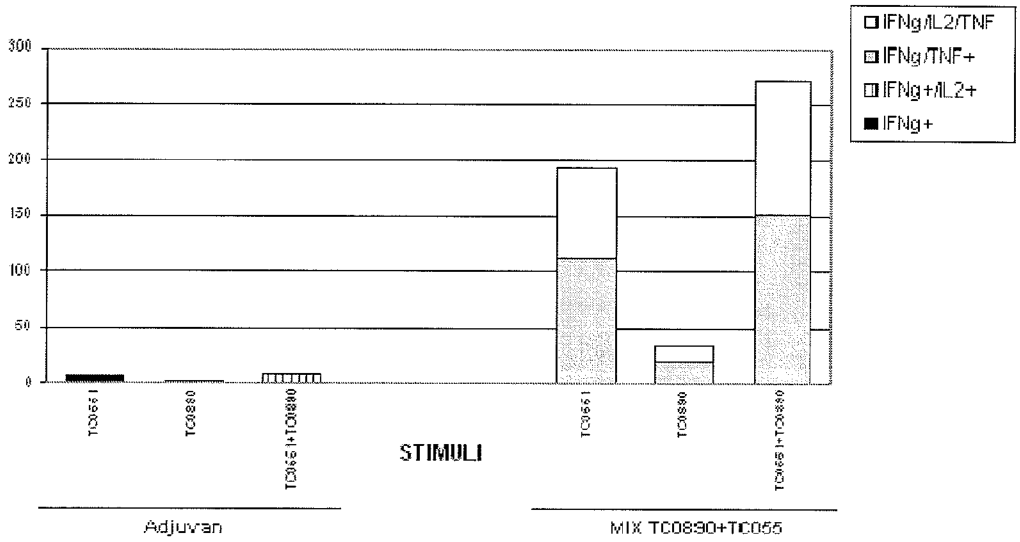

FIGURE 12
FIGURE 12A
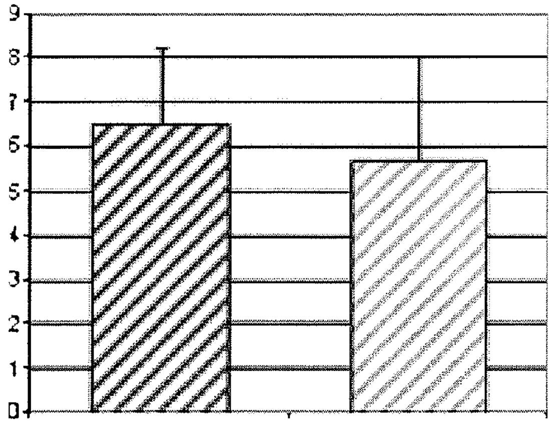
FIGURE 12B
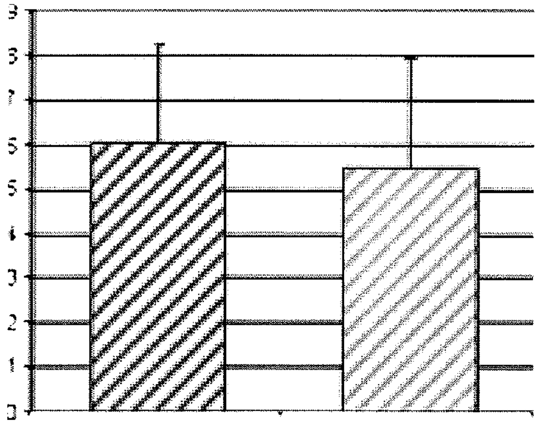
FIGURE 12C
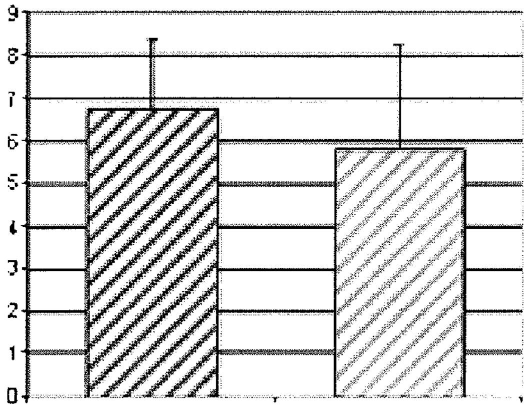
FIGURE 12D
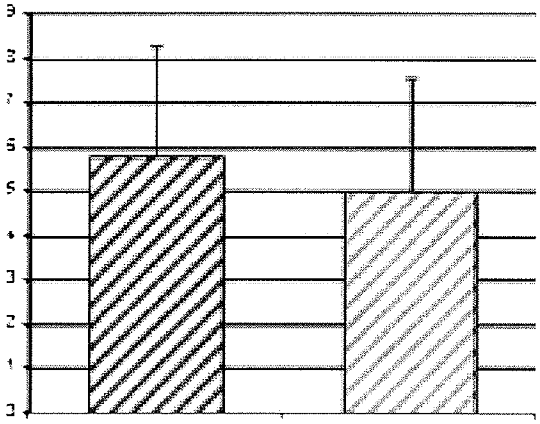
FIGURE 12E
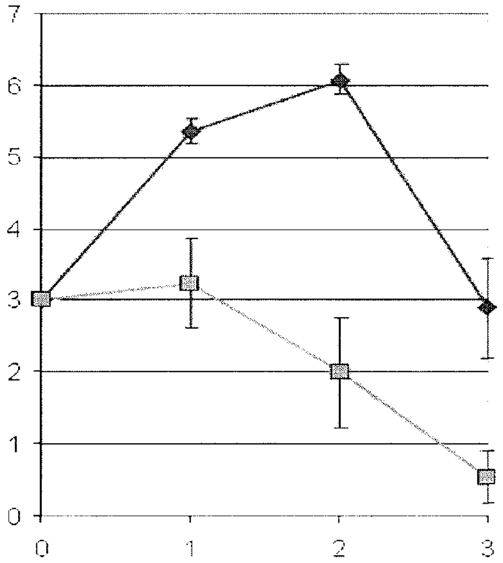

CHLAMYDIA ANTIGENS

This patent application is a §371 filing of PCT/IB2010/050988, filed Mar. 8, 2010, and claims priority benefit of U.S. provisional application 61/157,921 filed on Mar. 6, 2009, the complete contents of which are hereby incorporated herein by reference.

TECHNICAL FIELD

This invention is in the field of *Chlamydia trahomatis* proteins and their uses.

BACKGROUND ART

Vaccine development has been identified as essential to controlling infection with *C. trachomatis*. Vaccines against *C. trachomatis* appear to elicit protective T-cell and/or B-cell immunity in the genital tract mucosa.

Protective immunity to *C. trachomatis* seems to depend on a Th1-polarized cell-mediated immune response, in particular on CD4+ lymphocytes secreting IFNγ. For example, depletion of CD4+ T cells in mice results in loss of protective immunity, and adoptive transfer of *Chlamydia*-specific CD4+ T cells confers protection against challenge with *C. trachomatis*. Furthermore, recent studies report that *C. trachomatis* infection in mice induces a CD4-Th1 protective immune response, indicating that critical *Chlamydia* antigens are processed and presented via the MHC class II pathway (Brunham R C and Rey-Ladino J (2005), Nat Rev Immunol 5: 149-1611; Su H and Caldwell H D (1995), Infect Immun 63: 3302-3308).

Although B-cells and antibodies do not have a decisive role in resolution of primary infection, they are likely to be important for enhancing the protective effector T-cell response and to be required to control re-infection with various mechanisms such as antibody-mediated neutralization and opsonization.

Because immune protection against infection with *C. trachomatis* is likely to be mediated by immunization with *C. trachomatis* proteins that are targets of CD4+ T cells and that are capable of inducing B-cell responses, identification of such proteins is particularly important. It is therefore an object of the invention to provide further antigens for use in *Chlamydia* vaccines.

DISCLOSURE OF THE INVENTION

The invention provides identifies *Chlamydia* antigens for use in the treatment, prevention and/or diagnosis of *Chlamydia* infection. In particular, the invention provides one or more of the following antigens (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) from *C. trachomatis* for the treatment, prevention or diagnosis of *Chlamydia* infection (and, in particular, *C. trachomatis* infection): CT733, CT153, CT601, CT279, CT443, CT372, CT456, CT381, CT255, CT341, CT716, CT745, CT812, CT869, CT387, CT166, CT175, CT163, CT214, CT721, CT127, CT043, CT823, CT600, CT711, CT114, CT480, CT089, CT734 and CT016 for example, one or more of CT733, CT153, CT601, CT279, CT443, CT372, CT456, CT381, CT255, CT341, CT716 and CT745.

In particular, the invention provides proteins for use in the treatment, prevention and/or diagnosis of *Chlamydia* infection (and, in particular, *C. trachomatis* infection). Immunisation with the proteins is preferably able to induce a specific CD4+ Th1 cell mediated response against *Chlamydia*.

In one embodiment, the nucleic acid sequence and/or amino acid sequence of the protein comprises the sequence presented in SEQ ID NO:1 and SEQ ID NO:2 respectively. This protein is also known as "CT733" and is annotated as a hypothetical protein from *C. trachomatis*. In another embodiment, the nucleic acid sequence and/or amino acid sequence of the protein comprises the sequence presented in SEQ ID NO:3 and SEQ ID NO:4 respectively. This protein is also known as "CT153" and is annotated as MACPF/membrane-attack complex (MAC)/perforin from *C. trachomatis*. In another embodiment, the nucleic acid sequence and/or amino acid sequence of the protein comprises the sequence presented in SEQ ID NO:5 and SEQ ID NO:6 respectively. This protein is also known as "CT601" from *C. trachomatis*. In another embodiment, the nucleic acid sequence and/or amino acid sequence of the protein comprises the sequence presented in SEQ ID NO:7 and SEQ ID NO:8 respectively. This protein is also known as "CT279" from *C. trachomatis*. In another embodiment, the nucleic acid sequence and/or amino acid sequence of the protein comprises the sequence presented in SEQ ID NO:9 and SEQ ID NO:10 respectively. This protein is also known as "CT443" from *C. trachomatis*. In another embodiment, the nucleic acid sequence and/or amino acid sequence of the protein comprises the sequence presented in SEQ ID NO:11 and SEQ ID NO:12 respectively. This protein is also known as "CT372" from *C. trachomatis*. In another embodiment, the nucleic acid sequence and/or amino acid sequence of the protein comprises the sequence presented in SEQ ID NO:13 and SEQ ID NO:14 respectively. This protein is also known as "CT456" from *C. trachomatis*. In another embodiment, the nucleic acid sequence and/or amino acid sequence of the protein comprises the sequence presented in SEQ ID NO:15 and SEQ ID NO:16 respectively. This protein is also known as "CT381" from *C. trachomatis*. In another embodiment, the nucleic acid sequence and/or amino acid sequence of the protein comprises the sequence presented in SEQ ID NO:39 and SEQ ID NO:40 respectively. This protein is also known as "CT255" from *C. trachomatis*. In another embodiment, the nucleic acid sequence and/or amino acid sequence of the protein comprises the sequence presented in SEQ ID NO:41 and SEQ ID NO:42 respectively. This protein is also known as "CT341" from *C. trachomatis*. In another embodiment, the nucleic acid sequence and/or amino acid sequence of the protein comprises the sequence presented in SEQ ID NO:43 and SEQ ID NO:44 respectively. This protein is also known as "CT716" from *C. trachomatis*. In another embodiment, the nucleic acid sequence and/or amino acid sequence of the protein comprises the sequence presented in SEQ ID NO:45 and SEQ ID NO:46 respectively. This protein is also known as "CT745" from *C. trachomatis*. In another embodiment, the nucleic acid sequence and/or amino acid sequence of the protein comprises the sequence presented in SEQ ID NO:47 and SEQ ID NO:48, respectively. This protein is also known as "CT387" from *C. trachomatis* and is annotated as a hypothetical protein. In another embodiment, the nucleic acid and/or amino acid sequence of the protein comprises the sequence presented in SEQ ID NO:49 and SEQ ID NO:50, respectively. This protein is also known as "CT812" from *C. trachomatis* and is annotated as a polymorphic outer membrane protein. In another embodiment, the nucleic acid and/or amino acid sequence of the protein comprises the sequence presented in SEQ ID NO:51 and SEQ ID NO:52, respectively. This protein is also known as "CT869" from *C. trachomatis* and is annotated as a polymorphic outer membrane protein. In another embodiment, the nucleic acid and/or amino acid sequence of the protein comprises the sequence presented in SEQ ID NO:53 and SEQ ID NO:54, respectively. This protein is also known as "CT166" from *C. trachomatis*. In another embodiment, the nucleic acid and/or amino acid sequence of the protein comprises the sequence presented in SEQ ID NO:55 and SEQ ID NO:56, respectively. This protein is also known as "CT175" from *C. trachomatis*. In another embodiment, the nucleic acid and/or amino acid sequence of the protein comprises the sequence presented in SEQ ID NO:155 and SEQ ID NO:156, respectively. This protein is also known as "CT163" from *C. trachomatis*. In another embodiment, the nucleic acid and/or amino acid sequence of the protein comprises the sequence presented in SEQ ID NO:159 and SEQ ID NO:160, respectively. This protein is also known as "CT214" from *C. trachomatis*. In another embodiment, the nucleic acid and/or amino acid sequence of the protein comprises the sequence presented in SEQ ID NO:163 and SEQ ID NO:164, respectively. This protein is also known as "CT721" from *C. trachomatis*. In another embodiment, the nucleic acid and/or amino acid sequence of the protein comprises the sequence presented in SEQ ID NO:167 and SEQ ID NO:168, respectively. This protein is also known as "CT127" from *C. trachomatis*.

In some embodiments, the protein is a variant of a protein as described above. For example, the protein may comprise one or more mutations (for example, 1, 2, 3, 4, 5, 6, 7, 8, 9, 10 or more mutations) in the sequence of SEQ ID NO: 2, 4, 6, 8, 10, 12, 14, 16, 18, 19, 20, 21, 22, 23, 24, 40, 42, 44, 46, 48, 50, 52, 54, 56, 136, 140, 156, 160, 164 or 168, for example, in the sequence of SEQ ID NO: 2, 4, 6, 8, 10, 12, 14, 16, 40, 42, 44, or 46. Preferred mutations are those which do not cause a significant conformational change in the protein such that the protein of the invention retains the ability to elicit an immune response against the wild-type *Chlamydia* protein. The proteins having the sequences presented in SEQ ID NO: 2, 4, 6, 8, 10, 12, 14, 16, 40, 42, 44, 46, 48, 50, 52, 54 and 56 are the wild-type proteins.

In some embodiments, the one or more mutations are present in the N-terminal portion of the protein, for example, between residues 1 and 20 of the protein, between residues 21 and 40, between residues 41 and 60, between residues 1 and 60 or between residues 1 and 40 of the protein. In some embodiments, the one or more mutations are present in the C-terminal portion of the protein, for example, between the C-terminal 20 residues of the protein, between residues 21 and 40 from the C-terminus, between residues 41 and 60 from the C-terminus; between residues 1 and 60 from the C-terminus or between residues 1 and 40 from the C-terminus of the protein.

Preferably, the amino acid sequences contain fewer than twenty mutations (e.g. 19, 18, 17, 16, 15, 14, 13, 12, 11, 10, 9, 8, 7, 6, 5, 4, 3, 2 or 1). Each mutation preferably involves a single amino acid and is preferably a point mutation. The mutations may each independently be a substitution, an insertion or a deletion. Preferred mutations are single amino acid substitutions. The proteins may also include one or more (e.g. 1, 2, 3, 4, 5, 6, 7, 8, 9, etc.) single amino acid deletions relative to the *Chlamydia* sequences. The proteins may also include one or more (e.g. 1, 2, 3, 4, 5, 6, 7, 8, 9, etc.) insertions (e.g. each of 1, 2, 3, 4 or 5 or more amino acids) relative to the *Chlamydia* sequences. Deletions, substitutions or insertions may be at the N-terminus and/or C-terminus, or may be between the two termini. Thus a truncation is an example of a deletion. Truncations may involve deletion of up to 40 (or more) amino acids at the N-terminus and/or C-terminus (for example, 1-10, 11-40, 41-70, 71-100 or more amino acids).

Amino acid substitutions may be to any one of the other nineteen naturally occurring amino acids. Preferably, a substitution mutation is a conservative substitution. Alternatively, a substitution mutation is a non-conservative substitution. A conservative substitution is commonly defined as a substitution introducing an amino acid having sufficiently similar chemical properties, e.g. having a related side chain (e.g. a basic, positively charged amino acid should be replaced by another basic, positively charged amino acid), in order to preserve the structure and the biological function of the molecule. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. Further examples of conversative substitutions that may be used in the invention are presented in Table 1.

TABLE 1

| Amino Acid | Synonymous Groups | More Preferred Synonymous Groups |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

Examples of non-conservative substitutions that may be used in the invention include the substitution of an uncharged polar amino acid with a nonpolar amino acid, the substitution of a nonpolar amino acid with an uncharged polar amino acid, the substitution of an acidic amino acid with a basic amino acid and the substitution of a basic amino acid with an acidic amino acid.

Mutations may also be introduced to improve stability, e.g., the insertion of disulphide bonds (van den Akker et al. Protein Sci., 1997, 6:2644-2649). For example, the protein may comprise an amino acid sequence having sequence identity to the amino acid sequence of any one of SEQ ID NOs: 2, 4, 6, 8, 10, 12, 14, 16, 18, 19, 20, 21, 22, 23, 24, 40, 42, 44, 46, 48, 50, 52, 54, 56, 136, 140, 156, 160, 164 and 168, for example, of any one of SEQ ID NOs: 2, 4, 6, 8, 10, 12, 14, 16, 40, 42, 44 and 46. The degree of sequence identity is preferably greater than 50% (e.g. 60%, 70%, 80%, 90%, 95%, 97%, 98%, 99% or more). These proteins include homologs, orthologs, allelic variants and functional mutants. Identity between proteins is preferably determined by the Smith-Waterman homology search algorithm as implemented in the MPSRCH program (Oxford Molecular), using an affine gap search with parameters gap open penalty=12 and gap extension penalty=1.

The *Chlamydia* protein of the invention may comprise one or more amino acid derivatives. By "amino acid derivative" is intended an amino acid or amino acid-like chemical entity other than one of the 20 genetically encoded naturally occurring amino acids. In particular, the amino acid derivative may contain substituted or non-substituted, linear, branched, or cyclic alkyl moieties, and may include one or more heteroatoms. The amino acid derivatives can be made de novo or obtained from commercial sources (Calbiochem-Novabiochem AG; Bachem).

In some embodiments, the variant protein is a homologous protein from *C. pneumoniae, C. psittaci, C. pecorum, C. muridarum* or *C. suis.*

The invention further provides a protein comprising or consisting of a fragment of a protein comprising or consisting of the amino acid sequence of any of SEQ ID NOs: 2, 4, 6, 8, 10, 12, 14, 16, 18, 19, 20, 21, 22, 23, 24, 40, 42, 44, 46, 48, 50, 52, 54, 56, 136, 140, 156, 160, 164 or 168, for example, of any one of SEQ ID NO: 2, 4, 6, 8, 10, 12, 14, 16, 40, 42, 44 or 46, or a fragment of a variant thereof. The fragment should comprise at least n consecutive amino acids from the protein and, depending on the particular sequence, n is 6 or more (e.g. 8, 11, 16, 31, 51, 76, 121, 181, 231, 281, 331, 381, 431, 440, 445, 446, 481, 531, 581, 631, 681, 731, 781, 801, 806, 808 or more). The fragment is n-1 amino acids or less in length, wherein n=the number of amino acids in the full length protein (e.g. n-5, n-20, n-50, n-110, n-180, n-240, n-310, n-380, n-445, n-515, n-595, n-675, n-745, n-785, n-800 amino acids or less in length). Preferably the fragment comprises one or more epitopes from the protein. Preferably, one or more of the epitopes is an MHC class II epitope, for example, a CD4+ T cell epitope. In some embodiments, the fragment comprises or consists of the amino acid sequence of any of SEQ ID NOs 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 142, 146, 150, 154, 158, 162, 166 and 170. In some embodiments, the invention provides a protein comprising or consisting of a fragment of a protein comprising or consisting of the amino acid sequence recited in SEQ ID NO: 122. Table 3 below shows which fragments correspond to which full length sequences.

TABLE 3

| Annotation | SEQ ID NO. for full length sequence | SEQ ID NO. for fragment |
|---|---|---|
| CT733 | 1 | 63 |
| CT733 | 2 | 64 |
| CT153 | 3 | 65 |
| CT153 | 4 | 66 |
| CT601 | 5 | 67 |
| CT601 | 6 | 68 |
| CT279 | 7 | 69 |
| CT279 | 8 | 70 |
| CT443 | 9 | 71 |
| CT443 | 10 | 72 |
| CT372 | 11 | 73 |
| CT372 | 12 | 74 |
| CT456 | 13 | 75 |
| CT456 | 14 | 76 |
| CT381 | 15 | 77 |
| CT381 | 16 | 78 |
| CT043 | 17 | 79 |
| CT043 | 18 | 80 |
| CT711 | 19 | 81 (nucleotide); 82 (protein) |
| CT114 | 20 | 83 (nucleotide); 84 (protein) |
| CT480 | 21 | 85 (nucleotide); 86 (protein) |
| CT089 | 22 | 87 (nucleotide); 88 (protein) |
| CT734 | 23 | 89 (nucleotide); 90 (protein) |
| CT016 | 24 | 91 (nucleotide); 92 (protein) |
| TC0551 (CT279) | 25 | 93 |
| TC0551 (CT279) | 26 | 94 |
| TC0651 (CT372) | 27 | 95 |
| TC0651 (CT372) | 28 | 96 |
| TC0727 (CT443) | 29 | 97 |
| TC0727 (CT443) | 30 | 98 |
| TC0313 (CT043) | 31 | 99 |
| TC0313 (CT043) | 32 | 100 |
| TC0890 (CT601) | 33 | 101 |
| TC0890 (CT601) | 34 | 102 |
| TC0741 (CT456) | 35 | 103 |
| TC0741 (CT456) | 36 | 104 |
| TC0660 (CT381) | 37 | 105 |
| TC0660 (CT381) | 38 | 106 |
| CT255 | 39 | 107 |
| CT255 | 40 | 108 |
| CT341 | 41 | 109 |
| CT341 | 42 | 110 |
| CT716 | 43 | 111 |
| CT716 | 44 | 112 |
| CT745 | 45 | 113 |
| CT745 | 46 | 114 |
| CT387 | 47 | 115 |
| CT387 | 48 | 116 |
| CT812 | 49 | 117 (mature full length); 119 (N-terminal fragment); 121 (C-terminal fragment) |
| CT812 | 50 | 118 (mature full length) 120 (N-terminal fragment) 122 (C-terminal fragment) |
| CT869 | 51 | 123 |
| CT869 | 52 | 124 |
| CT166 | 53 | 125 |
| CT166 | 54 | 126 |
| CT175 | 55 | 127 |
| CT175 | 56 | 128 |
| TC0666 (CT387) | 57 | 129 |
| TC0666 (CT387) | 58 | 130 |
| TC0197 | 59 | 131 |
| TC0197 | 60 | 132 |
| TC0261 | 61 | 133 |
| TC0261 | 62 | 134 |
| CT600 | 135 | 137 |
| CT600 | 136 | 138 |
| CT823 | 139 | 141 |
| CT823 | 140 | 142 |
| TC0106 | 143 | 145 |
| TC0106 | 144 | 146 |
| TC0431 | 147 | 149 |
| TC0431 | 148 | 150 |
| TC0210 | 151 | 153 |
| TC0210 | 152 | 154 |
| CT163 | 155 | 157 |
| CT163 | 156 | 158 |
| CT214 | 159 | 161 |
| CT214 | 160 | 162 |
| CT721 | 163 | 165 |
| CT721 | 164 | 166 |
| CT127 | 167 | 169 |
| CT127 | 168 | 170 |

The protein of the invention, for example the variant protein or the fragment, is preferably immunogenic.

The term "immunogenic" in the context of "an immunogenic variant" and "immunogenic fragment", is used to mean that the protein is capable of eliciting an immune response, such as a cell-mediated and/or an antibody response, against the wild-type *Chlamydia* protein from which it is derived, for example, when used to immunise a subject (preferably a mammal, more preferably a human or a mouse). For example, the protein of the invention (for example, the variant or fragment) is preferably capable of stimulating in vitro CD4+ IFNγ+ cells in splenocytes purified from mice infected with live *C. trachomatis* to a level comparable with the wild-type *Chlamydia* protein. The protein of the invention preferably retains the ability to elicit antibodies that recognise the wild-type protein. For example, the protein of the invention preferably elicits antibodies that can bind to, and preferably neutralise the activity of, the wild-type protein. In a further embodiment, the protein of the invention is capable of eliciting antibodies that are capable of neutralising *Chlamydia* infectivity and/or virulence. In some embodiments, the antibodies are able to cross-react with the protein of the invention and the wild-type protein, but with no other homologous protein (e.g. from another *Chlamydia* species). In other embodiments, the antibodies are cross-reactive with the wild-type protein and with homologous proteins from other *Chlamydia* species. In some embodiments, the antibodies are cross-reactive with the wild-type protein and with homologous protein from other organisms (for example from *E. coli* or *H. influenzae*). Mice immunized with the protein of the invention and the wild-type *Chlamydia* protein preferably show similar antigen-specific antibody titers. Antibody titres and specificities can be measured using standard methods available in the art. Other methods of testing the immunogenicity of proteins are also well known in the art.

For example, the variant or fragment is preferably capable of eliciting an immune response, such as a cell-mediated and/or an antibody response, against the wild-type *Chlamydia* protein. In one embodiment the fragment is capable of stimulating in vitro CD4+ IFNγ+ cells in splenocytes purified from mice infected with live *C. trachomatis* to a level comparable with the wild-type *Chlamydia* protein and/or retains the ability to elicit antibodies that recognise the wild-type protein.

Preferably, the variant or the fragment is capable of inducing a specific CD4-Th1 cell mediated response against the wild type *Chlamydia* protein.

The proteins of the invention can, of course, be prepared by various means (e.g. recombinant expression, purification from native host, purification from cell culture, chemical synthesis etc.) and in various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). Generally, the recombinant fusion proteins of the present invention are prepared as a GST-fusion protein and/or a His-tagged fusion protein.

The proteins of the invention are preferably prepared in purified or substantially pure form (i.e. substantially free from host cell proteins and/or other *Chlamydia* proteins), and are generally at least about 50% pure (by weight), and usually at least about 90% pure, i.e. less than about 50%, and more preferably less than about 10% (e.g. 5%) of a composition is made up of other expressed polypeptides. Thus the antigens in the compositions are separated from the whole organism with which the molecule is expressed.

Whilst expression of the proteins of the invention may take place in *Chlamydia*, the invention preferably utilises a heterologous host. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc.

The term "polypeptide" or "protein" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included are, for example, polypeptides containing one or more analogs of an amino acid (including, for example, unnatural amino acids, etc.), as well as other modifications known in the art. Polypeptides can occur as single chains or associated chains.

The invention provides polypeptides comprising a sequence —P-Q- or -Q-P—, wherein: —P— is an amino acid sequence as defined above and -Q- is not a sequence as defined above i.e. the invention provides fusion proteins. Where the N-terminus codon of —P— is not ATG, but this codon is not present at the N-terminus of a polypeptide, it will be translated as the standard amino acid for that codon rather than as a Met. Where this codon is at the N-terminus of a polypeptide, however, it will be translated as Met. Examples of -Q- moieties include, but are not limited to, histidine tags (i.e. $His_n$ where n=3, 4, 5, 6, 7, 8, 9, 10 or more), maltose-binding protein, or glutathione-S-transferase (GST).

Proteins of the invention may be attached to a solid support. They may comprise a detectable label (e.g. a radioactive or fluorescent label, or a biotin label).

Antibodies

The proteins of the invention induce antibodies that may be used as a vaccine capable of neutralising the activity of infectious EB. The antibodies may alternatively be used for the diagnosis of *Chlamydia* infection. Thus, the invention provides antibodies for use in the treatment, prevention or diagnosis of *Chlamydia* infection. Preferably, the infection is by *C. trachomatis*, but may alternatively be by *C. psittaci, C. pecorum, C. muridarum* or *C. suis*.

The term "antibody" includes intact immunoglobulin molecules, as well as fragments thereof which are capable of binding an antigen. These include hybrid (chimeric) antibody molecules (Winter et al., (1991) *Nature* 349:293-99; U.S. Pat. No. 4,816,567); F(ab')2 and F(ab) fragments and Fv molecules; non-covalent heterodimers (Inbar et al., (1972) *Proc. Natl. Acad. Sci. U.S.A.* 69:2659-62; Ehrlich et al., (1980) *Biochem* 19:4091-96); single-chain Fv molecules (sFv) (Huston et al., (1988) Proc. Natl. Acad. Sci. U.S.A. 85:5897-83); dimeric and trimeric antibody fragment constructs; minibodies Pack et al., (1992) *Biochem* 31, 1579-84; Cumber et al., (1992) *J. Immunology* 149B, 120-26); humanized antibody molecules (Riechmann et al., (1988) *Nature* 332, 323-27; Verhoeyan et al., (1988) *Science* 239, 1534-36; and GB 2,276,169); and any functional fragments obtained from such molecules, as well as antibodies obtained through non-conventional processes such as phage display. Preferably, the antibodies are monoclonal antibodies. Methods of obtaining monoclonal antibodies are well known in the art. Humanised or fully-human antibodies are preferred.

The antibodies may be polyclonal or monoclonal and may be produced by any suitable means. The antibody may include a detectable label.

Also provided is a method for preparing antibodies comprising immunising a mammal (such as a mouse or a rabbit) with a protein of the invention and obtainining polyclonal antibodies or monoclonal antibodies by conventional techniques. For example, polyclonal antisera may be obtained by bleeding the immunized animal into a glass or plastic container, incubating the blood at 25° C. for one hour, followed by incubating at 4° C. for 2-18 hours. The serum is recovered by centrifugation (eg. 1,000 g for 10 minutes). Monoclonal antibodies may be prepared using the standard method of Kohler & Milstein [Nature (1975) 256:495-96], or a modification thereof, or by any other suitable method.

Nucleic Acids

According to a further aspect, the invention provides a nucleic acid encoding a protein or antibody of the invention. In some embodiments, the nucleic acid sequence encoding a protein of the invention preferably comprises or consists of any one of SEQ ID NOs:1, 3, 5, 7, 9, 11, 13, 15, 17, 39, 41, 43, 45, 47, 49, 51, 53, 55, 135, 139, 155, 159, 163 or 167, for example, of any one of SEQ ID NOs:1, 3, 5, 7, 9, 11, 13, 15, 39, 41, 43 or 45. In some embodiments, the nucleic acid sequence encoding a protein of the invention comprises or consists of any one of SEQ ID NOs: 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131 and 133.

The invention also provides nucleic acid comprising nucleotide sequences having sequence identity to such nucleotide sequences. Identity between sequences is preferably determined by the Smith-Waterman homology search algorithm as described above. Such nucleic acids include those using alternative codons to encode the same amino acid.

The invention also provides nucleic acid which can hybridize to these nucleic acids. Hybridization reactions can be performed under conditions of different "stringency". Conditions that increase stringency of a hybridization reaction of widely known and published in the art (e.g. page 7.52 of Kaplitt, *Nature Genetics* (1994) 6:148). Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art (e.g. see U.S. Pat. No. 5,707,829, *Current Protocols in Molecular Biology* (F. M. Ausubel et al. eds., 1987) Supplement 30, Kaplitt, *Nature Genetics* (1994) 6:148, and WO 94/03622, etc.).

The nucleic acid may be used in hybridisation reactions (e.g. Northern or Southern blots, or in nucleic acid microarrays or 'gene chips') or in amplification reactions (e.g. PCR, SDA, SSSR, LCR, NASBA, TMA) etc.

The invention also provides a nucleic acid comprising sequences complementary to those described above (e.g. for antisense or probing, or for use as primers). In one embodiment, the nucleic acid is complementary to the full length of the nucleic acid described above.

Nucleic acid according to the invention may be labelled e.g. with a radioactive or fluorescent label. This is particularly useful where the nucleic acid is to be used as a primer or probe e.g. in PCR, LCR or TMA.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids of the invention can take various forms (e.g. single stranded, double stranded, vectors, primers, probes etc.). Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids of the invention are preferably prepared in substantially pure form (i.e. substantially free from naturally-occuring nucleic acids, particularly from chlamydial or other host cell nucleic acids), generally being at least about 50% pure (by weight), and usually at least about 90% pure.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

The invention provides vectors comprising nucleotide sequences of the invention (e.g. cloning or expression vectors) and host cells transformed with such vectors. Nucleic acids of the invention may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which are designed to result in the production of a recombinant virus or virus-like particle, or "shuttle vectors", which comprise the attributes of more than one type of vector. Preferred vectors are plasmids.

Also provided is a host cell comprising a nucleic acid of the invention. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention, for example, with a vector of the invention.

Where a nucleic acid is DNA, it will be appreciated that "U" in a RNA sequence will be replaced by "T" in the DNA. Similarly, where a nucleic acid is RNA, it will be appreciated that "T" in a DNA sequence will be replaced by "U" in the RNA.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T).

Nucleic acids of the invention can be used, for example: to produce polypeptides; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid of the invention, wherein the nucleic acid is synthesised in part or in whole using chemical means.

For certain embodiments of the invention, nucleic acids are preferably at least 24 nucleotides in length (e.g. 60, 120, 240, 390, 540, 720, 900, 1200, 1320, 1500, 1800, 2100, 2400, 2415 nucleotides or longer).

For certain embodiments of the invention, nucleic acids are preferably at most 2430 nucleotides in length (e.g. 2427, 2394, 2250, 2034, 1450, 1300, 1150, 1000, 850, 700, 500 nucleotides or shorter).

Primers and probes of the invention, and other nucleic acids used for hybridization, are preferably between 10 and 30 nucleotides in length (e.g. 10, 11, 12, 13, 14, 15, 16, 17, 18, 19, 20, 21, 22, 23, 24, 25, 26, 27, 28, 29, or 30 nucleotides).

Immunogenic Compositions and Medicaments

The protein, antibody, and/or nucleic acid or medicament may be in the form of a composition. These compositions may be suitable as immunogenic compositions (e.g. vaccines), or as diagnostic reagents.

Preferably, the composition is an immunogenic composition. It is particularly advantageous to use a protein of the invention in an immunogenic composition such as a vaccine. It is also envisaged that the immunogenic composition may comprise a nucleic acid which encodes a protein of the invention such that the protein is generated in vivo.

An immunogenic composition of the invention comprises a protein, antibody, nucleic acid, vector and/or host cell according to the invention. Immunogenic compositions according to the invention may either be prophylactic (i.e. to prevent infection) or therapeutic (i.e. to treat infection), but will typically be prophylactic. Where the immunogenic composition is for prophylactic use, the human is preferably a child (e.g. a toddler or infant) or a teenager; where the immunogenic composition is for therapeutic use, the human is preferably a teenager or an adult. An immunogenic composition intended for children may also be administered to adults e.g. to assess safety, dosage, immunogenicity, etc.

In some embodiments, the immunogenic composition is for treatment or prevention of *Chlamydia* infection or an associated condition (e.g. trachoma, blindness, cervicitis, pelvic inflammatory disease, infertility, ectopic pregnancy, chronic pelvic pain, salpingitis, urethritis, epididymitis, infant pneumonia, patients infected with cervical squamous cell carcinoma, and/or HIV infection, etc.), preferably, *C. trachomatis* infection. The immunogenic composition may be effective against *C. pneumoniae.*

Immunogenic compositions used as vaccines comprise an immunologically effective amount of the protein of the invention, as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of the individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Antigens in the composition will typically be present at a concentration of at least 1 μg/ml each.

In general, the concentration of any given antigen will be sufficient to elicit an immune response against that antigen.

Dosage treatment can be a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In some embodiments, three or more doses are provided (for example, three, four or five) doses. In some embodiments, three doses are given intramuscularly at 2 week-intervals, for example, three doses of 10-20 μg of each protein, at 2 week-intervals, given intramuscularly.

The pH of an immunogenic composition is preferably between 6 and 8, preferably about 7. pH may be maintained by the use of a buffer. The composition may be sterile and/or pyrogen-free. The composition may be isotonic with respect to humans.

Immunogenic compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal (See e.g. WO99/27961) or transcutaneous (See e.g. WO02/074244 and WO02/064162), intranasal (See e.g. WO03/028760), ocular, aural, pulmonary or other mucosal administration.

*Chlamydia* infections affect various areas of the body and so the immunogenic compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition may be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops.

The invention also provides a delivery device pre-filled with an immunogenic composition of the invention.

The invention also provides a kit comprising a first component and a second component wherein neither the first component nor the second component is a composition of the invention as described herein, but wherein the first component and the second component can be combined to provide a composition of the invention as described herein. The kit may further include a third component comprising one or more of the following: instructions, syringe or other delivery device, adjuvant, or pharmaceutically acceptable formulating solution.

A composition as described above may alternatively and/or additionally be used for diagnosis of *chlamydia* infection.

Combinations with Other Antigens

The therapeutic or diagnostic efficiency of a *Chlamydia* antigen may be improved by combination with a different *Chlamydia* antigen. For example, the immunogenicity of a protein of the invention may be improved by comaintion with antoher protein of the invention or with another known *Chlamydia* antigen. The invention thus includes an immunogenic composition comprising a combination of *Chlamydia* antigens, said combination comprising a protein of the invention in combination with one or more additional *Chlamydia* antigens. The one or more additional *Chlamydia* antigens that are present in the composition may be in the form of a protein or nucleic acid or any other suitable form. A protein of the invention may be combined with one or more (e.g. 2, 3, 4, 5, 6, 7, 8, 9, 10, 15, 20 or more) different proteins of the invention and/or with one or more (e.g. 2, 3, 4, 5, 6, 7, 8, 9, 10, 15, 20 or more) other known *Chlamydia* antigens. For example, an immunogenic composition is provided comprising two or more (e.g. 3, 4, 5, 6, 7, 8, 9, 10, 15, 20 or more) proteins of the invention. The proteins of the invention may alternatively and/or additionally be provided in the composition in the form of their corresponding nucleic acids, vectors, host cells, etc. Also provided is a protein or nucleic acid of the invention for a use as described above, wherein the protein or nucleic acid is for use in combination with one or more additional *Chlamydia* antigens (or their encoding nucleic acids). The one or more additional antigens (e.g. 2, 3, 4, 5, 6, 7 or more additional antigens) may be administered simultaneously, separately or sequentially with the protein or nucleic acid of the invention, for example as a combined preparation.

Likewise, the antibodies of the invention may be used in combination with one or more antibodies specific for one or more additional *Chlamydia* antigens for use in diagnosis of *Chlamydia* infections.

In one embodiment, one or more of the additional *Chlamydia* antigens is selected from the antigens presented in Table 2, or their variants. For example, one or more (for example, all) of the additional antigens are selected from the *Chlamydia trachomatis* antigens listed in Table 2, but may alternatively or additionally be selected from the *Chlamydia pneumoniae* antigens listed in Table 2. In some embodiments, the one or more (for example, all) of the additional antigens are selected from the *Chlamydia trachomatis* antigens and/or *Chlamydia pneumoniae* antigens listed in Table 2 and CT387, CT812, CT869, CT166, CT175, CT163, CT214, CT721 and CT127. In one embodiment, one or more of the one or more additional antigens are selected from CT372, CT443, CT043, CT153, CT279, CT601, CT711, CT114, CT480, CT456, CT381, CT089, CT734, CT016, CT600, CT823, CT387, CT812, CT869, CT166, CT175, CT163, CT214, CT721 and CT127 (or their variants), for example, from CT372, CT443, CT043, CT153, CT279, CT601, CT711, CT114, CT480, CT456, CT381, CT089, CT734, CT016, CT600 and CT823. These additional antigens are listed in Table 2 and their sequences are set out in the "Sequences" section that follows Table 2. In one embodiment, one or more proteins of the invention is combined with CT089. In another embodiment, one or more proteins of the invention is combined with CT089 and CT381 (or their variants). In some embodiments, the C-terminal fragment of CT812 "CT812C" (for example, a protein comprising or consisting of the amino acid sequence set out in SEQ ID NO:122 or a fragment or variant thereof) is used instead of full length CT812.

In some embodiments, the following combinations of antigens (or their variants) are used: CT733+CT601, CT733+CT279, CT733+CT443, CT733+CT372, CT733+CT456, CT733+CT381, CT153+CT601, CT153+CT279, CT153+CT443, CT153+CT372, CT153+CT456, CT153+CT381, CT601+CT443, CT601+CT372, CT601+CT456, CT601+CT381, CT279+CT443, CT279+CT372, CT279+CT456, CT279+CT381, CT443+CT372, CT443+CT456, CT443+CT381, CT372+CT456, CT372+CT381, CT387+CT812+CT869, CT387+CT812C+CT869. These combinations may be used in the absence of any other *chlamydia* antigens or in the presence of one or more additional *chlamydia* antigens. Particularly preferred combinations are: (i) CT279+CT601; (ii) CT372+CT443; (iii) CT733+CT153; (iv) CT456+CT381; (v) CT279+CT601+CT733+CT153; (vi) CT279+CT601+CT372+CT443; (vii) CT823+CT733+CT043+CT456; (viii) CT387+CT812+CT869; and (ix) CT387+CT812C+CT869 (or their variants).

The human serovariants ("serovars") of *C. trachomatis* are divided into two biovariants ("biovars"). Serovars A-K elicit epithelial infections primarily in the ocular tissue (A-C) or urogenital tract (D-K). Serovars L1, L2 and L3 are the agents of invasive lymphogranuloma venereum (LGV). In some embodiments, one or more of the additional Chlamydial antigens may, for example, be of any of Serovars A-K or L1, L2 or L3. One or more of the additional *Chlamydia* antigens is preferably from *C. trachomatis* serovar D, or from another epidemiologically prevalent serotype.

In some embodiments, one or more of the additional *Chlamydia* antigens is a homologous antigen from *C. pneumoniae, C. psittaci, C. pecorum, C. muridarum* or *C. suis.*

In some embodiments, TC0551 (the *C. muridarum* homologue of CT279) is used in place of the *C. trachomatis* protein. *C. muridarum* is the mouse adapted strain of *Chlamydia trachomatis*. Although *C. muridarum* is not a human pathogen, infection of mice with *C. muridarum* phenotypically mimics many aspects of *C. trachomatis* infection in humans and is frequently used to measure immunoprotective responses against *C. trachomatis.* In some embodiments, TC0890 (the *C. muridarum* homologue of CT601) is used in place of the *C. trachomatis* protein. In some embodiments, TC0651 (the *C. muridarum* homologue of CT372) is used in place of the *C. trachomatis* protein. In some embodiments, TC0727 (the *C. muridarum* homologue of CT443) is used in place of the *C. trachomatis* protein. In some embodiments, TC0106 (the *C. muridarum* homologue of CT733) is used in place of the *C. trachomatis* protein. In some embodiments, TC0431 (the *C. muridarum* homologue of CTI 53) is used in place of the *C. trachomatis* protein. In some embodiments, TC0660 (the *C. muridarum* homologue of CT381) is used in place of the *C. trachomatis* protein. In some embodiments, TC0741 (the *C. muridarum* homologue of CT456) is used in place of the *C. trachomatis* protein. In some embodiments, TC0210 (the *C. muridarum* homologue of CT823) is used in place of the *C. trachomatis* protein. In some embodiments, TC0666 (the *C. muridarum* homologue of CT387) is used in place of the *C. trachomatis* protein. TC0666 is annotated as a hypothetical protein. In some embodiments, TC0197 (the *C. muridarum* homologue of CT812) is used in place of the *C. trachomatis* protein. TC0197 is annotated as polymorphic membrane protein D family protein. In some embodiments, TC0261 (the *C. muridarum* homologue of CT869) is used in place of the *C. trachomatis* protein. TC0261 is annotated as polymorphic membrane protein E/F family protein. In some embodiments, TC0313 (the *C. muridarum* homologue of CT043) is used in place of the *C. trachomatis* protein. In some embodiments, TC0889 (the *C. muridarum* homologue of CT600) is used in place of the *C. trachomatis* protein. In some embodiments, TC0210 (the *C. muridarum* homologue of CT823) is used in place of the *C. trachomatis* protein. In some embodiments in which the composition comprises a single *Chlamydia* antigen, the *C. muridarum* homologue is used in place of the single *C. trachomatis* antigen. In some embodiments in which the composition comprises a combination of *Chlamydia* antigens, the *C. muridarum* homologue is used in place of one or more (for example, 1, 2, 3, 4, 5, 6, 7, 8, 9, 10) or all *C. trachomatis* antigens.

Advantageous combinations of the invention are those in which two or more antigens (for example, two, three or four antigens) act synergistically. Thus, the protection against *Chlamydia* achieved by their combined administration exceeds that expected by mere addition of their individual protective efficacy.

In some embodiments, the one or more additional *Chlamydia* antigens may comprise an amino acid sequence: (a) which is a variant of a Table 2 antigen (i.e. has 50% or more identity (e.g. 60%, 65%, 70%, 75%, 80%, 85%, 90%, 91%, 92%, 93%, 94%, 95%, 96%, 97%, 98%, 99%, 99.5% or more) to a sequence presented in Table 2); and/or (b) comprising a fragment of at least 'n' consecutive amino acids of a sequence presented in Table 2 or of a variant of a Table 2 antigen, wherein 'n' is 7 or more (e.g. 8, 10, 12, 14, 16, 18, 20, 25, 30, 35, 40, 50, 60, 70, 80, 90, 100, 150, 200, 250, 350, 450, 550, 650, 750, 780, 800 or more). Preferred fragments of (b) comprise an epitope from a sequence presented in Table 2. Preferably, the epitope is a MHC class II epitope, for example, a CD4+ T cell epitope. Other preferred fragments lack one or more amino acids (e.g. 1, 2, 3, 4, 5, 6, 7, 8, 9, 10, 15, 20, 25 or more) from the C-terminus and/or one or more amino acids (e.g. I, 2, 3, 4, 5, 6, 7, 8, 9, 10, 15, 20, 25 or more) from the N-terminus of a sequence presented in Table 2, while retaining at least one epitope of a sequence presented in Table 2. Other fragments omit one or more protein domains. When an additional *Chlamydia* antigen comprises a sequence that is not identical to a complete sequence from Table 2 (e.g. when it comprises a sequence with less than 100% sequence identity thereto, or when it comprises a fragment thereof), it is preferred in each individual instance that the additional *Chlamydia* antigen can elicit an antibody that recognises a protein having the complete sequence from the Table 2 antigen from which it is derived.

In some embodiments, the combination of two or more *chlamydia* antigens is provided as a combined preparation for simultaneous, separate or sequential administration. The invention also provides a kit comprising a protein of the invention and one or more additional antigens for simultaneous, separate or sequential administration.

The *Chlamydia* antigens used in the invention may be present in the composition as individual separate polypeptides. Alternatively, the combination may be present as a hybrid polypeptide in which two or more (i.e. 2, 3, 4, 5, 6, 7, 8, 9, 10, 11, 12, 13, 14, 15, 16, 17, 18, 19 or 20 or more) of the antigens are expressed as a single polypeptide chain. Hybrid polypeptides offer two principal advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful. Different hybrid polypeptides may be mixed together in a single formulation. Within such combinations, a *Chlamydia trachomatis* antigen may be present in more than one hybrid polypeptide and/or as a non-hybrid polypeptide. It is preferred, however, that an antigen is present either as a hybrid or as a non-hybrid, but not as both.

Hybrid polypeptides can be represented by the formula $NH_2$-A-{-X-L-}$_n$-B—COOH, wherein: at least one X is an amino acid sequence of a *Chlamydia* protein according to the invention as described above; L is an optional linker amino acid sequence; A is an optional N-terminal amino acid sequence; B is an optional C-terminal amino acid sequence; n is an integer of 2 or more (e.g. 2, 3, 4, 5, 6, etc.). Usually n is 2 or 3.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2$ . . . $X_n$ will be omitted. This is equivalent to deleting all leader peptides and using the leader peptide of $X_1$ as moiety -A-.

For each n instances of {—X-L-}, linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COON, $NH_2$—$X_1$—$X_2$-$L_2$-COOH, etc. Linker amino acid sequence(s) -L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG, with the Gly-Ser dipeptide being formed from a BamHI restriction site, thus aiding cloning and manipulation, and the $(Gly)_4$ tetrapeptide being a typical poly-glycine linker.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more), or sequences which enhance protein stability. Other suitable C-terminal amino acid sequences will be apparent to those skilled in the art.

Where hybrid polypeptides are used, the individual antigens within the hybrid (i.e. individual —X— moieties) may be from one or more strains. Where n=2, for instance, $X_2$ may be from the same strain as $X_1$ or from a different strain. Where n=3, the strains might be (i) $X_1$=$X_2$=$X_3$ (ii) $X_1$=$X_2$≠$X_3$ (iii) $X_1$≠$X_2$=$X_3$ (iv) $X_1$≠$X_2$≠$X_3$ or (v) $X_1$=$X_3$≠$X_2$, etc.

The invention also provides a nucleic acid encoding a hybrid polypeptide of the invention. Furthermore, the invention provides a nucleic acid which can hybridise to this nucleic acid, preferably under "high stringency" conditions (e.g. 65° C. in a 0.1×SSC, 0.5% SDS solution).

Further Components of the Composition

Compositions may thus be pharmaceutically acceptable. They will usually include components in addition to the antigens e.g. they typically include one or more pharmaceutical carrier(s) and/or excipient(s). A thorough discussion of such components is available in *Remington The Science and Practice of Pharmacy*.

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilised during manufacture and are reconstituted into an aqueous form at the time of use. Thus a composition of the invention may be dried, such as a lyophilised formulation.

The composition may include preservatives such as thiomersal or 2-phenoxyethanol. It is preferred, however, that the vaccine should be substantially free from (i.e. less than 5 μg/ml) mercurial material e.g. thiomersal-free. Vaccines containing no mercury are more preferred. Preservative-free vaccines are particularly preferred.

To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

Immunogenic compositions of the invention may also comprise one or more immunoregulatory agents. Preferably, one or more of the immunoregulatory agents include one or more adjuvants. The adjuvants may include a TH1 adjuvant and/or a TH2 adjuvant, further discussed below.

Adjuvants which may be used in compositions of the invention include, but are not limited to:

A. Mineral-Containing Compositions

Mineral containing compositions suitable for use as adjuvants in the invention include mineral salts, such as aluminium salts and calcium salts (or mixtures thereof). Calcium salts include calcium phosphate (e.g. the "CAP" particles disclosed in U.S. Pat. No. 6,355,271). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [WO00/23105].

The adjuvants known as aluminum hydroxide and aluminum phosphate may be used. These names are conventional, but are used for convenience only, as neither is a precise description of the actual chemical compound which is present (e.g. see chapter 9 of *Vaccine Design* . . . (1995) eds. Powell & Newman. ISBN: 030644867X. Plenum). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

Aluminium phosphate adjuvants generally have a $PO_4/Al$ molar ratio between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4/Al$ molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

Aluminium phosphates are particularly preferred, particularly in compositions which include a *H. influenzae* saccharide antigen, and a typical adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where there is more than one conjugate in a composition, not all conjugates need to be adsorbed.

B. Oil Emulsions

Oil emulsion compositions suitable for use as adjuvants in the invention include squalene-water emulsions, such as MF59 [Chapter 10 of *Vaccine Design* . . . (1995) eds.

Powell & Newman. ISBN: 030644867X. Plenum; see also WO90/14837] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

Various oil-in-water emulsion adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferred emulsion adjuvants have an average droplets size of <1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

- A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' (WO90/14837, Podda & Del Giudice (2003) *Expert Rev Vaccines* 2:197-203, Podda (2001) *Vaccine* 19: 2673-2680; as described in more detail in Chapter 10 of *Vaccine Design: The Subunit and Adjuvant Approach* (eds. Powell & Newman) Plenum Press 1995 (ISBN 0-306-44867-X) and chapter 12 of *Vaccine Adjuvants: Preparation Methods and Research Protocols* (Volume 42 of *Methods in Molecular Medicine* series). ISBN: 1-59259-083-7. Ed. O'Hagan). The MF59 emulsion advantageously includes citrate ions e.g. 10 mM sodium citrate buffer.
- An emulsion of squalene, a tocopherol, and Tween 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene:tocopherol is preferably ≤1 as this provides a more stable emulsion. Squalene and Tween 80 may be present volume ratio of about 5:2. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.
- An emulsion of squalene, a tocopherol, and a Triton detergent (e.g. Triton X-100). The emulsion may also include a 3d-MPL (see below). The emulsion may contain a phosphate buffer.
- An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.
- An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant (Allison & Byars (1992) *Res Immunol* 143: 519-25) (0.05-1% Thr-MDP, 5% squalane, 2.5% Pluronic L121 and 0.2% polysorbate 80). It can also be used without the Thr-MDP, as in the "AF" adjuvant (Hariharan et al. (1995) *Cancer Res* 55:3486-9) (5% squalane, 1.25% Pluronic L121 and 0.2% polysorbate 80). Microfluidisation is preferred.

- An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm (US-2007/014805.). The emulsion may also include one or more of: alditol; a cryoprotective agent (e.g. a sugar, such as dodecylmaltoside and/or sucrose); and/or an alkylpolyglycoside. Such emulsions may be lyophilized.
- An emulsion o US-2007/014805.f squalene, poloxamer 105 and Abil-Care (Suli et al. (2004) *Vaccine* 22(25-26): 3464-9). The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; capryl ic/capric triglyceride).
- An emulsion having from 0.5-50% of an oil, 0.1-10% of a phospholipid, and 0.05-5% of a non-ionic surfactant. As described in WO95/11700, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.
- A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in U.S. Pat. No. 6,080,725, produced by addition of aliphatic amine to desacylsaponin via the carboxyl group of glucuronic acid), dimethyidioctadecylammonium bromide and/or N,N-dioctadecyl-N,N-bis(2-hydroxyethyl)propanediamine.
- An emulsion in which a saponin (e.g. QuilA or QS21) and a sterol (e.g. a cholesterol) are associated as helical micelles (WO2005/097181).
- An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) (WO2006/113373).
- An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) (Wu et al. (2004) *Antiviral Res.* 64(2):79-83).

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease. Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Where a composition includes a tocopherol, any of the α, β, γ, δ, ϵ or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g. aged 60 years or older) because vitamin E has been reported to have a positive effect on the immune response in this patient group (Han et al. (2005) *Impact of Vitamin E on Immune Function and Infectious Diseases in the Aged at Nutrition, Immune functions and Health* EuroConference, Paris, 9-10 Jun. 2005). They also have antioxidant properties that may help to stabilize the emulsions (U.S. Pat. No. 6,630,161). A preferred α-tocopherol is DL-α-tocopherol, and the preferred salt of this tocopherol is the succinate. The succinate salt has been found to cooperate with TNF-related ligands in vivo.

*C. Saponin* Formulations (Chapter 22 of *Vaccine Design* . . . (1995) eds. Powell & Newman. ISBN. 030644867*X. Plenum*)

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officinalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (WO96/33739).

Combinations of saponins and cholesterols can be used to form unique particles called immunostimulating complexs (ISCOMs) (chapter 23 of *Vaccine Design* . . . (1995) eds. Powell & Newman. ISBN: 030644867X. Plenum). ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in Podda & Del Giudice (2003) *Expert Rev Vaccines* 2:197-203; Podda (2001) *Vaccine* 19: 2673-2680; *Vaccine Design: The Subunit and Adjuvant Approach* (eds. Powell & Newman) Plenum Press 1995 (ISBN 0-306-44867-X); *Vaccine Adjuvants: Preparation Methods and Research Protocols* (Volume 42 of *Methods in Molecular Medicine* series). ISBN: 1-59259-083-7. Ed. O'Hagan; Allison & Byars (1992) *Res Immunol* 143:519-25; Hariharan et al. (1995) *Cancer Res* 55:3486-9; US-2007/014805; Suli et al. (2004) *Vaccine* 22(25-26):3464-9; WO95/11700; U.S. Pat. No. 6,080,725; WO2005/097181; WO2006/113373; Han et al. (2005) *Impact of Vitamin E on Immune Function and Infectious Diseases in the Aged at Nutrition, Immune functions and Health* EuroConference, Paris, 9-10 Jun. 2005; U.S. Pat. No. 6,630,161; U.S. Pat. No. 5,057,540; WO96/33739; EP-A-0109942; and WO96/11711. Optionally, the ISCOMS may be devoid of additional detergent (WO00/07621).

A review of the development of saponin based adjuvants can be found in Barr et al. (1998) *Advanced Drug Delivery Reviews* 32:247-271 and Sjolanderet et al. (1998) *Advanced Drug Delivery Reviews* 32:321-338.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in Niikura et al. (2002) *Virology* 293:273-280; Lenz et al. (2001) *J Immunol* 166:5346-5355; Pinto et al. (2003) *J Infect Dis* 188:327-338; Gerber et al. (2001) *J Virol* 75:4752-4760; WO03/024480 and WO03/024481. Virosomes are discussed further in, for example, Gluck et al. (2002) *Vaccine* 20:B10-B16.

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in EP-A-0689454. Such "small particles" of 3dMPL are small enough to be sterile filtered through a 0.22 μm membrane (U.S. Pat. No. 6,630,161). Other non-toxic LPS derivatives include monophosphoryl lipid A mimics, such as aminoalkyl glucosaminide phosphate derivatives e.g. RC-529 (Johnson et al. (1999) *Bioorg Med Chem Lett* 9:2273-2278; and Evans et al. (2003) *Expert Rev Vaccines* 2:219-229).

Lipid A derivatives include derivatives of lipid A from *Escherichia coli* such as OM-174. OM-174 is described for example in Meraldi et al. (2003) *Vaccine* 21:2485-2491 and Pajak et al. (2003) *Vaccine* 21:836-842.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. Kandimalla et al. (2003) *Nucleic Acids Research* 31:2393-2400, WO02/26757 and WO99/62923 disclose possible analog substitutions e.g. replacement of guanosine with 2'-deoxy-7-deazaguanosine. The adjuvant effect of CpG oligonucleotides is further discussed in Krieg (2003) *Nature Medicine* 9:831-835; McCluskie et al. (2002) *FEMS Immunology and Medical Microbiology* 32:179-185; WO98/40100; U.S. Pat. No. 6,207,646; U.S. Pat. No. 6,239,116 and U.S. Pat. No. 6,429,199.

The CpG sequence may be directed to TLR9, such as the motif GTCGTT or TTCGTT (Kandimalla et al. (2003) *Biochemical Society Transactions* 31 (part 3):654-658). The CpG sequence may be specific for inducing a Th1 immune response, such as a CpG-A ODN, or it may be more specific for inducing a B cell response, such a CpG-B ODN. CpG-A and CpG-B ODNs are discussed in Blackwell et al. (2003) *J Immunol* 170:4061-4068; Krieg (2002) *Trends Immunol* 23:64-65; and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Gluck et al. (2002) *Vaccine* 20:B10-B16; Kandimalla et al. (2003) *BBRC* 306:948-953; Bhagat et al. (2003) *BBRC* 300:853-861; and WO03/035836.

A useful CpG adjuvant is CpG7909, also known as ProMune™ (Coley Pharmaceutical Group, Inc.). Another is CpG1826. As an alternative, or in addition, to using CpG sequences, TpG sequences can be used (WO01/22972), and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in Pajak et al. (2003) *Vaccine* 21:836-842), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in Pajak et al. (2003) *Vaccine* 21:836-842), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC-31™ (Schellack et al. (2006) *Vaccine* 24:5461-72). Thus an adjuvant used with the invention may comprise a mixture of (i) an oligonucleotide (e.g, between 15-40 nucleotides) including at least one (and preferably multiple) CpI motifs (i.e, a cytosine linked to an inosine to form a dinucleotide), and (ii) a polycationic polymer, such as an oligopeptide (e.g, between 5-20 amino acids) including at least one (and preferably multiple) Lys-Arg-Lys tripeptide sequence(s). The oligonucleotide may be a deoxynucleotide comprising 26-mer sequence 5'-(IC) 13-3'. The polycationic polymer may be a peptide comprising 11-mer amino acid sequence KLKLLLLLKLK (SEQ ID NO:171).

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in Beignon et al. (2002) *Infect Immun* 70:3012-3019; Pizza et al. (2001) *Vaccine* 19:2534-2541; Pizza et al. (2000) *Int J Med Microbiol* 290:455-461; Scharton-Kersten et al. (2000) *Infect Immun* 68:5306-5313; Ryan et al. (1999) *Infect Immun* 67:6270-6280; Partidos et al. (1999) *Immunol Lett* 67:209-216; Peppoloni et al. (2003) *Expert Rev Vaccines* 2:285-293; and Pine et al. (2002) *J Control Release* 85:263-270.

A useful CT mutant is or CT-E29H (Tebbey et al. (2000) *Vaccine* 18:2723-34). Numerical reference for amino acid substitutions is preferably based on the alignments of the A and B subunits of ADP-ribosylating toxins set forth in Domenighini et al. (1995) *Mol Microbiol* 15:1165-1167, specifically incorporated herein by reference in its entirety.

F. Human Immunomodulators

Human immunomodulators suitable for use as adjuvants in the invention include cytokines, such as interleukins (e.g.

IL-1, IL-2, IL-4, IL-5, IL-6, IL-7, IL-12 (WO99/40936), etc.) (WO99/44636), interferons (e.g. interferon-γ), macrophage colony stimulating factor, and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres (Singh et al. (2001) *J Cont Release* 70:267-276) or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention (WO99/27960).

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (*Chapters* 13 & 14 *of Vaccine Design* . . . (1995) eds. Powell & Newman. ISBN: 030644867*X Plenum*.)

Examples of liposome formulations suitable for use as adjuvants are described in U.S. Pat. No. 6,090,406; U.S. Pat. No. 5,916,588; and EP-A-0626169.

J. Polyoxyethylene Ether and Polyoxyethylene Ester Formulations

Adjuvants suitable for use in the invention include polyoxyethylene ethers and polyoxyethylene esters (WO99/52549). Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152). Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Phosphazenes

A phosphazene, such as poly[di(carboxylatophenoxy) phosphazene] ("PCPP") as described, for example, in Andrianov et al. (1998) *Biomaterials* 19:109-115 and Payne et al. (1998) *Adv Drug Delivery Review* 31:185-196, may be used.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquimod ("R-837") (U.S. Pat. No. 4,680,338; U.S. Pat. No. 4,988,815), Resiquimod ("R-848") (WO92/15582), and their analogs; and salts thereof (e.g. the hydrochloride salts). Further details about immunostimulatory imidazoquinolines can be found in Stanley (2002) *Clin Exp Dermatol* 27:571-577; Wu et al. (2004) *Antiviral Res.* 64(2):79-83; Vasilakos et al. (2000) *Cell Immunol.* 204(1):64-74; U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293; and Jones (2003) *Curr Opin Investig Drugs* 4:214-218.

N. Substituted Ureas

Substituted ureas useful as adjuvants include compounds of formula I, II or III, or salts thereof:

I

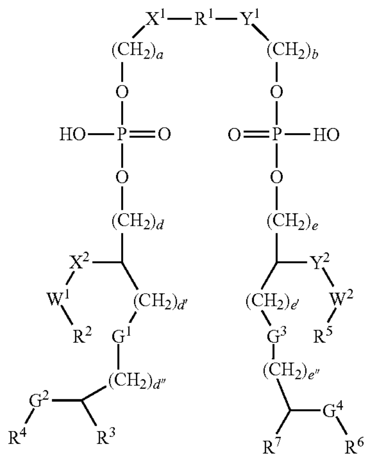

II

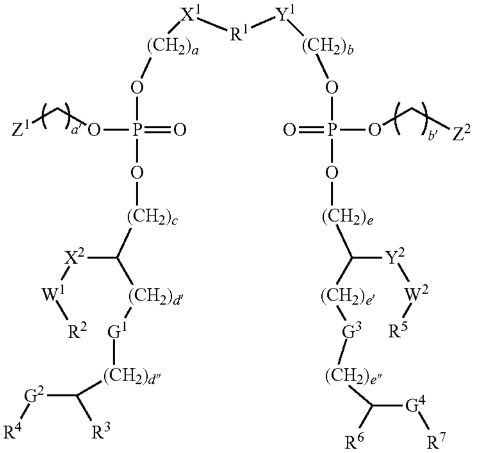

III

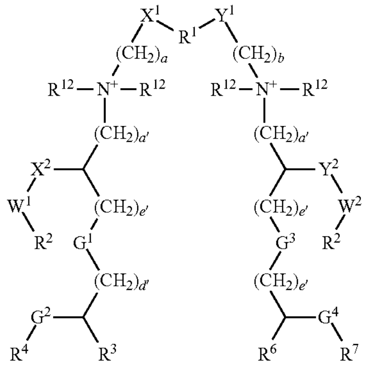

as defined in WO03/011223, such as 'ER 803058', 'ER 803732', 'ER 804053', ER 804058', 'ER 804059', 'ER 804442', 'ER 804680', 'ER 804764', ER 803022 or 'ER 804057' e.g.:

ER804057

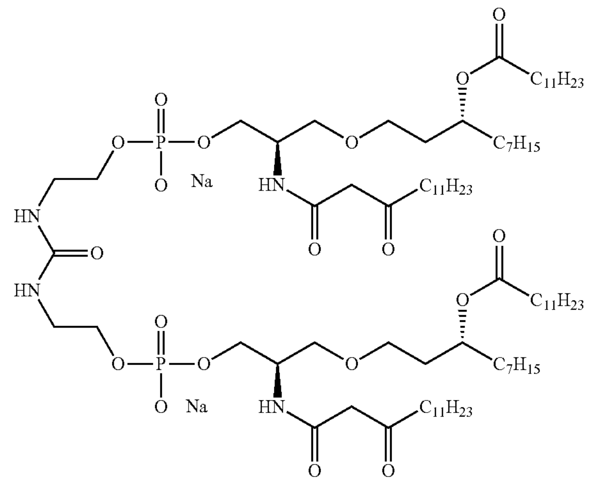

ER-803022

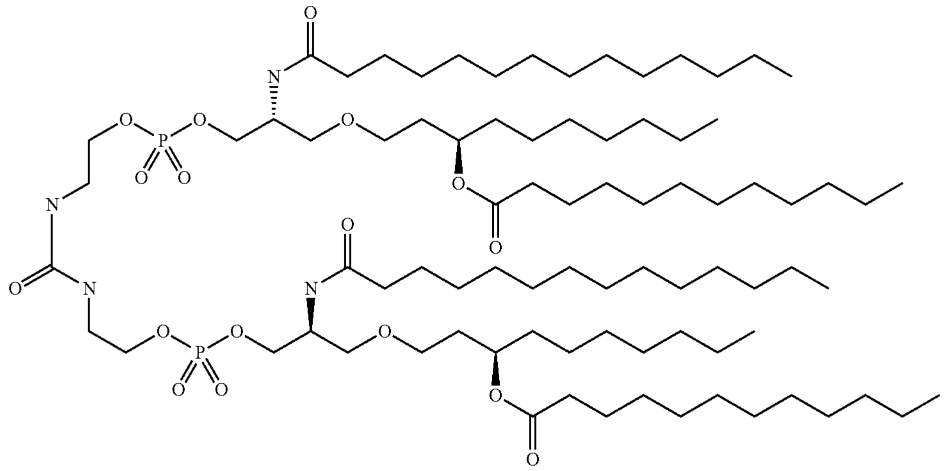

O. Further Adjuvants

Further adjuvants that may be used with the invention include:

An aminoalkyl glucosaminide phosphate derivative, such as RC-529 (Johnson et al. (1999) *Bioorg Med Chem Lett* 9:2273-2278; Evans et al. (2003) *Expert Rev Vaccines* 2:219-229).

A thiosemicarbazone compound, such as those disclosed in WO2004/060308. Methods of formulating, manufacturing, and screening for active compounds are also described in Bhagat et al. (2003) *BBRC* 300:853-861. The thiosemicarbazones are particularly effective in the stimulation of human peripheral blood mononuclear cells for the production of cytokines, such as TNF-α.

A tryptanthrin compound, such as those disclosed in WO2004/064759. Methods of formulating, manufacturing, and screening for active compounds are also described in WO03/035836. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

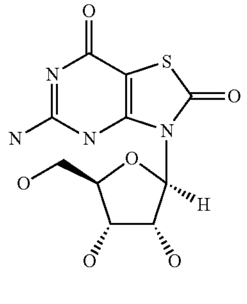 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in U.S. Pat. No. 6,924,271, US2005/0070556 and U.S. Pat. No. 5,658,731, oxoribine (7-allyl-8-oxoguanosine) (U.S. Pat. No. 5,011,828).

Compounds disclosed in WO2004/87153, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds (U.S. Pat. No. 6,605,617, WO02/18383), Hydrapthalamide compounds, Benzophenone compounds, Isoxazole compounds, Sterol compounds, Quinazilinone compounds, Pyrrole compounds (WO2004/018455), Anthraquinone compounds, Quinoxaline compounds, Triazine compounds, Pyrazalopyrimidine compounds, and Benzazole compounds (WO03/082272).

Compounds containing lipids linked to a phosphate-containing acyclic backbone, such as the TLR4 antagonist E5564 (Wong et al. (2003) *J Clin Pharmacol* 43(7):735-42; US2005/0215517).

A polyoxidonium polymer (Dyakonova et al. (2004) Int Inimunopharmacol 4(13):1615-23; FR-2859633) or other N-oxidized polyethylene-piperazine derivative.

Methyl inosine 5'-monophosphate ("MIMP") (Signorelli & Hadden (2003) *Int Immitnopharmacol* 3(8):1 177-86).

A polyhydroxlated pyrrolizidine compound (WO2004/064715), such as one having formula:

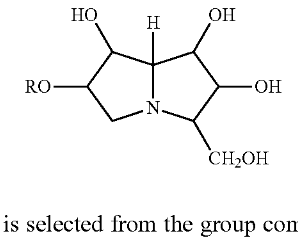

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide (De Libero et al, *Nature Reviews Immunology,* 2005, 5: 485-496; U.S. Pat. No. 5,936,076; Oki et al, *J. Clin. Investig.,* 113: 1631-1640; US2005/0192248; Yang et al, *Angew. Chem. Int. Ed.,* 2004, 43: 3818-3822; WO2005/102049; Goff et al, *J. Am. Chem., Soc.,* 2004, 126: 13602-13603; WO03/105769) e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin (Cooper (1995) *Pharm Biotechnol* 6:559-80) or derivative thereof, such as algammulin.

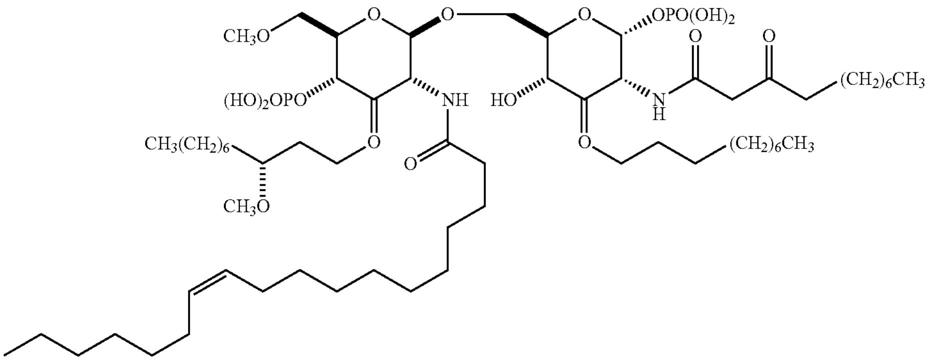

Adjuvant Combinations

The invention may also comprise combinations of aspects of one or more of the adjuvants identified above. For example, the following adjuvant compositions may be used in the invention: (1) a saponin and an oil-in-water emulsion (WO99/11241); (2) a saponin (e.g. QS21)+a non-toxic LPS derivative (e.g. 3dMPL) (WO94/00153); (3) a saponin (e.g. QS21)+a non-toxic LPS derivative (e.g. 3dMPL)+a cholesterol; (4) a saponin (e.g. QS21)+3dMPL+IL-12 (optionally+a sterol) (WO98/57659); (5) combinations of 3dMPL with, for example, QS21 and/or oil-in-water emulsions (European patent applications 08/35,318, 07/35,898 and 07/61,231); (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL). In some embodiments a combination of a toxin (e.g. LTK63) and an immunostimulatory oligonucleotide (e.g. CpG) is used. In some embodiments, a combination of an emulsion (e.g. montanide) and an immunostimulatory oligonucleotide (e.g. CpG) is used.

Other substances that act as immunostimulating agents are disclosed in chapter 7 of *Vaccine Design,* (1995) eds. Powell & Newman. ISBN: 030644867X. Plenum.

The use of an aluminium hydroxide and/or aluminium phosphate adjuvant is particularly preferred, and antigens are generally adsorbed to these salts. Calcium phosphate is another preferred adjuvant. Other preferred adjuvant combinations include combinations of Th1 and Th2 adjuvants such as CpG & alum or resiquimod & alum. A combination of aluminium phosphate and 3dMPL may be used.

To improve thermal stability, a composition may include a temperature protective agent. This component may be particularly useful in adjuvanted compositions (particularly those containing a mineral adjuvant, such as an aluminium salt). As described in WO2006/110603, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human administration, readily miscible/soluble in water, and should not damage other components (e.g. antigen and adjuvant) in the composition. Examples include glycerin, propylene glycol, and/or polyethylene glycol (PEG). Suitable PEGs may have an average molecular weight ranging from 200-20,000 Da. In a preferred embodiment, the polyethylene glycol can have an average molecular weight of about 300 Da ('PEG-300').

The invention provides an immunogenic composition comprising: (i) one or more proteins of the invention; and (ii) a temperature protective agent. This composition may be formed by mixing (i) an aqueous composition comprising one or more proteins of the invention, with (ii) a temperature protective agent. The mixture may then be stored e.g. below 0° C., from 0-20° C., from 20-35° C., from 35-55° C., or higher. It may be stored in liquid or frozen form. The mixture may be lyophilised. The composition may alternatively be formed by mixing (i) a dried composition comprising one or more proteins of the invention, with (ii) a liquid composition comprising the temperature protective agent. Thus component (ii) can be used to reconstitute component (i).

The compositions of the invention may elicit either or both of a cell mediated immune response and a humoral immune response. This immune response will preferably induce long lasting (e.g. neutralising) antibodies and a cell mediated immunity that can quickly respond upon exposure to *chlamydia*.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFNγ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFNγ, and TNF-β), an increase in activated macrophages, an increase in NK activity, or an increase in the production of IgG2a. Preferably, the enhanced TH 1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune resonse will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response. Preferably, the immune response includes an increase in the production of IgG1 and/or IgG2 and/or IgGA.

The invention is preferably used to elicit systemic and/or mucosal immunity. The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

Methods of Treatment, and Administration of the Vaccine

The invention also provides a method for raising an immune response in a mammal comprising the step of administering an effective amount of a protein, antibody, nucleic acid, vector, host cell or composition of the invention. The immune response is preferably protective and preferably involves antibodies and/or cell-mediated immunity. The method may raise a booster response.

The invention also provides a protein or combination, as defiend above, for use as a medicament e.g. for use in raising an immune response in a mammal.

The invention also provides the use of a protein or combination of the invention in the manufacture of a medicament for raising an immune response in a mammal. By raising an immune response in the mammal by these uses and methods, the mammal can be protected against *Chlamydia* infection. More particularly, the mammal may be protected against *Chlamydia trachomatis*. The invention is effective against *Chlamydia* of various different serotypes, but can be particularly useful in protecting against disease resulting from *Chlamydia* infection by strains in serovar D.

Thus, according to a further aspect, the invention also provides a nucleic acid, protein, antibody, vector or host cell according to the invention for use as a medicament (e.g. a vaccine) or a diagnostic reagent. In one embodiment, the protein, nucleic acid or antibody is used for treatment, prevention or diagnosis of *Chlamydia* infection (preferably *C. trachomatis*) in a mammal. The invention also provides a method of treating, preventing of diagnosing *Chlamydia* infection (preferably, *C. trachomatis* infection) in a patient (preferably a mammal), comprising administering a therapeutically effective amount of a nucleic acid, protein or antibody of the invention.

Preferably, the nucleic acid, protein or antibody according to the invention is for treatment or prevention of *Chlamydia* infection or an associated condition (e.g. trachoma, blindness, cervicitis, pelvic inflammatory disease, infertility, ectopic pregnancy, chronic pelvic pain, salpingitis, urethritis, epididymitis, infant pneumonia, cervical squamous cell carcinoma, etc.), preferably, *C. trachomatis* infection. The immunogenic composition may additionally or alternatively be effective against *C. pneumoniae*.

The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc. Thus a human patient may be less than 1 year old, 1-5 years old, 5-15 years old, 15-55 years old, or at least 55 years old. Preferred patients for receiving the vaccines are people going through purberty, teenagers, sexually active people, the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Vaccines produced by the invention may be administered to patients at substantially the same time as (e.g. during the same medical consultation or visit to a healthcare professional or vaccination centre) other vaccines e.g. at substantially the same time as a human papillomavirus vaccine such as Cervarix™ or Gardasil™; a tetanus, diphtheria and acellular pertussis vaccine such as TDaP, DTaP or Boostrix™; a rubella vaccine such as MMR; or a tubercolosis vaccine such as the BCG. Examples of other vaccines that the vaccine produced by the invention may be administered at substantially the same time as are a measles vaccine, a mumps vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, etc.

In a preferred embodiment, the protein of the invention is used to elicit antibodies that are capable of neutralising the activity of the wild type *Chlamydia* protein, for example, of one or more of wild-type *Chlamydia* CT733, CT153, CT601, CT279, CT443, CT372, CT456, CT381, CT255, CT341, CT716, CT745, CT387, CT812, CT869, CT166, CT175, CT163, CT214, CT721, CT127, CT043, CT600 and/or CT823 for example, of one or more of wild-type *Chlamydia* CT733, CT153, CT601, CT279, CT443, CT372, CT456 and/or CT381. Neutralizing antibodies may be used as a vaccine capable of neutralising the activity of a native *Chlamydia* protein expressed by infectious EB. In one embodiment, the protein of the invention is used to elicit antibodies that are capable of neutralising *Chlamydia* infectivity and/or virulence. Thus, the invention also provides the antibodies of the invention for neutralising wild-type *Chlamydia* proteins and/or *Chlamydia* infectivity and/or virulence.

The invention also provides the use of a nucleic acid, protein, or antibody of the invention in the manufacture of: (i) a medicament for treating or preventing bacterial infection; (ii) a diagnostic reagent for detecting the presence of bacteria or of antibodies raised against bacteria; and/or (iii) a reagent which can raise antibodies against bacteria. Said bacteria is preferably a *Chlamydia*, e.g. *Chlamydia trachomatis* or *Chlamydia pneumoniae*, but is preferably *Chlamydia trachomatis*.

Also provided is a method for diagnosing *Chlamydia* infection, comprising:

(a) raising an antibody against a protein of the invention;
(b) contacting the antibody of step (a) with a biological sample suspected of being infected with *Chlamydia* under conditions suitable for the formation of antibody-antigen complexes; and
(c) detecting said complexes, wherein detection of said complex is indicative of *Chlamydia* infection.

Also provided is a method for diagnosing *Chlamydia* infection, comprising: (a) contacting an antibody which was raised against a protein of the invention with a biological sample suspected of being infected with *Chlamydia* under conditions suitable for the formation of antibody-antigen complexes; and (b) detecting said complexes, wherein detection of said complex is indicative of *Chlamydia* infection.

Proteins of the invention can be used in immunoassays to detect antibody levels (or, conversely, antibodies of the invention can be used to detect protein levels). Immunoassays based on well defined, recombinant antigens can be developed to replace invasive diagnostics methods. Antibodies to proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Testing Efficacy of Compositions

The efficacy of the immunogenic compositions of the present invention can be evaluated in in vitro and in vivo animal models prior to host, e.g., human, administration. For example, in vitro neutralization by Peterson et al (1988) is suitable for testing vaccine compositions directed toward *Chlamydia trachomatis.*

One way of checking efficacy of therapeutic treatment involves monitoring *C. trachomatis* infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the *Chlamydia trachomatis* antigens in the compositions of the invention after administration of the composition. Typically, serum *Chlamydia* specific antibody responses are determined post-immunisation but pre-challenge whereas mucosal *Chlamydia* specific antibody body responses are determined post-immunisation and post-challenge.

One example of such an in vitro test is described as follows. Hyper-immune antisera is diluted in PBS containing 5% guinea pig serum, as a complement source. *Chlamydia trachomatis* ($10^4$ IFU; inclusion forming units) are added to the antisera dilutions. The antigen-antibody mixtures are incubated at 37° C. for 45 minutes and inoculated into duplicate confluent Hep-2 or HeLa cell monolayers contained in glass vials (e.g., 15 by 45 mm), which have been washed twice with PBS prior to inoculation. The monolayer cells are infected by centrifugation at 1000×g for 1 hour followed by stationary incubation at 37° C. for 1 hour. Infected monolayers are incubated for 48 or 72 hours, fixed and stained with *Chlamydia* specific antibody, such as anti-MOMP. Inclusion-bearing cells are counted in ten fields at a magnification of 200×. Neutralization titer is assigned on the dilution that gives 50% inhibition as compared to control monolayers/IFU.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within antigens.

The efficacy of vaccine compositions can also be determined in vivo by challenging animal models of *Chlamydia trachomatis* infection, e.g., guinea pigs or mice, with the vaccine compositions. For example, in vivo vaccine composition challenge studies in the guinea pig model of *Chlamydia trachomatis* infection can be performed. A description of one example of this type of approach follows. Female guinea pigs weighing 450-500 g are housed in an environmentally controlled room with a 12 hour light-dark cycle and immunized with vaccine compositions via a variety of immunization routes. Post-vaccination, guinea pigs are infected in the genital tract with the agent of guinea pig inclusion conjunctivitis (GPIC), which has been grown in HeLa or McCoy cells (Rank et al. (1988)). Each animal receives approximately $1.4\times10^7$ inclusion forming units (IFU) contained in 0.05 ml of sucrose-phosphate-glutamate buffer, pH 7.4 (Schacter, 1980). The course of infection monitored by determining the percentage of inclusion-bearing cells by indirect immunofluorescence with GPIC specific antisera, or by Giemsa-stained smear from a scraping from the genital tract (Rank et al 1988). Antibody titers in the serum is determined by an enzyme-linked immunosorbent assay.

Alternatively, in vivo vaccine compositions challenge studies can be performed in the murine model of *Chlamydia trachomatis* (Morrison et al 1995). A description of one example of this type of approach is as follows. Female mice 7 to 12 weeks of age receive 2.5 mg of depo-provera subcutaneously at 10 and 3 days before vaginal infection. Post-vaccination, mice are infected in the genital tract with 1,500 inclusion-forming units of *Chlamydia trachomatis* contained in 5 ml of sucrose-phosphate-glutamate buffer, pH 7.4. The course of infection is monitored by determining the percentage of inclusion-bearing cells by indirect immunofluorescence with *Chlamydia trachomatis* specific antisera, or by a Giemsa-stained smear from a scraping from the genital tract of an infected mouse. The presence of antibody titers in the serum of a mouse is determined by an enzyme-linked immunosorbent assay.

Nucleic Acid Immunisation

The immunogenic compositions described above include *Chlamydia* antigens. In all cases, however, the polypeptide antigens can be replaced by nucleic acids (typically DNA) encoding those polypeptides, to give compositions, methods and uses based on nucleic acid immunisation. Nucleic acid immunisation is now a developed field (e.g. see Donnelly et al. (1997) *Annu Rev Immunol* 15:617-648; Strugnell et al. (1997) *Immunol Cell Biol* 75(4):364-369; Cui (2005) *Adv Genet* 54:257-89; Robinson & Torres (1997) *Seminars in Immunol* 9:271-283; Brunham et al. (2000) *J Infect Dis* 181 Suppl 3:S538-43; Svanholm et al. (2000) *Scand J Immunol* 51(4):345-53; *DNA Vaccination—Genetic Vaccination* (1998) eds. Koprowski et al. (ISBN 3540633928); *Gene Vaccination: Theory and Practice* (1998) ed. Raz (ISBN 3540644288), etc.).

The nucleic acid encoding the immunogen is expressed in vivo after delivery to a patient and the expressed immunogen then stimulates the immune system. The active ingredient will typically take the form of a nucleic acid vector comprising: (i) a promoter; (ii) a sequence encoding the immunogen, operably linked to the promoter; and optionally (iii) a selectable marker. Preferred vectors may further comprise (iv) an origin of replication; and (v) a transcription terminator downstream of and operably linked to (ii). In general, (i) & (v) will be eukaryotic and (iii) & (iv) will be prokaryotic.

Preferred promoters are viral promoters e.g. from cytomegalovirus (CMV). The vector may also include transcriptional regulatory sequences (e.g. enhancers) in addition to the promoter and which interact functionally with the promoter. Preferred vectors include the immediate-early CMV enhancer/promoter, and more preferred vectors also include CMV intron A. The promoter is operably linked to a downstream sequence encoding an immunogen, such that expression of the immunogen-encoding sequence is under the promoter's control.

Where a marker is used, it preferably functions in a microbial host (e.g. in a prokaryote, in a bacteria, in a yeast). The marker is preferably a prokaryotic selectable marker (e.g. transcribed under the control of a prokaryotic promoter). For convenience, typical markers are antibiotic resistance genes.

The vector of the invention is preferably an autonomously replicating episomal or extrachromosomal vector, such as a plasmid.

The vector of the invention preferably comprises an origin of replication. It is preferred that the origin of replication is active in prokaryotes but not in eukaryotes.

Preferred vectors thus include a prokaryotic marker for selection of the vector, a prokaryotic origin of replication, but a eukaryotic promoter for driving transcription of the immunogen-encoding sequence. The vectors will therefore (a) be amplified and selected in prokaryotic hosts without polypeptide expression, but (b) be expressed in eukaryotic hosts without being amplified. This arrangement is ideal for nucleic acid immunization vectors.

The vector of the invention may comprise a eukaryotic transcriptional terminator sequence downstream of the coding sequence. This can enhance transcription levels. Where the coding sequence does not have its own, the vector of the invention preferably comprises a polyadenylation sequence. A preferred polyadenylation sequence is from bovine growth hormone.

The vector of the invention may comprise a multiple cloning site.

In addition to sequences encoding the immunogen and a marker, the vector may comprise a second eukaryotic coding sequence. The vector may also comprise an IRES upstream of said second sequence in order to permit translation of a second eukaryotic polypeptide from the same transcript as the immunogen. Alternatively, the immunogen-coding sequence may be downstream of an IRES.

The vector of the invention may comprise unmethylated CpG motifs e.g. unmethylated DNA sequences which have in common a cytosine preceding a guanosine, flanked by two 5' purines and two 3' pyrimidines. In their unmethylated form these DNA motifs have been demonstrated to be potent stimulators of several types of immune cell.

Vectors may be delivered in a targeted way. Receptor-mediated DNA delivery techniques are described in, for example, Findeis et al., *Trends Biotechnol.* (1993) 11:202; Chiou et al. (1994) *Gene Therapeutics: Methods And Applications Of Direct Gene Transfer*. ed. Wolff; Wu et al., *J. Biol. Chem.* (1988) 263:621; Wu et al., *J. Biol. Chem.* (1994) 269: 542; Zenke et al., *Proc. Natl. Acad. Sci.* (*USA*) (1990) 87:3655; and Wu et al., *J. Biol. Chem.* (1991) 266:338.

Therapeutic compositions containing a nucleic acid are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. Factors such as method of action (e.g. for enhancing or inhibiting levels of the encoded gene product) and efficacy of transformation and expression are considerations which will affect the dosage required for ultimate efficacy. Where greater expression is desired over a larger area of tissue, larger amounts of vector or the same amounts re-administered in a successive protocol of administrations, or several administrations to different adjacent or close tissue portions may be required to effect a positive therapeutic outcome. In all cases, routine experimentation in clinical trials will determine specific ranges for optimal therapeutic effect.

Vectors can be delivered using gene delivery vehicles. The gene delivery vehicle can be of viral or non-viral origin (see generally Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148).

Viral-based vectors for delivery of a desired nucleic acid and expression in a desired cell are well known in the art. Exemplary viral-based vehicles include, but are not limited to, recombinant retroviruses (e.g. WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP-A-0345242; and WO 91/02805), alphavirus-based vectors (e.g. Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532); hybrids or chimeras of these viruses may also be used), poxvirus vectors (e.g. vaccinia, fowlpox, canarypox, modified vaccinia Ankara, etc.), adenovirus vectors, and adeno-associated virus (AAV) vectors (e.g. see WO 90/07936; WO 94/03622; WO 93/25698; WO 93/25234; U.S. Pat. No. 5,219,740; WO 93/11230; WO 93/10218; U.S. Pat. No. 4,777,127; GB Patent No. 2,200,651; EP-A-0345242; WO 91/02805; WO 94/12649; WO 93/03769; WO 93/19191; WO 94/28938; WO 95/11984; and WO 95/00655). Administration of DNA linked to killed adenovirus (Curiel, *Hum. Gene Ther.* (1992) 3:147) can also be employed.

Non-viral delivery vehicles and methods can also be employed, including, but not limited to, polycationic condensed DNA linked or unlinked to killed adenovirus alone (e.g. De Libero et al, *Nature Reviews Immunology,* 2005, 5: 485-496), ligand-linked DNA (Wu, *J. Biol. Chem.* (1989) 264:16985), eukaryotic cell delivery vehicles cells (U.S. Pat. No. 5,814,482; WO 95/07994; WO 96/17072; WO 95/30763; and WO 97/42338) and nucleic charge neutralization or fusion with cell membranes. Naked DNA can also be employed. Exemplary naked DNA introduction methods are described in WO 90/11092 and U.S. Pat. No. 5,580,859. Liposomes (e.g. immunoliposomes) that can act as gene delivery vehicles are described in U.S. Pat. No. 5,422,120; WO 95/13796; WO 94/23697; WO 91/14445; and EP-0524968. Additional approaches are described in Philip, *Mol. Cell Biol.* (1994) 14:2411 and Woffendin, *Proc. Natl. Acad. Sci.* (1994) 91:11581.

Further non-viral delivery suitable for use includes mechanical delivery systems such as the approach described in Donnelly et al. (1997) *Annu Rev Immunol* 15:617-648. Moreover, the coding sequence and the product of expression of such can be delivered through deposition of photopolymerized hydrogel materials or use of ionizing radiation (e.g. U.S. Pat. No. 5,206,152 and WO 92/11033). Other conventional methods for gene delivery that can be used for delivery of the coding sequence include, for example, use of hand-held gene transfer particle gun (U.S. Pat. No. 5,149,655) or use of ionizing radiation for activating transferred genes (Strugnell et al. (1997) *Immunol Cell Biol* 75(4):364-369 and Cui (2005) *Adv Genet* 54:257-89).

Delivery DNA using PLG {poly(lactide-co-glycolide)} microparticles is a particularly preferred method e.g. by adsorption to the microparticles, which are optionally treated to have a negatively-charged surface (e.g. treated with SDS) or a positively-charged surface (e.g. treated with a cationic detergent, such as CTAB).

Antibody Immunisation

The antibodies of the invention may be used, for example, for neutralising the activity of the wild-type *Chlamydia* protein. Antibodies against *Chlamydia* antigens can be used for passive immunisation (Brandt et al. (2006) *J Antimicrob Chemother.* 58(6):1291-4. Epub 2006 Oct. 26). Thus the invention provides the use of antibodies of the invention in therapy. The invention also provides the use of such antibodies in the manufacture of a medicament. The invention also provides a method for treating a mammal comprising the step of administering an effective amount of an antibody of the invention. As described above for immunogenic compositions, these methods and uses allow a mammal to be protected against *Chlamydia* infection.

Processes

According to further aspects, the invention provides various processes.

A process for producing a protein of the invention is provided, comprising the step of culturing a host cell of the invention under conditions which induce protein expression.

A process for producing protein or nucleic acid of the invention is provided, wherein the protein or nucleic acid is synthesised in part or in whole using chemical means.

A process for detecting *Chlamydia* (preferably *C. trachomatis*) in a biological sample is also provided, comprising the step of contacting a nucleic acid according to the invention with the biological sample under hybridising conditions. The process may involve nucleic acid amplification (e.g. PCR, SDA, SSSR, LCR, TMA etc.) or hybridisation (e.g. microarrays, blots, hybridisation with probe in solution etc.).

A process for detecting wild-type *Chlamydia* (preferably, *C. trachomatis*) is provided, comprising the steps of: (a) contacting an antibody of the invention with a biological sample under conditions suitable for the formation of an antibody-antigen complex(es); and (b) detecting said complex(es). This process may advantageously be used to diagnose *Chlamydia* infection.

General

The practice of the present invention will employ, unless otherwise indicated, conventional methods of chemistry, biochemistry, molecular biology, immunology and pharmacology, within the skill of the art. Such techniques are explained fully in the literature. See, e.g., Gennaro (2000) *Remington: The Science and Practice of Pharmacy.* 20th edition, ISBN: 0683306472; *Methods In Enzymology* (S. Colowick and N. Kaplan, eds., Academic Press, Inc.); *Handbook of Experimental Immunology*, Vols. I-IV (D. M. Weir and C. C. Blackwell, eds, 1986, Blackwell Scientific Publications); Sambrook et al. (2001) *Molecular Cloning: A Laboratory Manual,* 3rd edition (Cold Spring Harbor Laboratory Press); *Handbook of Surface and Colloidal Chemistry* (Birdi, K. S. ed., CRC Press, 1997); Ausubel et al. (eds) (2002) *Short protocols in molecular biology,* 5th edition (Current Protocols); *Molecular Biology Techniques: An Intensive Laboratory Course*, (Ream et al., eds., 1998, Academic Press); and *PCR* (*Introduction to Biotechniques Series*), 2nd ed. (Newton & Graham eds., 1997, Springer Verlag) etc.

"GI" numbering is used herein. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

Where the invention concerns an "epitope", this epitope may be a B-cell epitope and/or a T-cell epitope. Such epitopes can be identified empirically (e.g. using PEPSCAN (Geysen el al. (1984) *PNAS USA* 81:3998-4002; Carter (1994) *Methods Mol Biol* 36:207-23) or similar methods), or they can be predicted (e.g. using the Jameson-Wolf antigenic index (Jameson, B A et al. 1988, *CABIOS* 4(1):181-186), matrix-based approaches (Raddrizzani & Hammer (2000) *Brief Bioinform* 1(2):179-89), MAPITOPE (Bublil et al. (2007) *Proteins* 68(1):294-304), TEPITOPE (De Lalla et al. (1999) *J. Immunol.* 163:1725-29; Kwok et al. (2001) *Trends Immunol* 22:583-88), neural networks (Brusic et al. (1998) *Bioinformatics* 14(2):121-30), OptiMer & EpiMer (Meister et al. (1995) *Vaccine* 13(6):581-91; Roberts et al. (1996) *AIDS Res Hum Retroviruses* 12(7):593-610), ADEPT (Maksyutov & Zagrebelnaya (1993) *Comput Appl Biosci* 9(3):291-7), Tsites (Feller & de la Cruz (1991) *Nature* 349(6311):720-1), hydrophilicity (Hopp (1993) *Peptide Research* 6:183-190), antigenic index (Welling et al. (1985) *FEBS Lett.* 188:215-218) or the methods disclosed in Davenport et al. (1995) *Immunogenetics* 42:392-297; Tsurui & Takahashi (2007) *J Pharmacol Sci.* 105(4):299-316; Tong et al. (2007) *Brief Bioinform.* 8(2):96-108; Schirle et al. (2001) *J Immunol Methods.* 257(1-2):1-16; and Chen et al. (2007) *Amino Acids* 33(3):423-8, etc.). Epitopes are the parts of an antigen that are recognised by and bind to the antigen binding sites of antibodies or T-cell receptors, and they may also be referred to as "antigenic determinants".

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of *Current Protocols in Molecular Biology* (F. M. Ausubel et al., eds., 1987) Supplement 30. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) *Adv. Appl. Math.* 2:482-489.

BRIEF DESCRIPTION OF DRAWINGS

FIG. 1 is a graph which shows the ability of 20 selected *C. trachomatis* antigens to induce IFNγ production by CD4+ T cells.

FIG. 2*a* shows the bacterial shedding (IFUs recovered from lungs) after *Chlamydia* challenge in mice to whom EB-CM CD4+ T cells had been adoptively transferred.

FIG. 10A shows the protection results achieved with various antigens combinations in the mouse model of *C. muridarum* intranasal challenge. FIG. 10B shows the frequency of IFNg-producing CD4+ T cells induced by vaccination with the antigen combination TC0890+TC0551. From left to right, the bars represent stimutaion with 1) TC0551, TC0890, TC0551+TC0890 (for adjuvant-immunized mice) and 2) TC0551, TC0890, TC0551+TC0890 (for MIX TC0890+TC0551-immunized mice).

FIG. 12 shows protective activity of antigens TC0313, TC0741, TC0106 and TC0210 given singly or in combination. In 12A to 12D the bars show mean IFU/lung (Log 10), with the left-hand bar being adjuvant alone (LTK61+CpG) and the right-hand bar being the TC antigen. FIG. 12E shows the IFU reduction over time (Mean IFU/lung against days post-challenge) using the combination (squares) or adjuvant alone (diamonds).

MODES FOR CARRYING OUT THE INVENTION

Example 1

Figure 2B:
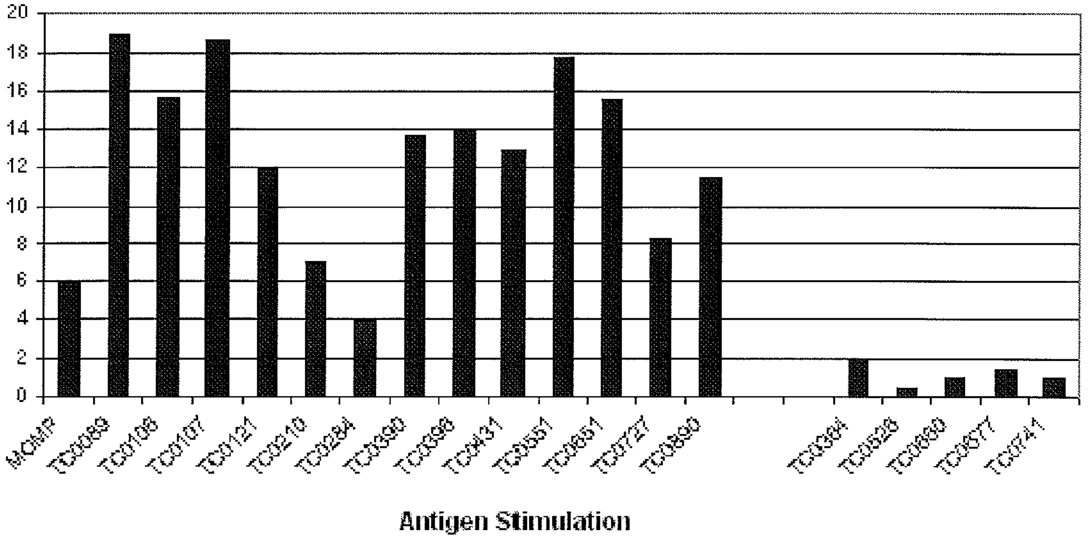
FIG. 2*b* shows the ability of various *C. muridarum* antigens to stimulate the protective EB-CD4+ T cell line to produce IFNγ.

Induction of Population of CD4+ T Cells to Produce IFNγ

20 antigens have been found which induce a population of CD4+ T cells to produce IFNγ (see FIG. 1). 17 of these are newly discovered (CT016, CT043, CT114, CT153, CT255, CT279, CT341, CT372, CT480, CT600, CT601, CT711, CT716, CT733, CT734. CT745, CT823), while three antigens (CT681-MOMP, CT396-Hsp60 and CT587-Enolase) have already been described as targets of CD4+ T cells (Goodall J C et al. 2001; Hassell A B et al. 1993). Significantly, some antigens were able to induce a frequency of antigen-specific CD4+ responding T cells at least comparable to what observed with the positive control antigen MOMP.

The 17 new antigens are as follows:

| Antigen | Annotation | Gene name |
|---|---|---|
| CT016 | Hypothetical protein | |
| CT043 | Hypothetical protein | |
| CT114 | Hypothetical protein | |
| CT153 | Hypothetical protein | |
| CT255 | Hypothetical protein | |
| CT279 | Na(+)-translocating NADH-quinone reductase subunit C | nqr3 |
| CT341 | Heat shock protein J (Hsp-J) | dnaJ |
| CT372 | Hypothetical protein | |
| CT480 | Oligopeptide Binding Lipoprotein | oppA_4 |
| CT600 | | |
| CT601 | Invasin repeat family phosphatase | papQ |
| CT711 | Hypothetical protein | |
| CT716 | Hypothetical protein | |
| CT733 | Hypothetical protein | |
| CT734 | Hypothetical protein | |
| CT745 | protoporphyrinogen oxidase | hemG |
| CT823 | DO serine protease | htrA |

Of these 17 new antigens, CT341 may be the least suitable for use in immunization because it is a heat shock protein.

Example 2

Characterization of the Antigen-Specifity of Protective *Chlamydia* Specific CD4+ Th1 Cell Lines The relevance of the newly discovered antigens for protective immunity to *Chlamydia* was further corroborated by showing that they were recognized by T cells belonging to a *Chlamydia*-specific CD4+/IFNγ+ cell line, conferring protection when adoptively transferred to naïve recipient mice. To this aim we have derived a short-term CD4+ T cell line, produced against the extracellular EB form of *C. muridarum* that showed a high capacity to protect adoptively transferred naïve mice from *C. muridarum* challenge. The protective CD4+ cell line, which had undergone only a few cycles of expansion, maintained a polyclonal cell population with broad specificity that should correlate more closely to the in vivo protective response than long-term lines or clones. The polyclonal cell line was analysed for its antigen recognition profile versus the *C. muridarum* antigens, homologous to the *C. trachomatis* CD4-Th1 inducing proteins. The dissection of the antigen specificity of the protective CD4+ T cell polyclonal population demonstrated that the *Chlamydia* CD4+/IFNγ+ inducing-antigens identified during an infection are also targets of CD4+ T cells that play a part in the rapid clearance of the bacterium in a protective response to the infection, in the absence of antibodies.

*Chlamydia* T cell lines were derived from Balb/c infected mice and their protective activity was verified in naïve mice against *C. muridarum* challenge. Subsequently, the antigen recognition profile of the *C. muridarum* CD4+ T cell line was characterized to define the possible contribution of each *C. muridarum* antigen in inducing protective CD4+ T cells. For the preparation of *Chlamydia*-specific CD4+ T cells, splenic CD4+ T lymphocytes were purified from donor Balb/c mice that had previously been infected intranasally with $10^3$ viable Elementary Bodies (EBs) of *C. muridarum*. An EB-responding CD4+ T cell line was derived (referred as EB-CD4+ cell line) and expanded in vitro with a short term stimulation with heat inactivated EBs. The line showed the capacity to respond to *C. muridarum* EBs by producing IFNγ with a high frequency (data not shown). To determine the efficacy of the EB-CD4+ cell line in resolving an infection, $10^7$ CD4+ T cells were adoptively transferred into 4 Balb/c recipient naïve mice. Mice were challenged intranasally 24 hours after i.v. infusion of CD4+ T cells with $10^3$ IFUs of *C. muridarum*. The protective effect of adoptive immunization was evaluated by quantitating the number of IFUs recovered from lungs taken 10 days after *Chlamydia* challenge. As shown in FIG. 2*a*, naïve mice adoptively transferred with EB-CM CD4+ T cells shed 3 $Log_{10}$ fewer IFUs in the lungs 10 days after intranasal challenge with $10^3$ IFUs of *C. muridarum*, as compared to either non treated mice (p value: 0.008) or mice receiving an unrelated CD4+ T cell line. Similarly, splenic CD4+ T cells isolated from mice that resolved an intravaginal primary infection with $10^5$ IFUs of *C. trachomatis* conferred significant IFU reduction in adoptively transferred mice (data not shown).

To characterize the antigen recognition profile of the *C. muridarum* CD4+ T cells, most of the *C. muridarum* proteins, homolog of the proteins identified as CD4+ Th1 inducers during *C. trachomatis* infection (FIG. 1), were obtained in recombinant form and tested for their ability to stimulate the protective EB-CD4+ T cell line to produce IFNγ. In this analysis we excluded both the proteins which after purification did not reach the purity/endoxin level required for the cytokine stimulation assay, or those which, due to their homology with human bacterial proteins were not suitable for developing a vaccine (e.g. heat shock proteins, enolase). The protective EB-CD4+ T cell line was stimulated in vitro with a panel of 19 *C. muridarum* recombinant proteins, including MOMP. Fourteen of them were homologs of *C. trachomatis* CD4+ Th1 inducing antigens identified in the primary screening in infected mice, and 5 were negative controls. As shown in FIG. 2*b*, all the 14 CD4+-inducing antigens tested were found also to be targets of the protective EB-CM CD4+ T cell line, and able to induce IFNγ production in a percentage of CD4+ T cells at least 3 times higher than the frequency of negative control antigens. Therefore the pattern of T cell antigens recognized by the protective *Chlamydia* EB-CM T cell line is comparable to the recognition profile of T cells identified in the *C. trachomatis* infected mice.

Example 3

CT733 and CT153 Specific CD4+ Th1 Response in BALB/c Mice after a Primary *C. trachomatis* Infection Splenocytes of primary infected BALB/c mice and non infected controls were collected 10 days after infection and stimulated with LPS-free recombinant antigens CT733 and CT153 (20 mg/ml). After 4 hours of stimulation, 5 mg/ml of Brefeldin A were added to the cells for the following 12 hrs to block cytokine secretion. Afterwards, cells were fixed, permeabilized and stained. Intracellular IFNγ and IL-5 expression were analyzed versus CD4 surface expression of the gated viable cells and assessed by flow cytometry.

Figure 3:
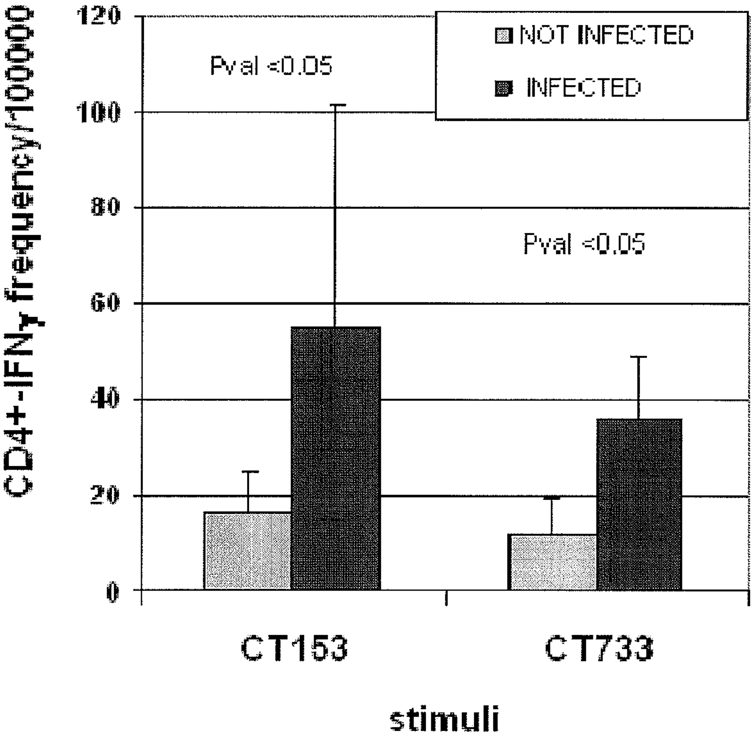
FIG. 3 is a histogram which shows the number of CD4+ T cells that produce IFNγ, upon specific stimulation with *C. trachomatis* recombinant antigens CT153 and CT733.

The histogram in FIG. 3 shows the number of CD4+ T cells per $10^5$ CD4+ T splenocytes of primary infected (dark gery bars) and non-infected (light grey bars) mice that produce IFNγ upon specific stimulation with the *C. trachomatis* recombinant antigens CT153 and CT733. The data were confirmed in several further experiments using the same protcol.

The results indicate that CT733 and CT153 are able to induce significant frequencies of specific CD4+/IFNγ+ cells in splenocytes from Balb/c mice that were infected intravaginally with *C. trachomatis*, suggesting a potential role as antigen candidates for these proteins.

Example 4

Protective Activity of Single Antigens TC0106 and TC0431 Against *C. muridarum* Challenge CT733 and CT153 were tested in a mouse model of chlamydial infection to evaluate their protective properties. This was done by adopting the mouse model of lung infection with the species *Chlamydia muridarum*.

The *C. muridarum* proteins TC0106 and TC0431, homologous to CT733 and CT153, respectively, were cloned and purified, and used for the mouse model.

Groups of BALB/c mice were immunized with either TC0106 or TC0431 recombinant antigens formulated with LTK63+CpG adjuvant (3 doses of 15 ug protein, at 2 week interval, given intramuscularly). As negative control, mice were immunized with the adjuvant only. Four weeks after the last immunization animals were infected intranasally with $10^3$ IFU of infectious *C. muridarum*. After 10 days, the protective activity conferred by the two antigens was measured by counting the infectious IFU in the lung of challenge animals.

Figure 4:
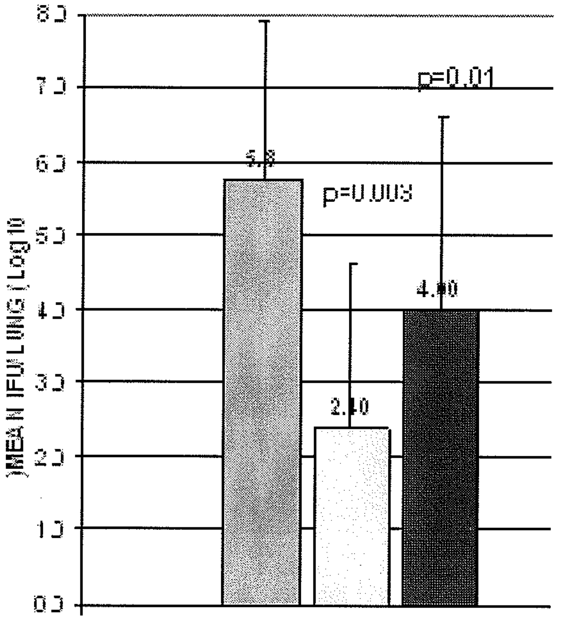
FIG. 4 shows the protective activity of TC0106 (*C. muridarum* homologue of CT733) and TC0431 (*C. muridarum* homologue of CT153) as single antigens. The graph shows mean IFU/ml in BALB/C mice immunised with the two antigens and then challendged with *C. muridarum*. The three bars are, from left to right: adjuvant alone; TC0106 as immunogen; and TC0431 as immunogen.

As shown in FIG. 4, each of the two antigens (middle and right hand columns of the histogram) was able to reduce significantly the number of IFU/lung in challenged mice as compared to adjuvant immunized mice (left hand column of the histogram), indicating that both TC0106 and TC0431 (and therefore CT733 and CT153) confer protective immunity to *Chlamydia* infection Example 5

Protective Activity of the Combination of TC0106+TC0431 Against *C. muridarum* Challenge Groups of BALB/c mice (10 to 15 mice) were immunized with the combination of TC0106+TC0431 recombinant antigens formulated with LTK63+CpG adjuvant (3 doses of 10 ug of each protein at 2 week-interval, given intramuscularly). As negative control, mice were immunized with the adjuvant only. Four weeks after the last immunization, animals were infected intranasally with $10^3$ IFU of infectious *C. muridarum*. After 10 days, the protective activity conferred by the two antigens was measured by counting the infectious IFU in the lung of challenge animals. As positive control, a group of mice receiving a primary and a secondary *C. muridarum* infection was also included (left column in the histogram of FIG. 5).

Figure 5:
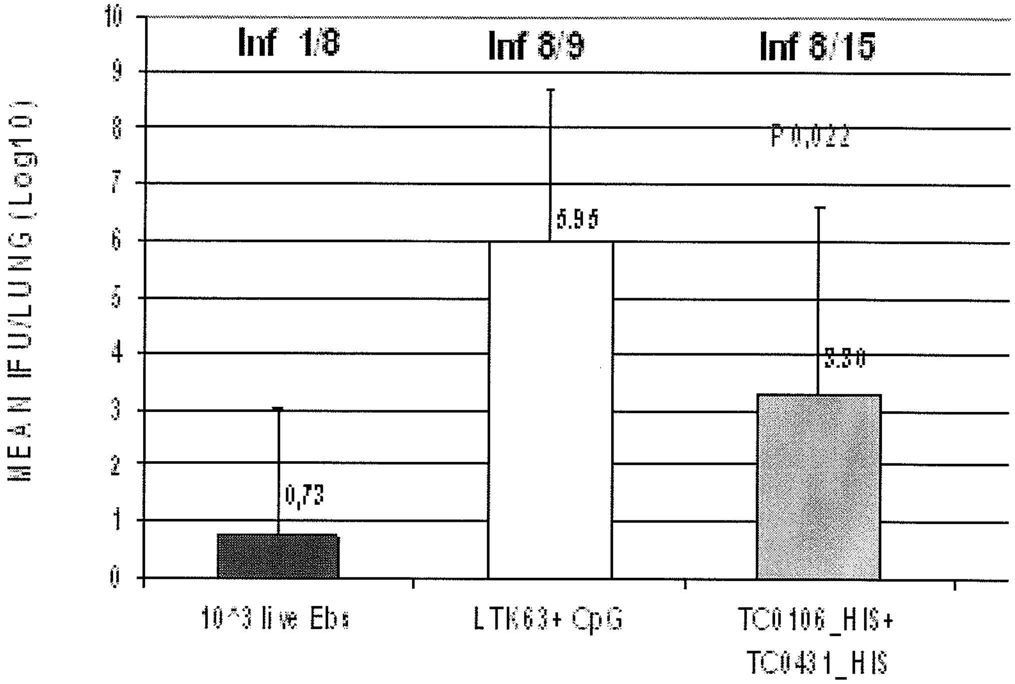
FIG. 5 shows the protective activity of the combination TC0106+TC0431. The graph shows mean IFU per lung (Log 10) recovered from infected lungs of mice immunised with the combination. The three bars are, from left to right: $10^3$ live Ebs; adjuvant alone; antigen combination.

As shown in FIG. 5, the antigen combination (right hand column of histogram) was able to significantly reduce the number of IFU/lung in challenged mice as compared to adjuvant immunized mice (middle column of histogram).

Thus, immunization with the CT733 and CT153, either alone or in combination, was able to significantly reduce the bacterial load in the lungs of challenged mice (see FIGS. 4 and 5).

Example 6

Figure 6:
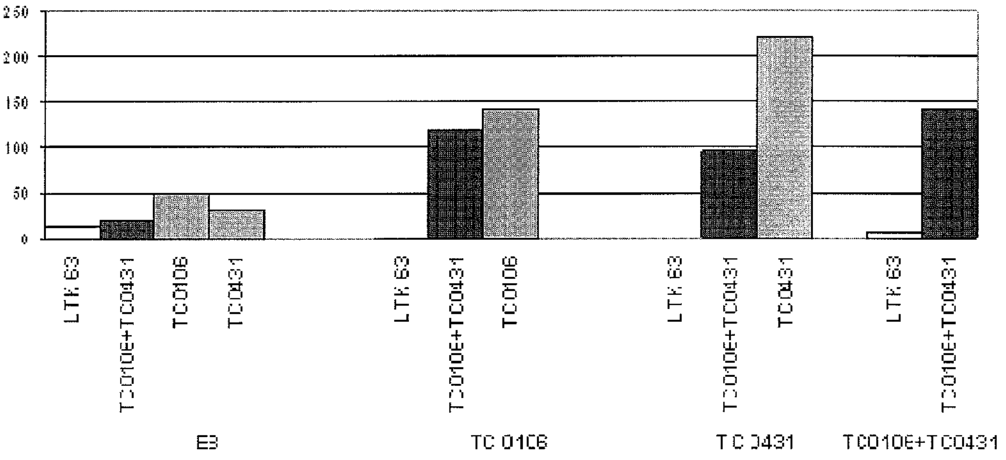
FIG. 6 shows CD4 T cells producing IFNγ in PBMC of mice immunized with TC0106+TC0431, TC0106, TC0431 and LTK 63+CpG. From left to right, the bars represent stimulation with 1) LTK 63, TC0106+TC0431, TC0106, TC0431 (all EB-immunized mice); 2) LTK 63, TC0106+TC0431, TC0106 (all TC 0106-immunized mice); 3) LTK63, TC0106+TC0431. TC0431 (all TC0431-immunized mice); and 4) LTK63 and TC0106+TC0431 (both TC0106+TC0431-immunized mice). It shows that immunization with TC0106 (*C. muridarum* homologue of CT733) and TC0431 (*C. muridarum* homologue of CT153) elicits a significant frequency of specific CD4+/IFNγ+ cells. The Y axis shows frequency on $10^6$ CD4.

Elicitation of CD4+ Th1 Cells in BALB/c Mice After Immunization with TC0431 and TC0106 Recombinant Antigens, Alone or in Combination Groups of BALB/c mice (10 to 15 mice) were immunized with the recombinant antigens TC0431 and TC0106 as single antigens or in combination (i.m., 10-15 micrograms/dose, 3 doses at 2 week-intervals) using LTK63+CpG adjuvant. Ten days after the third immunization dose, splenocytes were collected and stimulated with LPS-free recombinant antigens (20 mg/ml). As negative control, splenocytes of adjuvant immunized mice were included. After 4 hours of stimulation, 5 mg/ml of Brefeldin A was added to the cells for the following 12 hrs to block cytokine secretion. Afterwards, cells were fixed, permeabilized and stained. The intracellular IFNγ was analyzed versus CD4 surface expression of the gated viable cells and assessed by flow cytometry. The histogram in FIG. 6 shows the number of CD4+ T cells per $10^5$ CD4+ T splenocytes that produce IFNγ upon specific stimulation with the recombinant antigens in mice immunized with TC0106, TC0431, the combination of TC0106+TC0431 and adjuvant immunized mice.

The results indicate that immunization with these antigens elicits a high frequency of CD4+ Th1 cells.

Example 7

Evaluation of the Protective Effect of the Chlamydial Antigen(s) Against *C. muridarum* Challenge The protective effect of combinations of two antigens selected from *C. trachomatis* CT279, CT601, CT372, CT443, CT733, CT153, CT456 and CT381 was tested in the *C. muridarum* mouse model using their *C. muridarum* homologues TC0551 (CT279), TC0651 (CT372), TC0727 (CT443), TC0890 (CT601), TC0106 (CT733), TC0431 (CT153), TC0660 (CT381) and TC0741 (CT456). The protective effect of CT733 and CT153 individually was also tested.

Figure 7:
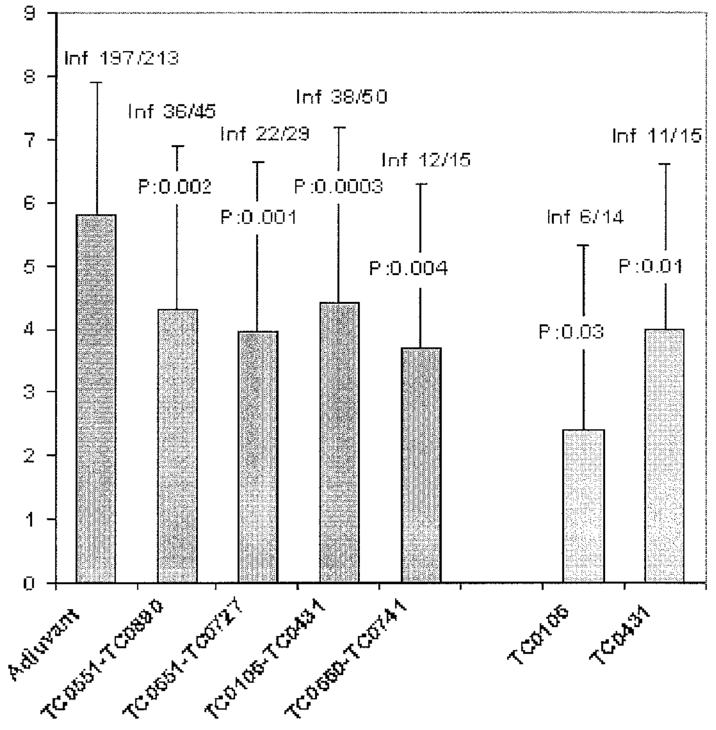
FIG. 7 is a summary of protection results for various combinations and single antigens in the mouse model of *C. muridarum* intransal challenge. It shows the mean IFU/lung of mice immunised imtramuscularly with single antigens, or antigen combinations, adjuvanted with LTK63 and CpG, then challenged intranasally with $10^3$ *C. muridarum* IFU.

BALB/c mice were immunized three times intramuscularly with a combination of two antigens or single antigens with LTK63+CpG as adjuvant. Twenty-four days post last immunization mice were challenged intranasally with $10^3$ IFU *C. muridarum*. After 10 days, lungs were collected, homogenized and the number of viable chlamydiae (IFU/lung) was measured. The data in FIG. 7 shows the mean IFU/lung counts in antigen-immunized mice and adjuvant-immunized control. From left to right, the lanes relate to (a) adjuvant only; (b) TC0551+TC0890 (CT279+CT601); (c) TC0651+TC0727 (CT372+CT443); (d) TC0106+TC0431 (CT733+CT153); (e) TC0660+TC0741 (CT456+CT381); (f) TC0106 (CT733); (g) TC0431 (CT153). For each antigen formulation, the numbers of infected mice out of the total immunized are reported in the form "Inf X/Y", wherein X is the number of infected mice and Y is the total number of mice challenged. The statistical significance of immunizing antigen/s (P), was determined by Student t-test.

Four combinations of two antigens have been identified as capable of conferring protection against *C. muridarum* intranasal challenge. For three of them (TC0431+TC0106; TC0727+TC0651; TC0551+TC0890; homologs of CT733+CT153; CT443+CT372; CT279+CT601) protection has been confirmed in a high number of mice using LTK63+CpG adjuvant (FIG. 7). Immunization experiments with TC0431 and TC0106 (CT153 and CT733) as single antigens indicate that the two antigens are both immunogenic individually and that either of the two antigens contributes to protection of the CT153+CT733 combination (FIG. 7). A fourth antigen combination has been recently identified (TC660+TC0741; homologs of CT456 and CT381) showing protection in an immunization experiment (15 mice) (FIG. 7).

Figure 8:
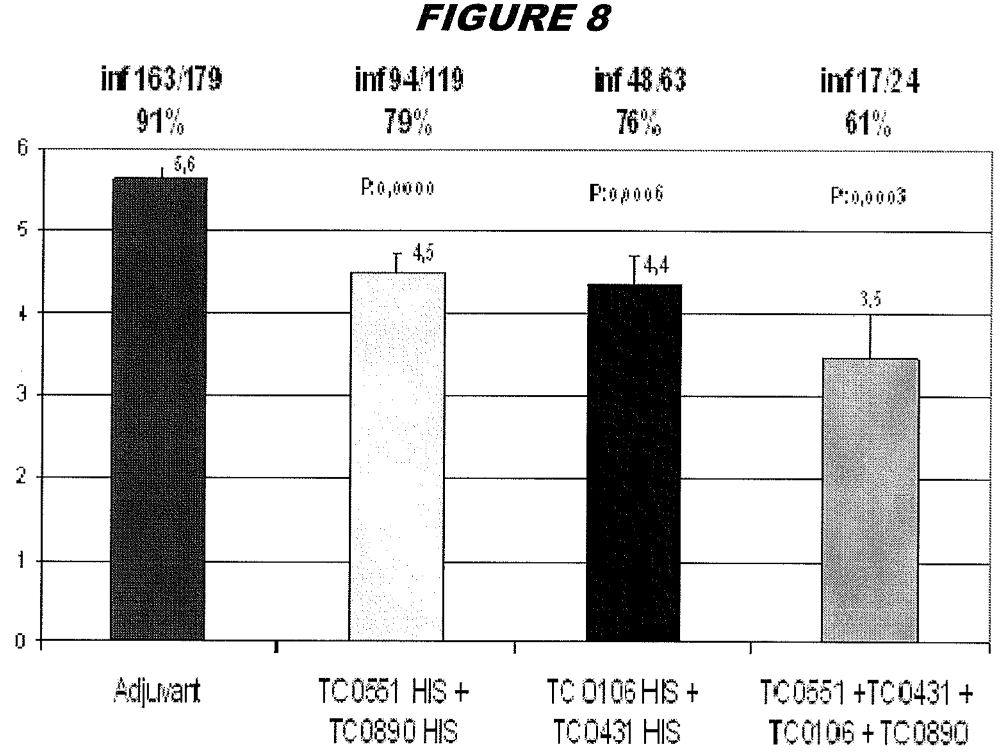
FIG. 8 is a summary of protection results for various combinations of antigens in the mouse model of *C. muridarum* intransal challenge. It shows mean IFU/lung (log 10) of *C. muridarum* recovered from infected lungs of immunised mice.

The experiments were repeated where the protocol differed from that described above in that the mice were challenged intranasally with $10^3$ IFUs of *C. muridarum* three weeks after the last immunization. Since differences in the duration of infections in the animals may occur, the presence of infectious Chlamydiae in the lungs was determined in each mouse at days 10 and 12 after challenge. Immunization experiments were repeated at least three times so as to generate data from a statistically significant number of mice. FIG. 8 reports the mean number of infectious chlamydiae recovered from lungs of mice immunized with each antigen formulation, in which data obtained at days 10 and 12 were averaged. As shown in FIG. 8, two of the four combinations tested in the mouse model, namely TC0551 (CT279 homolog, 82.6% identity)+TC0890 (CT0601 homolog, 87.6% identity) and TC0106 (CT733 homolog, 84.8% identity)+TC0431 (CT153 homolog, 64.6% identity), showed a statistically significant protective effect in the immunized groups with an IFU reduction of more than 1 Log as compared to the adjuvant-injected mice (P:<0.001). Moreover, 20-25% of the animals immunized with either of the two combinations resolved completely the infection by days 10-12, as compared to 9% of the adjuvant group.

Example 8

Evaluation of the Protective Activity of the Combination TC0551+TC0890+TC0106+TC0431 Against Challenge with *C. muridarum*

On the basis of the result discussed in the preceeding Example, groups of mice were immunized with a combination of four antigens TC0551+TC0890+TC0106+TC0431 using the same immunization regimen as in the Example above. As shown in FIG. 8, the 4-antigen combination appeared to have an additive protective effect over the 2-antigen combinations, showing 2.2 Logs reduction of bacterial shedding in the lung (P:0.0003). Moreover, 39% of animals totally resolved the infection, indicating a higher efficacy of this antigen combination in accelerating the bacterial clearance.

The remarkable reduction observed in the number of viable Chlamydiae recovered from the lungs of immunized mice is the first demonstration of a high level of protection induced by systemic immunization with recombinant *Chlamydia* proteins. It has also to be pointed out that, since denatured forms of the recombinant antigens were used, further optimization of antigen conformation could maximize their protective activity.

Preliminary data aimed at defining whether any of the 4 recombinant antigens were protective when given as single antigens, indicated that a lower level of IFU reduction was observed (less than 1 log) was obtained with any of them (data not shown). This is in agreement with the notion that, in general, combinatorial vaccination approaches are more effective in conferring protective immunity against a given pathogen than single vaccine approaches, since elicited immune responses target different aspects of the bacterial developmental cycle.

Example 9

Evaluation of the Protective Activity of the Combination TC0551+TC0651+TC0727+TC0890 Against Intraovarian Bursa Challenge with *C. muridarum*

The protective effect of the combination TC0551+TC0651+TC0727+TC0890 (homologs of *C. trachomatis* CT279+CT372+CT443+CT601) was tested in the mouse model of ovarian bursa challenge with *C. muridarum* using the Montanide+CpG adjuvant. This model has previously been described to assess the protective activity of native MOMP (nMOMP), the chlamydial major outer membrane protein (Pal S et al, Infect Immun., 73:8153, 2005). In this model, the protective activity of the antigens is assessed against progression of infection by counting the *chlamydia* shedding in vaginals swabs.

BALB/c mice were immunized three times intranasally with a combination of the four antigens or with MOMP, with LTK63+CpG as adjuvant. As negative control, a group of mice immunized with ovalbumin was also included. Four weeks after the last immunization, mice received a *C. muridarum* challenge in the ovarian bursa and chlamydial shedding was measured by counting the IFU in the vaginal swabs of infected animals.

Figure 9:
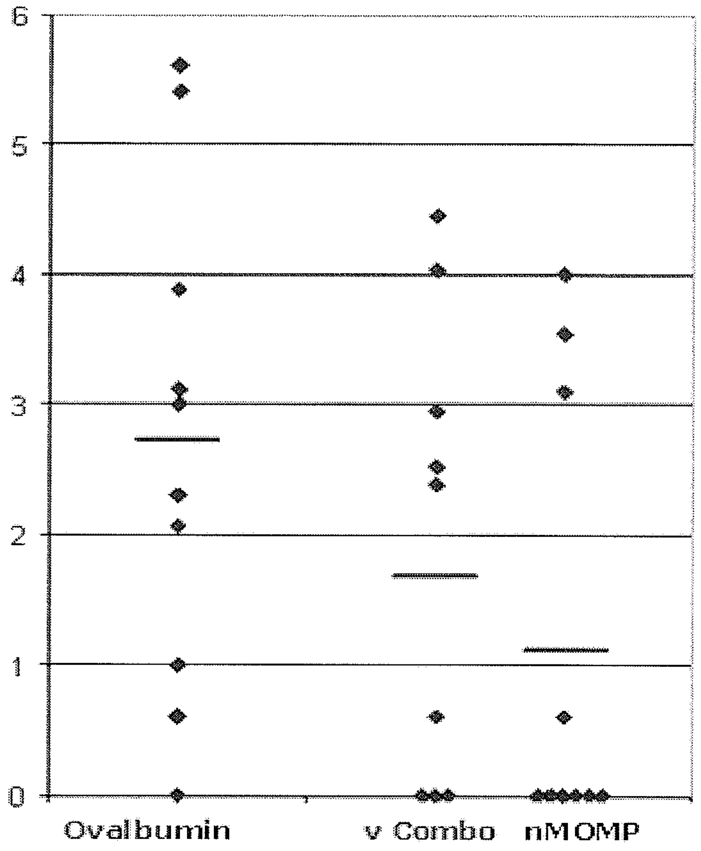
FIG. 9 shows the results of the combination TC0551+TC0651+TC0727+TC0890 in the mouse model of ovarian bursa challenge with *C. muridarum*. The Y axis shows IFU/swab (log 10). The three groups, from left to right, are for different immunizing antigens: ovalbiumin; the combination; and nMOMP.

The results shown in FIG. 9 represent the number of IFU/vaginal swab at two weeks post challenge. As shown in FIG. 9, mice receiving the combination of all four antigens show a reduced bacterial shedding as compared to the negative control group (Ovalbumin). Thus, the combination reduced the progression of infection. Interestingly, the protection level obtained with the combination does not differ significantly from that obtained with nMOMP, which is the most protective antigen that has been identified so far. Thus, this combination of four antigens is a particularly immunogenic combination.

Example 10

Antigen-Specific Cytokine Profiles of Protective CD4+ T Cells

Figure 10C:
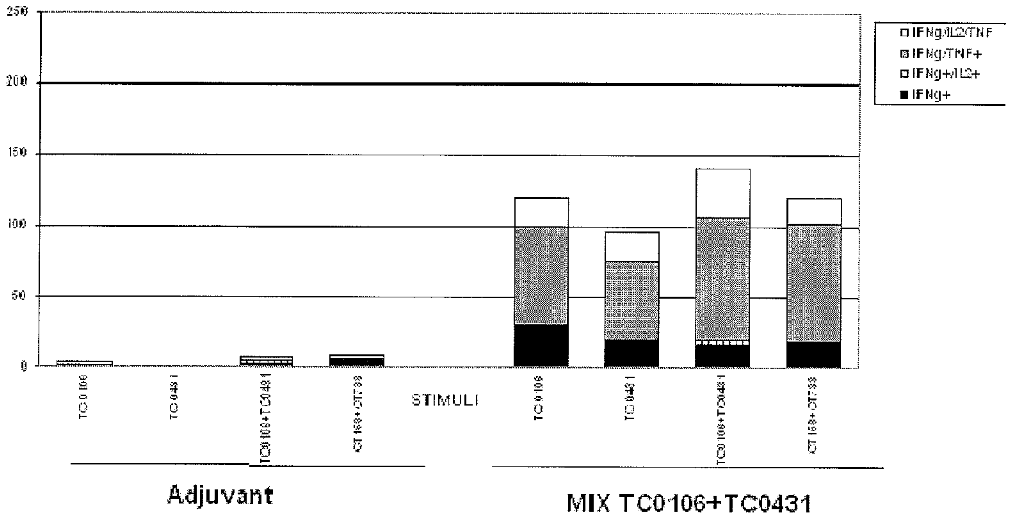
FIG. 10C shows CD4 T cells producing TFNg and IL2/TNF in PBMC of mice immunized with TC0106+TC0431 with Ltk63+CpG. From left to right, the bars represent stimulation with a) TC0106. TC0431, TC0106+TC0431, CT153+CT733 (all adjuvant-immunized mice); 2) TC0106, TC0431, TC0106+TC0431, CT153+CT733 (all MIX TC0106+TC0431-immunized mice).

Given the importance of the CD4-Th1 response in mediating protection from *Chlamydia* infection, the type of immune response induced by vaccination with two antigen combinations that elicited protection in mice was analysed (TC0551+TC0890 and TC0106+TC0431). In particular, we measured the simultaneous production from antigen-specific CD4+ T cells of IFNγ, TNF-α and IL-2, considering this as an indication of optimal effector functions of CD4+ T cells, possibly improving protection for vaccines aimed at targeting T-cell responses. The assessment of the cytokine profile induced in a single antigen specific CD4+ T cell by vaccination was performed by multiparametric flow cytometric analysis (Perfetto S P et al., Nat. Rev. Immunol. 4, 648-655, 2004) in immunized mice. Peripheral blood was collected 12 days after the last immunization with antigen combinations TC0551+TC0890 and TC0106+TC0431. PBMC were prepared and the frequency of CD3+, CD4+ antigen-specific IFNγ, IL-2 and TNF-producing cells was assessed by intracellular cytokine staining and flow cytometric determination. As shown in FIG. 10B, vaccination with the antigen combination TC0551-TC0890 induced a high frequency of TC0551-responding CD4+ T cells producing IFNγ (93 TC0551 specific CD4+ T cells on $10^5$ CD4+ cells), while the response to TC0890 was very low, with a frequency of 16 IFNγ+ responding T cells on $10^5$ CD4+ cells. The response to the antigen combination used for immunization showed an increased response compared to single antigens, with 132 IFNγ producing T cells on $10^5$ CD4+ cells. Furthermore, there was a predominant frequency of multifunctional CD4+ T cells, producing either IFNγ and TNF-α or IFNγ/TNF-α/IL-2 simultaneously. In the control group of mock immunized mice there was no cytokine secretion in response to any recombinant antigen used for stimulation, indicating the specificity of the response observed in the vaccinated mice. As far as the CD4+ response to the antigen combination TC0106-TC0431 is concerned (FIG. 10C) both antigens. TC0106 and TC0431 induced a similar response with a frequency respectively of 120 and 98 IFNγ antigen-specific T cells on $10^5$ CD4+, while the antigen combination showed a frequency of 145 IFNγ+ responding T cells on $10^5$ CD4+ cells. The further analysis of cytokines produced simultaneously with IFNγ showed that about 50% of IFNγ+ cells produced also TNF-α and IL-2, while about 30% of them produced TNF-α. Overall these data underline that the Th1 cytokines produced by antigen-specific CD4+ T cells induced by vaccination showed a functional difference that could reflect differences in the capacity to clear the infection.

Example: 11

Expression Analysis of CD4+ Inducing *Chlamydia* Antigens

Figure 11:
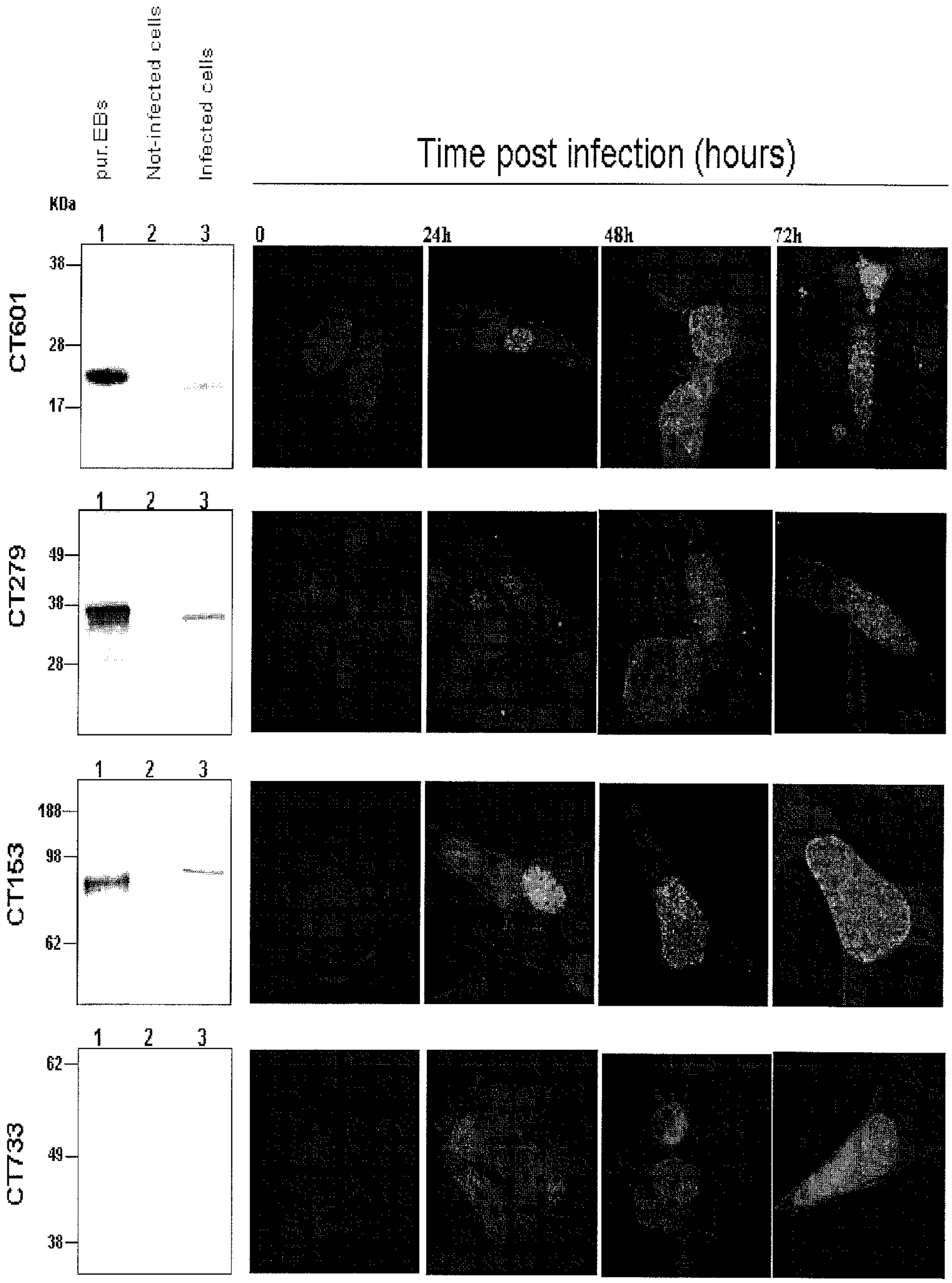
FIG. 11 shows an immunoblot analysis of CT601, CT279, CT153 and CT733 in Ct-EBs and *C. trachomatis*-infected HeLa cells using their specific mouse immune antisera.

We then investigated the expression of CT279 (subunit C of Na(+)-translocating NADH-quinone reductase), CT601 (Invasin repeat family phosphatase), CT733 (-Hypothetical protein) and CT153 (MAC-Perforin Protein) by immunoblot analysis both in Ct-EBs and within *C. trachomatis* infected HeLa cells, using their specific mouse immune antisera (FIG. 11A). Total protein lysates of renografin-purified EBs (corresponding to approximately $10^7$ EBs per lane) showed that each tested antiserum was able to react with a protein band of the expected molecular weight in both EB samples, showing in general a higher reactivity against CM EBs. For analysis of antigen expression in *Chlamydia*-infected cells, total protein extracts were prepared from Hela 229 cells at different time points after infection (24-48-72 h) and tested by immunoblot.

The amount of Chlamydial proteins loaded on the gel was normalized on the basis of MOMP expression as described.

As shown in FIG. 11B, the four antigens appeared to be expressed at different phases of the *Chlamydia* development.

Finally, we also investigated antigen cellular localization within infected HeLa cells by confocal microscopy in infected Hela cells at 6, 24, 48 and 72 h post infection. As shown in FIG. 11B, expression of all antigens was clearly detected within the inclusions at 24 h post infection and was still visible at 72 h. Interestingly, CT153 staining appeared to accumulate at the inclusion membrane while the other proteins were homogeneously distributed. Since CT153 encodes a MAC-Perforin protein, belonging to a protein family capable of disrupting the cell membrane, the ammassing of this protein at the inclusion membrane might anticipate its involvement in the *Chlamydia* exit from infected cells.

The analysis of the immune response after vaccination with the combinations has shown that all the recombinant antigens induced a robust humoral response, with the production of IgG2a antibody titers higher than IgG1, as expected for a Th1 driven immune response. Since the resolution of a *Chlamydia* infection requires a Th1 type of cellular immune response, the regulation of CD4+ Th1 effector and memory cells after vaccination has also been investigated. Differences in the type of cytokines produced by individual cells have important implications for their capacity to mediate effector functions, be sustained as memory T cells or both. CD4+ T cells that secrete only IFNγ have limited capacity to develop into memory T cells as compared with IL-2-IFNγ double positive cells (Hayashi N. et al. 2002). Therefore vaccines eliciting high frequency of single-positive IFNγ producing cells may be limited in their ability to provide long-lasting protection. Furthermore the majority of CD4+ T cells that produce IL-2, IFNγ and TNF are classified as effector memory cells, playing an essential role for mediating protection against intracellular pathogens (Darrah P A et al. 2007). We demonstrated that antigen-specific CD4+ T cells induced by immunization with the protective combinations were predominantly multifunctional, being differentiated to ensure a population of Th1 cells that included either effectors and memory cells. An appropriate balance of Th1 lineage cells that can be maintained and those with immediate protective functions might be the successful formula for an effective vaccine.

Example 12

Combination of CT823+CT733+CT043+CT456

To evaluate the protective activity of antigens TC0106, TC0313, TC0210, TC0741 and their combination, groups of mice were immunized with the 4 antigens either as single or in a 4 antigen-combination, using the same immunization regimen described in Example 7. The protective activity of the single antigens was assessed by measuring the IFU/Lung at day 12 post infection. The protective activity of the 4-ag combination was measured at days 10, 12, 14 post infection, to evaluate the kinetics of the infection clearance. As shown in FIG. 12, the single antigens conferred approximately 0.5-1 log IFU reduction in the lung of infected animals.

The four antigens combination showed a highest protective property, indicating a synergic activity of the four antigens in conferring protection, eliciting approximately 4 logs reduction of bacterial shedding in the lung (P<0.0001) at day 12 and showing the tendency to resolve the infection at day 12. Moreover a high number of mice (42%) totally resolved the infection, indicating the efficacy of the antigen combination in accelerating the bacterial clearance.

Example 13

Evaluation of Antigenicity of CT812, CT387, CT869, CT166 and CT175

Figure 13A:
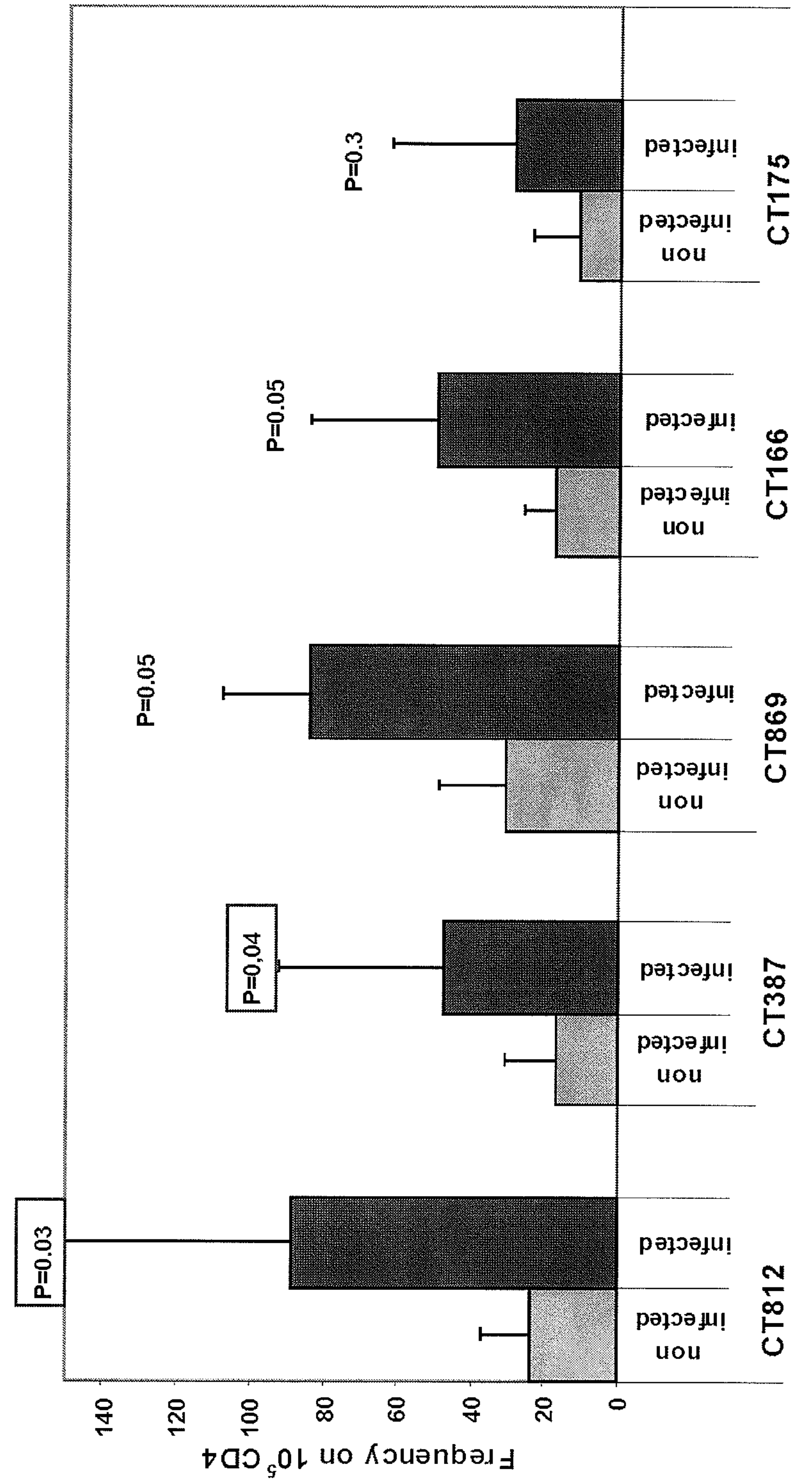
FIGS. 13A and 13B are histograms showing the antigen specific CD4 Th1 response in BALB/c mice after a primary *C. trachomatis* (CT) infection. Results are the mean of 4 independent experiments. Two results are shown for each experiment: non-infected mice (left hand bar) and primary infected mice (right hand bar). From left to right in FIG. 13A, the results relate to stimulation with CT812C, CT387, CT869, CT166 and CT175. From left to right in FIG. 13B, the results relate to stimulation with MOMP, CT163, CT812, CT812C, CT166, CT869, CT163, CT812, CT214, CT387, CT721, CT127 and CT175. The frequency on $10^5$ CD4 T cells is shown on the Y axis.
Figure 13B:
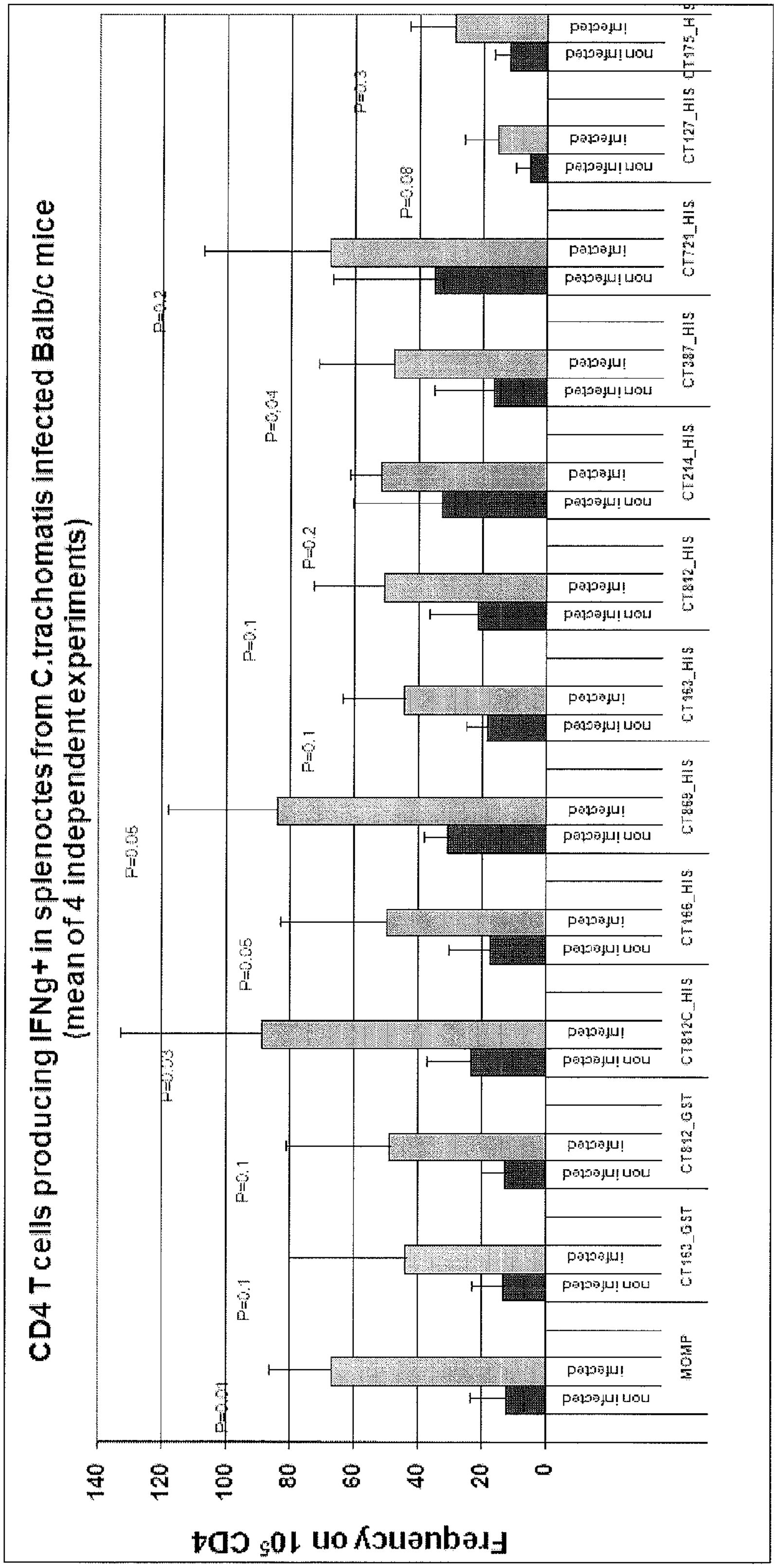

Antigen Specific CD4 Tg1 Response in BALB/c Mice After a Primary Ctrachomatis (CT Infection The antigen specific CD4 Th1 response in BALB/c mice after a primary *C. trachomatis* (CT) infection was evaluated. *C. trachomatis* antigens identified by the proteomic characterization of the membrane fraction of CT infected HeLa cells were tested for their capability to induce specific CD4+ Th1 response in mice that received an experimental CT infection. Splenocytes of primary infected BALB/c mice and non infected controls were collected 10 days after infection and stimulated with LPS-free recombinant antigens (20 μg/ml). After 4 hours of stimulation, 5 μg/ml of Brefeldin A was added to the cells for the following 12 hrs, to block cytokine secretion. Afterwards, cells were fixed, permeabilized and stained. The intracellular IFN-γ expression was analyzed versus CD4 surface expression of the gated viable cells, and assessed by flow cytometry. The histogram in FIG. 13A and FIG. 13B show the number of CD4+ T cells that produce IFNγ, upon specific stimulation with CT recombinant antigens per $10^5$ CD4+ T splenocytes of primary infected (right hand bars) and not-infected (left hand bars) mice. Data are representative of 4 different experiments. As shown in FIG. 13A, CT812C, CT387, CT869 and CT166 induced a significant frequency of $CD4^+$-IFNγ+ cells in splenocytes of infected animals (Pval<0.05). As shown in FIG. 13B, CT812C (a C-terminal fragment of CT812) surprisingly induced a higher frequency of $CD4^+$-IFNγ+ cells in splenocytes of infected animals than did the full length CT812 sequence.

Figure 14:
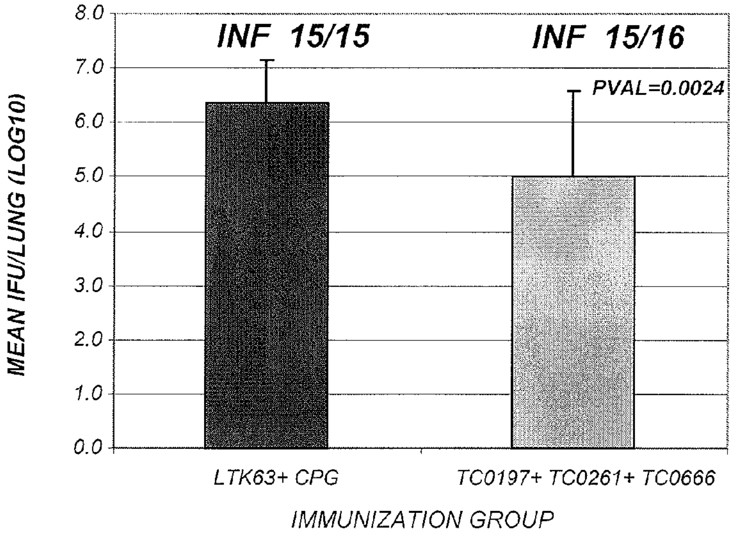
FIG. 14 is a histogram showing *C. muridarum* IFUs recovered from infected lungs of immunised mice (Day 12 post I.N. challenge with $10^3$ IFUs). The immunisation group is shown on the X axis: the left hand bar relates to mice immuised with LTK63+CpG; the right hand bar relates to mice immunised with TC0197+TC0261+TC0666+LTK63+CpG. Mean IFU/lung (Log 10) is shown on the Y axis.

Protective Activity of the Combination of TC0197+TC0261+TC0666 Against *C. muridarum* Challenge The protective effect of the combination of the three *C. trachomatis* antigens CT387+CT812+CT869 was tested in the *C. muridarum* mouse model using their *C. muridarum* orthologues TC0666, TC0197 and TC0261, respectively. TC0197, TC0261 and TC0666 were cloned and purified for protection studies in the mouse model of intranasal infection with *C. muridarum*. Groups of BALB/c mice (16 mice per group) were immunized with the combination of the three recombinant antigens TC0197+TC0261+TC0666 formulated with LTK63+CpG adjuvant (3 doses of 10 μg of each protein, at 2 week-interval, given intramuscularly). As a negative control, mice were immunized with the adjuvant only. Four weeks after the last immunization, animals were infected intranasally with $10^3$ IFU of infectious *C. muridarum*. After 12 days, the protective activity conferred by the two antigens was measured by counting the infectious IFU in the lung of challenge animals. As shown in FIG. 14, the antigen combination TC0197+TC0261+TC0666 was able to reduce significantly the number of IFU/lung in challenged mice as compared to adjuvant immunized mice (1.4 log IFU reduction with Pval<0.05). The finding that the combination of TC0197+TC0261+TC0666 is able to protect mice against *C. muridarum* challenge (FIG. 14) provides evidence that the combinations CT812+CT869+CT387 and CT812C+CT869+CT387 from *C. trachomatis* are protective against infection by *C. trachomatis*.

Figure 15:
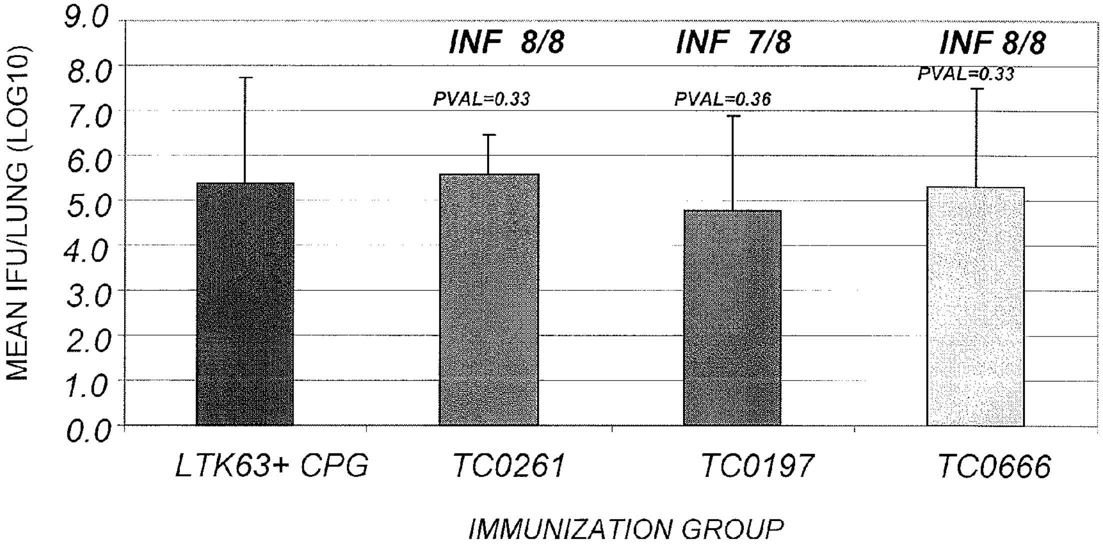
FIG. 15 is a histogram showing *C. muridarum* IFUs recovered from infected lungs of immunised mice (Day 12 post I.N. challenge with $10^3$ IFUs). The immunisation group is shown on the X axis: from left to right, the results relate to mice immunised with i) LTK63+CpG, ii) TC0261+LTK63+CpG, iii) TC0197+LTK63+CpG, and iv) TC0666+LTK63+CpG. Mean IFU/lung (Log 10) is shown on the Y axis.

Protective Activity of TC0197, TC0261 and TC0666 as Single Antigens Against *C. muridarum* Challenge The protective activity of TC0197, TC0261 and TC0666 as single antigens against *C. muridarum* challenge was assessed. 3 Groups of BALB/c mice (16 mice per group) were immunized with the three recombinant antigens individually formulated with LTK63+CpG adjuvant (3 doses of 20 ug of each protein, at 2 week-interval, given intramuscularly). As a negative control, mice were immunized with the adjuvant only. Four weeks after the last immunization, animals were infected intranasally (I.N.) with $10^3$ IFU of infectious *C. muridarum*. After 12 days, the protective activity conferred by the three single antigens was measured by counting the infectious IFU in the lung of challenge animals. As shown in FIG. 15, none of the 3 antigens individually were able to reduce significantly the number of IFU/lung in challenged mice as compared to adjuvant immunized mice.

Thus, the combination of TC0197+TC0261+TC0666 is able to protect mice against *C. muridarum* challenge (FIG. 14). In particular, FIG. 14 shows protection in terms of reduction in the mean number of IFUs recovered from lungs of immunized mice versus adjuvant immunized controls [p=0.0024]. In contrast, the three antigens are not protective when administered individually (FIG. 15).

Example 14

Materials and Methods

The experimental protocols used in Examples 1, 2, 7 (repeated experiments), 8, 10 and 11 are described in further detail in this Example.

Bacterial Strains, Cultures and Reagents

*Chlamydia muridarum* Nigg and *Chlamydia trachomatis* serovar D strain D/UW-3/CX were grown on confluent monolayers of LLCMK2 (ATCC CCL7) or HeLa 229 cells (ATCC CCL 2.1) in Earle minimal essential medium (EMEM) as described (Caldwell et al. (1981) *Infect Immun* 31: 1161-1176). Purification of *C. trachomatis* and *C. muridarum* EBs was carried out by Renografin density gradient centrifugation as described (Montigiani et al. (2002) *Infect Immun* 70: 368-379.). Bacteria were aliquoted and stored at −70° C. in sucrose-phosphate-glutamine buffer (SPG) until use. When indicated, EBs were heat inactivated at 56° C. for 3 hours.

*E. coli* DH5α or BL21 (DE3) was grown aerobically in Luria Broth (LB) medium (Difco) at 37° C. When appropriate, ampicillin (100 μg/ml) and isopropyl-beta-D-galactopyranoside (IPTG, 0.5 mM) were added to the medium.

Unless specified, all chemicals were purchased from Sigma. Restriction enzymes and DNA modification enzymes were from New England Biolabs. Unless differently stated, all reagents and antibody for intracellular cytokine staining were from BD Biosciences Pharmingen. Confocal microscopy reagents were from Molecular Probes.

Gene Cloning, Protein Expression and Preparation of Antisera

To produce *C. trachomatis* recombinant proteins and their *C. muridarum* homologs, genes were PCR-amplified from *C. trachomatis* and *C. muridarum* chromosomal DNA using specific primers annealing at the 5' and 3' ends of either gene. The genes were cloned into plasmid pET21b$^+$ (Invitrogen) or pGEXKG (Amersham) in order to express them both as a C-terminal His-tag fusion and as a double fusion protein with an N-terminal Glutathione transferase-encoding sequence and a C-terminal His-tag.

Cloning and purification of His- and GST fusions were performed as already described (Montigiani et al., 2002). CT0681 and TC0052, encoding for *C. trachomatis* and *C. muridarum* MOMP respectively (Ct MOMP and Cm MOMP, respectively) were expressed as His fusions and purified from the insoluble protein fraction. With the exception of TC0313 and TC0210, all the *C. muridarum* proteins used in this work were purified only from the insoluble protein fraction in a denatured form.

For T cell in vitro stimulation assays, LPS-free proteins were prepared by washing of column—immobilized proteins with buffer Tris-HCl 10 mM, pH 8, containing 1% Triton X114 (35 ml) at 4° C. The amount of residual endotoxin was determined using a Limulus Amebocyte Lysate Analysis Kit (QCL-100, BioWhittaker, Walkerville, Md.).

Mouse antisera were generated and treated as described (Montigiani et al., 2002). Where specified, sera from mice immunized with 20 μg of *E. coli* contaminant proteins (IMAC-purified proteins from *E. coli* bacteria containing pET21b+ empty vector) were used as negative control. Western blot, ELISA and Flow cytometry of *C. trachomatis* EBs were performed as described (Finco et al. (2005) *Vaccine* 23: 1178-1188.).

Screening of Antigen Specific CD4-Th1 Response in Splenocytes from Infected Mice Groups of 6 week-old female BALB/c mice purchased from Charles River Laboratories (3 mice/group) received a subcutaneus hormonal treatment with 2.5 mg of Depo-provera (Medroxyprogesterone acetate) and after five days mice were inoculated intravaginally with 15 μl of SPG buffer containing $10^6$ of *C. trachomatis* IFU. The level of infection was analyzed 7 days post-challenge, by collecting vaginal swabs and counting chlamydial inclusions 48 h later stained with FITC-conjugated anti *Chlamydia* antibody (Merifluor) using a UV microscope.

The swabs were collected in 400 μl of SPG and were inoculated on LLCMK2 cell monolayers seeded on 96 w flat bottom plates. After 48 hours incubation the number of infectious chlamydiae was determined by counting chlamydial inclusions.

Ten days post challenge mice were sacrificed and their spleens were taken. Splenocytes were prepared by homogenization through a nylon filter (BD) and the erythrocytes were removed by hypotonic lysis in Ack lysis buffer ($NH_4Cl$ 0.155 M, $KHCO_3$ 10 mM, $Na_2EDTA$ 0.1 mM) for 3 minutes at RT, then the cells were plated in 96 wells plates at $2\times10^6$ cells per well and stimulated with 20 μg/ml of endotoxin-free specific antigen or with 4 μg/ml of purified EBS in presence of 1 μg/ml anti-CD28 antibody (BD Biosciences Pharmingen) for 4 h at 37° C. Brefeldin A (BFA; Sigma-Aldrich) was then added at a final concentration of 2.5 μg/ml and cells were incubated for an additional 16 h before intracellular cytokine staining. Cells were stained for viability with LIVE/DEAD® (Molecular Probes) dye according to the manufacturer's instructions. Cells were then fixed and permeabilized using the Cytofix/Cytoperm kit (BD Biosciences Pharmingen) and stained with fluorochrome-labelled monoclonal antibodies for the detection of cells expressing CD3, CD4 on the surface and intracellular IFNγ and IL-4. Finally, cells were resuspended in PBS 1% BSA. All antibodies for intracellular cytokine staining were purchased from BD Pharmingen. Acquisition of the samples was performed using a BD Canto flow cytometer and data were analyzed using FlowJo software (Tree Star Inc., Ashland, USA). The intracellular expression of IFNγ and IL-4 was analysed in CD4 expressing singlet cells, previously gated for, morphology, CD3 expression and viability. Cells were then harvested and stained for CD4 surface expression and IFNγ, or IL-4 intracellular production, to investigate whether the observed responses were of the Th1 (IFNγ) or Th2 (IL-4) type. As negative control, spleens from not infected mice were harvested and analyzed in parallel.

Preparation of CD4+ Th1 Cell Lines and of Antigen Presenting Cells (APCs)

Splenocytes were prepared by homogenization from spleens from donor Balb/c mice that had previously been infected intranasally with $10^3$ viable Elementary Bodies (EBs) of *Chlamydia muridarum* (*C. muridarum*) as decribed above. Following centrifugation at 1200 rpm and suspension in Macs Buffer (PBS PH 7.2 0.5% BSA and 2 mM EDTA), the cells were incubated with CD4 (L3T4) microbeads (Milteny Biotec) for 15 minutes and then loaded on a LS columns. The CD4 cells bound to the magnet were recovered, washed and suspended in RPMI 1640 supplemented with 2.5% fetal bovine serum (Hyclone), antibiotics, L-Glutammine 2 mM, Sodium Piruvate 1 mM, MEM Not essential amino Acids, MEM Vitamins (Gibco) and Beta-mercaptoethanol 0.5 μM. Then the cells were plated in 6 multiwell plates, $10^7$ cells/wells. After the first stimulation, the purified CD4 were washed twice and then plated with APCs as described below.

Also a CD4+ cell line with *C. trachomatis* was obtained by spleens from donor Balb/c mice that had previously been infected intravaginally with $10^6$ viable Elementary Bodies (EBs) of *Chlamydia trachomatis* and it was performed as described above for *Chlamydia muridarum.*

The CD4 cells were plated ($6\times10^6$/well) with APCs ($2\times10^7$/well) prepared by naive mice spleens. Splenocytes were prepared as described above, then were washed twice with the medium, gamma irradiated for 7 minutes washed again and suspended in medium.

Cultures were then incubated at 37° C. in a humidified atmosphere containing 5% $CO_2$. After 24 h, Aldesleukin Proleukin (IL2) was added at a concentration of 20 U/ml.

*C. muridarum* and *C. trachomatis*-Mouse Model of Adoptive Transfer

Groups of 6 week-old female BALB/c mice purchased from Charles River Laboratories (4 mice/group), were adoptively transferred by intravenous administration of $10^7$ CD4+ T cells in 100 μl of RPMI-1640 medium (Sigma). Mice were challenged intranasally 24 hours after with $10^3$ IFUs of *C. muridarum* or $10^5$ IFUs of *C. trachomatis*. The effect of adoptive immunization was evaluated by quantitating the number of IFUs recovered from lungs taken 10 days after *C. muridarum* challenge or 6 days after *C. trachomatis* challenge, as described above.

Characterization of the *C. muridarum* CD4+ T Cell Line

The same day of the adoptive transfer, an aliquot of purified CD4+ T cells were taken to assess the capability of *C. muridarum* antigens identified in the previous CD4+ Th1+ screening to stimulate them in vitro. 250000 cells/w were plated in 96 multiwell plates with $10^6$ mouse splenocytes CD4 depleted as APC and stimulated with 20 μg/ml of *C. muridarum* proteins, homologous to the *C. trachomatis* proteins identified as CD4+ Th1 inducers, in presence of 1 μg/ml anti-CD28 antibody (BD Biosciences Pharmingen) for 3 h at 37° C. Then BFA was added and intracellular staining was carried out as described for the splenocytes.

Mouse Protection Model

Groups of 6 week-old female BALB/c mice (10-15 mice/group), were immunized intramuscularly (i.m.) with 3 doses of the antigen combinations TC0551-TC890 (15 μg/dose) and TC0106-TC0431 (containing 10 μg of each protein/dose) at days 1, 15, and 28 formulated with 5 μg of LTK63 (Ryan et al., 2000)+10 μg of CpG (ODN 1826) adjuvant dissolved in 50 μl PBS. As negative control, groups of mice that received the adjuvant alone were included and treated in parallel.

Three weeks after the last immunization mice were inoculated intranasally (i.n.) with 40 μl of SPG buffer containing $10^3$ IFU of *C. muridarum*. The *Chlamydia* challenge dose given to each mouse was confirmed by culturing in triplicate serial dilutions of the inoculating dose on LLCMK2 cell monolayers seeded on 96 wells flat bottom plates. After 24 hours incubation the number of infectious chlamydiae was determined by counting chlamydial inclusions. In the time period between 10- and 12 days post challenge mice were sacrificed, lungs were isolated and their homogenates were used to assess *chlamydia* growth.

Analysis of Antigen Specific CD4-Th1 Response in PBMC of Mice

PBMC from mouse were isolated from up to 2 ml of heparinized blood, diluted ⅕ in HBSS (Hanks' Balanced Salt Solution) and separated by density gradient centrifugation over Lympholite-M (Cedarlane). $10^6$ PBMC were plated in duplicate in 96 multiwell plates with $10^6$ mouse splenocytes CD4 depleted as APC and stimulated and stained as described above for mouse splenocytes for 16 h. In this staining was analyzed the expression of IFNγ, TNFα and IL-2.

Confocal Microscopy

To examine cellular localization of *C. trachomatis* proteins after infection, HeLa cells (20000) were plated on onto glass coverslides (Ø 13 mm) and after 24 hours were infected with CT EBs in 1:1 ratio as described above. At 6, 24, 48 and 72 hours post infection the cells were fixed in 2% paraformaldehyde in PBS buffer for 20 minutes at room temperature. After 2 washes with PBS the cells were permeabilized with a solution of 1%/saponin-0.1% Triton in PBS for 20 minutes.

After washing twice and blocking with PBS containing 1% BSA (PBS-BSA), the cell samples were subjected to antibody and chemical staining. The samples were incubated for 1 h at RT (standard dilution 1:5000 in PBS-BSA) with polyclonal antisera obtained from mice immunized with TC601, TC279, TC733 and TC153, previously pre-adsorbed overnight at 4° C. onto nitrocellulose strips containing *E. coli* BL21 cell total proteins. Goat anti-mouse Alexa Fluor (Molecular Probes) conjugated antibodies (excitation at 488) were used to visualize the localization of each antigen. Propidium Iodide and Phalloidin conjugated with Alexa Fluor dye A620 (Molecular Probes) were used to visualize respectively DNA and actin.

After extensive washes in PBS, cells were mounted with Anti-Fade reagent (Molecular Probes) and observed under a laser scanning confocal microscope (Bio-Rad) with 100× oil immersion objective lens.

It will be understood that the invention has been described by way of example only and modifications may be made whilst remaining within the scope and spirit of the invention.

TABLE 2

| *C. pneumoniae* accession number & annotation | *C. trachomatis* accession number & annotation | CT No. |
|---|---|---|
| | Hypothetical protein (AAC67968) | CT372 |
| | omcB (AAC68042) | CT443 |
| | Hypothetical protein (AAC67634) | CT043 |
| | Hypothetical protein (AAC67744) | CT153 |
| | Nqr3 (AAC67872) | CT279 |
| | papQ (AAC68203) | CT601 |

TABLE 2-continued

| *C. pneumoniae* accession number & annotation | *C. trachomatis* accession number & annotation | CT No. |
|---|---|---|
| | Hypothetical protein (AAC68306) | CT711 |
| | Hypothetical protein (AAC67705) | CT114 |
| | oppA_4 (AAC68080) | CT480 |
| | Hypothetical protein (AAC68056) | CT456 |
| | ArtJ (AAC67977) | CT381 |
| | IcrE (AAC67680) | CT089 |
| | Hypothetical protein (AAC68329) | CT734 |
| | Hypothetical protein (AAC67606) | CT016 |
| gi\|4376729\|gb\|AAD18590.1\| Polymorphic Outer Membrane Protein G Family | gi\|3329346\|gb\|AAC68469.1\| Putative Outer Membrane Protein G | |
| gi\|4376729\|gb\|AAD18590.1\| Polymorphic Outer Membrane Protein G Family | gi\|3329346\|gb\|AAC68469.1\| Putative Outer Membrane Protein G | |
| gi\|4376731\|gb\|AAD18591.1\| Polymorphic Outer Membrane Protein G/I Family | gi\|3329346\|gb\|AAC68469.1\| Putative Outer Membrane Protein G | |
| gi\|4376731\|gb\|AAD18591.1\| Polymorphic Outer Membrane Protein G/I Family | gi\|3329350\|gb\|AAC68472.1\| Putative Outer Membrane Protein I | |
| gi\|4376731\|gb\|AAD18591.1\| Polymorphic Outer Membrane Protein G/I Family | gi\|3329346\|gb\|AAC68469.1\| Putative Outer Membrane Protein G | |
| gi\|4376733\|gb\|AAD18593.1\| Polymorphic Outer Membrane Protein G Family | gi\|3328840\|gb\|AAC68009.1\| Putative outer membrane protein A | |
| gi\|4376731\|gb\|AAD18591.1\| Polymorphic Outer Membrane Protein G/I Family | gi\|3329346\|gb\|AAC68469.1\| Putative Outer Membrane Protein G | |
| gi\|4376754\|gb\|AAD18611.1\| Polymorphic Outer Membrane Protein (Frame-shift with C | gi\|3329344\|gb\|AAC68467.1\| Putative Outer Membrane Protein E | |
| gi\|4376260\|gb\|AAD18163.1\| Polymorphic Outer Membrane Protein G Family | gi\|3329346\|gb\|AAC68469.1\| Putative Outer Membrane Protein G | |
| gi\|4376262\|gb\|AAD18165.1\| hypothetical protein | gi\|3328765\|gb\|AAC67940.1\| hypothetical protein | |
| gi\|4376269\|gb\|AAD18171.1\| hypothetical protein | gi\|3328825\|gb\|AAC67995.1\| hypothetical protein | |
| gi\|4376270\|gb\|AAD18172.1\| Polymorphic Outer Membrane Protein G Family | gi\|3329350\|gb\|AAC68472.1\| Putative Outer Membrane Protein I | |
| gi\|4376272\|gb\|AAD18173.1\| Predicted OMP {leader peptide: outer membrane} | gi\|3328772\|gb\|AAC67946.1\| hypothetical protein | CT351 |
| gi\|4376273\|gb\|AAD18174.1\| Predicted OMP {leader peptide} | gi\|3328771\|gb\|AAC67945.1\| hypothetical protein | CT350 |
| gi\|4376296\|gb\|AAD18195.1\| hypothetical protein | gi\|3328520\|gb\|AAC67712.1\| Ribulose-P Epimerase | |
| gi\|4376362\|gb\|AAD18254.1\| YbbP family hypothetical protein | gi\|3328401\|gb\|AAC67602.1\| hypothetical protein | |
| gi\|4376372\|gb\|AAD18263.1\| Signal Peptidase I | gi\|3328410\|gb\|AAC67610.1\| Signal Peptidase I | |
| gi\|4376397\|gb\|AAD18286.1\| CHLPS hypothetical protein | gi\|3328506\|gb\|AAC67700.1\| CHLPS hypothetical protein | |
| gi\|4376402\|gb\|AAD18290.1\| ACR family | gi\|3328505\|gb\|AAC67699.1\| ACR family | |
| gi\|4376419\|gb\|AAD18305.1\| CT149 hypothetical protein | gi\|3328551\|gb\|AAC67740.1\| possible hydrolase | |
| gi\|4376446\|gb\|AAD18330.1\| hypothetical protein | gi\|3329261\|gb\|AAC68390.1\| hypothetical protein | |
| gi\|4376466\|gb\|AAD18348.1\| Oligopeptide Binding Protein | gi\|3328604\|gb\|AAC67790.1\| Oligopeptide Binding Protein | CT198 |
| gi\|4376467\|gb\|AAD18349.1\| Oligopeptide Binding Protein | gi\|3328604\|gb\|AAC67790.1\| Oligopeptide Binding Protein | |
| gi\|4376468\|gb\|AAD18350.1\| Oligopeptide Binding Protein | gi\|3328539\|gb\|AAC67730.1\| Oligopeptide Binding Protein | |
| gi\|4376469\|gb\|AAD18351.1\| Oligopeptide Binding Protein | gi\|3328579\|gb\|AAC67766.1\| Oligopeptide binding protein permease | |
| gi\|4376520\|gb\|AAD18398.1\| Polysaccharide Hydrolase-Invasin Repeat Family | gi\|3328526\|gb\|AAC67718.1\| predicted polysaccharide hydrolase-invasin repeat family | |
| gi\|4376567\|gb\|AAD18441.1\| Inclusion Membrane Protein C | gi\|3328642\|gb\|AAC67825.1\| Inclusion Membrane Protein C | |
| gi\|4376576\|gb\|AAD18449.1\| Omp85 Analog | gi\|3328651\|gb\|AAC67834.1\| Omp85 Analog | CT241 |
| gi\|4376577\|gb\|AAD18450.1\| (OmpH-Like Outer Membrane Protein) | gi\|3328652\|gb\|AAC67835.1\| (OmpH-Like Outer Membrane Protein) | CT242 |
| gi\|4376601\|gb\|AAD18472.1\| Low Calcium Response D | gi\|3328486\|gb\|AAC67681.1\| Low Calcium Response D | |
| gi\|4376602\|gb\|AAD18473.1\| Low Calcium Response E | gi\|3328485\|gb\|AAC67680.1\| Low Calcium Response E | CT089 |
| gi\|4376607\|gb\|AAD18478.1\| Phopholipase D Superfamily | gi\|3328479\|gb\|AAC67675.1\| Phopholipase D Superfamily {leader (33) peptide} | |
| gi\|4376615\|gb\|AAD18485.1\| YojL hypothetical protein | gi\|3328472\|gb\|AAC67668.1\| hypothetical protein | CT077 |
| gi\|4376624\|gb\|AAD18493.1\| Solute Protein Binding Family | gi\|3328461\|gb\|AAC67658.1\| Solute Protein Binding Family | |
| gi\|4376639\|gb\|AAD18507.1\| Flagellar Secretion Protein | gi\|3328453\|gb\|AAC67651.1\| Flagellar Secretion Protein | |
| gi\|4376664\|gb\|AAD18529.1\| Leucyl Aminopeptidase A | gi\|3328437\|gb\|AAC67636.1\| Leucyl Aminopeptidase A | CT045 |
| gi\|4376672\|gb\|AAD18537.1\| CBS Domain protein (Hemolysin Homolog) | gi\|3328667\|gb\|AAC67849.1\| Hypothetical protein containing CBS domains | |
| gi\|4376679\|gb\|AAD18543.1\| CT253 hypothetical protein | gi\|3328664\|gb\|AAC67846.1\| hypothetical protein | |
| gi\|4376696\|gb\|AAD18559.1\| CT266 hypothetical protein | gi\|3328678\|gb\|AAC67859.1\| hypothetical protein | CT266 |
| gi\|4376717\|gb\|AAD18579.1\| Phospholipase D superfamily | gi\|3328698\|gb\|AAC67877.1\| Phospholipase D superfamily | |
| gi\|4376727\|gb\|AAD18588.1\| Polymorphic Outer Membrane Protein G/I Family | gi\|3329346\|gb\|AAC68469.1\| Putative Outer Membrane Protein G | |
| gi\|4376728\|gb\|AAD18589.1\| Polymorphic Outer Membrane Protein G Family | gi\|3329346\|gb\|AAC68469.1\| Putative Outer Membrane Protein G | |
| gi\|4376729\|gb\|AAD18590.1\| Polymorphic Outer Membrane Protein G Family | gi\|3329350\|gb\|AAC68472.1\| Putative Outer Membrane Protein I | |
| gi\|4376731\|gb\|AAD18591.1\| Polymorphic Outer Membrane Protein G/I Family | gi\|3329350\|gb\|AAC68472.1\| Putative Outer Membrane Protein I | |
| gi\|4376733\|gb\|AAD18593.1\| Polymorphic Outer Membrane Protein G Family | gi\|3328840\|gb\|AAC68009.1\| Putative outer membrane protein A | |
| gi\|4376735\|gb\|AAD18594.1\| Polymorphic Outer Membrane Protein (truncated) A/I Fam | gi\|3328840\|gb\|AAC68009.1\| Putative outer membrane protein A | |
| gi\|4376736\|gb\|AAD18595.1\| Polymorphic Outer Membrane Protein G Family | gi\|3329346\|gb\|AAC68469.1\| Putative Outer Membrane Protein G | |

TABLE 2-continued

| *C. pneumoniae* accession number & annotation | *C. trachomatis* accession number & annotation | CT No. |
|---|---|---|
| gi\|4376737\|gb\|AAD18596.1\| Polymorphic Outer Membrane Protein H Family | gi\|3329347\|gb\|AAC68470.1\| Putative Outer Membrane Protein H | |
| gi\|4376751\|gb\|AAD18608.1\| Polymorphic Outer Membrane Protein E Family | gi\|3329344\|gb\|AAC68467.1\| Putative Outer Membrane Protein E | |
| gi\|4376752\|gb\|AAD18609.1\| Polymorphic Outer Membrane Protein E Family | gi\|3329344\|gb\|AAC68467.1\| Putative Outer Membrane Protein E | |
| gi\|4376753\|gb\|AAD18610.1\| Polymorphic Outer Membrane Protein E/F Family | gi\|3329344\|gb\|AAC68467.1\| Putative Outer Membrane Protein E | |
| gi\|4376757\|gb\|AAD18613.1\| hypothetical protein | gi\|3328701\|gb\|AAC67880.1\| PP-loop superfamily ATPase | |
| gi\|4376767\|gb\|AAD18622.1\| Arginine Periplasmic Binding Protein | gi\|3328806\|gb\|AAC67977.1\| Arginine Binding Protein | CT381 |
| gi\|4376790\|gb\|AAD18643.1\| Heat Shock Protein-70 | gi\|3328822\|gb\|AAC67993.1\| HSP-70 | CT396 |
| gi\|4376802\|gb\|AAD18654.1\| CT427 hypothetical protein | gi\|3328857\|gb\|AAC68024.1\| hypothetical protein | |
| gi\|4376814\|gb\|AAD18665.1\| CT398 hypothetical protein | gi\|3328825\|gb\|AAC67995.1\| hypothetical protein | CT398 |
| gi\|4376829\|gb\|AAD18679.1\| polymorphic membrane protein A Family | gi\|3328840\|gb\|AAC68009.1\| Putative outer membrane protein A | |
| gi\|4376830\|gb\|AAD18680.1\| polymorphic membrane protein B Family | gi\|3328841\|gb\|AAC68010.1\| Putative outer membrane protein B | |
| gi\|4376832\|gb\|AAD18681.1\| Solute binding protein | gi\|3328844\|gb\|AAC68012.1\| Solute-binding protein | CT415 |
| gi\|4376834\|gb\|AAD18683.1\| (Metal Transport Protein) | gi\|3328846\|gb\|AAC68014.1\| (Metal Transport Protein) | |
| gi\|4376847\|gb\|AAD18695.1\| Tail-Specific Protease | gi\|3328872\|gb\|AAC68040.1\| Tail-Specific Protease | |
| gi\|4376848\|gb\|AAD18696.1\| 15 kDa Cysteine-Rich Protein | gi\|3328873\|gb\|AAC68041.1\| 15 kDa Cysteine-Rich Protein | |
| gi\|4376849\|gb\|AAD18697.1\| 60 kDa Cysteine-Rich OMP | gi\|3328874\|gb\|AAC68042.1\| 60 kDa Cysteine-Rich OMP | CT443 |
| gi\|4376850\|gb\|AAD18698.1\| 9 kDa-Cysteine-Rich Lipoprotein | gi\|3328876\|gb\|AAC68043.1\| 9 kDa-Cysteine-Rich Lipoprotein | CT444 |
| gi\|4376878\|gb\|AAD18723.1\| 2-Component Sensor | gi\|3328901\|gb\|AAC68067.1\| 2-component regulatory system-sensor histidine kinase | CT467 |
| gi\|4376879\|gb\|AAD18724.1\| similarity to CHLPS IncA | gi\|3328451\|gb\|AAC67649.1\| hypothetical protein | |
| gi\|4376884\|gb\|AAD18729.1\| CT471 hypothetical protein | gi\|3328905\|gb\|AAC68071.1\| hypothetical protein | |
| gi\|4376886\|gb\|AAD18731.1\| YidD family | gi\|3328908\|gb\|AAC68073.1\| hypothetical protein | |
| gi\|4376890\|gb\|AAD18734.1\| CT476 hypothetical protein | gi\|3328911\|gb\|AAC68076.1\| hypothetical protein | |
| gi\|4376892\|gb\|AAD18736.1\| Oligopeptide Permease | gi\|3328913\|gb\|AAC68078.1\| Oligopeptide Permease | |
| gi\|4376894\|gb\|AAD18738.1\| Oligopeptide Binding Lipoprotein | gi\|3328915\|gb\|AAC68080.1\| oligopeptide Binding Lipoprotein | |
| gi\|4376900\|gb\|AAD18743.1\| Glutamine Binding Protein | gi\|3328922\|gb\|AAC68086.1\| Glutamine Binding Protein | |
| gi\|4376909\|gb\|AAD18752.1\| Protease | gi\|6578107\|gb\|AAC68094.2\| Protease | |
| gi\|4376952\|gb\|AAD18792.1\| Apolipoprotein N-Acetyltransferase | gi\|3328972\|gb\|AAC68136.1\| Apolipoprotein N-Acetyltransferase | |
| gi\|4376960\|gb\|AAD18800.1\| FKBP-type peptidyl-prolyl cis-trans isomerise | gi\|3328979\|gb\|AAC68143.1\| FKBP-type peptidyl-prolyl cis-trans isomerise | CT541 |
| gi\|4376968\|gb\|AAD18807.1\| CT547 hypothetical protein | gi\|3328986\|gb\|AAC68149.1\| hypothetical protein | CT547 |
| gi\|4376969\|gb\|AAD18808.1\| CT548 hypothetical protein | gi\|3328987\|gb\|AAC68150.1\| hypothetical protein | |
| gi\|4376998\|gb\|AAD18834.1\| Major Outer Membrane Protein | gi\|3329133\|gb\|AAC68276.1\| Major Outer Membrane Protein | CT681 |
| gi\|4377005\|gb\|AAD18841.1\| YopC/Gen Secretion Protein D | gi\|3329125\|gb\|AAC68269.1\| probable Yop proteins translocation protein | |
| gi\|4377015\|gb\|AAD18851.1\| FHA domain; (homology to adenylate cyclase) | gi\|3329115\|gb\|AAC68259.1\| (FHA domain; homology to adenylate cyclase) | |
| gi\|4377033\|gb\|AAD18867.1\| CHLPN 76 kDa Homolog_1 (CT622) | gi\|3329069\|gb\|AAC68226.1\| CHLPN 76 kDa Homolog | CT622 |
| gi\|4377034\|gb\|AAD18868.1\| CHLPN 76 kDa Homolog_2 (CT623) | gi\|6578109\|gb\|AAC68227.2\| CHLPN 76 kDa Homolog | CT623 |
| gi\|4377035\|gb\|AAD18869.1\| Integral Membrane Protein | gi\|3329071\|gb\|AAC68228.1\| Integral Membrane Protein | |
| gi\|4377072\|gb\|AAD18902.1\| CT648 hypothetical protein | gi\|3329097\|gb\|AAC68825.1\| hypothetical protein | |
| gi\|4377073\|gb\|AAD18903.1\| CT647 hypothetical protein | gi\|3329096\|gb\|AAC68824.1\| hypothetical protein | CT647 |
| gi\|4377085\|gb\|AAD18914.1\| CT605 hypothetical protein | gi\|3329050\|gb\|AAC68208.1\| hypothetical protein | |
| gi\|4377090\|gb\|AAD18919.1\| Peptidoglycan-Associated Lipoprotein | gi\|3329044\|gb\|AAC68202.1\| Peptidoglycan-Associated Lipoprotein | CT600 |
| gi\|4377091\|gb\|AAD18920.1\| macromolecule transporter | gi\|3329043\|gb\|AAC68201.1\| component of a macromolecule transport system | |
| gi\|4377092\|gb\|AAD18921.1\| CT598 hypothetical protein | gi\|3329042\|gb\|AAC68200.1\| hypothetical protein | |
| gi\|4377093\|gb\|AAD18922.1\| Biopolymer Transport Protein | gi\|3329041\|gb\|AAC68199.1\| Biopolymer Transport Protein | CT597 |
| gi\|4377094\|gb\|AAD18923.1\| Macromolecule transporter | gi\|3329040\|gb\|AAC68198.1\| polysaccharide transporter | |
| gi\|4377101\|gb\|AAD18929.1\| CT590 hypothetical protein | gi\|3329033\|gb\|AAC68192.1\| hypothetical protein | |
| gi\|4377102\|gb\|AAD18930.1\| CT589 hypothetical protein | gi\|3329032\|gb\|AAC68191.1\| hypothetical protein | CT589 |
| gi\|4377106\|gb\|AAD18933.1\| hypothetical protein | gi\|3328796\|gb\|AAC67968.1\| hypothetical protein | |
| gi\|4377111\|gb\|AAD18938.1\| Enolase | gi\|3329030\|gb\|AAC68189.1\| Enolase | CT587 |
| gi\|4377127\|gb\|AAD18953.1\| General Secretion Protein D | gi\|3329013\|gb\|AAC68174.1\| Gen. Secretion Protein D | |
| gi\|4377130\|gb\|AAD18956.1\| predicted OMP {leader peptide} | gi\|3329010\|gb\|AAC68171.1\| predicted OMP | CT569 |
| gi\|4377132\|gb\|AAD18958.1\| CT567 hypothetical protein | gi\|3329008\|gb\|AAC68169.1\| hypothetical protein | CT567 |
| gi\|4377133\|gb\|AAD18959.1\| CT566 hypothetical protein | gi\|3329007\|gb\|AAC68168.1\| hypothetical protein | |
| gi\|4377140\|gb\|AAD18965.1\| Yop Translocation J | gi\|3329000\|gb\|AAC68161.1\| Yop proteins translocation lipoprotein J | CT559 |
| gi\|4377170\|gb\|AAD18992.1\| Outer Membrane Protein B | gi\|3329169\|gb\|AAC68308.1\| Outer Membrane Protein Analog | CT713 |
| gi\|4377177\|gb\|AAD18998.1\| Flagellar M-Ring Protein | gi\|3329175\|gb\|AAC68314.1\| Flagellar M-Ring Protein | |
| gi\|4377182\|gb\|AAD19003.1\| CT724 hypothetical protein | gi\|3329181\|gb\|AAC68319.1\| hypothetical protein | |
| gi\|4377184\|gb\|AAD19005.1\| Rod Shape Protein | gi\|3329183\|gb\|AAC68321.1\| Rod Shape Protein | |
| gi\|4377193\|gb\|AAD19013.1\| CT734 hypothetical protein | gi\|3329192\|gb\|AAC68329.1\| hypothetical protein | |
| gi\|4377206\|gb\|AAD19025.1\| CHLTR possible phosphoprotein | gi\|3329204\|gb\|AAC68339.1\| CHLTR possible phosphoprotein | |

TABLE 2-continued

| *C. pneumoniae* accession number & annotation | *C. trachomatis* accession number & annotation | CT No. |
|---|---|---|
| gi\|4377222\|gb\|AAD19040.1\| Muramidase (invasin repeat family) | gi\|3329221\|gb\|AAC68354.1\| Muramidase (invasin repeat family) | CT759 |
| gi\|4377223\|gb\|AAD19041.1\| Cell Division Protein FtsW | gi\|3329222\|gb\|AAC68355.1\| Cell Division Protein FtsW | |
| gi\|4377224\|gb\|AAD19042.1\| Peptidoglycan Transferase | gi\|3329223\|gb\|AAC68356.1\| Peptidoglycan Transferase | CT761 |
| gi\|4377225\|gb\|AAD19043.1\| Muramate-Ala Ligase & D-Ala-D-Ala Ligase | gi\|3329224\|gb\|AAC68357.1\| UDP-N-acetylmuramate-alanine ligase | |
| gi\|4377248\|gb\|AAD19064.1\| Thioredoxin Disulfide Isomerase | gi\|3329244\|gb\|AAC68375.1\| Thioredoxin Disulfide Isomerase | |
| gi\|4377261\|gb\|AAD19076.1\| CT788 hypothetical protein - {leader peptide-periplasmi | gi\|3329253\|gb\|AAC68383.1\| {leader (60) peptide-periplasmic} | |
| gi\|4377280\|gb\|AAD19093.1\| Insulinase family/Protease III | gi\|3329273\|gb\|AAC68402.1\| Insulinase family/Protease III | |
| gi\|4377287\|gb\|AAD19099.1\| Putative Outer Membrane Protein D Family | gi\|3329279\|gb\|AAC68408.1\| Putative Outer Membrane Protein D | |
| gi\|4377306\|gb\|AAD19116.1\| DO Serine Protease | gi\|3329293\|gb\|AAC68420.1\| DO Serine Protease | CT823 |
| gi\|4377342\|gb\|AAD19149.1\| ABC transporter permease | gi\|3329327\|gb\|AAC68451.1\| ABC transporter permease — pyrimidine biosynthesis protein | |
| gi\|4377347\|gb\|AAD19153.1\| CT858 hypothetical protein | gi\|6578118\|gb\|AAC68456.2\| predicted Protease containing IRBP and DHR domains | |
| gi\|4377353\|gb\|AAD19159.1\| CT863 hypothetical protein | gi\|3329337\|gb\|AAC68461.1\| hypothetical protein | |
| gi\|4377367\|gb\|AAD19171.1\| Predicted OMP | gi\|3328795\|gb\|AAC67967.1\| hypothetical protein | |
| gi\|4377408\|gb\|AAD19209.1\| hypothetical protein | gi\|3328795\|gb\|AAC67967.1\| hypothetical protein | |
| gi\|4377409\|gb\|AAD19210.1\| Predicted Outer Membrane Protein (CT371) | gi\|3328795\|gb\|AAC67967.1\| hypothetical protein | |
| gi\|4376411\|gb\| | gi\|3328512\|gb\|AAC67705.1\| hypothetical protein | CT114 |
| gi\|4376508\|gb\| | gi\|3328585\|gb\|AAC67772.1\| hypothetical protein | CT181 |
| gi\|4376710\|gb\| | gi\|3328692\|gb\|AAC67872.1\| NADH (Ubiquinone) Oxidoreductase, Gamma | CT279 |
| gi\|4376777\|gb\| | gi\|3328815\|gb\|AAC67986.1\| hypothetical protein | CT389 |
| gi\|4376782\|gb\| | gi\|3328817\|gb\|AAC67988.1\| hypothetical protein | CT391 |
| gi\|4376863\|gb\| | gi\|3328887\|gb\|AAC68054.1\| Arginyl tRNA transferase | CT454 |
| gi\|4376866\|gb\| | gi\|3328889\|gb\|AAC68056.1\| hypothetical protein | CT456 |
| gi\|4376972\|gb\| | gi\|3328991\|gb\|AAC68153.1\| D-Ala-D-Ala Carboxypeptidase | CT551 |
| gi\|4377139\|gb\| | gi\|3329001\|gb\|AAC68162.1\| hypothetical protein | CT560 |
| gi\|4377154\|gb\| | gi\|3329154\|gb\|AAC68295.1\| hypothetical protein | CT700 |

SEQUENCE LISTING

SEQ ID NO: 1 - CT733 nucleotide sequence

```
ATGTTAATAAACTTTACCTTTCGCAACTGTCTTTTGTTCCTTGTCACACTGTCTAGTGTCCCTGTTTTCTCAGCACC

TCAACCTCGCGGAACGCTTCCTAGCTCGACCACAAAAATTGGATCAGAAGTTTGGATTGAACAAAAAGTCCGCCAAT

ATCCAGAGCTTTTATGGTTAGTAGAGCCGTCCTCTACGGGAGCCTCTTTAAAATCTCCTTCAGGAGCCATCTTTTCT

CCAACATTATTCCAAAAAAAGGTCCCTGCTTTCGATATCGCAGTGCGCAGTTTGATTCACTTACATTTATTAATCCA

GGGTTCCCGCCAAGCCTATGCTCAACTGATCCAACTACAGACCAGCGAATCCCCTCTAACATTTAAGCAATTCCTTG

CATTGCATAAGCAATTAACTCTATTTTTAAATTCCCCTAAGGAATTTTATGACTCTGTTAAAGTGTTAGAGACAGCT

ATCGTCTTACGTCACTTAGGCTGTTCAACTAAGGCTGTTGCTGCGTTTAAACCTTATTTCTCAGAAATGCAAAGAGA

GGCTTTTTACACTAAGGCTCTGCATGTACTACACACCTTCCCAGAGCTAAGCCCATCATTTGCTCGCCTCTCTCCGG

AGCAGAAAACTCTCTTCTTCTCCTTGAGAAAATTGGCGAATTACGATGAGTTACTCTCGCTGACGAACACCCCAAGT

TTTCAGCTTCTGTCTGCTGGGCGCTCGCAACGAGCTCTTTTAGCTCTGGACTTGTACCTCTATGCTTTGGATTCCTG

TGGAGAACAGGGGATGTCCTCTCAATTCCACACAAACTTCGCACCTCTACAGTCCATGTTGCAACAATACGCTACTG

TAGAAGAGGCCTTTTCTCGTTATTTTACTTACCGAGCTAATCGATTAGGATTTGATGGCTCTTCTCGATCCGAGATG

GCTTTAGTAAGAATGGCCACCTTGATGAACTTGTCTCCTTCCGAAGCTGCGATTTTAACCACAAGCTTCAAAACCCT

TCCTACAGAAGAAGCGGATACTTTGATCAATAGTTTCTATACCAATAAGGGCGATTCGTTGGCTCTTTCTCTGCGAG

GGTTGCCTACACTTGTATCCGAACTGACGCGAACTGCCCATGGCAATACCAATGCAGAAGCTCGATCTCAGCAAATT

TATGCAACTACCCTATCGCTAGTAGTAAAGAGTCTGAAAGCGCACAAAGAAATGCTAAACAAGCAAATTCTTTCTAA

GGAAATTGTTTTAGATTTCTCAGAAACTGCAGCTTCTTGCCAAGGATTGGATATCTTTTCCGAGAATGTCGCTGTTC

AAATTCACTTAAATGGAACCGTTAGTATCCATTTATAA
```

-continued

SEQUENCE LISTING

SEQ ID NO: 2 - CT733 protein sequence
MLINFTFRNCLLFLVTLSSVPVFSAPQPRGTLPSSTTKIGSEVWIEQKVRQYPELLWLVEPSSTGASLKSPSGAIFS

PTLFQKKVPAFDIAVRSLIHLHLLIQGSRQAYAQLIQLQTSESPLTFKQFLALHKQLTLFLNSPKEFYDSVKVLETA

IVLRHLGCSTKAVAAFKPYFSEMQREAFYTKALHVLHTFPELSPSFARLSPEQKTLFFSLRKLANYDELLSLTNTPS

FQLLSAGRSQRALLALDLYLYALDSCGEQGMSSQFHTNFAPLQSMLQQYATVEEAFSRYFTYRANRLGFDGSSRSEM

ALVRMATLMNLSPSEAAILTTSFKTLPTEEADTLINSFYTNKGDSLALSLRGLPTLVSELTRTAHGNTNAEARSQQI

YATTLSLVVKSLKAHKEMLNKQILSKEIVLDFSETAASCQGLDIFSENVAVQIHLNGTVSIHL

SEQ ID NO: 3 - CT153 nucleotide sequence
ATGACTAAGCCTTCTTTCTTATACGTTATTCAACCTTTTTCCGTATTTAATCCACGATTAGGACGTTTCTCTACAGA

CTCAGATACTTATATCGAAGAAGAAAACCGCCTAGCATCGTTCATTGAGAGTTTGCCACTGGAGATCTTCGATATAC

CTTCTTTCATGGAAACCGCGATTTCCAATAGCCCCTATATTTTATCTTGGGAGACAACTAAAGACGGCGCTCTGTTC

ACTATTCTTGAACCCAAACTCTCAGCTTGCGCAGCCACTTGCCTGGTAGCCCCTTCTATACAAATGAAATCCGATGC

GGAGCTCCTAGAAGAAATTAAGCAAGCGTTATTACGCAGCTCTCATGACGGTGTGAAATATCGCATCACCAGAGAAT

CCTTCTCTCCAGAAAAGAAAACTCCTAAGGTTGCTCTAGTCGATGACGATATTGAATTGATTCGCAATGTCGACTTT

TTGGGTAGAGCTGTTGACATTGTCAAATTAGACCCTATTAATATTCTGAATACCGTAAGCGAAGAGAATATTCTAGA

TTACTCTTTTACAAGAGAAACGGCTCAGCTGAGCGCGGATGGTCGTTTTGGTATTCCTCCAGGGACTAAGCTATTCC

CTAAACCTTCTTTTGATGTAGAAATCAGTACCTCCATTTTCGAAGAAACAACTTCATTTACTCGAAGTTTTTCTGCA

TCGGTTACTTTTAGTGTACCAGACCTCGCGGCGACTATGCCTCTTCAAAGCCCTCCCATGGTAGAAAATGGTCAAAA

AGAAATTTGTGTCATTCAAAAACACTTATTCCCAAGCTACTCTCCTAAACTAGTCGATATTGTTAAACGATACAAAA

GAGAGGCTAAGATCTTGATTAACAAGCTTGCCTTTGGAATGTTATGGCGACATCGGGCTAAAAGCCAAATCCTCACC

GAGGGAAGCGTACGTCTAGACTTACAAGGATTCACAGAATCGAAGTACAATTACCAGATTCAAGTAGGATCCCATAC

GATTGCAGCTGTATTAATCGATATGGATATTTCCAAGATTCAATCCAAATCAGAACAAGCTTATGCAATTAGGAAAA

TCAAATCAGGCTTTCAACGTAGCTTGGATGACTATCATATTTATCAAATTGAAAGAAAACAAACCTTTTCTTTTTCT

CCGAAGCATCGCAGCCTCTCATCCACATCCCATTCCGAAGATTCTGATTTGGATCTTTCTGAAGCAGCCGCCTTTTC

AGGAAGTCTTACCTGCGAGTTTGTAAAAAAAAGCACTCAACATGCCAAGAATACCGTCACATGTTCCACAGCCGCTC

ATTCCCTATACACACTCAAAGAAGATGACAGCTCGAACCCCTCTGAAAAACGATTAGATAGTTGTTTCCGCAATTGG

ATTGAAAACAAACTAAGCGCCAATTCTCCAGATTCCTGGTCAGCGTTTATTCAAAAATTCGGAACACACTATATTGC

ATCAGCAACTTTTGGAGGGATAGGTTTCCAAGTGCTCAAACTATCTTTTGAACAGGTGGAGGATCTACATAGCAAAA

AGATCTCCTTAGAAACCGCAGCAGCCAACTCTCTATTAAAAGGTTCTGTATCCAGCAGCACAGAATCTGGATACTCC

AGCTATAGCTCCACGTCTTCTTCTCATACGGTATTTTTAGGAGGAACGGTCTTACCTTCGGTTCATGATGAACGTTT

AGACTTTAAAGATTGGTCGGAAAGTGTGCACCTGGAACCTGTTCCTATCCAGGTTTCTTTACAACCTATAACGAATT

TACTAGTTCCTCTCCATTTTCCTAATATCGGTGCTGCAGAGCTCTCTAATAAACGAGAATCTCTTCAACAAGCGATT

CGAGTCTATCTCAAAGAACATAAAGTAGATGAGCAAGGAGAACGTACTACATTTACATCAGGAATCGATAATCCTTC

TTCCTGGTTTACCTTAGAAGCTGCCCACTCTCCTCTTATAGTCAGTACTCCTTACATTGCTTCGTGGTCTACGCTTC

CTTATTTGTTCCCAACATTAAGAGAACGTTCTTCGGCAACCCCTATCGTTTTCTATTTTTGTGTAGATAATAATGAA

CATGCTTCGCAAAAAATATTAAACCAATCGTATTGCTTCCTCGGGTCCTTGCCTATTCGACAAAAAATTTTTGGTAG

CGAATTTGCTAGTTTCCCCTATCTATCTTTCTATGGAAATGCAAAAGAGGCGTACTTTGATAACACGTACTACCCAA

CGCGTTGTGGGTGGATTGTTGAAAAGTTAAATACTACACAAGATCAATTCCTCCGGGATGGAGACGAGGTGCGACTA

AAACATGTTTCCAGCGGAAAGTATCTAGCAACAACTCCTCTTAAGGATACCCATGGTACACTCACGCGTACAACGAA

CTGTGAAGATGCTATCTTTATTATTAAAAAATCTTCAGGTTATTGA

-continued

SEQUENCE LISTING

SEQ ID NO: 4 - CT153 protein sequence
MTKPSFLYVIQPFSVFNPRLGRFSTDSDTYIEEENRLASFIESLPLEIFDIPSFMETAISNSPYILSWETTKDGALF

TILEPKLSACAATCLVAPSIQMKSDAELLEEIKQALLRSSHDGVKYRITRESFSPEKKTPKVALVDDDIELIRNVDF

LGRAVDIVKLDPINILNTVSEENILDYSFTRETAQLSADGRFGIPPGTKLFPKPSFDVEISTSIFEETTSFTRSFSA

SVTFSVPDLAATMPLQSPPMVENGQKEICVIQKHLFPSYSPKLVDIVKRYKREAKILINKLAFGMLWRHRAKSQILT

EGSVRLDLQGFTESKYNYQIQVGSHTIAAVLIDMDISKIQSKSEQAYAIRKIKSGFQRSLDDYHIYQIERKQTFSFS

PKHRSLSSTSHSEDSDLDLSEAAAFSGSLTCEFVKKSTQHAKNTVTCSTAAHSLYTLKEDDSSNPSEKRLDSCFRNW

IENKLSANSPDSWSAFIQKFGTHYIASATFGGIGFQVLKLSFEQVEDLHSKKISLETAAANSLLKGSVSSSTESGYS

SYSSTSSSHTVFLGGTVLPSVHDERLDFKDWSESVHLEPVPIQVSLQPITNLLVPLHFPNIGAAELSNKRESLQQAI

RVYLKEHKVDEQGERTTFTSGIDNPSSWFTLEAAHSPLIVSTPYIASWSTLPYLFPTLRERSSATPIVFYFCVDNNE

HASQKILNQSYCFLGSLPIRQKIFGSEFASFPYLSFYGNAKEAYFDNTYYPTRCGWIVEKLNTTQDQFLRDGDEVRL

KHVSSGKYLATTPLKDTHGTLTRTTNCEDAIFIIKKSSGY

SEQ ID NO: 5 - CT601 nucleotide sequence
ATGCTCGCTAATCGCTTATTCTTAATAACCCTTTTAGGGTTAAGTTCGTCTGTTTACGGCGCAGGTAAAGCACCGTC

TTTGCAGGCTATTCTAGCCGAAGTCGAAGACACCTCCTCTCGTCTACACGCTCATCACAATGAGCTTGCTATGATCT

CTGAACGCCTCGATGAGCAAGACACGAAACTACAGCAACTTTCGTCAACACAAGATCATAACCTACCTCGACAAGTT

CAGCGACTAGAAACGGACCAAAAAGCTTTGGCAAAAACACTGGCGATTCTTTCGCAATCCGTCCAAGATATTCGGTC

TTCTGTACAAAATAAATTACAAGAAATCCAACAAGAACAAAAAAAATTAGCACAAAATTTGCGAGCGCTTCGTAACT

CTTTACAAGCTCTCGTTGATGGCTCTTCTCCAGAAAATTATATTGATTTCCTAACTGGTGAAACCCCGGAACATATT

CATATTGTTAAACAAGGAGAGACCCTGAGCAAGATCGCGAGTAAATATAACATCCCCGTCGTAGAATTAAAAAAACT

TAATAAACTAAATTCGGATACTATTTTTACAGATCAAAGAATTCGCCTTCCGAAAAAGAAATAG

SEQ ID NO: 6 - CT601 protein sequence
MLANRLFLITLLGLSSSVYGAGKAPSLQAILAEVEDTSSRLHAHHNELAMISERLDEQDTKLQQLSSTQDHNLPRQV

QRLETDQKALAKTLAILSQSVQDIRSSVQNKLQEIQQEQKKLAQNLRALRNSLQALVDGSSPENYIDFLTGETPEHI

HIVKQGETLSKIASKYNIPVVELKKLNKLNSDTIFTDQRIRLPKKK

SEQ ID NO: 7 - CT279 nucleotide sequence
ATGGCATCCAAGTCTCGCCATTATCTTAATCAGCCTTGGTACATTATCTTATTCATCTTTGTTCTTAGTTTAATTGC

TGGTACCCTCCTGTCTTCTGTGTATTATGTCCTTGCACCTATCCAACAGCAAGCTGCGGAATTCGATCGCAATCAAC

AAATGCTAATGGCTGCACAAGTAATTTCTTCCGATAACACATTCCAAGTCTATGAAAAGGGAGATTGGCACCCAGCC

CTATATAATACTAAAAAGCAGTTGCTAGAGATCTCCTCTACTCCTCCTAAAGTAACCGTGACAACTTTAAGCTCATA

TTTTCAAAACTTTGTTAGAGTCTTGCTTACAGATACACAAGGAAATCTTTCTTCATTCGAAGACCATAATCTCAATC

TAGAAGAATTTTTATCTCAACCAACTCCTGTAATACATGGTCTTGCCCTTTATGTGGTCTACGCTATCCTACACAAC

GATGCAGCTTCCTCTAAATTATCTGCTTCCCAAGTAGCGAAAAATCCAACAGCTATAGAATCTATAGTTCTTCCTAT

AGAAGGTTTTGGTTTGTGGGGACCTATCTATGGATTCCTTGCTCTAGAAAAAGACGGGAATACTGTTCTTGGTACTT

CTTGGTATCAACATGGCGAGACTCCTGGATTAGGAGCAAATATCGCTAACCCTCAATGGCAAAAAAATTTCAGAGGC

AAAAAAGTATTTCTAGTCTCAGCTTCTGGAGAAACAGATTTTGCTAAGACAACCCTAGGACTGGAAGTTATAAAAGG

ATCTGTATCTGCAGCATTAGGAGACTCACCTAAAGCTGCTTCTTCCATCGACGGAATTTCAGGAGCTACTTTGACTT

GTAATGGTGTTACCGAATCCTTCTCTCATTCTCTAGCTCCCTACCGCGCTTTGTTGACTTTCTTCGCCAACTCTAAA

CCTAGTGGAGAGTCTCATGACCACTAA

SEQ ID NO: 8 - CT279 protein sequence
MASKSRHYLNQPWYIILFIFVLSLIAGTLLSSVYYVLAPIQQQAAEFDRNQQMLMAAQVISSDNTFQVYEKGDWHPA

LYNTKKQLLEISSTPPKVTVTTLSSYFQNFVRVLLTDTQGNLSSFEDHNLNLEEFLSQPTPVIHGLALYVVYAILHN

-continued

SEQUENCE LISTING

DAASSKLSASQVAKNPTAIESIVLPIEGFGLWGPIYGFLALEKDGNTVLGTSWYQHGETPGLGANIANPQWQKNFRG

KKVFLVSASGETDFAKTTLGLEVIKGSVSAALGDSPKAASSIDGISGATLTCNGVTESFSHSLAPYRALLTFFANSK

PSGESHDH

SEQ ID NO: 9 - CT443 nucleotide sequence
ATGCGAATAGGAGATCCTATGAACAAACTCATCAGACGAGCAGTGACGATCTTCGCGGTGACTAGTGTGGCGAGTTT

ATTTGCTAGCGGGGTGTTAGAGACCTCTATGGCAGAGTCTCTCTCTACAAACGTTATTAGCTTAGCTGACACCAAAG

CGAAAGACAACACTTCTCATAAAAGCAAAAAAGCAAGAAAAAACCACAGCAAAGAGACTCCCGTAGACCGTAAAGAG

GTTGCTCCGGTTCATGAGTCTAAAGCTACAGGACCTAAACAGGATTCTTGCTTTGGCAGAATGTATACAGTCAAAGT

TAATGATGATCGCAATGTTGAAATCACACAAGCTGTTCCTGAATATGCTACGGTAGGATCTCCCTATCCTATTGAAA

TTACTGCTACAGGTAAAAGGGATTGTGTTGATGTTATCATTACTCAGCAATTACCATGTGAAGCAGAGTTCGTACGC

AGTGATCCAGCGACAACTCCTACTGCTGATGGTAAGCTAGTTTGGAAAATTGACCGCTTAGGACAAGGCGAAAAGAG

TAAAATTACTGTATGGGTAAAACCTCTTAAAGAAGGTTGCTGCTTTACAGCTGCAACAGTATGCGCTTGTCCAGAGA

TCCGTTCGGTTACAAAATGTGGACAACCTGCTATCTGTGTTAAACAAGAAGGCCCAGAGAATGCTTGTTTGCGTTGC

CCAGTAGTTTACAAAATTAATATAGTGAACCAAGGAACAGCAACAGCTCGTAACGTTGTTGTTGAAAATCCTGTTCC

AGATGGTTACGCTCATTCTTCTGGACAGCGTGTACTGACGTTTACTCTTGGAGATATGCAACCTGGAGAGCACAGAA

CAATTACTGTAGAGTTTTGTCCGCTTAAACGTGGTCGTGCTACCAATATAGCAACGGTTTCTTACTGTGGAGGACAT

AAAAATACAGCAAGCGTAACAACTGTGATCAACGAGCCTTGCGTACAAGTAAGTATTGCAGGAGCAGATTGGTCTTA

TGTTTGTAAGCCTGTAGAATATGTGATCTCCGTTTCCAATCCTGGAGATCTTGTGTTGCGAGATGTCGTCGTTGAAG

ACACTCTTTCTCCCGGAGTCACAGTTCTTGAAGCTGCAGGAGCTCAAATTTCTTGTAATAAAGTAGTTTGGACTGTG

AAAGAACTGAATCCTGGAGAGTCTCTACAGTATAAAGTTCTAGTAAGAGCACAAACTCCTGGACAATTCACAAATAA

TGTTGTTGTGAAGAGCTGCTCTGACTGTGGTACTTGTACTTCTTGCGCAGAAGCGACAACTTACTGGAAAGGAGTTG

CTGCTACTCATATGTGCGTAGTAGATACTTGTGACCCTGTTTGTGTAGGAGAAAATACTGTTTACCGTATTTGTGTC

ACCAACAGAGGTTCTGCAGAAGATACAAATGTTTCTTTAATGCTTAAATTCTCTAAAGAACTGCAACCTGTATCCTT

CTCTGGACCAACTAAAGGAACGATTACAGGCAATACAGTAGTATTCGATTCGTTACCTAGATTAGGTTCTAAAGAAA

CTGTAGAGTTTTCTGTAACATTGAAAGCAGTATCAGCTGGAGATGCTCGTGGGGAAGCGATTCTTTCTTCCGATACA

TTGACTGTTCCAGTTTCTGATACAGAGAATACACACATCTATTAA

SEQ ID NO: 10 - CT443 protein sequence
MRIGDPMNKLIRRAVTIFAVTSVASLFASGVLETSMAESLSTNVISLADTKAKDNTSHKSKKARKNHSKETPVDRKE

VAPVHESKATGPKQDSCFGRMYTVKVNDDRNVEITQAVPEYATVGSPYPIEITATGKRDCVDVIITQQLPCEAEFVR

SDPATTPTADGKLVWKIDRLGQGEKSKITVWVKPLKEGCCFTAATVCACPEIRSVTKCGQPAICVKQEGPENACLRC

PVVYKINIVNQGTATARNVVVENPVPDGYAHSSGQRVLIFTLGDMQPGEHRTITVEFCPLKRGRATNIATVSYCGGH

KNTASVTTVINEPCVQVSIAGADWSYVCKPVEYVISVSNPGDLVLRDVVVEDTLSPGVTVLEAAGAQISCNKVVWTV

KELNPGESLQYKVLVRAQTPGQFTNNVVVKSCSDCGTCTSCAEATTYWKGVAATHMCVVDTCDPVCVGENTVYRICV

TNRGSAEDTNVSLMLKFSKELQPVSFSGPTKGTITGNTVVFDSLPRLGSKETVEFSVTLKAVSAGDARGEAILSSDT

LTVPVSDTENTHIY

SEQ ID NO: 11 - CT372 nucleotide sequence
ATGCAGGCTGCACACCATCACTATCACCGCTACACAGATAAACTGCACAGACAAAACCATAAAAAAGATCTCATCTC

TCCCAAACCTACCGAACAAGAGGCGTGCAATACTTCTTCCCTTAGTAAGGAATTAATCCCTCTATCAGAACAAAGAG

GCCTTTTATCCCCCATCTGTGACTTTATTTCGGAACGCCCTTGCTTACACGGAGTTTCTGTTAGAAATCTCAAGCAA

GCGCTAAAAAATTCTGCAGGAACCCAAATTGCACTGGATTGGTCTATTCTCCCTCAATGGTTCAATCCTCGGGTCTC

-continued

SEQUENCE LISTING

TCATGCCCCTAAGCTTTCTATCCGAGACTTTGGGTATAGCGCACACCAAACTGTTACCGAAGCCACTCCTCCTTGCT

GGCAAAACTGCTTTAATCCATCTGCGGCCGTTACTATCTATGATTCCTCATATGGGAAAGGGGTCTTTCAAATATCC

TATACCCTTGTCCGCTATTGGAGAGAGAATGCTGCGACTGCTGGCGATGCTATGATGCTCGCAGGGAGTATCAATGA

TTATCCCTCTCGTCAGAACATTTTCTCTCAGTTTACTTTCTCCCAAAACTTCCCAAATGAACGGGTGAGTCTGACAA

TTGGTCAGTACTCACTCTATGCAATAGACGGAACATTATACAATAACGATCAACAACTTGGATTCATTAGTTACGCA

TTATCACAAAATCCAACAGCAACTTATTCCTCTGGAAGTCTTGGAGCTTACCTACAAGTCGCTCCTACCGCAAGCAC

AAGTCTTCAAATAGGATTTCAAGACGCTTATAATATCTCCGGATCCTCTATCAAATGGAGTAACCTTACAAAAAATA

GATACAATTTTCACGGTTTTGCTTCCTGGGCTCCCCGCTGTTGCTTAGGATCTGGCCAGTACTCCGTGCTTCTTTAT

GTGACTAGACAAGTTCCAGAACAGATGGAACAAACAATGGGATGGTCAGTCAATGCGAGTCAACACATATCTTCTAA

ACTGTATGTGTTTGGAAGATACAGCGGTGTTACAGGACATGTGTTCCCGATTAACCGCACGTATTCATTCGGTATGG

CCTCTGCAAATTTATTTAACCGTAACCCACAAGATTTATTTGGAATTGCTTGCGCATTCAATAATGTACACCTCTCT

GCTTCTCCAAATACTAAAAGAAAATACGAAACTGTAATCGAAGGGTTTGCAACTATCGGTTGCGGCCCCTATCTTTC

TTTCGCTCCAGACTTCCAACTCTACCTCTACCCAGCTCTTCGTCCAAACAAACAATCTGCCCGTGTTTATAGCGTGC

GAGCTAATTTAGCTATCTAA

SEQ ID NO: 12 - CT372 protein sequence
MQAAHHHYHRYTDKLHRQNHKKDLISPKPTEQEACNTSSLSKELIPLSEQRGLLSPICDFISERPCLHGVSVRNLKQ

ALKNSAGTQIALDWSILPQWFNPRVSHAPKLSIRDFGYSAHQTVTEATPPCWQNCFNPSAAVTIYDSSYGKGVFQIS

YTLVRYWRENAATAGDAMMLAGSINDYPSRQNIFSQFTFSQNFPNERVSLTIGQYSLYAIDGTLYNNDQQLGFISYA

LSQNPTATYSSGSLGAYLQVAPTASTSLQIGFQDAYNISGSSIKWSNLTKNRYNFHGFASWAPRCCLGSGQYSVLLY

VTRQVPEQMEQTMGWSVNASQHISSKLYVFGRYSGVTGHVFPINRTYSFGMASANLFNRNPQDLFGIACAFNNVHLS

ASPNTKRKYETVIEGFATIGCGPYLSFAPDFQLYLYPALRPNKQSARVYSVRANLAI

SEQ ID NO: 13 - CT456 nucleotide sequence
ATGACGAATTCTATATCAGGTTATCAACCTACTGTTACAACTTCTACATCATCAACCACTTCGGCATCAGGTGCTTC

CGGATCTCTGGGAGCTTCTTCTGTATCTACTACCGCAAACGCTACAGTTACACAAACAGCAAACGCAACAAATTCAG

CGGCTACATCTTCTATCCAAACGACTGGAGAGACTGTAGTAAACTATACGAATTCAGCCTCCGCCCCCAATGTAACT

GTATCGACCTCCTCTTCTTCCACACAAGCCACAGCCACTTCGAATAAAACTTCCCAAGCCGTTGCTGGAAAAAATCAC

TTCTCCAGATACTTCAGAAAGCTCAGAAACTAGCTCTACCTCATCAAGCGATCATATCCCTAGCGATTACGATGACG

TTGGTAGCAATAGTGGAGATATTAGCAACAACTACGATGACGTAGGTAGTAACAACGGAGATATCAGTAGCAATTAT

GACGATGCTGCTGCTGATTACGAGCCGATAAGAACTACTGAAAATATTTATGAGAGTATTGGTGGCTCTAGAACAAG

TGGCCCAGAAAATACAAGTGGTGGTGCAGCAGCAGCACTCAATTCTCTAAGAGGCTCCTCCTACAGCAATTATGACG

ATGCTGCTGCTGATTACGAGCCGATAAGAACTACTGAAAATATTTATGAGAGTATTGGTGGCTCTAGAACAAGTGGC

CCAGAAAATACGAGTGGTGGTGCAGCAGCAGCACTCAATTCTCTAAGAGGCTCCTCCTACAGCAATTATGACGATGC

TGCTGCTGATTACGAGCCGATAAGAACTACTGAAAATATTTATGAGAGTATTGGTGGCTCTAGAACAAGTGGCCCAG

AAAATACGAGTGATGGTGCAGCAGCAGCAGCACTCAATTCTCTAAGAGGCTCCTCCTACACAACAGGGCCTCGTAAC

GAGGGTGTATTCGGCCCTGGACCGGAAGGACTACCAGACATGTCTCTTCCTTCATACGATCCTACAAATAAAACCTC

GTTATTGACTTTCCTCTCCAACCCTCATGTAAAGTCGAAAATGCTTGAAAACTCGGGGCATTTCGTCTTCATTGATA

CAGATAGAAGTAGTTTCATTCTTGTTCCTAACGGAAATTGGGACCAAGTCTGTTCAATTAAAGTTCAAAATGGAAAG

ACCAAAGAAGATCTCGACATCAAAGACTTGGAAAACATGTGTGCAAAATTCTGTACAGGGTTTAGCAAATTCTCTGG

TGACTGGGACAGTCTTGTAGAACCTATGGTGTCAGCCAAAGCTGGAGTGGCCAGCGGAGGCAATCTTCCCAATACAG

TGATTATCAATAATAAATTCAAAACTTGCGTTGCTTATGGTCCTTGGAATAGCCAGGAAGCAAGTTCTGGTTATACA

-continued

SEQUENCE LISTING

CCTTCTGCTTGGAGACGTGGTCATCGAGTAGATTTTGGAGGAATTTTTGAGAAAGCCAACGACTTTAATAAAATCAA

CTGGGGAACTCAAGCCGGGCCTAGTAGCGAAGACGATGGCATTTCCTTCTCCAATGAAACTCCTGGAGCTGGTCCTG

CAGCTGCTCCATCACCAACGCCATCCTCTATTCCTATCATCAATGTCAATGTCAATGTTGGCGGAACTAATGTGAAT

ATTGGAGATACGAATGTCAACACGACTAACACCACACCAACAACTCAATCTACAGACGCCTCTACAGATACAAGCGA

TATCGATGACATAAATACCAACAACCAAACTGATGATATCAATACGACAGACAAAGACTCTGACGGAGCTGGTGGAG

TCAATGGCGATATATCCGAAACAGAATCCTCTTCTGGAGATGATTCAGGAAGTGTCTCTTCCTCAGAATCAGACAAG

AATGCCTCTGTCGGAAATGACGGACCTGCTATGAAAGATATCCTTTCTGCCGTGCGTAAACACCTAGACGTCGTTTA

CCCTGGCGAAAATGGCGGTTCTACAGAAGGGCCTCTCCCAGCTAACCAAACTCTCGGAGACGTAATCTCTGATGTAG

AGAATAAAGGCTCCGCTCAGGATACAAAATTGTCAGGAAATACAGGAGCTGGGGATGACGATCCAACAACCACAGCT

GCTGTAGGTAATGGAGCGGAAGAGATCACTCTTTCCGACACAGATTCTGGTATCGGAGATGATGTATCCGATACAGC

GTCTTCATCTGGGGATGAATCCGGAGGAGTCTCCTCTCCCTCTTCAGAATCCAATAAAAATACTGCCGTTGGAAATG

ACGGACCTTCTGGACTAGATATCCTCGCTGCCGTACGTAAACATTTAGATAAGGTTTACCCTGGCGACAATGGTGGT

TCTACAGAAGGGCCTCTCCAAGCTAACCAAACTCTTGGAGATATCGTCCAGGATATGGAAACAACAGGGACATCCCA

AGAAACCGTTGTATCCCCATGGAAAGGAAGCACTTCTTCAACGGAATCAGCAGGAGGAAGTGGTAGCGTACAAACAC

TACTGCCTTCACCACCTCCAACCCCGTCAACTACAACATTAAGAACGGGCACAGGAGCTACCACCACATCCTTGATG

ATGGGAGGACCAATCAAAGCTGACATAATAACAACTGGTGGCGGAGGACGAATTCCTGGAGGAGGAACGTTAGAAAA

GCTGCTCCCTCGTATACGTGCGCACTTAGACATATCCTTTGATGCGCAAGGCGATCTCGTAAGTACTGAAGAGCCTC

AGCTTGGCTCGATTGTAAACAAATTCCGCCAAGAAACTGGTTCAAGAGGAATCTTAGCTTTCGTTGAGAGTGCTCCA

GGCAAGCCGGGATCTGCACAGGTCTTAACGGGTACAGGGGGAGATAAAGGCAACCTATTCCAAGCAGCTGCCGCAGT

CACCCAAGCCTTAGGAAATGTTGCAGGGAAAGTCAACCTTGCGATACAAGGCCAAAAACTATCATCCCTAGTCAATG

ACGACGGGAAGGGGTCTGTTGGAAGAGATTTATTCCAAGCAGCAGCCCAAACAACTCAAGTGCTAAGCGCACTGATT

GATACCGTAGGATAA

SEQ ID NO: 14 - CT456 protein sequence
MTNSISGYQPTVTTSTSSTTSASGASGSLGASSVSTTANATVTQTANATNSAATSSIQTTGETVVNYTNSASAPNVT

VSTSSSSTQATATSNKTSQAVAGKITSPDTSESSETSSTSSSDHIPSDYDDVGSNSGDISNNYDDVGSNNGDISSNY

DDAAADYEPIRTTENIYESIGGSRTSGPENTSGGAAAALNSLRGSSYSNYDDAAADYEPIRTTENIYESIGGSRTSG

PENTSGGAAAALNSLRGSSYSNYDDAAADYEPIRTTENIYESIGGSRTSGPENTSDGAAAAALNSLRGSSYTTGPRN

EGVFGPGPEGLPDMSLPSYDPTNKTSLLTFLSNPHVKSKMLENSGHFVFIDTDRSSFILVPNGNWDQVCSIKVQNGK

TKEDLDIKDLENMCAKFCTGFSKFSGDWDSLVEPMVSAKAGVASGGNLPNTVIINNKFKTCVAYGPWNSQEASSGYT

PSAWRRGHRVDFGGIFEKANDFNKINWGTQAGPSSEDDGISFSNETPGAGPAAAPSPTPSSIPIINVNVNVGGTNVN

IGDTNVNTTNTTPTTQSTDASTDTSDIDDINTNNQTDDINTTDKDSDGAGGVNGDISETESSSGDDSGSVSSSESDK

NASVGNDGPAMKDILSAVRKHLDVVYPGENGGSTEGPLPANQTLGDVISDVENKGSAQDTKLSGNTGAGDDDPTTTA

AVGNGAEEITLSDTDSGIGDDVSDTASSSGDESGGVSSPSSESNKNTAVGNDGPSGLDILAAVRKHLDKVYPGDNGG

STEGPLQANQTLGDIVQDMETTGTSQETVVSPWKGSTSSTESAGGSGSVQTLLPSPPPTPSTTTLRTGTGATTTSLM

MGGPIKADIITTGGGGRIPGGGTLEKLLPRIRAHLDISFDAQGDLVSTEEPQLGSIVNKFRQETGSRGILAFVESAP

GKPGSAQVLTGTGGDKGNLFQAAAAVTQALGNVAGKVNLAIQGQKLSSLVNDDGKGSVGRDLFQAAAQTTQVLSALI

DTVG

SEQ ID NO: 15: CT381 nucleotide sequence
ATGTGCATAAAAAGAAAAAAAACATGGATAGCTTTTTTAGCAGTTGTCTGTAGTTTTTGTTTGACGGGTTGTTTAAA

AGAAGGGGGAGACTCCAATAGTGAAAAATTTATTGTAGGGACTAATGCAACCTACCCTCCTTTTGAGTTTGTTGATA

-continued

SEQUENCE LISTING

AGCGAGGAGAGGTTGTAGGCTTCGATATAGACTTGGCTAGAGAGATTAGTAACAAGCTGGGGAAAACGCTGGACGTT

CGGGAGTTTTCCTTTGATGCACTCATTCTAAACCTAAAACAGCATCGGATTGATGCGGTTATAACAGGGATGTCCAT

TACTCCTTCTAGATTGAAGGAAATTCTTATGATTCCCTATTATGGGGAGGAAATAAAACACTTGGTTTTAGTGTTTA

AAGGAGAGAATAAGCATCCATTGCCACTCACTCAATATCGTTCTGTAGCTGTTCAAACAGGAACCTATCAAGAGGCC

TATTTACAGTCTCTTTCTGAAGTTCATATTCGCTCTTTTGATAGCACTCTAGAAGTACTCATGGAAGTCATGCATGG

TAAATCTCCCGTCGCTGTTTTAGAGCCATCTATCGCTCAAGTTGTCTTGAAAGATTTCCCGGCTCTTTCTACAGCAA

CCATAGATCTCCCTGAAGATCAGTGGGTTTTAGGATACGGGATTGGCGTTGCTTCAGATCGCCCAGCTTTAGCCTTG

AAAATCGAGGCAGCTGTGCAAGAGATCCGAAAAGAAGGAGTGCTAGCAGAGTTGGAACAGAAGTGGGGTTTGAACAA

CTAA

SEQ ID NO: 16: CT381 protein sequence
MCIKRKKTWIAFLAVVCSFCLTGCLKEGGDSNSEKFIVGTNATYPPFEFVDKRGEVVGFDIDLAREISNKLGKTLDV

REFSFDALILNLKQHRIDAVITGMSITPSRLKEILMIPYYGEEIKHLVLVFKGENKHPLPLTQYRSVAVQTGTYQEA

YLQSLSEVHIRSFDSTLEVLMEVMHGKSPVAVLEPSIAQVVLKDFPALSTATIDLPEDQWVLGYGIGVASDRPALAL

KIEAAVQEIRKEGVLAELEQKWGLNN

SEQ ID NO: 17: CT043 nucleotide sequence
ATGTCCAGGCAGAATGCTGAGGAAAATCTAAAAAATTTTGCTAAAGAGCTTAAACTCCCCGACGTGGCCTTCGATCA

GAATAATACGTGCATTTTGTTTGTTGATGGAGAGTTTTCTCTTCACCTGACCTACGAAGAACACTCTGATCGCCTTT

ATGTTTACGCACCTCTTCTTGACGGACTGCCAGACAATCCGCAAAGAAGGTTAGCTCTATATGAGAAGTTGTTAGAA

GGCTCTATGCTCGGAGGCCAAATGGCTGGTGGAGGGGTAGGAGTCGCTACTAAGGAACAGTTGATCTTAATGCACTG

CGTGTTAGACATGAAGTATGCAGAGACCAACCTACTCAAAGCTTTTGCACAGCTTTTTATTGAAACCGTTGTGAAAT

GGCGAACTGTTTGTTCTGATATCAGCGCTGGACGAGAACCCACTGTTGATACCATGCCACAAATGCCTCAAGGGGGT

GGCGGAGGAATTCAACCTCCTCCAGCAGGAATCCGTGCATAA

SEQ ID NO: 18: CT043 protein sequence
MSRQNAEENLKNFAKELKLPDVAFDQNNTCILFVDGEFSLHLTYEEHSDRLYVYAPLLDGLPDNPQRRLALYEKLLE

GSMLGGQMAGGGVGVATKEQLILMHCVLDMKYAETNLLKAFAQLFIETVVKWRTVCSDISAGREPTVDTMPQMPQGG

GGGIQPPPAGIRA

SEQ ID NO: 19: CT711/hypothetical protein (AAC68306)
MSIQPTSISLTKNITAALAGEQVDAAAVYMPQAVFFFQQLDEKSKGLKQALGLLEEVDLEKFIPSLEKSPTPITTGT

TSKISADGIEIVGELSSETILADPNKAAAQVFGEGLADSFDDWLRLSENGGIQDPTAIEEEIVTKYQTELNTLRNKL

KQQSLTDDEYTKLYAIPQNFVKEIESLKNENNVRLIPKSKVTNFWQNIMLTYNSVTSLSEPVTDAMNTTMAEYSLYI

ERATEAAKLIREITNTIKDIFNPVWDVREQTGIFGLKGAEYNALEGNMIQSLLSFAGLFRQLMSRTATVDEIGALYP

KNDKNEDVIHTAIDDYVNSLADLKANEQVKLNGLLSLVYAYYASTLGFAKKDVFNNAQASFTDYTNFLNQEIQYWTP

RETSSFNISNQALQTFKNKPSADYNGVYLFDNKGLETNLFNPTFFFDVVSLMTADPTKTMSRQDYNKVITASESSIQ

KINQAITAWELAIAECGTKKAKLEPSSLNYFNAMVEAKKTFVETSPIQMVYSSLMLDKYLPNQQYILETLGSQMTFS

NKAARYLNDIIAYAVSFQTADVYYSLGMYLRQMNQQEFPEVISRANDTVKKEIDRSRADLFHCKKAIEKIKELVTSV

NADTELTSSQRAELLETLASYAFEFENLYHNLSNVYVMVSKVQISGVSKPDEVDEAFTAKIGSKEFDTWIQQLTTFE

SAVIEGGRNGVMPGGEQQVLQSLESKQQDYTSFNQNQQLALQMESAAIQQEWTMVAAALALMNQIFAKLIRRFK

SEQ ID NO: 20: CT114/hypothetical protein (AAC67705)
MCFIGIGSLLLPTALRATERMRKEPIPLLDKQQSFWNVDPYCLESICACFVAHRDPLSAKQLMYLFPQLSEEDVSVF

ARCILSSKRPEYLFSKSEEELFAKLILPRVSLGVHRDDDLARVLVLAEPSAEEQKARYYSLYLDVLALRAYVERERL

ASAAHGDPERIDLATIEAINTILFQEEGWRYPSKQEMFENRFSELAAVTDSKFGVCLGTVVLYQAVAQRLDLSLDPV

TPPGHIYLRYKDKVNIETTSGGRHLPTERYCECIKESQLKVRSQMELIGLTFMNRGAFFLQKGEFLQASLAYEQAQS

-continued

SEQUENCE LISTING

YLSDEQISDLLGITYVLLGKKAAGEALLKKSAEKTRRGSSIYDYFQGYISPEILGVLFADSGVTYQETLEYRKKLVM

LSKKYPKSGSLRLRLATTALELGLVKEGVQLLEESVKDAPEDLSLRLQFCKILCNRHDYVRAKYHFDQAQALLIKEG

LFSEKTSYTLLKTIGKKLSLFAPS

SEQ ID NO: 21: CT480/oppA_4 (AAC68080)
MIDKIIRTILVLSLFLLYWSSDLLEKDVKSIKRELKALHEDVLELVRISHQQKNWVQSTDFSVSPEISVLKDCGDPA

FPNLLCEDPYVEKVVPSLLKEGFVPKGILRTAQVGRPDNLSPFNGFVNIVRFYELCVPNLAVEHVGKYEEFAPSLAL

KIEEHYVEDGSGDKEFHIYLRPNMFWEPIDPTLFPKNITLADSFLRPHPVTAHDVKFYYDVVMNPYVAEMRAVAMRS

YFEDMVSVRVENDLKLIVRWRAHTVRNEQGEEEKKVLYSAFANTLALQPLPCFVYQHFANGEKIVPEDSDPDTYRKD

SVWAQNFSSHWAYNYIVSCGAFRFAGMDDEKITLVRNPNYHNPFAALVEKRYIYMKDSTDSLFQDFKAGKVDIAYFP

PNHVDNLASFMQTSAYKEQAARGEAILEKNSSDRSYSYIGWNCLSLFFNNRSVRQAMNMLIDRDRIIEQCLDGRGVS

VSGPFSLCSPSYNRDVEGWQYSPEEAARKLEEEGWIDADGDGIREKVIDGVVVPFRFRLCYYVKSVTARTIAEYVAT

VCKEVGIECCLLGLDMADYSQALEEKNFDAILSGWCLGTPPEDPRALWHSEGALEKGSANAVGFCNEEADRIIEQLS

YEYDSNKRQALYHRFHEVIHEESPYAFLYSRQYSLVYKEFVKNIFVPTEHQDLIPGAQDETVNLSMLWVDKEEGRCS

AIS

SEQ ID NO: 22: CT089/lcrE (AAC67680)
MTASGGAGGLGSTQTVDVARAQAAAATQDAQEVIGSQEASEASMLKGCEDLINPAAATRIKKKGEKFESLEARRKPT

ADKAEKKSESTEEKGDTPLEDRFTEDLSEVSGEDFRGLKNSFDDDSSPDEILDALTSKFSDPTIKDLALDYLIQTAP

SDGKLKSTLIQAKHQLMSQNPQAIVGGRNVLLASETFASRANTSPSSLRSLYFQVTSSPSNCANLHQMLASYLPSEK

TAVMEFLVNGMVADLKSEGPSIPPAKLQVYMTELSNLQALHSVNSFFDRNIGNLENSLKHEGHAPIPSLTTGNLTKT

FLQLVEDKFPSSSKAQKALNELVGPDTGPQTEVLNLFFRALNGCSPRIFSGAEKKQQLASVITNTLDAINADNEDYP

KPGDFPRSSFSSTPPHAPVPQSEIPTSPTSTQPPSP

SEQ ID NO: 23: CT734/hypothetical protein (AAC68329)
MKKFIYKYSFGALLLLSGLSGLSSCCANSYGSTLAKNTAEIKEESVTLREKPDAGCKKKSSCYLRKFFSRKKPKEKT

EPVLPNFKSYADPMTDSERKDLSFVVSAAADKSSIALAMAQGEIKGALSRIREIHPLALLQALAEDPALIAGMKKMQ

GRDWVWNIFITELSKVFSQAASLGAFSVADVAAFASTLGLDSGTVTSIVDGERWAELIDVVIQNPAI

SEQ ID NO: 24: CT016/hypothetical protein (AAC67606)
MKVKINDQFICISPYISARWNQIAFIESCDGGTEGGITLKLHLIDGETVSIPNLGQAIVDEVFQEHLLYLESTAPQK

NKEEEKISSLLGAVQQMAKGCEVQVFSQKGLVSMLLGGAGSINVLLQHSPEHKDHPDLPTDLLERIAQMMRSLSIGP

TSILAKPEPHCNCLHCQIGRATVEEEDAGVSDEDLTFRSWDISQSGEKMYTVTDPLNPEEQFNVYLGTPIGCTCGQP

YCEHVKAVLYT

SEQ ID NO: 25: CM homolog of CT279 = TC_0551
ATGGCATCCAAGTCTCGTCATTATCTTAACCAGCCTTGGTACATTATCTTATTCATCTTTGTTCTTAGTCTGGTTGC

TGGTACCCTTCTTTCTTCAGTTTCCTATGTTCTATCTCCAATCCAAAAACAAGCTGCAGAATTTGATCGTAATCAGC

AAATGTTGATGGCCGCACAAATTATTTCCTATGACAATAAATTCCAAATATATGCTGAAGGGGATTGGCAACCTGCT

GTCTATAATACAAAAAAACAGATACTAGAAAAAAGCTCTTCCACTCCACCACAAGTGACTGTGGCGACTCTATGCTC

TTATTTTCAAAATTTTGTTAGAGTTTTGCTTACAGACTCCCAAGGGAATCTTTCTTCTTTTGAAGATCACAATCTTA

ACCTAGAAGAGTTCTTATCCCACCCCACATCTTCAGTACAAGATCACTCTCTGCATGTAATTTATGCTATTCTAGCA

AACGATGAATCCTCTAAAAAGTTATCATCCTCCCAAGTAGCAAAAAATCCGGTATCCATAGAGTCTATTATTCTTCC

TATAAAAGGATTTGGTTTATGGGGACCAATCTATGGATTTCTTGCTTTAGAAAAGGACGGTAATACGGTTCTAGGGA

CATGCTGGTATCAACATGGTGAGACTCCAGGATTAGGAGCAAATATAACTAATCCCCAATGGCAACAAAATTTCAGA

GGAAAAAAAGTATTTCTCGCTTCCTCTTCCGGAGAAACCGATTTTGCTAAAACAACTCTAGGACTAGAAGTTATAAA

```
AGGATCTGTTTCTGCATTATTAGGGGACTCTCCCAAAGCTAATTCCGCTGTTGATGGAATTTCAGGAGCTACACTGA

CCTGTAATGGAGTTACTGAAGCTTTTGCTAATTCGCTAGCTCCTTACCGCCCCTTATTGACTTTCTTCGCCAATCTT

AACTCTAGTGGAGAATCTCATGACAACCAATAA

SEQ ID NO: 26: CM homologue of CT279 protein sequence = TC_0551 protein sequence
MASKSRHYLNQPWYIILFIFVLSLVAGTLLSSVSYVLSPIQKQAAEFDRNQQMLMAAQIISYDNKFQIYAEGDWQPA

VYNTKKQILEKSSSTPPQVTVATLCSYFQNFVRVLLTDSQGNLSSFEDHNLNLEEFLSHPTSSVQDHSLHVIYAILA

NDESSKKLSSSQVAKNPVSIESIILPIKGFGLWGPIYGFLALEKDGNTVLGTCWYQHGETPGLGANITNPQWQQNFR

GKKVFLASSSGETDFAKTTLGLEVIKGSVSALLGDSPKANSAVDGISGATLTCNGVTEAFANSLAPYRPLLTFFANL

NSSGESHDNQ

SEQ ID NO: 27: CM homologue of CT372 = TC_0651 nucleotide sequence
ATGAATGGAAAAGTTCTGTGTGAGGTTTCTGTGTCCTTCCGTTCGATTCTGCTGACGGCTCTGCTTTCACTTTCTTT

TACAAACACTATGCAGGCTGCACACCATCATTATCACCGTTATGATGATAAACTACGCAGACAATACCATAAAAAGG

ACTTGCCCACTCAAGAGAATGTTCGGAAAGAGTTTTGTAATCCCTACTCTCATAGTAGTGATCCTATCCCTTTGTCA

CAACAACGAGGAGTCCTATCTCCTATCTGTGATTTAGTCTCAGAGTGCTCGTTTTTGAACGGGATTTCCGTTAGGAG

TCTTAAACAAACACTGAAAAATTCTGCTGGGACTCAAGTTGCTTTAGACTGGTCTATCCTTCCTCAATGGTTCAATC

CTAGATCCTCTTGGGCTCCTAAGCTCTCTATTCGAGATCTTGGATATGGTAAACCCCAGTCCCTTATTGAAGCAGAT

TCCCCTTGTTGTCAAACCTGCTTCAACCCATCTGCTGCTATTACGATTTACGATTCTTCATGTGGGAAGGGTGTTGT

CCAAGTGTCATACACCCTTGTTCGTTATTGGAGAGAAACGGCTGCACTTGCAGGGCAAACTATGATGCTTGCAGGAA

GTATTAATGATTATCCTGCTCGCCAAAACATATTCTCTCAACTTACATTTTCCCAAACTTTCCCTAATGAGAGAGTA

AATCTAACTGTTGGTCAATACTCTCTTTACTCGATAGACGGAACGCTGTACAACAATGATCAGCAGCTAGGATTTAT

TAGTTATGCGTTGTCGCAAAATCCAACAGCGACTTATTCCTCTGGAAGCCTTGGCGCCTATCTACAAGTCGCTCCAA

CAGAAAGCACCTGTCTTCAAGTTGGGTTCCAAGATGCCTATAATATTTCAGGTTCCTCGATCAAATGGAATAATCTT

ACAAAAAATAAGTATAACTTCCATGGCTATGCATCTTGGGCTCCACACTGTTGCTTAGGACCTGGACAATACTCTGT

TCTTCTTTATGTAACCAGAAAGGTTCCTGAGCAAATGATGCAGACAATGGGCTGGTCTGTGAATGCAAGTCAATACA

TCTCTTCTAAACTTTATGTATTTGGAAGATACAGCGGAGTCACAGGCCAATTGTCTCCTATTAACCGAACCTATTCA

TTTGGCTTAGTCTCTCCTAATTTATTGAACCGTAACCCACAAGACTTATTTGGAGTAGCTTGCGCATTCAATAATAT

ACACGCCTCCGCCTTTCAAAATGCTCAAAGAAAATATGAAACTGTGATCGAGGGATTTGCAACTATTGGTTGCGGAC

CTTACATCTCCTTTGCTCCAGATTTCCAACTTTACCTCTATCCTGCTCTGCGTCCAAATAAACAAAGCGCCCGAGTC

TATAGCGTTCGCGCAAACCTAGCTATTTAG

SEQ ID NO: 28: CM homologue of CT372 = TC_0651 protein sequence
MNGKVLCEVSVSFRSILLTALLSLSFTNTMQAAHHHYHRYDDKLRRQYHKKDLPTQENVRKEFCNPYSHSSDPIPLS

QQRGVLSPICDLVSECSFLNGISVRSLKQTLKNSAGTQVALDWSILPQWFNPRSSWAPKLSIRDLGYGKPQSLIEAD

SPCCQTCFNPSAAITIYDSSCGKGVVQVSYTLVRYWRETAALAGQTMMLAGSINDYPARQNIFSQLTFSQTFPNERV

NLTVGQYSLYSIDGTLYNNDQQLGFISYALSQNPTATYSSGSLGAYLQVAPTESTCLQVGFQDAYNISGSSIKWNNL

TKNKYNFHGYASWAPHCCLGPGQYSVLLYVTRKVPEQMMQTMGWSVNASQYISSKLYVFGRYSGVTGQLSPINRTYS

FGLVSPNLLNRNPQDLFGVACAFNNIHASAFQNAQRKYETVIEGFATIGCGPYISFAPDFQLYLYPALRPNKQSARV

YSVRANLAI

SEQ ID NO: 29: CM homologue of CT443 = TC_0727
ATGCGAATAGGAGATCCTATGAACAAACTCATCAGACGAGCTGTGACGATCTTCGCGGTGACTAGTGTGGCGAGTTT

ATTTGCTAGCGGGGTGTTAGAGACCTCTATGGCAGAGTCTCTCTCTACCAACGTTATTAGCTTAGCTGACACCAAAG

CGAAAGAGACCACTTCTCATCAAAAAGACAGAAAAGCAAGAAAAAATCATCAAAATAGGACTTCCGTAGTCCGTAAA
```

-continued

SEQUENCE LISTING

GAGGTTACTGCAGTTCGTGATACTAAAGCTGTAGAGCCTAGACAGGATTCTTGCTTTGGCAAAATGTATACAGTCAA

AGTTAATGATGATCGTAATGTAGAAATCGTGCAGTCCGTTCCTGAATATGCTACGGTAGGATCTCCATATCCTATTG

AGATTACTGCTATAGGGAAAAGAGACTGTGTTGATGTAATCATTACACAGCAATTACCATGCGAAGCAGAGTTTGTT

AGCAGTGATCCAGCTACTACTCCTACTGCTGATGGTAAGCTAGTTTGGAAAATTGATCGGTTAGGACAGGGCGAAAA

GAGTAAAATTACTGTATGGGTAAAACCTCTTAAAGAAGGTTGCTGCTTTACAGCTGCAACGGTTTGTGCTTGTCCAG

AGATCCGTTCGGTTACGAAATGTGGCCAGCCTGCTATCTGTGTTAAACAGGAAGGTCCAGAAAGCGCATGTTTGCGT

TGCCCAGTAACTTATAGAATTAATGTAGTCAACCAAGGAACAGCAACAGCACGTAATGTTGTTGTGGAAAATCCTGT

TCCAGATGGCTATGCTCATGCATCCGGACAGCGTGTATTGACATATACTCTTGGGGATATGCAACCTGGAGAACAGA

GAACAATCACCGTGGAGTTTTGTCCGCTTAAACGTGGTCGAGTCACAAATATTGCTACAGTTTCTTACTGTGGTGGA

CACAAAAATACTGCTAGCGTAACAACAGTGATCAATGAGCCTTGCGTGCAAGTTAACATCGAGGGAGCAGATTGGTC

TTATGTTTGTAAGCCTGTAGAATATGTTATCTCTGTTTCTAACCCTGGTGACTTAGTTTTACGAGACGTTGTAATTG

AAGATACGCTTTCTCCTGGAATAACTGTTGTTGAAGCAGCTGGAGCTCAGATTTCTTGTAATAAATTGGTTTGGACT

TTGAAGGAACTCAATCCTGGAGAGTCTTTACAATATAAGGTTCTAGTAAGAGCTCAAACTCCAGGGCAATTCACAAA

CAACGTTGTTGTGAAAAGTTGCTCTGATTGCGGTATTTGTACTTCTTGCGCAGAAGCAACAACTTACTGGAAAGGAG

TTGCTGCTACTCATATGTGCGTAGTAGATACTTGTGATCCTATTTGCGTAGGAGAGAACACTGTTTATCGTATCTGT

GTGACAAACAGAGGTTCTGCTGAAGATACAAATGTGTCCTTAATTTTGAAATTCTCTAAAGAATTACAACCTATATC

TTTCTCTGGACCAACTAAAGGAACCATTACAGGAAACACGGTAGTGTTTGATTCGTTACCTAGATTAGGTTCTAAAG

AAACTGTAGAGTTTTCTGTAACGTTGAAAGCAGTATCCGCTGGAGATGCTCGTGGGGAAGCTATTCTTTCTTCCGAT

ACATTGACAGTTCCTGTATCTGATACGGAGAATACACATATCTATTAA

SEQ ID NO: 30: CM homologue of CT443 = TC_0727
MRIGDPMNKLIRRAVTIFAVTSVASLFASGVLETSMAESLSTNVISLADTKAKETTSHQKDRKARKNHQNRTSVVRK

EVTAVRDTKAVEPRQDSCFGKMYTVKVNDDRNVEIVQSVPEYATVGSPYPIEITAIGKRDCVDVIITQQLPCEAEFV

SSDPATTPTADGKLVWKIDRLGQGEKSKITVWVKPLKEGCCFTAATVCACPEIRSVTKCGQPAICVKQEGPESACLR

CPVTYRINVVNQGTATARNVVVENPVPDGYAHASGQRVLTYTLGDMQPGEQRTITVEFCPLKRGRVTNIATVSYCGG

HKNTASVTTVINEPCVQVNIEGADWSYVCKPVEYVISVSNPGDLVLRDVVIEDTLSPGITVVEAAGAQISCNKLVWT

LKELNPGESLQYKVLVRAQTPGQFTNNVVVKSCSDCGICTSCAEATTYWKGVAATHMCVVDTCDPICVGENTVYRIC

VTNRGSAEDTNVSLILKFSKELQPISFSGPTKGTITGNTVVFDSLPRLGSKETVEFSVTLKAVSAGDARGEAILSSD

TLTVPVSDTENTHIY

SEQ ID NO: 31: CM homologue of CT043 = TC_0313 nucleotide sequence
ATGTCCAGACAGAATGCTGAGGAAAATCTAAAAAATTTTGCTAAAGAGCTCAAGCTCCCCGACGTGGCCTTCGATCA

GAATAATACGTGCATTTTGTTTGTTGATGGAGAGTTTTCTCTTCACCTGACCTACGAAGAGCACTCTGATCGCCTTT

ATGTTTACGCACCTCTCCTTGACGGACTCCCAGATAATCCGCAAAGAAAGTTGGCTCTGTATGAGAAATTGTTGGAA

GGCTCTATGCTCGGAGGCCAAATGGCTGGTGGAGGAGTAGGAGTTGCTACTAAAGAACAGTTGATCCTAATGCATTG

CGTGTTAGATATGAAATATGCAGAGACTAATCTATTGAAAGCTTTTGCACAGCTTTTCATTGAAACTGTTGTGAAAT

GGCGAACGGTCTGTTCTGATATCAGCGCTGGACGAGAACCTTCCGTTGACACTATGCCTCAAATGCCTCAAGGAGGC

AGCGGAGGAATTCAACCTCCTCCAACAGGAATTCGTGCGTAG

SEQ ID NO: 32: CM homologue of CT043 = TC_0313 protein sequence
MSRQNAEENLKNFAKELKLPDVAFDQNNTCILFVDGEFSLHLTYEEHSDRLYVYAPLLDGLPDNPQRKLALYEKLLE

GSMLGGQMAGGGVGVATKEQLILMHCVLDMKYAETNLLKAFAQLFIETVVKWRTVCSDISAGREPSVDTMPQMPQGG

SGGIQPPPTGIRA

-continued

SEQUENCE LISTING

SEQ ID NO: 33: CM homologue of CT601 = TC_0890 nucleotide sequence
ATGCTCGCTAATCGGTTATTTCTAATCACCCTTATAGGTTTTGGCTATTCTGCTTACGGTGCCAGCACAGGGAAATC

ACCTTCTTTACAGGTTATTTTAGCTGAAGTCGAGGATACATCTTCGCGCTTACAAGCTCATCAGAATGAGCTTGTTA

TGCTCTCGGAACGTTTAGATGAGCAAGACACAAAACTTCAACAACTCTCGTCAACTCAGGCCCGTAATCTTCCTCAA

CAAGTTCAACGGCTTGAGATTGATCTGAGAGCTCTGGCTAAAACAGCTGCTGTGCTCTCGCAATCTGTTCAGGATAT

CCGATCATCCGTGCAAAATAAATTACAAGAAATCCAACAAGAACAAAAAAATTTAGCTCAAAATTTACGAGCGCTTC

GCAACTCCTTACAAGCACTAGTTGATGGCTCTTCCCCAGAAAATTATATTGATTTTTTGGCCGGGGAGACACCTGAA

CATATTCACGTTGTTAAACAAGGAGAAACCCTGAGTAAAATCGCTAGTAAGTACAATATCCCTGTCGCAGAATTGAA

AAAACTTAATAAATTAAATTCCGATACTATTTTTACTGATCAAAGAATCCGACTTCCAAAAAAGAAATAA

SEQ ID NO: 34: CM homologue of CT601 = TC_0890 protein sequence
MLANRLFLITLIGFGYSAYGASTGKSPSLQVILAEVEDTSSRLQAHQNELVMLSERLDEQDTKLQQLSSTQARNLPQ

QVQRLEIDLRALAKTAAVLSQSVQDIRSSVQNKLQEIQQEQKNLAQNLRALRNSLQALVDGSSPENYIDFLAGETPE

HIHVVKQGETLSKIASKYNIPVAELKKLNKLNSDTIFTDQRIRLPKKK

SEQ ID NO: 35: CM homologue of CT456 = TC_0741
ATGACGACTCCAATAAGTAATTCTCCATCTTCTATTCCAACTGTTACAGTATCAACTACTACAGCATCTTCTGGATC

TCTCGGAACTTCTACTGTATCATCAACGACTACAAGTACTTCAGTCGCACAAACAGCAACAACAACATCTTCTGCTT

CTACATCTATAATTCAGTCTAGTGGAGAAAACATCCAATCCACTACAGGTACCCCTTCTCCTATTACGTCTAGTGTT

TCAACATCCGCTCCATCTCCTAAAGCCTCCGCCACTGCAAACAAAACTTCAAGCGCTGTTTCTGGGAAAATTACCTC

ACAAGAAACTTCTGAGGAATCCGAAACCCAAGCCACTACATCTGATGGAGAAGTTAGTAGTAATTACGATGATGTTG

ATACCCCGACCAATTCGTCCGATTCGACAGTTGATAGTGATTACCAAGATGTTGAGACTCAGTACAAAACAATTAGC

AACAATGGTGAAAACACTTATGAAACAATCGGAAGTCATGGTGAGAAAAACACACACGTCCAGGAAAGCCATGCATC

CGGAACAGGAAATCCCATAAATAATCAGCAAGAAGCTATTAGACAGCTCCGATCATCTACCTATACAACCAGCCCTC

GTAATGAGAATATATTTAGTCCAGGACCGGAAGGTCTACCTAATATGTCTCTTCCTAGTTACAGCCCTACAGATAAA

AGTTCTCTACTAGCTTTCCTATCTAATCCCAATACAAAAGCAAAAATGCTCGAACACTCCGGGCATTTAGTCTTTAT

AGACACAACTAGAAGTAGCTTTATCTTTGTTCCGAATGGAAATTGGGATCAAGTCTGTTCCATGAAGGTTCAGAATG

GGAAAACTAAAGAAGACCTTGGCTTAAAGGACTTAGAAGATATGTGTGCAAAGTTTTGCACAGGATACAATAAATTC

TCCTCTGATTGGGGAAATCGAGTTGACCCCTTGGTCTCTTCTAAGGCCGGGATAGAAAGTGGGGGGCACCTCCCAAG

CTCAGTTATCATCAACAACAAATTTAGAACCTGTGTTGCCTATGGGCCGTGGAACCCCAAAGAAAACGGCCCCAATT

ATACTCCTTCAGCCTGGAGACGTGGGCATCGAGTAGATTTTGGAAAGATCTTTGATGGAACAGCGCCGTTTAATAAA

ATCAACTGGGGCTCTTCCCCTACCCCTGGTGATGACGGCATCTCCTTCTCTAATGAAACTATTGGGTCTGAACCATT

CGCGACACCTCCCTCATCCCCATCGCAAACCCCCGTTATCAACGTCAATGTTAATGTCGGTGGAACCAATGTTAATA

TTGGGGATACAAACGTATCTAAAGGATCCGGCACACCAACATCTTCTCAATCTGTGGACATGTCTACAGATACTAGC

GATTTAGATACCAGTGATATTGATACAAACAACCAAACTAACGGCGATATCAACACGAATGACAACTCCAATAATGT

CGATGGAAGTTTATCTGACGTTGATTCAAGGGTGGAAGACGATGACGGTGTATCGGATACAGAGTCCACTAATGGCA

ATGACTCTGGTAAAACTACTTCCACAGAAGAAAATGGTGACCCAAGCGGACCAGACATCCTGGCTGCTGTACGTAAA

CACCTAGACACTGTCTATCCAGGAGAAAATGGCGGATCTACAGAAGGACCTCTCCCTGCTAATCAAAATCTGGGGAA

CGTTATCCATGATGTGGAGCAGAATGGATCTGCTAAAGAAACTATTATCACTCCAGGAGATACAGGGCCTACAGACT

CAAGCTCCTCTGTAGATGCTGATGCAGACGTTGAAGATACTTCTGATACTGACTCTGGAATCGGAGACGACGACGGT

GTATCGGATACAGAGTCCACTAATGGTAATAACTCTGGTAAAACTACTTCCACAGAAGAAAATGGTGACCCAAGCGG

ACCAGACATCCTGGCTGCTGTACGTAAACACCTAGACACTGTCTATCCAGGAGAAAATGGCGGATCTACAGAAGGAC

CTCTCCCTGCTAATCAAAATCTGGGGAACGTTATCCATGATGTAGAACAAAACGGAGCCGCTCAAGAAACTATTATC

-continued

SEQUENCE LISTING

ACTCCAGGAGATACGGAATCTACAGACACAAGCTCTAGTGTAAATGCTAATGCAGACTTAGAAGATGTTTCTGATGC

TGATTCAGGATTCGGGGATGATGACGGTATATCGGATACAGAGTCCACTAATGGTAACGACTCTGGAAAAAATACTC

CTGTAGGGGATGGTGGTACACCAAGCGGACCAGATATCCTAGCTGCTGTACGCAAACATCTAGACACTGTCTATCCA

GGAGAAAATGGTGGATCTACAGAGAGACCTTTACCCGCTAATCAAAATTTAGGAGATATCATTCATGATGTAGAACA

AAACGGAAGCGCTAAAGAAACTGTAGTATCGCCTTATCGAGGAGGAGGAGGAAATACATCTTCCCCAATTGGATTAG

CCTCCCTGCTTCCAGCAACACCATCCACACCTTTGATGACAACACCTAGAACAAATGGGAAAGCTGCAGCTTCTTCT

TTGATGATAAAAGGAGGAGAAACTCAAGCCAAGCTAGTTAAGAATGGCGGCAATATCCCTGGAGAAACCACATTAGC

AGAATTACTCCCTCGTTTAAGAGGACACCTTGACAAAGTCTTTACTTCAGACGGGAAGTTTACAAATCTTAATGGAC

CTCAACTTGGAGCCATCATAGACCAATTCCGCAAAGAAACGGGTTCCGGAGGAATCATAGCTCATACAGATAGTGTT

CCAGGAGAGAACGGAACAGCCTCTCCTCTCACAGGAAGTTCAGGGGAAAAAGTCTCTCTCTATGATGCAGCGAAAAA

CGTCACTCAAGCTTTAACAAGTGTTACGAACAAAGTAACCCTAGCAATGCAAGGACAAAAACTGGAAGGAATTATAA

ACAACAACAATACCCCCTCTTCTATTGGACAAAATCTTTTCGCAGCAGCGAGGGCAACGACACAATCCCTCAGTTCA

TTAATTGGAACCGTACAATAA

SEQ ID NO: 36: CM homologue of CT456 = TC_0741 protein sequence
MTTPISNSPSSIPTVIVSTTTASSGSLGTSTVSSTTTSTSVAQTATTTSSASTSIIQSSGENIQSTTGTPSPITSSV

STSAPSPKASATANKTSSAVSGKITSQETSEESETQATTSDGEVSSNYDDVDTPTNSSDSTVDSDYQDVETQYKTIS

NNGENTYETIGSHGEKNTHVQESHASGTGNPINNQQEAIRQLRSSTYTTSPRNENIFSPGPEGLPNMSLPSYSPTDK

SSLLAFLSNPNTKAKMLEHSGHLVFIDTTRSSFIFVPNGNWDQVCSMKVQNGKTKEDLGLKDLEDMCAKFCTGYNKF

SSDWGNRVDPLVSSKAGIESGGHLPSSVIINNKFRTCVAYGPWNPKENGPNYTPSAWRRGHRVDFGKIFDGTAPFNK

INWGSSPTPGDDGISFSNETIGSEPFATPPSSPSQTPVINVNVNVGGTNVNIGDTNVSKGSGTPTSSQSVDMSTDTS

DLDTSDIDTNNQTNGDINTNDNSNNVDGSLSDVDSRVEDDDGVSDTESTNGNDSGKTTSTEENGDPSGPDILAAVRK

HLDTVYPGENGGSTEGPLPANQNLGNVIHDVEQNGSAKETIITPGDTGPTDSSSSVDADADVEDTSDTDSGIGDDDG

VSDTESTNGNNSGKTTSTEENGDPSGPDILAAVRKHLDTVYPGENGGSTEGPLPANQNLGNVIHDVEQNGAAQETII

TPGDTESTDTSSSVNANADLEDVSDADSGFGDDDGISDTESTNGNDSGKNTPVGDGGTPSGPDILAAVRKHLDTVYP

GENGGSTERPLPANQNLGDIIHDVEQNGSAKETVVSPYRGGGGNTSSPIGLASLLPATPSTPLMTTPRTNGKAAASS

LMIKGGETQAKLVKNGGNIPGETTLAELLPRLRGHLDKVFTSDGKFTNLNGPQLGAIIDQFRKETGSGGIIAHTDSV

PGENGTASPLTGSSGEKVSLYDAAKNVTQALTSVTNKVTLAMQGQKLEGIINNNNTPSSIGQNLFAAARATTQSLSS

LIGTVQ

SEQ ID NO: 37: CM homologue of CT381 = TC_0660
GTGAGTATGTATATAAAAAGAAAGAAAGCTTGGATGACTTTCTTAGCAATTGTCTGTAGTTTCTGTTTGGCGGGCTG

TTCAAAAGAGAGCAAAGACTCTGTTAGTGAAAAATTTATTGTAGGAACTAACGCAACGTATCCTCCTTTTGAGTTTG

TTGATGAAAGAGGTGAGACGGTTGGCTTTGATATTGATTTAGCTAGGGAGATTAGTAAAAAGCTAGGGAAAAAATTA

GAAGTCCGAGAATTTGCTTTTGATGCACTCGTTCTCAATTTAAAACAGCATCGTATTGATGCAATTATGGCAGGGGT

GTCCATTACGTCTTCTCGATTGAAAGAAATTTTGATGATTCCCTACTATGGCGAAGAAATAAAGAGTTTGGTTTTAG

TGTTTAAGGATGGAGACTCAAAGTCTTTACCACTAGATCAGTATAATTCTGTTGCTGTTCAAACTGGCACGTACCAA

GAGGAATATTTACAGTCTCTTCCAGGGGTGCGTATTCGCTCTTTTGATAGTACTTTAGAAGTGCTTATGGAAGTTTT

GCATAGCAAGTCTCCTATAGCTGTTTTAGAACCGTCTATTGCGCAGGTCGTTTTAAAAGATTTTCCGACGCTCACTA

CTGAAACGATAGATCTTCCTGAAGATAAATGGGTTTTAGGGTATGGAATTGGAGTTGCTTCTGATCGACCATCTCTA

GCTTCTGATATAGAAGCTGCTGTACAAGAGATCAAGAAAGAAGGAGTGTTAGCAGAGTTAGAGCAAAAATGGGGTTT

GAACGGCTAA

-continued

SEQUENCE LISTING

SEQ ID NO: 38: CM homologue of CT381 = TC_0660
MSMYIKRKKAWMTFLAIVCSFCLAGCSKESKDSVSEKFIVGTNATYPPFEFVDERGETVGFDIDLAREISKKLGKKL

EVREFAFDALVLNLKQHRIDAIMAGVSITSSRLKEILMIPYYGEEIKSLVLVFKDGDSKSLPLDQYNSVAVQTGTYQ

EEYLQSLPGVRIRSFDSTLEVLMEVLHSKSPIAVLEPSIAQVVLKDFPTLTTETIDLPEDKWVLGYGIGVASDRPSL

ASDIEAAVQEIKKEGVLAELEQKWGLNG

SEQ ID NO: 39 - CT255 nucleotide sequence
ATGGAAGAAAAAGGCATCTTACAATTGGTTGAAATTTCGCGAGCAATGGCTTTACAGGGAGTTTGTCCTTGGACTAA

TTTACAGAGTGTGGAGTCTATGTTGCAGTATATAGCAGGGGAGTGTCAGGAGTTGGCTGATGCTGTACAAGAAAATA

AAGCTTCGTTGGAAATCGCTTCGGAAGCCGGAGACGTACTTACTTTAGTATTGACCTTGTGTTTCTTGCTAGAAAGA

GAAGGAAAGCTTAAAGCTGAAGAAGTATTTGTAGAAGCTTTGGCTAAGTTGCGTCGTCGATCTCCTCATGTTTTTGA

TCCTCATAATCAAATTTCTTTAGAACAGGCTGAAGAATACTGGGCTCGTATGAAACAGCAAGAAAAAATTTCTTAA

SEQ ID NO: 40 - CT255 protein sequence
MEEKGILQLVEISRAMALQGVCPWTNLQSVESMLQYIAGECQELADAVQENKASLEIASEAGDVLTLVLTLCFLLER

EGKLKAEEVFVEALAKLRRRSPHVFDPHNQISLEQAEEYWARMKQQEKIS

SEQ ID NO: 41 - CT341 nucleotide sequence
ATGGATTACTACACGATATTGGGTGTAGCGAAGACTGCTACTCCTGAAGAAATAAAGAAAGCTTACCGTAAGCTCGC

TGTAAAGTACCATCCAGATAAGAATCCTGGGGATGCTGAAGCGGAGCGACGCTTTAAAGAAGTTTCTGAAGCCTATG

AAGTATTAGGTGATGCGCAGAAGCGGGAGTCATATGATCGTTACGGCAAAGACGGTCCATTTGCTGGTGCTGGAGGA

TTCGGTGGCGCTGGCATGGGGAATATGGAAGACGCTTTGCGAACATTTATGGGAGCTTTTGGCGGCGATTTCGGTGG

TAATGGAGGCGGTTTCTTTGAAGGGCTTTTTGGAGGACTTGGAGAAGCTTTCGGAATGCGTGGAGGCTCAGAAAGTT

CTCGACAAGGAGCTAGTAAGAAGGTGCATATTACGCTGTCCTTCGAGGAGGCGGCAAAAGGTGTTGAAAAAGAACTT

CTTGTTTCAGGCTATAAATCTTGTGATGCTTGTTCTGGTAGTGGAGCCAATACTGCTAAAGGTGTAAAAGTTTGTGA

TCGATGCAAGGGCTCTGGTCAGGTAGTGCAAAGCCGAGGCTTTTTCTCCATGGCTTCTACTTGCCCTGATTGTAGTG

GTGAAGGTCGGGTTATCACAGATCCTTGTTCAGTTTGTCGTGGGCAGGGACGTATCAAGGATAAACGTAGCGTCCAT

GTTAATATCCCAGCTGGAGTCGATTCTGGGATGAGATTAAAGATGGAAGGCTATGGAGATGCTGGCCAAAATGGAGC

GCCTGCAGGGGATCTGTATGTTTTTATTGATGTAGAGCCTCATCCTGTTTTCGAGCGCCATGGGGATGATTTAGTTT

TAGAGCTTCCTATTGGATTTGTTGATGCGGCTTTAGGGATCAAGAAGGAAATCCCTACACTCTTAAAAGAAGGTACT

TGCCGTTTGAGTATCCCAGAAGGGATTCAGAGCGGAACAGTTCTTAAAGTTAGAGGGCAGGGATTCCCTAATGTGCA

TGGGAAATCCAGAGGAGATCTTTTAGTAAGAGTATCTGTGGAGACTCCCCAGCACCTATCTAATGAACAAAAAGATT

TATTGAGACAGTTTGCTGCTACGGAGAAGGCTGAAAATTTCCCTAAGAAACGGAGTTTCTTAGACAAAATCAAAGGT

TTTTTTTCTGACTTTGCTGTATAG

SEQ ID NO: 42 - CT341 protein sequence
MDYYTILGVAKTATPEEIKKAYRKLAVKYHPDKNPGDAEAERRFKEVSEAYEVLGDAQKRESYDRYGKDGPFAGAGG

FGGAGMGNMEDALRTFMGAFGGDFGGNGGGFFEGLFGGLGEAFGMRGGSESSRQGASKKVHITLSFEEAAKGVEKEL

LVSGYKSCDACSGSGANTAKGVKVCDRCKGSGQVVQSRGFFSMASTCPDCSGEGRVITDPCSVCRGQGRIKDKRSVH

VNIPAGVDSGMRLKMEGYGDAGQNGAPAGDLYVFIDVEPHPVFERHGDDLVLELPIGFVDAALGIKKEIPTLLKEGT

CRLSIPEGIQSGTVLKVRGQGFPNVHGKSRGDLLVRVSVETPQHLSNEQKDLLRQFAATEKAENFPKKRSFLDKIKG

FFSDFAV

SEQ ID NO: 43 - CT716 nucleotide sequence
ATGAATAAAAAACTCCAAGATCTGTCTAAACTGCTCACTATTGAGCTTTTCAAGAAACGTACACGGTTGGAAACAGT

AAAAAAAGCGCTCTCCACAATAGAACATCGCTTACAACAAATACAGGAGCACATCGCGAAAATTTCCTTAACAAGGC

ACAAACAATTCCTATGTCGGTCATATACCCATGAATATGACCAACATTTAGAACATTTACAAAGAGAGCAAACTTCT

-continued

SEQUENCE LISTING

CTATATAAACAGCATCAGACCCTGAAAACGTCTTTGAAAGATGCTTATGGCGACATACAAAAACAACTAGACCAAAG

AAAAATTATCGAAAAGATCCATGACAGTAAATATCCTATAAAGAGCGCGAATAACTAA

SEQ ID NO: 44 - CT716 protein sequence
MNKKLQDLSKLLTIELFKKRTRLETVKKALSTIEHRLQQIQEHIAKISLTRHKQFLCRSYTHEYDQHLEHLQREQTS

LYKQHQTLKTSLKDAYGDIQKQLDQRKIIEKIHDSKYPIKSANN

SEQ ID NO: 45 - CT745 nucleotide sequence
ATGAAACATGCTCTCATTGTTGGCTCAGGTATTGCCGGCCTTTCTGCCGCGTGGTGGCTACACAAACGATTCCCTCA

TGTGCAGCTGTCTATTCTAGAAAAAGAGTCTCGATCTGGAGGGCTAATTGTCACAGAGAAACAACAAGGGTTTTCCC

TCAATATGGGCCCTAAAGGTTTTGTTTTAGCTCATGATGGGCAACACACCCTTCACCTCATTCAGTCTTTAGGCCTA

GCAGACGAGCTATTATATAGCTCTCCAGAGGCTAAAAACCGCTTTATCCACTATAATAATAAAACCCGAAAAGTCTC

GCCTTGGACTATTTTCAAACAAAATCTCCCTCTCTCTTTTGCTAAGGATTTCTTTGCGCGTCCTTACAAACAAGACA

GCTCCGTGGAAGCCTTCTTTAAAAGACACAGTTCTTCCAAGCTTAGAAGAAATCTTTTAAATCCCATTAGCATTGCT

ATTCGTGCAGGACATAGTCATATATTGTCTGCACAGATGGCTTACCCAGAATTAACACGAAGAGAAGCTCAAACAGG

ATCGTTGTTACGTAGTTATCTCAAAGATTTTCCTAAAGAGAAACGCACAGGCCCTTATTTAGCTACCTTGCGGTCTG

GGATGGGAATGCTAACCCAGGCTTTGCATGATAAATTGCCTGCTACCTGGTATTTTTCTGCACCCGTCAGCAAAATC

CGTCAGTTGGCGAATGGGAAAATTTCTCTTTCATCTCCTCAAGGAGAAATAACGGGAGATATGCTCATTTATGCTGG

GTCCGTGCACGATCTCCCTTCCTGTCTAGAAGGGATCCCTGAAACCAAGCTTATCAAGCAAACGACTTCATCTTGGG

ATCTCTCTTGTGTATCTTTAGGATGGCATGCATCCTTCCCTATCCCTCATGGATATGGCATGCTTTTCGCTGATACG

CCTCCCTTATTAGGGATCGTGTTTAATACGGAAGTGTTCCCTCAACCCGAGCGGCCTAATACAATAGTCTCTCTTCT

TTTAGAAGGTCGATGGCACCAAGAAGAAGCGTATGCTTTCTCACTAGCAGCTATTTCTGAGTACCTGCAAATTTACA

CTCCTCCCCAAGCTTTCTCACTATTCTCTCCTCGAGAGGGACTTCCCCAACACCATGTTGGATTTATCCAATCCCGC

CAACGCCTTCTATCTAAACTTCCTCACAATATAAAAATTGTAGGGCAGAATTTTGCAGGTCCAGGTCTCAACCGCGC

TACAGCGTCTGCTTATAAAGCTATAGCTTCTTTACTATCATGA

SEQ ID NO: 46 - CT745 protein sequence
MKHALIVGSGIAGLSAAWWLHKRFPHVQLSILEKESRSGGLIVTEKQQGFSLNMGPKGFVLAHDGQHTLHLIQSLGL

ADELLYSSPEAKNRFIHYNNKTRKVSPWTIFKQNLPLSFAKDFFARPYKQDSSVEAFFKRHSSSKLRRNLLNPISIA

IRAGHSHILSAQMAYPELTRREAQTGSLLRSYLKDFPKEKRTGPYLATLRSGMGMLTQALHDKLPATWYFSAPVSKI

RQLANGKISLSSPQGEITGDMLIYAGSVHDLPSCLEGIPETKLIKQTTSSWDLSCVSLGWHASFPIPHGYGMLFADT

PPLLGIVFNTEVFPQPERPNTIVSLLLEGRWHQEEAYAFSLAAISEYLQIYTPPQAFSLFSPREGLPQHHVGFIQSR

QRLLSKLPHNIKIVGQNFAGPGLNRATASAYKAIASLLS

SEQ ID NO: 47 - CT387 nucleotide sequence
ATGACGCTCTTTCATTCTCATCATGATGCCGTCTCTCCAGACAGCTACCTATGTTCTTCCCTTCAGTTAGTTGGTAC

TGGCGTATACGAAGGAGAAATCGAGATTCAAAATATCCCCTCTTATTTCCTTGGATTCCAATTACCCTCTCATTGCA

TACACCTTAATTTAAAGAGCTCTCTAGCTCAATTAGGAATAGATGCCTCCCTTCTTCACTGCGAATTGAGCAAAAAT

CAACATCGAGCACATATACATGCTCAATTTACCGGTCATGGCCCCATTGCTGAATCTATGCTAGCCCTTCTCCAACC

AGGAGATCGTGTAGCAAAACTATTTGCTGCAGACGATCGCAGACTGGTCCGATCTCCAGATTACCTCGAAAGCATGC

TGAAAAATACAGATAAAGCTGGCCATCCTTTGCTCTGTTTTGGGAAAAAAATTAGAACACTTGATTTCTTTTGATGTG

GTAGATGATCGCCTTGTCGTCTCCCTTCCTACCCTGCCGGGAGTTGTTCGTTATGATTCGGATATTTATGGACTCCT

TCCTCTTATTCAAAAATCACTCAGTAATCCCAAACTCAGCATTCGTCACTTTTTAGCTCTGTACCAACAGATTGTGG

AAGGGCAACATGTCTCTTGCGGAAACCATATTCTTCTGATCAAAACAGAACCGCTGCACATCCGCACTGTATTTGCT

CGCGTGGTAAATCAACTCCTCCCTCAAGGTCTCTCCCACACTTCTGCCAATATTTTGGAACCAACCACTCGAGAATC

-continued

SEQUENCE LISTING

CGGGGATATCTTTGAATTTTTTGGGAACCCTTCTGCACAGATAGAAAGAATTCCTTTAGAATTTTTCACTATCGAAC

CCTATAAAGAACATTCTTACTTCTGTAATCGGGATTTATTACAAACCATCTTACAATCAGAAAGCGAAATCAAAAAA

ATATTCGAAACAGCGCCCAAAGAACCTGTCAAAGCTGCCACCTATTTATCAAAAGGCAGTGAAATCTCTTCCCTGCA

CACAGACTCTTGGCTCACAGGATCCGCAGCTGCCTATCAATATAGTGAGCAAGCAGATAAAAACGAGTACACTCATG

CTCAACCTTGCTATCCTTTCTTAGAAGCAATGGAAATGGGCCTGATCAATAGCGAAGGAGCCTTACTCACTCGTTAT

TTCCCTTCAGCTAGCTTAAAAGGAATGTTGATTTCCTACCATGTGCGCCACTATCTCAAACAAATCTACTTTCAAGT

TCCCTCTTATACACATGGAAACTATTTCTCTCATAATGACAGAGGTTTGCTATTAGATCTGCAGCAAGCAGATATTG

ATGTTTTCTGGGCAGATGAAGAAAGCGGCCGTGTGTTGCAATATACAAAACGACGCGATAAGAATAGCGGTATGTTC

GTGATCAAAAATCGTGTTGAAGAGTTTCGATCAGCTTATTTTATTGCTATTTATGGCTCTCGTCTCCTTGAGAATAA

TTTCTCTGCTCAGCTCCATACCCTCCTAGCGGGCTTACAGCAAGCAGCACATACTCTCGGCATTCCTGGATTCTCAA

AGCCTACCCCACTTGCAGTCATCACCGGAGGCGGCACTGGAGTTATGGCCACAGGAAATCGTGTAGCTAAAGAACTA

GGAATCCTATCTTGTGGAACCGTTCTTGATTTAGAAGCTTCTCCAGCACAAATCGACCAACCTACCAATGAATTCTT

AGATGCTAAAATGACATACCGCCTACCTCAACTTATAGAAAGGCAAGAACACTTTTATGCAGACCTTCCTATCCTTG

TAGTTGGCGGTGTAGGAACCGATTTCGAACTCTACCTAGAACTTGTCTATCTCAAAACAGGAGCTAAACCACCGACT

CCCATTTTCCTAATTGGACCTATTGAATACTGGAAAGAAAAAGTGGCCCACGCCTACGAGATCAACCTCAAAGCAGG

AACCATCCGTGGATCCGAATGGATCAGCAACTGCCTATATTGTATCACTTCTCCGGAAGCTGGAATTGCCGTATTCG

AACAATTCCTAGCTGGAGAACTCCCTATAGGATACGACTATCCTCCAGCTCCAGATGGATTAGTGATCGTCTAA

SEQ ID NO: 48 - CT387 protein sequence
MTLFHSHHDAVSPDSYLCSSLQLVGTGVYEGEIEIQNIPSYFLGFQLPSHCIHLNLKSSLAQLGIDASLLHCELSKN

QHRAHIHAQFTGHGPIAESMLALLQPGDRVAKLFAADDRRLVRSPDYLESMLKNTDKAGHPLLCFGKKLEHLISFDV

VDDRLVVSLPTLPGVVRYDSDIYGLLPLIQKSLSNPKLSIRHFLALYQQIVEGQHVSCGNHILLIKTEPLHIRTVFA

RVVNQLLPQGLSHTSANILEPTTRESGDIFEFFGNPSAQIERIPLEFFTIEPYKEHSYFCNRDLLQTILQSESEIKK

IFETAPKEPVKAATYLSKGSEISSLHTDSWLIGSAAAYQYSEQADKNEYTHAQPCYPFLEAMEMGLINSEGALLTRY

FPSASLKGMLISYHVRHYLKQIYFQVPSYTHGNYFSHNDRGLLLDLQQADIDVFWADEESGRVLQYTKRRDKNSGMF

VIKNRVEEFRSAYFIAIYGSRLLENNFSAQLHTLLAGLQQAAHTLGIPGFSKPTPLAVITGGGTGVMATGNRVAKEL

GILSCGTVLDLEASPAQIDQPTNEFLDAKMTYRLPQLIERQEHFYADLPILVVGGVGTDFELYLELVYLKTGAKPPT

PIFLIGPIEYWKEKVAHAYEINLKAGTIRGSEWISNCLYCITSPEAGIAVFEQFLAGELPIGYDYPPAPDGLVIV

SEQ ID NO: 49 - CT812 nucleotide sequence
ATGAGTTCCGAGAAAGATATAAAAAGCACCTGTTCTAAGTTTTCTTTGTCTGTAGTAGCAGCTATCCTTGCCTCTGT

TAGCGGGTTAGCTAGTTGCGTAGATCTTCATGCTGGAGGACAGTCTGTAAATGAGCTGGTATATGTAGGCCCTCAAG

CGGTTTTATTGTTAGACCAAATTCGAGATCTATTCGTTGGGTCTAAAGATAGTCAGGCTGAAGGACAGTATAGGTTA

ATTGTAGGAGATCCAAGTTCTTTCCAAGAGAAAGATGCGGATACTCTTCCCGGGAAGGTAGAGCAAAGTACTTTGTT

CTCAGTAACCAATCCCGTGGTTTTCCAAGGTGTGGACCAACAGGATCAAGTCTCTTCCCAAGGGTTAATTTGTAGTT

TTACGAGCAGCAACCTTGATTCTCCTCGTGACGGAGAATCTTTTTTAGGTATTGCTTTTGTTGGGGATAGTAGTAAG

GCTGGAATCACATTAACTGACGTGAAAGCTTCTTTGTCTGGAGCGGCTTTATATTCTACAGAAGATCTTATCTTTGA

AAAGATTAAGGGTGGATTGGAATTTGCATCATGTTCTTCTCTAGAACAGGGGGGAGCTTGTGCAGCTCAAAGTATTT

TGATTCATGATTGTCAAGGATTGCAGGTTAAACACTGTACTACAGCCGTGAATGCTGAGGGGTCTAGTGCGAATGAT

CATCTTGGATTTGGAGGAGGCGCTTTCTTTGTTACGGGTTCTCTTTCTGGAGAGAAAAGTCTCTATATGCCTGCAGG

AGATATGGTAGTTGCGAATTGTGATGGGGCTATATCTTTTGAAGGAAACAGCGCGAACTTTGCTAATGGAGGAGCGA

TTGCTGCCTCTGGGAAAGTGCTTTTTGTCGCTAATGATAAAAAGACTTCTTTTATAGAGAACCGAGCTTTGTCTGGA

-continued

SEQUENCE LISTING

GGAGCGATTGCAGCCTCTTCTGATATTGCCTTTCAAAACTGCGCAGAACTAGTTTTCAAAGGCAATTGTGCAATTGG

AACAGAGGATAAAGGTTCTTTAGGTGGAGGGGCTATATCTTCTCTAGGCACCGTTCTTTTGCAAGGGAATCACGGGA

TAACTTGTGATAAGAATGAGTCTGCTTCGCAAGGAGGCGCCATTTTTGGCAAAAATTGTCAGATTTCTGACAACGAG

GGGCCAGTGGTTTTCAGAGATAGTACAGCTTGCTTAGGAGGAGGCGCTATTGCAGCTCAAGAAATTGTTTCTATTCA

GAACAATCAGGCTGGGATTTCCTTCGAGGGAGGTAAGGCTAGTTTCGGAGGAGGTATTGCGTGTGGATCTTTTTCTT

CCGCAGGTGGTGCTTCTGTTTTAGGGACCATTGATATTTCGAAGAATTTAGGCGCGATTTCGTTCTCTCGTACTTTA

TGTACGACCTCAGATTTAGGACAAATGGAGTACCAGGGAGGAGGAGCTCTATTTGGTGAAAATATTTCTCTTTCTGA

GAATGCTGGTGTGCTCACCTTTAAAGACAACATTGTGAAGACTTTTGCTTCGAATGGGAAAATTCTGGGAGGAGGAG

CGATTTTAGCTACTGGTAAGGTGGAAATTACTAATAATTCCGAAGGAATTTCTTTTACAGGAAATGCGAGAGCTCCA

CAAGCTCTTCCAACTCAAGAGGAGTTTCCTTTATTCAGCAAAAAAGAAGGGCGACCACTCTCTTCAGGATATTCTGG

GGGAGGAGCGATTTTAGGAAGAGAAGTAGCTATTCTCCACAACGCTGCAGTAGTATTTGAGCAAAATCGTTTGCAGT

GCAGCGAAGAAGAAGCGACATTATTAGGTTGTTGTGGAGGAGGCGCTGTTCATGGGATGGATAGCACTTCGATTGTT

GGCAACTCTTCAGTAAGATTTGGTAATAATTACGCAATGGGACAAGGAGTCTCAGGAGGAGCTCTTTTATCTAAAAC

AGTGCAGTTAGCTGGGAATGGAAGCGTCGATTTTTCTCGAAATATTGCTAGTTTGGGAGGAGGAGCTCTTCAAGCTT

CTGAAGGAAATTGTGAGCTAGTTGATAACGGCTATGTGCTATTCAGAGATAATCGAGGGAGGGTTTATGGGGGTGCT

ATTTCTTGCTTACGTGGAGATGTAGTCATTTCTGGAAACAAGGGTAGAGTTGAATTTAAAGACAACATAGCAACACG

TCTTTATGTGGAAGAAACTGTAGAAAAGGTTGAAGAGGTAGAGCCAGCTCCTGAGCAAAAAGACAATAATGAGCTTT

CTTTCTTAGGGAGAGCAGAACAGAGTTTTATTACTGCAGCTAATCAAGCTCTTTTCGCATCTGAAGATGGGGATTTA

TCACCTGAGTCATCCATTTCTTCTGAAGAACTTGCGAAAAGAAGAGAGTGTGCTGGAGGAGCTATTTTTGCAAAACG

GGTTCGTATTGTAGATAACCAAGAGGCCGTTGTATTCTCGAATAACTTCTCTGATATTTATGGCGGCGCCATTTTTA

CAGGTTCTCTTCGAGAAGAGGATAAGTTAGATGGGCAAATCCCTGAAGTCTTGATCTCAGGCAATGCAGGGGATGTT

GTTTTTTCCGGAAATTCCTCGAAGCGTGATGAGCATCTTCCTCATACAGGTGGGGGAGCCATTTGTACTCAAAATTT

GACGATTTCTCAGAATACAGGGAATGTTCTGTTTTATAACAACGTGGCCTGTTCGGGAGGAGCTGTTCGTATAGAGG

ATCATGGTAATGTTCTTTTAGAAGCTTTTGGAGGAGATATTGTTTTTAAAGGAAATTCTTCTTTCAGAGCACAAGGA

TCCGATGCTATCTATTTTGCAGGTAAAGAATCGCATATTACAGCCCTGAATGCTACGGAAGGACATGCTATTGTTTT

CCACGACGCATTAGTTTTTGAAAATCTAGAAGAAAGGAAATCTGCTGAAGTATTGTTAATCAATAGTCGAGAAAATC

CAGGTTACACTGGATCTATTCGATTTTTAGAAGCAGAAAGTAAAGTTCCTCAATGTATTCATGTACAACAAGGAAGC

CTTGAGTTGCTAAATGGAGCCACATTATGTAGTTATGGTTTTAAACAAGATGCTGGAGCTAAGTTGGTATTGGCTGC

TGGAGCTAAACTGAAGATTTTAGATTCAGGAACTCCTGTACAACAAGGGCATGCTATCAGTAAACCTGAAGCAGAAA

TCGAGTCATCTTCTGAACCAGAGGGTGCACATTCTCTTTGGATTGCGAAGAATGCTCAAACAACAGTTCCTATGGTT

GATATCCATACTATTTCTGTAGATTTAGCCTCCTTCTCTTCTAGTCAACAGGAGGGGACAGTAGAAGCTCCTCAGGT

TATTGTTCCTGGAGGAAGTTATGTTCGATCTGGAGAGCTTAATTTGGAGTTAGTTAACACAACAGGTACTGGTTATG

AAAATCATGCTTTATTGAAGAATGAGGCTAAAGTTCCATTGATGTCTTTCGTTGCTTCTGGTGATGAAGCTTCAGCC

GAAATCAGTAACTTGTCGGTTTCTGATTTACAGATTCATGTAGTAACTCCAGAGATTGAAGAAGACACATACGGCCA

TATGGGAGATTGGTCTGAGGCTAAAATTCAAGATGGAACTCTTGTCATTAGTTGGAATCCTACTGGATATCGATTAG

ATCCTCAAAAAGCAGGGGCTTTAGTATTTAATGCATTATGGGAAGAAGGGGCTGTCTTGTCTGCTCTGAAAAATGCA

CGCTTTGCTCATAATCTCACTGCTCAGCGTATGGAATTCGATTATTCTACAAATGTGTGGGGATTCGCCTTTGGTGG

TTTCCGAACTCTATCTGCAGAGAATCTGGTTGCTATTGATGGATACAAAGGAGCTTATGGTGGTGCTTCTGCTGGAG

TCGATATTCAATTGATGGAAGATTTTGTTCTAGGAGTTAGTGGAGCTGCTTTCCTAGGTAAAATGGATAGTCAGAAG

-continued

SEQUENCE LISTING

TTTGATGCGGAGGTTTCTCGGAAGGGAGTTGTTGGTTCTGTATATACAGGATTTTTAGCTGGATCCTGGTTCTTCAA

AGGACAATATAGCCTTGGAGAAACACAGAACGATATGAAAACGCGTTATGGAGTACTAGGAGAGTCGAGTGCTTCTT

GGACATCTCGAGGAGTACTGGCAGATGCTTTAGTTGAATACCGAAGTTTAGTTGGTCCTGTGAGACCTACTTTTTAT

GCTTTGCATTTCAATCCTTATGTCGAAGTATCTTATGCTTCTATGAAATTCCCTGGCTTTACAGAACAAGGAAGAGA

AGCGCGTTCTTTTGAAGACGCTTCCCTTACCAATATCACCATTCCTTTAGGGATGAAGTTTGAATTGGCGTTCATAA

AAGGACAGTTTTCAGAGGTGAACTCTTTGGGAATAAGTTATGCATGGGAAGCTTATCGAAAAGTAGAAGGAGGCGCG

GTGCAGCTTTTAGAAGCTGGGTTTGATTGGGAGGGAGCTCCAATGGATCTTCCTAGACAGGAGCTGCGTGTCGCTCT

GGAAAATAATACGGAATGGAGTTCTTACTTCAGCACAGTCTTAGGATTAACAGCTTTTTGTGGAGGATTTACTTCTA

CAGATAGTAAACTAGGATATGAGGCGAATACTGGATTGCGATTGATCTTTTAA

SEQ ID NO: 50 - CT812 protein sequence
MSSEKDIKSTCSKFSLSVVAAILASVSGLASCVDLHAGGQSVNELVYVGPQAVLLLDQIRDLFVGSKDSQAEGQYRL

IVGDPSSFQEKDADTLPGKVEQSTLFSVTNPVVFQGVDQQDQVSSQGLICSFTSSNLDSPRDGESFLGIAFVGDSSK

AGITLTDVKASLSGAALYSTEDLIFEKIKGGLEFASCSSLEQGGACAAQSILIHDCQGLQVKHCTTAVNAEGSSAND

HLGFGGGAFFVTGSLSGEKSLYMPAGDMVVANCDGAISFEGNSANFANGGAIAASGKVLFVANDKKTSFIENRALSG

GAIAASSDIAFQNCAELVFKGNCAIGTEDKGSLGGGAISSLGTVLLQGNHGITCDKNESASQGGAIFGKNCQISDNE

GPVVFRDSTACLGGGAIAAQEIVSIQNNQAGISFEGGKASFGGGIACGSFSSAGGASVLGTIDISKNLGAISFSRTL

CTTSDLGQMEYQGGGALFGENISLSENAGVLTFKDNIVKTFASNGKILGGGAILATGKVEITNNSEGISFTGNARAP

QALPTQEEFPLFSKKEGRPLSSGYSGGGAILGREVAILHNAAVVFEQNRLQCSEEEATLLGCCGGGAVHGMDSTSIV

GNSSVRFGNNYAMGQGVSGGALLSKTVQLAGNGSVDFSRNIASLGGGALQASEGNCELVDNGYVLFRDNRGRVYGGA

ISCLRGDVVISGNKGRVEFKDNIATRLYVEETVEKVEEVEPAPEQKDNNELSFLGRAEQSFITAANQALFASEDGDL

SPESSISSEELAKRRECAGGAIFAKRVRIVDNQEAVVFSNNFSDIYGGAIFTGSLREEDKLDGQIPEVLISGNAGDV

VFSGNSSKRDEHLPHTGGGAICTQNLTISQNTGNVLFYNNVACSGGAVRIEDHGNVLLEAFGGDIVFKGNSSFRAQG

SDAIYFAGKESHITALNATEGHAIVFHDALVFENLEERKSAEVLLINSRENPGYTGSIRFLEAESKVPQCIHVQQGS

LELLNGATLCSYGFKQDAGAKLVLAAGAKLKILDSGTPVQQGHAISKPEAEIESSSEPEGAHSLWIAKNAQTTVPMV

DIHTISVDLASFSSSQQEGTVEAPQVIVPGGSYVRSGELNLELVNTTGTGYENHALLKNEAKVPLMSFVASGDEASA

EISNLSVSDLQIHVVTPEIEEDTYGHMGDWSEAKIQDGTLVISWNPTGYRLDPQKAGALVFNALWEEGAVLSALKNA

RFAHNLTAQRMEFDYSTNVWGFAFGGFRTLSAENLVAIDGYKGAYGGASAGVDIQLMEDFVLGVSGAAFLGKMDSQK

FDAEVSRKGVVGSVYTGFLAGSWFFKGQYSLGETQNDMKTRYGVLGESSASWTSRGVLADALVEYRSLVGPVRPTFY

ALHFNPYVEVSYASMKFPGFTEQGREARSFEDASLTNITIPLGMKFELAFIKGQFSEVNSLGISYAWEAYRKVEGGA

VQLLEAGFDWEGAPMDLPRQELRVALENNTEWSSYFSTVLGLTAFCGGFTSTDSKLGYEANTGLRLIF

SEQ ID NO: 51 - CT869 nucleotide sequence
ATGAAAAAAGCGTTTTTCTTTTTCCTTATCGGAAACTCCCTATCAGGACTAGCTAGAGAGGTTCCTTCTAGAATCTT

TCTTATGCCCAACTCAGTTCCAGATCCTACGAAAGAGTCGCTATCAAATAAAATTAGTTTGACAGGAGACACTCACA

ATCTCACTAACTGCTATCTCGATAACCTACGCTACATACTGGCTATTCTACAAAAAACTCCCAATGAAGGAGCTGCT

GTCACAATAACAGATTACCTAAGCTTTTTTGATACACAAAAAGAAGGTATTTATTTTGCAAAAAATCTCACCCCTGA

AAGTGGTGGTGCGATTGGTTATGCGAGTCCCAATTCTCCTACCGTGGAGATTCGTGATACAATAGGTCCTGTAATCT

TTGAAAATAATACTTGTTGCAGACTATTTACATGGAGAAATCCTTATGCTGCTGATAAAATAAGAGAAGGCGGAGCC

ATTCATGCTCAAAATCTTTACATAAATCATAATCATGATGTGGTCGGATTTATGAAGAACTTTTCTTATGTCCAAGG

AGGAGCCATTAGTACCGCTAATACCTTTGTTGTGAGCGAGAATCAGTCTTGTTTTCTCTTTATGGACAACATCTGTA

TTCAAACTAATACAGCAGGAAAAGGTGGCGCTATCTATGCTGGAACGAGCAATTCTTTTGAGAGTAATAACTGCGAT

-continued

SEQUENCE LISTING

CTCTTCTTCATCAATAACGCCTGTTGTGCAGGAGGAGCGATCTTCTCCCCTATCTGTTCTCTAACAGGAAATCGTGG

TAACATCGTTTTCTATAACAATCGCTGCTTTAAAAATGTAGAAACAGCTTCTTCAGAAGCTTCTGATGGAGGAGCAA

TTAAAGTAACTACTCGCCTAGATGTTACAGGCAATCGTGGTAGGATCTTTTTTAGTGACAATATCACAAAAAATTAT

GGCGGAGCTATTTACGCTCCTGTAGTTACCCTAGTGGATAATGGCCCTACCTACTTTATAAACAATATCGCCAATAA

TAAGGGGGGCGCTATCTATATAGACGGAACCAGTAACTCCAAAATTTCTGCCGACCGCCATGCTATTATTTTTAATG

AAAATATTGTGACTAATGTAACTAATGCAAATGGTACCAGTACGTCAGCTAATCCTCCTAGAAGAAATGCAATAACA

GTAGCAAGCTCCTCTGGTGAAATTCTATTAGGAGCAGGGAGTAGCCAAAATTTAATTTTTTATGATCCTATTGAAGT

TAGCAATGCAGGGGTCTCTGTGTCCTTCAATAAGGAAGCTGATCAAACAGGCTCTGTAGTATTTTCAGGAGCTACTG

TTAATTCTGCAGATTTTCATCAACGCAATTTACAAACAAAAACACCTGCACCCCTTACTCTCAGTAATGGTTTTCTA

TGTATCGAAGATCATGCTCAGCTTACAGTGAATCGATTCACACAAACTGGGGGTGTTGTTTCTCTTGGGAATGGAGC

AGTTCTGAGTTGCTATAAAAATGGTACAGGAGATTCTGCTAGCAATGCCTCTATAACACTGAAGCATATTGGATTGA

ATCTTTCTTCCATTCTGAAAAGTGGTGCTGAGATTCCTTTATTGTGGGTAGAGCCTACAAATAACAGCAATAACTAT

ACAGCAGATACTGCAGCTACCTTTTCATTAAGTGATGTAAAACTCTCACTCATTGATGACTACGGGAACTCTCCTTA

TGAATCCACAGATCTGACCCATGCTCTGTCATCACAGCCTATGCTATCTATTTCTGAAGCTAGCGATAACCAGCTAC

AATCAGAAAATATAGATTTTTCGGGACTAAATGTCCCTCATTATGGATGGCAAGGACTTTGGACTTGGGGCTGGGCA

AAAACTCAAGATCCAGAACCAGCATCTTCAGCAACAATCACTGATCCACAAAAAGCCAATAGATTTCATAGAACCTT

ACTACTAACATGGCTTCCTGCCGGGTATGTTCCTAGCCCAAAACACAGAAGTCCCCTCATAGCTAACACCTTATGGG

GGAATATGCTGCTTGCAACAGAAAGCTTAAAAAATAGTGCAGAGCTGACACCTAGTGGTCATCCTTTCTGGGGAATT

ACAGGAGGAGGACTAGGCATGATGGTTTACCAAGATCCTCGAGAAAATCATCCTGGATTCCATATGCGCTCTTCCGG

ATACTCTGCGGGGATGATAGCAGGGCAGACACACACCTTCTCATTGAAATTCAGTCAGACCTACACCAAACTCAATG

AGCGTTACGCAAAAAACAACGTATCTTCTAAAAATTACTCATGCCAAGGAGAAATGCTCTTCTCATTGCAAGAAGGT

TTCTTGCTGACTAAATTAGTTGGGCTTTACAGCTATGGAGACCATAACTGTCACCATTTCTATACTCAAGGAGAAAA

TCTAACATCTCAAGGGACGTTCCGCAGTCAAACGATGGGAGGTGCTGTCTTTTTTGATCTCCCTATGAAACCCTTTG

GATCAACGCATATACTGACAGCTCCCTTTTTAGGTGCTCTTGGTATTTATTCTAGCCTGTCTCACTTTACTGAGGTG

GGAGCCTATCCGCGAAGCTTTTCTACAAAGACTCCTTTGATCAATGTCCTAGTCCCTATTGGAGTTAAAGGTAGCTT

TATGAATGCTACCCACAGACCTCAAGCCTGGACTGTAGAATTGGCATACCAACCCGTTCTGTATAGACAAGAACCAG

GGATCGCAGCCCAGCTCCTAGCCAGTAAGGGTATTTGGTTCGGTAGTGGAAGCCCCTCATCGCGTCATGCCATGTCC

TATAAAATCTCACAGCAAACACAACCTTTGAGTTGGTTAACTCTCCATTTCCAGTATCATGGATTCTACTCCTCTTC

AACCTTCTGTAATTATCTCAATGGGGAAATTGCTCTGCGATTCTAG

SEQ ID NO: 52 - CT869 protein sequence
MKKAFFFFLIGNSLSGLAREVPSRIFLMPNSVPDPTKESLSNKISLTGDTHNLTNCYLDNLRYILAILQKTPNEGAA

VTITDYLSFFDTQKEGIYFAKNLTPESGGAIGYASPNSPTVEIRDTIGPVIFENNTCCRLFTWRNPYAADKIREGGA

IHAQNLYINHNHDVVGFMKNFSYVQGGAISTANTFVVSENQSCFLFMDNICIQTNTAGKGGAIYAGTSNSFESNNCD

LFFINNACCAGGAIFSPICSLTGNRGNIVFYNNRCFKNVETASSEASDGGAIKVTTRLDVTGNRGRIFFSDNITKNY

GGAIYAPVVTLVDNGPTYFINNIANNKGGAIYIDGTSNSKISADRHAIIFNENIVTNVTNANGTSTSANPPRRNAIT

VASSSGEILLGAGSSQNLIFYDPIEVSNAGVSVSFNKEADQTGSVVFSGATVNSADFHQRNLQTKTPAPLTLSNGFL

CIEDHAQLTVNRFTQTGGVVSLGNGAVLSCYKNGTGDSASNASITLKHIGLNLSSILKSGAEIPLLWVEPTNNSNNY

TADTAATFSLSDVKLSLIDDYGNSPYESTDLTHALSSQPMLSISEASDNQLQSENIDFSGLNVPHYGWQGLWTWGWA

KTQDPEPASSATITDPQKANRFHRTLLLTWLPAGYVPSPKHRSPLIANTLWGNMLLATESLKNSAELTPSGHPFWGI

-continued

SEQUENCE LISTING

TGGGLGMMVYQDPRENHPGFHMRSSGYSAGMIAGQTHTFSLKFSQTYTKLNERYAKNNVSSKNYSCQGEMLFSLQEG

FLLTKLVGLYSYGDHNCHHFYTQGENLTSQGTFRSQTMGGAVFFDLPMKPFGSTHILTAPFLGALGIYSSLSHFTEV

GAYPRSFSTKTPLINVLVPIGVKGSFMNATHRPQAWTVELAYQPVLYRQEPGIAAQLLASKGIWFGSGSPSSRHAMS

YKISQQTQPLSWLTLHFQYHGFYSSSTFCNYLNGEIALRF

SEQ ID NO: 53 - CT166 nucleotide sequence
GTGAACGTTCGTACGTACTCTGTTCAGAGGGGGGGGGTAAAAACGATTTCTGCTAGTGCAGTTCCTCCTACAGCAGC

TGTTTTATCGAGAAAAAAGCGTGCTATAGAAGAGAAGAAGGAGGAAGCTTCTTCTGGAAAGATAGAAAATCTTGATG

CTAGCAAATACGATCTTACTCCCAAGAACATAGAAGAAAAACTAGGAATTACTCCTGAACAGAAATCTACTGTTAAA

GACCTATTAAATAAACTGAAAAAGGTCATTAGTGCTTACAACTCTATGCCAGATAAAAATTCGGAAGCGGGACAGAA

TTCCTTGATTCAACAAGGAAAATACGTCGATGCCATTCAGAAGAAGCTTCCAGCATCATCGCAGGCTCAGCCTAAAC

AGGCAAAAGCTAAGGAACAGAAAGCCGAAGAAAAACCTAAGACGACTCCGATTGAAGGTGTTCTTGAAACCATCAAA

ACAGAATTTAAAGGCCATCGTGTACCTGTTGAGAAAATCATCCATGGAATATGGATCGCAGGAGCGCCTCCGGATGG

TATCGAAGATTATATGCGAGTCTTTTTAGATACTTATGAAGGTTTTGACTTCTACTTCTGGGTAGATGAGAATGCTT

ATGCAGCAGCTAAATTTTCTAGCATTTTGAAGAAGGTCGCTTTCGATGCGGCTATTCAAGATCTACGATCTGCCACA

GATGAGTCTACGAAGGCCTTTGTTAAAGACTACGATGAATTAAAACAGAAATATGAAAAGAAAGTTGCGGAGACGAC

TTCTCAAGCAGAAAAAGACCAATATCTCAAAGATCTAAAGGATCTTTTAGAGAAATTTACAAAAATCAGTGATGAGA

TTCGTGGAAAATTTGATCGGCTGTTTCTTAAGAATGTGATTGTTGCTCAGAACGGATTCTTTAATTTCTGCTTGCTG

AAAGGCCTCGGCAATATCAATGACGAAACGCGTGCAGAGTATTTAGAGAAAGAACTCAAACTTCCTACTGAGGAGAT

CGAACAGTATAAAAAGCTTAAAGAGACGAACAAAGAGAAGATAGCCGCTATTGTAAAACAACTAAACGAGAAACTTG

GATCGGATCGGGTAAAAATCAAAGACATTAAAGAGCTGCAATCTATGAAGCAAGCTCGAAATGTCTACAATTATGAA

CAGGAAATGTTTCTGCGCTGGAACTATGCAGCCGCAACAGATCAGATTCGTATGTATATGTTGGAGGAACTTGGAGG

TCTTTATACTGATCTGGATATGATGCCTTCATACTCTCAGGAAGTATTGGAGCTTATCAAAAAGCACAGTGATGGAA

ACCGAATGTTTGAGGATATGAGCTCTAGACGGGCGATTTCTGATGCGGTTTTAAAGATGGCTGTAGGTAAGGCGACA

ACAGTTTCCATGGAAGAGGTAGCAAAGGATATCGATGTTTCTCGCTTAACAGAAGAGGATAAGACAAAATTAAATGC

TCTATTTAAGGATCTAGAGCCATTTGCAAAACCGGATTCTAAAGGAGCTGAAGCAGAAGGGGGTGAAGGAGCAAAAG

GTATGAAAAAGAGCTTTTTCCAGCCCATAGATCTGAATATTGTCAGAAATACCATGCCTATCTTGAGACGCTATCAT

CACTATCCTGAGTTAGGATGGTTTATTCGAGGATTGAACGGATTGATGGTCTCTCATAAGGGAAGCACTGCGGTTTC

TGCTGTCATTGTAGGGCAACAGGCTGCCTACCAGGAACTAGCAGCACTTAGACAAGATGTCCTTTCAGGGGAGTTTT

TCCATTCTTTAGAAAATTTGACACATAGAAACCATAAGGAGCGTATTGGAAATCATCTCGTCGCTAATTATTTGGCT

AAAAGTCTCTTTTTTGATTACTGCCAAGATTCAGTGATGCCGGAGGCTGTAAGTACCTTAGGTATTAGATGA

SEQ ID NO: 54 - CT166 protein sequence
MNVRTYSVQRGGVKTISASAVPPTAAVLSRKKRAIEEKKEEASSGKIENLDASKYDLTPKNIEEKLGITPEQKSTVK

DLLNKLKKVISAYNSMPDKNSEAGQNSLIQQGKYVDAIQKKLPASSQAQPKQAKAKEQKAEEKPKTTPIEGVLETIK

TEFKGHRVPVEKIIHGIWIAGAPPDGIEDYMRVFLDTYEGFDFYFWVDENAYAAAKFSSILKKVAFDAAIQDLRSAT

DESTKAFVKDYDELKQKYEKKVAETTSQAEKDQYLKDLKDLLEKFTKISDEIRGKFDRLFLKNVIVAQNGFFNFCLL

KGLGNINDETRAEYLEKELKLPTEEIEQYKKLKETNKEKIAAIVKQLNEKLGSDRVKIKDIKELQSMKQARNVYNYE

QEMFLRWNYAAATDQIRMYMLEELGGLYTDLDMMPSYSQEVLELIKKHSDGNRMFEDMSSRRAISDAVLKMAVGKAT

TVSMEEVAKDIDVSRLTEEDKTKLNALFKDLEPFAKPDSKGAEAEGGEGAKGMKKSFFQPIDLNIVRNTMPILRRYH

HYPELGWFIRGLNGLMVSHKGSTAVSAVIVGQQAAYQELAALRQDVLSGEFFHSLENLTHRNHKERIGNHLVANYLA

KSLFFDYCQDSVMPEAVSTLGIR

-continued

SEQUENCE LISTING

SEQ ID NO: 55 - CT175 nucleotide sequence
ATGCATCACAGGAAGTTTTTAGCAGTTTCCATTGCTTTCGTAAGTTTAGCTTTTGGGCTAACATCTTGTTATCATAA

AAAAGAAGAACCAAAAGATGTTTTGCGGATTGCGATCTGTCATGATCCAATGTCTTTAGATCCGCGTCAGGTTTTTT

TAAGCAAAGATGTTTCTATTGTAAAAGCTCTCTATGAAGGGTTAGTCCGGGAAAAAGAAGCTGCGTTCCAGCTAGCT

TTGGCAGAAAGATATCATCAATCTGATGATGGTTGTGTTTATACTTTTTTTCTAAAAAATACATTCTGGAGCAACGG

AGATGTTGTAACAGCATATGATTTTGAAGAGTCTATTAAACAAATTTATTTCCGAGAAATTGATAACCCTTCGTTAC

GCTCTCTTGCATTAATTAAAAATTCTCATGCTGTTTTAACAGGAGCTCTCCCTGTTGAAGATTTAGGTGTTAGAGCT

TTGAATGCGAAAACTCTAGAAATTGTTTTAGAAAACCCGTTTCCTTATTTTCTAGAGATATTGGCGCACCCGGTTTT

TTATCCGGTGCACACCTCTTTACGAGAATATTACAAAGATAAGCGTAACAAACGCGTTTTCCCGATAATTTCTAATG

GTCCTTTTGCGATTCAATGTTATGAGCCGCAAAGATATTTACTAATCAACAAAAACCCTCTGTATCATGCCAAGCAC

GATGTTCTGTTAAATTCGGTATGTTTGCAGATAGTTCCTGATATCCATACAGCTATGCAGTTATTCCAAAAAAATCA

TATCGATTTAGTTGGGTTACCCTGGAGCTCCTCCTTTTCTTTAGAAGAACAAAGAAATCTCCCTAGAGAAAAATTAT

TTGATTATCCTGTATTGAGTTGCTCTGTTTTATTCTGTAACATTCATCAAACACCTTTAAATAATCCCTCGCTGAGA

ACAGCCCTCTCTTTAGCAATCAATCGAGAAACTTTATTAAAACTAGCAGGTAAAGGCTGTAGCGCTACGAGCTTTGT

TCACCCACAATTATCTCAGATACCTGCTACTACTTTGTCTCAAGATGAGCGGATTGCTTTAGCAAAAGGCTACTTGA

CCGAAGCTTTAAAGACTTTATCTCAAGAAGATTTAGAAAAAATTACATTAATTTATCCTATAGAATCTGTTTGCTTA

CGAGCCGTTGTTCAAGAAATTCGCCAACAATTATTTGATGTACTGGGATTTAAAATTTCTACATTAGGATTAGAATA

TCATTGTTTTTTAGACAAACGTTCCAGAGGAGAATTCTCCTTAGCAACTGGTAATTGGATTGCAGACTATCATCAAG

CTAGTGCTTTCCTGTCTGTCCTAGGTAATGGGACAAGATATAAAGACTTTCAATTGATTAACTGGCAGAACCAAAAG

TACACAAATATAGTTGCTCAACTTCTGATTCAAGAATCAAGCGACCTACAGCTTATGGCAGAGCAGTTGTTGCTTAA

AGAAAGTCCTCTTATTCCTCTATACCACCTCGATTATGTGTATGCGAAACAGCCTCGGGTGTCTGATCTCCAAACCT

CTTCTCGTGGAGAAATTGATTTAAAAAGAGTTTCATTAGCTGAAGGATAG

SEQ ID NO: 56 - CT175 protein sequence
MHHRKFLAVSIAFVSLAFGLTSCYHKKEEPKDVLRIAICHDPMSLDPRQVFLSKDVSIVKALYEGLVREKEAAFQLA

LAERYHQSDDGCVYTFFLKNTFWSNGDVVTAYDFEESIKQIYFREIDNPSLRSLALIKNSHAVLTGALPVEDLGVRA

LNAKTLEIVLENPFPYFLEILAHPVFYPVHTSLREYYKDKRNKRVFPIISNGPFAIQCYEPQRYLLINKNPLYHAKH

DVLLNSVCLQIVPDIHTAMQLFQKNHIDLVGLPWSSSFSLEEQRNLPREKLFDYPVLSCSVLFCNIHQTPLNNPSLR

TALSLAINRETLLKLAGKGCSATSFVHPQLSQIPATTLSQDERIALAKGYLTEALKTLSQEDLEKITLIYPIESVCL

RAVVQEIRQQLFDVLGFKISTLGLEYHCFLDKRSRGEFSLATGNWIADYHQASAFLSVLGNGTRYKDFQLINWQNQK

YTNIVAQLLIQESSDLQLMAEQLLLKESPLIPLYHLDYVYAKQPRVSDLQTSSRGEIDLKRVSLAEG

SEQ ID NO: 57 - TC0666 nucleotide sequence (homologue of CT387)
ATGAGGATTCCAATGACACTCTTTCACACTCATCACGATGCCGTCTCTCCGGACGGCTACTTATGTTCTTCCCTTCA

GTTAGTTGGCTCTGGCACATATGAAGGAGAAATCGAAATCCAAAATATTCCTTCTTATTTCCTTGGATTCCGATTAC

CCACCCATTGCGTTCATCTTAATTTGAAGAGTTCTCTAGCCCAGTTAGGAGTAGATGCATCTCTTCTTCACTGCGAA

CTAAGCAAAAATCAACAACGTGCACATATGCACGTGCAGTTCACCGGCTATGGCCCTATCGCTGAGTCCATGCTATC

TCTTCTCAAACCCGGAGATCGAGTAGCCAAACTGTTTGCTGCAGATGATCGTAGACTAGTCCGCTCCCCTGATTATC

TTGAAAGCATGCTAAAAAATACTGATAAGACAGGACATCCTCTGCTCCGATTTGGAAAAAAACTCGAGCATCTTATC

TCTTTTGATGTGGTGGACGATCGCCTCGTTGTATCACTCCCCACCTTGCCAGGCATAGTCAATTATGACCCAGACAT

CTATGGACTTCTTCCCTTAATTCAAAAATCACTAAGCAATCCTAAATTGAGTATTCGCCACTTCTTGTCTCTCTATC

AGAAGATCGTAGAAGGACCACACATCCCTTATGAAGGAAACATTTTGTTAATCAAAACAGAGCCTCTTCATATCCGC

ACAGTATTTGCTCGCGTGGTCGATCAAATGCTCCCTCAAGGTCTATTTCACACTTCTGCCAACATTTTAGAACCCAC

-continued

SEQUENCE LISTING

AACGCGAGAGTCTGGAGATATTTTTGAATTTTTTGGAAATCCCTCCACTCTTGTAGAAAGAATCCCTCTAGAATTCT

TCACTATCGAACCCTACAAAGAACACTCTTACTTCTGTAATCGAGATCTATTGCAAACTACCTTGCAATCGGAAAGT

GAAATCAAAAAAATATTCGATACAGCTCCTCAAGAGCCTGTAAAAGCCGCCACTTATTTATCAAAAGGAAGTGAAAT

TTCTTCTCTTGATGCAGATTCTTGGCTTACGGGATCCGCAGCTGCATACCAATGTAGCGAAAAACAGGCAGCTAAAG

ACGAATACATCCACGCTCAACCCTGTTATCCATTTTTGGAAGCAATGGAAACGGGACTCATCAATAGCGAAGGAGCT

TTACTCACTCGGTTTTTCCCCTCTTCCAGCTTAAAAGGGATGTTGATCTCCTATCATGTACGCCACTATCTTAAGCA

AATTTACTTTCAAGTTCCTTCTTATACATATGGAGACTACTTCTCTCATAATGACCGAGGATTACTGTTAGATCTAT

ATCAGGCGAACATTGATGTGTTCTGGGCTGATGAAGAGAGCGGCCGTGTATTGCAATATACAAAACGGCGCGACAAA

AATAGTGGAATGTTCGTCGTTAAAAATCGAGTAGAAGAGTTCCAATCAGCATATTTCGTAGCGATTTATGGATCACG

TCTCCTGGAAAATAATTTCTCGGCCCAACTAAACACGCTTCTTGCAGGGTTACAAAAAGCTGCACACACTCTAGGCA

TTCCAGGCTTCTCAAAACCCACTCCTCTTGCCGTAATCACAGGAGGAGGGACTGGCGTTATGGCTACAGGAAATCGT

GTTGCAAAAGAGTTGGGAATTCTTTCTTGCGGGACCGTTCTCGATTTGGAAGCTTCACCTGCACAAATAGATCAGCC

TGCAAACGAATTTTTAGATGCCAAAATGACATACCGTCTACCGCAACTTATAGAAAGACAAGAACATTTTTATTCAG

ACCTTGCCATTTTAGTTGTTGGTGGTGTTGGAACAGATTTCGAACTTTACCTAGAACTCGTCTACTTGAAAACAGGC

GCCAAACCTCCTACTCCAATTTTCCTTATTGGGCCTGTTGAATACTGGAAAGAGAAAGTTGCTCATGCCTATGAGAT

TAATCTTAAAGCAGGAACTATTCGTGGTTCTGAGTGGATCAGCAACTGCTTATTCTGCATTACATCTCCTGAAGCAG

GAATTGCTGTATTCGAACAGTTCCTCGCTGGAGAACTTCCCATAGGATATGATTATCCTCCAGCTCCAGACGGATTA

GTTATCGTCTAA

SEQ ID NO: 58 - TC0666 protein sequence (homologue of CT387)
MRIPMTLFHTHHDAVSPDGYLCSSLQLVGSGTYEGEIEIQNIPSYFLGFRLPTHCVHLNLKSSLAQLGVDASLLHCE

LSKNQQRAHMHVQFTGYGPIAESMLSLLKPGDRVAKLFAADDRRLVRSPDYLESMLKNTDKTGHPLLRFGKKLEHLI

SFDVVDDRLVVSLPTLPGIVNYDPDIYGLLPLIQKSLSNPKLSIRHFLSLYQKIVEGPHIPYEGNILLIKTEPLHIR

TVFARVVDQMLPQGLFHTSANILEPTTRESGDIFEFFGNPSTLVERIPLEFFTIEPYKEHSYFCNRDLLQTTLQSES

EIKKIFDTAPQEPVKAATYLSKGSEISSLDADSWLTGSAAAYQCSEKQAAKDEYIHAQPCYPFLEAMETGLINSEGA

LLTRFFPSSSLKGMLISYHVRHYLKQIYFQVPSYTYGDYFSHNDRGLLLDLYQANIDVFWADEESGRVLQYTKRRDK

NSGMFVVKNRVEEFQSAYFVAIYGSRLLENNFSAQLNTLLAGLQKAAHTLGIPGFSKPTPLAVITGGGTGVMATGNR

VAKELGILSCGTVLDLEASPAQIDQPANEFLDAKMTYRLPQLIERQEHFYSDLAILVVGGVGTDFELYLELVYLKTG

AKPPTPIFLIGPVEYWKEKVAHAYEINLKAGTIRGSEWISNCLFCITSPEAGIAVFEQFLAGELPIGYDYPPAPDGL

VIV

SEQ ID NO: 59 - TC0197 nucleotide sequence
ATGAGTTCCGAGAAAGATAAAAAAAACTCCTGTTCTAAGTTTTCCTTATCGGTAGTAGCAGCTATTCTCGCTTCTAT

GAGTGGTTTATCGAATTGTTCCGATCTTTATGCCGTAGGAAGTTCTGCAGACCATCCTGCCTACTTGATTCCTCAAG

CGGGGTTATTATTGGATCATATTAAGGATATATTCATTGGCCCTAAAGATAGTCAGGATAAGGGGCAGTATAAGTTG

ATTATTGGTGAGGCTGGCTCTTTCCAAGATAGTAATGCAGAGACTCTTCCTCAAAAGGTAGAGCACAGCACTTTGTT

TTCAGTTACAACACCTATAATTGTGCAAGGAATAGATCAACAAGATCAGGTCTCTTCGCAGGGATTGGTCTGTAATT

TTTCAGGAGATCATTCAGAGGAGATTTTTGAGAGAGAATCCTTTTTAGGGATCGCTTTCCTAGGGAATGGTAGCAAG

GATGGAATCACGTTAACAGATATAAAATCTTCGTTATCTGGTGCTGCCTTGTATTCTTCAGATGATCTTATTTTTGA

AAGAATTAAGGGAGATATAGAGCTTTCTTCTTGTTCATCTTTAGAAAGAGGAGGAGCTTGTTCAGCTCAAAGTATTT

TAATTCATGATTGTCAAGGATTAACGGTAAAACATTGTGCCGCAGGGGTGAATGTTGAAGGAGTTAGTGCTAGCGAC

CATCTCGGATTTGGGGGCGGGGCCTTCTCTACTACAAGTTCTCTTTCTGGAGAGAAGAGTTTGTATATGCCTGCAGG

-continued

SEQUENCE LISTING

CGATATTGTGGTGGCTACCTGCGATGGTCCTGTGTGTTTCGAAGGAAATAGTGCTCAGTTAGCAAATGGTGGCGCTA

TTGCCGCTTCTGGTAAAGTTCTTTTTGTAGCTAACGAAAAAAAGATTTCCTTTACAGACAACCAAGCTTTGTCTGGA

GGAGCTATTTCTGCATCTTCTAGTATTTCTTTCCAAAATTGTGCTGAGCTTGTGTTCAAGAGTAATCTTGCAAAAGG

AGTTAAAGATAAATGTTCTTTGGGAGGAGGTGCTTTAGCCTCTTTAGAATCCGTAGTTTTGAAAGATAATCTCGGTA

TTACTTATGAAAAAAATCAGTCCTATTCGGAAGGAGGGGCTATTTTTGGGAAGGATTGTGAGATTTTTGAAAACAGG

GGGCCTGTTGTATTCAGAGATAATACAGCTGCTTTAGGAGGCGGAGCTATTTTGGCGCAACAAACTGTGGCGATTTG

TGGTAATAAGTCTGGAATATCTTTTGAAGGAAGTAAGTCTAGTTTTGGAGGGGCCATTGCTTGTGGAAATTTCTCTT

CTGAGAATAATTCTTCAGCTTTGGGATCAATTGATATCTCTAACAATCTAGGAGATATCTCTTTTCTTCGGACTCTG

TGTACTACTTCGGATTTAGGGCAAACGGATTACCAAGGGGGAGGGGCCTTATTCGCTGAAAATATTTCTCTTTCTGA

GAATGCTGGTGCAATTACTTTCAAAGACAATATTGTGAAGACATTTGCCTCAAATGGAAAAATGTTGGGTGGAGGGG

CAATTTTAGCTTCAGGAAATGTTTTGATTAGCAAAAACTCTGGAGAGATTTCTTTTGTAGGGAATGCTCGAGCTCCT

CAGGCTATTCCGACTCGTTCATCTGACGAATTGTCTTTTGGCGCACAATTAACTCAAACTACTTCAGGATGTTCTGG

AGGAGGAGCTCTTTTTGGTAAAGAGGTTGCCATTGTTCAAAATGCCACTGTTGTATTCGAGCAAAATCGCTTACAGT

GTGGCGAGCAGGAAACACATGGTGGAGGCGGTGCTGTTTATGGTATGGAGAGTGCCTCTATTATTGGAAACTCTTTT

GTGAGATTCGGAAATAATTACGCTGTAGGGAATCAGATTTCTGGAGGAGCTCTTTTATCCAAGAAGGTCCGTTTAGC

TGAAAATACAAGGGTAGATTTTTCTCGAAATATCGCTACTTTCTGCGGCGGGGCTGTTCAAGTTTCTGATGGAAGTT

GCGAATTGATCAACAATGGGTATGTGCTATTCAGAGATAACCGAGGGCAGACATTTGGTGGGGCTATTTCTTGCTTG

AAAGGAGATGTGATCATTTCCGGAAATAAAGATAGGGTTGAGTTTAGAGATAACATTGTGACGCGGCCTTATTTTGA

AGAAAATGAAGAAAAAGTTGAGACAGCAGATATTAATTCAGATAAGCAAGAAGCAGAAGAGCGCTCTTTATTAGAGA

ACATTGAGCAGAGCTTTATTACTGCAACTAATCAGACCTTTTTCTTAGAGGAAGAGAAACTCCCATCAGAAGCTTTT

ATCTCTGCTGAAGAACTTTCAAAGAGAAGAGAATGTGCTGGTGGGGCGATTTTTGCAAAACGGGTCTACATTACGGA

TAATAAAGAACCTATCTTGTTTTCGCATAATTTTTCTGATGTTTATGGGGGAGCTATTTTTACGGGTTCTCTACAGG

AAACTGATAAACAAGATGTTGTAACTCCTGAAGTTGTGATATCAGGCAACGATGGGGATGTCATTTTTTCTGGAAAT

GCAGCTAAACATGATAAGCATTTACCTGATACAGGTGGTGGAGCCATTTGTACACAGAATTTGACGATTTCCCAAAA

CAATGGGAATGTCTTGTTCTTGAACAATTTTGCTTGTTCTGGTGGAGCAGTTCGCATAGAGGATCATGGAGAAGTTC

TTTTAGAGGCTTTTGGGGGAGATATTATTTTCAATGGAAACTCTTCTTTCAGAGCTCAAGGATCGGATGCGATCTAT

TTTGCTGGTAAGGACTCTAGAATTAAAGCTTTAAATGCTACTGAAGGACATGCGATTGTGTTCCAAGATGCATTGGT

GTTTGAAAATATAGAAGAAAGAAAGTCTTCGGGACTATTGGTGATTAACTCTCAGGAAAATGAGGGTTATACGGGAT

CCGTCCGATTTTTAGGATCTGAAAGTAAGGTTCCTCAATGGATTCATGTGCAACAGGGAGGTCTTGAGTTGCTACAT

GGAGCTATTTTATGTAGTTATGGGGTTAAACAAGATCCTAGAGCTAAAATAGTATTATCTGCTGGATCTAAATTGAA

GATTCTAGATTCAGAGCAAGAAAATAACGCAGAAATTGGAGATCTTGAAGATTCTGTTAATTCAGAAAAAAACACCAT

CTCTTTGGATTGGGAAGAACGCTCAAGCAAAAGTCCCTCTGGTTGATATCCATACTATTTCTATTGATTTAGCATCA

TTTTCTTCTAAAGCTCAGGAAACCCCTGAGGAAGCTCCACAAGTCATCGTCCCTAAGGGAAGTTGTGTCCACTCGGG

AGAGTTAAGTTTGGAGTTGGTTAATACAACAGGAAAAGGTTATGAGAATCATGCGTTGTTAAAAAATGATACTCAGG

TTTCTCTCATGTCTTTCAAAGAGGAAAATGATGGATCTTTAGAAGATTTGAGTAAGTTGTCTGTTTCGGATTTACGC

ATTAAAGTTTCTACTCCAGATATTGTAGAAGAAACTTATGGCCATATGGGGGATTGGTCTGAAGCTACAATTCAAGA

TGGGGCTCTTGTCATTAATTGGCATCCTACTGGATATAAATTAGATCCGCAAAAAGCTGGTTCTTTGGTATTCAATG

CATTATGGGAGGAAGAGGCTGTATTGTCTACTCTAAAAAATGCTCGGATTGCCCATAACCTTACCATTCAGAGAATG

GAATTTGATTATTCTACAAATGCTTGGGGATTAGCTTTTAGTAGCTTTAGAGAGCTATCTTCAGAGAAGCTTGTTTC

-continued

SEQUENCE LISTING

TGTTGATGGATATAGAGGCTCTTATATAGGGGCTTCTGCAGGCATTGATACTCAGTTGATGGAAGATTTTGTTTTGG

GAATCAGCACGGCTTCCTTCTTCGGGAAAATGCATAGTCAGAATTTTGATGCAGAGATTTCTCGACATGGTTTTGTT

GGTTCGGTCTATACAGGCTTCCTAGCTGGGGCCTGGTTCTTCAAGGGGCAGTACAGTCTTGGCGAAACACATAACGA

TATGACAACTCGTTACGGGGTTTTGGGAGAATCTAATGCTACTTGGAAGTCTCGAGGAGTACTAGCAGATGCTTTAG

TTGAATATCGTAGTTTAGTCGGTCCAGCACGACCTAAATTTTATGCTTTGCATTTTAATCCTTATGTCGAGGTATCT

TATGCATCTGCGAAGTTCCCTAGTTTTGTAGAACAAGGAGGAGAAGCTCGTGCTTTTGAAGAAACCTCTTTAACAAA

CATTACCGTTCCCTTTGGTATGAAATTTGAACTATCTTTTACAAAAGGACAGTTTTCAGAGACTAATTCTCTTGGAA

TAGGTTGTGCATGGGAAATGTATCGGAAAGTCGAAGGAAGATCTGTAGAGCTACTAGAAGCTGGTTTTGATTGGGAA

GGATCTCCTATAGATCTCCCTAAACAAGAGCTGAGAGTGGCTTTAGAAAACAATACGGAATGGAGTTCGTATTTTAG

TACAGCTCTAGGAGTAACAGCATTTTGTGGAGGATTTTCTTCTATGGATAATAAACTAGGATACGAAGCGAATGCTG

GAATGCGTTTGATTTTCTAG

SEQ ID NO: 60 - TC0197 protein sequence
MSSEKDKKNSCSKFSLSVVAAILASMSGLSNCSDLYAVGSSADHPAYLIPQAGLLLDHIKDIFIGPKDSQDKGQYKL

IIGEAGSFQDSNAETLPQKVEHSTLFSVTTPIIVQGIDQQDQVSSQGLVCNFSGDHSEEIFERESFLGIAFLGNGSK

DGITLTDIKSSLSGAALYSSDDLIFERIKGDIELSSCSSLERGGACSAQSILIHDCQGLTVKHCAAGVNVEGVSASD

HLGFGGGAFSTTSSLSGEKSLYMPAGDIVVATCDGPVCFEGNSAQLANGGAIAASGKVLFVANEKKISFTDNQALSG

GAISASSSISFQNCAELVFKSNLAKGVKDKCSLGGGALASLESVVLKDNLGITYEKNQSYSEGGAIFGKDCEIFENR

GPVVFRDNTAALGGGAILAQQTVAICGNKSGISFEGSKSSFGGAIACGNFSSENNSSALGSIDISNNLGDISFLRTL

CTTSDLGQTDYQGGGALFAENISLSENAGAITFKDNIVKTFASNGKMLGGGAILASGNVLISKNSGEISFVGNARAP

QAIPTRSSDELSFGAQLTQTTSGCSGGGALFGKEVAIVQNATVVFEQNRLQCGEQETHGGGGAVYGMESASIIGNSF

VRFGNNYAVGNQISGGALLSKKVRLAENTRVDFSRNIATFCGGAVQVSDGSCELINNGYVLFRDNRGQTFGGAISCL

KGDVIISGNKDRVEFRDNIVTRPYFEENEEKVETADINSDKQEAEERSLLENIEQSFITATNQTFFLEEEKLPSEAF

ISAEELSKRRECAGGAIFAKRVYITDNKEPILFSHNFSDVYGGAIFTGSLQETDKQDVVTPEVVISGNDGDVIFSGN

AAKHDKHLPDTGGGAICTQNLTISQNNGNVLFLNNFACSGGAVRIEDHGEVLLEAFGGDIIFNGNSSFRAQGSDAIY

FACKDSRIKALNATEGHAIVFQDALVFENIEERKSSGLLVINSQENEGYTGSVRFLGSESKVPQWIHVQQGGLELLH

GAILCSYGVKQDPRAKIVLSAGSKLKILDSEQENNAEIGDLEDSVNSEKTPSLWIGKNAQAKVPLVDIHTISIDLAS

FSSKAQETPEEAPQVIVPKGSCVHSGELSLELVNTTGKGYENHALLKNDTQVSLMSFKEENDGSLEDLSKLSVSDLR

IKVSTPDIVEETYGHMGDWSEATIQDGALVINWHPTGYKLDPQKAGSLVFNALWEEEAVLSTLKNARIAHNLTIQRM

EFDYSTNAWGLAFSSFRELSSEKLVSVDGYRGSYIGASAGIDTQLMEDFVLGISTASFFGKMHSQNFDAEISRHGFV

GSVYTGFLAGAWFFKGQYSLGETHNDMTTRYGVLGESNATWKSRGVLADALVEYRSLVGPARPKFYALHFNPYVEVS

YASAKFPSFVEQGGEARAFEETSLTNITVPFGMKFELSFTKGQFSETNSLGIGCAWEMYRKVEGRSVELLEAGFDWE

GSPIDLPKQELRVALENNTEWSSYFSTALGVTAFCGGFSSMDNKLGYEANAGMRLIF

SEQ ID NO: 61 - TC0261 nucleotide sequence
ATGAAAAAACTGTTCTTTTTTGTCCTTATTGGAAGCTCTATACTGGGATTTACTCGAGAAGTCCCTCCTTCGATTCT

TTTAAAGCCTATACTAAATCCATACCATATGACCGGGTTATTTTTTCCCAAGGTTAATTTGCTTGGAGACACACATA

ATCTCACTGATTACCATTTGGATAATCTAAAATGCATTCTGGCTTGCCTACAAAGAACTCCTTATGAAGGAGCTGCT

TTCACAGTAACCGATTACTTAGGTTTTTCAGATACACAAAAGGATGGTATTTTTTGTTTTAAAAATCTTACTCCAGA

GAGTGGAGGGGTTATTGGTTCCCCAACTCAAAACACTCCTACTATAAAAATTCATAATACAATCGGCCCCGTTCTTT

TCGAAAATAATACCTGTCATAGACTGTGGACACAGACCGATCCCGAAAATGAAGGAAACAAAGCACGCGAAGGCGGG

GCAATTCATGCTGGGGACGTTTACATAAGCAATAACCAGAACCTTGTCGGATTCATAAAGAACTTTGCTTATGTTCA

-continued

SEQUENCE LISTING

AGGTGGAGCTATTAGTGCTAATACTTTTGCCTATAAAGAAAATAAATCGAGCTTTCTTTGCCTAAATAACTCTTGTA

TACAAACTAAGACGGGAGGGAAAGGTGGTGCTATTTACGTTAGTACGAGCTGCTCTTTCGAGAACAATAACAAGGAT

CTGCTTTTCATCCAAAACTCCGGCTGTGCAGGAGGAGCTATCTTCTCTCCAACCTGTTCTCTAATAGGAAACCAAGG

AGATATTGTTTTTTACAGCAACCACGGTTTTAAAAATGTTGATAATGCAACTAACGAATCTGGGGATGGAGGAGCTA

TTAAAGTAACTACCCGCTTGGACATCACCAATAATGGTAGTCAAATCTTTTTTTCTGATAATATCTCAAGAAATTTT

GGAGGAGCTATTCATGCTCCTTGTCTTCATCTTGTTGGTAATGGGCCAACCTATTTTACAAACAATATAGCTAATCA

CACAGGTGGGGCTATTTATATAACAGGAACAGAAACCTCAAAGATTTCTGCAGATCACCATGCTATTATTTTTGATA

ATAACATTTCTGCAAACGCCACCAATGCGGACGGATCTAGCAGCAACACTAATCCTCCTCACAGAAATGCGATCACT

ATGGACAATTCCGCTGGAGGAATAGAACTTGGTGCAGGGAAGAGCCAGAATCTTATTTTCTATGATCCTATTCAAGT

GACGAATGCTGGAGTTACCGTAGACTTCAATAAGGATGCCTCCCAAACCGGATGTGTAGTTTTCTCTGGAGCGACTG

TCCTTTCTGCAGATATTTCTCAGGCTAATTTGCAAACTAAAACACCTGCAACGCTTACTCTCAGTCACGGTCTTCTG

TGTATCGAAGATCGTGCTCAGCTCACAGTGAACAATTTTACACAAACAGGAGGGATTGTAGCCTTAGGAAATGGAGC

AGTTTTAAGCAGCTACCAACACAGCACTACAGACGCCACTCAAACTCCCCCTACAACCACCACTACAGATGCTTCCG

TAACTCTTAATCACATTGGATTAAATCTCCCCTCTATTCTTAAGGATGGAGCAGAGATGCCTCTATTATGGGTAGAA

CCTATAAGCACAACTCAAGGTAACACTACAACATATACGTCAGATACCGCGGCTTCCTTCTCATTAAATGGAGCCAC

ACTCTCTCTCATTGATGAAGATGGAAATTCTCCCTATGAAAACACGGACCTCTCTCGTGCATTGTACGCTCAACCTA

TGCTAGCAATTTCTGAGGCCAGTGATAACCAATTGCAATCCGAAAGCATGGACTTTTCTAAAGTTAATGTTCCTCAC

TATGGATGGCAAGGACTTTGGACCTGGGGGTGGGCAAAAACTGAAAATCCAACAACAACTCCTCCAGCAACAATTAC

TGATCCGAAAAAAGCTAATCAGTTTCATAGAACTTTATTATTAACGTGGCTCCCTGCTGGTTATATCCCCAGCCCTA

AACATAAAAGCCCTTTAATAGCTAATACCTTGTGGGGGAATATACTTTTTGCAACGGAAAACTTAAAAAATAGCTCA

GGGCAAGAACTTCTTGATCGTCCTTTCTGGGGAATTACAGGAGGGGGCTTGGGGATGATGGTCTATCAAGAACCTAG

AAAAGACCATCCTGGATTCCACATGCATACCTCCGGATATTCAGCAGGAATGATTACAGGAAACACACATACCTTCT

CATTACGATTCAGCCAGTCCTATACAAAACTCAATGAACGTTATGCCAAGAACTATGTGTCTTCTAAAAATTACTCT

TGCCAAGGGGAAATGCTTTTGTCCTTACAAGAAGGACTCATGCTGACTAAACTAATTGGTCTCTATAGTTATGGGAA

TCACAACAGCCACCATTTCTATACCCAAGGAGAAGACCTATCGTCTCAAGGGGAGTTCCATAGTCAGACTTTTGGAG

GGGCTGTCTTTTTTGATCTACCTCTGAAACCTTTTGGAAGAACACACATACTTACAGCTCCTTTCTTAGGTGCCATT

GGTATGTATTCTAAGCTGTCTAGCTTTACAGAAGTAGGAGCCTATCCAAGAACCTTTATTACAGAAACGCCTTTAAT

CAATGTCCTGATTCCTATCGGAGTAAAAGGTAGCTTCATGAATGCCACCCATAGACCTCAGGCCTGGACTGTAGAGC

TTGCTTACCAACCTGTTCTTTACAGACAAGAACCTAGTATCTCTACCCAATTACTCGCTGGTAAAGGTATGTGGTTT

GGGCATGGAAGTCCTGCATCTCGCCACGCTCTAGCTTATAAAATTTCACAGAAAACACAGCTTTTGCGATTTGCAAC

ACTTCAACTCCAGTATCACGGATACTATTCGTCTTCCACTTTCTGTAATTATCTGAATGGAGAGGTATCTTTACGTT

TCTAA

SEQ ID NO: 62 - TC0261 protein sequence
MKKLFFFVLIGSSILGFTREVPPSILLKPILNPYHMTGLFFPKVNLLGDTHNLTDYHLDNLKCILACLQRTPYEGAA

FTVTDYLGFSDTQKDGIFCFKNLTPESGGVIGSPTQNTPTIKIHNTIGPVLFENNTCHRLWTQTDPENEGNKAREGG

AIHAGDVYISNNQNLVGFIKNFAYVQGGAISANTFAYKENKSSFLCLNNSCIQTKTGGKGGAIYVSTSCSFENNNKD

LLFIQNSGCAGGAIFSPTCSLIGNQGDIVFYSNHGFKNVDNATNESGDGGAIKVTTRLDITNNGSQIFFSDNISRNF

GGAIHAPCLHLVGNGPTYFTNNIANHTGGAIYITGTETSKISADHHAIIFDNNISANATNADGSSSNTNPPHRNAIT

MDNSAGGIELGAGKSQNLIFYDPIQVTNAGVTVDFNKDASQTGCVVFSGATVLSADISQANLQTKTPATLTLSHGLL

-continued

SEQUENCE LISTING

CIEDRAQLTVNNFTQTGGIVALGNGAVLSSYQHSTTDATQTPPTTTTTDASVTLNHIGLNLPSILKDGAEMPLLWVE

PISTTQGNTTTYTSDTAASFSLNGATLSLIDEDGNSPYENTDLSRALYAQPMLAISEASDNQLQSESMDFSKVNVPH

YGWQGLWTWGWAKTENPTTTPPATITDPKKANQFHRTLLLTWLPAGYIPSPKHKSPLIANTLWGNILFATENLKNSS

GQELLDRPFWGITGGGLGMMVYQEPRKDHPGFHMHTSGYSAGMITGNTHTFSLRFSQSYTKLNERYAKNYVSSKNYS

CQGEMLLSLQEGLMLTKLIGLYSYGNHNSHHFYTQGEDLSSQGEFHSQTFGGAVFFDLPLKPFGRTHILTAPFLGAI

GMYSKLSSFTEVGAYPRTFITETPLINVLIPIGVKGSFMNATHRPQAWTVELAYQPVLYRQEPSISTQLLAGKGMWF

GHGSPASRHALAYKISQKTQLLRFATLQLQYHGYYSSSTFCNYLNGEVSLRF

SEQ ID NO: 63 - CT733 fragment nucleotide sequence
GCACCTCAACCTCGCGGAACGCTTCCTAGCTCGACCACAAAAATTGGATCAGAAGTTTGGATTGAACAAAAAGTCCG

CCAATATCCAGAGCTTTTATGGTTAGTAGAGCCGTCCTCTACGGGAGCCTCTTTAAAATCTCCTTCAGGAGCCATCT

TTTCTCCAACATTATTCCAAAAAAAGGTCCCTGCTTTCGATATCGCAGTGCGCAGTTTGATTCACTTACATTTATTA

ATCCAGGGTTCCCGCCAAGCCTATGCTCAACTGATCCAACTACAGACCAGCGAATCCCCTCTAACATTTAAGCAATT

CCTTGCATTGCATAAGCAATTAACTCTATTTTTAAATTCCCCTAAGGAATTTTATGACTCTGTTAAAGTGTTAGAGA

CAGCTATCGTCTTACGTCACTTAGGCTGTTCAACTAAGGCTGTTGCTGCGTTTAAACCTTATTTCTCAGAAATGCAA

AGAGAGGCTTTTTACACTAAGGCTCTGCATGTACTACACACCTTCCCAGAGCTAAGCCCATCATTTGCTCGCCTCTC

TCCGGAGCAGAAAACTCTCTTCTTCTCCTTGAGAAAATTGGCGAATTACGATGAGTTACTCTCGCTGACGAACACCC

CAAGTTTTCAGCTTCTGTCTGCTGGGCGCTCGCAACGAGCTCTTTTAGCTCTGGACTTGTACCTCTATGCTTTGGAT

TCCTGTGGAGAACAGGGGATGTCCTCTCAATTCCACACAAACTTCGCACCTCTACAGTCCATGTTGCAACAATACGC

TACTGTAGAAGAGGCCTTTTCTCGTTATTTTACTTACCGAGCTAATCGATTAGGATTTGATGGCTCTTCTCGATCCG

AGATGGCTTTAGTAAGAATGGCCACCTTGATGAACTTGTCTCCTTCCGAAGCTGCGATTTTAACCACAAGCTTCAAA

ACCCTTCCTACAGAAGAAGCGGATACTTTGATCAATAGTTTCTATACCAATAAGGGCGATTCGTTGGCTCTTTCTCT

GCGAGGGTTGCCTACACTTGTATCCGAACTGACGCGAACTGCCCATGGCAATACCAATGCAGAAGCTCGATCTCAGC

AAATTTATGCAACTACCCTATCGCTAGTAGTAAAGAGTCTGAAAGCGCACAAAGAAATGCTAAACAAGCAAATTCTT

TCTAAGGAAATTGTTTTAGATTTCTCAGAAACTGCAGCTTCTTGCCAAGGATTGGATATCTTTTCCGAGAATGTCGC

TGTTCAAATTCACTTAAATGGAACCGTTAGTATCCATTTA

SEQ ID NO: 64 - CT733 fragment protein sequence
APQPRGTLPSSTTKIGSEVWIEQKVRQYPELLWLVEPSSTGASLKSPSGAIFSPTLFQKKVPAFDIAVRSLIHLHLL

IQGSRQAYAQLIQLQTSESPLTFKQFLALHKQLTLFLNSPKEFYDSVKVLETAIVLRHLGCSTKAVAAFKPYFSEMQ

REAFYTKALHVLHTFPELSPSFARLSPEQKTLFFSLRKLANYDELLSLTNTPSFQLLSAGRSQRALLALDLYLYALD

SCGEQGMSSQFHTNFAPLQSMLQQYATVEEAFSRYFTYRANRLGFDGSSRSEMALVRMATLMNLSPSEAAILTTSFK

TLPTEEADTLINSFYTNKGDSLALSLRGLPTLVSELTRTAHGNTNAEARSQQIYATTLSLVVKSLKAHKEMLNKQIL

SKEIVLDFSETAASCQGLDIFSENVAVQIHLNGTVSIHL

SEQ ID NO: 65 - CT153 fragment nucleotide sequence
ACTAAGCCTTCTTTCTTATACGTTATTCAACCTTTTTCCGTATTTAATCCACGATTAGGACGTTTCTCTACAGACTC

AGATACTTATATCGAAGAAGAAAACCGCCTAGCATCGTTCATTGAGAGTTTGCCACTGGAGATCTTCGATATACCTT

CTTTCATGGAAACCGCGATTTCCAATAGCCCCTATATTTTATCTTGGGAGACAACTAAAGACGGCGCTCTGTTCACT

ATTCTTGAACCCAAACTCTCAGCTTGCGCAGCCACTTGCCTGGTAGCCCCTTCTATACAAATGAAATCCGATGCGGA

GCTCCTAGAAGAAATTAAGCAAGCGTTATTACGCAGCTCTCATGACGGTGTGAAATATCGCATCACCAGAGAATCCT

TCTCTCCAGAAAAGAAAACTCCTAAGGTTGCTCTAGTCGATGACGATATTGAATTGATTCGCAATGTCGACTTTTTG

GGTAGAGCTGTTGACATTGTCAAATTAGACCCTATTAATATTCTGAATACCGTAAGCGAAGAGAATATTCTAGATTA

CTCTTTTACAAGAGAAACGGCTCAGCTGAGCGCGGATGGTCGTTTTGGTATTCCTCCAGGGACTAAGCTATTCCCTA

-continued

SEQUENCE LISTING

AACCTTCTTTTGATGTAGAAATCAGTACCTCCATTTTCGAAGAAACAACTTCATTTACTCGAAGTTTTTCTGCATCG

GTTACTTTTAGTGTACCAGACCTCGCGGCGACTATGCCTCTTCAAAGCCCTCCCATGGTAGAAAATGGTCAAAAAGA

AATTTGTGTCATTCAAAAACACTTATTCCCAAGCTACTCTCCTAAACTAGTCGATATTGTTAAACGATACAAAAGAG

AGGCTAAGATCTTGATTAACAAGCTTGCCTTTGGAATGTTATGGCGACATCGGGCTAAAAGCCAAATCCTCACCGAG

GGAAGCGTACGTCTAGACTTACAAGGATTCACAGAATCGAAGTACAATTACCAGATTCAAGTAGGATCCCATACGAT

TGCAGCTGTATTAATCGATATGGATATTTCCAAGATTCAATCCAAATCAGAACAAGCTTATGCAATTAGGAAAATCA

AATCAGGCTTTCAACGTAGCTTGGATGACTATCATATTTATCAAATTGAAAGAAAACAAACCTTTTCTTTTTCTCCG

AAGCATCGCAGCCTCTCATCCACATCCCATTCCGAAGATTCTGATTTGGATCTTTCTGAAGCAGCCGCCTTTTCAGG

AAGTCTTACCTGCGAGTTTGTAAAAAAAAGCACTCAACATGCCAAGAATACCGTCACATGTTCCACAGCCGCTCATT

CCCTATACACACTCAAAGAAGATGACAGCTCGAACCCCTCTGAAAAACGATTAGATAGTTGTTTCCGCAATTGGATT

GAAAACAAACTAAGCGCCAATTCTCCAGATTCCTGGTCAGCGTTTATTCAAAAATTCGGAACACACTATATTGCATC

AGCAACTTTTGGAGGGATAGGTTTCCAAGTGCTCAAACTATCTTTTGAACAGGTGGAGGATCTACATAGCAAAAAGA

TCTCCTTAGAAACCGCAGCAGCCAACTCTCTATTAAAAGGTTCTGTATCCAGCAGCACAGAATCTGGATACTCCAGC

TATAGCTCCACGTCTTCTTCTCATACGGTATTTTTAGGAGGAACGGTCTTACCTTCGGTTCATGATGAACGTTTAGA

CTTTAAAGATTGGTCGGAAAGTGTGCACCTGGAACCTGTTCCTATCCAGGTTTCTTTACAACCTATAACGAATTTAC

TAGTTCCTCTCCATTTTCCTAATATCGGTGCTGCAGAGCTCTCTAATAAACGAGAATCTCTTCAACAAGCGATTCGA

GTCTATCTCAAAGAACATAAAGTAGATGAGCAAGGAGAACGTACTACATTTACATCAGGAATCGATAATCCTTCTTC

CTGGTTTACCTTAGAAGCTGCCCACTCTCCTCTTATAGTCAGTACTCCTTACATTGCTTCGTGGTCTACGCTTCCTT

ATTTGTTCCCAACATTAAGAGAACGTTCTTCGGCAACCCCTATCGTTTTCTATTTTTGTGTAGATAATAATGAACAT

GCTTCGCAAAAAATATTAAACCAATCGTATTGCTTCCTCGGGTCCTTGCCTATTCGACAAAAAATTTTTGGTAGCGA

ATTTGCTAGTTTCCCCTATCTATCTTTCTATGGAAATGCAAAAGAGGCGTACTTTGATAACACGTACTACCCAACGC

GTTGTGGGTGGATTGTTGAAAAGTTAAATACTACACAAGATCAATTCCTCCGGGATGGAGACGAGGTGCGACTAAAA

CATGTTTCCAGCGGAAAGTATCTAGCAACAACTCCTCTTAAGGATACCCATGGTACACTCACGCGTACAACGAACTG

TGAAGATGCTATCTTTATTATTAAAAAATCTTCAGGTTAT

SEQ ID NO: 66 - CT153 fragment protein sequence
TKPSFLYVIQPFSVFNPRLGRFSTDSDTYIEEENRLASFIESLPLEIFDIPSFMETAISNSPYILSWETTKDGALFT

ILEPKLSACAATCLVAPSIQMKSDAELLEEIKQALLRSSHDGVKYRITRESFSPEKKTPKVALVDDDIELIRNVDFL

GRAVDIVKLDPINILNTVSEENILDYSFTRETAQLSADGRFGIPPGTKLFPKPSFDVEISTSIFEETTSFTRSFSAS

VTFSVPDLAATMPLQSPPMVENGQKEICVIQKHLFPSYSPKLVDIVKRYKREAKILINKLAFGMLWRHRAKSQILTE

GSVRLDLQGFTESKYNYQIQVGSHTIAAVLIDMDISKIQSKSEQAYAIRKIKSGFQRSLDDYHIYQIERKQTFSFSP

KHRSLSSTSHSEDSDLDLSEAAAFSGSLTCEFVKKSTQHAKNTVTCSTAAHSLYTLKEDDSSNPSEKRLDSCFRNWI

ENKLSANSPDSWSAFIQKFGTHYIASATFGGIGFQVLKLSFEQVEDLHSKKISLETAAANSLLKGSVSSSTESGYSS

YSSTSSSHTVFLGGTVLPSVHDERLDFKDWSESVHLEPVPIQVSLQPITNLLVPLHFPNIGAAELSNKRESLQQAIR

VYLKEHKVDEQGERTTFTSGIDNPSSWFTLEAAHSPLIVSTPYIASWSTLPYLFPTLRERSSATPIVFYFCVDNNEH

ASQKILNQSYCFLGSLPIRQKIFGSEFASFPYLSFYGNAKEAYFDNTYYPTRCGWIVEKLNTTQDQFLRDGDEVRLK

HVSSGKYLATTPLKDTHGTLTRTTNCEDAIFIIKKSSGY

SEQ ID NO: 67 - CT601 fragment nucleotide sequence
GGTAAAGCACCGTCTTTGCAGGCTATTCTAGCCGAAGTCGAAGACACCTCCTCTCGTCTACACGCTCATCACAATGA

GCTTGCTATGATCTCTGAACGCCTCGATGAGCAAGACACGAAACTACAGCAACTTTCGTCAACACAAGATCATAACC

TACCTCGACAAGTTCAGCGACTAGAAACGGACCAAAAAGCTTTGGCAAAAACACTGGCGATTCTTTCGCAATCCGTC

-continued

SEQUENCE LISTING

CAAGATATTCGGTCTTCTGTACAAAATAAATTACAAGAAATCCAACAAGAACAAAAAAAATTAGCACAAAATTTGCG

AGCGCTTCGTAACTCTTTACAAGCTCTCGTTGATGGCTCTTCTCCAGAAAATTATATTGATTTCCTAACTGGTGAAA

CCCCGGAACATATTCATATTGTTAAACAAGGAGAGACCCTGAGCAAGATCGCGAGTAAATATAACATCCCCGTCGTA

GAATTAAAAAAACTTAATAAACTAAATTCGGATACTATTTTTACAGATCAAAGAATTCGCCTTCCGAAAAAGAAA

SEQ ID NO: 68 - CT601 fragment protein sequence
GKAPSLQAILAEVEDTSSRLHAHHNELAMISERLDEQDTKLQQLSSTQDHNLPRQVQRLETDQKALAKTLAILSQSV

QDIRSSVQNKLQEIQQEQKKLAQNLRALRNSLQALVDGSSPENYIDFLTGETPEHIHIVKQGETLSKIASKYNIPVV

ELKKLNKLNSDTIFTDQRIRLPKKK

SEQ ID NO: 69 - CT279 fragment nucleotide sequence
GCACAAGTAATTTCTTCCGATAACACATTCCAAGTCTATGAAAAGGGAGATTGGCACCCAGCCCTATATAATACTAA

AAAGCAGTTGCTAGAGATCTCCTCTACTCCTCCTAAAGTAACCGTGACAACTTTAAGCTCATATTTTCAAAACTTTG

TTAGAGTCTTGCTTACAGATACACAAGGAAATCTTTCTTCATTCGAAGACCATAATCTCAATCTAGAAGAATTTTTA

TCTCAACCAACTCCTGTAATACATGGTCTTGCCCTTTATGTGGTCTACGCTATCCTACACAACGATGCAGCTTCCTC

TAAATTATCTGCTTCCCAAGTAGCGAAAAATCCAACAGCTATAGAATCTATAGTTCTTCCTATAGAAGGTTTTGGTT

TGTGGGGACCTATCTATGGATTCCTTGCTCTAGAAAAAGACGGGAATACTGTTCTTGGTACTTCTTGGTATCAACAT

GGCGAGACTCCTGGATTAGGAGCAAATATCGCTAACCCTCAATGGCAAAAAAATTTCAGAGGCAAAAAAGTATTTCT

AGTCTCAGCTTCTGGAGAAACAGATTTTGCTAAGACAACCCTAGGACTGGAAGTTATAAAAGGATCTGTATCTGCAG

CATTAGGAGACTCACCTAAAGCTGCTTCTTCCATCGACGGAATTTCAGGAGCTACTTTGACTTGTAATGGTGTTACC

GAATCCTTCTCTCATTCTCTAGCTCCCTACCGCGCTTTGTTGACTTTCTTCGCCAACTCTAAACCTAGTGGAGAGTC

TCATGACCAC

SEQ ID NO: 70 - CT279 fragment protein sequence
AQVISSDNTFQVYEKGDWHPALYNTKKQLLEISSTPPKVTVTTLSSYFQNFVRVLLTDTQGNLSSFEDHNLNLEEFL

SQPTPVIHGLALYVVYAILHNDAASSKLSASQVAKNPTAIESIVLPIEGFGLWGPIYGFLALEKDGNTVLGTSWYQH

GETPGLGANIANPQWQKNFRGKKVFLVSASGETDFAKTTLGLEVIKGSVSAALGDSPKAASSIDGISGATLTCNGVT

ESFSHSLAPYRALLTFFANSKPSGESHDH

SEQ ID NO: 71 - CT443 fragment nucleotide sequence
GGGGTGTTAGAGACCTCTATGGCAGAGTCTCTCTCTACAAACGTTATTAGCTTAGCTGACACCAAAGCGAAAGACAA

CACTTCTCATAAAAGCAAAAAAGCAAGAAAAAACCACAGCAAAGAGACTCCCGTAGACCGTAAAGAGGTTGCTCCGG

TTCATGAGTCTAAAGCTACAGGACCTAAACAGGATTCTTGCTTTGGCAGAATGTATACAGTCAAAGTTAATGATGAT

CGCAATGTTGAAATCACACAAGCTGTTCCTGAATATGCTACGGTAGGATCTCCCTATCCTATTGAAATTACTGCTAC

AGGTAAAAGGGATTGTGTTGATGTTATCATTACTCAGCAATTACCATGTGAAGCAGAGTTCGTACGCAGTGATCCAG

CGACAACTCCTACTGCTGATGGTAAGCTAGTTTGGAAAATTGACCGCTTAGGACAAGGCGAAAAGAGTAAAATTACT

GTATGGGTAAAACCTCTTAAAGAAGGTTGCTGCTTTACAGCTGCAACAGTATGCGCTTGTCCAGAGATCCGTTCGGT

TACAAAATGTGGACAACCTGCTATCTGTGTTAAACAAGAAGGCCCAGAGAATGCTTGTTTGCGTTGCCCAGTAGTTT

ACAAAATTAATATAGTGAACCAAGGAACAGCAACAGCTCGTAACGTTGTTGTTGAAAATCCTGTTCCAGATGGTTAC

GCTCATTCTTCTGGACAGCGTGTACTGACGTTTACTCTTGGAGATATGCAACCTGGAGAGCACAGAACAATTACTGT

AGAGTTTTGTCCGCTTAAACGTGGTCGTGCTACCAATATAGCAACGGTTTCTTACTGTGGAGGACATAAAAATACAG

CAAGCGTAACAACTGTGATCAACGAGCCTTGCGTACAAGTAAGTATTGCAGGAGCAGATTGGTCTTATGTTTGTAAG

CCTGTAGAATATGTGATCTCCGTTTCCAATCCTGGAGATCTTGTGTTGCGAGATGTCGTCGTTGAAGACACTCTTTC

TCCCGGAGTCACAGTTCTTGAAGCTGCAGGAGCTCAAATTTCTTGTAATAAAGTAGTTTGGACTGTGAAAGAACTGA

ATCCTGGAGAGTCTCTACAGTATAAAGTTCTAGTAAGAGCACAAACTCCTGGACAATTCACAAATAATGTTGTTGTG

-continued

SEQUENCE LISTING

AAGAGCTGCTCTGACTGTGGTACTTGTACTTCTTGCGCAGAAGCGACAACTTACTGGAAAGGAGTTGCTGCTACTCA

TATGTGCGTAGTAGATACTTGTGACCCTGTTTGTGTAGGAGAAAATACTGTTTACCGTATTTGTGTCACCAACAGAG

GTTCTGCAGAAGATACAAATGTTTCTTTAATGCTTAAATTCTCTAAAGAACTGCAACCTGTATCCTTCTCTGGACCA

ACTAAAGGAACGATTACAGGCAATACAGTAGTATTCGATTCGTTACCTAGATTAGGTTCTAAAGAAACTGTAGAGTT

TTCTGTAACATTGAAAGCAGTATCAGCTGGAGATGCTCGTGGGGAAGCGATTCTTTCTTCCGATACATTGACTGTTC

CAGTTTCTGATACAGAGAATACACACATCTAT

SEQ ID NO: 72 - CT443 fragment protein sequence
GVLETSMAESLSTNVISLADTKAKDNTSHKSKKARKNHSKETPVDRKEVAPVHESKATGPKQDSCFGRMYTVKVNDD

RNVEITQAVPEYATVGSPYPIEITATGKRDCVDVIITQQLPCEAEFVRSDPATTPTADGKLVWKIDRLGQGEKSKIT

VWVKPLKEGCCFTAATVCACPEIRSVTKCGQPAICVKQEGPENACLRCPVVYKINIVNQGTATARNVVVENPVPDGY

AHSSGQRVLTFTLGDMQPGEHRTITVEFCPLKRGRATNIATVSYCGGHKNTASVTTVINEPCVQVSIAGADWSYVCK

PVEYVISVSNPGDLVLRDVVVEDTLSPGVTVLEAAGAQISCNKVVWTVKELNPGESLQYKVLVRAQTPGQFTNNVVV

KSCSDCGTCTSCAEATTYWKGVAATHMCVVDTCDPVCVGENTVYRICVTNRGSAEDTNVSLMLKFSKELQPVSFSGP

TKGTITGNTVVFDSLPRLGSKETVEFSVTLKAVSAGDARGEAILSSDTLTVPVSDTENTHIY

SEQ ID NO: 73 - CT372 fragment nucleotide sequence
CAGGCTGCACACCATCACTATCACCGCTACACAGATAAACTGCACAGACAAAACCATAAAAAAGATCTCATCTCTCC

CAAACCTACCGAACAAGAGGCGTGCAATACTTCTTCCCTTAGTAAGGAATTAATCCCTCTATCAGAACAAAGAGGCC

TTTTATCCCCCATCTGTGACTTTATTTCGGAACGCCCTTGCTTACACGGAGTTTCTGTTAGAAATCTCAAGCAAGCG

CTAAAAAATTCTGCAGGAACCCAAATTGCACTGGATTGGTCTATTCTCCCTCAATGGTTCAATCCTCGGGTCTCTCA

TGCCCCTAAGCTTTCTATCCGAGACTTTGGGTATAGCGCACACCAAACTGTTACCGAAGCCACTCCTCCTTGCTGGC

AAAACTGCTTTAATCCATCTGCGGCCGTTACTATCTATGATTCCTCATATGGGAAAGGGGTCTTTCAAATATCCTAT

ACCCTTGTCCGCTATTGGAGAGAGAATGCTGCGACTGCTGGCGATGCTATGATGCTCGCAGGGAGTATCAATGATTA

TCCCTCTCGTCAGAACATTTTCTCTCAGTTTACTTTCTCCCAAAACTTCCCAAATGAACGGGTGAGTCTGACAATTG

GTCAGTACTCACTCTATGCAATAGACGGAACATTATACAATAACGATCAACAACTTGGATTCATTAGTTACGCATTA

TCACAAAATCCAACAGCAACTTATTCCTCTGGAAGTCTTGGAGCTTACCTACAAGTCGCTCCTACCGCAAGCACAAG

TCTTCAAATAGGATTTCAAGACGCTTATAATATCTCCGGATCCTCTATCAAATGGAGTAACCTTACAAAAAATAGAT

ACAATTTTCACGGTTTTGCTTCCTGGGCTCCCCGCTGTTGCTTAGGATCTGGCCAGTACTCCGTGCTTCTTTATGTG

ACTAGACAAGTTCCAGAACAGATGGAACAAACAATGGGATGGTCAGTCAATGCGAGTCAACACATATCTTCTAAACT

GTATGTGTTTGGAAGATACAGCGGTGTTACAGGACATGTGTTCCCGATTAACCGCACGTATTCATTCGGTATGGCCT

CTGCAAATTTATTTAACCGTAACCCACAAGATTTATTTGGAATTGCTTGCGCATTCAATAATGTACACCTCTCTGCT

TCTCCAAATACTAAAAGAAAATACGAAACTGTAATCGAAGGGTTTGCAACTATCGGTTGCGGCCCCTATCTTTCTTT

CGCTCCAGACTTCCAACTCTACCTCTACCCAGCTCTTCGTCCAAACAAACAATCTGCCCGTGTTTATAGCGTGCGAG

CTAATTTAGCTATC

SEQ ID NO: 74 - CT372 fragment protein sequence
QAAHNHYHRYTDKLHRQNHKKDLISPKPTEQEACNTSSLSKELIPLSEQRGLLSPICDFISERPCLHGVSVRNLKQA

LKNSAGTQIALDWSILPQWFNPRVSHAPKLSIRDFGYSAHQTVTEATPPCWQNCFNPSAAVTIYDSSYGKGVFQISY

TLVRYWRENAATAGDAMMLAGSINDYPSRQNIFSQFTFSQNFPNERVSLTIGQYSLYAIDGTLYNNDQQLGFISYAL

SQNPTATYSSGSLGAYLQVAPTASTSLQIGFQDAYNISGSSIKWSNLTKNRYNFHGFASWAPRCCLGSGQYSVLLYV

TRQVPEQMEQTMGWSVNASQHISSKLYVFGRYSGVTGHVFPINRTYSFGMASANLFNRNPQDLFGIACAFNNVHLSA

SPNTKRKYETVIEGFATIGCGPYLSFAPDFQLYLYPALRPNKQSARVYSVRANLAI

-continued

SEQUENCE LISTING

SEQ ID NO: 75 - CT456 fragment nucleotide sequence
ACAAATTCAGCGGCTACATCTTCTATCCAAACGACTGGAGAGACTGTAGTAAACTATACGAATTCAGCCTCCGCCCC

CAATGTAACTGTATCGACCTCCTCTTCTTCCACACAAGCCACAGCCACTTCGAATAAAACTTCCCAAGCCGTTGCTG

GAAAAATCACTTCTCCAGATACTTCAGAAAGCTCAGAAACTAGCTCTACCTCATCAAGCGATCATATCCCTAGCGAT

TACGATGACGTTGGTAGCAATAGTGGAGATATTAGCAACAACTACGATGACGTAGGTAGTAACAACGGAGATATCAG

TAGCAATTATGACGATGCTGCTGCTGATTACGAGCCGATAAGAACTACTGAAAATATTTATGAGAGTATTGGTGGCT

CTAGAACAAGTGGCCCAGAAAATACAAGTGGTGGTGCAGCAGCAGCACTCAATTCTCTAAGAGGCTCCTCCTACAGC

AATTATGACGATGCTGCTGCTGATTACGAGCCGATAAGAACTACTGAAAATATTTATGAGAGTATTGGTGGCTCTAG

AACAAGTGGCCCAGAAAATACGAGTGGTGGTGCAGCAGCAGCACTCAATTCTCTAAGAGGCTCCTCCTACAGCAATT

ATGACGATGCTGCTGCTGATTACGAGCCGATAAGAACTACTGAAAATATTTATGAGAGTATTGGTGGCTCTAGAACA

AGTGGCCCAGAAAATACGAGTGATGGTGCAGCAGCAGCAGCACTCAATTCTCTAAGAGGCTCCTCCTACACAACAGG

GCCTCGTAACGAGGGTGTATTCGGCCCTGGACCGGAAGGACTACCAGACATGTCTCTTCCTTCATACGATCCTACAA

ATAAAACCTCGTTATTGACTTTCCTCTCCAACCCTCATGTAAAGTCGAAAATGCTTGAAAACTCGGGGCATTTCGTC

TTCATTGATACAGATAGAAGTAGTTTCATTCTTGTTCCTAACGGAAATTGGGACCAAGTCTGTTCAATTAAAGTTCA

AAATGGAAAGACCAAAGAAGATCTCGACATCAAAGACTTGGAAAACATGTGTGCAAAATTCTGTACAGGGTTTAGCA

AATTCTCTGGTGACTGGGACAGTCTTGTAGAACCTATGGTGTCAGCCAAAGCTGGAGTGGCCAGCGGAGGCAATCTT

CCCAATACAGTGATTATCAATAATAAATTCAAAACTTGCGTTGCTTATGGTCCTTGGAATAGCCAGGAAGCAAGTTC

TGGTTATACACCTTCTGCTTGGAGACGTGGTCATCGAGTAGATTTTGGAGGAATTTTTGAGAAAGCCAACGACTTTA

ATAAAATCAACTGGGGAACTCAAGCCGGGCCTAGTAGCGAAGACGATGGCATTTCCTTCTCCAATGAAACTCCTGGA

GCTGGTCCTGCAGCTGCTCCATCACCAACGCCATCCTCTATTCCTATCATCAATGTCAATGTCAATGTTGGCGGAAC

TAATGTGAATATTGGAGATACGAATGTCAACACGACTAACACCACACCAACAACTCAATCTACAGACGCCTCTACAG

ATACAAGCGATATCGATGACATAAATACCAACAACCAAACTGATGATATCAATACGACAGACAAAGACTCTGACGGA

GCTGGTGGAGTCAATGGCGATATATCCGAAACAGAATCCTCTTCTGGAGATGATTCAGGAAGTGTCTCTTCCTCAGA

ATCAGACAAGAATGCCTCTGTCGGAAATGACGGACCTGCTATGAAAGATATCCTTTCTGCCGTGCGTAAACACCTAG

ACGTCGTTTACCCTGGCGAAAATGGCGGTTCTACAGAAGGGCCTCTCCCAGCTAACCAAACTCTCGGAGACGTAATC

TCTGATGTAGAGAATAAAGGCTCCGCTCAGGATACAAAATTGTCAGGAAATACAGGAGCTGGGGATGACGATCCAAC

AACCACAGCTGCTGTAGGTAATGGAGCGGAAGAGATCACTCTTTCCGACACAGATTCTGGTATCGGAGATGATGTAT

CCGATACAGCGTCTTCATCTGGGGATGAATCCGGAGGAGTCTCCTCTCCCTCTTCAGAATCCAATAAAAATACTGCC

GTTGGAAATGACGGACCTTCTGGACTAGATATCCTCGCTGCCGTACGTAAACATTTAGATAAGGTTTACCCTGGCGA

CAATGGTGGTTCTACAGAAGGGCCTCTCCAAGCTAACCAAACTCTTGGAGATATCGTCCAGGATATGGAAACAACAG

GGACATCCCAAGAAACCGTTGTATCCCCATGGAAAGGAAGCACTTCTTCAACGGAATCAGCAGGAGGAAGTGGTAGC

GTACAAACACTACTGCCTTCACCACCTCCAACCCCGTCAACTACAACATTAAGAACGGGCACAGGAGCTACCACCAC

ATCCTTGATGATGGGAGGACCAATCAAAGCTGACATAATAACAACTGGTGGCGGAGGACGAATTCCTGGAGGAGGAA

CGTTAGAAAAGCTGCTCCCTCGTATACGTGCGCACTTAGACATATCCTTTGATGCGCAAGGCGATCTCGTAAGTACT

GAAGAGCCTCAGCTTGGCTCGATTGTAAACAAATTCCGCCAAGAAACTGGTTCAAGAGGAATCTTAGCTTTCGTTGA

GAGTGCTCCAGGCAAGCCGGGATCTGCACAGGTCTTAACGGGTACAGGGGGAGATAAAGGCAACCTATTCCAAGCAG

CTGCCGCAGTCACCCAAGCCTTAGGAAATGTTGCAGGGAAAGTCAACCTTGCGATACAAGGCCAAAAACTATCATCC

CTAGTCAATGACGACGGGAAGGGGTCTGTTGGAAGAGATTTATTCCAAGCAGCAGCCCAAACAACTCAAGTGCTAAG

CGCACTGATTGATACCGTAGGA

```
SEQUENCE LISTING

SEQ ID NO: 76 - CT456 fragment protein sequence
TNSAATSSIQTTGETVVNYTNSASAPNVTVSTSSSSTQATATSNKTSQAVAGKITSPDTSESSETSSTSSSDHIPSD

YDDVGSNSGDISNNYDDVGSNNGDISSNYDDAAADYEPIRTTENIYESIGGSRTSGPENTSGGAAAALNSLRGSSYS

NYDDAAADYEPIRTTENIYESIGGSRTSGPENTSGGAAAALNSLRGSSYSNYDDAAADYEPIRTTENIYESIGGSRT

SGPENTSDGAAAAALNSLRGSSYTTGPRNEGVFGPGPEGLPDMSLPSYDPTNKTSLLTFLSNPHVKSKMLENSGHFV

FIDTDRSSFILVPNGNWDQVCSIKVQNGKTKEDLDIKDLENMCAKFCTGFSKFSGDWDSLVEPMVSAKAGVASGGNL

PNTVIINNKFKTCVAYGPWNSQEASSGYTPSAWRRGHRVDFGGIFEKANDFNKINWGTQAGPSSEDDGISFSNETPG

AGPAAAPSPTPSSIPIINVNVNVGGTNVNIGDTNVNTTNTTPTTQSTDASTDTSDIDDINTNNQTDDINTTDKDSDG

AGGVNGDISETESSSGDDSGSVSSSESDKNASVGNDGPAMKDILSAVRKHLDVVYPGENGGSTEGPLPANQTLGDVI

SDVENKGSAQDTKLSGNTGAGDDDPTTTAAVGNGAEEITLSDTDSGIGDDVSDTASSSGDESGGVSSPSSESNKNTA

VGNDGPSGLDILAAVRKHLDKVYPGDNGGSTEGPLQANQTLGDIVQDMETTGTSQETVVSPWKGSTSSTESAGGSGS

VQTLLPSPPPTPSTTTLRTGTGATTTSLMMGGPIKADIITTGGGGRIPGGGTLEKLLPRIRAHLDISFDAQGDLVST

EEPQLGSIVNKFRQETGSRGILAFVESAPGKPGSAQVLTGTGGDKGNLFQAAAAVTQALGNVAGKVNLAIQGQKLSS

LVNDDGKGSVGRDLFQAAAQTTQVLSALIDTVG

SEQ ID NO: 77: CT381 fragment nucleotide sequence
TGTTTAAAAGAAGGGGGAGACTCCAATAGTGAAAAATTTATTGTAGGGACTAATGCAACCTACCCTCCTTTTGAGTT

TGTTGATAAGCGAGGAGAGGTTGTAGGCTTCGATATAGACTTGGCTAGAGAGATTAGTAACAAGCTGGGGAAAACGC

TGGACGTTCGGGAGTTTTCCTTTGATGCACTCATTCTAAACCTAAAACAGCATCGGATTGATGCGGTTATAACAGGG

ATGTCCATTACTCCTTCTAGATTGAAGGAAATTCTTATGATTCCCTATTATGGGGAGGAAATAAAACACTTGGTTTT

AGTGTTTAAAGGAGAGAATAAGCATCCATTGCCACTCACTCAATATCGTTCTGTAGCTGTTCAAACAGGAACCTATC

AAGAGGCCTATTTACAGTCTCTTTCTGAAGTTCATATTCGCTCTTTTGATAGCACTCTAGAAGTACTCATGGAAGTC

ATGCATGGTAAATCTCCCGTCGCTGTTTTAGAGCCATCTATCGCTCAAGTTGTCTTGAAAGATTTCCCGGCTCTTTC

TACAGCAACCATAGATCTCCCTGAAGATCAGTGGGTTTTAGGATACGGGATTGGCGTTGCTTCAGATCGCCCAGCTT

TAGCCTTGAAAATCGAGGCAGCTGTGCAAGAGATCCGAAAAGAAGGAGTGCTAGCAGAGTTGGAACAGAAGTGGGGT

TTGAACAAC

SEQ ID NO: 78: CT381 fragment protein sequence
CLKEGGDSNSEKFIVGTNATYPPFEFVDKRGEVVGFDIDLAREISNKLGKTLDVREFSFDALILNLKQHRIDAVITG

MSITPSRLKEILMIPYYGEEIKHLVLVFKGENKHPLPLTQYRSVAVQTGTYQEAYLQSLSEVHIRSFDSTLEVLMEV

MHGKSPVAVLEPSIAQVVLKDFPALSTATIDLPEDQWVLGYGIGVASDRPALALKIEAAVQEIRKEGVLAELEQKWG

LNN

SEQ ID NO: 79: CT043 fragment nucleotide sequence
TCCAGGCAGAATGCTGAGGAAAATCTAAAAAATTTTGCTAAAGAGCTTAAACTCCCCGACGTGGCCTTCGATCAGAA

TAATACGTGCATTTTGTTTGTTGATGGAGAGTTTTCTCTTCACCTGACCTACGAAGAACACTCTGATCGCCTTTATG

TTTACGCACCTCTTCTTGACGGACTGCCAGACAATCCGCAAAGAAGGTTAGCTCTATATGAGAAGTTGTTAGAAGGC

TCTATGCTCGGAGGCCAAATGGCTGGTGGAGGGGTAGGAGTCGCTACTAAGGAACAGTTGATCTTAATGCACTGCGT

GTTAGACATGAAGTATGCAGAGACCAACCTACTCAAAGCTTTTGCACAGCTTTTTATTGAAACCGTTGTGAAATGGC

GAACTGTTTGTTCTGATATCAGCGCTGGACGAGAACCCACTGTTGATACCATGCCACAAATGCCTCAAGGGGGTGGC

GGAGGAATTCAACCTCCTCCAGCAGGAATCCGTGCA

SEQ ID NO: 80: CT043 fragment protein sequence
SRQNAEENLKNFAKELKLPDVAFDQNNTCILFVDGEFSLHLTYEEHSDRLYVYAPLLDGLPDNPQRRLALYEKLLEG

SMLGGQMAGGGVGVATKEQLILMHCVLDMKYAETNLLKAFAQLFIETVVKWRTVCSDISAGREPTVDTMPQMPQGGG

GGIQPPPAGIRA
```

-continued

SEQUENCE LISTING

SEQ ID NO: 81: CT711 fragment nucleotide.seq Length: 2298
TCAATACAACCTACATCCATTTCTTTAACTAAGAATATAACGGCAGCTTTAGCCGGAGAGCAGGTCGATGCTGCTGC

AGTGTATATGCCGCAGGCTGTTTTTTTCTTTCAGCAACTGGATGAAAAAAGCAAGGGGCTGAAACAGGCTTTAGGAT

TGCTCGAAGAGGTTGATCTAGAAAAATTTATACCGTCTTTAGAAAAATCACCTACACCTATCACTACGGGAACAACG

AGTAAAATTTCCGCTGATGGGATTGAGATTGTTGGAGAGCTTTCTTCAGAAACAATTTTGGCAGATCCTAATAAAGC

TGCAGCTCAGGTTTTTGGAGAGGGGCTTGCAGATAGTTTTGATGATTGGCTCAGATTATCTGAAAATGGGGGGATTC

AAGATCCTACAGCAATAGAAGAAGAGATTGTTACTAAGTATCAAACAGAACTCAATACTCTGCGCAATAAACTCAAG

CAACAATCTTTAACAGACGATGAGTATACGAAGCTTTATGCTATTCCTCAAAACTTTGTTAAAGAGATAGAAAGCTT

AAAGAATGAAAATAATGTGAGGTTAATTCCCAAAAGTAAAGTCACTAACTTTTGGCAGAATATCATGCTCACTTACA

ACTCGGTAACCTCGTTATCAGAACCTGTTACCGATGCGATGAATACGACTATGGCGGAGTACTCTCTTTATATTGAG

AGAGCTACAGAGGCTGCCAAGTTGATACGGGAGATAACCAACACGATCAAAGACATTTTCAATCCAGTTTGGGATGT

GCGTGAACAAACAGGAATTTTTGGGTTAAAAGGAGCTGAGTATAACGCTTTAGAAGGCAATATGATTCAAAGCTTGC

TTAGCTTTGCGGGTCTATTCCGGCAGTTAATGAGTCGTACTGCAACAGTTGATGAGATAGGCGCACTTTATCCTAAA

AATGATAAAAACGAAGACGTCATTCATACTGCTATTGATGATTATGTGAATTCTTTAGCTGATTTGAAAGCCAATGA

ACAGGTCAAACTCAACGGTCTGTTGAGTTTAGTATATGCTTATTATGCTAGTACTTTAGGTTTTGCTAAGAAGGATG

TATTCAATAATGCACAAGCTTCTTTTACAGATTATACTAATTTTCTAAACCAAGAGATCCAATATTGGACGCCTAGA

GAGACTTCAAGTTTTAATATCTCCAATCAAGCATTGCAAACCTTTAAAAATAAGCCTTCGGCTGATTATAACGGCGT

ATATCTTTTTGATAATAAAGGATTAGAGACTAATCTCTTTAATCCTACGTTCTTCTTTGATGTTGTGAGTCTCATGA

CAGCTGATCCTACGAAGACTATGTCTCGACAGGATTACAATAAGGTGATTACAGCCTCGGAATCCAGTATTCAGAAG

ATTAATCAGGCTATTACCGCTTGGGAACTAGCTATTGCAGAATGTGGGACTAAAAAAGCGAAGCTCGAACCATCCAG

TTTAAATTATTTTAATGCTATGGTCGAAGCGAAGAAGACCTTCGTAGAGACCTCTCCAATACAGATGGTCTATTCAT

CTTTGATGTTGGATAAGTATCTTCCGAATCAGCAGTACATATTAGAGACATTAGGAAGTCAGATGACTTTCTCTAAC

AAGGCTGCTCGGTATTTAAATGATATCATTGCGTATGCAGTTAGCTTCCAAACAGCTGACGTCTATTATTCTTTAGG

GATGTATCTTCGACAAATGAACCAGCAGGAATTTCCTGAGGTGATTTCTCGTGCTAACGATACTGTGAAAAAAGAGA

TAGATCGGAGTCGTGCGGATCTCTTTCACTGTAAAAAAGCTATCGAAAAGATTAAAGAATTAGTGACTTCTGTAAAT

GCGGATACTGAATTGACCTCATCTCAGCGTGCAGAGTTATTAGAGACGTTAGCTAGTTATGCTTTTGAATTTGAGAA

TCTCTATCACAACCTCTCTAATGTTTACGTCATGGTTTCTAAGGTACAGATTTCTGGCGTAAGCAAGCCTGATGAAG

TGGATGAGGCTTTTACTGCTAAGATTGGATCGAAGGAATTCGATACTTGGATTCAGCAGCTTACAACATTTGAAAGT

GCTGTGATTGAAGGTGGGCGTAATGGTGTGATGCCTGGGGGAGAGCAGCAGGTTTTACAGAGTTTAGAGAGCAAGCA

GCAAGATTACACGTCGTTCAACCAGAATCAGCAATTAGCTCTACAAATGGAGTCCGCAGCGATTCAACAAGAGTGGA

CTATGGTAGCAGCAGCCTTAGCATTAATGAATCAGATTTTTGCTAAGTTGATCCGTAGATTTAAA

SEQ ID NO: 82: CT711 fragment protein sequence (AAC68306)
SIQPTSISLTKNITAALAGEQVDAAAVYMPQAVFFFQQLDEKSKGLKQALGLLEEVDLEKFIPSLEKSPTPITTGTT

SKISADGIEIVGELSSETILADPNKAAAQVFGEGLADSFDDWLRLSENGGIQDPTAIEEEIVTKYQTELNTLRNKLK

QQSLTDDEYTKLYAIPQNFVKEIESLKNENNVRLIPKSKVTNFWQNIMLTYNSVTSLSEPVTDAMNTTMAEYSLYIE

RATEAAKLIREITNTIKDIFNPVWDVREQTGIFGLKGAEYNALEGNMIQSLLSFAGLFRQLMSRTATVDEIGALYPK

NDKNEDVIHTAIDDYVNSLADLKANEQVKLNGLLSLVYAYYASTLGFAKKDVFNNAQASFTDYTNFLNQEIQYWTPR

ETSSFNISNQALQTFKNKPSADYNGVYLFDNKGLETNLFNPTFFFDVVSLMTADPTKTMSRQDYNKVITASESSIQK

INQAITAWELAIAECGTKKAKLEPSSLNYFNAMVEAKKTFVETSPIQMVYSSLMLDKYLPNQQYILETLGSQMTFSN

KAARYLNDIIAYAVSFQTADVYYSLGMYLRQMNQQEFPEVISRANDTVKKEIDRSRADLFHCKKAIEKIKELVTSVN

-continued

SEQUENCE LISTING

ADTELTSSQRAELLETLASYAFEFENLYHNLSNVYVMVSKVQISGVSKPDEVDEAFTAKIGSKEFDTWIQQLTTFES

AVIEGGRNGVMPGGEQQVLQSLESKQQDYTSFNQNQQLALQMESAAIQQEWTMVAAALALMNQIFAKLIRRFK

SEQ ID NO: 83: CT114 fragment nucleotide sequence—Length: 1296
GATCCTTTGAGTGCAAAACAGTTAATGTATCTGTTTCCTCAGCTCTCAGAAGAGGATGTATCTGTTTTTGCTCGATG

CATTTTGTCTTCAAAGCGTCCAGAATACCTCTTTTCAAAATCGGAGGAAGAGCTCTTTGCAAAATTGATTTTGCCAA

GGGTTTCTCTAGGTGTTCATCGGGACGATGATTTAGCGAGAGTGTTGGTGTTAGCGGAGCCTTCTGCAGAAGAGCAG

AAGGCTCGATACTATTCATTGTATCTGGATGTTTTAGCTTTGCGTGCATACGTTGAAAGAGAGCGTTTGGCGAGTGC

TGCACACGGAGATCCTGAGCGGATAGATTTGGCAACCATAGAAGCTATTAATACCATCCTTTTTCAGGAAGAAGGAT

GGAGGTATCCTTCAAAACAAGAGATGTTTGAAAACAGGTTTTCTGAGTTAGCTGCTGTTACAGATAGTAAGTTTGGA

GTTTGCTTGGGAACTGTAGTGCTTTATCAAGCTGTCGCCCAGCGGCTTGATTTGTCTCTGGACCCTGTCACCCCTCC

TGGACATATTTACTTACGCTATAAGGACAAGGTGAATATTGAAACCACTTCTGGAGGAAGGCATCTTCCTACTGAAA

GGTATTGTGAATGCATAAAAGAGTCGCAGTTAAAGGTGCGTTCGCAGATGGAGCTTATAGGGTTAACTTTTATGAAT

AGAGGAGCTTTCTTTTTGCAAAAAGGAGAGTTTCTTCAGGCGTCCTTAGCTTATGAGCAAGCTCAATCATATTTATC

AGACGAGCAGATTTCTGATTTGTTAGGGATTACTTATGTTCTTTTAGGAAAGAAGGCGGCGGGAGAGGCTCTTTTAA

AGAAATCTGCAGAAAAGACTCGGCGAGGGTCATCTATCTATGACTATTTCCAAGGATATATTTCCCCCGAAATCCTA

GGGGTGTTGTTTGCCGATTCAGGGGTGACCTATCAAGAAACTTTGGAGTATCGAAAAAAACTAGTGATGCTTTCCAA

GAAGTATCCAAAAAGTGGATCTCTTAGGTTGAGGTTGGCGACAACAGCATTGGAGCTAGGGCTGGTCAAGGAGGGGG

TGCAGTTGTTAGAAGAGAGTGTTAAGGATGCCCCAGAGGACCTCTCTTTACGTCTGCAGTTTTGTAAAATTCTTTGC

AATCGACATGATTATGTCCGAGCAAAATATCATTTTGATCAAGCGCAAGCTCTTCTCATTAAAGAAGGGTTGTTTTC

CGAAAAAACTTCCTATACTCTCTTAAAAACTATCGGGAAAAAGCTATCTCTTTTTGCTCCGAGT

SEQ ID NO: 84: CT114 fragment protein sequence (AAC67705)
DPLSAKQLMYLFPQLSEEDVSVFARCILSSKRPEYLFSKSEEELFAKLILPRVSLGVHRDDDLARVLVLAEPSAEEQ

KARYYSLYLDVLALRAYVERERLASAAHGDPERIDLATIEAINTILFQEEGWRYPSKQEMFENRFSELAAVTDSKFG

VCLGTVVLYQAVAQRLDLSLDPVTPPGHIYLRYKDKVNIETTSGGRHLPTERYCECIKESQLKVRSQMELIGLTFMN

RGAFFLQKGEFLQASLAYEQAQSYLSDEQISDLLGITYVLLGKKAAGEALLKKSAEKTRRGSSIYDYFQGYISPEIL

GVLFADSGVTYQETLEYRKKLVMLSKKYPKSGSLRLRLATTALELGLVKEGVQLLEESVKDAPEDLSLRLQFCKILC

NRHDYVRAKYHFDQAQALLIKEGLFSEKTSYTLLKTIGKKLSLFAPS

SEQ ID NO: 85: CT480 fragment nucleotide sequence
TCTTCAGATCTACTTGAAAAAGATGTGAAATCGATCAAAAGAGAACTCAAGGCTTTACATGAAGATGTTCTTGAGTT

AGTCCGGATCTCGCATCAGCAAAAAAATTGGGTCCAGTCTACAGATTTTTCTGTTTCTCCAGAGATCAGTGTATTGA

AGGATTGCGGAGATCCTGCGTTCCCTAATTTATTATGCGAAGACCCCTTATGTTGAAAAAGTGGTCCCTTCGTTGTTA

AAGGAAGGTTTTGTTCCGAAAGGTATTTTGCGTACAGCTCAAGTAGGAAGGCCTGATAACCTAAGTCCGTTTAATGG

CTTTGTTAATATCGTTCGATTTTATGAATTGTGCGTTCCTAATTTGGCTGTTGAGCATGTTGGTAAATACGAGGAGT

TTGCGCCTAGTTTAGCCTTAAAGATAGAAGAGCATTATGTAGAGGATGGGTCTGGGGATAAAGAATTTCATATTTAT

TTGCGTCCTAATATGTTTTGGGAGCCGATAGATCCTACGCTGTTCCCTAAAAATATAACTTTAGCAGACAGCTTCTT

AAGACCACATCCTGTCACCGCTCATGATGTGAAGTTCTATTACGATGTAGTCATGAATCCCTATGTTGCAGAAATGC

GTGCAGTGGCTATGAGATCTTATTTTGAGGATATGGTTTCGGTTCGGGTAGAAAACGATTTGAAATTAATCGTTCGT

TGGAGAGCTCATACTGTACGTAATGAACAGGGAGAGGAAGAGAAAAAAGTGCTCTATTCTGCTTTCGCGAATACATT

GGCACTCCAACCGTTACCTTGTTTCGTGTATCAGCATTTCGCAAATGGAGAGAAGATCGTTCCAGAAGATTCTGATC

CCGATACGTATCGCAAAGATTCGGTATGGGCGCAAAACTTTTCTTCACATTGGGCGTATAATTACATAGTGAGCTGT

-continued

SEQUENCE LISTING

GGAGCATTCCGATTTGCAGGGATGGATGATGAGAAAATTACTTTAGTTCGTAATCCTAATTATCATAATCCGTTTGC

GGCTCTTGTGGAGAAGCGCTATATCTATATGAAAGATAGTACAGATTCTCTCTTCCAAGATTTCAAAGCTGGGAAGG

TGGATATTGCGTATTTCCCTCCTAACCATGTCGATAATCTAGCGAGCTTCATGCAAACCTCTGCTTATAAGGAACAA

GCTGCTAGAGGAGAGGCAATTTTAGAAAAAAATTCATCAGACCGGTCCTATTCTTACATCGGATGGAATTGTCTTTC

TCTTTTCTTTAACAATCGTTCGGTACGACAAGCCATGAATATGTTGATCGATCGGGATCGCATTATTGAGCAGTGCT

TGGATGGTCGTGGAGTCTCTGTGAGTGGGCCTTTTTCTCTCTGCTCTCCATCATACAACAGAGATGTAGAGGGATGG

CAATACTCTCCGGAAGAGGCCGCACGTAAATTAGAGGAAGAGGGCTGGATCGATGCTGATGGAGATGGTATTCGTGA

GAAAGTAATCGATGGAGTTGTAGTGCCTTTCCGTTTCCGGTTATGCTACTATGTGAAAAGTGTAACAGCACGAACGA

TTGCCGAATATGTAGCTACGGTATGTAAAGAGGTGGGTATCGAGTGTTGCTTACTCGGGTTAGATATGGCGGATTAT

TCACAAGCCCTCGAGGAGAAAAATTTCGATGCTATTCTTTCCGGATGGTGTTTAGGAACCCCTCCAGAAGATCCTCG

TGCTCTATGGCATTCGGAAGGAGCTTTGGAGAAAGGATCTGCCAATGCTGTTGGATTTTGTAATGAGGAAGCAGACC

GTATCATCGAACAGCTCAGTTACGAGTATGATTCTAATAAGCGCCAAGCCTTGTATCACCGTTTTCACGAGGTGATT

CATGAGGAATCTCCTTACGCGTTTCTCTATTCAAGACAGTACTCCCTTGTCTATAAGGAGTTTGTAAAAAATATTTT

TGTGCCAACAGAACATCAGGATTTGATTCCTGGAGCTCAAGATGAGACAGTGAATTTATCCATGTTGTGGGTAGATA

AAGAGGAGGGTCGATGCTCCGCTATATCT

SEQ ID NO: 86: CT480/oppA_4 fragment protein sequence (AAC68080)
SSDLLEKDVKSIKRELKALHEDVLELVRISHQQKNWVQSTDFSVSPEISVLKDCGDPAFPNLLCEDPYVEKVVPSLL

KEGFVPKGILRTAQVGRPDNLSPFNGFVNIVRFYELCVPNLAVEHVGKYEEFAPSLALKIEEHYVEDGSGDKEFHIY

LRPNMFWEPIDPTLFPKNITLADSFLRPHPVTAHDVKFYYDVVMNPYVAEMRAVAMRSYFEDMVSVRVENDLKLIVR

WRAHTVRNEQGEEEKKVLYSAFANTLALQPLPCFVYQHFANGEKIVPEDSDPDTYRKDSVWAQNFSSHWAYNYIVSC

GAFRFAGMDDEKITLVRNPNYHNPFAALVEKRYIYMKDSTDSLFQDFKAGKVDIAYFPPNHVDNLASFMQTSAYKEQ

AARGEAILEKNSSDRSYSYIGWNCLSLFFNNRSVRQAMNMLIDRDRIIEQCLDGRGVSVSGPFSLCSPSYNRDVEGW

QYSPEEAARKLEEEGWIDADGDGIREKVIDGVVVPFRFRLCYYVKSVTARTIAEYVATVCKEVGIECCLLGLDMADY

SQALEEKNFDAILSGWCLGTPPEDPRALWHSEGALEKGSANAVGFCNEEADRIIEQLSYEYDSNKRQALYHRFHEVI

HEESPYAFLYSRQYSLVYKEFVKNIFVPTEHQDLIPGAQDETVNLSMLWVDKEEGRCSAIS

SEQ ID NO: 87: CT089 fragment nucleotide.sequence-Length: 1194
GCTGCAGCTACTCAAGATGCACAAGAGGTTATCGGCTCTCAGGAAGCTTCTGAGGCAAGTATGCTCAAAGGATGTGA

GGATCTCATAAATCCTGCAGCTGCAACCCGAATCAAAAAAAAAGGAGAGAAGTTTGAATCATTAGAAGCTCGTCGCA

AACCAACAGCGGATAAAGCAGAAAAGAAATCCGAGAGCACAGAGGAAAAAGGCGATACTCCTCTTGAAGATCGTTTC

ACAGAAGATCTTTCCGAAGTCTCCGGAGAAGATTTTCGAGGATTGAAAAATTCGTTCGATGATGATTCTTCTCCTGA

CGAAATTCTCGATGCGCTCACAAGTAAATTTTCTGATCCCACAATAAAGGATCTAGCTCTTGATTATCTAATTCAAA

CAGCTCCCTCTGATGGGAAACTTAAGTCCACTCTCATTCAGGCAAAGCATCAACTGATGAGCCAGAATCCTCAGGCG

ATTGTTGGAGGACGCAATGTTCTGTTAGCTTCAGAAACCTTTGCTTCCAGAGCAAATACATCTCCTTCATCGCTTCG

CTCCTTATATTTCCAAGTAACCTCATCCCCCTCTAATTGCGCTAATTTACATCAAATGCTTGCTTCTTACTTGCCAT

CAGAGAAAACCGCTGTTATGGAGTTTCTAGTAAATGGCATGGTAGCAGATTTAAAATCGGAGGGCCCTTCCATTCCT

CCTGCAAAATTGCAAGTATATATGACGGAACTAAGCAATCTCCAAGCCTTACACTCTGTAAATAGCTTTTTTGATAG

AAATATTGGGAACTTGGAAAATAGCTTAAAGCATGAAGGACATGCCCCTATTCCATCCTTAACGACAGGAAATTTAA

CTAAAACCTTCTTACAATTAGTAGAAGATAAATTCCCTTCCTCTTCCAAAGCTCAAAAGGCATTAAATGAACTGGTA

GGCCCAGATACTGGTCCTCAAACTGAAGTTTTAAACTTATTCTTCCGCGCTCTTAATGGCTGTTCGCCTAGAATATT

CTCTGGAGCTGAAAAAAAACAGCAGCTGGCATCGGTTATCACAAATACGCTAGATGCGATAAATGCGGATAATGAGG

-continued

SEQUENCE LISTING

ATTATCCTAAACCAGGTGACTTCCCACGATCTTCCTTCTCTAGTACGCCTCCTCATGCTCCAGTACCTCAATCTGAG

ATTCCAACGTCACCTACCTCAACACAGCCTCCATCACCC

SEQ ID NO: 88: CT089/lcrE fragment protein sequence (AAC67680)
AAATQDAQEVIGSQEASEASMLKGCEDLINPAAATRIKKKGEKFESLEARRKPTADKAEKKSESTEEKGDTPLEDRF

TEDLSEVSGEDFRGLKNSFDDDSSPDEILDALTSKFSDPTIKDLALDYLIQTAPSDGKLKSTLIQAKHQLMSQNPQA

IVGGRNVLLASETFASRANTSPSSLRSLYFQVTSSPSNCANLHQMLASYLPSEKTAVMEFLVNGMVADLKSEGPSIP

PAKLQVYMTELSNLQALHSVNSFFDRNIGNLENSLKHEGHAPIPSLTTGNLTKTFLQLVEDKFPSSSKAQKALNELV

GPDTGPQTEVLNLFFRALNGCSPRIFSGAEKKQQLASVITNTLDAINADNEDYPKPGDFPRSSFSSTPPHAPVPQSE

IPTSPTSTQPPSP

SEQ ID NO: 89: CT734 fragment nucleotide sequence-Length: 591
TGTTGCGCCAACTCTTATGGATCGACTCTTGCAAAAAATACAGCCGAGATAAAAGAAGAATCTGTTACACTTCGCGA

GAAGCCGGATGCCGGCTGTAAAAAGAAATCTTCTTGTTACTTGAGAAAATTTTTCTCGCGCAAGAAACCTAAAGAGA

AGACAGAGCCTGTGTTGCCGAACTTTAAGTCTTACGCAGATCCAATGACAGATTCCGAAAGAAAAGACCTTTCTTTC

GTAGTATCTGCTGCTGCTGATAAGTCTTCTATTGCTTTGGCTATGGCTCAGGGGGAAATTAAAGGCGCATTATCGCG

TATTAGAGAGATCCATCCTCTTGCATTGTTACAAGCTCTTGCAGAAGATCCTGCTTTAATTGCTGGAATGAAAAAGA

TGCAAGGACGGGATTGGGTCTGGAATATCTTTATCACAGAATTAAGCAAAGTTTTTTCTCAAGCAGCATCTTTAGGG

GCTTTCAGCGTTGCAGACGTTGCCGCGTTCGCGTCGACCTTAGGATTAGACTCGGGGACCGTTACCTCAATTGTTGA

TGGGGAAAGGTGGGCTGAGCTGATCGATGTCGTGATTCAGAACCCTGCTATA

SEQ ID NO: 90: CT734 fragment protein sequence (AAC68329)
CCANSYGSTLAKNTAEIKEESVTLREKPDAGCKKKSSCYLRKFFSRKKPKEKTEPVLPNFKSYADPMTDSERKDLSF

VVSAAADKSSIALAMAQGEIKGALSRIREIHPLALLQALAEDPALIAGMKKMQGRDWVWNIFITELSKVFSQAASLG

AFSVADVAAFASTLGLDSGTVTSIVDGERWAELIDVVIQNPAI

SEQ ID NO: 91: CT016 fragment nucleotide sequence
AAAGTTAAAATTAATGATCAGTTCATTTGTATTTCCCCATACATTTCTGCTCGATGGAATCAGATAGCTTTCATAGA

GTCTTGTGATGGAGGGACGGAAGGGGGTATTACTTTGAAACTCCATTTAATTGATGGAGAGACAGTCTCTATACCTA

ATCTAGGACAAGCGATTGTTGATGAGGTGTTCCAAGAGCACTTGCTATATTTAGAGTCCACAGCTCCTCAGAAAAAC

AAGGAAGAGGAAAAAATTAGCTCTTTGTTAGGAGCTGTTCAACAAATGGCTAAAGGATGCGAAGTACAGGTTTTTTC

TCAAAAGGGCTTGGTTTCTATGTTACTAGGAGGAGCTGGTTCGATTAATGTGTTGTTGCAACATTCTCCAGAACATA

AGGATCATCCTGATCTTCCTACCGATTTACTGGAGAGGATAGCGCAAATGATGCGTTCATTATCTATAGGACCAACT

TCTATTTTAGCTAAGCCAGAGCCTCATTGCAACTGTTTGCATTGTCAAATTGGACGAGCTACAGTGGAAGAAGAGGA

TGCCGGAGTATCGGATGAGGATCTTACTTTTCGTTCATGGGATATCTCTCAAAGTGGAGAAAAGATGTACACTGTTA

CAGATCCTTTGAATCCAGAAGAGCAGTTTAATGTGTATTTAGGAACGCCGATTGGATGCACATGTGGGCAGCCATAC

TGTGAACACGTGAAAGCTGTTCTTTATACT

SEQ ID NO: 92: CT016 fragment protein sequence (AAC67606)
KVKINDQFICISPYISARWNQIAFIESCDGGTEGGITLKLHLIDGETVSIPNLGQAIVDEVFQEHLLYLESTAPQKN

KEEEKISSLLGAVQQMAKGCEVQVFSQKGLVSMLLGGAGSINVLLQHSPEHKDHPDLPTDLLERIAQMMRSLSIGPT

SILAKPEPHCNCLHCQIGRATVEEEDAGVSDEDLTFRSWDISQSGEKMYTVTDPLNPEEQFNVYLGTPIGCTCGQPY

CEHVKAVLYT

SEQ ID NO: 93: CM homolog of CT279 = TC_0551 fragment nucleotide sequence
GCATCCAAGTCTCGTCATTATCTTAACCAGCCTTGGTACATTATCTTATTCATCTTTGTTCTTAGTCTGGTTGCTGG

TACCCTTCTTTCTTCAGTTTCCTATGTTCTATCTCCAATCCAAAAACAAGCTGCAGAATTTGATCGTAATCAGCAAA

TGTTGATGGCCGCACAAATTATTTCCTATGACAATAAATTCCAAATATATGCTGAAGGGGATTGGCAACCTGCTGTC

-continued

SEQUENCE LISTING

TATAATACAAAAAAACAGATACTAGAAAAAAGCTCTTCCACTCCACCACAAGTGACTGTGGCGACTCTATGCTCTTA

TTTTCAAAATTTTGTTAGAGTTTTGCTTACAGACTCCCAAGGGAATCTTTCTTCTTTTGAAGATCACAATCTTAACC

TAGAAGAGTTCTTATCCCACCCCACATCTTCAGTACAAGATCACTCTCTGCATGTAATTTATGCTATTCTAGCAAAC

GATGAATCCTCTAAAAAGTTATCATCCTCCCAAGTAGCAAAAAATCCGGTATCCATAGAGTCTATTATTCTTCCTAT

AAAAGGATTTGGTTTATGGGGACCAATCTATGGATTTCTTGCTTTAGAAAAGGACGGTAATACGGTTCTAGGGACAT

GCTGGTATCAACATGGTGAGACTCCAGGATTAGGAGCAAATATAACTAATCCCCAATGGCAACAAAATTTCAGAGGA

AAAAAAGTATTTCTCGCTTCCTCTTCCGGAGAAACCGATTTTGCTAAAACAACTCTAGGACTAGAAGTTATAAAAGG

ATCTGTTTCTGCATTATTAGGGGACTCTCCCAAAGCTAATTCCGCTGTTGATGGAATTTCAGGAGCTACACTGACCT

GTAATGGAGTTACTGAAGCTTTTGCTAATTCGCTAGCTCCTTACCGCCCCTTATTGACTTTCTTCGCCAATCTTAAC

TCTAGTGGAGAATCTCATGACAACCAA

SEQ ID NO: 94: CM homologue of CT279 = TC_0551 fragment protein sequence
ASKSRHYLNQPWYIILFIFVLSLVAGTLLSSVSYVLSPIQKQAAEFDRNQQMLMAAQIISYDNKFQIYAEGDWQPAV

YNTKKQILEKSSSTPPQVTVATLCSYFQNFVRVLLTDSQGNLSSFEDHNLNLEEFLSHPTSSVQDHSLHVIYAILAN

DESSKKLSSSQVAKNPVSIESIILPIKGFGLWGPIYGFLALEKDGNTVLGTCWYQHGETPGLGANITNPQWQQNFRG

KKVFLASSSGETDFAKTTLGLEVIKGSVSALLGDSPKANSAVDGISGATLTCNGVTEAFANSLAPYRPLLTFFANLN

SSGESHDNQ

SEQ ID NO: 95: CM homologue of CT372 = TC_0651 fragment nucleotide sequence
AATGGAAAAGTTCTGTGTGAGGTTTCTGTGTCCTTCCGTTCGATTCTGCTGACGGCTCTGCTTTCACTTTCTTTTAC

AAACACTATGCAGGCTGCACACCATCATTATCACCGTTATGATGATAAACTACGCAGACAATACCATAAAAAGGACT

TGCCCACTCAAGAGAATGTTCGGAAAGAGTTTTGTAATCCCTACTCTCATAGTAGTGATCCTATCCCTTTGTCACAA

CAACGAGGAGTCCTATCTCCTATCTGTGATTTAGTCTCAGAGTGCTCGTTTTTGAACGGGATTTCCGTTAGGAGTCT

TAAACAAACACTGAAAAATTCTGCTGGGACTCAAGTTGCTTTAGACTGGTCTATCCTTCCTCAATGGTTCAATCCTA

GATCCTCTTGGGCTCCTAAGCTCTCTATTCGAGATCTTGGATATGGTAAACCCCAGTCCCTTATTGAAGCAGATTCC

CCTTGTTGTCAAACCTGCTTCAACCCATCTGCTGCTATTACGATTTACGATTCTTCATGTGGGAAGGGTGTTGTCCA

AGTGTCATACACCCTTGTTCGTTATTGGAGAGAAACGGCTGCACTTGCAGGGCAAACTATGATGCTTGCAGGAAGTA

TTAATGATTATCCTGCTCGCCAAAACATATTCTCTCAACTTACATTTTCCCAAACTTTCCCTAATGAGAGAGTAAAT

CTAACTGTTGGTCAATACTCTCTTTACTCGATAGACGGAACGCTGTACAACAATGATCAGCAGCTAGGATTTATTAG

TTATGCGTTGTCGCAAAATCCAACAGCGACTTATTCCTCTGGAAGCCTTGGCGCCTATCTACAAGTCGCTCCAACAG

AAAGCACCTGTCTTCAAGTTGGGTTCCAAGATGCCTATAATATTTCAGGTTCCTCGATCAAATGGAATAATCTTACA

AAAAATAAGTATAACTTCCATGGCTATGCATCTTGGGCTCCACACTGTTGCTTAGGACCTGGACAATACTCTGTTCT

TCTTTATGTAACCAGAAAGGTTCCTGAGCAAATGATGCAGACAATGGGCTGGTCTGTGAATGCAAGTCAATACATCT

CTTCTAAACTTTATGTATTTGGAAGATACAGCGGAGTCACAGGCCAATTGTCTCCTATTAACCGAACCTATTCATTT

GGCTTAGTCTCTCCTAATTTATTGAACCGTAACCCACAAGACTTATTTGGAGTAGCTTGCGCATTCAATAATATACA

CGCCTCCGCCTTTCAAAATGCTCAAAGAAAATATGAAACTGTGATCGAGGGATTTGCAACTATTGGTTGCGGACCTT

ACATCTCCTTTGCTCCAGATTTCCAACTTTACCTCTATCCTGCTCTGCGTCCAAATAAACAAAGCGCCCGAGTCTAT

AGCGTTCGCGCAAACCTAGCTATT

SEQ ID NO: 96: CM homologue of CT372 = TC_0651 fragment protein sequence
NGKVLCEVSVSFRSILLTALLSLSFTNTMQAAHHHYHRYDDKLRRQYHKKDLPTQENVRKEFCNPYSHSSDPIPLSQ

QRGVLSPICDLVSECSFLNGISVRSLKQTLKNSAGTQVALDWSILPQWFNPRSSWAPKLSIRDLGYGKPQSLIEADS

PCCQTCFNPSAAITIYDSSCGKGVVQVSYTLVRYWRETAALAGQTMMLAGSINDYPARQNIFSQLTFSQTFPNERVN

LTVGQYSLYSIDGTLYNNDQQLGFISYALSQNPTATYSSGSLGAYLQVAPTESTCLQVGFQDAYNISGSSIKWNNLT

KNKYNFHGYASWAPHCCLGPGQYSVLLYVTRKVPEQMMQTMGWSVNASQYISSKLYVFGRYSGVTGQLSPINRTYSF
GLVSPNLLNRNPQDLFGVACAFNNIHASAFQNAQRKYETVIEGFATIGCGPYISFAPDFQLYLYPALRPNKQSARVY
SVRANLAI

SEQ ID NO: 97: CM homologue of CT443 = TC_0727 fragment nucleotide sequence
AGCGGGGTGTTAGAGACCTCTATGGCAGAGTCTCTCTCTACCAACGTTATTAGCTTAGCTGACACCAAAGCGAAAGA
GACCACTTCTCATCAAAAAGACAGAAAAGCAAGAAAAAATCATCAAAATAGGACTTCCGTAGTCCGTAAAGAGGTTA
CTGCAGTTCGTGATACTAAAGCTGTAGAGCCTAGACAGGATTCTTGCTTTGGCAAAATGTATACAGTCAAAGTTAAT
GATGATCGTAATGTAGAAATCGTGCAGTCCGTTCCTGAATATGCTACGGTAGGATCTCCATATCCTATTGAGATTAC
TGCTATAGGGAAAAGAGACTGTGTTGATGTAATCATTACACAGCAATTACCATGCGAAGCAGAGTTTGTTAGCAGTG
ATCCAGCTACTACTCCTACTGCTGATGGTAAGCTAGTTTGGAAAATTGATCGGTTAGGACAGGGCGAAAAGAGTAAA
ATTACTGTATGGGTAAAACCTCTTAAAGAAGGTTGCTGCTTTACAGCTGCAACGGTTTGTGCTTGTCCAGAGATCCG
TTCGGTTACGAAATGTGGCCAGCCTGCTATCTGTGTTAAACAGGAAGGTCCAGAAAGCGCATGTTTGCGTTGCCCAG
TAACTTATAGAATTAATGTAGTCAACCAAGGAACAGCAACAGCACGTAATGTTGTTGTGGAAAATCCTGTTCCAGAT
GGCTATGCTCATGCATCCGGACAGCGTGTATTGACATATACTCTTGGGGATATGCAACCTGGAGAACAGAGAACAAT
CACCGTGGAGTTTTGTCCGCTTAAACGTGGTCGAGTCACAAATATTGCTACAGTTTCTTACTGTGGTGGACACAAAA
ATACTGCTAGCGTAACAACAGTGATCAATGAGCCTTGCGTGCAAGTTAACATCGAGGGAGCAGATTGGTCTTATGTT
TGTAAGCCTGTAGAATATGTTATCTCTGTTTCTAACCCTGGTGACTTAGTTTTACGAGACGTTGTAATTGAAGATAC
GCTTTCTCCTGGAATAACTGTTGTTGAAGCAGCTGGAGCTCAGATTTCTTGTAATAAATTGGTTTGGACTTTGAAGG
AACTCAATCCTGGAGAGTCTTTACAATATAAGGTTCTAGTAAGAGCTCAAACTCCAGGGCAATTCACAAACAACGTT
GTTGTGAAAAGTTGCTCTGATTGCGGTATTTGTACTTCTTGCGCAGAAGCAACAACTTACTGGAAAGGAGTTGCTGC
TACTCATATGTGCGTAGTAGATACTTGTGATCCTATTTGCGTAGGAGAGAACACTGTTTATCGTATCTGTGTGACAA
ACAGAGGTTCTGCTGAAGATACAAATGTGTCCTTAATTTTGAAATTCTCTAAAGAATTACAACCTATATCTTTCTCT
GGACCAACTAAAGGAACCATTACAGGAAACACGGTAGTGTTTGATTCGTTACCTAGATTAGGTTCTAAAGAAACTGT
AGAGTTTTCTGTAACGTTGAAAGCAGTATCCGCTGGAGATGCTCGTGGGGAAGCTATTCTTTCTTCCGATACATTGA
CAGTTCCTGTATCTGATACGGAGAATACACATATCTAT SEQ ID NO: 98: CM homologue of CT443 = TC_0727 fragment protein sequence
SGVLETSMAESLSTNVISLADTKAKETTSHQKDRKARKNHQNRTSVVRKEVTAVRDTKAVEPRQDSCFGKMYTVKVN
DDRNVEIVQSVPEYATVGSPYPIEITAIGKRDCVDVIITQQLPCEAEFVSSDPATTPTADGKLVWKIDRLGQGEKSK
ITVWVKPLKEGCCFTAATVCACPEIRSVTKCGQPAICVKQEGPESACLRCPVTYRINVVNQGTATARNVVVENPVPD
GYAHASGQRVLTYTLGDMQPGEQRTITVEFCPLKRGRVTNIATVSYCGGHKNTASVTTVINEPCVQVNIEGADWSYV
CKPVEYVISVSNPGDLVLRDVVIEDTLSPGITVVEAAGAQISCNKLVWTLKELNPGESLQYKVLVRAQTPGQFTNNV
VVKSCSDCGICTSCAEATTYWKGVAATHMCVVDTCDPICVGENTVYRICVTNRGSAEDTNVSLILKFSKELQPISFS
GPTKGTITGNTVVFDSLPRLGSKETVEFSVTLKAVSAGDARGEAILSSDTLTVPVSDTENTHIY SEQ ID NO: 99: CM homologue of CT043 = TC_0313 fragment nucleotide sequence
TCCAGACAGAATGCTGAGGAAAATCTAAAAAATTTTGCTAAAGAGCTCAAGCTCCCCGACGTGGCCTTCGATCAGAA
TAATACGTGCATTTTGTTTGTTGATGGAGAGTTTTCTCTTCACCTGACCTACGAAGAGCACTCTGATCGCCTTTATG
TTTACGCACCTCTCCTTGACGGACTCCCAGATAATCCGCAAAGAAAGTTGGCTCTGTATGAGAAATTGTTGGAAGGC
TCTATGCTCGGAGGCCAAATGGCTGGTGGAGGAGTAGGAGTTGCTACTAAAGAACAGTTGATCCTAATGCATTGCGT -continued

SEQUENCE LISTING

GTTAGATATGAAATATGCAGAGACTAATCTATTGAAAGCTTTTGCACAGCTTTTCATTGAAACTGTTGTGAAATGGC

GAACGGTCTGTTCTGATATCAGCGCTGGACGAGAACCTTCCGTTGACACTATGCCTCAAATGCCTCAAGGAGGCAGC

GGAGGAATTCAACCTCCTCCAACAGGAATTCGTGCG

SEQ ID NO: 100: CM homologue of CT043 = TC_0313 fragment protein sequence
SRQNAEENLKNFAKELKLPDVAFDQNNTCILFVDGEFSLHLTYEEHSDRLYVYAPLLDGLPDNPQRKLALYEKLLEG

SMLGGQMAGGGVGVATKEQLILMHCVLDMKYAETNLLKAFAQLFIETVVKWRTVCSDISAGREPSVDTMPQMPQGGS

GGIQPPPTGIRA

SEQ ID NO: 101: CM homologue of CT601 = TC_0890 fragment nucleotide sequence
CTCGCTAATCGGTTATTTCTAATCACCCTTATAGGTTTTGGCTATTCTGCTTACGGTGCCAGCACAGGGAAATCACC

TTCTTTACAGGTTATTTTAGCTGAAGTCGAGGATACATCTTCGCGCTTACAAGCTCATCAGAATGAGCTTGTTATGC

TCTCGGAACGTTTAGATGAGCAAGACACAAAACTTCAACAACTCTCGTCAACTCAGGCCCGTAATCTTCCTCAACAA

GTTCAACGGCTTGAGATTGATCTGAGAGCTCTGGCTAAAACAGCTGCTGTGCTCTCGCAATCTGTTCAGGATATCCG

ATCATCCGTGCAAAATAAATTACAAGAAATCCAACAAGAACAAAAAAATTTAGCTCAAAATTTACGAGCGCTTCGCA

ACTCCTTACAAGCACTAGTTGATGGCTCTTCCCCAGAAAATTATATTGATTTTTTGGCCGGGGAGACACCTGAACAT

ATTCACGTTGTTAAACAAGGAGAAACCCTGAGTAAAATCGCTAGTAAGTACAATATCCCTGTCGCAGAATTGAAAAA

ACTTAATAAATTAAATTCCGATACTATTTTTACTGATCAAAGAATCCGACTTCCAAAAAAGAAA

SEQ ID NO: 102: CM homologue of CT601 = TC_0890 fragment protein sequence
LANRLFLITLIGFGYSAYGASTGKSPSLQVILAEVEDTSSRLQAHQNELVMLSERLDEQDTKLQQLSSTQARNLPQQ

VQRLEIDLRALAKTAAVLSQSVQDIRSSVQNKLQEIQQEQKNLAQNLRALRNSLQALVDGSSPENYIDFLAGETPEH

IHVVKQGETLSKIASKYNIPVAELKKLNKLNSDTIFTDQRIRLPKKK

SEQ ID NO: 103: CM homologue of CT456 = TC_0741 fragment nucleotide sequence
ACGACTCCAATAAGTAATTCTCCATCTTCTATTCCAACTGTTACAGTATCAACTACTACAGCATCTTCTGGATCTCT

CGGAACTTCTACTGTATCATCAACGACTACAAGTACTTCAGTCGCACAAACAGCAACAACAACATCTTCTGCTTCTA

CATCTATAATTCAGTCTAGTGGAGAAAACATCCAATCCACTACAGGTACCCCTTCTCCTATTACGTCTAGTGTTTCA

ACATCCGCTCCATCTCCTAAAGCCTCCGCCACTGCAAACAAAACTTCAAGCGCTGTTTCTGGGAAAATTACCTCACA

AGAAACTTCTGAGGAATCCGAAACCCAAGCCACTACATCTGATGGAGAAGTTAGTAGTAATTACGATGATGTTGATA

CCCCGACCAATTCGTCCGATTCGACAGTTGATAGTGATTACCAAGATGTTGAGACTCAGTACAAAACAATTAGCAAC

AATGGTGAAAACACTTATGAAACAATCGGAAGTCATGGTGAGAAAAACACACACGTCCAGGAAAGCCATGCATCCGG

AACAGGAAATCCCATAAATAATCAGCAAGAAGCTATTAGACAGCTCCCGATCATCTACCTATACAACCAGCCCTCGTA

ATGAGAATATATTTAGTCCAGGACCGGAAGGTCTACCTAATATGTCTCTTCCTAGTTACAGCCCTACAGATAAAAGT

TCTCTACTAGCTTTCCTATCTAATCCCAATACAAAAGCAAAAATGCTCGAACACTCCGGGCATTTAGTCTTTATAGA

CACAACTAGAAGTAGCTTTATCTTTGTTCCGAATGGAAATTGGGATCAAGTCTGTTCCATGAAGGTTCAGAATGGGA

AAACTAAAGAAGACCTTGGCTTAAAGGACTTAGAAGATATGTGTGCAAAGTTTTGCACAGGATACAATAAATTCTCC

TCTGATTGGGGAAATCGAGTTGACCCCTTGGTCTCTTCTAAGGCCGGGATAGAAAGTGGGGGGCACCTCCCAAGCTC

AGTTATCATCAACAACAAATTTAGAACCTGIGTTGCCTATGGGCCGTGGAACCCCAAAGAAAACGGCCCCAATTATA

CTCCTTCAGCCTGGAGACGTGGGCATCGAGTAGATTTTGGAAAGATCTTTGATGGAACAGCGCCGTTTAATAAAATC

AACTGGGGCTCTTCCCCTACCCCTGGTGATGACGGCATCTCCTTCTCTAATGAAACTATTGGGTCTGAACCATTCGC

GACACCTCCCTCATCCCCATCGCAAACCCCCGTTATCAACGTCAATGTTAATGTCGGTGGAACCAATGTTAATATTG

GGGATACAAACGTATCTAAAGGATCCGGCACACCAACATCTTCTCAATCTGTGGACATGTCTACAGATACTAGCGAT

TTAGATACCAGTGATATTGATACAAACAACCAAACTAACGGCGATATCAACACGAATGACAACTCCAATAATGTCGA

TGGAAGTTTATCTGACGTTGATTCAAGGGTGGAAGACGATGACGGTGTATCGGATACAGAGTCCACTAATGGCAATG

-continued

SEQUENCE LISTING

ACTCTGGTAAAACTACTTCCACAGAAGAAAATGGTGACCCAAGCGGACCAGACATCCTGGCTGCTGTACGTAAACAC

CTAGACACTGTCTATCCAGGAGAAAATGGCGGATCTACAGAAGGACCTCTCCCTGCTAATCAAAATCTGGGGAACGT

TATCCATGATGTGGAGCAGAATGGATCTGCTAAAGAAACTATTATCACTCCAGGAGATACAGGGCCTACAGACTCAA

GCTCCTCTGTAGATGCTGATGCAGACGTTGAAGATACTTCTGATACTGACTCTGGAATCGGAGACGACGACGGTGTA

TCGGATACAGAGTCCACTAATGGTAATAACTCTGGTAAAACTACTTCCACAGAAGAAAATGGTGACCCAAGCGGACC

AGACATCCTGGCTGCTGTACGTAAACACCTAGACACTGTCTATCCAGGAGAAAATGGCGGATCTACAGAAGGACCTC

TCCCTGCTAATCAAAATCTGGGGAACGTTATCCATGATGTAGAACAAAACGGAGCCGCTCAAGAAACTATTATCACT

CCAGGAGATACGGAATCTACAGACACAAGCTCTAGTGTAAATGCTAATGCAGACTTAGAAGATGTTTCTGATGCTGA

TTCAGGATTCGGGGATGATGACGGTATATCGGATACAGAGTCCACTAATGGTAACGACTCTGGAAAAAAATACTCCTG

TAGGGGATGGTGGTACACCAAGCGGACCAGATATCCTAGCTGCTGTACGCAAACATCTAGACACTGTCTATCCAGGA

GAAAATGGTGGATCTACAGAGAGACCTTTACCCGCTAATCAAAATTTAGGAGATATCATTCATGATGTAGAACAAAA

CGGAAGCGCTAAAGAAACTGTAGTATCGCCTTATCGAGGAGGAGGAGGAAATACATCTTCCCCAATTGGATTAGCCT

CCCTGCTTCCAGCAACACCATCCACACCTTTGATGACAACACCTAGAACAAATGGGAAAGCTGCAGCTTCTTCTTTG

ATGATAAAAGGAGGAGAAACTCAAGCCAAGCTAGTTAAGAATGGCGGCAATATCCCTGGAGAAACCACATTAGCAGA

ATTACTCCCTCGTTTAAGAGGACACCTTGACAAAGTCTTTACTTCAGACGGGAAGTTTACAAATCTTAATGGACCTC

AACTTGGAGCCATCATAGACCAATTCCGCAAAGAAACGGGTTCCGGAGGAATCATAGCTCATACAGATAGTGTTCCA

GGAGAGAACGGAACAGCCTCTCCTCTCACAGGAAGTTCAGGGGAAAAAGTCTCTCTCTATGATGCAGCGAAAAACGT

CACTCAAGCTTTAACAAGTGTTACGAACAAAGTAACCCTAGCAATGCAAGGACAAAAACTGGAAGGAATTATAAACA

ACAACAATACCCCCTCTTCTATTGGACAAAATCTTTTCGCAGCAGCGAGGGCAACGACACAATCCCTCAGTTCATTA

ATTGGAACCGTACAA

SEQ ID NO: 104: CM homologue of CT456 = TC_0741 fragment protein sequence
TTPISNSPSSIPTVTVSTTTASSGSLGTSTVSSTTTSTSVAQTATTTSSASTSIIQSSGENIQSTTGTPSPITSSVS

TSAPSPKASATANKTSSAVSGKITSQETSEESETQATTSDGEVSSNYDDVDTPTNSSDSTVDSDYQDVETQYKTISN

NGENTYETIGSHGEKNTHVQESHASGTGNPINNQQEAIRQLRSSTYTTSPRNENIFSPGPEGLPNMSLPSYSPTDKS

SLLAFLSNPNTKAKMLEHSGHLVFIDTTRSSFIFVPNGNWDQVCSMKVQNGKTKEDLGLKDLEDMCAKFCTGYNKFS

SDWGNRVDPLVSSKAGIESGGHLPSSVIINNKFRTCVAYGPWNPKENGPNYTPSAWRRGHRVDFGKIFDGTAPFNKI

NWGSSPTPGDDGISFSNETIGSEPFATPPSSPSQTPVINVNVNVGGTNVNIGDTNVSKGSGTPTSSQSVDMSTDTSD

LDTSDIDTNNQTNGDINTNDNSNNVDGSLSDVDSRVEDDDGVSDTESTNGNDSGKTTSTEENGDPSGPDILAAVRKH

LDTVYPGENGGSTEGPLPANQNLGNVIHDVEQNGSAKETIITPGDTGPTDSSSSVDADADVEDTSDTDSGIGDDDGV

SDTESTNGNNSGKTTSTEENGDPSGPDILAAVRKHLDTVYPGENGGSTEGPLPANQNLGNVIHDVEQNGAAQETIIT

PGDTESTDTSSSVNANADLEDVSDADSGFGDDDGISDTESTNGNDSGKNTPVGDGGTPSGPDILAAVRKHLDTVYPG

ENGGSTERPLPANQNLGDIIHDVEQNGSAKETVVSPYRGGGGNTSSPIGLASLLPATPSTPLMTTPRTNGKAAASSL

MIKGGETQAKLVKNGGNIPGETTLAELLPRLRGHLDKVFTSDGKFTNLNGPQLGAIIDQFRKETGSGGIIAHTDSVP

GENGTASPLIGSSGEKVSLYDAAKNVTQALTSVTNKVTLAMQGQKLEGIINNNNTPSSIGQNLFAAARATTQSLSSL

IGTVQ

SEQ ID NO: 105: CM homologue of CT381 = TC_0660 fragment nucleotide sequence
TGTTCAAAAGAGAGCAAAGACTCTGTTAGTGAAAAATTTATTGTAGGAACTAACGCAACGTATCCTCCTTTTGAGTT

TGTTGATGAAAGAGGTGAGACGGTTGGCTTTGATATTGATTTAGCTAGGGAGATTAGTAAAAAGCTAGGGAAAAAAT

TAGAAGTCCGAGAATTTGCTTTTGATGCACTCGTTCTCAATTTAAAACAGCATCGTATTGATGCAATTATGGCAGGG

GTGTCCATTACGTCTTCTCGATTGAAAGAAATTTTGATGATTCCCTACTATGGCGAAGAAATAAAGAGTTTGGTTTT

SEQUENCE LISTING

AGTGTTTAAGGATGGAGACTCAAAGTCTTTACCACTAGATCAGTATAATTCTGTTGCTGTTCAAACTGGCACGTACC

AAGAGGAATATTTACAGTCTCTTCCAGGGGTGCGTATTCGCTCTTTTGATAGTACTTTAGAAGTGCTTATGGAAGTT

TTGCATAGCAAGTCTCCTATAGCTGTTTTAGAACCGTCTATTGCGCAGGTCGTTTTAAAAGATTTTCCGACGCTCAC

TACTGAAACGATAGATCTTCCTGAAGATAAATGGGTTTTAGGGTATGGAATTGGAGTTGCTTCTGATCGACCATCTC

TAGCTTCTGATATAGAAGCTGCTGTACAAGAGATCAAGAAAGAAGGAGTGTTAGCAGAGTTAGAGCAAAAATGGGGT

TTGAACGGC

SEQ ID NO: 106: CM homologue of CT381 = TC_0660 fragment protein sequence
CSKESKDSVSEKFIVGTNATYPPFEFVDERGETVGFDIDLAREISKKLGKKLEVREFAFDALVLNLKQHRIDAIMAG

VSITSSRLKEILMIPYYGEEIKSLVLVFKDGDSKSLPLDQYNSVAVQTGTYQEEYLQSLPGVRIRSFDSTLEVLMEV

LHSKSPIAVLEPSIAQVVLKDFPTLTTETIDLPEDKWVLGYGIGVASDRPSLASDIEAAVQEIKKEGVLAELEQKWG

LNG

SEQ ID NO: 107 - CT255 fragment nucleotide sequence
GAAGAAAAAGGCATCTTACAATTGGTTGAAATTTCGCGAGCAATGGCTTTACAGGGAGTTTGTCCTTGGACTAATTT

ACAGAGTGTGGAGTCTATGTTGCAGTATATAGCAGGGGAGTGTCAGGAGTTGGCTGATGCTGTACAAGAAAATAAAG

CTTCGTTGGAAATCGCTTCGGAAGCCGGAGACGTACTTACTTTAGTATTGACCTTGTGTTTCTTGCTAGAAAGAGAA

GGAAAGCTTAAAGCTGAAGAAGTATTTGTAGAAGCTTTGGCTAAGTTGCGTCGTCGATCTCCTCATGTTTTTGATCC

TCATAATCAAATTTCTTTAGAACAGGCTGAAGAATACTGGGCTCGTATGAAACAGCAAGAAAAAATTTCT

SEQ ID NO: 108 - CT255 fragment protein sequence
EEKGILQLVEISRAMALQGVCPWTNLQSVESMLQYIAGECQELADAVQENKASLEIASEAGDVLTLVLTLCFLLERE

GKLKAEEVFVEALAKLRRRSPHVFDPHNQISLEQAEEYWARMKQQEKIS

SEQ ID NO: 109 - CT341 fragment nucleotide sequence
GATTACTACACGATATTGGGTGTAGCGAAGACTGCTACTCCTGAAGAAATAAAGAAAGCTTACCGTAAGCTCGCTGT

AAAGTACCATCCAGATAAGAATCCTGGGGATGCTGAAGCGGAGCGACGCTTTAAAGAAGTTTCTGAAGCCTATGAAG

TATTAGGTGATGCGCAGAAGCGGGAGTCATATGATCGTTACGGCAAAGACGGTCCATTTGCTGGTGCTGGAGGATTC

GGTGGCGCTGGCATGGGGAATATGGAAGACGCTTTGCGAACATTTATGGGAGCTTTTGGCGGCGATTTCGGTGGTAA

TGGAGGCGGTTTCTTTGAAGGGCTTTTTGGAGGACTTGGAGAAGCTTTCGGAATGCGTGGAGGCTCAGAAAGTTCTC

GACAAGGAGCTAGTAAGAAGGTGCATATTACGCTGTCCTTCGAGGAGGCGGCAAAAGGTGTTGAAAAAGAACTTCTT

GTTTCAGGCTATAAATCTTGTGATGCTTGTTCTGGTAGTGGAGCCAATACTGCTAAAGGTGTAAAAGTTTGTGATCG

ATGCAAGGGCTCTGGTCAGGTAGTGCAAAGCCGAGGCTTTTTCTCCATGGCTTCTACTTGCCCTGATTGTAGTGGTG

AAGGTCGGGTTATCACAGATCCTTGTTCAGTTTGTCGTGGGCAGGGACGTATCAAGGATAAACGTAGCGTCCATGTT

AATATCCCAGCTGGAGTCGATTCTGGGATGAGATTAAAGATGGAAGGCTATGGAGATGCTGGCCAAAATGGAGCGCC

TGCAGGGGATCTGTATGTTTTTATTGATGTAGAGCCTCATCCTGTTTTCGAGCGCCATGGGGATGATTTAGTTTTAG

AGCTTCCTATTGGATTTGTTGATGCGGCTTTAGGGATCAAGAAGGAAATCCCTACACTCTTAAAAGAAGGTACTTGC

CGTTTGAGTATCCCAGAAGGGATTCAGAGCGGAACAGTTCTTAAAGTTAGAGGGCAGGGATTCCCTAATGTGCATGG

GAAATCCAGAGGAGATCTTTTAGTAAGAGTATCTGTGGAGACTCCCCAGCACCTATCTAATGAACAAAAAGATTTAT

TGAGACAGTTTGCTGCTACGGAGAAGGCTGAAAATTTCCCTAAGAAACGGAGTTTCTTAGACAAAATCAAAGGTTTT

TTTTCTGACTTTGCTGTA

SEQ ID NO: 110 - CT341 fragment protein sequence
DYYTILGVAKTATPEEIKKAYRKLAVKYHPDKNPGDAEAERRFKEVSEAYEVLGDAQKRESYDRYGKDGPFAGAGGF

GGAGMGNMEDALRTFMGAFGGDFGGNGGGFFEGLFGGLGEAFGMRGGSESSRQGASKKVHITLSFEEAAKGVEKELL

VSGYKSCDACSGSGANTAKGVKVCDRCKGSGQVVQSRGFFSMASTCPDCSGEGRVITDPCSVCRGQGRIKDKRSVHV

-continued

SEQUENCE LISTING

NIPAGVDSGMRLKMEGYGDAGQNGAPAGDLYVFIDVEPHPVFERHGDDLVLELPIGFVDAALGIKKEIPTLLKEGTC

RLSIPEGIQSGTVLKVRGQGFPNVHGKSRGDLLVRVSVETPQHLSNEQKDLLRQFAATEKAENFPKKRSFLDKIKGF

FSDFAV

SEQ ID NO: 111 - CT716 fragment nucleotide sequence
AATAAAAAACTCCAAGATCTGTCTAAACTGCTCACTATTGAGCTTTTCAAGAAACGTACACGGTTGGAAACAGTAAA

AAAAGCGCTCTCCACAATAGAACATCGCTTACAACAAATACAGGAGCACATCGCGAAAATTTCCTTAACAAGGCACA

AACAATTCCTATGTCGGTCATATACCCATGAATATGACCAACATTTAGAACATTTACAAAGAGAGCAAACTTCTCTA

TATAAACAGCATCAGACCCTGAAAACGTCTTTGAAAGATGCTTATGGCGACATACAAAAACAACTAGACCAAAGAAA

AATTATCGAAAAGATCCATGACAGTAAATATCCTATAAAGAGCGCGAATAAC

SEQ ID NO: 112 - CT716 fragment protein sequence
NKKLQDLSKLLTIELFKKRTRLETVKKALSTIEHRLQQIQEHIAKISLTRHKQFLCRSYTHEYDQHLEHLQREQTSL

YKQHQTLKTSLKDAYGDIQKQLDQRKIIEKIHDSKYPIKSANN

SEQ ID NO: 113 - CT745 fragment nucleotide sequence
GCGTGGTGGCTACACAAACGATTCCCTCATGTGCAGCTGTCTATTCTAGAAAAAGAGTCTCGATCTGGAGGGCTAAT

TGTCACAGAGAAACAACAAGGGTTTTCCCTCAATATGGGCCCTAAAGGTTTTGTTTTAGCTCATGATGGGCAACACA

CCCTTCACCTCATTCAGTCTTTAGGCCTAGCAGACGAGCTATTATATAGCTCTCCAGAGGCTAAAAACCGCTTTATC

CACTATAATAATAAAACCCGAAAAGTCTCGCCTTGGACTATTTTCAAACAAAATCTCCCTCTCTCTTTTGCTAAGGA

TTTCTTTGCGCGTCCTTACAAACAAGACAGCTCCGTGGAAGCCTTCTTTAAAAGACACAGTTCTTCCAAGCTTAGAA

GAAATCTTTTAAATCCCATTAGCATTGCTATTCGTGCAGGACATAGTCATATATTGTCTGCACAGATGGCTTACCCA

GAATTAACACGAAGAGAAGCTCAAACAGGATCGTTGTTACGTAGTTATCTCAAAGATTTTCCTAAAGAGAAACGCAC

AGGCCCTTATTTAGCTACCTTGCGGTCTGGGATGGGAATGCTAACCCAGGCTTTGCATGATAAATTGCCTGCTACCT

GGTATTTTTCTGCACCCGTCAGCAAAATCCGTCAGTTGGCGAATGGGAAAATTTCTCTTTCATCTCCTCAAGGAGAA

ATAACGGGAGATATGCTCATTTATGCTGGGTCCGTGCACGATCTCCCTTCCTGTCTAGAAGGGATCCCTGAAACCAA

GCTTATCAAGCAAACGACTTCATCTTGGGATCTCTCTTGTGTATCTTTAGGATGGCATGCATCCTTCCCTATCCCTC

ATGGATATGGCATGCTTTTCGCTGATACGCCTCCCTTATTAGGGATCGTGTTTAATACGGAAGTGTTCCCTCAACCC

GAGCGGCCTAATACAATAGTCTCTCTTCTTTTAGAAGGTCGATGGCACCAAGAAGAAGCGTATGCTTTCTCACTAGC

AGCTATTTCTGAGTACCTGCAAATTTACACTCCTCCCCAAGCTTTCTCACTATTCTCTCCTCGAGAGGGACTTCCCC

AACACCATGTTGGATTTATCCAATCCCGCCAACGCCTTCTATCTAAACTTCCTCACAATATAAAAATTGTAGGGCAG

AATTTTGCAGGTCCAGGTCTCAACCGCGCTACAGCGTCTGCTTATAAAGCTATAGCTTCTTTACTATCA

SEQ ID NO: 114 - CT745 fragment protein sequence
AWWLHKRFPHVQLSILEKESRSGGLIVTEKQQGFSLNMGPKGFVLAHDGQHTLHLIQSLGLADELLYSSPEAKNRFI

HYNNKTRKVSPWTIFKQNLPLSFAKDFFARPYKQDSSVEAFFKRHSSSKLRRNLLNPISIAIRAGHSHILSAQMAYP

ELTRREAQTGSLLRSYLKDFPKEKRTGPYLATLRSGMGMLTQALHDKLPATWYFSAPVSKIRQLANGKISLSSPQGE

ITGDMLIYAGSVHDLPSCLEGIPETKLIKQTTSSWDLSCVSLGWHASFPIPHGYGMLFADTPPLLGIVFNTEVFPQP

ERPNTIVSLLLEGRWHQEEAYAFSLAAISEYLQIYTPPQAFSLFSPREGLPQHHVGFIQSRQRLLSKLPHNIKIVGQ

NFAGPGLNRATASAYKAIASLLS

SEQ ID NO: 115 - CT387 fragment nucleotide sequence
ACGCTCTTTCATTCTCATCATGATGCCGTCTCTCCAGACAGCTACCTATGTTCTTCCCTTCAGTTAGTTGGTACTGG

CGTATACGAAGGAGAAATCGAGATTCAAAATATCCCCTCTTATTTCCTTGGATTCCAATTACCCTCTCATTGCATAC

ACCTTAATTTAAAGAGCTCTCTAGCTCAATTAGGAATAGATGCCTCCCTTCTTCACTGCGAATTGAGCAAAAATCAA

CATCGAGCACATATACATGCTCAATTTACCGGTCATGGCCCCATTGCTGAATCTATGCTAGCCCTTCTCCAACCAGG

AGATCGTGTAGCAAAACTATTTGCTGCAGACGATCGCAGACTGGTCCGATCTCCAGATTACCTCGAAAGCATGCTGA

-continued

SEQUENCE LISTING

AAAATACAGATAAAGCTGGCCATCCTTTGCTCTGTTTTGGGAAAAAATTAGAACACTTGATTTCTTTTGATGTGGTA

GATGATCGCCTTGTCGTCTCCCTTCCTACCCTGCCGGGAGTTGTTCGTTATGATTCGGATATTTATGGACTCCTTCC

TCTTATTCAAAAATCACTCAGTAATCCCAAACTCAGCATTCGTCACTTTTTAGCTCTGTACCAACAGATTGTGGAAG

GGCAACATGTCTCTTGCGGAAACCATATTCTTCTGATCAAAACAGAACCGCTGCACATCCGCACTGTATTTGCTCGC

GTGGTAAATCAACTCCTCCCTCAAGGTCTCTCCCACACTTCTGCCAATATTTTGGAACCAACCACTCGAGAATCCGG

GGATATCTTTGAATTTTTTGGGAACCCTTCTGCACAGATAGAAAGAATTCCTTTAGAATTTTTCACTATCGAACCCT

ATAAAGAACATTCTTACTTCTGTAATCGGGATTTATTACAAACCATCTTACAATCAGAAAGCGAAATCAAAAAAATA

TTCGAAACAGCGCCCAAAGAACCTGTCAAAGCTGCCACCTATTTATCAAAAGGCAGTGAAATCTCTTCCCTGCACAC

AGACTCTTGGCTCACAGGATCCGCAGCTGCCTATCAATATAGTGAGCAAGCAGATAAAAACGAGTACACTCATGCTC

AACCTTGCTATCCTTTCTTAGAAGCAATGGAAATGGGCCTGATCAATAGCGAAGGAGCCTTACTCACTCGTTATTTC

CCTTCAGCTAGCTTAAAAGGAATGTTGATTTCCTACCATGTGCGCCACTATCTCAAACAAATCTACTTTCAAGTTCC

CTCTTATACACATGGAAACTATTTCTCTCATAATGACAGAGGTTTGCTATTAGATCTGCAGCAAGCAGATATTGATG

TTTTCTGGGCAGATGAAGAAAGCGGCCGTGTGTTGCAATATACAAAACGACGCGATAAGAATAGCGGTATGTTCGTG

ATCAAAAATCGTGTTGAAGAGTTTCGATCAGCTTATTTTATTGCTATTTATGGCTCTCGTCTCCTTGAGAATAATTT

CTCTGCTCAGCTCCATACCCTCCTAGCGGGCTTACAGCAAGCAGCACATACTCTCGGCATTCCTGGATTCTCAAAGC

CTACCCCACTTGCAGTCATCACCGGAGGCGGCACTGGAGTTATGGCCACAGGAAATCGTGTAGCTAAAGAACTAGGA

ATCCTATCTTGTGGAACCGTTCTTGATTTAGAAGCTTCTCCAGCACAAATCGACCAACCTACCAATGAATTCTTAGA

TGCTAAAATGACATACCGCCTACCTCAACTTATAGAAAGGCAAGAACACTTTTATGCAGACCTTCCTATCCTTGTAG

TTGGCGGTGTAGGAACCGATTTCGAACTCTACCTAGAACTTGTCTATCTCAAAACAGGAGCTAAACCACCGACTCCC

ATTTTCCTAATTGGACCTATTGAATACTGGAAAGAAAAAGTGGCCCACGCCTACGAGATCAACCTCAAAGCAGGAAC

CATCCGTGGATCCGAATGGATCAGCAACTGCCTATATTGTATCACTTCTCCGGAAGCTGGAATTGCCGTATTCGAAC

AATTCCTAGCTGGAGAACTCCCTATAGGATACGACTATCCTCCAGCTCCAGATGGATTAGTGATCGTC

SEQ ID NO: 116 - CT387 fragment protein sequence
TLFHSHHDAVSPDSYLCSSLQLVGTGVYEGEIEIQNIPSYFLGFQLPSHCIHLNLKSSLAQLGIDASLLHCELSKNQ

HRAHIHAQFTGHGPIAESMLALLQPGDRVAKLFAADDRRLVRSPDYLESMLKNTDKAGHPLLCFGKKLEHLISFDVV

DDRLVVSLPTLPGVVRYDSDIYGLLPLIQKSLSNPKLSIRHFLALYQQIVEGQHVSCGNHILLIKTEPLHIRTVFAR

VVNQLLPQGLSHTSANILEPTTRESGDIFEFFGNPSAQIERIPLEFFTIEPYKEHSYFCNRDLLQTILQSESEIKKI

FETAPKEPVKAATYLSKGSEISSLHTDSWLTGSAAAYQYSEQADKNEYTHAQPCYPFLEAMEMGLINSEGALLTRYF

PSASLKGMLISYHVRHYLKQIYFQVPSYTHGNYFSHNDIRGLLLDLQQADIDVFWADEESGRVLQYTKRRDKNSGMFV

IKNRVEEFRSAYFIAIYGSRLLENNFSAQLHTLLAGLQQAAHTLGIPGFSKPTPLAVITGGGTGVMATGNRVAKELG

ILSCGTVLDLEASPAQIDQPTNEFLDAKMTYRLPQLIERQEHFYADLPILVVGGVGTDFELYLELVYLKTGAKPPTP

IFLIGPIEYWKEKVAHAYEINLKAGTIRGSEWISNCLYCITSPEAGIAVFEQFLAGELPIGYDYPPAPDGLVIV

SEQ ID NO: 117 - CT812 fragment nucleotide sequence
TGCGTAGATCTTCATGCTGGAGGACAGTCTGTAAATGAGCTGGTATATGTAGGCCCTCAAGCGGTTTTATTGTTAGA

CCAAATTCGAGATCTATTCGTTGGGTCTAAAGATAGTCAGGCTGAAGGACAGTATAGGTTAATTGTAGGAGATCCAA

GTTCTTTCCAAGAGAAAGATGCGGATACTCTTCCCGGGAAGGTAGAGCAAAGTACTTTGTTCTCAGTAACCAATCCC

GTGGTTTTCCAAGGTGTGGACCAACAGGATCAAGTCTCTTCCCAAGGGTTAATTTGTAGTTTTACGAGCAGCAACCT

TGATTCTCCTCGTGACGGAGAATCTTTTTTAGGTATTGCTTTTGTTGGGGATAGTAGTAAGGCTGGAATCACATTAA

CTGACGTGAAAGCTTCTTTGTCTGGAGCGGCTTTATATTCTACAGAAGATCTTATCTTTGAAAAGATTAAGGGTGGA

TTGGAATTTGCATCATGTTCTTCTCTAGAACAGGGGGGAGCTTGTGCAGCTCAAAGTATTTTGATTCATGATTGTCA

-continued

SEQUENCE LISTING

AGGATTGCAGGTTAAACACTGTACTACAGCCGTGAATGCTGAGGGGTCTAGTGCGAATGATCATCTTGGATTTGGAG

GAGGCGCTTTCTTTGTTACGGGTTCTCTTTCTGGAGAGAAAAGTCTCTATATGCCTGCAGGAGATATGGTAGTTGCG

AATTGTGATGGGGCTATATCTTTTGAAGGAAACAGCGCGAACTTTGCTAATGGAGGAGCGATTGCTGCCTCTGGGAA

AGTGCTTTTTGTCGCTAATGATAAAAAGACTTCTTTTATAGAGAACCGAGCTTTGTCTGGAGGAGCGATTGCAGCCT

CTTCTGATATTGCCTTTCAAAACTGCGCAGAACTAGTTTTCAAAGGCAATTGTGCAATTGGAACAGAGGATAAAGGT

TCTTTAGGTGGAGGGGCTATATCTTCTCTAGGCACCGTTCTTTTGCAAGGGAATCACGGGATAACTTGTGATAAGAA

TGAGTCTGCTTCGCAAGGAGGCGCCATTTTTGGCAAAAATTGTCAGATTTCTGACAACGAGGGGCCAGTGGTTTTCA

GAGATAGTACAGCTTGCTTAGGAGGAGGCGCTATTGCAGCTCAAGAAATTGTTTCTATTCAGAACAATCAGGCTGGG

ATTTCCTTCGAGGGAGGTAAGGCTAGTTTCGGAGGAGGTATTGCGTGTGGATCTTTTTCTTCCGCAGGTGGTGCTTC

TGTTTTAGGGACCATTGATATTTCGAAGAATTTAGGCGCGATTTCGTTCTCTCGTACTTTATGTACGACCTCAGATT

TAGGACAAATGGAGTACCAGGGAGGAGGAGCTCTATTTGGTGAAAATATTTCTCTTTCTGAGAATGCTGGTGTGCTC

ACCTTTAAAGACAACATTGTGAAGACTTTTGCTTCGAATGGGAAAATTCTGGGAGGAGGAGCGATTTTAGCTACTGG

TAAGGTGGAAATTACTAATAATTCCGAAGGAATTTCTTTTACAGGAAATGCGAGAGCTCCACAAGCTCTTCCAACTC

AAGAGGAGTTTCCTTTATTCAGCAAAAAAGAAGGGCGACCACTCTCTTCAGGATATTCTGGGGGAGGAGCGATTTTA

GGAAGAGAAGTAGCTATTCTCCACAACGCTGCAGTAGTATTTGAGCAAAATCGTTTGCAGTGCAGCGAAGAAGAAGC

GACATTATTAGGTTGTTGTGGAGGAGGCGCTGTTCATGGGATGGATAGCACTTCGATTGTTGGCAACTCTTCAGTAA

GATTTGGTAATAATTACGCAATGGGACAAGGAGTCTCAGGAGGAGCTCTTTTATCTAAAACAGTGCAGTTAGCTGGG

AATGGAAGCGTCGATTTTTCTCGAAATATTGCTAGTTTGGGAGGAGGAGCTCTTCAAGCTTCTGAAGGAAATTGTGA

GCTAGTTGATAACGGCTATGTGCTATTCAGAGATAATCGAGGGAGGGTTTATGGGGGTGCTATTTCTTGCTTACGTG

GAGATGTAGTCATTTCTGGAAACAAGGGTAGAGTTGAATTTAAAGACAACATAGCAACACGTCTTTATGTGGAAGAA

ACTGTAGAAAAGGTTGAAGAGGTAGAGCCAGCTCCTGAGCAAAAAGACAATAATGAGCTTTCTTTCTTAGGGAGAGC

AGAACAGAGTTTTATTACTGCAGCTAATCAAGCTCTTTTCGCATCTGAAGATGGGGATTTATCACCTGAGTCATCCA

TTTCTTCTGAAGAACTTGCGAAAAGAAGAGAGTGTGCTGGAGGAGCTATTTTTGCAAAACGGGTTCGTATTGTAGAT

AACCAAGAGGCCGTTGTATTCTCGAATAACTTCTCTGATATTTATGGCGGCGCCATTTTTACAGGTTCTCTTCGAGA

AGAGGATAAGTTAGATGGGCAAATCCCTGAAGTCTTGATCTCAGGCAATGCAGGGGATGTTGTTTTTTCCGGAAATT

CCTCGAAGCGTGATGAGCATCTTCCTCATACAGGTGGGGGAGCCATTTGTACTCAAAATTTGACGATTTCTCAGAAT

ACAGGGAATGTTCTGTTTTATAACAACGTGGCCTGTTCGGGAGGAGCTGTTCGTATAGAGGATCATGGTAATGTTCT

TTTAGAAGCTTTTGGAGGAGATATTGTTTTTAAAGGAAATTCTTCTTTCAGAGCACAAGGATCCGATGCTATCTATT

TTGCAGGTAAAGAATCGCATATTACAGCCCTGAATGCTACGGAAGGACATGCTATTGTTTTCCACGACGCATTAGTT

TTTGAAAATCTAGAAGAAAGGAAATCTGCTGAAGTATTGTTAATCAATAGTCGAGAAAATCCAGGTTACACTGGATC

TATTCGATTTTTAGAAGCAGAAAGTAAAGTTCCTCAATGTATTCATGTACAACAAGGAAGCCTTGAGTTGCTAAATG

GAGCCACATTATGTAGTTATGGTTTTAAACAAGATGCTGGAGCTAAGTTGGTATTGGCTGCTGGAGCTAAACTGAAG

ATTTTAGATTCAGGAACTCCTGTACAACAAGGGCATGCTATCAGTAAACCTGAAGCAGAAATCGAGTCATCTTCTGA

ACCAGAGGGTGCACATTCTCTTTGGATTGCGAAGAATGCTCAAACAACAGTTCCTATGGTTGATATCCATACTATTT

CTGTAGATTTAGCCTCCTTCTCTTCTAGTCAACAGGAGGGGACAGTAGAAGCTCCTCAGGTTATTGTTCCTGGAGGA

AGTTATGTTCGATCTGGAGAGCTTAATTTGGAGTTAGTTAACACAACAGGTACTGGTTATGAAAATCATGCTTTATT

GAAGAATGAGGCTAAAGTTCCATTGATGTCTTTCGTTGCTTCTGGTGATGAAGCTTCAGCCGAAATCAGTAACTTGT

CGGTTTCTGATTTACAGATTCATGTAGTAACTCCAGAGATTGAAGAAGACACATACGGCCATATGGGAGATTGGTCT

GAGGCTAAAATTCAAGATGGAACTCTTGTCATTAGTTGGAATCCTACTGGATATCGATTAGATCCTCAAAAAGCAGG

SEQUENCE LISTING

GGCTTTAGTATTTAATGCATTATGGGAAGAAGGGGCTGTCTTGTCTGCTCTGAAAAATGCACGCTTTGCTCATAATC

TCACTGCTCAGCGTATGGAATTCGATTATTCTACAAATGTGTGGGGATTCGCCTTTGGTGGTTTCCGAACTCTATCT

GCAGAGAATCTGGTTGCTATTGATGGATACAAAGGAGCTTATGGTGGTGCTTCTGCTGGAGTCGATATTCAATTGAT

GGAAGATTTTGTTCTAGGAGTTAGTGGAGCTGCTTTCCTAGGTAAAATGGATAGTCAGAAGTTTGATGCGGAGGTTT

CTCGGAAGGGAGTTGTTGGTTCTGTATATACAGGATTTTTAGCTGGATCCTGGTTCTTCAAAGGACAATATAGCCTT

GGAGAAACACAGAACGATATGAAAACGCGTTATGGAGTACTAGGAGAGTCGAGTGCTTCTTGGACATCTCGAGGAGT

ACTGGCAGATGCTTTAGTTGAATACCGAAGTTTAGTTGGTCCTGTGAGACCTACTTTTTATGCTTTGCATTTCAATC

CTTATGTCGAAGTATCTTATGCTTCTATGAAATTCCCTGGCTTTACAGAACAAGGAAGAGAAGCGCGTTCTTTTGAA

GACGCTTCCCTTACCAATATCACCATTCCTTTAGGGATGAAGTTTGAATTGGCGTTCATAAAAGGACAGTTTTCAGA

GGTGAACTCTTTGGGAATAAGTTATGCATGGGAAGCTTATCGAAAAGTAGAAGGAGGCGCGGTGCAGCTTTTAGAAG

CTGGGTTTGATTGGGAGGGAGCTCCAATGGATCTTCCTAGACAGGAGCTGCGTGTCGCTCTGGAAAATAATACGGAA

TGGAGTTCTTACTTCAGCACAGTCTTAGGATTAACAGCTTTTTGTGGAGGATTTACTTCTACAGATAGTAAACTAGG

ATATGAGGCGAATACTGGATTGCGATTGATCTTT

SEQ ID NO: 118 - CT812 fragment protein sequence
CVDLHAGGQSVNELVYVGPQAVLLLDQIRDLFVGSKDSQAEGQYRLIVGDPSSFQEKDADTLPGKVEQSTLFSVTNP

VVFQGVDQQDQVSSQGLICSFTSSNLDSPRDGESFLGIAFVGDSSKAGITLTDVKASLSGAALYSTEDLIFEKIKGG

LEFASCSSLEQGGACAAQSILIHDCQGLQVKHCTTAVNAEGSSANDHLGFGGGAFFVTGSLSGEKSLYMPAGDMVVA

NCDGAISFEGNSANFANGGAIAASGKVLFVANDKKTSFIENRALSGGAIAASSDIAFQNCAELVFKGNCAIGTEDKG

SLGGGAISSLGTVLLQGNHGITCDKNESASQGGAIFGKNCQISDNEGPVVFRDSTACLGGGAIAAQEIVSIQNNQAG

ISFEGGKASFGGGIACGSFSSAGGASVLGTIDISKNLGAISFSRTLCTTSDLGQMEYQGGGALFGENISLSENAGVL

TFKDNIVKTFASNGKILGGGAILATGKVEITNNSEGISFTGNARAPQALPTQEEFPLFSKKEGRPLSSGYSGGGAIL

GREVAILHNAAVVFEQNRLQCSEEEATLLGCCGGGAVHGMDSTSIVGNSSVRFGNNYAMGQGVSGGALLSKTVQLAG

NGSVDFSRNIASLGGGALQASEGNCELVDNGYVLFRDNRGRVYGGAISCLRGDVVISGNKGRVEFKDNIATRLYVEE

TVEKVEEVEPAPEQKDNNELSFLGRAEQSFITAANQALFASEDGDLSPESSISSEELAKRRECAGGAIFAKRVRIVD

NQEAVVFSNNFSDIYGGAIFTGSLREEDKLDGQIPEVLISGNAGDVVFSGNSSKRDEHLPHTGGGAICTQNLTISQN

TGNVLFYNNVACSGGAVRIEDHGNVLLEAFGGDIVFKGNSSFRAQGSDAIYFAGKESHITALNATEGHAIVFHDALV

FENLEERKSAEVLLINSRENPGYTGSIRFLEAESKVPQCIHVQQGSLELLNGATLCSYGFKQDAGAKLVLAAGAKLK

ILDSGTPVQQGHAISKPEAEIESSSEPEGAHSLWIAKNAQTTVPMVDIHTISVDLASFSSSQQEGTVEAPQVIVPGG

SYVRSGELNLELVNTTGTGYENHALLKNEAKVPLMSFVASGDEASAEISNLSVSDLQIHVVTPEIEEDTYGHMGDWS

EAKIQDGTLVISWNPTGYRLDPQKAGALVFNALWEEGAVLSALKNARFAHNLTAQRMEFDYSTNVWGFAFGGFRTLS

AENLVAIDGYKGAYGGASAGVDIQLMEDFVLGVSGAAFLGKMDSQKFDAEVSRKGVVGSVYTGFLAGSWFFKGQYSL

GETQNDMKTRYGVLGESSASWTSRGVLADALVEYRSLVGPVRPTFYALHFNPYVEVSYASMKFPGFTEQGREARSFE

DASLTNITIPLGMKFELAFIKGQFSEVNSLGISYAWEAYRKVEGGAVQLLEAGFDWEGAPMDLPRQELRVALENNTE

WSSYFSTVLGLTAFCGGFTSTDSKLGYEANTGLRLIF

SEQ ID NO: 119 - CT812N nucleotide sequence
TGCGTAGATCTTCATGCTGGAGGACAGTCTGTAAATGAGCTGGTATATGTAGGCCCTCAAGCGGTTTTATTGTTAGA

CCAAATTCGAGATCTATTCGTTGGGTCTAAAGATAGTCAGGCTGAAGGACAGTATAGGTTAATTGTAGGAGATCCAA

GTTCTTTCCAAGAGAAAGATGCGGATACTCTTCCCGGGAAGGTAGAGCAAAGTACTTTGTTCTCAGTAACCAATCCC

GTGGTTTTCCAAGGTGTGGACCAACAGGATCAAGTCTCTTCCCAAGGGTTAATTTGTAGTTTTACGAGCAGCAACCT

TGATTCTCCTCGTGACGGAGAATCTTTTTTAGGTATTGCTTTTGTTGGGGATAGTAGTAAGGCTGGAATCACATTAA

-continued

SEQUENCE LISTING

CTGACGTGAAAGCTTCTTTGTCTGGAGCGGCTTTATATTCTACAGAAGATCTTATCTTTGAAAAGATTAAGGGTGGA

TTGGAATTTGCATCATGTTCTTCTCTAGAACAGGGGGGAGCTTGTGCAGCTCAAAGTATTTTGATTCATGATTGTCA

AGGATTGCAGGTTAAACACTGTACTACAGCCGTGAATGCTGAGGGGTCTAGTGCGAATGATCATCTTGGATTTGGAG

GAGGCGCTTTCTTTGTTACGGGTTCTCTTTCTGGAGAGAAAAGTCTCTATATGCCTGCAGGAGATATGGTAGTTGCG

AATTGTGATGGGGCTATATCTTTTGAAGGAAACAGCGCGAACTTTGCTAATGGAGGAGCGATTGCTGCCTCTGGGAA

AGTGCTTTTTGTCGCTAATGATAAAAAGACTTCTTTTATAGAGAACCGAGCTTTGTCTGGAGGAGCGATTGCAGCCT

CTTCTGATATTGCCTTTCAAAACTGCGCAGAACTAGTTTTCAAAGGCAATTGTGCAATTGGAACAGAGGATAAAGGT

TCTTTAGGTGGAGGGGCTATATCTTCTCTAGGCACCGTTCTTTTGCAAGGGAATCACGGGATAACTTGTGATAAGAA

TGAGTCTGCTTCGCAAGGAGGCGCCATTTTTGGCAAAAATTGTCAGATTTCTGACAACGAGGGGCCAGTGGTTTTCA

GAGATAGTACAGCTTGCTTAGGAGGAGGCGCTATTGCAGCTCAAGAAATTGTTTCTATTCAGAACAATCAGGCTGGG

ATTTCCTTCGAGGGAGGTAAGGCTAGTTTCGGAGGAGGTATTGCGTGTGGATCTTTTTCTTCCGCAGGTGGTGCTTC

TGTTTTAGGGACCATTGATATTTCGAAGAATTTAGGCGCGATTTCGTTCTCTCGTACTTTATGTACGACCTCAGATT

TAGGACAAATGGAGTACCAGGGAGGAGGAGCTCTATTTGGTGAAAATATTTCTCTTTCTGAGAATGCTGGTGTGCTC

ACCTTTAAAGACAACATTGTGAAGACTTTTGCTTCGAATGGGAAAATTCTGGGAGGAGGAGCGATTTTAGCTACTGG

TAAGGTGGAAATTACTAATAATTCCGAAGGAATTTCTTTTACAGGAAATGCGAGAGCTCCACAAGCTCTTCCAACTC

AAGAGGAGTTTCCTTTATTCAGCAAAAAAGAAGGGCGACCACTCTCTTCAGGATATTCTGGGGGAGGAGCGATTTTA

GGAAGAGAAGTAGCTATTCTCCACAACGCTGCAGTAGTATTTGAGCAAAATCGTTTGCAGTGCAGCGAAGAAGAAGC

GACATTATTAGGTTGTTGTGGAGGAGGCGCTGTTCATGGGATGGATAGCACTTCGATTGTTGGCAACTCTTCAGTAA

GATTTGGTAATAATTACGCAATGGGACAAGGAGTCTCAGGAGGAGCTCTTTTATCTAAAACAGTGCAGTTAGCTGGG

AATGGAAGCGTCGATTTTTCTCGAAATATTGCTAGTTTGGGAGGAGGAGCTCTTCAAGCTTCTGAAGGAAATTGTGA

GCTAGTTGATAACGGCTATGTGCTATTCAGAGATAATCGAGGGAGGGTTTATGGGGGTGCTATTTCTTGCTTACGTG

GAGATGTAGTCATTTCTGGAAACAAGGGTAGAGTTGAATTTAAAGACAACATAGCAACACGTCTTTATGTGGAAGAA

ACTGTAGAAAAGGTTGAAGAGGTAGAGCCAGCTCCTGAGCAAAAAGACAATAATGAGCTTTCTTTCTTAGGGAGAGC

AGAACAGAGTTTTATTACTGCAGCTAATCAAGCTCTTTTCGCATCTGAAGATGGGGATTTATCACCTGAGTCATCCA

TTTCTTCTGAAGAA

SEQ ID NO: 120: CT812N protein sequence
CVDLHAGGQSVNELVYVGPQAVLLLDQIRDLFVGSKDSQAEGQYRLIVGDPSSFQEKDADTLPGKVEQSTLFSVTNP

VVFQGVDQQDQVSSQGLICSFTSSNLDSPRDGESFLGIAFVGDSSKAGITLTDVKASLSGAALYSTEDLIFEKIKGG

LEFASCSSLEQGGACAAQSILIHDCQGLQVKHCTTAVNAEGSSANDHLGFGGGAFFVTGSLSGEKSLYMPAGDMVVA

NCDGAISFEGNSANFANGGAIAASGKVLFVANDKKTSFIENRALSGGAIAASSDIAFQNCAELVFKGNCAIGTEDKG

SLGGGAISSLGTVLLQGNHGITCDKNESASQGGAIFGKNCQISDNEGPVVFRDSTACLGGGAIAAQEIVSIQNNQAG

ISFEGGKASFGGGIACGSFSSAGGASVLGTIDISKNLGAISFSRTLCTTSDLGQMEYQGGGALFGENISLSENAGVL

TFKDNIVKTFASNGKILGGGAILATGKVEITNNSEGISFTGNARAPQALPTQEEFPLFSKKEGRPLSSGYSGGGAIL

GREVAILHNAAVVFEQNRLQCSEEEATLLGCCGGGAVHGMDSTSIVGNSSVRFGNNYAMGQGVSGGALLSKTVQLAG

NGSVDFSRNIASLGGGALQASEGNCELVDNGYVLFRDNRGRVYGGAISCLRGDVVISGNKGRVEFKDNIATRLYVEE

TVEKVEEVEPAPEQKDNNELSFLGRAEQSFITAANQALFASEDGDLSPESSISSEE

SEQ ID NO: 121: CT812C nucleotide sequence
GAAGAACTTGCGAAAAGAAGAGAGTGTGCTGGAGGAGCTATTTTTGCAAAACGGGTTCGTATTGTAGATAACCAAGA

GGCCGTTGTATTCTCGAATAACTTCTCTGATATTTATGGCGGCGCCATTTTTACAGGTTCTCTTCGAGAAGAGGATA

AGTTAGATGGGCAAATCCCTGAAGTCTTGATCTCAGGCAATGCAGGGGATGTTGTTTTTTCCGGAAATTCCTCGAAG

-continued

SEQUENCE LISTING

CGTGATGAGCATCTTCCTCATACAGGTGGGGGAGCCATTTGTACTCAAAATTTGACGATTTCTCAGAATACAGGGAA

TGTTCTGTTTTATAACAACGTGGCCTGTTCGGGAGGAGCTGTTCGTATAGAGGATCATGGTAATGTTCTTTTAGAAG

CTTTTGGAGGAGATATTGTTTTTAAAGGAAATTCTTCTTTCAGAGCACAAGGATCCGATGCTATCTATTTTGCAGGT

AAAGAATCGCATATTACAGCCCTGAATGCTACGGAAGGACATGCTATTGTTTTCCACGACGCATTAGTTTTTGAAAA

TCTAGAAGAAAGGAAATCTGCTGAAGTATTGTTAATCAATAGTCGAGAAAATCCAGGTTACACTGGATCTATTCGAT

TTTTAGAAGCAGAAAGTAAAGTTCCTCAATGTATTCATGTACAACAAGGAAGCCTTGAGTTGCTAAATGGAGCCACA

TTATGTAGTTATGGTTTTAAACAAGATGCTGGAGCTAAGTTGGTATTGGCTGCTGGAGCTAAACTGAAGATTTTAGA

TTCAGGAACTCCTGTACAACAAGGGCATGCTATCAGTAAACCTGAAGCAGAAATCGAGTCATCTTCTGAACCAGAGG

GTGCACATTCTCTTTGGATTGCGAAGAATGCTCAAACAACAGTTCCTATGGTTGATATCCATACTATTTCTGTAGAT

TTAGCCTCCTTCTCTTCTAGTCAACAGGAGGGGACAGTAGAAGCTCCTCAGGTTATTGTTCCTGGAGGAAGTTATGT

TCGATCTGGAGAGCTTAATTTGGAGTTAGTTAACACAACAGGTACTGGTTATGAAAATCATGCTTTATTGAAGAATG

AGGCTAAAGTTCCATTGATGTCTTTCGTTGCTTCTGGTGATGAAGCTTCAGCCGAAATCAGTAACTTGTCGGTTTCT

GATTTACAGATTCATGTAGTAACTCCAGAGATTGAAGAAGACACATACGGCCATATGGGAGATTGGTCTGAGGCTAA

AATTCAAGATGGAACTCTTGTCATTAGTTGGAATCCTACTGGATATCGATTAGATCCTCAAAAAGCAGGGGCTTTAG

TATTTAATGCATTATGGGAAGAAGGGGCTGTCTTGTCTGCTCTGAAAAATGCACGCTTTGCTCATAATCTCACTGCT

CAGCGTATGGAATTCGATTATTCTACAAATGTGTGGGGATTCGCCTTTGGTGGTTTCCGAACTCTATCTGCAGAGAA

TCTGGTTGCTATTGATGGATACAAAGGAGCTTATGGTGGTGCTTCTGCTGGAGTCGATATTCAATTGATGGAAGATT

TTGTTCTAGGAGTTAGTGGAGCTGCTTTCCTAGGTAAAATGGATAGTCAGAAGTTTGATGCGGAGGTTTCTCGGAAG

GGAGTTGTTGGTTCTGTATATACAGGATTTTTAGCTGGATCCTGGTTCTTCAAAGGACAATATAGCCTTGGAGAAAC

ACAGAACGATATGAAAACGCGTTATGGAGTACTAGGAGAGTCGAGTGCTTCTTGGACATCTCGAGGAGTACTGGCAG

ATGCTTTAGTTGAATACCGAAGTTTAGTTGGTCCTGTGAGACCTACTTTTTATGCTTTGCATTTCAATCCTTATGTC

GAAGTATCTTATGCTTCTATGAAATTCCCTGGCTTTACAGAACAAGGAAGAGAAGCGCGTTCTTTTGAAGACGCTTC

CCTTACCAATATCACCATTCCTTTAGGGATGAAGTTTGAATTGGCGTTCATAAAAGGACAGTTTTCAGAGGTGAACT

CTTTGGGAATAAGTTATGCATGGGAAGCTTATCGAAAAGTAGAAGGAGGCGCGGTGCAGCTTTTAGAAGCTGGGTTT

GATTGGGAGGGAGCTCCAATGGATCTTCCTAGACAGGAGCTGCGTGTCGCTCTGGAAAATAATACGGAATGGAGTTC

TTACTTCAGCACAGTCTTAGGATTAACAGCTTTTTGTGGAGGATTTACTTCTACAGATAGTAAACTAGGATATGAGG

CGAATACTGGATTGCGATTGATCTTT

SEQ ID NO: 122: CT812C protein sequence
EELAKRRECAGGAIFAKRVRIVDNQEAVVFSNNFSDIYGGAIFTGSLREEDKLDGQIPEVLISGNAGDVVFSGNSSK

RDEHLPHTGGGAICTQNLTISQNTGNVLFYNNVACSGGAVRIEDHGNVLLEAFGGDIVFKGNSSFRAQGSDAIYFAG

KESHITALNATEGHAIVFHDALVFENLEERKSAEVLLINSRENPGYTGSIRFLEAESKVPQCIHVQQGSLELLNGAT

LCSYGFKQDAGAKLVLAAGAKLKILDSGTPVQQGHAISKPEAEIESSSEPEGAHSLWIAKNAQTTVPMVDIHTISVD

LASFSSSQQEGTVEAPQVIVPGGSYVRSGELNLELVNTTGTGYENHALLKNEAKVPLMSFVASGDEASAEISNLSVS

DLQIHVVTPEIEEDTYGHMGDWSEAKIQDGTLVISWNPTGYRLDPQKAGALVFNALWEEGAVLSALKNARFAHNLTA

QRMEFDYSTNVWGFAFGGFRTLSAENLVAIDGYKGAYGGASAGVDIQLMEDFVLGVSGAAFLGKMDSQKFDAEVSRK

GVVGSVYTGFLAGSWFFKGQYSLGETQNDMKTRYGVLGESSASWTSRGVLADALVEYRSLVGPVRPTFYALHFNPYV

EVSYASMKFPGFTEQGREARSFEDASLTNITIPLGMKFELAFIKGQFSEVNSLGISYAWEAYRKVEGGAVQLLEAGF

DWEGAPMDLPRQELRVALENNTEWSSYFSTVLGLTAFCGGFTSTDSKLGYEANTGLRLIF

-continued

SEQUENCE LISTING

SEQ ID NO: 123: CT869 fragment nucleotide sequence

AGAGAGGTTCCTTCTAGAATCTTTCTTATGCCCAACTCAGTTCCAGATCCTACGAAAGAGTCGCTATCAAATAAAAT

TAGTTTGACAGGAGACACTCACAATCTCACTAACTGCTATCTCGATAACCTACGCTACATACTGGCTATTCTACAAA

AAACTCCCAATGAAGGAGCTGCTGTCACAATAACAGATTACCTAAGCTTTTTTGATACACAAAAAGAAGGTATTTAT

TTTGCAAAAAATCTCACCCCTGAAAGTGGTGGTGCGATTGGTTATGCGAGTCCCAATTCTCCTACCGTGGAGATTCG

TGATACAATAGGTCCTGTAATCTTTGAAAATAATACTTGTTGCAGACTATTTACATGGAGAAATCCTTATGCTGCTG

ATAAAATAAGAGAAGGCGGAGCCATTCATGCTCAAAATCTTTACATAAATCATAATCATGATGTGGTCGGATTTATG

AAGAACTTTTCTTATGTCCAAGGAGGAGCCATTAGTACCGCTAATACCTTTGTTGTGAGCGAGAATCAGTCTTGTTT

TCTCTTTATGGACAACATCTGTATTCAAACTAATACAGCAGGAAAAGGTGGCGCTATCTATGCTGGAACGAGCAATT

CTTTTGAGAGTAATAACTGCGATCTCTTCTTCATCAATAACGCCTGTTGTGCAGGAGGAGCGATCTTCTCCCCTATC

TGTTCTCTAACAGGAAATCGTGGTAACATCGTTTTCTATAACAATCGCTGCTTTAAAAATGTAGAAACAGCTTCTTC

AGAAGCTTCTGATGGAGGAGCAATTAAAGTAACTACTCGCCTAGATGTTACAGGCAATCGTGGTAGGATCTTTTTTA

GTGACAATATCACAAAAAATTATGGCGGAGCTATTTACGCTCCTGTAGTTACCCTAGTGGATAATGGCCCTACCTAC

TTTATAAACAATATCGCCAATAATAAGGGGGGCGCTATCTATATAGACGGAACCAGTAACTCCAAAATTTCTGCCGA

CCGCCATGCTATTATTTTTAATGAAAATATTGTGACTAATGTAACTAATGCAAATGGTACCAGTACGTCAGCTAATC

CTCCTAGAAGAAATGCAATAACAGTAGCAAGCTCCTCTGGTGAAATTCTATTAGGAGCAGGGAGTAGCCAAAATTTA

ATTTTTTATGATCCTATTGAAGTTAGCAATGCAGGGGTCTCTGTGTCCTTCAATAAGGAAGCTGATCAAACAGGCTC

TGTAGTATTTTCAGGAGCTACTGTTAATTCTGCAGATTTTCATCAACGCAATTTACAAACAAAAACACCTGCACCCC

TTACTCTCAGTAATGGTTTTCTATGTATCGAAGATCATGCTCAGCTTACAGTGAATCGATTCACACAAACTGGGGGT

GTTGTTTCTCTTGGGAATGGAGCAGTTCTGAGTTGCTATAAAAATGGTACAGGAGATTCTGCTAGCAATGCCTCTAT

AACACTGAAGCATATTGGATTGAATCTTTCTTCCATTCTGAAAAGTGGTGCTGAGATTCCTTTATTGTGGGTAGAGC

CTACAAATAACAGCAATAACTATACAGCAGATACTGCAGCTACCTTTTCATTAAGTGATGTAAAACTCTCACTCATT

GATGACTACGGGAACTCTCCTTATGAATCCACAGATCTGACCCATGCTCTGTCATCACAGCCTATGCTATCTATTTC

TGAAGCTAGCGATAACCAGCTACAATCAGAAAATATAGATTTTTCGGGACTAAATGTCCCTCATTATGGATGGCAAG

GACTTTGGACTTGGGGCTGGGCAAAAACTCAAGATCCAGAACCAGCATCTTCAGCAACAATCACTGATCCACAAAAA

GCCAATAGATTTCATAGAACCTTACTACTAACATGGCTTCCTGCCGGGTATGTTCCTAGCCCAAAACACAGAAGTCC

CCTCATAGCTAACACCTTATGGGGGAATATGCTGCTTGCAACAGAAAGCTTAAAAAATAGTGCAGAGCTGACACCTA

GTGGTCATCCTTTCTGGGGAATTACAGGAGGAGGACTAGGCATGATGGTTTACCAAGATCCTCGAGAAAATCATCCT

GGATTCCATATGCGCTCTTCCGGATACTCTGCGGGGATGATAGCAGGGCAGACACACACCTTCTCATTGAAATTCAG

TCAGACCTACACCAAACTCAATGAGCGTTACGCAAAAAACAACGTATCTTCTAAAAATTACTCATGCCAAGGAGAAA

TGCTCTTCTCATTGCAAGAAGGTTTCTTGCTGACTAAATTAGTTGGGCTTTACAGCTATGGAGACCATAACTGTCAC

CATTTCTATACTCAAGGAGAAAATCTAACATCTCAAGGGACGTTCCGCAGTCAAACGATGGGAGGTGCTGTCTTTTT

TGATCTCCCTATGAAACCCTTTGGATCAACGCATATACTGACAGCTCCCTTTTTAGGTGCTCTTGGTATTTATTCTA

GCCTGTCTCACTTTACTGAGGTGGGAGCCTATCCGCGAAGCTTTTCTACAAAGACTCCTTTGATCAATGTCCTAGTC

CCTATTGGAGTTAAAGGTAGCTTTATGAATGCTACCCACAGACCTCAAGCCTGGACTGTAGAATTGGCATACCAACC

CGTTCTGTATAGACAAGAACCAGGGATCGCAGCCCAGCTCCTAGCCAGTAAGGGTATTTGGTTCGGTAGTGGAAGCC

CCTCATCGCGTCATGCCATGTCCTATAAAATCTCACAGCAAACACAACCTTTGAGTTGGTTAACTCTCCATTTCCAG

TATCATGGATTCTACTCCTCTTCAACCTTCTGTAATTATCTCAATGGGGAAATTGCTCTGCGATTC

-continued

SEQUENCE LISTING

SEQ ID NO: 124: CT869 fragment protein sequence
REVPSRIFLMPNSVPDPTKESLSNKISLTGDTHNLTNCYLDNLRYILAILQKTPNEGAAVTITDYLSFFDTQKEGIY

FAKNLTPESGGAIGYASPNSPTVEIRDTIGPVIFENNTCCRLFTWRNPYAADKIREGGAIHAQNLYINHNHDVVGFM

KNFSYVQGGAISTANTFVVSENQSCFLFMDNICIQTNTAGKGGAIYAGTSNSFESNNCDLFFINNACCAGGAIFSPI

CSLTGNRGNIVFYNNRCFKNVETASSEASDGGAIKVTTRLDVTGNRGRIFFSDNITKNYGGAIYAPVVTLVDNGPTY

FINNIANNKGGAIYIDGTSNSKISADRHAIIFNENIVTNVTNANGTSTSANPPRRNAITVASSSGEILLGAGSSQNL

IFYDPIEVSNAGVSVSFNKEADQTGSVVFSGATVNSADFHQRNLQTKTPAPLTLSNGFLCIEDHAQLTVNRFTQTGG

VVSLGNGAVLSCYKNGTGDSASNASITLKHIGLNLSSILKSGAEIPLLWVEPTNNSNNYTADTAATFSLSDVKLSLI

DDYGNSPYESTDLTHALSSQPMLSISEASDNQLQSENIDFSGLNVPHYGWQGLWTWGWAKTQDPEPASSATITDPQK

ANRFHRTLLLTWLPAGYVPSPKHRSPLIANTLWGNMLLATESLKNSAELTPSGHPFWGITGGGLGMMVYQDPRENHP

GFHMRSSGYSAGMIAGQTHTFSLKFSQTYTKLNERYAKNNVSSKNYSCQGEMLFSLQEGFLLTKLVGLYSYGDHNCH

HFYTQGENLTSQGTFRSQTMGGAVFFDLPMKPFGSTHILTAPFLGALGIYSSLSHFTEVGAYPRSFSTKTPLINVLV

PIGVKGSFMNATHRPQAWTVELAYQPVLYRQEPGIAAQLLASKGIWFGSGSPSSRHAMSYKISQQTQPLSWLTLHFQ

YHGFYSSSTFCNYLNGEIALRF

SEQ ID NO: 125: CT166 fragment nucleotide sequence
AACGTTCGTACGTACTCTGTTCAGAGGGGGGGGGTAAAAACGATTTCTGCTAGTGCAGTTCCTCCTACAGCAGCTGT

TTTATCGAGAAAAAAGCGTGCTATAGAAGAGAAGAAGGAGGAAGCTTCTTCTGGAAAGATAGAAAATCTTGATGCTA

GCAAATACGATCTTACTCCCAAGAACATAGAAGAAAAACTAGGAATTACTCCTGAACAGAAATCTACTGTTAAAGAC

CTATTAAATAAACTGAAAAAGGTCATTAGTGCTTACAACTCTATGCCAGATAAAAATTCGGAAGCGGGACAGAATTC

CTTGATTCAACAAGGAAAATACGTCGATGCCATTCAGAAGAAGCTTCCAGCATCATCGCAGGCTCAGCCTAAACAGG

CAAAAGCTAAGGAACAGAAAGCCGAAGAAAAACCTAAGACGACTCCGATTGAAGGTGTTCTTGAAACCATCAAAACA

GAATTTAAAGGCCATCGTGTACCTGTTGAGAAAATCATCCATGGAATATGGATCGCAGGAGCGCCTCCGGATGGTAT

CGAAGATTATATGCGAGTCTTTTTAGATACTTATGAAGGTTTTGACTTCTACTTCTGGGTAGATGAGAATGCTTATG

CAGCAGCTAAATTTTCTAGCATTTTGAAGAAGGTCGCTTTCGATGCGGCTATTCAAGATCTACGATCTGCCACAGAT

GAGTCTACGAAGGCCTTTGTTAAAGACTACGATGAATTAAAACAGAAATATGAAAAGAAAGTTGCGGAGACGACTTC

TCAAGCAGAAAAAGACCAATATCTCAAAGATCTAAAGGATCTTTTAGAGAAATTTACAAAAATCAGTGATGAGATTC

GTGGAAAATTTGATCGGCTGTTTCTTAAGAATGTGATTGTTGCTCAGAACGGATTCTTTAATTTCTGCTTGCTGAAA

GGCCTCGGCAATATCAATGACGAAACGCGTGCAGAGTATTTAGAGAAAGAACTCAAACTTCCTACTGAGGAGATCGA

ACAGTATAAAAAGCTTAAAGAGACGAACAAAGAGAAGATAGCCGCTATTGTAAAACAACTAAACGAGAAACTTGGAT

CGGATCGGGTAAAAATCAAAGACATTAAAGAGCTGCAATCTATGAAGCAAGCTCGAAATGTCTACAATTATGAACAG

GAAATGTTTCTGCGCTGGAACTATGCAGCCGCAACAGATCAGATTCGTATGTATATGTTGGAGGAACTTGGAGGTCT

TTATACTGATCTGGATATGATGCCTTCATACTCTCAGGAAGTATTGGAGCTTATCAAAAAGCACAGTGATGGAAACC

GAATGTTTGAGGATATGAGCTCTAGACGGGCGATTTCTGATGCGGTTTTAAAGATGGCTGTAGGTAAGGCGACAACA

GTTTCCATGGAAGAGGTAGCAAAGGATATCGATGTTTCTCGCTTAACAGAAGAGGATAAGACAAAATTAAATGCTCT

ATTTAAGGATCTAGAGCCATTTGCAAAACCGGATTCTAAAGGAGCTGAAGCAGAAGGGGGTGAAGGAGCAAAAGGTA

TGAAAAAGAGCTTTTTCCAGCCCATAGATCTGAATATTGTCAGAAATACCATGCCTATCTTGAGACGCTATCATCAC

TATCCTGAGTTAGGATGGTTTATTCGAGGATTGAACGGATTGATGGTCTCTCATAAGGGAAGCACTGCGGTTTCTGC

TGTCATTGTAGGGCAACAGGCTGCCTACCAGGAACTAGCAGCACTTAGACAAGATGTCCTTTCAGGGGAGTTTTTCC

ATTCTTTAGAAAATTTGACACATAGAAACCATAAGGAGCGTATTGGAAATCATCTCGTCGCTAATTATTTGGCTAAA

AGTCTCTTTTTTGATTACTGCCAAGATTCAGTGATGCCGGAGGCTGTAAGTACCTTAGGTATTAGA

-continued

SEQUENCE LISTING

SEQ ID NO: 126 - CT166 fragment protein sequence
NVRTYSVQRGGVKTISASAVPPTAAVLSRKKRAIEEKKEEASSGKIENLDASKYDLTPKNIEEKLGITPEQKSTVKD

LLNKLKKVISAYNSMPDKNSEAGQNSLIQQGKYVDAIQKKLPASSQAQPKQAKAKEQKAEEKPKTTPIEGVLETIKT

EFKGHRVPVEKIIHGIWIAGAPPDGIEDYMRVFLDTYEGFDFYFWVDENAYAAAKFSSILKKVAFDAAIQDLRSATD

ESTKAFVKDYDELKQKYEKKVAETTSQAEKDQYLKDLKDLLEKFTKISDEIRGKFDRLFLKNVIVAQNGFFNFCLLK

GLGNINDETRAEYLEKELKLPTEEIEQYKKLKETNKEKIAAIVKQLNEKLGSDRVKIKDIKELQSMKQARNVYNYEQ

EMFLRWNYAAATDQIRMYMLEELGGLYTDLDMMPSYSQEVLELIKKHSDGNRMFEDMSSRRAISDAVLKMAVGKATT

VSMEEVAKDIDVSRLTEEDKTKLNALFKDLEPFAKPDSKGAEAEGGEGAKGMKKSFFQPIDLNIVRNTMPILRRYHH

YPELGWFIRGLNGLMVSHKGSTAVSAVIVGQQAAYQELAALRQDVLSGEFFHSLENLTHRNHKERIGNHLVANYLAK

SLFFDYCQDSVMPEAVSTLGIR

SEQ ID NO: 127 - CT175 fragment nucleotide sequence
TGTTATCATAAAAAAGAAGAACCAAAAGATGTTTTGCGGATTGCGATCTGTCATGATCCAATGTCTTTAGATCCGCG

TCAGGTTTTTTTAAGCAAAGATGTTTCTATTGTAAAAGCTCTCTATGAAGGGTTAGTCCGGGAAAAAGAAGCTGCGT

TCCAGCTAGCTTTGGCAGAAAGATATCATCAATCTGATGATGGTTGTGTTTATACTTTTTTTCTAAAAAATACATTC

TGGAGCAACGGAGATGTTGTAACAGCATATGATTTTGAAGAGTCTATTAAACAAATTTATTTCCGAGAAATTGATAA

CCCTTCGTTACGCTCTCTTGCATTAATTAAAAATTCTCATGCTGTTTTAACAGGAGCTCTCCCTGTTGAAGATTTAG

GTGTTAGAGCTTTGAATGCGAAAACTCTAGAAATTGTTTTAGAAAACCCGTTTCCTTATTTTCTAGAGATATTGGCG

CACCCGGTTTTTTATCCGGTGCACACCTCTTTACGAGAATATTACAAAGATAAGCGTAACAAACGCGTTTTCCCGAT

AATTTCTAATGGTCCTTTTGCGATTCAATGTTATGAGCCGCAAAGATATTTACTAATCAACAAAAACCCTCTGTATC

ATGCCAAGCACGATGTTCTGTTAAATTCGGTATGTTTGCAGATAGTTCCTGATATCCATACAGCTATGCAGTTATTC

CAAAAAAATCATATCGATTTAGTTGGGTTACCCTGGAGCTCCTCCTTTTCTTTAGAAGAACAAAGAAATCTCCCTAG

AGAAAAATTATTTGATTATCCTGTATTGAGTTGCTCTGTTTTATTCTGTAACATTCATCAAACACCTTTAAATAATC

CCTCGCTGAGAACAGCCCTCTCTTTAGCAATCAATCGAGAAACTTTATTAAAACTAGCAGGTAAAGGCTGTAGCGCT

ACGAGCTTTGTTCACCCACAATTATCTCAGATACCTGCTACTACTTTGTCTCAAGATGAGCGGATTGCTTTAGCAAA

AGGCTACTTGACCGAAGCTTTAAAGACTTTATCTCAAGAAGATTTAGAAAAAATTACATTAATTTATCCTATAGAAT

CTGTTTGCTTACGAGCCGTTGTTCAAGAAATTCGCCAACAATTATTTGATGTACTGGGATTTAAAATTTCTACATTA

GGATTAGAATATCATTGTTTTTTAGACAAACGTTCCAGAGGAGAATTCTCCTTAGCAACTGGTAATTGGATTGCAGA

CTATCATCAAGCTAGTGCTTTCCTGTCTGTCCTAGGTAATGGGACAAGATATAAAGACTTTCAATTGATTAACTGGC

AGAACCAAAAGTACACAAATATAGTTGCTCAACTTCTGATTCAAGAATCAAGCGACCTACAGCTTATGGCAGAGCAG

TTGTTGCTTAAAGAAAGTCCTCTTATTCCTCTATACCACCTCGATTATGTGTATGCGAAACAGCCTCGGGTGTCTGA

TCTCCAAACCTCTTCTCGTGGAGAAATTGATTTAAAAAGAGTTTCATTAGCTGAAGGATAG

SEQ ID NO: 128 - CT175 fragment protein sequence
CYHKKEEPKDVLRIAICHDPMSLDPRQVFLSKDVSIVKALYEGLVREKEAAFQLALAERYHQSDDGCVYTFFLKNTF

WSNGDVVTAYDFEESIKQIYFREIDNPSLRSLALIKNSHAVLTGALPVEDLGVRALNAKTLEIVLENPFPYFLEILA

HPVFYPVHTSLREYYKDKRNKRVFPIISNGPFAIQCYEPQRYLLINKNPLYHAKHDVLLNSVCLQIVPDIHTAMQLF

QKNHIDLVGLPWSSSFSLEEQRNLPREKLFDYPVLSCSVLFCNIHQTPLNNPSLRTALSLAINRETLLKLAGKGCSA

TSFVHPQLSQIPATTLSQDERIALAKGYLTEALKTLSQEDLEKITLIYPIESVCLRAVVQEIRQQLFDVLGFKISTL

GLEYHCFLDKRSRGEFSLATGNWIADYHQASAFLSVLGNGTRYKDFQLINWQNQKYTNIVAQLLIQESSDLQLMAEQ

LLLKESPLIPLYHLDYVYAKQPRVSDLQTSSRGEIDLKRVSLAEG

-continued

SEQUENCE LISTING

SEQ ID NO: 129 - TC0666 fragment nucleotide sequence (homologue of CT387)
ATGACACTCTTTCACACTCATCACGATGCCGTCTCTCCGGACGGCTACTTATGTTCTTCCCTTCAGTTAGTTGGCTC

TGGCACATATGAAGGAGAAATCGAAATCCAAAATATTCCTTCTTATTTCCTTGGATTCCGATTACCCACCCATTGCG

TTCATCTTAATTTGAAGAGTTCTCTAGCCCAGTTAGGAGTAGATGCATCTCTTCTTCACTGCGAACTAAGCAAAAAT

CAACAACGTGCACATATGCACGTGCAGTTCACCGGCTATGGCCCTATCGCTGAGTCCATGCTATCTCTTCTCAAACC

CGGAGATCGAGTAGCCAAACTGTTTGCTGCAGATGATCGTAGACTAGTCCGCTCCCCTGATTATCTTGAAAGCATGC

TAAAAAATACTGATAAGACAGGACATCCTCTGCTCCGATTTGGAAAAAAACTCGAGCATCTTATCTCTTTTGATGTG

GTGGACGATCGCCTCGTTGTATCACTCCCCACCTTGCCAGGCATAGTCAATTATGACCCAGACATCTATGGACTTCT

TCCCTTAATTCAAAAATCACTAAGCAATCCTAAATTGAGTATTCGCCACTTCTTGTCTCTCTATCAGAAGATCGTAG

AAGGACCACACATCCCTTATGAAGGAAACATTTTGTTAATCAAAACAGAGCCTCTTCATATCCGCACAGTATTTGCT

CGCGTGGTCGATCAAATGCTCCCTCAAGGTCTATTTCACACTTCTGCCAACATTTTAGAACCCACAACGCGAGAGTC

TGGAGATATTTTTGAATTTTTTGGAAATCCCTCCACTCTTGTAGAAAGAATCCCTCTAGAATTCTTCACTATCGAAC

CCTACAAAGAACACTCTTACTTCTGTAATCGAGATCTATTGCAAACTACCTTGCAATCGGAAAGTGAAATCAAAAAA

ATATTCGATACAGCTCCTCAAGAGCCTGTAAAAGCCGCCACTTATTTATCAAAAGGAAGTGAAATTTCTTCTCTTGA

TGCAGATTCTTGGCTTACGGGATCCGCAGCTGCATACCAATGTAGCGAAAAACAGGCAGCTAAAGACGAATACATCC

ACGCTCAACCCTGTTATCCATTTTTGGAAGCAATGGAAACGGGACTCATCAATAGCGAAGGAGCTTTACTCACTCGG

TTTTTCCCCTCTTCCAGCTTAAAAGGGATGTTGATCTCCTATCATGTACGCCACTATCTTAAGCAAATTTACTTTCA

AGTTCCTTCTTATACATATGGAGACTACTTCTCTCATAATGACCGAGGATTACTGTTAGATCTATATCAGGCGAACA

TTGATGTGTTCTGGGCTGATGAAGAGAGCGGCCGTGTATTGCAATATACAAAACGGCGCGACAAAAATAGTGGAATG

TTCGTCGTTAAAAATCGAGTAGAAGAGTTCCAATCAGCATATTTCGTAGCGATTTATGGATCACGTCTCCTGGAAAA

TAATTTCTCGGCCCAACTAAACACGCTTCTTGCAGGGTTACAAAAAGCTGCACACACTCTAGGCATTCCAGGCTTCT

CAAAACCCACTCCTCTTGCCGTAATCACAGGAGGAGGGACTGGCGTTATGGCTACAGGAAATCGTGTTGCAAAAGAG

TTGGGAATTCTTTCTTGCGGGACCGTTCTCGATTTGGAAGCTTCACCTGCACAAATAGATCAGCCTGCAAACGAATT

TTTAGATGCCAAAATGACATACCGTCTACCGCAACTTATAGAAAGACAAGAACATTTTTATTCAGACCTTGCCATTT

TAGTTGTTGGTGGTGTTGGAACAGATTTCGAACTTTACCTAGAACTCGTCTACTTGAAAACAGGCGCCAAACCTCCT

ACTCCAATTTTCCTTATTGGGCCTGTTGAATACTGGAAAGAGAAAGTTGCTCATGCCTATGAGATTAATCTTAAAGC

AGGAACTATTCGTGGTTCTGAGTGGATCAGCAACTGCTTATTCTGCATTACATCTCCTGAAGCAGGAATTGCTGTAT

TCGAACAGTTCCTCGCTGGAGAACTTCCCATAGGATATGATTATCCTCCAGCTCCAGACGGATTAGTTATCGTC

SEQ ID NO: 130 - TC0666 fragment protein sequence (homologue of CT387)
MTLFHTHHDAVSPDGYLCSSLQLVGSGTYEGEIEIQNIPSYFLGFRLPTHCVHLNLKSSLAQLGVDASLLHCELSKN

QQRAHMHVQFTGYGPIAESMLSLLKPGDRVAKLFAADDRRLVRSPDYLESMLKNTDKTGHPLLRFGKKLEHLISFDV

VDDRLVVSLPTLPGIVNYDPDIYGLLPLIQKSLSNPKLSIRHFLSLYQKIVEGPHIPYEGNILLIKTEPLHIRTVFA

RVVDQMLPQGLFHTSANILEPTTRESGDIFEFFGNPSTLVERIPLEFFTIEPYKEHSYFCNRDLLQTTLQSESEIKK

IFDTAPQEPVKAATYLSKGSEISSLDADSWLTGSAAAYQCSEKQAAKDEYIHAQPCYPFLEAMETGLINSEGALLTR

FFPSSSLKGMLISYHVRHYLKQIYFQVPSYTYGDYFSHNDRGLLLDLYQANIDVFWADEESGRVLQYTKRRDKNSGM

FVVKNRVEEFQSAYFVAIYGSRLLENNFSAQLNTLLAGLQKAAHTLGIPGFSKPTPLAVITGGGTGVMATGNRVAKE

LGILSCGTVLDLEASPAQIDQPANEFLDAKMTYRLPQLIERQEHFYSDLAILVVGGVGTDFELYLELVYLKTGAKPP

TPIFLIGPVEYWKEKVAHAYEINLKAGTIRGSEWISNCLFCITSPEAGIAVFEQFLAGELPIGYDYPPAPDGLVIV

SEQ ID NO: 131 - TC0197 fragment nucleotide sequence
AATTGTTCCGATCTTTATGCCGTAGGAAGTTCTGCAGACCATCCTGCCTACTTGATTCCTCAAGCGGGGTTATTATT

GGATCATATTAAGGATATATTCATTGGCCCTAAAGATAGTCAGGATAAGGGGCAGTATAAGTTGATTATTGGTGAGG

-continued

SEQUENCE LISTING

CTGGCTCTTTCCAAGATAGTAATGCAGAGACTCTTCCTCAAAAGGTAGAGCACAGCACTTTGTTTTCAGTTACAACA

CCTATAATTGTGCAAGGAATAGATCAACAAGATCAGGTCTCTTCGCAGGGATTGGTCTGTAATTTTTCAGGAGATCA

TTCAGAGGAGATTTTTGAGAGAGAATCCTTTTTAGGGATCGCTTTCCTAGGGAATGGTAGCAAGGATGGAATCACGT

TAACAGATATAAAATCTTCGTTATCTGGTGCTGCCTTGTATTCTTCAGATGATCTTATTTTTGAAAGAATTAAGGGA

GATATAGAGCTTTCTTCTTGTTCATCTTTAGAAAGAGGAGGAGCTTGTTCAGCTCAAAGTATTTTAATTCATGATTG

TCAAGGATTAACGGTAAAACATTGTGCCGCAGGGGTGAATGTTGAAGGAGTTAGTGCTAGCGACCATCTCGGATTTG

GGGGCGGGGCCTTCTCTACTACAAGTTCTCTTTCTGGAGAGAAGAGTTTGTATATGCCTGCAGGCGATATTGTGGTG

GCTACCTGCGATGGTCCTGTGTGTTTCGAAGGAAATAGTGCTCAGTTAGCAAATGGTGGCGCTATTGCCGCTTCTGG

TAAAGTTCTTTTTGTAGCTAACGAAAAAAAGATTTCCTTTACAGACAACCAAGCTTTGTCTGGAGGAGCTATTTCTG

CATCTTCTAGTATTTCTTTCCAAAATTGTGCTGAGCTTGTGTTCAAGAGTAATCTTGCAAAAGGAGTTAAAGATAAA

TGTTCTTTGGGAGGAGGTGCTTTAGCCTCTTTAGAATCCGTAGTTTTGAAAGATAATCTCGGTATTACTTATGAAAA

AAATCAGTCCTATTCGGAAGGAGGGGCTATTTTTGGGAAGGATTGTGAGATTTTTGAAAACAGGGGGCCTGTTGTAT

TCAGAGATAATACAGCTGCTTTAGGAGGCGGAGCTATTTTGGCGCAACAAACTGTGGCGATTTGTGGTAATAAGTCT

GGAATATCTTTTGAAGGAAGTAAGTCTAGTTTTGGAGGGGCCATTGCTTGTGGAAATTTCTCTTCTGAGAATAATTC

TTCAGCTTTGGGATCAATTGATATCTCTAACAATCTAGGAGATATCTCTTTTCTTCGGACTCTGTGTACTACTTCGG

ATTTAGGGCAAACGGATTACCAAGGGGGAGGGGCCTTATTCGCTGAAAATATTTCTCTTTCTGAGAATGCTGGTGCA

ATTACTTTCAAAGACAATATTGTGAAGACATTTGCCTCAAATGGAAAAATGTTGGGTGGAGGGGCAATTTTAGCTTC

AGGAAATGTTTTGATTAGCAAAAACTCTGGAGAGATTTCTTTTGTAGGGAATGCTCGAGCTCCTCAGGCTATTCCGA

CTCGTTCATCTGACGAATTGTCTTTTGGCGCACAATTAACTCAAACTACTTCAGGATGTTCTGGAGGAGGAGCTCTT

TTTGGTAAAGAGGTTGCCATTGTTCAAAATGCCACTGTTGTATTCGAGCAAAATCGCTTACAGTGTGGCGAGCAGGA

AACACATGGTGGAGGCGGTGCTGTTTATGGTATGGAGAGTGCCTCTATTATTGGAAACTCTTTTGTGAGATTCGGAA

ATAATTACGCTGTAGGGAATCAGATTTCTGGAGGAGCTCTTTTATCCAAGAAGGTCCGTTTAGCTGAAAATACAAGG

GTAGATTTTTCTCGAAATATCGCTACTTTCTGCGGCGGGGCTGTTCAAGTTTCTGATGGAAGTTGCGAATTGATCAA

CAATGGGTATGTGCTATTCAGAGATAACCGAGGGCAGACATTTGGTGGGGCTATTTCTTGCTTGAAAGGAGATGTGA

TCATTTCCGGAAATAAAGATAGGGTTGAGTTTAGAGATAACATTGTGACGCGGCCTTATTTTGAAGAAAATGAAGAA

AAAGTTGAGACAGCAGATATTAATTCAGATAAGCAAGAAGCAGAAGAGCGCTCTTATTAGAGAACATTGAGCAGAG

CTTTATTACTGCAACTAATCAGACCTTTTTCTTAGAGGAAGAGAAACTCCCATCAGAAGCTTTTATCTCTGCTGAAG

AACTTTCAAAGAGAAGAGAATGTGCTGGTGGGGCGATTTTTGCAAAACGGGTCTACATTACGGATAATAAAGAACCT

ATCTTGTTTTCGCATAATTTTTCTGATGTTTATGGGGGAGCTATTTTTACGGGTTCTCTACAGGAAACTGATAAACA

AGATGTTGTAACTCCTGAAGTTGTGATATCAGGCAACGATGGGGATGTCATTTTTTCTGGAAATGCAGCTAAACATG

ATAAGCATTTACCTGATACAGGTGGTGGAGCCATTTGTACACAGAATTTGACGATTTCCCAAAACAATGGGAATGTC

TTGTTCTTGAACAATTTTGCTTGTTCTGGTGGAGCAGTTCGCATAGAGGATCATGGAGAAGTTCTTTTAGAGGCTTT

TGGGGGAGATATTATTTTCAATGGAAACTCTTCTTTCAGAGCTCAAGGATCGGATGCGATCTATTTTGCTGGTAAGG

ACTCTAGAATTAAAGCTTTAAATGCTACTGAAGGACATGCGATTGTGTTCCAAGATGCATTGGTGTTTGAAAATATA

GAAGAAAGAAAGTCTTCGGGACTATTGGTGATTAACTCTCAGGAAAATGAGGGTTATACGGGATCCGTCCGATTTTT

AGGATCTGAAAGTAAGGTTCCTCAATGGATTCATGTGCAACAGGGAGGTCTTGAGTTGCTACATGGAGCTATTTTAT

GTAGTTATGGGGTTAAACAAGATCCTAGAGCTAAAATAGTATTATCTGCTGGATCTAAATTGAAGATTCTAGATTCA

GAGCAAGAAAATAACGCAGAAATTGGAGATCTTGAAGATTCTGTTAATTCAGAAAAAAACACCATCTCTTTGGATTGG

GAAGAACGCTCAAGCAAAAGTCCCTCTGGTTGATATCCATACTATTTCTATTGATTTAGCATCATTTTCTTCTAAAG

-continued

SEQUENCE LISTING

CTCAGGAAACCCCTGAGGAAGCTCCACAAGTCATCGTCCCTAAGGGAAGTTGTGTCCACTCGGGAGAGTTAAGTTTG

GAGTTGGTTAATACAACAGGAAAAGGTTATGAGAATCATGCGTTGTTAAAAAATGATACTCAGGTTTCTCTCATGTC

TTTCAAAGAGGAAAATGATGGATCTTTAGAAGATTTGAGTAAGTTGTCTGTTTCGGATTTACGCATTAAAGTTTCTA

CTCCAGATATTGTAGAAGAAACTTATGGCCATATGGGGGATTGGTCTGAAGCTACAATTCAAGATGGGGCTCTTGTC

ATTAATTGGCATCCTACTGGATATAAATTAGATCCGCAAAAAGCTGGTTCTTTGGTATTCAATGCATTATGGGAGGA

AGAGGCTGTATTGTCTACTCTAAAAAATGCTCGGATTGCCCATAACCTTACCATTCAGAGAATGGAATTTGATTATT

CTACAAATGCTTGGGGATTAGCTTTTAGTAGCTTTAGAGAGCTATCTTCAGAGAAGCTTGTTTCTGTTGATGGATAT

AGAGGCTCTTATATAGGGGCTTCTGCAGGCATTGATACTCAGTTGATGGAAGATTTTGTTTTGGGAATCAGCACGGC

TTCCTTCTTCGGGAAAATGCATAGTCAGAATTTTGATGCAGAGATTTCTCGACATGGTTTTGTTGGTTCGGTCTATA

CAGGCTTCCTAGCTGGGGCCTGGTTCTTCAAGGGGCAGTACAGTCTTGGCGAAACACATAACGATATGACAACTCGT

TACGGGGTTTTGGGAGAATCTAATGCTACTTGGAAGTCTCGAGGAGTACTAGCAGATGCTTTAGTTGAATATCGTAG

TTTAGTCGGTCCAGCACGACCTAAATTTTATGCTTTGCATTTTAATCCTTATGTCGAGGTATCTTATGCATCTGCGA

AGTTCCCTAGTTTTGTAGAACAAGGAGGAGAAGCTCGTGCTTTTGAAGAAACCTCTTTAACAAACATTACCGTTCCC

TTTGGTATGAAATTTGAACTATCTTTTACAAAAGGACAGTTTTCAGAGACTAATTCTCTTGGAATAGGTTGTGCATG

GGAAATGTATCGGAAAGTCGAAGGAAGATCTGTAGAGCTACTAGAAGCTGGTTTTGATTGGGAAGGATCTCCTATAG

ATCTCCCTAAACAAGAGCTGAGAGTGGCTTTAGAAAACAATACGGAATGGAGTTCGTATTTTAGTACAGCTCTAGGA

GTAACAGCATTTTGTGGAGGATTTTCTTCTATGGATAATAAACTAGGATACGAAGCGAATGCTGGAATGCGTTTGAT

TTTCTAG

SEQ ID NO: 132 - C0197 fragment protein sequence
NCSDLYAVGSSADHPAYLIPQAGLLLDHIKDIFIGPKDSQDKGQYKLIIGEAGSFQDSNAETLPQKVEHSTLFSVTT

PIIVQGIDQQDQVSSQGLVCNFSGDHSEEIFERESFLGIAFLGNGSKDGITLTDIKSSLSGAALYSSDDLIFERIKG

DIELSSCSSLERGGACSAQSILIHDCQGLTVKHCAAGVNVEGVSASDHLGFGGGAFSTTSSLSGEKSLYMPAGDIVV

ATCDGPVCFEGNSAQLANGGAIAASGKVLFVANEKKISFTDNQALSGGAISASSSISFQNCAELVFKSNLAKGVKDK

CSLGGGALASLESVVLKDNLGITYEKNQSYSEGGAIFGKDCEIFENRGPVVFRDNTAALGGGAILAQQTVAICGNKS

GISFEGSKSSFGGAIACGNFSSENNSSALGSIDISNNLGDISFLRTLCTTSDLGQTDYQGGGALFAENISLSENAGA

ITFKDNIVKTFASNGKMLGGGAILASGNVLISKNSGEISFVGNARAPQAIPTRSSDELSFGAQLTQTTSGCSGGGAL

FGKEVAIVQNATVVFEQNRLQCGEQETHGGGGAVYGMESASIIGNSFVRFGNNYAVGNQISGGALLSKKVRLAENTR

VDFSRNIATFCGGAVQVSDGSCELINNGYVLFRDNRGQTFGGAISCLKGDVIISGNKDRVEFRDNIVTRPYFEENEE

KVETADINSDKQEAEERSLLENIEQSFITATNQTFFLEEEKLPSEAFISAEELSKRRECAGGAIFAKRVYITDNKEP

ILFSHNFSDVYGGAIFTGSLQETDKQDVVTPEVVISGNDGDVIFSGNAAKHDKHLPDTGGGAICTQNLTISQNNGNV

LFLNNFACSGGAVRIEDHGEVLLEAFGGDIIFNGNSSFRAQGSDAIYFACKDSRIKALNATEGHAIVFQDALVFENI

EERKSSGLLVINSQENEGYTGSVRFLGSESKVPQWIHVQQGGLELLHGAILCSYGVKQDPRAKIVLSAGSKLKILDS

EQENNAEIGDLEDSVNSEKTPSLWIGKNAQAKVPLVDIHTISIDLASFSSKAQETPEEAPQVIVPKGSCVHSGELSL

ELVNTTGKGYENHALLKNDTQVSLMSFKEENDGSLEDLSKLSVSDLRIKVSTPDIVEETYGHMGDWSEATIQDGALV

INWHPTGYKLDPQKAGSLVFNALWEEEAVLSTLKNARIAHNLTIQRMEFDYSTNAWGLAFSSFRELSSEKLVSVDGY

RGSYIGASAGIDTQLMEDFVLGISTASFFGKMHSQNFDAEISRHGFVGSVYTGFLAGAWFFKGQYSLGETHNDMTTR

YGVLGESNATWKSRGVLADALVEYRSLVGPARPKFYALHFNPYVEVSYASAKFPSFVEQGGEARAFEETSLTNITVP

FGMKFELSFTKGQFSETNSLGIGCAWEMYRKVEGRSVELLEAGFDWEGSPIDLPKQELRVALENNTEWSSYFSTALG

VTAFCGGFSSMDNKLGYEANAGMRLIF

-continued

SEQUENCE LISTING

SEQ ID NO: 133 - C0261 fragment nucleotide sequence

ACTCGAGAAGTCCCTCCTTCGATTCTTTTAAAGCCTATACTAAATCCATACCATATGACCGGGTTATTTTTTCCCAA

GGTTAATTTGCTTGGAGACACACATAATCTCACTGATTACCATTTGGATAATCTAAAATGCATTCTGGCTTGCCTAC

AAAGAACTCCTTATGAAGGAGCTGCTTTCACAGTAACCGATTACTTAGGTTTTTCAGATACACAAAAGGATGGTATT

TTTTGTTTTAAAAATCTTACTCCAGAGAGTGGAGGGGTTATTGGTTCCCCAACTCAAAACACTCCTACTATAAAAAT

TCATAATACAATCGGCCCCGTTCTTTTCGAAAATAATACCTGTCATAGACTGTGGACACAGACCGATCCCGAAAATG

AAGGAAACAAAGCACGCGAAGGCGGGGCAATTCATGCTGGGGACGTTTACATAAGCAATAACCAGAACCTTGTCGGA

TTCATAAAGAACTTTGCTTATGTTCAAGGTGGAGCTATTAGTGCTAATACTTTTGCCTATAAAGAAAATAAATCGAG

CTTTCTTTGCCTAAATAACTCTTGTATACAAACTAAGACGGGAGGGAAAGGTGGTGCTATTTACGTTAGTACGAGCT

GCTCTTTCGAGAACAATAACAAGGATCTGCTTTTCATCCAAAACTCCGGCTGTGCAGGAGGAGCTATCTTCTCTCCA

ACCTGTTCTCTAATAGGAAACCAAGGAGATATTGTTTTTTACAGCAACCACGGTTTTAAAAATGTTGATAATGCAAC

TAACGAATCTGGGGATGGAGGAGCTATTAAAGTAACTACCCGCTTGGACATCACCAATAATGGTAGTCAAATCTTTT

TTTCTGATAATATCTCAAGAAATTTTGGAGGAGCTATTCATGCTCCTTGTCTTCATCTTGTTGGTAATGGGCCAACC

TATTTTACAAACAATATAGCTAATCACACAGGTGGGGCTATTTATATAACAGGAACAGAAACCTCAAAGATTTCTGC

AGATCACCATGCTATTATTTTTGATAATAACATTTCTGCAAACGCCACCAATGCGGACGGATCTAGCAGCAACACTA

ATCCTCCTCACAGAAATGCGATCACTATGGACAATTCCGCTGGAGGAATAGAACTTGGTGCAGGGAAGAGCCAGAAT

CTTATTTTCTATGATCCTATTCAAGTGACGAATGCTGGAGTTACCGTAGACTTCAATAAGGATGCCTCCCAAACCGG

ATGTGTAGTTTTCTCTGGAGCGACTGTCCTTTCTGCAGATATTTCTCAGGCTAATTTGCAAACTAAAACACCTGCAA

CGCTTACTCTCAGTCACGGTCTTCTGTGTATCGAAGATCGTGCTCAGCTCACAGTGAACAATTTTACACAAACAGGA

GGGATTGTAGCCTTAGGAAATGGAGCAGTTTTAAGCAGCTACCAACACAGCACTACAGACGCCACTCAAACTCCCCC

TACAACCACCACTACAGATGCTTCCGTAACTCTTAATCACATTGGATTAAATCTCCCCTCTATTCTTAAGGATGGAG

CAGAGATGCCTCTATTATGGGTAGAACCTATAAGCACAACTCAAGGTAACACTACAACATATACGTCAGATACCGCG

GCTTCCTTCTCATTAAATGGAGCCACACTCTCTCTCATTGATGAAGATGGAAATTCTCCCTATGAAAACACGGACCT

CTCTCGTGCATTGTACGCTCAACCTATGCTAGCAATTTCTGAGGCCAGTGATAACCAATTGCAATCCGAAAGCATGG

ACTTTTCTAAAGTTAATGTTCCTCACTATGGATGGCAAGGACTTTGGACCTGGGGGTGGGCAAAAACTGAAAATCCA

ACAACAACTCCTCCAGCAACAATTACTGATCCGAAAAAAGCTAATCAGTTTCATAGAACTTTATTATTAACGTGGCT

CCCTGCTGGTTATATCCCCAGCCCTAAACATAAAAGCCCTTTAATAGCTAATACCTTGTGGGGGAATATACTTTTTG

CAACGGAAAACTTAAAAAATAGCTCAGGGCAAGAACTTCTTGATCGTCCTTTCTGGGGAATTACAGGAGGGGGCTTG

GGGATGATGGTCTATCAAGAACCTAGAAAAGACCATCCTGGATTCCACATGCATACCTCCGGATATTCAGCAGGAAT

GATTACAGGAAACACACATACCTTCTCATTACGATTCAGCCAGTCCTATACAAAACTCAATGAACGTTATGCCAAGA

ACTATGTGTCTTCTAAAAATTACTCTTGCCAAGGGGAAATGCTTTTGTCCTTACAAGAAGGACTCATGCTGACTAAA

CTAATTGGTCTCTATAGTTATGGGAATCACAACAGCCACCATTTCTATACCCAAGGAGAAGACCTATCGTCTCAAGG

GGAGTTCCATAGTCAGACTTTTGGAGGGGCTGTCTTTTTTGATCTACCTCTGAAACCTTTTGGAAGAACACACATAC

TTACAGCTCCTTTCTTAGGTGCCATTGGTATGTATTCTAAGCTGTCTAGCTTTACAGAAGTAGGAGCCTATCCAAGA

ACCTTTATTACAGAAACGCCTTTAATCAATGTCCTGATTCCTATCGGAGTAAAAGGTAGCTTCATGAATGCCACCCA

TAGACCTCAGGCCTGGACTGTAGAGCTTGCTTACCAACCTGTTCTTTACAGACAAGAACCTAGTATCTCTACCCAAT

TACTCGCTGGTAAAGGTATGTGGTTTGGGCATGGAAGTCCTGCATCTCGCCACGCTCTAGCTTATAAAATTTCACAG

AAAACACAGCTTTTGCGATTTGCAACACTTCAACTCCAGTATCACGGATACTATTCGTCTTCCACTTTCTGTAATTA

TCTGAATGGAGAGGTATCTTTACGTTTC

-continued

SEQUENCE LISTING

SEQ ID NO: 134 - C0261 fragment protein sequence
TREVPPSILLKPILNPYHMTGLFFPKVNLLGDTHNLTDYHLDNLKCILACLQRTPYEGAAFTVTDYLGFSDTQKDGI

FCFKNLTPESGGVIGSPTQNTPTIKIHNTIGPVLFENNTCHRLWTQTDPENEGNKAREGGAIHAGDVYISNNQNLVG

FIKNFAYVQGGAISANTFAYKENKSSFLCLNNSCIQTKTGGKGGAIYVSTSCSFENNNKDLLFIQNSGCAGGAIFSP

TCSLIGNQGDIVFYSNHGFKNVDNATNESGDGGAIKVTTRLDITNNGSQIFFSDNISRNFGGAIHAPCLHLVGNGPT

YFTNNIANHTGGAIYITGTETSKISADHHAIIFDNNISANATNADGSSSNTNPPHRNAITMDNSAGGIELGAGKSQN

LIFYDPIQVTNAGVTVDFNKDASQTGCVVFSGATVLSADISQANLQTKTPATLTLSHGLLCIEDRAQLTVNNFTQTG

GIVALGNGAVLSSYQHSTTDATQTPPTTTTTDASVTLNHIGLNLPSILKDGAEMPLLWVEPISTTQGNTTTYTSDTA

ASFSLNGATLSLIDEDGNSPYENTDLSRALYAQPMLAISEASDNQLQSESMDFSKVNVPHYGWQGLWTWGWAKTENP

TTTPPATITDPKKANQFHRTLLLTWLPAGYIPSPKHKSPLIANTLWGNILFATENLKNSSGQELLDRPFWGITGGGL

GMMVYQEPRKDHPGFHMHTSGYSAGMITGNTHTFSLRFSQSYTKLNERYAKNYVSSKNYSCQGEMLLSLQEGLMLTK

LIGLYSYGNHNSHHFYTQGEDLSSQGEFHSQTFGGAVFFDLPLKPFGRTHILTAPFLGAIGMYSKLSSFTEVGAYPR

TFITETPLINVLIPIGVKGSFMNATHRPQAWTVELAYQPVLYRQEPSISTQLLAGKGMWFGHGSPASRHALAYKISQ

KTQLLRFATLQLQYHGYYSSSTFCNYLNGEVSLRF

SEQ ID NO: 135 - CT600 nucleotide sequence
ATGAGAAAGACTATTTTTAAAGCGTTTAATTTATTATTCTCCCTTCTTTTTCTTTCTTCATGCTCTTATCCTTGCAG

AGATTGGGAATGCCATGGTTGCGACTCCGCAAGACCTCGTAAATCCTCTTTTGGATTCGTACCTTTCTACTCCGATG

AAGAAATTCAACAAGCTTTTGTTGAAGATTTTGATTCCAAAGAAGAGCAGCTGTACAAAACGAGCGCACAGAGTACC

TCTTTCCGAAATATCACTTTCGCTACAGATAGTTATTCTATTAAAGGAGAGGATAACCTCACGATTCTTGCAAGCTT

AGTTCGTCATTTGCATAAATCTCCTAAAGCTACGCTATATATAGAGGGCCATACAGATGAACGTGGAGCTGCAGCTT

ATAACCTAGCTTTAGGAGCTCGTCGTGCGAATGCTGTAAAACAATACCTCATCAAACAGGGAATCGCTGCAGACCGC

TTATTCACTATTTCTTACGGAAAAGAACATCCTGTTCATCCAGGCCATAATGAATTAGCTTGGCAACAAAATCGTCG

TACTGAATTTAAGATCCATGCTCGCTAA

SEQ ID NO: 136 - CT600 protein sequence
MRKTIFKAFNLLFSLLFLSSCSYPCRDWECHGCDSARPRKSSFGFVPFYSDEEIQQAFVEDFDSKEEQLYKTSAQST

SFRNITFATDSYSIKGEDNLTILASLVRHLHKSPKATLYIEGHTDERGAAAYNLALGARRANAVKQYLIKQGIAADR

LFTISYGKEHPVHPGHNELAWQQNRRTEFKIHAR

SEQ ID NO: 137 - CT600 fragment nucleotide sequence
TGCTCTTATCCTTGCAGAGATTGGGAATGCCATGGTTGCGACTCCGCAAGACCTCGTAAATCCTCTTTTGGATTCGT

ACCTTTCTACTCCGATGAAGAAATTCAACAAGCTTTTGTTGAAGATTTTGATTCCAAAGAAGAGCAGCTGTACAAAA

CGAGCGCACAGAGTACCTCTTTCCGAAATATCACTTTCGCTACAGATAGTTATTCTATTAAAGGAGAGGATAACCTC

ACGATTCTTGCAAGCTTAGTTCGTCATTTGCATAAATCTCCTAAAGCTACGCTATATATAGAGGGCCATACAGATGA

ACGTGGAGCTGCAGCTTATAACCTAGCTTTAGGAGCTCGTCGTGCGAATGCTGTAAAACAATACCTCATCAAACAGG

GAATCGCTGCAGACCGCTTATTCACTATTTCTTACGGAAAAGAACATCCTGTTCATCCAGGCCATAATGAATTAGCT

TGGCAACAAAATCGTCGTACTGAATTTAAGATCCATGCTCGC

SEQ ID NO: 138 - CT600 fragment protein sequence
CSYPCRDWECHGCDSARPRKSSFGFVPFYSDEEIQQAFVEDFDSKEEQLYKTSAQSTSFRNITFATDSYSIKGEDNL

TILASLVRHLHKSPKATLYIEGHTDERGAAAYNLALGARRANAVKQYLIKQGIAADRLFTISYGKEHPVHPGHNELA

WQQNRRTEFKIHAR

SEQ ID NO: 139 - CT823 nucleotide sequence
ATGATGAAAAGATTATTATGTGTGTTGCTATCGACATCAGTTTTCTCTTCGCCAATGCTAGGCTATAGTGCGTCAAA

GAAAGATTCTAAGGCTGATATTTGTCTTGCAGTATCCTCAGGAGATCAAGAGGTTTCACAAGAAGATCTGCTCAAAG

-continued

SEQUENCE LISTING

AAGTATCCCGAGGATTTTCTCGGGTCGCTGCTAAGGCAACGCCTGGAGTTGTATATATAGAAAATTTTCCTAAAACA

GGGAACCAGGCTATTGCTTCTCCAGGAAACAAAAGAGGCTTTCAAGAGAACCCTTTTGATTATTTTAATGACGAATT

TTTTAATCGATTTTTTGGATTGCCTTCGCATAGAGAGCAGCAGCGTCCGCAGCAGCGTGATGCTGTAAGAGGAACTG

GGTTCATTGTTTCTGAAGATGGTTATGTTGTTACTAACCATCATGTAGTCGAGGATGCAGGAAAAATTCATGTTACT

CTCCACGACGGACAAAAATACACAGCTAAGATCGTGGGGTTAGATCCAAAAACAGATCTTGCTGTGATCAAAATTCA

AGCGGAGAAATTACCATTTTTGACTTTTGGGAATTCTGATCAGCTGCAGATAGGTGACTGGGCTATTGCTATTGGAA

ATCCTTTTGGATTGCAAGCAACGGTCACTGTCGGGGTCATTAGTGCTAAAGGAAGAAATCAGCTACATATTGTAGAT

TTCGAAGACTTTATTCAAACAGATGCTGCCATTAATCCTGGGAATTCAGGCGGTCCATTGTTAAACATCAATGGTCA

AGTTATCGGGGTTAATACTGCCATTGTCAGTGGTAGCGGGGGATATATTGGAATAGGGTTTGCTATTCCTAGCTTGA

TGGCTAAACGAGTCATTGATCAATTGATTAGTGATGGGCAGGTAACAAGAGGCTTTTTGGGAGTTACCTTGCAACCG

ATAGATTCTGAATTGGCTACTTGTTACAAATTGGAAAAAGTGTACGGAGCTTTGGTGACGGATGTTGTTAAAGGTTC

TCCAGCAGAAAAAGCAGGGCTGCGCCAAGAAGATGTCATTGTGGCTTACAATGGAAAAGAAGTAGAGTCTTTGAGTG

CGTTGCGTAATGCCATTTCCCTAATGATGCCAGGGACTCGTGTTGTTTTAAAAATCGTTCGTGAAGGGAAAACAATC

GAGATACCTGTGACGGTTACACAGATCCCAACAGAGGATGGCGTTTCAGCGTTGCAGAAGATGGGAGTCCGTGTTCA

GAACATTACTCCAGAAATTTGTAAGAAACTCGGATTGGCAGCAGATACCCGAGGGATTCTGGTAGTTGCTGTGGAGG

CAGGCTCGCCTGCAGCTTCTGCAGGCGTCGCTCCTGGACAGCTTATCTTAGCGGTGAATAGGCAGCGAGTCGCTTCC

GTTGAAGAGTTAAATCAGGTTTTGAAAAACTCGAAAGGAGAGAATGTTCTCCTTATGGTTTCTCAAGGAGATGTGGT

GCGATTCATCGTCTTGAAATCAGACGAGTAG

SEQ ID NO: 140 - CT823 protein sequence
MMKRLLCVLLSTSVFSSPMLGYSASKKDSKADICLAVSSGDQEVSQEDLLKEVSRGFSRVAAKATPGVVYIENFPKT

GNQAIASPGNKRGFQENPFDYFNDEFFNRFFGLPSHREQQRPQQRDAVRGTGFIVSEDGYVVTNHHVVEDAGKIHVT

LHDGQKYTAKIVGLDPKTDLAVIKIQAEKLPFLTFGNSDQLQIGDWAIAIGNPFGLQATVTGVISAKGRNQLHIVD

FEDFIQTDAAINPGNSGGPLLNINGQVIGVNTAIVSGSGGYIGIGFAIPSLMAKRVIDQLISDGQVTRGFLGVTLQP

IDSELATCYKLEKVYGALVTDVVKGSPAEKAGLRQEDVIVAYNGKEVESLSALRNAISLMMPGTRVVLKIVREGKTI

EIPVTVTQIPTEDGVSALQKMGVRVQNITPEICKKLGLAADTRGILVVAVEAGSPAASAGVAPGQLILAVNRQRVAS

VEELNQVLKNSKGENVLLMVSQGDVVRFIVLKSDE

SEQ ID NO: 141 - CT823 fragment nucleotide sequence
TCGCCAATGCTAGGCTATAGTGCGTCAAAGAAAGATTCTAAGGCTGATATTTGTCTTGCAGTATCCTCAGGAGATCA

AGAGGTTTCACAAGAAGATCTGCTCAAAGAAGTATCCCGAGGATTTTCTCGGGTCGCTGCTAAGGCAACGCCTGGAG

TTGTATATATAGAAAATTTTCCTAAAACAGGGAACCAGGCTATTGCTTCTCCAGGAAACAAAAGAGGCTTTCAAGAG

AACCCTTTTGATTATTTTAATGACGAATTTTTTAATCGATTTTTTGGATTGCCTTCGCATAGAGAGCAGCAGCGTCC

GCAGCAGCGTGATGCTGTAAGAGGAACTGGGTTCATTGTTTCTGAAGATGGTTATGTTGTTACTAACCATCATGTAG

TCGAGGATGCAGGAAAAATTCATGTTACTCTCCACGACGGACAAAAATACACAGCTAAGATCGTGGGGTTAGATCCA

AAAACAGATCTTGCTGTGATCAAAATTCAAGCGGAGAAATTACCATTTTTGACTTTTGGGAATTCTGATCAGCTGCA

GATAGGTGACTGGGCTATTGCTATTGGAAATCCTTTTGGATTGCAAGCAACGGTCACTGTCGGGGTCATTAGTGCTA

AAGGAAGAAATCAGCTACATATTGTAGATTTCGAAGACTTTATTCAAACAGATGCTGCCATTAATCCTGGGAATTCA

GGCGGTCCATTGTTAAACATCAATGGTCAAGTTATCGGGGTTAATACTGCCATTGTCAGTGGTAGCGGGGGATATAT

TGGAATAGGGTTTGCTATTCCTAGCTTGATGGCTAAACGAGTCATTGATCAATTGATTAGTGATGGGCAGGTAACAA

GAGGCTTTTTGGGAGTTACCTTGCAACCGATAGATTCTGAATTGGCTACTTGTTACAAATTGGAAAAAGTGTACGGA

GCTTTGGTGACGGATGTTGTTAAAGGTTCTCCAGCAGAAAAAGCAGGGCTGCGCCAAGAAGATGTCATTGTGGCTTA

-continued

SEQUENCE LISTING

CAATGGAAAAGAAGTAGAGTCTTTGAGTGCGTTGCGTAATGCCATTTCCCTAATGATGCCAGGGACTCGTGTTGTTT

TAAAAATCGTTCGTGAAGGGAAAACAATCGAGATACCTGTGACGGTTACACAGATCCCAACAGAGGATGGCGTTTCA

GCGTTGCAGAAGATGGGAGTCCGTGTTCAGAACATTACTCCAGAAATTTGTAAGAAACTCGGATTGGCAGCAGATAC

CCGAGGGATTCTGGTAGTTGCTGTGGAGGCAGGCTCGCCTGCAGCTTCTGCAGGCGTCGCTCCTGGACAGCTTATCT

TAGCGGTGAATAGGCAGCGAGTCGCTTCCGTTGAAGAGTTAAATCAGGTTTTGAAAAACTCGAAAGGAGAGAATGTT

CTCCTTATGGTTTCTCAAGGAGATGTGGTGCGATTCATCGTCTTGAAATCAGACGAG

SEQ ID NO: 142 - CT823 fragment protein sequence
SPMLGYSASKKDSKADICLAVSSGDQEVSQEDLLKEVSRGFSRVAAKATPGVVYIENFPKTGNQAIASPGNKRGFQE

NPFDYFNDEFFNRFFGLPSHREQQRPQQRDAVRGTGFIVSEDGYVVTNHHVVEDAGKIHVTLHDGQKYTAKIVGLDP

KTDLAVIKIQAEKLPFLTFGNSDQLQIGDWAIAIGNPFGLQATVTVGVISAKGRNQLHIVDFEDFIQTDAAINPGNS

GGPLLNINGQVIGVNTAIVSGSGGYIGIGFAIPSLMAKRVIDQLISDGQVTRGFLGVTLQPIDSELATCYKLEKVYG

ALVTDVVKGSPAEKAGLRQEDVIVAYNGKEVESLSALRNAISLMMPGTRVVLKIVREGKTIEIPVTVTQIPTEDGVS

ALQKMGVRVQNITPEICKKLGLAADTRGILVVAVEAGSPAASAGVAPGQLILAVNRQRVASVEELNQVLKNSKGENV

LLMVSQGDVVRFIVLKSDE

SEQ ID NO: 143 - C0106 nucleotide sequence
ATGCTAACTAACTTTACCTTTCGCAACTGTCTTTTGTTTTTCGTCACATTGTCCAGTGTCCCTGTTTTCTCGGCACC

CCAACCTCGCGTAACGCTTCCTAGTGGAGCCAATAAAATCGGATCAGAAGCTTGGATAGAGCAAAAAGTCCGTCAAT

ATCCAGAACTTTTGTGGTTAGTTGAACCTTCTCCTGCAGGAACTTCTTTAAACGCTCCTTCGGGGATGATCTTTTCT

CCCCTATTGTTCCAAAAGAAAGTCCCTGCTTTTGATATCGCAGTACGCAGTCTGATTCACCTACACCTGCTTATCCA

GGGCTCCCGCCAAGCTTATGCTCAGCTTGTCCAGCTGCAGGCTAATGAATCCCCTATGACATTTAAACAGTTCCTTA

CCCTACATAAGCAGCTCTCCTTATTCCTAAATTCTCCTAAAGAGTTTTATGATTCCGTCAAAATTTTAGAAACTGCT

ATCATCCTACGCCACTTAGGATGTTCAACAAAAGCTGTTGCCACATTTAAGCCTTATTTTTCAGAAACGCAAAAAGA

GGTCTTCTATACAAAAGCTTTGCATGTTCTGCATACTTTCCCAGAATTGAGCCCTTCGTTTGCTAGACTCTCTCCAG

AACAAAAAACGCTCTTCTTCTCATTGAGAAAGCTCGCTAATTATGATGAGTTACTTTCCCTGACAAATGCCCCTAGT

TTACAACTACTATCTGCTGTACGCTCGCGACGCGCGCTTTTGGCTCTAGACTTGTATCTCTATGCTTTAGATTTTTG

TGGAGAACAGGGGATATCCTCTCAGTTTCATATGGACTTTTCTCCTTTACAGTCCATGTTGCAACAATATGCTACGG

TTGAAGAAGCCTTCTCCCGCTACTTTACTTACCGAGCTAATCGCCTAGGATTTGCGGGTTCTTCTCGAACTGAAATG

GCCTTAGTTAGAATAGCTACTTTAATGAACCTATCCCCTTCAGAAGCTGCTATTTTAACAACAAGCTTTAAGTCTCT

TTCCTTGGAAGATGCTGAAAGCTTAGTGAATAGCTTTTATACAAATAAGGGAGACTCTTTAGCTCTTTCTTTACGAG

GACTACCAACTCTTATATCTGAACTAACACGCGCTGCGCATGGAAATACGAATGCGGAAGCTCGAGCTCAGCAAATT

TACGCCACAACGTTATCATTGGTAGCAAAAAGCTTGAAAGCTCACAAAGAGATGCAAAACAAACAAATTCTTCCCGA

AGAAGTCGTTTTAGATTTCTCTGAAACTGCTTCTTCCTGTCAAGGATTGGACATCTTCTCTGAGAACGTTGCTGTTC

AAATCCACTTGAATGGATCTGTCAGCATCCATCTATAA

SEQ ID NO: 144 - C0106 protein sequence
MLTNFTFRNCLLFFVTLSSVPVFSAPQPRVTLPSGANKIGSEAWIEQKVRQYPELLWLVEPSPAGTSLNAPSGMIFS

PLLFQKKVPAFDIAVRSLIHLHLLIQGSRQAYAQLVQLQANESPMTFKQFLTLHKQLSLFLNSPKEFYDSVKILETA

IILRHLGCSTKAVATFKPYFSETQKEVFYTKALHVLHTFPELSPSFARLSPEQKTLFFSLRKLANYDELLSLTNAPS

LQLLSAVRSRRALLALDLYLYALDFCGEQGISSQFHMDFSPLQSMLQQYATVEEAFSRYFTYRANRLGFAGSSRTEM

ALVRIATLMNLSPSEAAILTTSFKSLSLEDAESLVNSFYTNKGDSLALSLRGLPTLISELTRAAHGNTNAEARAQQI

YATTLSLVAKSLKAHKEMQNKQILPEEVVLDFSETASSCQGLDIFSENVAVQIHLNGSVSIHL

-continued

SEQUENCE LISTING

SEQ ID NO: 145 - C0106 fragment nucleotide sequence
TCAGAAGCTTGGATAGAGCAAAAAGTCCGTCAATATCCAGAACTTTTGTGGTTAGTTGAACCTTCTCCTGCAGGAAC

TTCTTTAAACGCTCCTTCGGGGATGATCTTTTCTCCCCTATTGTTCCAAAAGAAAGTCCCTGCTTTTGATATCGCAG

TACGCAGTCTGATTCACCTACACCTGCTTATCCAGGGCTCCCGCCAAGCTTATGCTCAGCTTGTCCAGCTGCAGGCT

AATGAATCCCCTATGACATTTAAACAGTTCCTTACCCTACATAAGCAGCTCTCCTTATTCCTAAATTCTCCTAAAGA

GTTTTATGATTCCGTCAAAATTTTAGAAACTGCTATCATCCTACGCCACTTAGGATGTTCAACAAAAGCTGTTGCCA

CATTTAAGCCTTATTTTTCAGAAACGCAAAAAGAGGTCTTCTATACAAAAGCTTTGCATGTTCTGCATACTTTCCCA

GAATTGAGCCCTTCGTTTGCTAGACTCTCTCCAGAACAAAAAACGCTCTTCTTCTCATTGAGAAAGCTCGCTAATTA

TGATGAGTTACTTTCCCTGACAAATGCCCCTAGTTTACAACTACTATCTGCTGTACGCTCGCGACGCGCGCTTTTGG

CTCTAGACTTGTATCTCTATGCTTTAGATTTTTGTGGAGAACAGGGGATATCCTCTCAGTTTCATATGGACTTTTCT

CCTTTACAGTCCATGTTGCAACAATATGCTACGGTTGAAGAAGCCTTCTCCCGCTACTTTACTTACCGAGCTAATCG

CCTAGGATTTGCGGGTTCTTCTCGAACTGAAATGGCCTTAGTTAGAATAGCTACTTTAATGAACCTATCCCCTTCAG

AAGCTGCTATTTTAACAACAAGCTTTAAGTCTCTTTCCTTGGAAGATGCTGAAAGCTTAGTGAATAGCTTTTATACA

AATAAGGGAGACTCTTTAGCTCTTTCTTTACGAGGACTACCAACTCTTATATCTGAACTAACACGCGCTGCGCATGG

AAATACGAATGCGGAAGCTCGAGCTCAGCAAATTTACGCCACAACGTTATCATTGGTAGCAAAAAGCTTGAAAGCTC

ACAAAGAGATGCAAAACAAACAAATTCTTCCCGAAGAAGTCGTTTTAGATTTCTCTGAAACTGCTTCTTCCTGTCAA

GGATTGGACATCTTCTCTGAGAACGTTGCTGTTCAAATCCACTTGAATGGATCTGTCAGCATCCATCTA

SEQ ID NO: 146 - C0106 fragment protein sequence
SEAWIEQKVRQYPELLWLVEPSPAGTSLNAPSGMIFSPLLFQKKVPAFDIAVRSLIHLHLLIQGSRQAYAQLVQLQA

NESPMTFKQFLTLHKQLSLFLNSPKEFYDSVKILETAIILRHLGCSTKAVATFKPYFSETQKEVFYTKALHVLHTFP

ELSPSFARLSPEQKTLFFSLRKLANYDELLSLTNAPSLQLLSAVRSRRALLALDLYLYALDFCGEQGISSQFHMDFS

PLQSMLQQYATVEEAFSRYFTYRANRLGFAGSSRTEMALVRIATLMNLSPSEAAILTTSFKSLSLEDAESLVNSFYT

NKGDSLALSLRGLPTLISELTRAAHGNTNAEARAQQIYATTLSLVAKSLKAHKEMQNKQILPEEVVLDFSETASSCQ

GLDIFSENVAVQIHLNGSVSIHL

SEQ ID NO: 147 - C0431 nucleotide sequence
ATGCCCCACTCTCCTTTTTATATGTTGTTCAACCGCATTCTGTTTTTAATCCTAGATTGGGAGAGCGGCACCCTAT

TACTTTAGATTTCATCAAAGAAAAGAATCGATTAGCTGATTTTATTGAAAACCTACCTTTAGAAATTTTTGGAGCCC

CTTCTTTCTTGGAAAATGCTTCTTTAGAAGCCTCTTATGTCTTGTCTAGGGAATCCACAAAAGATGGCACTCTTTTT

ACCGTTCTAGAACCCAAACTATCTGCCTGCGTAGCTACTTGCCTTGTGGATTCTTCTATTCCTATGGAGCCCGATAA

CGAGCTCTTAGAAGAAATTAAACACACTTTGTTGAAAAGCTCTTGTGATGGCGTACAATATCGTGTAACCCGAGAGA

CTCTCCAAAACAAAGATGAAGCCCCCAGAGTCTCTTTAGTTGCTGATGATATCGAACTTATCCGCAATGTAGATTTT

TTAGGACGTTCCGTTGATATTGTAAAATTGGATCCCTTGAATATTCCTAATACCGTAAGCGAGGAGAATGCTCTCGA

TTACTCTTTCACAAGGGAAACCGCCAAACTTAGCCCTGACGGACGAGTTGGCATCCCTCAAGGGACAAAAATTTTGC

CAGCTCCCTCTCTTGAAGTTGAAATTAGCACCTCTATTTTTGAGGAAACCTCTTCTTTTGAACAAAACTTTTCTTCC

TCTATTACTTTTTGTGTACCACCTCTTACCTCTTTTTCTCCTTTGCAAGAACCTCCTCTAGTGGGAGCTGGACAGCA

GGAAATTCTTGTGACTAAAAAGCACTTATTCCCTAGCTATACCCCTAAACTTATTGATATTGTCAAACGACACAAAA

GAGACGCAAAGATTCTAGTAAACAAGATCCAGTTCGAGAAACTATGGAGAAGTCATGCCAAAAGTCAAATCTTAAAA

GAAGGCTCTGTTCGCTTGGATTTACAAGGATTTACAGGGGAGCTGTTTAACTACCAACTTCAAGTAGGATCTCATAC

AATTGCAGCCGTGTTAATTGATCCGGAAATTGCTAACGTCAAATCCCTCCCCGAACAAACTTACGCTGTAAGAAAAA

TTAAATCAGGGTTCCAATGTAGTTTGGATGACCAACACATTTATCAAGTCGCAGTAAAAAAACATCTTTCTCTGTCT

TCACAACCTCCGAAGATATCTCCGTTATCTCAATCCGAAAGCTCCGATTTAAGTCTCTTTGAAGCAGCAGCGTTTTC

-continued

SEQUENCE LISTING

AGCAAGCCTAACTTACGAGTTCGTAAAGAAAAATACATATCATGCTAAGAATACTGTAACTTGCTCCACGGTATCGC

ACTCTCTGTATATTCTCAAAGAAGATGACGGGGCTAATGCTGCAGAAAAACGCTTAGACAACAGTTTCCGAAACTGG

GTCGAAAATAAGTTGAACGCAAATTCTCCAGATTCTTGTACTGCATTTATTCAAAAATTCGGCACACATTACATCAC

ATCGGCAACTTTTGGAGGATCTGGGTTCCAAGTTCTTAAATTATCCTTTGAACAGGTAGAAGGCCTCCGTAGTAAGA

AGATCTCCCTAGAAGCAGCAGCAGCAAATTCCTTATTAAAAAGCTCTGTGTCAAACAGCACGGAATCTGGCTACTCT

ACTTACGATTCCTCTTCTTCTTCTCATACAGTATTCCTAGGGGGCACTGTATTACCCTCTGTTCATGATGGACAGTT

AGATTTTAAAGATTGGTCTGAAAGTGTCTGTTTAGAACCTGTTCCCATTCACATTTCTTTACTCCCCTTAACAGACT

TGCTCACCCCTCTTTATTTTCCTGAAACGGATACAACCGAACTATCTAATAAACGTAATGCTCTCCAACAAGCGGTT

CGAGTTTACCTTAAAGACCATCGTTCAGCTAAACAAAGCGAACGCTCCGTATTCACAGCGGGGATCAATAGTCCTTC

TTCCTGGTTCACATTAGAATCTGCTAATTCACCTCTTGTTGTGAGTTCTCCTTACATGACGTATTGGTCTACTCTCC

CCTATCTCTTCCCCACATTAAAAGAGCGTTCTTCAGCAGCTCCCATCGTTTTTTATTTTTGTGTGGATAATAATGAA

CACGCCTCCCAAAAAATTTTAAACCAAACATATTGCTTCATAGGTTCTTTACCTATTCGACAAAAGATTTTTGGCAG

AGAATTTGCTGAGAATCCTTATTTATCTTTCTATGGAAGGTTTGGAGAAGCTTATTTTGATGGCGGTTATCCAGAAC

GTTGTGGATGGATTGTTGAAAAGTTAAATACTACTAAAGATCAAATTCTCCGCGATGAGGATGAAGTGCAACTAAAG

CATGTTTATAGCGGAGAGTATCTGTCTACAATTCCTATTAAGGATTCCCATTGCACACTCTCGCGTACATGCACCGA

ATCGAATGCTGTTTTTATTATCAAAAAACCTTCGAGCTATTGA

SEQ ID NO: 148 - C0431 protein sequence
MPHSPFLYVVQPHSVFNPRLGERHPITLDFIKEKNRLADFIENLPLEIFGAPSFLENASLEASYVLSRESTKDGTLF

TVLEPKLSACVATCLVDSSIPMEPDNELLEEIKHTLLKSSCDGVQYRVTRETLQNKDEAPRVSLVADDIELIRNVDF

LGRSVDIVKLDPLNIPNTVSEENALDYSFTRETAKLSPDGRVGIPQGTKILPAPSLEVEISTSIFEETSSFEQNFSS

SITFCVPPLTSFSPLQEPPLVGAGQQEILVTKKHLFPSYTPKLIDIVKRHKRDAKILVNKIQFEKLWRSHAKSQILK

EGSVRLDLQGFTGELFNYQLQVGSHTIAAVLIDPEIANVKSLPEQTYAVRKIKSGFQCSLDDQHIYQVAVKKHLSLS

SQPPKISPLSQSESSDLSLFEAAAFSASLTYEFVKKNTYHAKNTVTCSTVSHSLYILKEDDGANAAEKRLDNSFRNW

VENKLNANSPDSCTAFIQKFGTHYITSATFGGSGFQVLKLSFEQVEGLRSKKISLEAAAANSLLKSSVSNSTESGYS

TYDSSSSSHTVFLGGTVLPSVHDGQLDFKDWSESVCLEPVPIHISLLPLTDLLTPLYFPETDTTELSNKRNALQQAV

RVYLKDHRSAKQSERSVFTAGINSPSSWFTLESANSPLVVSSPYMTYWSTLPYLFPTLKERSSAAPIVFYFCVDNNE

HASQKILNQTYCFIGSLPIRQKIFGREFAENPYLSFYGRFGEAYFDGGYPERCGWIVEKLNTTKDQILRDEDEVQLK

HVYSGEYLSTIPIKDSHCTLSRTCTESNAVFIIKKPSSY

SEQ ID NO: 149 - C0431 fragment nucleotide sequence
CCCCACTCTCCTTTTTTATATGTTGTTCAACCGCATTCTGTTTTTAATCCTAGATTGGGAGAGCGGCACCCTATTAC

TTTAGATTTCATCAAAGAAAAGAATCGATTAGCTGATTTTATTGAAAACCTACCTTTAGAAATTTTTGGAGCCCCTT

CTTTCTTGGAAAATGCTTCTTTAGAAGCCTCTTATGTCTTGTCTAGGGAATCCACAAAAGATGGCACTCTTTTTACC

GTTCTAGAACCCAAACTATCTGCCTGCGTAGCTACTTGCCTTGTGGATTCTTCTATTCCTATGGAGCCCGATAACGA

GCTCTTAGAAGAAATTAAACACACTTTGTTGAAAAGCTCTTGTGATGGCGTACAATATCGTGTAACCCGAGAGACTC

TCCAAAACAAAGATGAAGCCCCCAGAGTCTCTTTAGTTGCTGATGATATCGAACTTATCCGCAATGTAGATTTTTTA

GGACGTTCCGTTGATATTGTAAAATTGGATCCCTTGAATATTCCTAATACCGTAAGCGAGGAGAATGCTCTCGATTA

CTCTTTCACAAGGGAAACCGCCAAACTTAGCCCTGACGGACGAGTTGGCATCCCTCAAGGGACAAAAATTTTGCCAG

CTCCCTCTCTTGAAGTTGAAATTAGCACCTCTATTTTTGAGGAAACCTCTTCTTTTGAACAAAACTTTTCTTCCTCT

ATTACTTTTTGTGTACCACCTCTTACCTCTTTTTCTCCTTTGCAAGAACCTCCTCTAGTGGGAGCTGGACAGCAGGA

AATTCTTGTGACTAAAAAGCACTTATTCCCTAGCTATACCCCTAAACTTATTGATATTGTCAAACGACACAAAAGAG

-continued

SEQUENCE LISTING

ACGCAAAGATTCTAGTAAACAAGATCCAGTTCGAGAAACTATGGAGAAGTCATGCCAAAAGTCAAATCTTAAAAGAA

GGCTCTGTTCGCTTGGATTTACAAGGATTTACAGGGGAGCTGTTTAACTACCAACTTCAAGTAGGATCTCATACAAT

TGCAGCCGTGTTAATTGATCCGGAAATTGCTAACGTCAAATCCCTCCCCGAACAAACTTACGCTGTAAGAAAAATTA

AATCAGGGTTCCAATGTAGTTTGGATGACCAACACATTTATCAAGTCGCAGTAAAAAAACATCTTTCTCTGTCTTCA

CAACCTCCGAAGATATCTCCGTTATCTCAATCCGAAAGCTCCGATTTAAGTCTCTTTGAAGCAGCAGCGTTTTCAGC

AAGCCTAACTTACGAGTTCGTAAAGAAAAATACATATCATGCTAAGAATACTGTAACTTGCTCCACGGTATCGCACT

CTCTGTATATTCTCAAAGAAGATGACGGGGCTAATGCTGCAGAAAAACGCTTAGACAACAGTTTCCGAAACTGGGTC

GAAAATAAGTTGAACGCAAATTCTCCAGATTCTTGTACTGCATTTATTCAAAAATTCGGCACACATTACATCACATC

GGCAACTTTTGGAGGATCTGGGTTCCAAGTTCTTAAATTATCCTTTGAACAGGTAGAAGGCCTCCGTAGTAAGAAGA

TCTCCCTAGAAGCAGCAGCAGCAAATTCCTTATTAAAAAGCTCTGTGTCAAACAGCACGGAATCTGGCTACTCTACT

TACGATTCCTCTTCTTCTTCTCATACAGTATTCCTAGGGGGCACTGTATTACCCTCTGTTCATGATGGACAGTTAGA

TTTTAAAGATTGGTCTGAAAGTGTCTGTTTAGAACCTGTTCCCATTCACATTTCTTTACTCCCCTTAACAGACTTGC

TCACCCCTCTTTATTTTCCTGAAACGGATACAACCGAACTATCTAATAAACGTAATGCTCTCCAACAAGCGGTTCGA

GTTTACCTTAAAGACCATCGTTCAGCTAAACAAAGCGAACGCTCCGTATTCACAGCGGGGATCAATAGTCCTTCTTC

CTGGTTCACATTAGAATCTGCTAATTCACCTCTTGTTGTGAGTTCTCCTTACATGACGTATTGGTCTACTCTCCCCT

ATCTCTTCCCCACATTAAAAGAGCGTTCTTCAGCAGCTCCCATCGTTTTTTATTTTTGTGTGGATAATAATGAACAC

GCCTCCCAAAAAATTTTAAACCAAACATATTGCTTCATAGGTTCTTTACCTATTCGACAAAAGATTTTTGGCAGAGA

ATTTGCTGAGAATCCTTATTTATCTTTCTATGGAAGGTTTGGAGAAGCTTATTTTGATGGCGGTTATCCAGAACGTT

GTGGATGGATTGTTGAAAAGTTAAATACTACTAAAGATCAAATTCTCCGCGATGAGGATGAAGTGCAACTAAAGCAT

GTTTATAGCGGAGAGTATCTGTCTACAATTCCTATTAAGGATTCCCATTGCACACTCTCGCGTACATGCACCGAATC

GAATGCTGTTTTTATTATCAAAAAACCTTCGAGCTAT

SEQ ID NO: 150 - C0431 fragment protein sequence
PHSPFLYVVQPHSVFNPRLGERHPITLDFIKEKNRLADFIENLPLEIFGAPSFLENASLEASYVLSRESTKDGTLFT

VLEPKLSACVATCLVDSSIPMEPDNELLEEIKHTLLKSSCDGVQYRVTRETLQNKDEAPRVSLVADDIELIRNVDFL

GRSVDIVKLDPLNIPNTVSEENALDYSFTRETAKLSPDGRVGIPQGTKILPAPSLEVEISTSIFEETSSFEQNFSSS

ITFCVPPLTSFSPLQEPPLVGAGQQEILVTKKHLFPSYTPKLIDIVKRHKRDAKILVNKIQFEKLWRSHAKSQILKE

GSVRLDLQGFTGELFNYQLQVGSHTIAAVLIDPEIANVKSLPEQTYAVRKIKSGFQCSLDDQHIYQVAVKKHLSLSS

QPPKISPLSQSESSDLSLFEAAAFSASLTYEFVKKNTYHAKNTVTCSTVSHSLYILKEDDGANAAEKRLDNSFRNWV

ENKLNANSPDSCTAFIQKFGTHYITSATFGGSGFQVLKLSFEQVEGLRSKKISLEAAAANSLLKSSVSNSTESGYST

YDSSSSSHTVFLGGTVLPSVHDGQLDFKDWSESVCLEPVPIHISLLPLTDLLTPLYFPETDTTELSNKRNALQQAVR

VYLKDHRSAKQSERSVFTAGINSPSSWFTLESANSPLVVSSPYMTYWSTLPYLFPTLKERSSAAPIVFYFCVDNNEH

ASQKILNQTYCFIGSLPIRQKIFGREFAENPYLSFYGRFGEAYFDGGYPERCGWIVEKLNTTKDQILRDEDEVQLKH

VYSGEYLSTIPIKDSHCTLSRTCTESNAVFIIKKPSSY

SEQ ID NO: 151 - C0210 nucleotide sequence
ATGATGAAAAGATTATTATGTGTGTTGCTATCGACATCAGTTTTCTCTTCGCCCATGTTGGGCTATAGTGCGCCAAA

GAAAGATTCCAGTACTGGCATTTGTCTTGCAGCATCTCAAAGTGATCGGGAACTTTCCCAAGAAGATTTGCTAAAAG

AAGTGTCTAGAGGATTTTCCAAAGTCGCTGCTCAGGCAACTCCAGGAGTTGTGTATATAGAAAATTTTCCTAAAACT

GGGAGTCAAGCTATTGCTTCTCCTGGGAATAAAAGGGGTTTTCAAGAGAATCCCTTTGATTATTTCAATGATGAGTT

TTTCAATCGATTTTTTGGTTTACCCTCGCATAGAGAGCAGCCTCGTCCCCAACAGCGTGATGCTGTAAGAGGAACAG

GTTTTATTGTGTCAGAAGATGGGTACGTTGTGACCAACCATCACGTAGTGGAAGATGCGGGGAAAATTCATGTTACT

-continued

SEQUENCE LISTING

TTACACGATGGACAAAAATACACCGCAAAAATCATAGGATTAGATCCTAAAACGGATCTCGCTGTGATTAAGATCCA

AGCAAAAAATCTCCCTTTTTTAACTTTTGGAAACTCTGATCAGCTTCAGATAGGGGATTGGTCAATAGCCATTGGAA

ATCCTTTCGGATTACAAGCCACAGTAACCGTTGGCGTGATTAGTGCTAAGGGAAGAAACCAATTACATATTGTTGAT

TTTGAAGATTTTATTCAGACGGATGCAGCAATTAATCCCGGGAATTCAGGTGGTCCATTATTGAACATTGATGGACA

GGTTATTGGAGTGAATACAGCAATCGTTAGCGGTAGCGGGGGATACATTGGAATAGGATTTGCCATTCCTAGCTTAA

TGGCTAAACGAGTTATTGACCAACTCATTAGCGATGGACAGGTGACGAGAGGATTTTTAGGAGTAACCTTACAGCCT

ATTGATTCGGAGCTTGCCGCTTGTTACAAATTAGAAAAGGTGTACGGAGCCTTGATTACGGATGTTGTTAAGGGATC

TCCTGCAGAAAAAGCAGGTTTGCGCCAGGAAGATGTCATTGTTGCTTACAATGGGAAAGAAGTGGAGTCTTTGAGTG

CTTTACGTAATGCGATTTCTTTGATGATGCCAGGGACTCGTGTTGTCTTAAAAGTTGTGCGTGAAGGGAAATTCATT

GAAATACCTGTCACTGTTACACAAATTCCTGCGGAGGATGGGGTATCTGCTCTTCAAAAAATGGGAGTTCGGGTACA

GAATCTTACTCCAGAGATATGCAAGAAACTAGGATTAGCGTCTGATACTCGAGGGATTTTTGTAGTGTCCGTAGAAG

CTGGTTCTCCTGCAGCTTCTGCAGGAGTGGTTCCAGGACAACTTATTCTGGCTGTAAACAGACAGAGAGTTTCTTCT

GTTGAAGAATTGAATCAGGTCTTGAAGAATGCAAAAGGAGAGAATGTTCTCCTTATGGTTTCTCAAGGAGAAGTCAT

TCGATTCGTTGTTTTAAAGTCTGATGAATAG

SEQ ID NO: 152 - C0210 protein sequence
MMKRLLCVLLSTSVFSSPMLGYSAPKKDSSTGICLAASQSDRELSQEDLLKEVSRGFSKVAAQATPGVVYIENFPKT

GSQAIASPGNKRGFQENPFDYFNDEFFNRFFGLPSHREQPRPQQRDAVRGTGFIVSEDGYVVTNHHVVEDAGKIHVT

LHDGQKYTAKIIGLDPKTDLAVIKIQAKNLPFLTFGNSDQLQIGDWSIAIGNPFGLQATVTVGVISAKGRNQLHIVD

FEDFIQTDAAINPGNSGGPLLNIDGQVIGVNTAIVSGSGGYIGIGFAIPSLMAKRVIDQLISDGQVTRGFLGVTLQP

IDSELAACYKLEKVYGALITDVVKGSPAEKAGLRQEDVIVAYNGKEVESLSALRNAISLMMPGTRVVLKVVREGKFI

EIPVTVTQIPAEDGVSALQKMGVRVQNLTPEICKKLGLASDTRGIFVVSVEAGSPAASAGVVPGQLILAVNRQRVSS

VEELNQVLKNAKGENVLLMVSQGEVIRFVVLKSDE

SEQ ID NO: 153 - C0210 fragment nucleotide sequence
TCGCCCATGTTGGGCTATAGTGCGCCAAAGAAAGATTCCAGTACTGGCATTTGTCTTGCAGCATCTCAAAGTGATCG

GGAACTTTCCCAAGAAGATTTGCTAAAAGAAGTGTCTAGAGGATTTTCCAAAGTCGCTGCTCAGGCAACTCCAGGAG

TTGTGTATATAGAAAATTTTCCTAAAACTGGGAGTCAAGCTATTGCTTCTCCTGGGAATAAAAGGGGTTTTCAAGAG

AATCCCTTTGATTATTTCAATGATGAGTTTTTCAATCGATTTTTTGGTTTACCCTCGCATAGAGAGCAGCCTCGTCC

CCAACAGCGTGATGCTGTAAGAGGAACAGGTTTTATTGTGTCAGAAGATGGGTACGTTGTGACCAACCATCACGTAG

TGGAAGATGCGGGGAAAATTCATGTTACTTTACACGATGGACAAAAATACACCGCAAAAATCATAGGATTAGATCCT

AAAACGGATCTCGCTGTGATTAAGATCCAAGCAAAAAATCTCCCTTTTTTAACTTTTGGAAACTCTGATCAGCTTCA

GATAGGGGATTGGTCAATAGCCATTGGAAATCCTTTCGGATTACAAGCCACAGTAACCGTTGGCGTGATTAGTGCTA

AGGGAAGAAACCAATTACATATTGTTGATTTTGAAGATTTTATTCAGACGGATGCAGCAATTAATCCCGGGAATTCA

GGTGGTCCATTATTGAACATTGATGGACAGGTTATTGGAGTGAATACAGCAATCGTTAGCGGTAGCGGGGGATACAT

TGGAATAGGATTTGCCATTCCTAGCTTAATGGCTAAACGAGTTATTGACCAACTCATTAGCGATGGACAGGTGACGA

GAGGATTTTTAGGAGTAACCTTACAGCCTATTGATTCGGAGCTTGCCGCTTGTTACAAATTAGAAAAGGTGTACGGA

GCCTTGATTACGGATGTTGTTAAGGGATCTCCTGCAGAAAAAGCAGGTTTGCGCCAGGAAGATGTCATTGTTGCTTA

CAATGGGAAAGAAGTGGAGTCTTTGAGTGCTTTACGTAATGCGATTTCTTTGATGATGCCAGGGACTCGTGTTGTCT

TAAAAGTTGTGCGTGAAGGGAAATTCATTGAAATACCTGTCACTGTTACACAAATTCCTGCGGAGGATGGGGTATCT

GCTCTTCAAAAAATGGGAGTTCGGGTACAGAATCTTACTCCAGAGATATGCAAGAAACTAGGATTAGCGTCTGATAC

TCGAGGGATTTTTGTAGTGTCCGTAGAAGCTGGTTCTCCTGCAGCTTCTGCAGGAGTGGTTCCAGGACAACTTATTC

-continued

SEQUENCE LISTING

TGGCTGTAAACAGACAGAGAGTTTCTTCTGTTGAAGAATTGAATCAGGTCTTGAAGAATGCAAAAGGAGAGAATGTT

CTCCTTATGGTTTCTCAAGGAGAAGTCATTCGATTCGTTGTTTTAAAGTCTGATGAA

SEQ ID NO: 154 - C0210 fragment protein sequence
SPMLGYSAPKKDSSTGICLAASQSDRELSQEDLLKEVSRGFSKVAAQATPGVVYIENFPKTGSQAIASPGNKRGFQE

NPFDYFNDEFFNRFFGLPSHREQPRPQQRDAVRGTGFIVSEDGYVVTNHHVVEDAGKIHVTLHDGQKYTAKIIGLDP

KTDLAVIKIQAKNLPFLTFGNSDQLQIGDWSIAIGNPFGLQATVTVGVISAKGRNQLHIVDFEDFIQTDAAINPGNS

GGPLLNIDGQVIGVNTAIVSGSGGYIGIGFAIPSLMAKRVIDQLISDGQVTRGFLGVTLQPIDSELAACYKLEKVYG

ALITDVVKGSPAEKAGLRQEDVIVAYNGKEVESLSALRNAISLMMPGTRVVLKVVREGKFIEIPVTVTQIPAEDGVS

ALQKMGVRVQNLTPEICKKLGLASDTRGIFVVSVEAGSPAASAGVVPGQLILAVNRQRVSSVEELNQVLKNAKGENV

LLMVSQGEVIRFVVLKSDE

SEQ ID NO: 155 - CT163 nucleotide sequence
ATGTTTGTGTCGTTCGATAAATCCCGTTGCAGAGCGGATGTCCCCGATTTTTTTGAAAGGACAGGAAACTTTCTTCT

CCATTGTGTGGCAAGAGGGATCAATGTTTTATATCGTGTGAAACAAATCTCTAACTATCCTTCATGCTATTTCTCAC

ATAAAGAGATTTCGTGTTGTCGTCGTATTGCAAACATTGTGATCTGTATTCTCACAGGGCCTCTGATGTTATTGGCC

ACTGTGTTAGGATTATTAGCGTATAGGTTTTCTTCTACTTACCAGACTTCTTTACAAGAACGCTTTCGTTATAAATA

TGAACAAAAGCAAGCTTTAGATGAATACCGTGATAGGGAAGAAAAAGTCATTACGCTTCAGAAGTTTTGTAGAGGAT

TTCTAGTTAGAAATCATTTGCTCAACCAAGAAACTTTAACAACGTGTAAGCAATGGGGGCAAAAACTATTAGAAGGA

GAAAAATTCCCAAGGGTCCCAGAAGGACGGTCTCTTGTATATATTTCAAAACAGTTTCCTTCTTTAGTAGCAAAACA

CGTTGGGGCTCAAGATGCCAGGTCTCGTTGGCATCATATTTTTTCTATGCGCAAAGCGCTTGCTTATTTAGATATTA

AGCGCATACGAGCACCACGCGCTAGAGTTTATCAAAACTTTATATTCGAAGAAAAACTTCCTGTTTCACGAATTTCT

GTAGATTCAATGTGTCTCTATAAAGAAAATCCACAAGCTTTCGATGAGGCGATCAAAGAACTCTTATTTCTATTTAA

AGAAGTGCATTTCAGGGATTTTGTTGTAGAAACAGAGTCTCCAACAGACGATTTCCCCTTAGCCGTGAAAGTACACA

ACTATTGGGTATGCCCACGATACGATAATTTACCTTTATTTATTCAAGAAGGAAAAGATGGCTCTCCAGAAGGGCGT

ATAGGACTGGTCGATCTAGAAACTTTTTCTTGGTCTCCACATCCATACCCCGTAGAAGAACTAGCTGTGATGTTTCC

TATGCATAAAGAGCTTCTTATGACAGAGGCGAAAAAACTACAAATCCCTTTCTCTACAAAGGAGGTCGAGCGCTCTG

TAGAGAAAGGGCTTGCTTTTTTTGAACATATGCTAGGGCATCAAGATTTTTGTTCCCAAAAAAGCGTAACGCCATTG

CGTAATTGTGCCCCTTATATTCATCTAGAAGTATGGAGATTCTCACTGAAAATTTTTGATATTTTAAAAGCTGCTAT

TCAACTAAATGGAGCACTCAATGTTCTGTTATCTCCAGATATTCGAGAGCGGTTGAGTGCTATTTCGGATAAGCAAT

GGTTGGCTATTAGCTCCCAGGTTACGTCATCGTTACTCGAGCAAGTTTCTACAAACATCTATCAGTCTCATACTGAA

GAGGCTAAACGAGTAAATTCTTCAGGGACTTTTATCATGTGTCGATCTCCTATCTTCCGGAAAAGCATCTTCATTAA

AAATCTCCCACAATTCTTAAACAAGAAATTGCAGTTGCTTCCAGAGGAGAAAGCAATCAGCGAGGCGCTTGCTTCTC

TATGTTTACGTGCAGTAATGGAAGAGCTAGTAGCAACAGGAAATATTTATTCTTATGATTCTATGGATGATTTTTTT

GAAGGGCAGTATTGTCGCATTCGTTATTAG

SEQ ID NO: 156 - CT163 protein sequence
MFVSFDKSRCRADVPDFFERTGNFLLHCVARGINVLYRVKQISNYPSCYFSHKEISCCRRIANIVICILTGPLMLLA

TVLGLLAYRFSSTYQTSLQERFRYKYEQKQALDEYRDREEKVITLQKFCRGFLVRNHLLNQETLTTCKQWGQKLLEG

EKFPRVPEGRSLVYISKQFPSLVAKHVGAQDARSRWHHIFSMRKALAYLDIKRIRAPRARVYQNFIFEEKLPVSRIS

VDSMCLYKENPQAFDEAIKELLFLFKEVHFRDFVVETESPTDDFPLAVKVHNYWVCPRYDNLPLFIQEGKDGSPEGR

IGLVDLETFSWSPHPYPVEELAVMFPMHKELLMTEAKKLQIPFSTKEVERSVEKGLAFFEHMLGHQDFCSQKSVTPL

RNCAPYIHLEVWRFSLKIFDILKAAIQLNGALNVLLSPDIRERLSAISDKQWLAISSQVTSSLLEQVSTNIYQSHTE

-continued

SEQUENCE LISTING

EAKRVNSSGTFIMCRSPIFRKSIFIKNLPQFLNKKLQLLPEEKAISEALASLCLRAVMEELVATGNIYSYDSMDDFF

EGQYCRIRY

SEQ ID NO: 157 - CT163 fragment nucleotide sequence
TTTGTGTCGTTCGATAAATCCCGTTGCAGAGCGGATGTCCCCGATTTTTTTGAAAGGACAGGAAACTTTCTTCTCCA

TTGTGTGGCAAGAGGGATCAATGTTTTATATCGTGTGAAACAAATCTCTAACTATCCTTCATGCTATTTCTCACATA

AAGAGATTTCGTGTTGTCGTCGTATTGCAAACATTGTGATCTGTATTCTCACAGGGCCTCTGATGTTATTGGCCACT

GTGTTAGGATTATTAGCGTATAGGTTTTCTTCTACTTACCAGACTTCTTTACAAGAACGCTTTCGTTATAAATATGA

ACAAAAGCAAGCTTTAGATGAATACCGTGATAGGGAAGAAAAAGTCATTACGCTTCAGAAGTTTTGTAGAGGATTTC

TAGTTAGAAATCATTTGCTCAACCAAGAAACTTTAACAACGTGTAAGCAATGGGGGCAAAAACTATTAGAAGGAGAA

AAATTCCCAAGGGTCCCAGAAGGACGGTCTCTTGTATATATTTCAAAACAGTTTCCTTCTTTAGTAGCAAAACACGT

TGGGGCTCAAGATGCCAGGTCTCGTTGGCATCATATTTTTTCTATGCGCAAAGCGCTTGCTTATTTAGATATTAAGC

GCATACGAGCACCACGCGCTAGAGTTTATCAAAACTTTATATTCGAAGAAAAACTTCCTGTTTCACGAATTTCTGTA

GATTCAATGTGTCTCTATAAAGAAAATCCACAAGCTTTCGATGAGGCGATCAAAGAACTCTTATTTCTATTTAAAGA

AGTGCATTTCAGGGATTTTGTTGTAGAAACAGAGTCTCCAACAGACGATTTCCCCTTAGCCGTGAAAGTACACAACT

ATTGGGTATGCCCACGATACGATAATTTACCTTTATTTATTCAAGAAGGAAAAGATGGCTCTCCAGAAGGGCGTATA

GGACTGGTCGATCTAGAAACTTTTTCTTGGTCTCCACATCCATACCCCGTAGAAGAACTAGCTGTGATGTTTCCTAT

GCATAAAGAGCTTCTTATGACAGAGGCGAAAAAACTACAAATCCCTTTCTCTACAAAGGAGGTCGAGCGCTCTGTAG

AGAAAGGGCTTGCTTTTTTTGAACATATGCTAGGGCATCAAGATTTTTGTTCCCAAAAAAGCGTAACGCCATTGCGT

AATTGTGCCCCTTATATTCATCTAGAAGTATGGAGATTCTCACTGAAAATTTTTGATATTTTAAAAGCTGCTATTCA

ACTAAATGGAGCACTCAATGTTCTGTTATCTCCAGATATTCGAGAGCGGTTGAGTGCTATTTCGGATAAGCAATGGT

TGGCTATTAGCTCCCAGGTTACGTCATCGTTACTCGAGCAAGTTTCTACAAACATCTATCAGTCTCATACTGAAGAG

GCTAAACGAGTAAATTCTTCAGGGACTTTTATCATGTGTCGATCTCCTATCTTCCGGAAAAGCATCTTCATTAAAAA

TCTCCCACAATTCTTAAACAAGAAATTGCAGTTGCTTCCAGAGGAGAAAGCAATCAGCGAGGCGCTTGCTTCTCTAT

GTTTACGTGCAGTAATGGAAGAGCTAGTAGCAACAGGAAATATTTATTCTTATGATTCTATGGATGATTTTTTTGAA

GGGCAGTATTGTCGCATTCGTTAT

SEQ ID NO: 158 - CT163 fragment protein sequence
FVSFDKSRCRADVPDFFERTGNFLLHCVARGINVLYRVKQISNYPSCYFSHKEISCCRRIANIVICILTGPLMLLAT

VLGLLAYRFSSTYQTSLQERFRYKYEQKQALDEYRDREEKVITLQKFCRGFLVRNHLLNQETLTTCKQWGQKLLEGE

KFPRVPEGRSLVYISKQFPSLVAKHVGAQDARSRWHHIFSMRKALAYLDIKRIRAPRARVYQNFIFEEKLPVSRISV

DSMCLYKENPQAFDEAIKELLFLFKEVHFRDFVVETESPTDDFPLAVKVHNYWVCPRYDNLPLFIQEGKDGSPEGRI

GLVDLETFSWSPHPYPVEELAVMFPMHKELLMTEAKKLQIPFSTKEVERSVEKGLAFFEHMLGHQDFCSQKSVTPLR

NCAPYIHLEVWRFSLKIFDILKAAIQLNGALNVLLSPDIRERLSAISDKQWLAISSQVTSSLLEQVSTNIYQSHTEE

AKRVNSSGTFIMCRSPIFRKSIFIKNLPQFLNKKLQLLPEEKAISEALASLCLRAVMEELVATGNIYSYDSMDDFFE

GQYCRIRY

SEQ ID NO: 159 - CT214 nucleotide sequence
ATGCGAACAGACTCTCTTTTCAATCCTCCCGACTCTACTAGAGGAGTTTTTCAGTTTTTAGAGACTCAGTGTGATCG

AGCCGTGGCTCGGTCCAGACAAAGCCAATTTATAGGGTTAGTCTCTGCTGTAGCAGCTGCAGCATTATTATTGTTGC

TTGTGGTCGCTCTATCTGTTCCAGGATTCCCAGTTGCAGCTTCAATTGTTGTAGGGGTTCTCTTTGCTTTATCGATC

GTAGCATTAACAGCTTCGTTTTTGGTATATATAGCTAATGCTAAGCTTGTTGCAATAAGAATTAAATTCTTGAGTAG

TGGTCTGCAAGATCACTTTTCGGAGTCATCTATTTTAGGGACTCTCCCGTAAAGGACGTGGTGCTAGTATTCCGCTTA

TTTCCGGACAAGCAGATGATCCTCTCCCTAATCGGATTGGGATCAAAAAAAGCACTGAAATGCGTGTTCTTCAAAAA

```
GGAATTGGGACAGATTATAAAAAATATAAGCAGCATCTTGATAGAGTGAATAATGATTTCACTTTTGTCTGTGAGGG

GATTAGCGCTTTAATTCCTACAGAAAAAGATGCTCCATTCCCTATAGAACCTTCTCATTTAGCAGGTGTTTTTTTAG

TATCATTTTCACCAGACAAGAATCCGATTCTAAAGATTACGCGTCATGCTGAGAAGATGTTACAGCCTCCTCAAGGC

GGATTCCCTAACGGGCTGGTTTGGTTGTGTGGAGCTCTTTCTGATCCTAAGAAATTTGCAGCTCCCTTTCTATCTTT

GATTGAGAAGACTCACCAAGGGATTTTGGTGAGTAAAGACTTGAAAGACAATAAGGAAAGAAAGCTAGCTTTAGAGG

CTTCCCTTCTTTCATTGAATATTTTCTTTTCCGGTTGGTGTTTGGGGAATCCGGAGTACAATCAGTATATCACAACT

GCTGTAGCTGAGAAATATAGGGATGTCTCTGTAAGAAATTGTATTTATGATTTCCTGGATACAGGGAATGTGATTTC

AGCTCTTGCTTTAGCAAGTAGTTATTCACAAGATTCCGCTTGGGCTGCAGGGTTGCAGAAAGTTTTACGTGAAGAAG

ATAAAAAGACTAAGAAAAAGTCACGTGAAGAAGTCTCTTGTTTGTATCGTGATATAGATCCAGGCTGTTGTTTAAGA

GCCCTTCCTAAGCGATTTGAATCCAAGTCTTCAGGTAGTCAAGGTAGTCCTAAAGAGCAGTTAAGCTCTTTGTTGAA

AGCTTTAGACCAGAAAATTCCTTCAGGGATTTTAGGATTGATTGCAAAAGCTTCTTCTGCAGATCTCAAGGCTGATT

TTGCAGGTATGCTTGAAGTTATTAAGCAATTACAAGCTTTATTCGATTCTTACCCACCTTTATGCGAAGACAATATT

CTCTTGTGGTTAAGCGCTTCTTTAGAACAAGTAGGCTTGCAGAAGAAATTGAGAACCTTTTTACCTTCATCAGAAAA

AAAACTCTTAGAAAGAGTTCTCTCTACATTTTTATTAGGTTTGTATACTCGAGGAGTCTTTTCTGTAGGGCAAGTGA

ATCAGCTAGCTACTATTTGTAATACTCAGGACTCTACAGAATTCTGCCAGAGAGTAAGTGACCTTTCGTTAATTAAA

CGAGCTCTACCTGCATTATTTGGTTAA

SEQ ID NO: 160 - CT214 protein sequence
MRTDSLFNPPDSTRGVFQFLETQCDRAVARSRQSQFIGLVSAVAAAALLLLLVVALSVPGFPVAASIVVGVLFALSI

VALTASFLVYIANAKLVAIRIKFLSSGLQDHFSESSILGTLRKGRGASIPLISGQADDPLPNRIGIKKSTEMRVLQK

GIGTDYKKYKQHLDRVNNDFTFVCEGISALIPTEKDAPFPIEPSHLAGVFLVSFSPDKNPILKITRHAEKMLQPPQG

GFPNGLVWLCGALSDPKKFAAPFLSLIEKTHQGILVSKDLKDNKERKLALEASLLSLNIFFSGWCLGNPEYNQYITT

AVAEKYRDVSVRNCIYDFLDTGNVISALALASSYSQDSAWAAGLQKVLREEDKKTKKKSREEVSCLYRDIDPGCCLR

ALPKRFESKSSGSQGSPKEQLSSLLKALDQKIPSGILGLIAKASSADLKADFAGMLEVIKQLQALFDSYPPLCEDNI

LLWLSASLEQVGLQKKLRTFLPSSEKKLLERVLSTFLLGLYTRGVFSVGQVNQLATICNTQDSTEFCQRVSDLSLIK

RALPALFG

SEQ ID NO: 161 - CT214 fragment nucleotide sequence
CGAACAGACTCTCTTTTCAATCCTCCCGACTCTACTAGAGGAGTTTTTCAGTTTTTAGAGACTCAGTGTGATCGAGC

CGTGGCTCGGTCCAGACAAAGCCAATTTATAGGGTTAGTCTCTGCTGTAGCAGCTGCAGCATTATTATTGTTGCTTG

TGGTCGCTCTATCTGTTCCAGGATTCCCAGTTGCAGCTTCAATTGTTGTAGGGGTTCTCTTTGCTTTATCGATCGTA

GCATTAACAGCTTCGTTTTTGGTATATATAGCTAATGCTAAGCTTGTTGCAATAAGAATTAAATTCTTGAGTAGTGG

TCTGCAAGATCACTTTTCGGAGTCATCTATTTTAGGGACTCTCCGTAAAGGACGTGGTGCTAGTATTCCGCTTATTT

CCGGACAAGCAGATGATCCTCTCCCTAATCGGATTGGGATCAAAAAAAGCACTGAAATGCGTGTTCTTCAAAAAGGA

ATTGGGACAGATTATAAAAAATATAAGCAGCATCTTGATAGAGTGAATAATGATTTCACTTTTGTCTGTGAGGGGAT

TAGCGCTTTAATTCCTACAGAAAAAGATGCTCCATTCCCTATAGAACCTTCTCATTTAGCAGGTGTTTTTTTAGTAT

CATTTTCACCAGACAAGAATCCGATTCTAAAGATTACGCGTCATGCTGAGAAGATGTTACAGCCTCCTCAAGGCGGA

TTCCCTAACGGGCTGGTTTGGTTGTGTGGAGCTCTTTCTGATCCTAAGAAATTTGCAGCTCCCTTTCTATCTTTGAT

TGAGAAGACTCACCAAGGGATTTTGGTGAGTAAAGACTTGAAAGACAATAAGGAAAGAAAGCTAGCTTTAGAGGCTT

CCCTTCTTTCATTGAATATTTTCTTTTCCGGTTGGTGTTTGGGGAATCCGGAGTACAATCAGTATATCACAACTGCT

GTAGCTGAGAAATATAGGGATGTCTCTGTAAGAAATTGTATTTATGATTTCCTGGATACAGGGAATGTGATTTCAGC

TCTTGCTTTAGCAAGTAGTTATTCACAAGATTCCGCTTGGGCTGCAGGGTTGCAGAAAGTTTTACGTGAAGAAGATA
```

-continued

SEQUENCE LISTING

AAAAGACTAAGAAAAAGTCACGTGAAGAAGTCTCTTGTTTGTATCGTGATATAGATCCAGGCTGTTGTTTAAGAGCC

CTTCCTAAGCGATTTGAATCCAAGTCTTCAGGTAGTCAAGGTAGTCCTAAAGAGCAGTTAAGCTCTTTGTTGAAAGC

TTTAGACCAGAAAATTCCTTCAGGGATTTTAGGATTGATTGCAAAAGCTTCTTCTGCAGATCTCAAGGCTGATTTTG

CAGGTATGCTTGAAGTTATTAAGCAATTACAAGCTTTATTCGATTCTTACCCACCTTTATGCGAAGACAATATTCTC

TTGTGGTTAAGCGCTTCTTTAGAACAAGTAGGCTTGCAGAAGAAATTGAGAACCTTTTTACCTTCATCAGAAAAAAA

ACTCTTAGAAAGAGTTCTCTCTACATTTTTATTAGGTTTGTATACTCGAGGAGTCTTTTCTGTAGGGCAAGTGAATC

AGCTAGCTACTATTTGTAATACTCAGGACTCTACAGAATTCTGCCAGAGAGTAAGTGACCTTTCGTTAATTAAACGA

GCTCTACCTGCATTATTTGGT

SEQ ID NO: 162 - CT214 fragment protein sequence
RTDSLFNPPDSTRGVFQFLETQCDRAVARSRQSQFIGLVSAVAAAALLLLLVVALSVPGFPVAASIVVGVLFALSIV

ALTASFLVYIANAKLVAIRIKFLSSGLQDHFSESSILGTLRKGRGASIPLISGQADDPLPNRIGIKKSTEMRVLQKG

IGTDYKKYKQHLDRVNNDFTFVCEGISALIPTEKDAPFPIEPSHLAGVFLVSFSPDKNPILKITRHAEKMLQPPQGG

FPNGLVWLCGALSDPKKFAAPFLSLIEKTHQGILVSKDLKDNKERKLALEASLLSLNIFFSGWCLGNPEYNQYITTA

VAEKYRDVSVRNCIYDFLDTGNVISALALASSYSQDSAWAAGLQKVLREEDKKTKKKSREEVSCLYRDIDPGCCLRA

LPKRFESKSSGSQGSPKEQLSSLLKALDQKIPSGILGLIAKASSADLKADFAGMLEVIKQLQALFDSYPPLCEDNIL

LWLSASLEQVGLQKKLRTFLPSSEKKLLERVLSTFLLGLYTRGVFSVGQVNQLATICNTQDSTEFCQRVSDLSLIKR

ALPALFG

SEQ ID NO: 163 - CT721 nucleotide sequence
ATGGACGGGACAAAAATTCACGAAACACGCTCCTTCTCTTGGTTAAACAACCAACAAGCCATCCCTCCTTCCGAAAT

GGTGAAGGAGGCTTTTCAACGTTACGCAGACGTATTTTCGTACAGCGCAAATACCTCCATTCTGACTTTACAAGCAG

AAGCTGAAGCTTCTGCCCGCAAACTCACAGGGTGTCAGGAGAAGGCTTTTACCTTTCATTTTATTCTTCATTACCCG

AATGTCACGGCCATTATCGTGGCCGCTCTTCTGGAAAACCAAAATGCCTTCCAGGGGCGTAATCACCTTCTTGTTCC

TTCTTGCGAGCAACAATTTATCATTAATGCTCTCTGCCGTCGGCAAAACTTAGGGACAACCTATGATTGGGTAACCA

GCAAAAACGGCCGCGTAAAAGAATCCGATCTAGCAGAAGCTCTTTCCCCGCGGACCTTGCTGTTTTCCATATCTGCT

GCGAATGGTATGACAGGATTTCTGGAAGCGATCCCTGAGCTTGCTGCGTTATGTAAAGAACGCGGGGTAATTTTCCA

CATAGACCTGAGTGATATCTTAGGAAGATGCGCGCTACCCGCAGAACTCTATCAAGCAGATATCCTTACTTTTTCTT

CACAGTCTCTTGGTGGGATTGGTCCCTCAGGAGCGATGTTTATTTCTCCCGCTTTAACAAAATATTTTTCCTTATGG

CTTCCTAGTAATCCACAAGTCCCTACCTGCCTGAGTTCTCTTGCAGCTTTTTCTCTTGCCTGTCAGGAACGTACAAC

CGCTTTCTCCTCTCTTGTGCTTTCTGCTATTTCTTCTCGAGCAGCTCTTAAACAGGCTCTTTCCGCTATTCCTCAAG

TCGAATTCCTTTTGGAAGACAGTGCCCCTCGTCTCCCTAATGTCGCTGTCTTTGCTATTCCTGGTATCCCTGCAGAG

TCCTTAGGATTTTTCCTTTCCCAGAAAAATATTTTTGTAGGGTTAGGCTATGAACGCTTCCAGCCTCTATCGCAGAT

TTTACAAAGTTCGGGCATCTCTCCCTTCTTATGCCACAGCGCTTTACACGTATCTTTTACTGAACGTACTCCTACTA

CACACTTCTCTGCATTAGCAACCGCCTTACAAGAAGGGATCTCTCACCTACAACCACTGGTTACTCAATCCTTATGA

SEQ ID NO: 164 - CT721 protein sequence
MDGTKIHETRSFSWLNNQQAIPPSEMVKEAFQRYADVFSYSANTSILTLQAEAEASARKLTGCQEKAFTFHFILHYP

NVTAIIVAALLENQNAFQGRNHLLVPSCEQQFIINALCRRQNLGTTYDWVTSKNGRVKESDLAEALSPRTLLFSISA

ANGMTGFLEAIPELAALCKERGVIFHIDLSDILGRCALPAELYQADILTFSSQSLGGIGPSGAMFISPALTKYFSLW

LPSNPQVPTCLSSLAAFSLACQERTTAFSSLVLSAISSRAALKQALSAIPQVEFLLEDSAPRLPNVAVFAIPGIPAE

SLGFFLSQKNIFVGLGYERFQPLSQILQSSGISPFLCHSALHVSFTERTPTTHFSALATALQEGISHLQPLVTQSL

-continued

SEQUENCE LISTING

SEQ ID NO: 165 - CT721 fragment nucleotide sequence
GACGGGACAAAAATTCACGAAACACGCTCCTTCTCTTGGTTAAACAACCAACAAGCCATCCCTCCTTCCGAAATGGT

GAAGGAGGCTTTTCAACGTTACGCAGACGTATTTTCGTACAGCGCAAATACCTCCATTCTGACTTTACAAGCAGAAG

CTGAAGCTTCTGCCCGCAAACTCACAGGGTGTCAGGAGAAGGCTTTTACCTTTCATTTTATTCTTCATTACCCGAAT

GTCACGGCCATTATCGTGGCCGCTCTTCTGGAAAACCAAAATGCCTTCCAGGGGCGTAATCACCTTCTTGTTCCTTC

TTGCGAGCAACAATTTATCATTAATGCTCTCTGCCGTCGGCAAAACTTAGGGACAACCTATGATTGGGTAACCAGCA

AAAACGGCCGCGTAAAAGAATCCGATCTAGCAGAAGCTCTTTCCCCGCGGACCTTGCTGTTTTCCATATCTGCTGCG

AATGGTATGACAGGATTTCTGGAAGCGATCCCTGAGCTTGCTGCGTTATGTAAAGAACGCGGGGTAATTTTCCACAT

AGACCTGAGTGATATCTTAGGAAGATGCGCGCTACCCGCAGAACTCTATCAAGCAGATATCCTTACTTTTTCTTCAC

AGTCTCTTGGTGGGATTGGTCCCTCAGGAGCGATGTTTATTTCTCCCGCTTTAACAAAATATTTTTCCTTATGGCTT

CCTAGTAATCCACAAGTCCCTACCTGCCTGAGTTCTCTTGCAGCTTTTTCTCTTGCCTGTCAGGAACGTACAACCGC

TTTCTCCTCTCTTGTGCTTTCTGCTATTTCTTCTCGAGCAGCTCTTAAACAGGCTCTTTCCGCTATTCCTCAAGTCG

AATTCCTTTTGGAAGACAGTGCCCCTCGTCTCCCTAATGTCGCTGTCTTTGCTATTCCTGGTATCCCTGCAGAGTCC

TTAGGATTTTTCCTTTCCCAGAAAAATATTTTTGTAGGGTTAGGCTATGAACGCTTCCAGCCTCTATCGCAGATTTT

ACAAAGTTCGGGCATCTCTCCCTTCTTATGCCACAGCGCTTTACACGTATCTTTTACTGAACGTACTCCTACTACAC

ACTTCTCTGCATTAGCAACCGCCTTACAAGAAGGGATCTCTCACCTACAACCACTGGTTACTCAATCCTTA

SEQ ID NO: 166 - CT721 fragment protein sequence
DGTKIHETRSFSWLNNQQAIPPSEMVKEAFQRYADVFSYSANTSILTLQAEAEASARKLTGCQEKAFTFHFILHYPN

VTAIIVAALLENQNAFQGRNHLLVPSCEQQFIINALCRRQNLGTTYDWVTSKNGRVKESDLAEALSPRTLLFSISAA

NGMTGFLEAIPELAALCKERGVIFHIDLSDILGRCALPAELYQADILTFSSQSLGGIGPSGAMFISPALTKYFSLWL

PSNPQVPTCLSSLAAFSLACQERTTAFSSLVLSAISSRAALKQALSAIPQVEFLLEDSAPRLPNVAVFAIPGIPAES

LGFFLSQKNIFVGLGYERFQPLSQILQSSGISPFLCHSALHVSFTERTPTTHFSALATALQEGISHLQPLVTQSL

SEQ ID NO: 167 - CT127 nucleotide sequence
ATGCCGCACCAAGTCTTATTGTCTCCTGTTTGCGATCTTTTATCGAATGCTGAAGGTATAGAGACGCAAGTACTGTT

TGGAGAAAGGATATGCAACCATAACCATCGACACTATGCCTATTCTCAACTAGTCTTTTCTTCTATATGGAAGCCAT

ACCCTGGCGACTCTCTACAGAATATTCCTCTATTCTCTTCCCAACTGCAGCCTCCTAATGCTGTTGTCTGCTCTCAA

GAAGCTTTTTTAGATCCTTGGCATATCCCCTTACCTTTTGCCGCTCCGCTCCACATAGATAACCAAAATCAAGTGTC

CCTATCTCCTGCTAGCATAGCATTATTAAATTCCAATTCCAGAAGTAACTATGCAAAAGCTTTCTGCTCTACCAAAG

AGATTCGTTTTTTAAATTCTTCATTCTCTCCAAGAGATTTAGTTTCTTTCGCAGAACAATTGATAGATACTCCGTAC

GTTTGGGGTGGCCGGTGCATTCATAAACAGCTTCCTCGTAATGGTGTAGATTGTTCGGGGTATATTCAACTACTTTA

CCAAGTCACAGGAAGAAATATCCCTCGCAATGCTAGAGATCAATACAGAGACTGTTCTCCAGTAAAAGATTTCTCGT

CTCTACCTATAGGAGGACTTATCTTCCTCAAGAAAGCAAGCACGGGACAAATCAACCATGTTATGATGAAAATCTCG

GAGCATGAATTCATTCATGCTGCGGAAAAAATAGGGAAAGTAGAAAAAGTAATCCTAGGAAATAGGGCTTTCTTTAA

AGGGAATCTATTCTGCTCATTAGGTGAACCGCCTATAGAAGCTGTTTTTGGCGTTCCTAAAAATAGAAAAGCCTTCT

TTTGA

SEQ ID NO: 168 - CT127 protein sequence
MPHQVLLSPVCDLLSNAEGIETQVLFGERICNHNHRHYAYSQLVFSSIWKPYPGDSLQNIPLFSSQLQPPNAVVCSQ

EAFLDPWHIPLPFAAPLHIDNQNQVSLSPASIALLNSNSRSNYAKAFCSTKEIRFLNSSFSPRDLVSFAEQLIDTPY

VWGGRCIHKQLPRNGVDCSGYIQLLYQVTGRNIPRNARDQYRDCSPVKDFSSLPIGGLIFLKKASTGQINHVMMKIS

EHEFIHAAEKIGKVEKVILGNRAFFKGNLFCSLGEPPIEAVFGVPKNRKAFF

-continued

SEQUENCE LISTING

SEQ ID NO: 169 - CT127 fragment nucleotide sequence
CCGCACCAAGTCTTATTGTCTCCTGTTTGCGATCTTTTATCGAATGCTGAAGGTATAGAGACGCAAGTACTGTTTGG

AGAAAGGATATGCAACCATAACCATCGACACTATGCCTATTCTCAACTAGTCTTTTCTTCTATATGGAAGCCATACC

CTGGCGACTCTCTACAGAATATTCCTCTATTCTCTTCCCAACTGCAGCCTCCTAATGCTGTTGTCTGCTCTCAAGAA

GCTTTTTTAGATCCTTGGCATATCCCCTTACCTTTTGCCGCTCCGCTCCACATAGATAACCAAAATCAAGTGTCCCT

ATCTCCTGCTAGCATAGCATTATTAAATTCCAATTCCAGAAGTAACTATGCAAAAGCTTTCTGCTCTACCAAAGAGA

TTCGTTTTTTAAATTCTTCATTCTCTCCAAGAGATTTAGTTTCTTTCGCAGAACAATTGATAGATACTCCGTACGTT

TGGGGTGGCCGGTGCATTCATAAACAGCTTCCTCGTAATGGTGTAGATTGTTCGGGGTATATTCAACTACTTTACCA

AGTCACAGGAAGAAATATCCCTCGCAATGCTAGAGATCAATACAGAGACTGTTCTCCAGTAAAAGATTTCTCGTCTC

TACCTATAGGAGGACTTATCTTCCTCAAGAAAGCAAGCACGGGACAAATCAACCATGTTATGATGAAAATCTCGGAG

CATGAATTCATTCATGCTGCGGAAAAAATAGGGAAAGTAGAAAAAGTAATCCTAGGAAATAGGGCTTTCTTTAAAGG

GAATCTATTCTGCTCATTAGGTGAACCGCCTATAGAAGCTGTTTTTGGCGTTCCTAAAAATAGAAAAGCCTTCTTT

SEQ ID NO: 170 - CT127 fragment protein sequence
PHQVLLSPVCDLLSNAEGIETQVLFGERICNHNHRHYAYSQLVFSSIWKPYPGDSLQNIPLFSSQLQPPNAVVCSQE

AFLDPWHIPLPFAAPLHIDNQNQVSLSPASIALLNSNSRSNYAKAFCSTKEIRFLNSSFSPRDLVSFAEQLIDTPYV

WGGRCIHKQLPRNGVDCSGYIQLLYQVTGRNIPRNARDQYRDCSPVKDFSSLPIGGLIFLKKASTGQINHVMMKISE

HEFIHAAEKIGKVEKVILGNRAFFKGNLFCSLGEPPIEAVFGVPKNRKAFF

The invention claimed is:

1. A method of inducing a CD4-Th1 cell-mediated immune response in a mammal against a *Chlamydia trachomatis* or *Chlamydia muridarum* protein, comprising administering an immunogenic composition comprising one or more proteins selected from the group consisting of (a) a protein comprising the amino acid sequence of SEQ ID NO: 2, or SEQ ID NO:144; (b) a protein comprising the amino acid sequence of SEQ ID NO:4, or SEQ ID NO:148; (c) a protein with at least 95% sequence identity to SEQ ID NO:2 and/or SEQ ID NO:4; (d) an immunogenic fragment of SEQ ID NO:2 that comprises the sequence of SEQ ID NO:64; and (d) an immunogenic fragment of SEQ ID NO:4 that comprises the sequence of SEQ ID NO:66.

2. The method of claim 1, wherein the protein is a *Chlamydia trachomatis* protein.

3. The method of claim 2, wherein the composition comprises the protein of SEQ ID NO: 2 and the protein of SEQ ID NO:4.

4. The method of claim 1, wherein the composition elicits antibodies capable of neutralizing *Chlamydia trachomatis* and/or *Chlamydia muridarum* infection.

* * * * *

SEQUENCE LISTING

<160> NUMBER OF SEQ ID NOS: 171

<210> SEQ ID NO 1
<211> LENGTH: 1347
<212> TYPE: DNA
<213> ORGANISM: Chlamydia trachomatis

<400> SEQUENCE: 1
atgttaataa actttacctt tcgcaactgt cttttgttcc ttgtcacact gtctagtgtc 60
cctgttttct cagcacctca acctcgcgga acgcttccta gctcgaccac aaaaattgga 120
tcagaagttt ggattgaaca aaaagtccgc caatatccag agcttttatg gttagtagag 180
ccgtcctcta cgggagcctc tttaaaatct ccttcaggag ccatcttttc tccaacatta 240
ttccaaaaaa aggtccctgc tttcgatatc gcagtgcgca gtttgattca cttacattta 300
ttaatccagg gttcccgcca agcctatgct caactgatcc aactacagac cagcgaatcc 360
cctctaacat ttaagcaatt ccttgcattg cataagcaat taactctatt tttaaattcc 420
cctaaggaat tttatgactc tgttaaagtg ttagagacag ctatcgtctt acgtcactta 480
ggctgttcaa ctaaggctgt tgctgcgttt aaaccttatt tctcagaaat gcaaagagag 540
gctttttaca ctaaggctct gcatgtacta cacaccttcc cagagctaag cccatcattt 600
gctcgcctct ctccggagca gaaaactctc ttcttctcct tgagaaaatt ggcgaattac 660
gatgagttac tctcgctgac gaacacccca agttttcagc ttctgtctgc tgggcgctcg 720
caacgagctc ttttagctct ggacttgtac ctctatgctt tggattcctg tggagaacag 780
gggatgtcct ctcaattcca cacaaacttc gcacctctac agtccatgtt gcaacaatac 840
gctactgtag aagaggcctt ttctcgttat tttacttacc gagctaatcg attaggattt 900

```
gatggctctt ctcgatccga gatggcttta gtaagaatgg ccaccttgat gaacttgtct    960

ccttccgaag ctgcgatttt aaccacaagc ttcaaaaccc ttcctacaga agaagcggat   1020

actttgatca atagtttcta taccaataag ggcgattcgt tggctctttc tctgcgaggg   1080

ttgcctacac ttgtatccga actgacgcga actgcccatg gcaataccaa tgcagaagct   1140

cgatctcagc aaatttatgc aactacccta tcgctagtag taaagagtct gaaagcgcac   1200

aaagaaatgc taaacaagca aattctttct aaggaaattg ttttagattt ctcagaaact   1260

gcagcttctt gccaaggatt ggatatcttt tccgagaatg tcgctgttca aattcactta   1320

aatggaaccg ttagtatcca tttataa                                       1347


<210> SEQ ID NO 2
<211> LENGTH: 448
<212> TYPE: PRT
<213> ORGANISM: Chlamydia trachomatis

<400> SEQUENCE: 2

Met Leu Ile Asn Phe Thr Phe Arg Asn Cys Leu Leu Phe Leu Val Thr
1               5                   10                  15

Leu Ser Ser Val Pro Val Phe Ser Ala Pro Gln Pro Arg Gly Thr Leu
            20                  25                  30

Pro Ser Ser Thr Thr Lys Ile Gly Ser Glu Val Trp Ile Glu Gln Lys
        35                  40                  45

Val Arg Gln Tyr Pro Glu Leu Leu Trp Leu Val Glu Pro Ser Ser Thr
    50                  55                  60

Gly Ala Ser Leu Lys Ser Pro Ser Gly Ala Ile Phe Ser Pro Thr Leu
65                  70                  75                  80

Phe Gln Lys Lys Val Pro Ala Phe Asp Ile Ala Val Arg Ser Leu Ile
                85                  90                  95

His Leu His Leu Leu Ile Gln Gly Ser Arg Gln Ala Tyr Ala Gln Leu
            100                 105                 110

Ile Gln Leu Gln Thr Ser Glu Ser Pro Leu Thr Phe Lys Gln Phe Leu
        115                 120                 125

Ala Leu His Lys Gln Leu Thr Leu Phe Leu Asn Ser Pro Lys Glu Phe
    130                 135                 140

Tyr Asp Ser Val Lys Val Leu Glu Thr Ala Ile Val Leu Arg His Leu
145                 150                 155                 160

Gly Cys Ser Thr Lys Ala Val Ala Ala Phe Lys Pro Tyr Phe Ser Glu
                165                 170                 175

Met Gln Arg Glu Ala Phe Tyr Thr Lys Ala Leu His Val Leu His Thr
            180                 185                 190

Phe Pro Glu Leu Ser Pro Ser Phe Ala Arg Leu Ser Pro Glu Gln Lys
        195                 200                 205

Thr Leu Phe Phe Ser Leu Arg Lys Leu Ala Asn Tyr Asp Glu Leu Leu
    210                 215                 220

Ser Leu Thr Asn Thr Pro Ser Phe Gln Leu Leu Ser Ala Gly Arg Ser
225                 230                 235                 240

Gln Arg Ala Leu Leu Ala Leu Asp Leu Tyr Leu Tyr Ala Leu Asp Ser
                245                 250                 255

Cys Gly Glu Gln Gly Met Ser Ser Gln Phe His Thr Asn Phe Ala Pro
            260                 265                 270

Leu Gln Ser Met Leu Gln Gln Tyr Ala Thr Val Glu Glu Ala Phe Ser
        275                 280                 285

Arg Tyr Phe Thr Tyr Arg Ala Asn Arg Leu Gly Phe Asp Gly Ser Ser
```

-continued

```
    290                 295                 300

Arg Ser Glu Met Ala Leu Val Arg Met Ala Thr Leu Met Asn Leu Ser
305                 310                 315                 320

Pro Ser Glu Ala Ala Ile Leu Thr Thr Ser Phe Lys Thr Leu Pro Thr
                325                 330                 335

Glu Glu Ala Asp Thr Leu Ile Asn Ser Phe Tyr Thr Asn Lys Gly Asp
            340                 345                 350

Ser Leu Ala Leu Ser Leu Arg Gly Leu Pro Thr Leu Val Ser Glu Leu
        355                 360                 365

Thr Arg Thr Ala His Gly Asn Thr Asn Ala Glu Ala Arg Ser Gln Gln
    370                 375                 380

Ile Tyr Ala Thr Thr Leu Ser Leu Val Val Lys Ser Leu Lys Ala His
385                 390                 395                 400

Lys Glu Met Leu Asn Lys Gln Ile Leu Ser Lys Glu Ile Val Leu Asp
                405                 410                 415

Phe Ser Glu Thr Ala Ala Ser Cys Gln Gly Leu Asp Ile Phe Ser Glu
            420                 425                 430

Asn Val Ala Val Gln Ile His Leu Asn Gly Thr Val Ser Ile His Leu
        435                 440                 445


<210> SEQ ID NO 3
<211> LENGTH: 2433
<212> TYPE: DNA
<213> ORGANISM: Chlamydia trachomatis

<400> SEQUENCE: 3

atgactaagc cttctttctt atacgttatt caaccttttt ccgtatttaa tccacgatta     60

ggacgtttct ctacagactc agatacttat atcgaagaag aaaaccgcct agcatcgttc    120

attgagagtt tgccactgga gatcttcgat ataccttctt tcatggaaac cgcgatttcc    180

aatagcccct atattttatc ttgggagaca actaaagacg gcgctctgtt cactattctt    240

gaacccaaac tctcagcttg cgcagccact tgcctggtag ccccttctat acaaatgaaa    300

tccgatgcgg agctcctaga agaaattaag caagcgttat tacgcagctc tcatgacggt    360

gtgaaatatc gcatcaccag agaatccttc tctccagaaa agaaaactcc taaggttgct    420

ctagtcgatg acgatattga attgattcgc aatgtcgact ttttgggtag agctgttgac    480

attgtcaaat tagaccctat taatattctg aataccgtaa gcgaagagaa tattctagat    540

tactctttta caagagaaac ggctcagctg agcgcggatg gtcgttttgg tattcctcca    600

gggactaagc tattccctaa accttctttt gatgtagaaa tcagtacctc cattttcgaa    660

gaaacaactt catttactcg aagtttttct gcatcggtta cttttagtgt accagacctc    720

gcggcgacta tgcctcttca aagccctccc atggtagaaa atggtcaaaa agaaatttgt    780

gtcattcaaa aacacttatt cccaagctac tctcctaaac tagtcgatat tgttaaacga    840

tacaaaagag aggctaagat cttgattaac aagcttgcct ttggaatgtt atggcgacat    900

cgggctaaaa gccaaatcct caccgaggga agcgtacgtc tagacttaca aggattcaca    960

gaatcgaagt acaattacca gattcaagta ggatcccata cgattgcagc tgtattaatc   1020

gatatggata tttccaagat tcaatccaaa tcagaacaag cttatgcaat taggaaaatc   1080

aaatcaggct ttcaacgtag cttggatgac tatcatattt atcaaattga aagaaaacaa   1140

accttttctt tttctccgaa gcatcgcagc ctctcatcca catcccattc cgaagattct   1200

gatttggatc tttctgaagc agccgccttt tcaggaagtc ttacctgcga gtttgtaaaa   1260

aaaagcactc aacatgccaa gaataccgtc acatgttcca cagccgctca ttccctatac   1320
```

```
acactcaaag aagatgacag ctcgaacccc tctgaaaaac gattagatag ttgtttccgc   1380

aattggattg aaaacaaact aagcgccaat tctccagatt cctggtcagc gtttattcaa   1440

aaattcggaa cacactatat tgcatcagca acttttggag ggataggttt ccaagtgctc   1500

aaactatctt ttgaacaggt ggaggatcta catagcaaaa agatctcctt agaaaccgca   1560

gcagccaact ctctattaaa aggttctgta tccagcagca cagaatctgg atactccagc   1620

tatagctcca cgtcttcttc tcatacggta tttttaggag gaacggtctt accttcggtt   1680

catgatgaac gtttagactt taaagattgg tcggaaagtg tgcacctgga acctgttcct   1740

atccaggttt ctttacaacc tataacgaat ttactagttc ctctccattt tcctaatatc   1800

ggtgctgcag agctctctaa taaacgagaa tctcttcaac aagcgattcg agtctatctc   1860

aaagaacata aagtagatga gcaaggagaa cgtactacat ttacatcagg aatcgataat   1920

ccttcttcct ggtttacctt agaagctgcc cactctcctc ttatagtcag tactccttac   1980

attgcttcgt ggtctacgct tccttatttg ttcccaacat taagagaacg ttcttcggca   2040

acccctatcg ttttctattt ttgtgtagat aataatgaac atgcttcgca aaaaatatta   2100

aaccaatcgt attgcttcct cgggtccttg cctattcgac aaaaaatttt tggtagcgaa   2160

tttgctagtt tcccctatct atctttctat ggaaatgcaa aagaggcgta ctttgataac   2220

acgtactacc caacgcgttg tgggtggatt gttgaaaagt taaatactac acaagatcaa   2280

ttcctccggg atggagacga ggtgcgacta aaacatgttt ccagcggaaa gtatctagca   2340

acaactcctc ttaaggatac ccatggtaca ctcacgcgta caacgaactg tgaagatgct   2400

atctttatta ttaaaaaatc ttcaggttat tga                                2433
```

<210> SEQ ID NO 4
<211> LENGTH: 810
<212> TYPE: PRT
<213> ORGANISM: Chlamydia trachomatis

<400> SEQUENCE: 4

```
Met Thr Lys Pro Ser Phe Leu Tyr Val Ile Gln Pro Phe Ser Val Phe
1               5                   10                  15

Asn Pro Arg Leu Gly Arg Phe Ser Thr Asp Ser Asp Thr Tyr Ile Glu
            20                  25                  30

Glu Glu Asn Arg Leu Ala Ser Phe Ile Glu Ser Leu Pro Leu Glu Ile
        35                  40                  45

Phe Asp Ile Pro Ser Phe Met Glu Thr Ala Ile Ser Asn Ser Pro Tyr
    50                  55                  60

Ile Leu Ser Trp Glu Thr Thr Lys Asp Gly Ala Leu Phe Thr Ile Leu
65                  70                  75                  80

Glu Pro Lys Leu Ser Ala Cys Ala Ala Thr Cys Leu Val Ala Pro Ser
                85                  90                  95

Ile Gln Met Lys Ser Asp Ala Glu Leu Leu Glu Glu Ile Lys Gln Ala
            100                 105                 110

Leu Leu Arg Ser Ser His Asp Gly Val Lys Tyr Arg Ile Thr Arg Glu
        115                 120                 125

Ser Phe Ser Pro Glu Lys Lys Thr Pro Lys Val Ala Leu Val Asp Asp
    130                 135                 140

Asp Ile Glu Leu Ile Arg Asn Val Asp Phe Leu Gly Arg Ala Val Asp
145                 150                 155                 160

Ile Val Lys Leu Asp Pro Ile Asn Ile Leu Asn Thr Val Ser Glu Glu
                165                 170                 175
```

```
Asn Ile Leu Asp Tyr Ser Phe Thr Arg Glu Thr Ala Gln Leu Ser Ala
        180                 185                 190

Asp Gly Arg Phe Gly Ile Pro Pro Gly Thr Lys Leu Phe Pro Lys Pro
    195                 200                 205

Ser Phe Asp Val Glu Ile Ser Thr Ser Ile Phe Glu Glu Thr Thr Ser
    210                 215                 220

Phe Thr Arg Ser Phe Ser Ala Ser Val Thr Phe Ser Val Pro Asp Leu
225                 230                 235                 240

Ala Ala Thr Met Pro Leu Gln Ser Pro Pro Met Val Glu Asn Gly Gln
                245                 250                 255

Lys Glu Ile Cys Val Ile Gln Lys His Leu Phe Pro Ser Tyr Ser Pro
            260                 265                 270

Lys Leu Val Asp Ile Val Lys Arg Tyr Lys Arg Glu Ala Lys Ile Leu
        275                 280                 285

Ile Asn Lys Leu Ala Phe Gly Met Leu Trp Arg His Arg Ala Lys Ser
    290                 295                 300

Gln Ile Leu Thr Glu Gly Ser Val Arg Leu Asp Leu Gln Gly Phe Thr
305                 310                 315                 320

Glu Ser Lys Tyr Asn Tyr Gln Ile Gln Val Gly Ser His Thr Ile Ala
                325                 330                 335

Ala Val Leu Ile Asp Met Asp Ile Ser Lys Ile Gln Ser Lys Ser Glu
            340                 345                 350

Gln Ala Tyr Ala Ile Arg Lys Ile Lys Ser Gly Phe Gln Arg Ser Leu
        355                 360                 365

Asp Asp Tyr His Ile Tyr Gln Ile Glu Arg Lys Gln Thr Phe Ser Phe
    370                 375                 380

Ser Pro Lys His Arg Ser Leu Ser Ser Thr Ser His Ser Glu Asp Ser
385                 390                 395                 400

Asp Leu Asp Leu Ser Glu Ala Ala Ala Phe Ser Gly Ser Leu Thr Cys
                405                 410                 415

Glu Phe Val Lys Lys Ser Thr Gln His Ala Lys Asn Thr Val Thr Cys
            420                 425                 430

Ser Thr Ala Ala His Ser Leu Tyr Thr Leu Lys Glu Asp Asp Ser Ser
        435                 440                 445

Asn Pro Ser Glu Lys Arg Leu Asp Ser Cys Phe Arg Asn Trp Ile Glu
    450                 455                 460

Asn Lys Leu Ser Ala Asn Ser Pro Asp Ser Trp Ser Ala Phe Ile Gln
465                 470                 475                 480

Lys Phe Gly Thr His Tyr Ile Ala Ser Ala Thr Phe Gly Gly Ile Gly
                485                 490                 495

Phe Gln Val Leu Lys Leu Ser Phe Glu Gln Val Glu Asp Leu His Ser
            500                 505                 510

Lys Lys Ile Ser Leu Glu Thr Ala Ala Ala Asn Ser Leu Leu Lys Gly
        515                 520                 525

Ser Val Ser Ser Ser Thr Glu Ser Gly Tyr Ser Ser Tyr Ser Ser Thr
    530                 535                 540

Ser Ser Ser His Thr Val Phe Leu Gly Gly Thr Val Leu Pro Ser Val
545                 550                 555                 560

His Asp Glu Arg Leu Asp Phe Lys Asp Trp Ser Glu Ser Val His Leu
                565                 570                 575

Glu Pro Val Pro Ile Gln Val Ser Leu Gln Pro Ile Thr Asn Leu Leu
            580                 585                 590

Val Pro Leu His Phe Pro Asn Ile Gly Ala Ala Glu Leu Ser Asn Lys
        595                 600                 605
```

```
Arg Glu Ser Leu Gln Gln Ala Ile Arg Val Tyr Leu Lys Glu His Lys
    610                 615                 620

Val Asp Glu Gln Gly Glu Arg Thr Thr Phe Thr Ser Gly Ile Asp Asn
625                 630                 635                 640

Pro Ser Ser Trp Phe Thr Leu Glu Ala Ala His Ser Pro Leu Ile Val
                645                 650                 655

Ser Thr Pro Tyr Ile Ala Ser Trp Ser Thr Leu Pro Tyr Leu Phe Pro
            660                 665                 670

Thr Leu Arg Glu Arg Ser Ser Ala Thr Pro Ile Val Phe Tyr Phe Cys
        675                 680                 685

Val Asp Asn Asn Glu His Ala Ser Gln Lys Ile Leu Asn Gln Ser Tyr
    690                 695                 700

Cys Phe Leu Gly Ser Leu Pro Ile Arg Gln Lys Ile Phe Gly Ser Glu
705                 710                 715                 720

Phe Ala Ser Phe Pro Tyr Leu Ser Phe Tyr Gly Asn Ala Lys Glu Ala
                725                 730                 735

Tyr Phe Asp Asn Thr Tyr Tyr Pro Thr Arg Cys Gly Trp Ile Val Glu
            740                 745                 750

Lys Leu Asn Thr Thr Gln Asp Gln Phe Leu Arg Asp Gly Asp Glu Val
        755                 760                 765

Arg Leu Lys His Val Ser Ser Gly Lys Tyr Leu Ala Thr Thr Pro Leu
    770                 775                 780

Lys Asp Thr His Gly Thr Leu Thr Arg Thr Thr Asn Cys Glu Asp Ala
785                 790                 795                 800

Ile Phe Ile Ile Lys Lys Ser Ser Gly Tyr
        805                 810
```

<210> SEQ ID NO 5
<211> LENGTH: 603
<212> TYPE: DNA
<213> ORGANISM: Chlamydia trachomatis

<400> SEQUENCE: 5

```
atgctcgcta atcgcttatt cttaataacc cttttagggt taagttcgtc tgtttacggc      60

gcaggtaaag caccgtcttt gcaggctatt ctagccgaag tcgaagacac ctcctctcgt     120

ctacacgctc atcacaatga gcttgctatg atctctgaac gcctcgatga gcaagacacg     180

aaactacagc aactttcgtc aacacaagat cataacctac ctcgacaagt tcagcgacta     240

gaaacggacc aaaaagcttt ggcaaaaaca ctggcgattc tttcgcaatc cgtccaagat     300

attcggtctt ctgtacaaaa taaattacaa gaaatccaac aagaacaaaa aaaattagca     360

caaaatttgc gagcgcttcg taactcttta caagctctcg ttgatggctc ttctccagaa     420

aattatattg atttcctaac tggtgaaacc ccggaacata ttcatattgt taaacaagga     480

gagaccctga gcaagatcgc gagtaaatat aacatccccg tcgtagaatt aaaaaaactt     540

aataaactaa attcggatac tatttttaca gatcaaagaa ttcgccttcc gaaaaagaaa     600

tag                                                                   603
```

<210> SEQ ID NO 6
<211> LENGTH: 200
<212> TYPE: PRT
<213> ORGANISM: Chlamydia trachomatis

<400> SEQUENCE: 6

```
Met Leu Ala Asn Arg Leu Phe Leu Ile Thr Leu Leu Gly Leu Ser Ser
1               5                   10                  15
```

```
Ser Val Tyr Gly Ala Gly Lys Ala Pro Ser Leu Gln Ala Ile Leu Ala
            20                  25                  30

Glu Val Glu Asp Thr Ser Ser Arg Leu His Ala His His Asn Glu Leu
        35                  40                  45

Ala Met Ile Ser Glu Arg Leu Asp Glu Gln Asp Thr Lys Leu Gln Gln
    50                  55                  60

Leu Ser Ser Thr Gln Asp His Asn Leu Pro Arg Gln Val Gln Arg Leu
65                  70                  75                  80

Glu Thr Asp Gln Lys Ala Leu Ala Lys Thr Leu Ala Ile Leu Ser Gln
                85                  90                  95

Ser Val Gln Asp Ile Arg Ser Ser Val Gln Asn Lys Leu Gln Glu Ile
            100                 105                 110

Gln Gln Glu Gln Lys Lys Leu Ala Gln Asn Leu Arg Ala Leu Arg Asn
        115                 120                 125

Ser Leu Gln Ala Leu Val Asp Gly Ser Ser Pro Glu Asn Tyr Ile Asp
    130                 135                 140

Phe Leu Thr Gly Glu Thr Pro Glu His Ile His Ile Val Lys Gln Gly
145                 150                 155                 160

Glu Thr Leu Ser Lys Ile Ala Ser Lys Tyr Asn Ile Pro Val Val Glu
                165                 170                 175

Leu Lys Lys Leu Asn Lys Leu Asn Ser Asp Thr Ile Phe Thr Asp Gln
            180                 185                 190

Arg Ile Arg Leu Pro Lys Lys Lys
        195                 200
```

<210> SEQ ID NO 7
<211> LENGTH: 951
<212> TYPE: DNA
<213> ORGANISM: Chlamydia trachomatis

<400> SEQUENCE: 7

```
atggcatcca agtctcgcca ttatcttaat cagccttggt acattatctt attcatcttt     60
gttcttagtt taattgctgg taccctcctg tcttctgtgt attatgtcct tgcacctatc    120
caacagcaag ctgcggaatt cgatcgcaat caacaaatgc taatggctgc acaagtaatt    180
tcttccgata acacattcca agtctatgaa aagggagatt ggcacccagc cctatataat    240
actaaaaagc agttgctaga gatctcctct actcctccta aagtaaccgt gacaacttta    300
agctcatatt ttcaaaactt tgttagagtc ttgcttacag atacacaagg aaatctttct    360
tcattcgaag accataatct caatctagaa gaatttttat ctcaaccaac tcctgtaata    420
catggtcttg ccctttatgt ggtctacgct atcctacaca acgatgcagc ttcctctaaa    480
ttatctgctt cccaagtagc gaaaaatcca acagctatag aatctatagt tcttcctata    540
gaaggttttg gtttgtgggg acctatctat ggattccttg ctctagaaaa agacgggaat    600
actgttcttg gtacttcttg gtatcaacat ggcgagactc ctggattagg agcaaatatc    660
gctaaccctc aatggcaaaa aaatttcaga ggcaaaaaag tatttctagt ctcagcttct    720
ggagaaacag attttgctaa gacaacccta ggactggaag ttataaaagg atctgtatct    780
gcagcattag gagactcacc taaagctgct tcttccatcg acggaatttc aggagctact    840
ttgacttgta atggtgttac cgaatccttc tctcattctc tagctcccta ccgcgctttg    900
ttgactttct tcgccaactc taaacctagt ggagagtctc atgaccacta a             951
```

<210> SEQ ID NO 8
<211> LENGTH: 316

<212> TYPE: PRT
<213> ORGANISM: Chlamydia trachomatis

<400> SEQUENCE: 8

Met Ala Ser Lys Ser Arg His Tyr Leu Asn Gln Pro Trp Tyr Ile Ile
1 5 10 15

Leu Phe Ile Phe Val Leu Ser Leu Ile Ala Gly Thr Leu Leu Ser Ser
20 25 30

Val Tyr Tyr Val Leu Ala Pro Ile Gln Gln Gln Ala Ala Glu Phe Asp
35 40 45

Arg Asn Gln Gln Met Leu Met Ala Ala Gln Val Ile Ser Ser Asp Asn
50 55 60

Thr Phe Gln Val Tyr Glu Lys Gly Asp Trp His Pro Ala Leu Tyr Asn
65 70 75 80

Thr Lys Lys Gln Leu Leu Glu Ile Ser Ser Thr Pro Pro Lys Val Thr
85 90 95

Val Thr Thr Leu Ser Ser Tyr Phe Gln Asn Phe Val Arg Val Leu Leu
100 105 110

Thr Asp Thr Gln Gly Asn Leu Ser Ser Phe Glu Asp His Asn Leu Asn
115 120 125

Leu Glu Glu Phe Leu Ser Gln Pro Thr Pro Val Ile His Gly Leu Ala
130 135 140

Leu Tyr Val Val Tyr Ala Ile Leu His Asn Asp Ala Ala Ser Ser Lys
145 150 155 160

Leu Ser Ala Ser Gln Val Ala Lys Asn Pro Thr Ala Ile Glu Ser Ile
165 170 175

Val Leu Pro Ile Glu Gly Phe Gly Leu Trp Gly Pro Ile Tyr Gly Phe
180 185 190

Leu Ala Leu Glu Lys Asp Gly Asn Thr Val Leu Gly Thr Ser Trp Tyr
195 200 205

Gln His Gly Glu Thr Pro Gly Leu Gly Ala Asn Ile Ala Asn Pro Gln
210 215 220

Trp Gln Lys Asn Phe Arg Gly Lys Lys Val Phe Leu Val Ser Ala Ser
225 230 235 240

Gly Glu Thr Asp Phe Ala Lys Thr Thr Leu Gly Leu Glu Val Ile Lys
245 250 255

Gly Ser Val Ser Ala Ala Leu Gly Asp Ser Pro Lys Ala Ala Ser Ser
260 265 270

Ile Asp Gly Ile Ser Gly Ala Thr Leu Thr Cys Asn Gly Val Thr Glu
275 280 285

Ser Phe Ser His Ser Leu Ala Pro Tyr Arg Ala Leu Leu Thr Phe Phe
290 295 300

Ala Asn Ser Lys Pro Ser Gly Glu Ser His Asp His
305 310 315

<210> SEQ ID NO 9
<211> LENGTH: 1662
<212> TYPE: DNA
<213> ORGANISM: Chlamydia trachomatis

<400> SEQUENCE: 9
atgcgaatag gagatcctat gaacaaactc atcagacgag cagtgacgat cttcgcggtg 60
actagtgtgg cgagtttatt tgctagcggg gtgttagaga cctctatggc agagtctctc 120
tctacaaacg ttattagctt agctgacacc aaagcgaaag acaacacttc tcataaaagc 180
aaaaaagcaa gaaaaaacca cagcaaagag actcccgtag accgtaaaga ggttgctccg 240

```
gttcatgagt ctaaagctac aggacctaaa caggattctt gctttggcag aatgtataca    300

gtcaaagtta atgatgatcg caatgttgaa atcacacaag ctgttcctga atatgctacg    360

gtaggatctc cctatcctat tgaaattact gctacaggta aaagggattg tgttgatgtt    420

atcattactc agcaattacc atgtgaagca gagttcgtac gcagtgatcc agcgacaact    480

cctactgctg atggtaagct agtttggaaa attgaccgct taggacaagg cgaaaagagt    540

aaaattactg tatgggtaaa acctcttaaa gaaggttgct gctttacagc tgcaacagta    600

tgcgcttgtc cagagatccg ttcggttaca aaatgtggac aacctgctat ctgtgttaaa    660

caagaaggcc cagagaatgc ttgtttgcgt tgcccagtag tttacaaaat taatatagtg    720

aaccaaggaa cagcaacagc tcgtaacgtt gttgttgaaa atcctgttcc agatggttac    780

gctcattctt ctggacagcg tgtactgacg tttactcttg gagatatgca acctggagag    840

cacagaacaa ttactgtaga gttttgtccg cttaaacgtg gtcgtgctac caatatagca    900

acggtttctt actgtggagg acataaaaat acagcaagcg taacaactgt gatcaacgag    960

ccttgcgtac aagtaagtat tgcaggagca gattggtctt atgtttgtaa gcctgtagaa   1020

tatgtgatct ccgtttccaa tcctggagat cttgtgttgc gagatgtcgt cgttgaagac   1080

actctttctc ccggagtcac agttcttgaa gctgcaggag ctcaaatttc ttgtaataaa   1140

gtagtttgga ctgtgaaaga actgaatcct ggagagtctc tacagtataa agttctagta   1200

agagcacaaa ctcctggaca attcacaaat aatgttgttg tgaagagctg ctctgactgt   1260

ggtacttgta cttcttgcgc agaagcgaca acttactgga aaggagttgc tgctactcat   1320

atgtgcgtag tagatacttg tgaccctgtt tgtgtaggag aaaatactgt ttaccgtatt   1380

tgtgtcacca acagaggttc tgcagaagat acaaatgttt ctttaatgct taaattctct   1440

aaagaactgc aacctgtatc cttctctgga ccaactaaag gaacgattac aggcaataca   1500

gtagtattcg attcgttacc tagattaggt tctaaagaaa ctgtagagtt ttctgtaaca   1560

ttgaaagcag tatcagctgg agatgctcgt ggggaagcga ttctttcttc cgatacattg   1620

actgttccag tttctgatac agagaataca cacatctatt aa                      1662
```

<210> SEQ ID NO 10
<211> LENGTH: 553
<212> TYPE: PRT
<213> ORGANISM: Chlamydia trachomatis

<400> SEQUENCE: 10

```
Met Arg Ile Gly Asp Pro Met Asn Lys Leu Ile Arg Arg Ala Val Thr
1               5                   10                  15

Ile Phe Ala Val Thr Ser Val Ala Ser Leu Phe Ala Ser Gly Val Leu
            20                  25                  30

Glu Thr Ser Met Ala Glu Ser Leu Ser Thr Asn Val Ile Ser Leu Ala
        35                  40                  45

Asp Thr Lys Ala Lys Asp Asn Thr Ser His Lys Ser Lys Lys Ala Arg
    50                  55                  60

Lys Asn His Ser Lys Glu Thr Pro Val Asp Arg Lys Glu Val Ala Pro
65                  70                  75                  80

Val His Glu Ser Lys Ala Thr Gly Pro Lys Gln Asp Ser Cys Phe Gly
                85                  90                  95

Arg Met Tyr Thr Val Lys Val Asn Asp Asp Arg Asn Val Glu Ile Thr
            100                 105                 110

Gln Ala Val Pro Glu Tyr Ala Thr Val Gly Ser Pro Tyr Pro Ile Glu
        115                 120                 125
```

-continued

```
Ile Thr Ala Thr Gly Lys Arg Asp Cys Val Asp Val Ile Ile Thr Gln
    130                 135                 140

Gln Leu Pro Cys Glu Ala Glu Phe Val Arg Ser Asp Pro Ala Thr Thr
145                 150                 155                 160

Pro Thr Ala Asp Gly Lys Leu Val Trp Lys Ile Asp Arg Leu Gly Gln
                165                 170                 175

Gly Glu Lys Ser Lys Ile Thr Val Trp Val Lys Pro Leu Lys Glu Gly
            180                 185                 190

Cys Cys Phe Thr Ala Ala Thr Val Cys Ala Cys Pro Glu Ile Arg Ser
        195                 200                 205

Val Thr Lys Cys Gly Gln Pro Ala Ile Cys Val Lys Gln Glu Gly Pro
    210                 215                 220

Glu Asn Ala Cys Leu Arg Cys Pro Val Val Tyr Lys Ile Asn Ile Val
225                 230                 235                 240

Asn Gln Gly Thr Ala Thr Ala Arg Asn Val Val Val Glu Asn Pro Val
                245                 250                 255

Pro Asp Gly Tyr Ala His Ser Ser Gly Gln Arg Val Leu Thr Phe Thr
            260                 265                 270

Leu Gly Asp Met Gln Pro Gly Glu His Arg Thr Ile Thr Val Glu Phe
        275                 280                 285

Cys Pro Leu Lys Arg Gly Arg Ala Thr Asn Ile Ala Thr Val Ser Tyr
    290                 295                 300

Cys Gly Gly His Lys Asn Thr Ala Ser Val Thr Thr Val Ile Asn Glu
305                 310                 315                 320

Pro Cys Val Gln Val Ser Ile Ala Gly Ala Asp Trp Ser Tyr Val Cys
                325                 330                 335

Lys Pro Val Glu Tyr Val Ile Ser Val Ser Asn Pro Gly Asp Leu Val
            340                 345                 350

Leu Arg Asp Val Val Val Glu Asp Thr Leu Ser Pro Gly Val Thr Val
        355                 360                 365

Leu Glu Ala Ala Gly Ala Gln Ile Ser Cys Asn Lys Val Val Trp Thr
    370                 375                 380

Val Lys Glu Leu Asn Pro Gly Glu Ser Leu Gln Tyr Lys Val Leu Val
385                 390                 395                 400

Arg Ala Gln Thr Pro Gly Gln Phe Thr Asn Asn Val Val Val Lys Ser
                405                 410                 415

Cys Ser Asp Cys Gly Thr Cys Thr Ser Cys Ala Glu Ala Thr Thr Tyr
            420                 425                 430

Trp Lys Gly Val Ala Ala Thr His Met Cys Val Val Asp Thr Cys Asp
        435                 440                 445

Pro Val Cys Val Gly Glu Asn Thr Val Tyr Arg Ile Cys Val Thr Asn
    450                 455                 460

Arg Gly Ser Ala Glu Asp Thr Asn Val Ser Leu Met Leu Lys Phe Ser
465                 470                 475                 480

Lys Glu Leu Gln Pro Val Ser Phe Ser Gly Pro Thr Lys Gly Thr Ile
                485                 490                 495

Thr Gly Asn Thr Val Val Phe Asp Ser Leu Pro Arg Leu Gly Ser Lys
            500                 505                 510

Glu Thr Val Glu Phe Ser Val Thr Leu Lys Ala Val Ser Ala Gly Asp
        515                 520                 525

Ala Arg Gly Glu Ala Ile Leu Ser Ser Asp Thr Leu Thr Val Pro Val
    530                 535                 540

Ser Asp Thr Glu Asn Thr His Ile Tyr
```

-continued 545 550

<210> SEQ ID NO 11
<211> LENGTH: 1329
<212> TYPE: DNA
<213> ORGANISM: Chlamydia trachomatis

<400> SEQUENCE: 11
atgcaggctg cacaccatca ctatcaccgc tacacagata aactgcacag acaaaaccat 60
aaaaaagatc tcatctctcc caaacctacc gaacaagagg cgtgcaatac ttcttccctt 120
agtaaggaat taatccctct atcagaacaa agaggccttt tatcccccat ctgtgacttt 180
atttcggaac gcccttgctt acacggagtt tctgttagaa atctcaagca agcgctaaaa 240
aattctgcag gaacccaaat tgcactggat tggtctattc tccctcaatg gttcaatcct 300
cgggtctctc atgcccctaa gctttctatc cgagactttg ggtatagcgc acaccaaact 360
gttaccgaag ccactcctcc ttgctggcaa aactgcttta atccatctgc ggccgttact 420
atctatgatt cctcatatgg gaaaggggtc tttcaaatat cctataccct tgtccgctat 480
tggagagaga atgctgcgac tgctggcgat gctatgatgc tcgcagggag tatcaatgat 540
tatccctctc gtcagaacat ttctctcag tttactttct cccaaaactt cccaaatgaa 600
cgggtgagtc tgacaattgg tcagtactca ctctatgcaa tagacggaac attatacaat 660
aacgatcaac aacttggatt cattagttac gcattatcac aaaatccaac agcaacttat 720
tcctctggaa gtcttggagc ttacctacaa gtcgctccta ccgcaagcac aagtcttcaa 780
ataggatttc aagacgctta taatatctcc ggatcctcta tcaaatggag taaccttaca 840
aaaaatagat acaattttca cggttttgct tcctgggctc cccgctgttg cttaggatct 900
ggccagtact ccgtgcttct ttatgtgact agacaagttc cagaacagat ggaacaaaca 960
atgggatggt cagtcaatgc gagtcaacac atatcttcta aactgtatgt gtttggaaga 1020
tacagcggtg ttacaggaca tgtgttcccg attaaccgca cgtattcatt cggtatggcc 1080
tctgcaaatt tatttaaccg taacccacaa gatttatttg gaattgcttg cgcattcaat 1140
aatgtacacc tctctgcttc tccaaatact aaaagaaaat acgaaactgt aatcgaaggg 1200
tttgcaacta tcggttgcgg cccctatctt tctttcgctc cagacttcca actctacctc 1260
tacccagctc ttcgtccaaa caaacaatct gcccgtgttt atagcgtgcg agctaattta 1320
gctatctaa 1329

<210> SEQ ID NO 12
<211> LENGTH: 442
<212> TYPE: PRT
<213> ORGANISM: Chlamydia trachomatis

<400> SEQUENCE: 12

Met Gln Ala Ala His His His Tyr His Arg Tyr Thr Asp Lys Leu His
1 5 10 15

Arg Gln Asn His Lys Lys Asp Leu Ile Ser Pro Lys Pro Thr Glu Gln
20 25 30

Glu Ala Cys Asn Thr Ser Ser Leu Ser Lys Glu Leu Ile Pro Leu Ser
35 40 45

Glu Gln Arg Gly Leu Leu Ser Pro Ile Cys Asp Phe Ile Ser Glu Arg
50 55 60

Pro Cys Leu His Gly Val Ser Val Arg Asn Leu Lys Gln Ala Leu Lys
65 70 75 80

Asn Ser Ala Gly Thr Gln Ile Ala Leu Asp Trp Ser Ile Leu Pro Gln

```
                85                  90                  95

Trp Phe Asn Pro Arg Val Ser His Ala Pro Lys Leu Ser Ile Arg Asp
            100                 105                 110

Phe Gly Tyr Ser Ala His Gln Thr Val Thr Glu Ala Thr Pro Pro Cys
        115                 120                 125

Trp Gln Asn Cys Phe Asn Pro Ser Ala Ala Val Thr Ile Tyr Asp Ser
    130                 135                 140

Ser Tyr Gly Lys Gly Val Phe Gln Ile Ser Tyr Thr Leu Val Arg Tyr
145                 150                 155                 160

Trp Arg Glu Asn Ala Ala Thr Ala Gly Asp Ala Met Met Leu Ala Gly
                165                 170                 175

Ser Ile Asn Asp Tyr Pro Ser Arg Gln Asn Ile Phe Ser Gln Phe Thr
            180                 185                 190

Phe Ser Gln Asn Phe Pro Asn Glu Arg Val Ser Leu Thr Ile Gly Gln
        195                 200                 205

Tyr Ser Leu Tyr Ala Ile Asp Gly Thr Leu Tyr Asn Asn Asp Gln Gln
    210                 215                 220

Leu Gly Phe Ile Ser Tyr Ala Leu Ser Gln Asn Pro Thr Ala Thr Tyr
225                 230                 235                 240

Ser Ser Gly Ser Leu Gly Ala Tyr Leu Gln Val Ala Pro Thr Ala Ser
                245                 250                 255

Thr Ser Leu Gln Ile Gly Phe Gln Asp Ala Tyr Asn Ile Ser Gly Ser
            260                 265                 270

Ser Ile Lys Trp Ser Asn Leu Thr Lys Asn Arg Tyr Asn Phe His Gly
        275                 280                 285

Phe Ala Ser Trp Ala Pro Arg Cys Cys Leu Gly Ser Gly Gln Tyr Ser
    290                 295                 300

Val Leu Leu Tyr Val Thr Arg Gln Val Pro Glu Gln Met Glu Gln Thr
305                 310                 315                 320

Met Gly Trp Ser Val Asn Ala Ser Gln His Ile Ser Ser Lys Leu Tyr
                325                 330                 335

Val Phe Gly Arg Tyr Ser Gly Val Thr Gly His Val Phe Pro Ile Asn
            340                 345                 350

Arg Thr Tyr Ser Phe Gly Met Ala Ser Ala Asn Leu Phe Asn Arg Asn
        355                 360                 365

Pro Gln Asp Leu Phe Gly Ile Ala Cys Ala Phe Asn Asn Val His Leu
    370                 375                 380

Ser Ala Ser Pro Asn Thr Lys Arg Lys Tyr Glu Thr Val Ile Glu Gly
385                 390                 395                 400

Phe Ala Thr Ile Gly Cys Gly Pro Tyr Leu Ser Phe Ala Pro Asp Phe
                405                 410                 415

Gln Leu Tyr Leu Tyr Pro Ala Leu Arg Pro Asn Lys Gln Ser Ala Arg
            420                 425                 430

Val Tyr Ser Val Arg Ala Asn Leu Ala Ile
        435                 440
```

<210> SEQ ID NO 13
<211> LENGTH: 3018
<212> TYPE: DNA
<213> ORGANISM: Chlamydia trachomatis

<400> SEQUENCE: 13

```
atgacgaatt ctatatcagg ttatcaacct actgttacaa cttctacatc atcaaccact      60

tcggcatcag gtgcttccgg atctctggga gcttcttctg tatctactac cgcaaacgct     120
```

-continued

```
acagttacac aaacagcaaa cgcaacaaat tcagcggcta catcttctat ccaaacgact    180
ggagagactg tagtaaacta tacgaattca gcctccgccc ccaatgtaac tgtatcgacc    240
tcctcttctt ccacacaagc cacagccact tcgaataaaa cttcccaagc cgttgctgga    300
aaaatcactt ctccagatac ttcagaaagc tcagaaacta gctctacctc atcaagcgat    360
catatcccta gcgattacga tgacgttggt agcaatagtg gagatattag caacaactac    420
gatgacgtag gtagtaacaa cggagatatc agtagcaatt atgacgatgc tgctgctgat    480
tacgagccga taagaactac tgaaaatatt tatgagagta ttggtggctc tagaacaagt    540
ggcccagaaa atacaagtgg tggtgcagca gcagcactca attctctaag aggctcctcc    600
tacagcaatt atgacgatgc tgctgctgat tacgagccga taagaactac tgaaaatatt    660
tatgagagta ttggtggctc tagaacaagt ggcccagaaa atacgagtgg tggtgcagca    720
gcagcactca attctctaag aggctcctcc tacagcaatt atgacgatgc tgctgctgat    780
tacgagccga taagaactac tgaaaatatt tatgagagta ttggtggctc tagaacaagt    840
ggcccagaaa atacgagtga tggtgcagca gcagcagcac tcaattctct aagaggctcc    900
tcctacacaa cagggcctcg taacgagggt gtattcggcc ctggaccgga aggactacca    960
gacatgtctc ttccttcata cgatcctaca aataaaacct cgttattgac tttcctctcc   1020
aaccctcatg taaagtcgaa aatgcttgaa aactcggggc atttcgtctt cattgataca   1080
gatagaagta gtttcattct tgttcctaac ggaaattggg accaagtctg ttcaattaaa   1140
gttcaaaatg gaaagaccaa agaagatctc gacatcaaag acttggaaaa catgtgtgca   1200
aaattctgta cagggtttag caaattctct ggtgactggg acagtcttgt agaacctatg   1260
gtgtcagcca aagctggagt ggccagcgga ggcaatcttc ccaatacagt gattatcaat   1320
aataaattca aaacttgcgt tgcttatggt ccttggaata gccaggaagc aagttctggt   1380
tatacacctt ctgcttggag acgtggtcat cgagtagatt ttggaggaat ttttgagaaa   1440
gccaacgact ttaataaaat caactgggga actcaagccg ggcctagtag cgaagacgat   1500
ggcatttcct tctccaatga aactcctgga gctggtcctg cagctgctcc atcaccaacg   1560
ccatcctcta ttcctatcat caatgtcaat gtcaatgttg gcggaactaa tgtgaatatt   1620
ggagatacga atgtcaacac gactaacacc acaccaacaa ctcaatctac agacgcctct   1680
acagatacaa gcgatatcga tgacataaat accaacaacc aaactgatga tatcaatacg   1740
acagacaaag actctgacgg agctggtgga gtcaatggcg atatatccga aacagaatcc   1800
tcttctggag atgattcagg aagtgtctct tcctcagaat cagacaagaa tgcctctgtc   1860
ggaaatgacg gacctgctat gaaagatatc ctttctgccg tgcgtaaaca cctagacgtc   1920
gtttaccctg gcgaaaatgg cggttctaca gaagggcctc tcccagctaa ccaaactctc   1980
ggagacgtaa tctctgatgt agagaataaa ggctccgctc aggatacaaa attgtcagga   2040
aatacaggag ctggggatga cgatccaaca accacagctg ctgtaggtaa tggagcggaa   2100
gagatcactc tttccgacac agattctggt atcggagatg atgtatccga tacagcgtct   2160
tcatctgggg atgaatccgg aggagtctcc tctccctctt cagaatccaa taaaaatact   2220
gccgttggaa atgacggacc ttctggacta gatatcctcg ctgccgtacg taaacattta   2280
gataaggttt accctggcga caatggtggt tctacagaag ggcctctcca agctaaccaa   2340
actcttggag atatcgtcca ggatatggaa acaacaggga catcccaaga aaccgttgta   2400
tccccatgga aaggaagcac ttcttcaacg gaatcagcag gaggaagtgg tagcgtacaa   2460
acactactgc cttcaccacc tccaaccccg tcaactacaa cattaagaac gggcacagga   2520
```

-continued

```
gctaccacca catccttgat gatgggagga ccaatcaaag ctgacataat aacaactggt   2580

ggcggaggac gaattcctgg aggaggaacg ttagaaaagc tgctccctcg tatacgtgcg   2640

cacttagaca tatcctttga tgcgcaaggc gatctcgtaa gtactgaaga gcctcagctt   2700

ggctcgattg taaacaaatt ccgccaagaa actggttcaa gaggaatctt agctttcgtt   2760

gagagtgctc caggcaagcc gggatctgca caggtcttaa cgggtacagg gggagataaa   2820

ggcaacctat tccaagcagc tgccgcagtc acccaagcct taggaaatgt tgcagggaaa   2880

gtcaaccttg cgatacaagg ccaaaaacta tcatccctag tcaatgacga cgggaagggg   2940

tctgttggaa gagatttatt ccaagcagca gcccaaacaa ctcaagtgct aagcgcactg   3000

attgataccg taggataa                                                 3018
```

```
<210> SEQ ID NO 14
<211> LENGTH: 1005
<212> TYPE: PRT
<213> ORGANISM: Chlamydia trachomatis

<400> SEQUENCE: 14

Met Thr Asn Ser Ile Ser Gly Tyr Gln Pro Thr Val Thr Thr Ser Thr
1               5                   10                  15

Ser Ser Thr Thr Ser Ala Ser Gly Ala Ser Gly Ser Leu Gly Ala Ser
            20                  25                  30

Ser Val Ser Thr Thr Ala Asn Ala Thr Val Thr Gln Thr Ala Asn Ala
        35                  40                  45

Thr Asn Ser Ala Ala Thr Ser Ser Ile Gln Thr Thr Gly Glu Thr Val
    50                  55                  60

Val Asn Tyr Thr Asn Ser Ala Ser Ala Pro Asn Val Thr Val Ser Thr
65                  70                  75                  80

Ser Ser Ser Ser Thr Gln Ala Thr Ala Thr Ser Asn Lys Thr Ser Gln
                85                  90                  95

Ala Val Ala Gly Lys Ile Thr Ser Pro Asp Thr Ser Glu Ser Ser Glu
            100                 105                 110

Thr Ser Ser Thr Ser Ser Ser Asp His Ile Pro Ser Asp Tyr Asp Asp
        115                 120                 125

Val Gly Ser Asn Ser Gly Asp Ile Ser Asn Asn Tyr Asp Asp Val Gly
    130                 135                 140

Ser Asn Asn Gly Asp Ile Ser Ser Asn Tyr Asp Asp Ala Ala Ala Asp
145                 150                 155                 160

Tyr Glu Pro Ile Arg Thr Thr Glu Asn Ile Tyr Glu Ser Ile Gly Gly
                165                 170                 175

Ser Arg Thr Ser Gly Pro Glu Asn Thr Ser Gly Gly Ala Ala Ala Ala
            180                 185                 190

Leu Asn Ser Leu Arg Gly Ser Ser Tyr Ser Asn Tyr Asp Asp Ala Ala
        195                 200                 205

Ala Asp Tyr Glu Pro Ile Arg Thr Thr Glu Asn Ile Tyr Glu Ser Ile
    210                 215                 220

Gly Gly Ser Arg Thr Ser Gly Pro Glu Asn Thr Ser Gly Gly Ala Ala
225                 230                 235                 240

Ala Ala Leu Asn Ser Leu Arg Gly Ser Ser Tyr Ser Asn Tyr Asp Asp
                245                 250                 255

Ala Ala Ala Asp Tyr Glu Pro Ile Arg Thr Thr Glu Asn Ile Tyr Glu
            260                 265                 270

Ser Ile Gly Gly Ser Arg Thr Ser Gly Pro Glu Asn Thr Ser Asp Gly
        275                 280                 285
```

```
Ala Ala Ala Ala Ala Leu Asn Ser Leu Arg Gly Ser Ser Tyr Thr Thr
    290                 295                 300

Gly Pro Arg Asn Glu Gly Val Phe Gly Pro Gly Pro Glu Gly Leu Pro
305                 310                 315                 320

Asp Met Ser Leu Pro Ser Tyr Asp Pro Thr Asn Lys Thr Ser Leu Leu
                325                 330                 335

Thr Phe Leu Ser Asn Pro His Val Lys Ser Lys Met Leu Glu Asn Ser
            340                 345                 350

Gly His Phe Val Phe Ile Asp Thr Asp Arg Ser Ser Phe Ile Leu Val
        355                 360                 365

Pro Asn Gly Asn Trp Asp Gln Val Cys Ser Ile Lys Val Gln Asn Gly
    370                 375                 380

Lys Thr Lys Glu Asp Leu Asp Ile Lys Asp Leu Glu Asn Met Cys Ala
385                 390                 395                 400

Lys Phe Cys Thr Gly Phe Ser Lys Phe Ser Gly Asp Trp Asp Ser Leu
                405                 410                 415

Val Glu Pro Met Val Ser Ala Lys Ala Gly Val Ala Ser Gly Gly Asn
            420                 425                 430

Leu Pro Asn Thr Val Ile Ile Asn Asn Lys Phe Lys Thr Cys Val Ala
        435                 440                 445

Tyr Gly Pro Trp Asn Ser Gln Glu Ala Ser Ser Gly Tyr Thr Pro Ser
    450                 455                 460

Ala Trp Arg Arg Gly His Arg Val Asp Phe Gly Gly Ile Phe Glu Lys
465                 470                 475                 480

Ala Asn Asp Phe Asn Lys Ile Asn Trp Gly Thr Gln Ala Gly Pro Ser
                485                 490                 495

Ser Glu Asp Asp Gly Ile Ser Phe Ser Asn Glu Thr Pro Gly Ala Gly
            500                 505                 510

Pro Ala Ala Ala Pro Ser Pro Thr Pro Ser Ser Ile Pro Ile Ile Asn
        515                 520                 525

Val Asn Val Asn Val Gly Gly Thr Asn Val Asn Ile Gly Asp Thr Asn
    530                 535                 540

Val Asn Thr Thr Asn Thr Thr Pro Thr Thr Gln Ser Thr Asp Ala Ser
545                 550                 555                 560

Thr Asp Thr Ser Asp Ile Asp Asp Ile Asn Thr Asn Asn Gln Thr Asp
                565                 570                 575

Asp Ile Asn Thr Thr Asp Lys Asp Ser Asp Gly Ala Gly Gly Val Asn
            580                 585                 590

Gly Asp Ile Ser Glu Thr Glu Ser Ser Ser Gly Asp Asp Ser Gly Ser
        595                 600                 605

Val Ser Ser Ser Glu Ser Asp Lys Asn Ala Ser Val Gly Asn Asp Gly
    610                 615                 620

Pro Ala Met Lys Asp Ile Leu Ser Ala Val Arg Lys His Leu Asp Val
625                 630                 635                 640

Val Tyr Pro Gly Glu Asn Gly Gly Ser Thr Glu Gly Pro Leu Pro Ala
                645                 650                 655

Asn Gln Thr Leu Gly Asp Val Ile Ser Asp Val Glu Asn Lys Gly Ser
            660                 665                 670

Ala Gln Asp Thr Lys Leu Ser Gly Asn Thr Gly Ala Gly Asp Asp Asp
        675                 680                 685

Pro Thr Thr Thr Ala Ala Val Gly Asn Gly Ala Glu Glu Ile Thr Leu
    690                 695                 700

Ser Asp Thr Asp Ser Gly Ile Gly Asp Asp Val Ser Asp Thr Ala Ser
705                 710                 715                 720
```

```
Ser Ser Gly Asp Glu Ser Gly Gly Val Ser Ser Pro Ser Ser Glu Ser
                725                 730                 735

Asn Lys Asn Thr Ala Val Gly Asn Asp Gly Pro Ser Gly Leu Asp Ile
            740                 745                 750

Leu Ala Ala Val Arg Lys His Leu Asp Lys Val Tyr Pro Gly Asp Asn
        755                 760                 765

Gly Gly Ser Thr Glu Gly Pro Leu Gln Ala Asn Gln Thr Leu Gly Asp
    770                 775                 780

Ile Val Gln Asp Met Glu Thr Thr Gly Thr Ser Gln Glu Thr Val Val
785                 790                 795                 800

Ser Pro Trp Lys Gly Ser Thr Ser Ser Thr Glu Ser Ala Gly Gly Ser
                805                 810                 815

Gly Ser Val Gln Thr Leu Leu Pro Ser Pro Pro Pro Thr Pro Ser Thr
            820                 825                 830

Thr Thr Leu Arg Thr Gly Thr Gly Ala Thr Thr Thr Ser Leu Met Met
        835                 840                 845

Gly Gly Pro Ile Lys Ala Asp Ile Ile Thr Thr Gly Gly Gly Gly Arg
    850                 855                 860

Ile Pro Gly Gly Gly Thr Leu Glu Lys Leu Leu Pro Arg Ile Arg Ala
865                 870                 875                 880

His Leu Asp Ile Ser Phe Asp Ala Gln Gly Asp Leu Val Ser Thr Glu
                885                 890                 895

Glu Pro Gln Leu Gly Ser Ile Val Asn Lys Phe Arg Gln Glu Thr Gly
            900                 905                 910

Ser Arg Gly Ile Leu Ala Phe Val Glu Ser Ala Pro Gly Lys Pro Gly
        915                 920                 925

Ser Ala Gln Val Leu Thr Gly Thr Gly Gly Asp Lys Gly Asn Leu Phe
    930                 935                 940

Gln Ala Ala Ala Ala Val Thr Gln Ala Leu Gly Asn Val Ala Gly Lys
945                 950                 955                 960

Val Asn Leu Ala Ile Gln Gly Gln Lys Leu Ser Ser Leu Val Asn Asp
                965                 970                 975

Asp Gly Lys Gly Ser Val Gly Arg Asp Leu Phe Gln Ala Ala Ala Gln
            980                 985                 990

Thr Thr Gln Val Leu Ser Ala Leu  Ile Asp Thr Val Gly
        995                 1000                1005
```

<210> SEQ ID NO 15
<211> LENGTH: 774
<212> TYPE: DNA
<213> ORGANISM: Chlamydia trachomatis

<400> SEQUENCE: 15

```
atgtgcataa aaagaaaaaa aacatggata gctttttag cagttgtctg tagtttttgt      60

ttgacgggtt gtttaaaaga agggggagac tccaatagtg aaaaatttat tgtagggact    120

aatgcaacct accctccttt tgagtttgtt gataagcgag gagaggttgt aggcttcgat    180

atagacttgg ctagagagat tagtaacaag ctggggaaaa cgctggacgt tcgggagttt    240

tcctttgatg cactcattct aaacctaaaa cagcatcgga ttgatgcggt tataacaggg    300

atgtccatta ctccttctag attgaaggaa attcttatga ttccctatta tggggaggaa    360

ataaaacact tggttttagt gtttaaagga gagaataagc atccattgcc actcactcaa    420

tatcgttctg tagctgttca aacaggaacc tatcaagagg cctatttaca gtctctttct    480

gaagttcata ttcgctcttt tgatagcact ctagaagtac tcatggaagt catgcatggt    540
```

aaatctcccg tcgctgtttt agagccatct atcgctcaag ttgtcttgaa agatttcccg 600
gctctttcta cagcaaccat agatctccct gaagatcagt gggttttagg atacgggatt 660
ggcgttgctt cagatcgccc agctttagcc ttgaaaatcg aggcagctgt gcaagagatc 720
cgaaaagaag gagtgctagc agagttggaa cagaagtggg gtttgaacaa ctaa 774

<210> SEQ ID NO 16
<211> LENGTH: 257
<212> TYPE: PRT
<213> ORGANISM: Chlamydia trachomatis

<400> SEQUENCE: 16

Met Cys Ile Lys Arg Lys Lys Thr Trp Ile Ala Phe Leu Ala Val Val
1 5 10 15

Cys Ser Phe Cys Leu Thr Gly Cys Leu Lys Glu Gly Gly Asp Ser Asn
20 25 30

Ser Glu Lys Phe Ile Val Gly Thr Asn Ala Thr Tyr Pro Pro Phe Glu
35 40 45

Phe Val Asp Lys Arg Gly Glu Val Val Gly Phe Asp Ile Asp Leu Ala
50 55 60

Arg Glu Ile Ser Asn Lys Leu Gly Lys Thr Leu Asp Val Arg Glu Phe
65 70 75 80

Ser Phe Asp Ala Leu Ile Leu Asn Leu Lys Gln His Arg Ile Asp Ala
85 90 95

Val Ile Thr Gly Met Ser Ile Thr Pro Ser Arg Leu Lys Glu Ile Leu
100 105 110

Met Ile Pro Tyr Tyr Gly Glu Glu Ile Lys His Leu Val Leu Val Phe
115 120 125

Lys Gly Glu Asn Lys His Pro Leu Pro Leu Thr Gln Tyr Arg Ser Val
130 135 140

Ala Val Gln Thr Gly Thr Tyr Gln Glu Ala Tyr Leu Gln Ser Leu Ser
145 150 155 160

Glu Val His Ile Arg Ser Phe Asp Ser Thr Leu Glu Val Leu Met Glu
165 170 175

Val Met His Gly Lys Ser Pro Val Ala Val Leu Glu Pro Ser Ile Ala
180 185 190

Gln Val Val Leu Lys Asp Phe Pro Ala Leu Ser Thr Ala Thr Ile Asp
195 200 205

Leu Pro Glu Asp Gln Trp Val Leu Gly Tyr Gly Ile Gly Val Ala Ser
210 215 220

Asp Arg Pro Ala Leu Ala Leu Lys Ile Glu Ala Ala Val Gln Glu Ile
225 230 235 240

Arg Lys Glu Gly Val Leu Ala Glu Leu Glu Gln Lys Trp Gly Leu Asn
245 250 255

Asn

<210> SEQ ID NO 17
<211> LENGTH: 504
<212> TYPE: DNA
<213> ORGANISM: Chlamydia trachomatis

<400> SEQUENCE: 17
atgtccaggc agaatgctga ggaaaatcta aaaaattttg ctaaagagct taaactcccc 60
gacgtggcct tcgatcagaa taatacgtgc attttgtttg ttgatggaga gttttctctt 120
cacctgacct acgaagaaca ctctgatcgc ctttatgttt acgcacctct tcttgacgga 180

```
ctgccagaca atccgcaaag aaggttagct ctatatgaga agttgttaga aggctctatg    240

ctcggaggcc aaatggctgg tggaggggta ggagtcgcta ctaaggaaca gttgatctta    300

atgcactgcg tgttagacat gaagtatgca gagaccaacc tactcaaagc ttttgcacag    360

ctttttattg aaaccgttgt gaaatggcga actgtttgtt ctgatatcag cgctggacga    420

gaacccactg ttgataccat gccacaaatg cctcaagggg gtggcggagg aattcaacct    480

cctccagcag gaatccgtgc ataa                                           504


<210> SEQ ID NO 18
<211> LENGTH: 167
<212> TYPE: PRT
<213> ORGANISM: Chlamydia trachomatis

<400> SEQUENCE: 18

Met Ser Arg Gln Asn Ala Glu Glu Asn Leu Lys Asn Phe Ala Lys Glu
1               5                   10                  15

Leu Lys Leu Pro Asp Val Ala Phe Asp Gln Asn Asn Thr Cys Ile Leu
            20                  25                  30

Phe Val Asp Gly Glu Phe Ser Leu His Leu Thr Tyr Glu Glu His Ser
        35                  40                  45

Asp Arg Leu Tyr Val Tyr Ala Pro Leu Leu Asp Gly Leu Pro Asp Asn
    50                  55                  60

Pro Gln Arg Arg Leu Ala Leu Tyr Glu Lys Leu Leu Glu Gly Ser Met
65                  70                  75                  80

Leu Gly Gly Gln Met Ala Gly Gly Gly Val Gly Val Ala Thr Lys Glu
                85                  90                  95

Gln Leu Ile Leu Met His Cys Val Leu Asp Met Lys Tyr Ala Glu Thr
            100                 105                 110

Asn Leu Leu Lys Ala Phe Ala Gln Leu Phe Ile Glu Thr Val Val Lys
        115                 120                 125

Trp Arg Thr Val Cys Ser Asp Ile Ser Ala Gly Arg Glu Pro Thr Val
    130                 135                 140

Asp Thr Met Pro Gln Met Pro Gln Gly Gly Gly Gly Gly Ile Gln Pro
145                 150                 155                 160

Pro Pro Ala Gly Ile Arg Ala
                165


<210> SEQ ID NO 19
<211> LENGTH: 767
<212> TYPE: PRT
<213> ORGANISM: Chlamydia trachomatis

<400> SEQUENCE: 19

Met Ser Ile Gln Pro Thr Ser Ile Ser Leu Thr Lys Asn Ile Thr Ala
1               5                   10                  15

Ala Leu Ala Gly Glu Gln Val Asp Ala Ala Ala Val Tyr Met Pro Gln
            20                  25                  30

Ala Val Phe Phe Phe Gln Gln Leu Asp Glu Lys Ser Lys Gly Leu Lys
        35                  40                  45

Gln Ala Leu Gly Leu Leu Glu Glu Val Asp Leu Glu Lys Phe Ile Pro
    50                  55                  60

Ser Leu Glu Lys Ser Pro Thr Pro Ile Thr Thr Gly Thr Thr Ser Lys
65                  70                  75                  80

Ile Ser Ala Asp Gly Ile Glu Ile Val Gly Glu Leu Ser Ser Glu Thr
                85                  90                  95
```

-continued

```
Ile Leu Ala Asp Pro Asn Lys Ala Ala Ala Gln Val Phe Gly Glu Gly
            100                 105                 110

Leu Ala Asp Ser Phe Asp Asp Trp Leu Arg Leu Ser Glu Asn Gly Gly
        115                 120                 125

Ile Gln Asp Pro Thr Ala Ile Glu Glu Glu Ile Val Thr Lys Tyr Gln
    130                 135                 140

Thr Glu Leu Asn Thr Leu Arg Asn Lys Leu Lys Gln Gln Ser Leu Thr
145                 150                 155                 160

Asp Asp Glu Tyr Thr Lys Leu Tyr Ala Ile Pro Gln Asn Phe Val Lys
                165                 170                 175

Glu Ile Glu Ser Leu Lys Asn Glu Asn Asn Val Arg Leu Ile Pro Lys
            180                 185                 190

Ser Lys Val Thr Asn Phe Trp Gln Asn Ile Met Leu Thr Tyr Asn Ser
        195                 200                 205

Val Thr Ser Leu Ser Glu Pro Val Thr Asp Ala Met Asn Thr Thr Met
    210                 215                 220

Ala Glu Tyr Ser Leu Tyr Ile Glu Arg Ala Thr Glu Ala Ala Lys Leu
225                 230                 235                 240

Ile Arg Glu Ile Thr Asn Thr Ile Lys Asp Ile Phe Asn Pro Val Trp
                245                 250                 255

Asp Val Arg Glu Gln Thr Gly Ile Phe Gly Leu Lys Gly Ala Glu Tyr
            260                 265                 270

Asn Ala Leu Glu Gly Asn Met Ile Gln Ser Leu Leu Ser Phe Ala Gly
        275                 280                 285

Leu Phe Arg Gln Leu Met Ser Arg Thr Ala Thr Val Asp Glu Ile Gly
    290                 295                 300

Ala Leu Tyr Pro Lys Asn Asp Lys Asn Glu Asp Val Ile His Thr Ala
305                 310                 315                 320

Ile Asp Asp Tyr Val Asn Ser Leu Ala Asp Leu Lys Ala Asn Glu Gln
                325                 330                 335

Val Lys Leu Asn Gly Leu Leu Ser Leu Val Tyr Ala Tyr Tyr Ala Ser
            340                 345                 350

Thr Leu Gly Phe Ala Lys Lys Asp Val Phe Asn Asn Ala Gln Ala Ser
        355                 360                 365

Phe Thr Asp Tyr Thr Asn Phe Leu Asn Gln Glu Ile Gln Tyr Trp Thr
    370                 375                 380

Pro Arg Glu Thr Ser Ser Phe Asn Ile Ser Asn Gln Ala Leu Gln Thr
385                 390                 395                 400

Phe Lys Asn Lys Pro Ser Ala Asp Tyr Asn Gly Val Tyr Leu Phe Asp
                405                 410                 415

Asn Lys Gly Leu Glu Thr Asn Leu Phe Asn Pro Thr Phe Phe Phe Asp
            420                 425                 430

Val Val Ser Leu Met Thr Ala Asp Pro Thr Lys Thr Met Ser Arg Gln
        435                 440                 445

Asp Tyr Asn Lys Val Ile Thr Ala Ser Glu Ser Ser Ile Gln Lys Ile
    450                 455                 460

Asn Gln Ala Ile Thr Ala Trp Glu Leu Ala Ile Ala Glu Cys Gly Thr
465                 470                 475                 480

Lys Lys Ala Lys Leu Glu Pro Ser Ser Leu Asn Tyr Phe Asn Ala Met
                485                 490                 495

Val Glu Ala Lys Lys Thr Phe Val Glu Thr Ser Pro Ile Gln Met Val
            500                 505                 510

Tyr Ser Ser Leu Met Leu Asp Lys Tyr Leu Pro Asn Gln Gln Tyr Ile
        515                 520                 525
```

Leu Glu Thr Leu Gly Ser Gln Met Thr Phe Ser Asn Lys Ala Ala Arg
    530                 535                 540

Tyr Leu Asn Asp Ile Ile Ala Tyr Ala Val Ser Phe Gln Thr Ala Asp
545                 550                 555                 560

Val Tyr Tyr Ser Leu Gly Met Tyr Leu Arg Gln Met Asn Gln Gln Glu
                565                 570                 575

Phe Pro Glu Val Ile Ser Arg Ala Asn Asp Thr Val Lys Lys Glu Ile
            580                 585                 590

Asp Arg Ser Arg Ala Asp Leu Phe His Cys Lys Lys Ala Ile Glu Lys
        595                 600                 605

Ile Lys Glu Leu Val Thr Ser Val Asn Ala Asp Thr Glu Leu Thr Ser
    610                 615                 620

Ser Gln Arg Ala Glu Leu Leu Glu Thr Leu Ala Ser Tyr Ala Phe Glu
625                 630                 635                 640

Phe Glu Asn Leu Tyr His Asn Leu Ser Asn Val Tyr Val Met Val Ser
                645                 650                 655

Lys Val Gln Ile Ser Gly Val Ser Lys Pro Asp Glu Val Asp Glu Ala
            660                 665                 670

Phe Thr Ala Lys Ile Gly Ser Lys Glu Phe Asp Thr Trp Ile Gln Gln
        675                 680                 685

Leu Thr Thr Phe Glu Ser Ala Val Ile Glu Gly Gly Arg Asn Gly Val
    690                 695                 700

Met Pro Gly Gly Glu Gln Gln Val Leu Gln Ser Leu Glu Ser Lys Gln
705                 710                 715                 720

Gln Asp Tyr Thr Ser Phe Asn Gln Asn Gln Gln Leu Ala Leu Gln Met
                725                 730                 735

Glu Ser Ala Ala Ile Gln Gln Glu Trp Thr Met Val Ala Ala Ala Leu
            740                 745                 750

Ala Leu Met Asn Gln Ile Phe Ala Lys Leu Ile Arg Arg Phe Lys
        755                 760                 765

<210> SEQ ID NO 20
<211> LENGTH: 486
<212> TYPE: PRT
<213> ORGANISM: Chlamydia trachomatis

<400> SEQUENCE: 20

Met Cys Phe Ile Gly Ile Gly Ser Leu Leu Leu Pro Thr Ala Leu Arg
1               5                   10                  15

Ala Thr Glu Arg Met Arg Lys Glu Pro Ile Pro Leu Leu Asp Lys Gln
            20                  25                  30

Gln Ser Phe Trp Asn Val Asp Pro Tyr Cys Leu Glu Ser Ile Cys Ala
        35                  40                  45

Cys Phe Val Ala His Arg Asp Pro Leu Ser Ala Lys Gln Leu Met Tyr
    50                  55                  60

Leu Phe Pro Gln Leu Ser Glu Glu Asp Val Ser Val Phe Ala Arg Cys
65                  70                  75                  80

Ile Leu Ser Ser Lys Arg Pro Glu Tyr Leu Phe Ser Lys Ser Glu Glu
                85                  90                  95

Glu Leu Phe Ala Lys Leu Ile Leu Pro Arg Val Ser Leu Gly Val His
            100                 105                 110

Arg Asp Asp Asp Leu Ala Arg Val Leu Val Leu Ala Glu Pro Ser Ala
        115                 120                 125

Glu Glu Gln Lys Ala Arg Tyr Tyr Ser Leu Tyr Leu Asp Val Leu Ala
    130                 135                 140

Leu Arg Ala Tyr Val Glu Arg Glu Arg Leu Ala Ser Ala Ala His Gly
145 150 155 160

Asp Pro Glu Arg Ile Asp Leu Ala Thr Ile Glu Ala Ile Asn Thr Ile
165 170 175

Leu Phe Gln Glu Glu Gly Trp Arg Tyr Pro Ser Lys Gln Glu Met Phe
180 185 190

Glu Asn Arg Phe Ser Glu Leu Ala Ala Val Thr Asp Ser Lys Phe Gly
195 200 205

Val Cys Leu Gly Thr Val Val Leu Tyr Gln Ala Val Ala Gln Arg Leu
210 215 220

Asp Leu Ser Leu Asp Pro Val Thr Pro Pro Gly His Ile Tyr Leu Arg
225 230 235 240

Tyr Lys Asp Lys Val Asn Ile Glu Thr Thr Ser Gly Gly Arg His Leu
245 250 255

Pro Thr Glu Arg Tyr Cys Glu Cys Ile Lys Glu Ser Gln Leu Lys Val
260 265 270

Arg Ser Gln Met Glu Leu Ile Gly Leu Thr Phe Met Asn Arg Gly Ala
275 280 285

Phe Phe Leu Gln Lys Gly Glu Phe Leu Gln Ala Ser Leu Ala Tyr Glu
290 295 300

Gln Ala Gln Ser Tyr Leu Ser Asp Glu Gln Ile Ser Asp Leu Leu Gly
305 310 315 320

Ile Thr Tyr Val Leu Leu Gly Lys Lys Ala Ala Gly Glu Ala Leu Leu
325 330 335

Lys Lys Ser Ala Glu Lys Thr Arg Arg Gly Ser Ser Ile Tyr Asp Tyr
340 345 350

Phe Gln Gly Tyr Ile Ser Pro Glu Ile Leu Gly Val Leu Phe Ala Asp
355 360 365

Ser Gly Val Thr Tyr Gln Glu Thr Leu Glu Tyr Arg Lys Lys Leu Val
370 375 380

Met Leu Ser Lys Lys Tyr Pro Lys Ser Gly Ser Leu Arg Leu Arg Leu
385 390 395 400

Ala Thr Thr Ala Leu Glu Leu Gly Leu Val Lys Glu Gly Val Gln Leu
405 410 415

Leu Glu Glu Ser Val Lys Asp Ala Pro Glu Asp Leu Ser Leu Arg Leu
420 425 430

Gln Phe Cys Lys Ile Leu Cys Asn Arg His Asp Tyr Val Arg Ala Lys
435 440 445

Tyr His Phe Asp Gln Ala Gln Ala Leu Leu Ile Lys Glu Gly Leu Phe
450 455 460

Ser Glu Lys Thr Ser Tyr Thr Leu Leu Lys Thr Ile Gly Lys Lys Leu
465 470 475 480

Ser Leu Phe Ala Pro Ser
485

<210> SEQ ID NO 21
<211> LENGTH: 696
<212> TYPE: PRT
<213> ORGANISM: Chlamydia trachomatis

<400> SEQUENCE: 21

Met Ile Asp Lys Ile Ile Arg Thr Ile Leu Val Leu Ser Leu Phe Leu
1 5 10 15

Leu Tyr Trp Ser Ser Asp Leu Leu Glu Lys Asp Val Lys Ser Ile Lys
20 25 30

```
Arg Glu Leu Lys Ala Leu His Glu Asp Val Leu Glu Leu Val Arg Ile
        35                  40                  45

Ser His Gln Gln Lys Asn Trp Val Gln Ser Thr Asp Phe Ser Val Ser
    50                  55                  60

Pro Glu Ile Ser Val Leu Lys Asp Cys Gly Asp Pro Ala Phe Pro Asn
65                  70                  75                  80

Leu Leu Cys Glu Asp Pro Tyr Val Glu Lys Val Val Pro Ser Leu Leu
                85                  90                  95

Lys Glu Gly Phe Val Pro Lys Gly Ile Leu Arg Thr Ala Gln Val Gly
            100                 105                 110

Arg Pro Asp Asn Leu Ser Pro Phe Asn Gly Phe Val Asn Ile Val Arg
        115                 120                 125

Phe Tyr Glu Leu Cys Val Pro Asn Leu Ala Val Glu His Val Gly Lys
    130                 135                 140

Tyr Glu Glu Phe Ala Pro Ser Leu Ala Leu Lys Ile Glu Glu His Tyr
145                 150                 155                 160

Val Glu Asp Gly Ser Gly Asp Lys Glu Phe His Ile Tyr Leu Arg Pro
                165                 170                 175

Asn Met Phe Trp Glu Pro Ile Asp Pro Thr Leu Phe Pro Lys Asn Ile
            180                 185                 190

Thr Leu Ala Asp Ser Phe Leu Arg Pro His Pro Val Thr Ala His Asp
        195                 200                 205

Val Lys Phe Tyr Tyr Asp Val Val Met Asn Pro Tyr Val Ala Glu Met
    210                 215                 220

Arg Ala Val Ala Met Arg Ser Tyr Phe Glu Asp Met Val Ser Val Arg
225                 230                 235                 240

Val Glu Asn Asp Leu Lys Leu Ile Val Arg Trp Arg Ala His Thr Val
                245                 250                 255

Arg Asn Glu Gln Gly Glu Glu Glu Lys Lys Val Leu Tyr Ser Ala Phe
            260                 265                 270

Ala Asn Thr Leu Ala Leu Gln Pro Leu Pro Cys Phe Val Tyr Gln His
        275                 280                 285

Phe Ala Asn Gly Glu Lys Ile Val Pro Glu Asp Ser Asp Pro Asp Thr
    290                 295                 300

Tyr Arg Lys Asp Ser Val Trp Ala Gln Asn Phe Ser Ser His Trp Ala
305                 310                 315                 320

Tyr Asn Tyr Ile Val Ser Cys Gly Ala Phe Arg Phe Ala Gly Met Asp
                325                 330                 335

Asp Glu Lys Ile Thr Leu Val Arg Asn Pro Asn Tyr His Asn Pro Phe
            340                 345                 350

Ala Ala Leu Val Glu Lys Arg Tyr Ile Tyr Met Lys Asp Ser Thr Asp
        355                 360                 365

Ser Leu Phe Gln Asp Phe Lys Ala Gly Lys Val Asp Ile Ala Tyr Phe
    370                 375                 380

Pro Pro Asn His Val Asp Asn Leu Ala Ser Phe Met Gln Thr Ser Ala
385                 390                 395                 400

Tyr Lys Glu Gln Ala Ala Arg Gly Glu Ala Ile Leu Glu Lys Asn Ser
                405                 410                 415

Ser Asp Arg Ser Tyr Ser Tyr Ile Gly Trp Asn Cys Leu Ser Leu Phe
            420                 425                 430

Phe Asn Asn Arg Ser Val Arg Gln Ala Met Asn Met Leu Ile Asp Arg
        435                 440                 445

Asp Arg Ile Ile Glu Gln Cys Leu Asp Gly Arg Gly Val Ser Val Ser
```

```
    450                 455                 460

Gly Pro Phe Ser Leu Cys Ser Pro Ser Tyr Asn Arg Asp Val Glu Gly
465                 470                 475                 480

Trp Gln Tyr Ser Pro Glu Glu Ala Ala Arg Lys Leu Glu Glu Glu Gly
                485                 490                 495

Trp Ile Asp Ala Asp Gly Asp Gly Ile Arg Glu Lys Val Ile Asp Gly
            500                 505                 510

Val Val Val Pro Phe Arg Phe Arg Leu Cys Tyr Tyr Val Lys Ser Val
        515                 520                 525

Thr Ala Arg Thr Ile Ala Glu Tyr Val Ala Thr Val Cys Lys Glu Val
    530                 535                 540

Gly Ile Glu Cys Cys Leu Leu Gly Leu Asp Met Ala Asp Tyr Ser Gln
545                 550                 555                 560

Ala Leu Glu Glu Lys Asn Phe Asp Ala Ile Leu Ser Gly Trp Cys Leu
                565                 570                 575

Gly Thr Pro Pro Glu Asp Pro Arg Ala Leu Trp His Ser Glu Gly Ala
            580                 585                 590

Leu Glu Lys Gly Ser Ala Asn Ala Val Gly Phe Cys Asn Glu Glu Ala
        595                 600                 605

Asp Arg Ile Ile Glu Gln Leu Ser Tyr Glu Tyr Asp Ser Asn Lys Arg
    610                 615                 620

Gln Ala Leu Tyr His Arg Phe His Glu Val Ile His Glu Glu Ser Pro
625                 630                 635                 640

Tyr Ala Phe Leu Tyr Ser Arg Gln Tyr Ser Leu Val Tyr Lys Glu Phe
                645                 650                 655

Val Lys Asn Ile Phe Val Pro Thr Glu His Gln Asp Leu Ile Pro Gly
            660                 665                 670

Ala Gln Asp Glu Thr Val Asn Leu Ser Met Leu Trp Val Asp Lys Glu
        675                 680                 685

Glu Gly Arg Cys Ser Ala Ile Ser
    690                 695


<210> SEQ ID NO 22
<211> LENGTH: 421
<212> TYPE: PRT
<213> ORGANISM: Chlamydia trachomatis

<400> SEQUENCE: 22

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
```

```
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400

His Ala Pro Val Pro Gln Ser Glu Ile Pro Thr Ser Pro Thr Ser Thr
                405                 410                 415

Gln Pro Pro Ser Pro
            420


<210> SEQ ID NO 23
<211> LENGTH: 221
<212> TYPE: PRT
<213> ORGANISM: Chlamydia trachomatis

<400> SEQUENCE: 23

Met Lys Lys Phe Ile Tyr Lys Tyr Ser Phe Gly Ala Leu Leu Leu Leu
1               5                   10                  15

Ser Gly Leu Ser Gly Leu Ser Ser Cys Cys Ala Asn Ser Tyr Gly Ser
            20                  25                  30

Thr Leu Ala Lys Asn Thr Ala Glu Ile Lys Glu Glu Ser Val Thr Leu
        35                  40                  45

Arg Glu Lys Pro Asp Ala Gly Cys Lys Lys Lys Ser Ser Cys Tyr Leu
    50                  55                  60

Arg Lys Phe Phe Ser Arg Lys Lys Pro Lys Glu Lys Thr Glu Pro Val
65                  70                  75                  80

Leu Pro Asn Phe Lys Ser Tyr Ala Asp Pro Met Thr Asp Ser Glu Arg
```

```
                85                  90                  95

Lys Asp Leu Ser Phe Val Val Ser Ala Ala Ala Asp Lys Ser Ser Ile
            100                 105                 110

Ala Leu Ala Met Ala Gln Gly Glu Ile Lys Gly Ala Leu Ser Arg Ile
        115                 120                 125

Arg Glu Ile His Pro Leu Ala Leu Leu Gln Ala Leu Ala Glu Asp Pro
    130                 135                 140

Ala Leu Ile Ala Gly Met Lys Lys Met Gln Gly Arg Asp Trp Val Trp
145                 150                 155                 160

Asn Ile Phe Ile Thr Glu Leu Ser Lys Val Phe Ser Gln Ala Ala Ser
                165                 170                 175

Leu Gly Ala Phe Ser Val Ala Asp Val Ala Ala Phe Ala Ser Thr Leu
            180                 185                 190

Gly Leu Asp Ser Gly Thr Val Thr Ser Ile Val Asp Gly Glu Arg Trp
        195                 200                 205

Ala Glu Leu Ile Asp Val Val Ile Gln Asn Pro Ala Ile
    210                 215                 220


<210> SEQ ID NO 24
<211> LENGTH: 242
<212> TYPE: PRT
<213> ORGANISM: Chlamydia trachomatis

<400> SEQUENCE: 24

Met Lys Val Lys Ile Asn Asp Gln Phe Ile Cys Ile Ser Pro Tyr Ile
1               5                   10                  15

Ser Ala Arg Trp Asn Gln Ile Ala Phe Ile Glu Ser Cys Asp Gly Gly
            20                  25                  30

Thr Glu Gly Gly Ile Thr Leu Lys Leu His Leu Ile Asp Gly Glu Thr
        35                  40                  45

Val Ser Ile Pro Asn Leu Gly Gln Ala Ile Val Asp Glu Val Phe Gln
    50                  55                  60

Glu His Leu Leu Tyr Leu Glu Ser Thr Ala Pro Gln Lys Asn Lys Glu
65                  70                  75                  80

Glu Glu Lys Ile Ser Ser Leu Leu Gly Ala Val Gln Gln Met Ala Lys
                85                  90                  95

Gly Cys Glu Val Gln Val Phe Ser Gln Lys Gly Leu Val Ser Met Leu
            100                 105                 110

Leu Gly Gly Ala Gly Ser Ile Asn Val Leu Leu Gln His Ser Pro Glu
        115                 120                 125

His Lys Asp His Pro Asp Leu Pro Thr Asp Leu Leu Glu Arg Ile Ala
    130                 135                 140

Gln Met Met Arg Ser Leu Ser Ile Gly Pro Thr Ser Ile Leu Ala Lys
145                 150                 155                 160

Pro Glu Pro His Cys Asn Cys Leu His Cys Gln Ile Gly Arg Ala Thr
                165                 170                 175

Val Glu Glu Glu Asp Ala Gly Val Ser Asp Glu Asp Leu Thr Phe Arg
            180                 185                 190

Ser Trp Asp Ile Ser Gln Ser Gly Glu Lys Met Tyr Thr Val Thr Asp
        195                 200                 205

Pro Leu Asn Pro Glu Glu Gln Phe Asn Val Tyr Leu Gly Thr Pro Ile
    210                 215                 220

Gly Cys Thr Cys Gly Gln Pro Tyr Cys Glu His Val Lys Ala Val Leu
225                 230                 235                 240

Tyr Thr
```

<210> SEQ ID NO 25
<211> LENGTH: 957
<212> TYPE: DNA
<213> ORGANISM: Chlamydia muridarum

<400> SEQUENCE: 25

```
atggcatcca agtctcgtca ttatcttaac cagccttggt acattatctt attcatcttt      60
gttcttagtc tggttgctgg tacccttctt tcttcagttt cctatgttct atctccaatc     120
caaaaacaag ctgcagaatt tgatcgtaat cagcaaatgt tgatggccgc acaaattatt     180
tcctatgaca ataaattcca aatatatgct gaaggggatt ggcaacctgc tgtctataat     240
acaaaaaaac agatactaga aaaaagctct tccactccac cacaagtgac tgtggcgact     300
ctatgctctt attttcaaaa ttttgttaga gttttgctta cagactccca agggaatctt     360
tcttcttttg aagatcacaa tcttaaccta gaagagttct tatcccaccc cacatcttca     420
gtacaagatc actctctgca tgtaatttat gctattctag caaacgatga atcctctaaa     480
aagttatcat cctcccaagt agcaaaaaat ccggtatcca tagagtctat tattcttcct     540
ataaaaggat ttggtttatg ggaccaatc tatggatttc ttgctttaga aaaggacggt      600
aatacggttc tagggacatg ctggtatcaa catggtgaga ctccaggatt aggagcaaat     660
ataactaatc cccaatggca acaaaatttc agaggaaaaa aagtatttct cgcttcctct     720
tccggagaaa ccgattttgc taaaacaact ctaggactag aagttataaa aggatctgtt     780
tctgcattat taggggactc tcccaaagct aattccgctg ttgatggaat ttcaggagct     840
acactgacct gtaatggagt tactgaagct tttgctaatt cgctagctcc ttaccgcccc     900
ttattgactt tcttcgccaa tcttaactct agtggagaat ctcatgacaa ccaataa        957
```

<210> SEQ ID NO 26
<211> LENGTH: 318
<212> TYPE: PRT
<213> ORGANISM: Chlamydia muridarum

<400> SEQUENCE: 26

```
Met Ala Ser Lys Ser Arg His Tyr Leu Asn Gln Pro Trp Tyr Ile Ile
1               5                   10                  15

Leu Phe Ile Phe Val Leu Ser Leu Val Ala Gly Thr Leu Leu Ser Ser
            20                  25                  30

Val Ser Tyr Val Leu Ser Pro Ile Gln Lys Gln Ala Ala Glu Phe Asp
        35                  40                  45

Arg Asn Gln Gln Met Leu Met Ala Ala Gln Ile Ile Ser Tyr Asp Asn
    50                  55                  60

Lys Phe Gln Ile Tyr Ala Glu Gly Asp Trp Gln Pro Ala Val Tyr Asn
65                  70                  75                  80

Thr Lys Lys Gln Ile Leu Glu Lys Ser Ser Ser Thr Pro Pro Gln Val
                85                  90                  95

Thr Val Ala Thr Leu Cys Ser Tyr Phe Gln Asn Phe Val Arg Val Leu
            100                 105                 110

Leu Thr Asp Ser Gln Gly Asn Leu Ser Ser Phe Glu Asp His Asn Leu
        115                 120                 125

Asn Leu Glu Glu Phe Leu Ser His Pro Thr Ser Ser Val Gln Asp His
    130                 135                 140

Ser Leu His Val Ile Tyr Ala Ile Leu Ala Asn Asp Glu Ser Ser Lys
145                 150                 155                 160

Lys Leu Ser Ser Ser Gln Val Ala Lys Asn Pro Val Ser Ile Glu Ser
```

```
                165                 170                 175

Ile Ile Leu Pro Ile Lys Gly Phe Gly Leu Trp Gly Pro Ile Tyr Gly
            180                 185                 190

Phe Leu Ala Leu Glu Lys Asp Gly Asn Thr Val Leu Gly Thr Cys Trp
        195                 200                 205

Tyr Gln His Gly Glu Thr Pro Gly Leu Gly Ala Asn Ile Thr Asn Pro
    210                 215                 220

Gln Trp Gln Gln Asn Phe Arg Gly Lys Lys Val Phe Leu Ala Ser Ser
225                 230                 235                 240

Ser Gly Glu Thr Asp Phe Ala Lys Thr Thr Leu Gly Leu Glu Val Ile
                245                 250                 255

Lys Gly Ser Val Ser Ala Leu Leu Gly Asp Ser Pro Lys Ala Asn Ser
            260                 265                 270

Ala Val Asp Gly Ile Ser Gly Ala Thr Leu Thr Cys Asn Gly Val Thr
        275                 280                 285

Glu Ala Phe Ala Asn Ser Leu Ala Pro Tyr Arg Pro Leu Leu Thr Phe
    290                 295                 300

Phe Ala Asn Leu Asn Ser Ser Gly Glu Ser His Asp Asn Gln
305                 310                 315


<210> SEQ ID NO 27
<211> LENGTH: 1416
<212> TYPE: DNA
<213> ORGANISM: Chlamydia muridarum

<400> SEQUENCE: 27

atgaatggaa aagttctgtg tgaggtttct gtgtccttcc gttcgattct gctgacggct      60

ctgctttcac tttcttttac aaacactatg caggctgcac accatcatta tcaccgttat     120

gatgataaac tacgcagaca ataccataaa aaggacttgc ccactcaaga gaatgttcgg     180

aaagagtttt gtaatcccta ctctcatagt agtgatccta tccctttgtc acaacaacga     240

ggagtcctat ctcctatctg tgatttagtc tcagagtgct cgtttttgaa cgggatttcc     300

gttaggagtc ttaaacaaac actgaaaaat tctgctggga ctcaagttgc tttagactgg     360

tctatccttc ctcaatggtt caatcctaga tcctcttggg ctcctaagct ctctattcga     420

gatcttggat atggtaaacc ccagtccctt attgaagcag attccccttg ttgtcaaacc     480

tgcttcaacc catctgctgc tattacgatt tacgattctt catgtgggaa gggtgttgtc     540

caagtgtcat acacccttgt tcgttattgg agagaaacgg ctgcacttgc agggcaaact     600

atgatgcttg caggaagtat taatgattat cctgctcgcc aaaacatatt ctctcaactt     660

acatttcccc aaactttccc taatgagaga gtaaatctaa ctgttggtca atactctctt     720

tactcgatag acggaacgct gtacaacaat gatcagcagc taggatttat tagttatgcg     780

ttgtcgcaaa atccaacagc gacttattcc tctggaagcc ttggcgccta tctacaagtc     840

gctccaacag aaagcacctg tcttcaagtt gggttccaag atgcctataa tatttcaggt     900

tcctcgatca aatggaataa tcttacaaaa aataagtata acttccatgg ctatgcatct     960

tgggctccac actgttgctt aggacctgga caatactctg ttcttcttta tgtaaccaga    1020

aaggttcctg agcaaatgat gcagacaatg ggctggtctg tgaatgcaag tcaatacatc    1080

tcttctaaac tttatgtatt tggaagatac agcggagtca caggccaatt gtctcctatt    1140

aaccgaacct attcatttgg cttagtctct cctaatttat tgaaccgtaa cccacaagac    1200

ttatttggag tagcttgcgc attcaataat atacacgcct ccgcctttca aaatgctcaa    1260

agaaaatatg aaactgtgat cgagggattt gcaactattg gttgcggacc ttacatctcc    1320
```

```
tttgctccag atttccaact ttacctctat cctgctctgc gtccaaataa acaaagcgcc   1380

cgagtctata gcgttcgcgc aaacctagct atttag                             1416


<210> SEQ ID NO 28
<211> LENGTH: 471
<212> TYPE: PRT
<213> ORGANISM: Chlamydia muridarum

<400> SEQUENCE: 28

Met Asn Gly Lys Val Leu Cys Glu Val Ser Val Ser Phe Arg Ser Ile
1               5                   10                  15

Leu Leu Thr Ala Leu Leu Ser Leu Ser Phe Thr Asn Thr Met Gln Ala
            20                  25                  30

Ala His His His Tyr His Arg Tyr Asp Asp Lys Leu Arg Arg Gln Tyr
        35                  40                  45

His Lys Lys Asp Leu Pro Thr Gln Glu Asn Val Arg Lys Glu Phe Cys
    50                  55                  60

Asn Pro Tyr Ser His Ser Ser Asp Pro Ile Pro Leu Ser Gln Gln Arg
65                  70                  75                  80

Gly Val Leu Ser Pro Ile Cys Asp Leu Val Ser Glu Cys Ser Phe Leu
                85                  90                  95

Asn Gly Ile Ser Val Arg Ser Leu Lys Gln Thr Leu Lys Asn Ser Ala
            100                 105                 110

Gly Thr Gln Val Ala Leu Asp Trp Ser Ile Leu Pro Gln Trp Phe Asn
        115                 120                 125

Pro Arg Ser Ser Trp Ala Pro Lys Leu Ser Ile Arg Asp Leu Gly Tyr
    130                 135                 140

Gly Lys Pro Gln Ser Leu Ile Glu Ala Asp Ser Pro Cys Cys Gln Thr
145                 150                 155                 160

Cys Phe Asn Pro Ser Ala Ala Ile Thr Ile Tyr Asp Ser Ser Cys Gly
                165                 170                 175

Lys Gly Val Val Gln Val Ser Tyr Thr Leu Val Arg Tyr Trp Arg Glu
            180                 185                 190

Thr Ala Ala Leu Ala Gly Gln Thr Met Met Leu Ala Gly Ser Ile Asn
        195                 200                 205

Asp Tyr Pro Ala Arg Gln Asn Ile Phe Ser Gln Leu Thr Phe Ser Gln
    210                 215                 220

Thr Phe Pro Asn Glu Arg Val Asn Leu Thr Val Gly Gln Tyr Ser Leu
225                 230                 235                 240

Tyr Ser Ile Asp Gly Thr Leu Tyr Asn Asn Asp Gln Gln Leu Gly Phe
                245                 250                 255

Ile Ser Tyr Ala Leu Ser Gln Asn Pro Thr Ala Thr Tyr Ser Ser Gly
            260                 265                 270

Ser Leu Gly Ala Tyr Leu Gln Val Ala Pro Thr Glu Ser Thr Cys Leu
        275                 280                 285

Gln Val Gly Phe Gln Asp Ala Tyr Asn Ile Ser Gly Ser Ser Ile Lys
    290                 295                 300

Trp Asn Asn Leu Thr Lys Asn Lys Tyr Asn Phe His Gly Tyr Ala Ser
305                 310                 315                 320

Trp Ala Pro His Cys Cys Leu Gly Pro Gly Gln Tyr Ser Val Leu Leu
                325                 330                 335

Tyr Val Thr Arg Lys Val Pro Glu Gln Met Met Gln Thr Met Gly Trp
            340                 345                 350

Ser Val Asn Ala Ser Gln Tyr Ile Ser Ser Lys Leu Tyr Val Phe Gly
```

-continued

```
        355                 360                 365

Arg Tyr Ser Gly Val Thr Gly Gln Leu Ser Pro Ile Asn Arg Thr Tyr
    370                 375                 380

Ser Phe Gly Leu Val Ser Pro Asn Leu Leu Asn Arg Asn Pro Gln Asp
385                 390                 395                 400

Leu Phe Gly Val Ala Cys Ala Phe Asn Asn Ile His Ala Ser Ala Phe
                405                 410                 415

Gln Asn Ala Gln Arg Lys Tyr Glu Thr Val Ile Glu Gly Phe Ala Thr
            420                 425                 430

Ile Gly Cys Gly Pro Tyr Ile Ser Phe Ala Pro Asp Phe Gln Leu Tyr
        435                 440                 445

Leu Tyr Pro Ala Leu Arg Pro Asn Lys Gln Ser Ala Arg Val Tyr Ser
    450                 455                 460

Val Arg Ala Asn Leu Ala Ile
465                 470


<210> SEQ ID NO 29
<211> LENGTH: 1665
<212> TYPE: DNA
<213> ORGANISM: Chlamydia muridarum

<400> SEQUENCE: 29

atgcgaatag gagatcctat gaacaaactc atcagacgag ctgtgacgat cttcgcggtg      60

actagtgtgg cgagtttatt tgctagcggg gtgttagaga cctctatggc agagtctctc     120

tctaccaacg ttattagctt agctgacacc aaagcgaaag agaccacttc tcatcaaaaa     180

gacagaaaag caagaaaaaa tcatcaaaat aggacttccg tagtccgtaa agaggttact     240

gcagttcgtg atactaaagc tgtagagcct agacaggatt cttgctttgg caaaatgtat     300

acagtcaaag ttaatgatga tcgtaatgta gaaatcgtgc agtccgttcc tgaatatgct     360

acggtaggat ctccatatcc tattgagatt actgctatag ggaaaagaga ctgtgttgat     420

gtaatcatta cacagcaatt accatgcgaa gcagagtttg ttagcagtga tccagctact     480

actcctactg ctgatggtaa gctagtttgg aaaattgatc ggttaggaca gggcgaaaag     540

agtaaaatta ctgtatgggt aaaacctctt aaagaaggtt gctgctttac agctgcaacg     600

gtttgtgctt gtccagagat ccgttcggtt acgaaatgtg gccagcctgc tatctgtgtt     660

aaacaggaag gtccagaaag cgcatgtttg cgttgcccag taacttatag aattaatgta     720

gtcaaccaag gaacagcaac agcacgtaat gttgttgtgg aaaatcctgt tccagatggc     780

tatgctcatg catccggaca gcgtgtattg acatatactc ttggggatat gcaacctgga     840

gaacagagaa caatcaccgt ggagttttgt ccgcttaaac gtggtcgagt cacaaatatt     900

gctacagttt cttactgtgg tggacacaaa aatactgcta gcgtaacaac agtgatcaat     960

gagccttgcg tgcaagttaa catcgaggga gcagattggt cttatgtttg taagcctgta    1020

gaatatgtta tctctgtttc taaccctggt gacttagttt tacgagacgt tgtaattgaa    1080

gatacgcttt ctcctggaat aactgttgtt gaagcagctg gagctcagat ttcttgtaat    1140

aaattggttt ggactttgaa ggaactcaat cctggagagt ctttacaata taaggttcta    1200

gtaagagctc aaactccagg gcaattcaca aacaacgttg ttgtgaaaag ttgctctgat    1260

tgcggtattt gtacttcttg cgcagaagca acaacttact ggaaaggagt tgctgctact    1320

catatgtgcg tagtagatac ttgtgatcct atttgcgtag gagagaacac tgtttatcgt    1380

atctgtgtga caaacagagg ttctgctgaa gatacaaatg tgtccttaat tttgaaattc    1440

tctaaagaat tacaacctat atctttctct ggaccaacta aaggaaccat tacaggaaac    1500
```

acggtagtgt ttgattcgtt acctagatta ggttctaaag aaactgtaga gttttctgta 1560
acgttgaaag cagtatccgc tggagatgct cgtggggaag ctattctttc ttccgataca 1620
ttgacagttc ctgtatctga tacggagaat acacatatct attaa 1665

<210> SEQ ID NO 30
<211> LENGTH: 554
<212> TYPE: PRT
<213> ORGANISM: Chlamydia muridarum

<400> SEQUENCE: 30

Met Arg Ile Gly Asp Pro Met Asn Lys Leu Ile Arg Arg Ala Val Thr
1 5 10 15

Ile Phe Ala Val Thr Ser Val Ala Ser Leu Phe Ala Ser Gly Val Leu
20 25 30

Glu Thr Ser Met Ala Glu Ser Leu Ser Thr Asn Val Ile Ser Leu Ala
35 40 45

Asp Thr Lys Ala Lys Glu Thr Thr Ser His Gln Lys Asp Arg Lys Ala
50 55 60

Arg Lys Asn His Gln Asn Arg Thr Ser Val Val Arg Lys Glu Val Thr
65 70 75 80

Ala Val Arg Asp Thr Lys Ala Val Glu Pro Arg Gln Asp Ser Cys Phe
85 90 95

Gly Lys Met Tyr Thr Val Lys Val Asn Asp Asp Arg Asn Val Glu Ile
100 105 110

Val Gln Ser Val Pro Glu Tyr Ala Thr Val Gly Ser Pro Tyr Pro Ile
115 120 125

Glu Ile Thr Ala Ile Gly Lys Arg Asp Cys Val Asp Val Ile Ile Thr
130 135 140

Gln Gln Leu Pro Cys Glu Ala Glu Phe Val Ser Ser Asp Pro Ala Thr
145 150 155 160

Thr Pro Thr Ala Asp Gly Lys Leu Val Trp Lys Ile Asp Arg Leu Gly
165 170 175

Gln Gly Glu Lys Ser Lys Ile Thr Val Trp Val Lys Pro Leu Lys Glu
180 185 190

Gly Cys Cys Phe Thr Ala Ala Thr Val Cys Ala Cys Pro Glu Ile Arg
195 200 205

Ser Val Thr Lys Cys Gly Gln Pro Ala Ile Cys Val Lys Gln Glu Gly
210 215 220

Pro Glu Ser Ala Cys Leu Arg Cys Pro Val Thr Tyr Arg Ile Asn Val
225 230 235 240

Val Asn Gln Gly Thr Ala Thr Ala Arg Asn Val Val Val Glu Asn Pro
245 250 255

Val Pro Asp Gly Tyr Ala His Ala Ser Gly Gln Arg Val Leu Thr Tyr
260 265 270

Thr Leu Gly Asp Met Gln Pro Gly Glu Gln Arg Thr Ile Thr Val Glu
275 280 285

Phe Cys Pro Leu Lys Arg Gly Arg Val Thr Asn Ile Ala Thr Val Ser
290 295 300

Tyr Cys Gly Gly His Lys Asn Thr Ala Ser Val Thr Thr Val Ile Asn
305 310 315 320

Glu Pro Cys Val Gln Val Asn Ile Glu Gly Ala Asp Trp Ser Tyr Val
325 330 335

Cys Lys Pro Val Glu Tyr Val Ile Ser Val Ser Asn Pro Gly Asp Leu
340 345 350

```
Val Leu Arg Asp Val Val Ile Glu Asp Thr Leu Ser Pro Gly Ile Thr
        355                 360                 365

Val Val Glu Ala Ala Gly Ala Gln Ile Ser Cys Asn Lys Leu Val Trp
    370                 375                 380

Thr Leu Lys Glu Leu Asn Pro Gly Glu Ser Leu Gln Tyr Lys Val Leu
385                 390                 395                 400

Val Arg Ala Gln Thr Pro Gly Gln Phe Thr Asn Asn Val Val Val Lys
                405                 410                 415

Ser Cys Ser Asp Cys Gly Ile Cys Thr Ser Cys Ala Glu Ala Thr Thr
            420                 425                 430

Tyr Trp Lys Gly Val Ala Ala Thr His Met Cys Val Val Asp Thr Cys
        435                 440                 445

Asp Pro Ile Cys Val Gly Glu Asn Thr Val Tyr Arg Ile Cys Val Thr
    450                 455                 460

Asn Arg Gly Ser Ala Glu Asp Thr Asn Val Ser Leu Ile Leu Lys Phe
465                 470                 475                 480

Ser Lys Glu Leu Gln Pro Ile Ser Phe Ser Gly Pro Thr Lys Gly Thr
                485                 490                 495

Ile Thr Gly Asn Thr Val Val Phe Asp Ser Leu Pro Arg Leu Gly Ser
            500                 505                 510

Lys Glu Thr Val Glu Phe Ser Val Thr Leu Lys Ala Val Ser Ala Gly
        515                 520                 525

Asp Ala Arg Gly Glu Ala Ile Leu Ser Ser Asp Thr Leu Thr Val Pro
    530                 535                 540

Val Ser Asp Thr Glu Asn Thr His Ile Tyr
545                 550
```

<210> SEQ ID NO 31
<211> LENGTH: 504
<212> TYPE: DNA
<213> ORGANISM: Chlamydia muridarum

<400> SEQUENCE: 31

```
atgtccagac agaatgctga ggaaaatcta aaaaattttg ctaaagagct caagctcccc      60

gacgtggcct tcgatcagaa taatacgtgc attttgtttg ttgatggaga gttttctctt     120

cacctgacct acgaagagca ctctgatcgc ctttatgttt acgcacctct ccttgacgga     180

ctcccagata atccgcaaag aaagttggct ctgtatgaga aattgttgga aggctctatg     240

ctcggaggcc aaatggctgg tggaggagta ggagttgcta ctaaagaaca gttgatccta     300

atgcattgcg tgttagatat gaaatatgca gagactaatc tattgaaagc ttttgcacag     360

cttttcattg aaactgttgt gaaatggcga acggtctgtt ctgatatcag cgctggacga     420

gaaccttccg ttgacactat gcctcaaatg cctcaaggag gcagcggagg aattcaacct     480

cctccaacag gaattcgtgc gtag                                            504
```

<210> SEQ ID NO 32
<211> LENGTH: 167
<212> TYPE: PRT
<213> ORGANISM: Chlamydia muridarum

<400> SEQUENCE: 32

```
Met Ser Arg Gln Asn Ala Glu Glu Asn Leu Lys Asn Phe Ala Lys Glu
1               5                   10                  15

Leu Lys Leu Pro Asp Val Ala Phe Asp Gln Asn Asn Thr Cys Ile Leu
            20                  25                  30
```

Phe Val Asp Gly Glu Phe Ser Leu His Leu Thr Tyr Glu Glu His Ser
35 40 45

Asp Arg Leu Tyr Val Tyr Ala Pro Leu Leu Asp Gly Leu Pro Asp Asn
50 55 60

Pro Gln Arg Lys Leu Ala Leu Tyr Glu Lys Leu Leu Glu Gly Ser Met
65 70 75 80

Leu Gly Gly Gln Met Ala Gly Gly Gly Val Gly Val Ala Thr Lys Glu
85 90 95

Gln Leu Ile Leu Met His Cys Val Leu Asp Met Lys Tyr Ala Glu Thr
100 105 110

Asn Leu Leu Lys Ala Phe Ala Gln Leu Phe Ile Glu Thr Val Val Lys
115 120 125

Trp Arg Thr Val Cys Ser Asp Ile Ser Ala Gly Arg Glu Pro Ser Val
130 135 140

Asp Thr Met Pro Gln Met Pro Gln Gly Gly Ser Gly Gly Ile Gln Pro
145 150 155 160

Pro Pro Thr Gly Ile Arg Ala
165

<210> SEQ ID NO 33
<211> LENGTH: 609
<212> TYPE: DNA
<213> ORGANISM: Chlamydia muridarum

<400> SEQUENCE: 33
atgctcgcta atcggttatt tctaatcacc cttataggtt ttggctattc tgcttacggt 60
gccagcacag ggaaatcacc ttctttacag gttattttag ctgaagtcga ggatacatct 120
tcgcgcttac aagctcatca gaatgagctt gttatgctct cggaacgttt agatgagcaa 180
gacacaaaac ttcaacaact ctcgtcaact caggcccgta atcttcctca acaagttcaa 240
cggcttgaga ttgatctgag agctctggct aaaacagctg ctgtgctctc gcaatctgtt 300
caggatatcc gatcatccgt gcaaaataaa ttacaagaaa tccaacaaga acaaaaaaat 360
ttagctcaaa atttacgagc gcttcgcaac tccttacaag cactagttga tggctcttcc 420
ccagaaaatt atattgattt tttggccggg gagacacctg aacatattca cgttgttaaa 480
caaggagaaa ccctgagtaa aatcgctagt aagtacaata tccctgtcgc agaattgaaa 540
aaacttaata aattaaattc cgatactatt tttactgatc aaagaatccg acttccaaaa 600
aagaaataa 609

<210> SEQ ID NO 34
<211> LENGTH: 202
<212> TYPE: PRT
<213> ORGANISM: Chlamydia muridarum

<400> SEQUENCE: 34

Met Leu Ala Asn Arg Leu Phe Leu Ile Thr Leu Ile Gly Phe Gly Tyr
1 5 10 15

Ser Ala Tyr Gly Ala Ser Thr Gly Lys Ser Pro Ser Leu Gln Val Ile
20 25 30

Leu Ala Glu Val Glu Asp Thr Ser Ser Arg Leu Gln Ala His Gln Asn
35 40 45

Glu Leu Val Met Leu Ser Glu Arg Leu Asp Glu Gln Asp Thr Lys Leu
50 55 60

Gln Gln Leu Ser Ser Thr Gln Ala Arg Asn Leu Pro Gln Gln Val Gln
65 70 75 80

```
Arg Leu Glu Ile Asp Leu Arg Ala Leu Ala Lys Thr Ala Ala Val Leu
                85                  90                  95

Ser Gln Ser Val Gln Asp Ile Arg Ser Ser Val Gln Asn Lys Leu Gln
            100                 105                 110

Glu Ile Gln Gln Glu Gln Lys Asn Leu Ala Gln Asn Leu Arg Ala Leu
        115                 120                 125

Arg Asn Ser Leu Gln Ala Leu Val Asp Gly Ser Ser Pro Glu Asn Tyr
    130                 135                 140

Ile Asp Phe Leu Ala Gly Glu Thr Pro Glu His Ile His Val Val Lys
145                 150                 155                 160

Gln Gly Glu Thr Leu Ser Lys Ile Ala Ser Lys Tyr Asn Ile Pro Val
                165                 170                 175

Ala Glu Leu Lys Lys Leu Asn Lys Leu Asn Ser Asp Thr Ile Phe Thr
            180                 185                 190

Asp Gln Arg Ile Arg Leu Pro Lys Lys Lys
        195                 200


<210> SEQ ID NO 35
<211> LENGTH: 3024
<212> TYPE: DNA
<213> ORGANISM: Chlamydia muridarum

<400> SEQUENCE: 35

atgacgactc caataagtaa ttctccatct tctattccaa ctgttacagt atcaactact     60

acagcatctt ctggatctct cggaacttct actgtatcat caacgactac aagtacttca    120

gtcgcacaaa cagcaacaac aacatcttct gcttctacat ctataattca gtctagtgga    180

gaaaacatcc aatccactac aggtacccct tctcctatta cgtctagtgt ttcaacatcc    240

gctccatctc ctaaagcctc cgccactgca aacaaaactt caagcgctgt ttctgggaaa    300

attacctcac aagaaacttc tgaggaatcc gaaacccaag ccactacatc tgatggagaa    360

gttagtagta attacgatga tgttgatacc ccgaccaatt cgtccgattc gacagttgat    420

agtgattacc aagatgttga gactcagtac aaaacaatta gcaacaatgg tgaaaacact    480

tatgaaacaa tcggaagtca tggtgagaaa aacacacacg tccaggaaag ccatgcatcc    540

ggaacaggaa atcccataaa taatcagcaa gaagctatta gacagctccg atcatctacc    600

tatacaacca gccctcgtaa tgagaatata tttagtccag gaccggaagg tctacctaat    660

atgtctcttc ctagttacag ccctacagat aaaagttctc tactagcttt cctatctaat    720

cccaatacaa aagcaaaaat gctcgaacac tccgggcatt tagtctttat agacacaact    780

agaagtagct ttatctttgt tccgaatgga aattgggatc aagtctgttc catgaaggtt    840

cagaatggga aaactaaaga agaccttggc ttaaaggact tagaagatat gtgtgcaaag    900

ttttgcacag gatacaataa attctcctct gattggggaa atcgagttga ccccttggtc    960

tcttctaagg ccgggataga aagtgggggg cacctcccaa gctcagttat catcaacaac   1020

aaatttagaa cctgtgttgc ctatgggccg tggaacccca aagaaaacgg ccccaattat   1080

actccttcag cctggagacg tgggcatcga gtagattttg gaaagatctt tgatggaaca   1140

gcgccgttta ataaaatcaa ctggggctct tcccctaccc ctggtgatga cggcatctcc   1200

ttctctaatg aaactattgg gtctgaacca ttcgcgacac ctccctcatc cccatcgcaa   1260

acccccgtta tcaacgtcaa tgttaatgtc ggtggaacca atgttaatat tggggataca   1320

aacgtatcta aaggatccgg cacaccaaca tcttctcaat ctgtggacat gtctacagat   1380

actagcgatt tagataccag tgatattgat acaaacaacc aaactaacgg cgatatcaac   1440
```

-continued

```
acgaatgaca actccaataa tgtcgatgga agtttatctg acgttgattc aagggtggaa   1500

gacgatgacg gtgtatcgga tacagagtcc actaatggca atgactctgg taaaactact   1560

tccacagaag aaaatggtga cccaagcgga ccagacatcc tggctgctgt acgtaaacac   1620

ctagacactg tctatccagg agaaaatggc ggatctacag aaggacctct ccctgctaat   1680

caaaatctgg ggaacgttat ccatgatgtg gagcagaatg gatctgctaa agaaactatt   1740

atcactccag gagatacagg gcctacagac tcaagctcct ctgtagatgc tgatgcagac   1800

gttgaagata cttctgatac tgactctgga atcggagacg acgacggtgt atcggataca   1860

gagtccacta atggtaataa ctctggtaaa actacttcca cagaagaaaa tggtgaccca   1920

agcggaccag acatcctggc tgctgtacgt aaacacctag acactgtcta tccaggagaa   1980

aatggcggat ctacagaagg acctctccct gctaatcaaa atctggggaa cgttatccat   2040

gatgtagaac aaaacggagc cgctcaagaa actattatca ctccaggaga tacggaatct   2100

acagacacaa gctctagtgt aaatgctaat gcagacttag aagatgtttc tgatgctgat   2160

tcaggattcg gggatgatga cggtatatcg gatacagagt ccactaatgg taacgactct   2220

ggaaaaaata ctcctgtagg ggatggtggt acaccaagcg gaccagatat cctagctgct   2280

gtacgcaaac atctagacac tgtctatcca ggagaaaatg gtggatctac agagagacct   2340

ttacccgcta atcaaaattt aggagatatc attcatgatg tagaacaaaa cggaagcgct   2400

aaagaaactg tagtatcgcc ttatcgagga ggaggaggaa atacatcttc cccaattgga   2460

ttagcctccc tgcttccagc aacaccatcc acacctttga tgacaacacc tagaacaaat   2520

gggaaagctg cagcttcttc tttgatgata aaaggaggag aaactcaagc caagctagtt   2580

aagaatggcg gcaatatccc tggagaaacc acattagcag aattactccc tcgtttaaga   2640

ggacaccttg acaaagtctt tacttcagac gggaagttta caaatcttaa tggacctcaa   2700

cttggagcca tcatagacca attccgcaaa gaaacgggtt ccggaggaat catagctcat   2760

acagatagtg ttccaggaga gaacggaaca gcctctcctc tcacaggaag ttcaggggaa   2820

aaagtctctc tctatgatgc agcgaaaaac gtcactcaag ctttaacaag tgttacgaac   2880

aaagtaaccc tagcaatgca aggacaaaaa ctggaaggaa ttataaacaa caacaatacc   2940

ccctcttcta ttggacaaaa tcttttcgca gcagcgaggg caacgacaca atccctcagt   3000

tcattaattg gaaccgtaca ataa                                          3024
```

<210> SEQ ID NO 36
<211> LENGTH: 1007
<212> TYPE: PRT
<213> ORGANISM: Chlamydia muridarum

<400> SEQUENCE: 36

```
Met Thr Thr Pro Ile Ser Asn Ser Pro Ser Ser Ile Pro Thr Val Thr
1               5                   10                  15

Val Ser Thr Thr Thr Ala Ser Ser Gly Ser Leu Gly Thr Ser Thr Val
            20                  25                  30

Ser Ser Thr Thr Thr Ser Thr Ser Val Ala Gln Thr Ala Thr Thr Thr
        35                  40                  45

Ser Ser Ala Ser Thr Ser Ile Ile Gln Ser Ser Gly Glu Asn Ile Gln
    50                  55                  60

Ser Thr Thr Gly Thr Pro Ser Pro Ile Thr Ser Ser Val Ser Thr Ser
65                  70                  75                  80

Ala Pro Ser Pro Lys Ala Ser Ala Thr Ala Asn Lys Thr Ser Ser Ala
                85                  90                  95
```

-continued

```
Val Ser Gly Lys Ile Thr Ser Gln Glu Thr Ser Glu Glu Ser Glu Thr
            100                 105                 110

Gln Ala Thr Thr Ser Asp Gly Glu Val Ser Ser Asn Tyr Asp Asp Val
        115                 120                 125

Asp Thr Pro Thr Asn Ser Ser Asp Ser Thr Val Asp Ser Asp Tyr Gln
    130                 135                 140

Asp Val Glu Thr Gln Tyr Lys Thr Ile Ser Asn Asn Gly Glu Asn Thr
145                 150                 155                 160

Tyr Glu Thr Ile Gly Ser His Gly Glu Lys Asn Thr His Val Gln Glu
                165                 170                 175

Ser His Ala Ser Gly Thr Gly Asn Pro Ile Asn Asn Gln Gln Glu Ala
            180                 185                 190

Ile Arg Gln Leu Arg Ser Ser Thr Tyr Thr Thr Ser Pro Arg Asn Glu
        195                 200                 205

Asn Ile Phe Ser Pro Gly Pro Glu Gly Leu Pro Asn Met Ser Leu Pro
    210                 215                 220

Ser Tyr Ser Pro Thr Asp Lys Ser Ser Leu Leu Ala Phe Leu Ser Asn
225                 230                 235                 240

Pro Asn Thr Lys Ala Lys Met Leu Glu His Ser Gly His Leu Val Phe
                245                 250                 255

Ile Asp Thr Thr Arg Ser Ser Phe Ile Phe Val Pro Asn Gly Asn Trp
            260                 265                 270

Asp Gln Val Cys Ser Met Lys Val Gln Asn Gly Lys Thr Lys Glu Asp
        275                 280                 285

Leu Gly Leu Lys Asp Leu Glu Asp Met Cys Ala Lys Phe Cys Thr Gly
    290                 295                 300

Tyr Asn Lys Phe Ser Ser Asp Trp Gly Asn Arg Val Asp Pro Leu Val
305                 310                 315                 320

Ser Ser Lys Ala Gly Ile Glu Ser Gly Gly His Leu Pro Ser Ser Val
                325                 330                 335

Ile Ile Asn Asn Lys Phe Arg Thr Cys Val Ala Tyr Gly Pro Trp Asn
            340                 345                 350

Pro Lys Glu Asn Gly Pro Asn Tyr Thr Pro Ser Ala Trp Arg Arg Gly
        355                 360                 365

His Arg Val Asp Phe Gly Lys Ile Phe Asp Gly Thr Ala Pro Phe Asn
    370                 375                 380

Lys Ile Asn Trp Gly Ser Ser Pro Thr Pro Gly Asp Asp Gly Ile Ser
385                 390                 395                 400

Phe Ser Asn Glu Thr Ile Gly Ser Glu Pro Phe Ala Thr Pro Pro Ser
                405                 410                 415

Ser Pro Ser Gln Thr Pro Val Ile Asn Val Asn Val Asn Val Gly Gly
            420                 425                 430

Thr Asn Val Asn Ile Gly Asp Thr Asn Val Ser Lys Gly Ser Gly Thr
        435                 440                 445

Pro Thr Ser Ser Gln Ser Val Asp Met Ser Thr Asp Thr Ser Asp Leu
    450                 455                 460

Asp Thr Ser Asp Ile Asp Thr Asn Asn Gln Thr Asn Gly Asp Ile Asn
465                 470                 475                 480

Thr Asn Asp Asn Ser Asn Asn Val Asp Gly Ser Leu Ser Asp Val Asp
                485                 490                 495

Ser Arg Val Glu Asp Asp Asp Gly Val Ser Asp Thr Glu Ser Thr Asn
            500                 505                 510

Gly Asn Asp Ser Gly Lys Thr Thr Ser Thr Glu Glu Asn Gly Asp Pro
        515                 520                 525
```

```
Ser Gly Pro Asp Ile Leu Ala Ala Val Arg Lys His Leu Asp Thr Val
    530                 535                 540

Tyr Pro Gly Glu Asn Gly Gly Ser Thr Glu Gly Pro Leu Pro Ala Asn
545                 550                 555                 560

Gln Asn Leu Gly Asn Val Ile His Asp Val Glu Gln Asn Gly Ser Ala
                565                 570                 575

Lys Glu Thr Ile Ile Thr Pro Gly Asp Thr Gly Pro Thr Asp Ser Ser
            580                 585                 590

Ser Ser Val Asp Ala Asp Ala Asp Val Glu Asp Thr Ser Asp Thr Asp
        595                 600                 605

Ser Gly Ile Gly Asp Asp Asp Gly Val Ser Asp Thr Glu Ser Thr Asn
    610                 615                 620

Gly Asn Asn Ser Gly Lys Thr Thr Ser Thr Glu Glu Asn Gly Asp Pro
625                 630                 635                 640

Ser Gly Pro Asp Ile Leu Ala Ala Val Arg Lys His Leu Asp Thr Val
                645                 650                 655

Tyr Pro Gly Glu Asn Gly Gly Ser Thr Glu Gly Pro Leu Pro Ala Asn
            660                 665                 670

Gln Asn Leu Gly Asn Val Ile His Asp Val Glu Gln Asn Gly Ala Ala
        675                 680                 685

Gln Glu Thr Ile Ile Thr Pro Gly Asp Thr Glu Ser Thr Asp Thr Ser
    690                 695                 700

Ser Ser Val Asn Ala Asn Ala Asp Leu Glu Asp Val Ser Asp Ala Asp
705                 710                 715                 720

Ser Gly Phe Gly Asp Asp Asp Gly Ile Ser Asp Thr Glu Ser Thr Asn
                725                 730                 735

Gly Asn Asp Ser Gly Lys Asn Thr Pro Val Gly Asp Gly Gly Thr Pro
            740                 745                 750

Ser Gly Pro Asp Ile Leu Ala Ala Val Arg Lys His Leu Asp Thr Val
        755                 760                 765

Tyr Pro Gly Glu Asn Gly Gly Ser Thr Glu Arg Pro Leu Pro Ala Asn
    770                 775                 780

Gln Asn Leu Gly Asp Ile Ile His Asp Val Glu Gln Asn Gly Ser Ala
785                 790                 795                 800

Lys Glu Thr Val Val Ser Pro Tyr Arg Gly Gly Gly Gly Asn Thr Ser
                805                 810                 815

Ser Pro Ile Gly Leu Ala Ser Leu Leu Pro Ala Thr Pro Ser Thr Pro
            820                 825                 830

Leu Met Thr Thr Pro Arg Thr Asn Gly Lys Ala Ala Ala Ser Ser Leu
        835                 840                 845

Met Ile Lys Gly Gly Glu Thr Gln Ala Lys Leu Val Lys Asn Gly Gly
    850                 855                 860

Asn Ile Pro Gly Glu Thr Thr Leu Ala Glu Leu Leu Pro Arg Leu Arg
865                 870                 875                 880

Gly His Leu Asp Lys Val Phe Thr Ser Asp Gly Lys Phe Thr Asn Leu
                885                 890                 895

Asn Gly Pro Gln Leu Gly Ala Ile Ile Asp Gln Phe Arg Lys Glu Thr
            900                 905                 910

Gly Ser Gly Gly Ile Ile Ala His Thr Asp Ser Val Pro Gly Glu Asn
        915                 920                 925

Gly Thr Ala Ser Pro Leu Thr Gly Ser Ser Gly Glu Lys Val Ser Leu
    930                 935                 940

Tyr Asp Ala Ala Lys Asn Val Thr Gln Ala Leu Thr Ser Val Thr Asn
```

945 950 955 960

Lys Val Thr Leu Ala Met Gln Gly Gln Lys Leu Glu Gly Ile Ile Asn
965 970 975

Asn Asn Asn Thr Pro Ser Ser Ile Gly Gln Asn Leu Phe Ala Ala Ala
980 985 990

Arg Ala Thr Thr Gln Ser Leu Ser Ser Leu Ile Gly Thr Val Gln
995 1000 1005

<210> SEQ ID NO 37
<211> LENGTH: 780
<212> TYPE: DNA
<213> ORGANISM: Chlamydia muridarum

<400> SEQUENCE: 37
gtgagtatgt atataaaaag aaagaaagct tggatgactt tcttagcaat tgtctgtagt 60
ttctgtttgg cgggctgttc aaaagagagc aaagactctg ttagtgaaaa atttattgta 120
ggaactaacg caacgtatcc tccttttgag tttgttgatg aaagaggtga gacggttggc 180
tttgatattg atttagctag ggagattagt aaaaagctag ggaaaaaatt agaagtccga 240
gaatttgctt ttgatgcact cgttctcaat ttaaaacagc atcgtattga tgcaattatg 300
gcaggggtgt ccattacgtc ttctcgattg aaagaaattt tgatgattcc ctactatggc 360
gaagaaataa agagtttggt tttagtgttt aaggatggag actcaaagtc tttaccacta 420
gatcagtata attctgttgc tgttcaaact ggcacgtacc aagaggaata tttacagtct 480
cttccagggg tgcgtattcg ctcttttgat agtactttag aagtgcttat ggaagttttg 540
catagcaagt ctcctatagc tgttttagaa ccgtctattg cgcaggtcgt tttaaaagat 600
tttccgacgc tcactactga aacgatagat cttcctgaag ataaatgggt tttagggtat 660
ggaattggag ttgcttctga tcgaccatct ctagcttctg atatagaagc tgctgtacaa 720
gagatcaaga aagaaggagt gttagcagag ttagagcaaa aatggggttt gaacggctaa 780

<210> SEQ ID NO 38
<211> LENGTH: 259
<212> TYPE: PRT
<213> ORGANISM: Chlamydia muridarum

<400> SEQUENCE: 38

Met Ser Met Tyr Ile Lys Arg Lys Lys Ala Trp Met Thr Phe Leu Ala
1 5 10 15

Ile Val Cys Ser Phe Cys Leu Ala Gly Cys Ser Lys Glu Ser Lys Asp
20 25 30

Ser Val Ser Glu Lys Phe Ile Val Gly Thr Asn Ala Thr Tyr Pro Pro
35 40 45

Phe Glu Phe Val Asp Glu Arg Gly Glu Thr Val Gly Phe Asp Ile Asp
50 55 60

Leu Ala Arg Glu Ile Ser Lys Lys Leu Gly Lys Lys Leu Glu Val Arg
65 70 75 80

Glu Phe Ala Phe Asp Ala Leu Val Leu Asn Leu Lys Gln His Arg Ile
85 90 95

Asp Ala Ile Met Ala Gly Val Ser Ile Thr Ser Ser Arg Leu Lys Glu
100 105 110

Ile Leu Met Ile Pro Tyr Tyr Gly Glu Glu Ile Lys Ser Leu Val Leu
115 120 125

Val Phe Lys Asp Gly Asp Ser Lys Ser Leu Pro Leu Asp Gln Tyr Asn
130 135 140

Ser Val Ala Val Gln Thr Gly Thr Tyr Gln Glu Glu Tyr Leu Gln Ser
145 150 155 160

Leu Pro Gly Val Arg Ile Arg Ser Phe Asp Ser Thr Leu Glu Val Leu
165 170 175

Met Glu Val Leu His Ser Lys Ser Pro Ile Ala Val Leu Glu Pro Ser
180 185 190

Ile Ala Gln Val Val Leu Lys Asp Phe Pro Thr Leu Thr Thr Glu Thr
195 200 205

Ile Asp Leu Pro Glu Asp Lys Trp Val Leu Gly Tyr Gly Ile Gly Val
210 215 220

Ala Ser Asp Arg Pro Ser Leu Ala Ser Asp Ile Glu Ala Ala Val Gln
225 230 235 240

Glu Ile Lys Lys Glu Gly Val Leu Ala Glu Leu Glu Gln Lys Trp Gly
245 250 255

Leu Asn Gly

<210> SEQ ID NO 39
<211> LENGTH: 384
<212> TYPE: DNA
<213> ORGANISM: Chlamydia trachomatis

<400> SEQUENCE: 39
atggaagaaa aaggcatctt acaattggtt gaaatttcgc gagcaatggc tttacaggga 60
gtttgtcctt ggactaattt acagagtgtg gagtctatgt tgcagtatat agcaggggag 120
tgtcaggagt tggctgatgc tgtacaagaa aataaagctt cgttggaaat cgcttcggaa 180
gccggagacg tacttacttt agtattgacc ttgtgtttct tgctagaaag agaaggaaag 240
cttaaagctg aagaagtatt tgtagaagct ttggctaagt tgcgtcgtcg atctcctcat 300
gtttttgatc ctcataatca aatttcttta gaacaggctg aagaatactg ggctcgtatg 360
aaacagcaag aaaaaatttc ttaa 384

<210> SEQ ID NO 40
<211> LENGTH: 127
<212> TYPE: PRT
<213> ORGANISM: Chlamydia trachomatis

<400> SEQUENCE: 40

Met Glu Glu Lys Gly Ile Leu Gln Leu Val Glu Ile Ser Arg Ala Met
1 5 10 15

Ala Leu Gln Gly Val Cys Pro Trp Thr Asn Leu Gln Ser Val Glu Ser
20 25 30

Met Leu Gln Tyr Ile Ala Gly Glu Cys Gln Glu Leu Ala Asp Ala Val
35 40 45

Gln Glu Asn Lys Ala Ser Leu Glu Ile Ala Ser Glu Ala Gly Asp Val
50 55 60

Leu Thr Leu Val Leu Thr Leu Cys Phe Leu Leu Glu Arg Glu Gly Lys
65 70 75 80

Leu Lys Ala Glu Glu Val Phe Val Glu Ala Leu Ala Lys Leu Arg Arg
85 90 95

Arg Ser Pro His Val Phe Asp Pro His Asn Gln Ile Ser Leu Glu Gln
100 105 110

Ala Glu Glu Tyr Trp Ala Arg Met Lys Gln Gln Glu Lys Ile Ser
115 120 125

<210> SEQ ID NO 41
<211> LENGTH: 1179

<212> TYPE: DNA
<213> ORGANISM: Chlamydia trachomatis

<400> SEQUENCE: 41
atggattact acacgatatt gggtgtagcg aagactgcta ctcctgaaga aataaagaaa 60
gcttaccgta agctcgctgt aaagtaccat ccagataaga atcctgggga tgctgaagcg 120
gagcgacgct ttaaagaagt ttctgaagcc tatgaagtat taggtgatgc gcagaagcgg 180
gagtcatatg atcgttacgg caaagacggt ccatttgctg gtgctggagg attcggtggc 240
gctggcatgg ggaatatgga agacgctttg cgaacattta tgggagcttt tggcggcgat 300
ttcggtggta atggaggcgg tttctttgaa gggctttttg gaggacttgg agaagctttc 360
ggaatgcgtg gaggctcaga aagttctcga caaggagcta gtaagaaggt gcatattacg 420
ctgtccttcg aggaggcggc aaaaggtgtt gaaaaagaac ttcttgtttc aggctataaa 480
tcttgtgatg cttgttctgg tagtggagcc aatactgcta aaggtgtaaa agtttgtgat 540
cgatgcaagg gctctggtca ggtagtgcaa agccgaggct tttctccat ggcttctact 600 tgccctgatt gtagtggtga aggtcgggtt atcacagatc cttgttcagt ttgtcgtggg 660
cagggacgta tcaaggataa acgtagcgtc catgttaata tcccagctgg agtcgattct 720
gggatgagat taaagatgga aggctatgga gatgctggcc aaaatggagc gcctgcaggg 780
gatctgtatg tttttattga tgtagagcct catcctgttt tcgagcgcca tggggatgat 840
ttagttttag agcttcctat tggatttgtt gatgcggctt tagggatcaa gaaggaaatc 900
cctacactct taaaagaagg tacttgccgt ttgagtatcc cagaagggat tcagagcgga 960
acagttctta aagttagagg gcagggattc cctaatgtgc atgggaaatc cagaggagat 1020
cttttagtaa gagtatctgt ggagactccc cagcacctat ctaatgaaca aaaagattta 1080
ttgagacagt ttgctgctac ggagaaggct gaaaatttcc ctaagaaacg gagtttctta 1140
gacaaaatca aaggtttttt ttctgacttt gctgtatag 1179

<210> SEQ ID NO 42
<211> LENGTH: 392
<212> TYPE: PRT
<213> ORGANISM: Chlamydia trachomatis

<400> SEQUENCE: 42

Met Asp Tyr Tyr Thr Ile Leu Gly Val Ala Lys Thr Ala Thr Pro Glu
1 5 10 15

Glu Ile Lys Lys Ala Tyr Arg Lys Leu Ala Val Lys Tyr His Pro Asp
20 25 30

Lys Asn Pro Gly Asp Ala Glu Ala Glu Arg Arg Phe Lys Glu Val Ser
35 40 45

Glu Ala Tyr Glu Val Leu Gly Asp Ala Gln Lys Arg Glu Ser Tyr Asp
50 55 60

Arg Tyr Gly Lys Asp Gly Pro Phe Ala Gly Ala Gly Gly Phe Gly Gly
65 70 75 80

Ala Gly Met Gly Asn Met Glu Asp Ala Leu Arg Thr Phe Met Gly Ala
85 90 95

Phe Gly Gly Asp Phe Gly Gly Asn Gly Gly Gly Phe Phe Glu Gly Leu
100 105 110

Phe Gly Gly Leu Gly Glu Ala Phe Gly Met Arg Gly Gly Ser Glu Ser
115 120 125

Ser Arg Gln Gly Ala Ser Lys Lys Val His Ile Thr Leu Ser Phe Glu
130 135 140

```
Glu Ala Ala Lys Gly Val Glu Lys Glu Leu Leu Val Ser Gly Tyr Lys
145                 150                 155                 160

Ser Cys Asp Ala Cys Ser Gly Ser Gly Ala Asn Thr Ala Lys Gly Val
            165                 170                 175

Lys Val Cys Asp Arg Cys Lys Gly Ser Gly Gln Val Val Gln Ser Arg
            180                 185                 190

Gly Phe Phe Ser Met Ala Ser Thr Cys Pro Asp Cys Ser Gly Glu Gly
        195                 200                 205

Arg Val Ile Thr Asp Pro Cys Ser Val Cys Arg Gly Gln Gly Arg Ile
    210                 215                 220

Lys Asp Lys Arg Ser Val His Val Asn Ile Pro Ala Gly Val Asp Ser
225                 230                 235                 240

Gly Met Arg Leu Lys Met Glu Gly Tyr Gly Asp Ala Gly Gln Asn Gly
            245                 250                 255

Ala Pro Ala Gly Asp Leu Tyr Val Phe Ile Asp Val Glu Pro His Pro
            260                 265                 270

Val Phe Glu Arg His Gly Asp Asp Leu Val Leu Glu Leu Pro Ile Gly
        275                 280                 285

Phe Val Asp Ala Ala Leu Gly Ile Lys Lys Glu Ile Pro Thr Leu Leu
    290                 295                 300

Lys Glu Gly Thr Cys Arg Leu Ser Ile Pro Glu Gly Ile Gln Ser Gly
305                 310                 315                 320

Thr Val Leu Lys Val Arg Gly Gln Gly Phe Pro Asn Val His Gly Lys
            325                 330                 335

Ser Arg Gly Asp Leu Leu Val Arg Val Ser Val Glu Thr Pro Gln His
            340                 345                 350

Leu Ser Asn Glu Gln Lys Asp Leu Leu Arg Gln Phe Ala Ala Thr Glu
        355                 360                 365

Lys Ala Glu Asn Phe Pro Lys Lys Arg Ser Phe Leu Asp Lys Ile Lys
    370                 375                 380

Gly Phe Phe Ser Asp Phe Ala Val
385                 390
```

<210> SEQ ID NO 43
<211> LENGTH: 366
<212> TYPE: DNA
<213> ORGANISM: Chlamydia trachomatis

<400> SEQUENCE: 43

```
atgaataaaa aactccaaga tctgtctaaa ctgctcacta ttgagctttt caagaaacgt      60

acacggttgg aaacagtaaa aaaagcgctc tccacaatag aacatcgctt acaacaaata     120

caggagcaca tcgcgaaaat ttccttaaca aggcacaaac aattcctatg tcggtcatat     180

acccatgaat atgaccaaca tttagaacat ttacaaagag agcaaacttc tctatataaa     240

cagcatcaga ccctgaaaac gtctttgaaa gatgcttatg gcgacataca aaaacaacta     300

gaccaaagaa aaattatcga aaagatccat gacagtaaat atcctataaa gagcgcgaat     360

aactaa                                                                366
```

<210> SEQ ID NO 44
<211> LENGTH: 121
<212> TYPE: PRT
<213> ORGANISM: Chlamydia trachomatis

<400> SEQUENCE: 44

```
Met Asn Lys Lys Leu Gln Asp Leu Ser Lys Leu Leu Thr Ile Glu Leu
1               5                   10                  15
```

```
Phe Lys Lys Arg Thr Arg Leu Glu Thr Val Lys Lys Ala Leu Ser Thr
            20                  25                  30

Ile Glu His Arg Leu Gln Gln Ile Gln Glu His Ile Ala Lys Ile Ser
        35                  40                  45

Leu Thr Arg His Lys Gln Phe Leu Cys Arg Ser Tyr Thr His Glu Tyr
    50                  55                  60

Asp Gln His Leu Glu His Leu Gln Arg Glu Gln Thr Ser Leu Tyr Lys
65                  70                  75                  80

Gln His Gln Thr Leu Lys Thr Ser Leu Lys Asp Ala Tyr Gly Asp Ile
                85                  90                  95

Gln Lys Gln Leu Asp Gln Arg Lys Ile Ile Glu Lys Ile His Asp Ser
            100                 105                 110

Lys Tyr Pro Ile Lys Ser Ala Asn Asn
        115                 120
```

<210> SEQ ID NO 45
<211> LENGTH: 1275
<212> TYPE: DNA
<213> ORGANISM: Chlamydia trachomatis

<400> SEQUENCE: 45

```
atgaaacatg ctctcattgt tggctcaggt attgccggcc tttctgccgc gtggtggcta     60

cacaaacgat tccctcatgt gcagctgtct attctagaaa aagagtctcg atctggaggg    120

ctaattgtca cagagaaaca acaagggttt tccctcaata tgggccctaa aggttttgtt    180

ttagctcatg atgggcaaca caccctcac ctcattcagt ctttaggcct agcagacgag    240

ctattatata gctctccaga ggctaaaaac cgctttatcc actataataa taaaacccga    300

aaagtctcgc cttggactat tttcaaacaa aatctccctc tctcttttgc taaggatttc    360

tttgcgcgtc cttacaaaca agacagctcc gtggaagcct tctttaaaag acacagttct    420

tccaagctta gaagaaatct tttaaatccc attagcattg ctattcgtgc aggacatagt    480

catatattgt ctgcacagat ggcttaccca gaattaacac gaagagaagc tcaaacagga    540

tcgttgttac gtagttatct caaagatttt cctaaagaga aacgcacagg cccttattta    600

gctaccttgc ggtctgggat gggaatgcta acccaggctt tgcatgataa attgcctgct    660

acctggtatt tttctgcacc cgtcagcaaa atccgtcagt tggcgaatgg gaaaatttct    720

ctttcatctc ctcaaggaga aataacggga gatatgctca tttatgctgg gtccgtgcac    780

gatctccctt cctgtctaga agggatccct gaaaccaagc ttatcaagca aacgacttca    840

tcttgggatc tctcttgtgt atctttagga tggcatgcat ccttccctat ccctcatgga    900

tatggcatgc ttttcgctga tacgcctccc ttattaggga tcgtgtttaa tacggaagtg    960

ttccctcaac ccgagcggcc taatacaata gtctctcttc ttttagaagg tcgatggcac   1020

caagaagaag cgtatgcttt ctcactagca gctatttctg agtacctgca aatttacact   1080

cctccccaag ctttctcact attctctcct cgagagggac ttccccaaca ccatgttgga   1140

tttatccaat cccgccaacg ccttctatct aaacttcctc acaatataaa aattgtaggg   1200

cagaattttg caggtccagg tctcaaccgc gctacagcgt ctgcttataa agctatagct   1260

tctttactat catga                                                    1275
```

<210> SEQ ID NO 46
<211> LENGTH: 424
<212> TYPE: PRT
<213> ORGANISM: Chlamydia trachomatis

<400> SEQUENCE: 46

```
Met Lys His Ala Leu Ile Val Gly Ser Gly Ile Ala Gly Leu Ser Ala
1               5                   10                  15

Ala Trp Trp Leu His Lys Arg Phe Pro His Val Gln Leu Ser Ile Leu
            20                  25                  30

Glu Lys Glu Ser Arg Ser Gly Gly Leu Ile Val Thr Glu Lys Gln Gln
        35                  40                  45

Gly Phe Ser Leu Asn Met Gly Pro Lys Gly Phe Val Leu Ala His Asp
    50                  55                  60

Gly Gln His Thr Leu His Leu Ile Gln Ser Leu Gly Leu Ala Asp Glu
65                  70                  75                  80

Leu Leu Tyr Ser Ser Pro Glu Ala Lys Asn Arg Phe Ile His Tyr Asn
                85                  90                  95

Asn Lys Thr Arg Lys Val Ser Pro Trp Thr Ile Phe Lys Gln Asn Leu
            100                 105                 110

Pro Leu Ser Phe Ala Lys Asp Phe Phe Ala Arg Pro Tyr Lys Gln Asp
        115                 120                 125

Ser Ser Val Glu Ala Phe Phe Lys Arg His Ser Ser Ser Lys Leu Arg
    130                 135                 140

Arg Asn Leu Leu Asn Pro Ile Ser Ile Ala Ile Arg Ala Gly His Ser
145                 150                 155                 160

His Ile Leu Ser Ala Gln Met Ala Tyr Pro Glu Leu Thr Arg Arg Glu
                165                 170                 175

Ala Gln Thr Gly Ser Leu Leu Arg Ser Tyr Leu Lys Asp Phe Pro Lys
            180                 185                 190

Glu Lys Arg Thr Gly Pro Tyr Leu Ala Thr Leu Arg Ser Gly Met Gly
        195                 200                 205

Met Leu Thr Gln Ala Leu His Asp Lys Leu Pro Ala Thr Trp Tyr Phe
    210                 215                 220

Ser Ala Pro Val Ser Lys Ile Arg Gln Leu Ala Asn Gly Lys Ile Ser
225                 230                 235                 240

Leu Ser Ser Pro Gln Gly Glu Ile Thr Gly Asp Met Leu Ile Tyr Ala
                245                 250                 255

Gly Ser Val His Asp Leu Pro Ser Cys Leu Glu Gly Ile Pro Glu Thr
            260                 265                 270

Lys Leu Ile Lys Gln Thr Thr Ser Ser Trp Asp Leu Ser Cys Val Ser
        275                 280                 285

Leu Gly Trp His Ala Ser Phe Pro Ile Pro His Gly Tyr Gly Met Leu
    290                 295                 300

Phe Ala Asp Thr Pro Pro Leu Leu Gly Ile Val Phe Asn Thr Glu Val
305                 310                 315                 320

Phe Pro Gln Pro Glu Arg Pro Asn Thr Ile Val Ser Leu Leu Leu Glu
                325                 330                 335

Gly Arg Trp His Gln Glu Glu Ala Tyr Ala Phe Ser Leu Ala Ala Ile
            340                 345                 350

Ser Glu Tyr Leu Gln Ile Tyr Thr Pro Pro Gln Ala Phe Ser Leu Phe
        355                 360                 365

Ser Pro Arg Glu Gly Leu Pro Gln His His Val Gly Phe Ile Gln Ser
    370                 375                 380

Arg Gln Arg Leu Leu Ser Lys Leu Pro His Asn Ile Lys Ile Val Gly
385                 390                 395                 400

Gln Asn Phe Ala Gly Pro Gly Leu Asn Arg Ala Thr Ala Ser Ala Tyr
                405                 410                 415
```

```
Lys Ala Ile Ala Ser Leu Leu Ser
            420


<210> SEQ ID NO 47
<211> LENGTH: 2076
<212> TYPE: DNA
<213> ORGANISM: Chlamydia trachomatis

<400> SEQUENCE: 47

atgacgctct ttcattctca tcatgatgcc gtctctccag acagctacct atgttcttcc      60

cttcagttag ttggtactgg cgtatacgaa ggagaaatcg agattcaaaa tatcccctct     120

tatttccttg gattccaatt accctctcat tgcatacacc ttaatttaaa gagctctcta     180

gctcaattag gaatagatgc ctcccttctt cactgcgaat tgagcaaaaa tcaacatcga     240

gcacatatac atgctcaatt taccggtcat ggccccattg ctgaatctat gctagccctt     300

ctccaaccag gagatcgtgt agcaaaacta tttgctgcag acgatcgcag actggtccga     360

tctccagatt acctcgaaag catgctgaaa aatacagata aagctggcca tcctttgctc     420

tgttttggga aaaaattaga acacttgatt tcttttgatg tggtagatga tcgccttgtc     480

gtctcccttc ctaccctgcc gggagttgtt cgttatgatt cggatattta tggactcctt     540

cctcttattc aaaaatcact cagtaatccc aaactcagca ttcgtcactt tttagctctg     600

taccaacaga ttgtggaagg gcaacatgtc tcttgcggaa accatattct tctgatcaaa     660

acagaaccgc tgcacatccg cactgtattt gctcgcgtgg taaatcaact cctccctcaa     720

ggtctctccc acacttctgc caatattttg gaaccaacca ctcgagaatc cggggatatc     780

tttgaatttt ttgggaaccc ttctgcacag atagaaagaa ttcctttaga atttttcact     840

atcgaaccct ataaagaaca ttcttacttc tgtaatcggg atttattaca aaccatctta     900

caatcagaaa gcgaaatcaa aaaaatattc gaaacagcgc ccaaagaacc tgtcaaagct     960

gccacctatt tatcaaaagg cagtgaaatc tcttccctgc acacagactc ttggctcaca    1020

ggatccgcag ctgcctatca atatagtgag caagcagata aaaacgagta cactcatgct    1080

caaccttgct atcctttctt agaagcaatg gaaatgggcc tgatcaatag cgaaggagcc    1140

ttactcactc gttatttccc ttcagctagc ttaaaaggaa tgttgatttc ctaccatgtg    1200

cgccactatc tcaaacaaat ctactttcaa gttccctctt atacacatgg aaactatttc    1260

tctcataatg acagaggttt gctattagat ctgcagcaag cagatattga tgttttctgg    1320

gcagatgaag aaagcggccg tgtgttgcaa tatacaaaac gacgcgataa gaatagcggt    1380

atgttcgtga tcaaaaatcg tgttgaagag tttcgatcag cttattttat tgctatttat    1440

ggctctcgtc tccttgagaa taatttctct gctcagctcc ataccctcct agcgggctta    1500

cagcaagcag cacatactct cggcattcct ggattctcaa agcctacccc acttgcagtc    1560

atcaccggag gcggcactgg agttatggcc acaggaaatc gtgtagctaa agaactagga    1620

atcctatctt gtggaaccgt tcttgattta gaagcttctc cagcacaaat cgaccaacct    1680

accaatgaat tcttagatgc taaaatgaca taccgcctac ctcaacttat agaaaggcaa    1740

gaacactttt atgcagacct tcctatcctt gtagttggcg gtgtaggaac cgatttcgaa    1800

ctctacctag aacttgtcta tctcaaaaca ggagctaaac caccgactcc cattttccta    1860

attggaccta ttgaatactg gaaagaaaaa gtggcccacg cctacgagat caacctcaaa    1920

gcaggaacca tccgtggatc cgaatggatc agcaactgcc tatattgtat cacttctccg    1980

gaagctggaa ttgccgtatt cgaacaattc ctagctggag aactccctat aggatacgac    2040

tatcctccag ctccagatgg attagtgatc gtctaa                              2076
```

<210> SEQ ID NO 48
<211> LENGTH: 691
<212> TYPE: PRT
<213> ORGANISM: Chlamydia trachomatis

<400> SEQUENCE: 48

```
Met Thr Leu Phe His Ser His His Asp Ala Val Ser Pro Asp Ser Tyr
1               5                   10                  15

Leu Cys Ser Ser Leu Gln Leu Val Gly Thr Gly Val Tyr Glu Gly Glu
            20                  25                  30

Ile Glu Ile Gln Asn Ile Pro Ser Tyr Phe Leu Gly Phe Gln Leu Pro
        35                  40                  45

Ser His Cys Ile His Leu Asn Leu Lys Ser Ser Leu Ala Gln Leu Gly
    50                  55                  60

Ile Asp Ala Ser Leu Leu His Cys Glu Leu Ser Lys Asn Gln His Arg
65                  70                  75                  80

Ala His Ile His Ala Gln Phe Thr Gly His Gly Pro Ile Ala Glu Ser
                85                  90                  95

Met Leu Ala Leu Leu Gln Pro Gly Asp Arg Val Ala Lys Leu Phe Ala
            100                 105                 110

Ala Asp Asp Arg Arg Leu Val Arg Ser Pro Asp Tyr Leu Glu Ser Met
        115                 120                 125

Leu Lys Asn Thr Asp Lys Ala Gly His Pro Leu Leu Cys Phe Gly Lys
    130                 135                 140

Lys Leu Glu His Leu Ile Ser Phe Asp Val Val Asp Asp Arg Leu Val
145                 150                 155                 160

Val Ser Leu Pro Thr Leu Pro Gly Val Val Arg Tyr Asp Ser Asp Ile
                165                 170                 175

Tyr Gly Leu Leu Pro Leu Ile Gln Lys Ser Leu Ser Asn Pro Lys Leu
            180                 185                 190

Ser Ile Arg His Phe Leu Ala Leu Tyr Gln Gln Ile Val Glu Gly Gln
        195                 200                 205

His Val Ser Cys Gly Asn His Ile Leu Leu Ile Lys Thr Glu Pro Leu
    210                 215                 220

His Ile Arg Thr Val Phe Ala Arg Val Val Asn Gln Leu Leu Pro Gln
225                 230                 235                 240

Gly Leu Ser His Thr Ser Ala Asn Ile Leu Glu Pro Thr Thr Arg Glu
                245                 250                 255

Ser Gly Asp Ile Phe Glu Phe Phe Gly Asn Pro Ser Ala Gln Ile Glu
            260                 265                 270

Arg Ile Pro Leu Glu Phe Phe Thr Ile Glu Pro Tyr Lys Glu His Ser
        275                 280                 285

Tyr Phe Cys Asn Arg Asp Leu Leu Gln Thr Ile Leu Gln Ser Glu Ser
    290                 295                 300

Glu Ile Lys Lys Ile Phe Glu Thr Ala Pro Lys Glu Pro Val Lys Ala
305                 310                 315                 320

Ala Thr Tyr Leu Ser Lys Gly Ser Glu Ile Ser Ser Leu His Thr Asp
                325                 330                 335

Ser Trp Leu Thr Gly Ser Ala Ala Ala Tyr Gln Tyr Ser Glu Gln Ala
            340                 345                 350

Asp Lys Asn Glu Tyr Thr His Ala Gln Pro Cys Tyr Pro Phe Leu Glu
        355                 360                 365

Ala Met Glu Met Gly Leu Ile Asn Ser Glu Gly Ala Leu Leu Thr Arg
    370                 375                 380
```

```
Tyr Phe Pro Ser Ala Ser Leu Lys Gly Met Leu Ile Ser Tyr His Val
385                 390                 395                 400

Arg His Tyr Leu Lys Gln Ile Tyr Phe Gln Val Pro Ser Tyr Thr His
                405                 410                 415

Gly Asn Tyr Phe Ser His Asn Asp Arg Gly Leu Leu Leu Asp Leu Gln
            420                 425                 430

Gln Ala Asp Ile Asp Val Phe Trp Ala Asp Glu Glu Ser Gly Arg Val
        435                 440                 445

Leu Gln Tyr Thr Lys Arg Arg Asp Lys Asn Ser Gly Met Phe Val Ile
    450                 455                 460

Lys Asn Arg Val Glu Glu Phe Arg Ser Ala Tyr Phe Ile Ala Ile Tyr
465                 470                 475                 480

Gly Ser Arg Leu Leu Glu Asn Asn Phe Ser Ala Gln Leu His Thr Leu
                485                 490                 495

Leu Ala Gly Leu Gln Gln Ala Ala His Thr Leu Gly Ile Pro Gly Phe
            500                 505                 510

Ser Lys Pro Thr Pro Leu Ala Val Ile Thr Gly Gly Gly Thr Gly Val
        515                 520                 525

Met Ala Thr Gly Asn Arg Val Ala Lys Glu Leu Gly Ile Leu Ser Cys
    530                 535                 540

Gly Thr Val Leu Asp Leu Glu Ala Ser Pro Ala Gln Ile Asp Gln Pro
545                 550                 555                 560

Thr Asn Glu Phe Leu Asp Ala Lys Met Thr Tyr Arg Leu Pro Gln Leu
                565                 570                 575

Ile Glu Arg Gln Glu His Phe Tyr Ala Asp Leu Pro Ile Leu Val Val
            580                 585                 590

Gly Gly Val Gly Thr Asp Phe Glu Leu Tyr Leu Glu Leu Val Tyr Leu
        595                 600                 605

Lys Thr Gly Ala Lys Pro Pro Thr Pro Ile Phe Leu Ile Gly Pro Ile
    610                 615                 620

Glu Tyr Trp Lys Glu Lys Val Ala His Ala Tyr Glu Ile Asn Leu Lys
625                 630                 635                 640

Ala Gly Thr Ile Arg Gly Ser Glu Trp Ile Ser Asn Cys Leu Tyr Cys
                645                 650                 655

Ile Thr Ser Pro Glu Ala Gly Ile Ala Val Phe Glu Gln Phe Leu Ala
            660                 665                 670

Gly Glu Leu Pro Ile Gly Tyr Asp Tyr Pro Pro Ala Pro Asp Gly Leu
        675                 680                 685

Val Ile Val
    690
```

<210> SEQ ID NO 49
<211> LENGTH: 4596
<212> TYPE: DNA
<213> ORGANISM: Chlamydia trachomatis

<400> SEQUENCE: 49

```
atgagttccg agaaagatat aaaaagcacc tgttctaagt tttctttgtc tgtagtagca      60

gctatccttg cctctgttag cgggttagct agttgcgtag atcttcatgc tggaggacag     120

tctgtaaatg agctggtata tgtaggccct caagcggttt tattgttaga ccaaattcga     180

gatctattcg ttgggtctaa agatagtcag gctgaaggac agtataggtt aattgtagga     240

gatccaagtt ctttccaaga gaaagatgcg gatactcttc ccgggaaggt agagcaaagt     300

actttgttct cagtaaccaa tcccgtggtt ttccaaggtg tggaccaaca ggatcaagtc     360
```

```
tcttcccaag ggttaatttg tagttttacg agcagcaacc ttgattctcc tcgtgacgga    420
gaatcttttt taggtattgc ttttgttggg gatagtagta aggctggaat cacattaact    480
gacgtgaaag cttctttgtc tggagcggct ttatattcta cagaagatct tatctttgaa    540
aagattaagg gtggattgga atttgcatca tgttcttctc tagaacaggg gggagcttgt    600
gcagctcaaa gtattttgat tcatgattgt caaggattgc aggttaaaca ctgtactaca    660
gccgtgaatg ctgaggggtc tagtgcgaat gatcatcttg gatttggagg aggcgctttc    720
tttgttacgg gttctctttc tggagagaaa agtctctata tgcctgcagg agatatggta    780
gttgcgaatt gtgatggggc tatatctttt gaaggaaaca gcgcgaactt tgctaatgga    840
ggagcgattg ctgcctctgg gaaagtgctt tttgtcgcta atgataaaaa gacttctttt    900
atagagaacc gagctttgtc tggaggagcg attgcagcct cttctgatat tgcctttcaa    960
aactgcgcag aactagtttt caaaggcaat tgtgcaattg gaacagagga taaaggttct   1020
ttaggtggag gggctatatc ttctctaggc accgttcttt tgcaagggaa tcacgggata   1080
acttgtgata agaatgagtc tgcttcgcaa ggaggcgcca tttttggcaa aaattgtcag   1140
atttctgaca acgaggggcc agtggttttc agagatagta cagcttgctt aggaggaggc   1200
gctattgcag ctcaagaaat tgtttctatt cagaacaatc aggctgggat ttccttcgag   1260
ggaggtaagg ctagtttcgg aggaggtatt gcgtgtggat ctttttcttc cgcaggtggt   1320
gcttctgttt tagggaccat tgatatttcg aagaatttag gcgcgatttc gttctctcgt   1380
actttatgta cgacctcaga tttaggacaa atggagtacc agggaggagg agctctattt   1440
ggtgaaaata tttctctttc tgagaatgct ggtgtgctca cctttaaaga caacattgtg   1500
aagacttttg cttcgaatgg gaaaattctg ggaggaggag cgattttagc tactggtaag   1560
gtggaaatta ctaataattc cgaaggaatt tcttttacag gaaatgcgag agctccacaa   1620
gctcttccaa ctcaagagga gtttccttta ttcagcaaaa aagaagggcg accactctct   1680
tcaggatatt ctgggggagg agcgatttta ggaagagaag tagctattct ccacaacgct   1740
gcagtagtat ttgagcaaaa tcgtttgcag tgcagcgaag aagaagcgac attattaggt   1800
tgttgtggag gaggcgctgt tcatgggatg gatagcactt cgattgttgg caactcttca   1860
gtaagatttg gtaataatta cgcaatggga caaggagtct caggaggagc tcttttatct   1920
aaaacagtgc agttagctgg gaatggaagc gtcgattttt ctcgaaatat tgctagtttg   1980
ggaggaggag ctcttcaagc ttctgaagga aattgtgagc tagttgataa cggctatgtg   2040
ctattcagag ataatcgagg gagggtttat gggggtgcta tttcttgctt acgtggagat   2100
gtagtcattt ctggaaacaa gggtagagtt gaatttaaag acaacatagc aacacgtctt   2160
tatgtggaag aaactgtaga aaaggttgaa gaggtagagc cagctcctga gcaaaaagac   2220
aataatgagc tttctttctt agggagagca gaacagagtt ttattactgc agctaatcaa   2280
gctcttttcg catctgaaga tggggattta tcacctgagt catccatttc ttctgaagaa   2340
cttgcgaaaa gaagagagtg tgctggagga gctatttttg caaaacgggt tcgtattgta   2400
gataaccaag aggccgttgt attctcgaat aacttctctg atatttatgg cggcgccatt   2460
tttacaggtt ctcttcgaga agaggataag ttagatgggc aaatccctga agtcttgatc   2520
tcaggcaatg caggggatgt tgtttttttcc ggaaattcct cgaagcgtga tgagcatctt   2580
cctcatacag gtgggggagc catttgtact caaaatttga cgatttctca gaatacaggg   2640
aatgttctgt tttataacaa cgtggcctgt tcgggaggag ctgttcgtat agaggatcat   2700
ggtaatgttc ttttagaagc ttttggagga gatattgttt ttaaaggaaa ttcttctttc   2760
```

-continued

```
agagcacaag gatccgatgc tatctatttt gcaggtaaag aatcgcatat tacagccctg   2820

aatgctacgg aaggacatgc tattgttttc cacgacgcat tagtttttga aaatctagaa   2880

gaaaggaaat ctgctgaagt attgttaatc aatagtcgag aaaatccagg ttacactgga   2940

tctattcgat ttttagaagc agaaagtaaa gttcctcaat gtattcatgt acaacaagga   3000

agccttgagt tgctaaatgg agccacatta tgtagttatg gttttaaaca agatgctgga   3060

gctaagttgg tattggctgc tggagctaaa ctgaagattt tagattcagg aactcctgta   3120

caacaagggc atgctatcag taaacctgaa gcagaaatcg agtcatcttc tgaaccagag   3180

ggtgcacatt ctctttggat tgcgaagaat gctcaaacaa cagttcctat ggttgatatc   3240

catactattt ctgtagattt agcctccttc tcttctagtc aacaggaggg gacagtagaa   3300

gctcctcagg ttattgttcc tggaggaagt tatgttcgat ctggagagct taatttggag   3360

ttagttaaca caacaggtac tggttatgaa aatcatgctt tattgaagaa tgaggctaaa   3420

gttccattga tgtctttcgt tgcttctggt gatgaagctt cagccgaaat cagtaacttg   3480

tcggtttctg atttacagat tcatgtagta actccagaga ttgaagaaga cacatacggc   3540

catatgggag attggtctga ggctaaaatt caagatggaa ctcttgtcat tagttggaat   3600

cctactggat atcgattaga tcctcaaaaa gcaggggctt tagtatttaa tgcattatgg   3660

gaagaagggg ctgtcttgtc tgctctgaaa aatgcacgct ttgctcataa tctcactgct   3720

cagcgtatgg aattcgatta ttctacaaat gtgtggggat tcgcctttgg tggtttccga   3780

actctatctg cagagaatct ggttgctatt gatggataca aaggagctta tggtggtgct   3840

tctgctggag tcgatattca attgatggaa gattttgttc taggagttag tggagctgct   3900

ttcctaggta aaatggatag tcagaagttt gatgcggagg tttctcggaa gggagttgtt   3960

ggttctgtat atacaggatt tttagctgga tcctggttct tcaaaggaca atatagcctt   4020

ggagaaacac agaacgatat gaaaacgcgt tatggagtac taggagagtc gagtgcttct   4080

tggacatctc gaggagtact ggcagatgct ttagttgaat accgaagttt agttggtcct   4140

gtgagaccta ctttttatgc tttgcatttc aatccttatg tcgaagtatc ttatgcttct   4200

atgaaattcc ctggctttac agaacaagga agagaagcgc gttcttttga agacgcttcc   4260

cttaccaata tcaccattcc tttagggatg aagtttgaat tggcgttcat aaaaggacag   4320

ttttcagagg tgaactcttt gggaataagt tatgcatggg aagcttatcg aaaagtagaa   4380

ggaggcgcgg tgcagctttt agaagctggg tttgattggg agggagctcc aatggatctt   4440

cctagacagg agctgcgtgt cgctctggaa aataatacgg aatggagttc ttacttcagc   4500

acagtcttag gattaacagc tttttgtgga ggatttactt ctacagatag taaactagga   4560

tatgaggcga atactggatt gcgattgatc ttttaa                             4596
```

<210> SEQ ID NO 50
<211> LENGTH: 1531
<212> TYPE: PRT
<213> ORGANISM: Chlamydia trachomatis

<400> SEQUENCE: 50

```
Met Ser Ser Glu Lys Asp Ile Lys Ser Thr Cys Ser Lys Phe Ser Leu
1               5                   10                  15

Ser Val Val Ala Ala Ile Leu Ala Ser Val Ser Gly Leu Ala Ser Cys
            20                  25                  30

Val Asp Leu His Ala Gly Gly Gln Ser Val Asn Glu Leu Val Tyr Val
        35                  40                  45
```

```
Gly Pro Gln Ala Val Leu Leu Leu Asp Gln Ile Arg Asp Leu Phe Val
    50                  55                  60

Gly Ser Lys Asp Ser Gln Ala Glu Gly Gln Tyr Arg Leu Ile Val Gly
65                  70                  75                  80

Asp Pro Ser Ser Phe Gln Glu Lys Asp Ala Asp Thr Leu Pro Gly Lys
                85                  90                  95

Val Glu Gln Ser Thr Leu Phe Ser Val Thr Asn Pro Val Val Phe Gln
            100                 105                 110

Gly Val Asp Gln Gln Asp Gln Val Ser Ser Gln Gly Leu Ile Cys Ser
        115                 120                 125

Phe Thr Ser Ser Asn Leu Asp Ser Pro Arg Asp Gly Glu Ser Phe Leu
    130                 135                 140

Gly Ile Ala Phe Val Gly Asp Ser Ser Lys Ala Gly Ile Thr Leu Thr
145                 150                 155                 160

Asp Val Lys Ala Ser Leu Ser Gly Ala Ala Leu Tyr Ser Thr Glu Asp
                165                 170                 175

Leu Ile Phe Glu Lys Ile Lys Gly Gly Leu Glu Phe Ala Ser Cys Ser
            180                 185                 190

Ser Leu Glu Gln Gly Gly Ala Cys Ala Ala Gln Ser Ile Leu Ile His
        195                 200                 205

Asp Cys Gln Gly Leu Gln Val Lys His Cys Thr Thr Ala Val Asn Ala
    210                 215                 220

Glu Gly Ser Ser Ala Asn Asp His Leu Gly Phe Gly Gly Gly Ala Phe
225                 230                 235                 240

Phe Val Thr Gly Ser Leu Ser Gly Glu Lys Ser Leu Tyr Met Pro Ala
                245                 250                 255

Gly Asp Met Val Val Ala Asn Cys Asp Gly Ala Ile Ser Phe Glu Gly
            260                 265                 270

Asn Ser Ala Asn Phe Ala Asn Gly Gly Ala Ile Ala Ala Ser Gly Lys
        275                 280                 285

Val Leu Phe Val Ala Asn Asp Lys Lys Thr Ser Phe Ile Glu Asn Arg
    290                 295                 300

Ala Leu Ser Gly Gly Ala Ile Ala Ala Ser Ser Asp Ile Ala Phe Gln
305                 310                 315                 320

Asn Cys Ala Glu Leu Val Phe Lys Gly Asn Cys Ala Ile Gly Thr Glu
                325                 330                 335

Asp Lys Gly Ser Leu Gly Gly Gly Ala Ile Ser Ser Leu Gly Thr Val
            340                 345                 350

Leu Leu Gln Gly Asn His Gly Ile Thr Cys Asp Lys Asn Glu Ser Ala
        355                 360                 365

Ser Gln Gly Gly Ala Ile Phe Gly Lys Asn Cys Gln Ile Ser Asp Asn
    370                 375                 380

Glu Gly Pro Val Val Phe Arg Asp Ser Thr Ala Cys Leu Gly Gly Gly
385                 390                 395                 400

Ala Ile Ala Ala Gln Glu Ile Val Ser Ile Gln Asn Asn Gln Ala Gly
                405                 410                 415

Ile Ser Phe Glu Gly Gly Lys Ala Ser Phe Gly Gly Gly Ile Ala Cys
            420                 425                 430

Gly Ser Phe Ser Ser Ala Gly Gly Ala Ser Val Leu Gly Thr Ile Asp
        435                 440                 445

Ile Ser Lys Asn Leu Gly Ala Ile Ser Phe Ser Arg Thr Leu Cys Thr
    450                 455                 460

Thr Ser Asp Leu Gly Gln Met Glu Tyr Gln Gly Gly Gly Ala Leu Phe
465                 470                 475                 480
```

-continued

```
Gly Glu Asn Ile Ser Leu Ser Glu Asn Ala Gly Val Leu Thr Phe Lys
                485                 490                 495

Asp Asn Ile Val Lys Thr Phe Ala Ser Asn Gly Lys Ile Leu Gly Gly
            500                 505                 510

Gly Ala Ile Leu Ala Thr Gly Lys Val Glu Ile Thr Asn Asn Ser Glu
        515                 520                 525

Gly Ile Ser Phe Thr Gly Asn Ala Arg Ala Pro Gln Ala Leu Pro Thr
    530                 535                 540

Gln Glu Glu Phe Pro Leu Phe Ser Lys Lys Glu Gly Arg Pro Leu Ser
545                 550                 555                 560

Ser Gly Tyr Ser Gly Gly Gly Ala Ile Leu Gly Arg Glu Val Ala Ile
                565                 570                 575

Leu His Asn Ala Ala Val Val Phe Glu Gln Asn Arg Leu Gln Cys Ser
            580                 585                 590

Glu Glu Glu Ala Thr Leu Leu Gly Cys Cys Gly Gly Gly Ala Val His
        595                 600                 605

Gly Met Asp Ser Thr Ser Ile Val Gly Asn Ser Ser Val Arg Phe Gly
    610                 615                 620

Asn Asn Tyr Ala Met Gly Gln Gly Val Ser Gly Gly Ala Leu Leu Ser
625                 630                 635                 640

Lys Thr Val Gln Leu Ala Gly Asn Gly Ser Val Asp Phe Ser Arg Asn
                645                 650                 655

Ile Ala Ser Leu Gly Gly Gly Ala Leu Gln Ala Ser Glu Gly Asn Cys
            660                 665                 670

Glu Leu Val Asp Asn Gly Tyr Val Leu Phe Arg Asp Asn Arg Gly Arg
        675                 680                 685

Val Tyr Gly Gly Ala Ile Ser Cys Leu Arg Gly Asp Val Val Ile Ser
    690                 695                 700

Gly Asn Lys Gly Arg Val Glu Phe Lys Asp Asn Ile Ala Thr Arg Leu
705                 710                 715                 720

Tyr Val Glu Glu Thr Val Glu Lys Val Glu Glu Val Glu Pro Ala Pro
                725                 730                 735

Glu Gln Lys Asp Asn Asn Glu Leu Ser Phe Leu Gly Arg Ala Glu Gln
            740                 745                 750

Ser Phe Ile Thr Ala Ala Asn Gln Ala Leu Phe Ala Ser Glu Asp Gly
        755                 760                 765

Asp Leu Ser Pro Glu Ser Ser Ile Ser Ser Glu Glu Leu Ala Lys Arg
    770                 775                 780

Arg Glu Cys Ala Gly Gly Ala Ile Phe Ala Lys Arg Val Arg Ile Val
785                 790                 795                 800

Asp Asn Gln Glu Ala Val Val Phe Ser Asn Asn Phe Ser Asp Ile Tyr
                805                 810                 815

Gly Gly Ala Ile Phe Thr Gly Ser Leu Arg Glu Glu Asp Lys Leu Asp
            820                 825                 830

Gly Gln Ile Pro Glu Val Leu Ile Ser Gly Asn Ala Gly Asp Val Val
        835                 840                 845

Phe Ser Gly Asn Ser Ser Lys Arg Asp Glu His Leu Pro His Thr Gly
    850                 855                 860

Gly Gly Ala Ile Cys Thr Gln Asn Leu Thr Ile Ser Gln Asn Thr Gly
865                 870                 875                 880

Asn Val Leu Phe Tyr Asn Asn Val Ala Cys Ser Gly Gly Ala Val Arg
                885                 890                 895

Ile Glu Asp His Gly Asn Val Leu Leu Glu Ala Phe Gly Gly Asp Ile
```

```
            900                 905                 910

Val Phe Lys Gly Asn Ser Ser Phe Arg Ala Gln Gly Ser Asp Ala Ile
        915                 920                 925

Tyr Phe Ala Gly Lys Glu Ser His Ile Thr Ala Leu Asn Ala Thr Glu
    930                 935                 940

Gly His Ala Ile Val Phe His Asp Ala Leu Val Phe Glu Asn Leu Glu
945                 950                 955                 960

Glu Arg Lys Ser Ala Glu Val Leu Leu Ile Asn Ser Arg Glu Asn Pro
                965                 970                 975

Gly Tyr Thr Gly Ser Ile Arg Phe Leu Glu Ala Glu Ser Lys Val Pro
            980                 985                 990

Gln Cys Ile His Val Gln Gln Gly  Ser Leu Glu Leu Leu  Asn Gly Ala
        995                 1000                 1005

Thr Leu  Cys Ser Tyr Gly Phe  Lys Gln Asp Ala Gly  Ala Lys Leu
    1010                 1015                 1020

Val Leu  Ala Ala Gly Ala Lys  Leu Lys Ile Leu Asp  Ser Gly Thr
    1025                 1030                 1035

Pro Val  Gln Gln Gly His Ala  Ile Ser Lys Pro Glu  Ala Glu Ile
    1040                 1045                 1050

Glu Ser  Ser Ser Glu Pro Glu  Gly Ala His Ser Leu  Trp Ile Ala
    1055                 1060                 1065

Lys Asn  Ala Gln Thr Thr Val  Pro Met Val Asp Ile  His Thr Ile
    1070                 1075                 1080

Ser Val  Asp Leu Ala Ser Phe  Ser Ser Ser Gln Gln  Glu Gly Thr
    1085                 1090                 1095

Val Glu  Ala Pro Gln Val Ile  Val Pro Gly Gly Ser  Tyr Val Arg
    1100                 1105                 1110

Ser Gly  Glu Leu Asn Leu Glu  Leu Val Asn Thr Thr  Gly Thr Gly
    1115                 1120                 1125

Tyr Glu  Asn His Ala Leu Leu  Lys Asn Glu Ala Lys  Val Pro Leu
    1130                 1135                 1140

Met Ser  Phe Val Ala Ser Gly  Asp Glu Ala Ser Ala  Glu Ile Ser
    1145                 1150                 1155

Asn Leu  Ser Val Ser Asp Leu  Gln Ile His Val Val  Thr Pro Glu
    1160                 1165                 1170

Ile Glu  Glu Asp Thr Tyr Gly  His Met Gly Asp Trp  Ser Glu Ala
    1175                 1180                 1185

Lys Ile  Gln Asp Gly Thr Leu  Val Ile Ser Trp Asn  Pro Thr Gly
    1190                 1195                 1200

Tyr Arg  Leu Asp Pro Gln Lys  Ala Gly Ala Leu Val  Phe Asn Ala
    1205                 1210                 1215

Leu Trp  Glu Glu Gly Ala Val  Leu Ser Ala Leu Lys  Asn Ala Arg
    1220                 1225                 1230

Phe Ala  His Asn Leu Thr Ala  Gln Arg Met Glu Phe  Asp Tyr Ser
    1235                 1240                 1245

Thr Asn  Val Trp Gly Phe Ala  Phe Gly Gly Phe Arg  Thr Leu Ser
    1250                 1255                 1260

Ala Glu  Asn Leu Val Ala Ile  Asp Gly Tyr Lys Gly  Ala Tyr Gly
    1265                 1270                 1275

Gly Ala  Ser Ala Gly Val Asp  Ile Gln Leu Met Glu  Asp Phe Val
    1280                 1285                 1290

Leu Gly  Val Ser Gly Ala Ala  Phe Leu Gly Lys Met  Asp Ser Gln
    1295                 1300                 1305
```

```
Lys Phe Asp Ala Glu Val Ser Arg Lys Gly Val Val Gly Ser Val
    1310                1315                1320

Tyr Thr Gly Phe Leu Ala Gly Ser Trp Phe Phe Lys Gly Gln Tyr
    1325                1330                1335

Ser Leu Gly Glu Thr Gln Asn Asp Met Lys Thr Arg Tyr Gly Val
    1340                1345                1350

Leu Gly Glu Ser Ser Ala Ser Trp Thr Ser Arg Gly Val Leu Ala
    1355                1360                1365

Asp Ala Leu Val Glu Tyr Arg Ser Leu Val Gly Pro Val Arg Pro
    1370                1375                1380

Thr Phe Tyr Ala Leu His Phe Asn Pro Tyr Val Glu Val Ser Tyr
    1385                1390                1395

Ala Ser Met Lys Phe Pro Gly Phe Thr Glu Gln Gly Arg Glu Ala
    1400                1405                1410

Arg Ser Phe Glu Asp Ala Ser Leu Thr Asn Ile Thr Ile Pro Leu
    1415                1420                1425

Gly Met Lys Phe Glu Leu Ala Phe Ile Lys Gly Gln Phe Ser Glu
    1430                1435                1440

Val Asn Ser Leu Gly Ile Ser Tyr Ala Trp Glu Ala Tyr Arg Lys
    1445                1450                1455

Val Glu Gly Gly Ala Val Gln Leu Leu Glu Ala Gly Phe Asp Trp
    1460                1465                1470

Glu Gly Ala Pro Met Asp Leu Pro Arg Gln Glu Leu Arg Val Ala
    1475                1480                1485

Leu Glu Asn Asn Thr Glu Trp Ser Ser Tyr Phe Ser Thr Val Leu
    1490                1495                1500

Gly Leu Thr Ala Phe Cys Gly Gly Phe Thr Ser Thr Asp Ser Lys
    1505                1510                1515

Leu Gly Tyr Glu Ala Asn Thr Gly Leu Arg Leu Ile Phe
    1520                1525                1530
```

<210> SEQ ID NO 51
<211> LENGTH: 2895
<212> TYPE: DNA
<213> ORGANISM: Chlamydia trachomatis

<400> SEQUENCE: 51

```
atgaaaaaag cgtttttctt tttccttatc ggaaactccc tatcaggact agctagagag     60

gttccttcta gaatctttct tatgcccaac tcagttccag atcctacgaa agagtcgcta    120

tcaaataaaa ttagtttgac aggagacact cacaatctca ctaactgcta tctcgataac    180

ctacgctaca tactggctat tctacaaaaa actcccaatg aaggagctgc tgtcacaata    240

acagattacc taagcttttt tgatacacaa aaagaaggta tttattttgc aaaaaatctc    300

acccctgaaa gtggtggtgc gattggttat gcgagtccca attctcctac cgtggagatt    360

cgtgatacaa taggtcctgt aatctttgaa aataatactt gttgcagact atttacatgg    420

agaaatcctt atgctgctga taaaataaga gaaggcggag ccattcatgc tcaaaatctt    480

tacataaatc ataatcatga tgtggtcgga tttatgaaga acttttctta tgtccaagga    540

ggagccatta gtaccgctaa tacctttgtt gtgagcgaga atcagtcttg ttttctcttt    600

atggacaaca tctgtattca aactaataca gcaggaaaag gtggcgctat ctatgctgga    660

acgagcaatt cttttgagag taataactgc gatctcttct tcatcaataa cgcctgttgt    720

gcaggaggag cgatcttctc ccctatctgt tctctaacag gaaatcgtgg taacatcgtt    780

ttctataaca atcgctgctt taaaaatgta gaaacagctt cttcagaagc ttctgatgga    840
```

ggagcaatta aagtaactac tcgcctagat gttacaggca atcgtggtag gatctttttt 900
agtgacaata tcacaaaaaa ttatggcgga gctatttacg ctcctgtagt taccctagtg 960
gataatggcc ctacctactt tataaacaat atcgccaata ataagggggg cgctatctat 1020
atagacggaa ccagtaactc caaaatttct gccgaccgcc atgctattat ttttaatgaa 1080
aatattgtga ctaatgtaac taatgcaaat ggtaccagta cgtcagctaa tcctcctaga 1140
agaaatgcaa taacagtagc aagctcctct ggtgaaattc tattaggagc agggagtagc 1200
caaaatttaa ttttttatga tcctattgaa gttagcaatg caggggtctc tgtgtccttc 1260
aataaggaag ctgatcaaac aggctctgta gtattttcag gagctactgt taattctgca 1320
gattttcatc aacgcaattt acaaacaaaa acacctgcac cccttactct cagtaatggt 1380
tttctatgta tcgaagatca tgctcagctt acagtgaatc gattcacaca aactgggggt 1440
gttgtttctc ttgggaatgg agcagttctg agttgctata aaaatggtac aggagattct 1500
gctagcaatg cctctataac actgaagcat attggattga atctttcttc cattctgaaa 1560
agtggtgctg agattccttt attgtgggta gagcctacaa ataacagcaa taactataca 1620
gcagatactg cagctacctt ttcattaagt gatgtaaaac tctcactcat tgatgactac 1680
gggaactctc cttatgaatc cacagatctg acccatgctc tgtcatcaca gcctatgcta 1740
tctatttctg aagctagcga taaccagcta caatcagaaa atatagattt ttcgggacta 1800
aatgtccctc attatggatg gcaaggactt tggacttggg gctgggcaaa aactcaagat 1860
ccagaaccag catcttcagc aacaatcact gatccacaaa aagccaatag atttcataga 1920
accttactac taacatggct tcctgccggg tatgttccta gcccaaaaca cagaagtccc 1980
ctcatagcta acaccttatg gggaatatg ctgcttgcaa cagaaagctt aaaaaatagt 2040
gcagagctga cacctagtgg tcatcccttc tggggaatta caggaggagg actaggcatg 2100
atggtttacc aagatcctcg agaaaatcat cctggattcc atatgcgctc ttccggatac 2160
tctgcgggga tgatagcagg gcagacacac accttctcat tgaaattcag tcagacctac 2220
accaaactca atgagcgtta cgcaaaaaac aacgtatctt ctaaaaatta ctcatgccaa 2280
ggagaaatgc tcttctcatt gcaagaaggt ttcttgctga ctaaattagt tgggctttac 2340
agctatggag accataactg tcaccatttc tatactcaag gagaaaatct aacatctcaa 2400
gggacgttcc gcagtcaaac gatgggaggt gctgtctttt ttgatctccc tatgaaaccc 2460
tttggatcaa cgcatatact gacagctccc tttttaggtg ctcttggtat ttattctagc 2520
ctgtctcact ttactgaggt gggagcctat ccgcgaagct tttctacaaa gactcctttg 2580
atcaatgtcc tagtccctat tggagttaaa ggtagcttta tgaatgctac ccacagacct 2640
caagcctgga ctgtagaatt ggcataccaa cccgttctgt atagacaaga accagggatc 2700
gcagcccagc tcctagccag taagggtatt tggttcggta gtggaagccc ctcatcgcgt 2760
catgccatgt cctataaaat ctcacagcaa acacaacctt tgagttggtt aactctccat 2820
ttccagtatc atggattcta ctcctcttca accttctgta attatctcaa tggggaaatt 2880
gctctgcgat tctag 2895

<210> SEQ ID NO 52
<211> LENGTH: 964
<212> TYPE: PRT
<213> ORGANISM: Chlamydia trachomatis

<400> SEQUENCE: 52

Met Lys Lys Ala Phe Phe Phe Phe Leu Ile Gly Asn Ser Leu Ser Gly

-continued

```
1               5                   10                  15

Leu Ala Arg Glu Val Pro Ser Arg Ile Phe Leu Met Pro Asn Ser Val
            20                  25                  30

Pro Asp Pro Thr Lys Glu Ser Leu Ser Asn Lys Ile Ser Leu Thr Gly
        35                  40                  45

Asp Thr His Asn Leu Thr Asn Cys Tyr Leu Asp Asn Leu Arg Tyr Ile
    50                  55                  60

Leu Ala Ile Leu Gln Lys Thr Pro Asn Glu Gly Ala Ala Val Thr Ile
65                  70                  75                  80

Thr Asp Tyr Leu Ser Phe Phe Asp Thr Gln Lys Glu Gly Ile Tyr Phe
                85                  90                  95

Ala Lys Asn Leu Thr Pro Glu Ser Gly Gly Ala Ile Gly Tyr Ala Ser
            100                 105                 110

Pro Asn Ser Pro Thr Val Glu Ile Arg Asp Thr Ile Gly Pro Val Ile
        115                 120                 125

Phe Glu Asn Asn Thr Cys Cys Arg Leu Phe Thr Trp Arg Asn Pro Tyr
    130                 135                 140

Ala Ala Asp Lys Ile Arg Glu Gly Gly Ala Ile His Ala Gln Asn Leu
145                 150                 155                 160

Tyr Ile Asn His Asn His Asp Val Val Gly Phe Met Lys Asn Phe Ser
                165                 170                 175

Tyr Val Gln Gly Gly Ala Ile Ser Thr Ala Asn Thr Phe Val Val Ser
            180                 185                 190

Glu Asn Gln Ser Cys Phe Leu Phe Met Asp Asn Ile Cys Ile Gln Thr
        195                 200                 205

Asn Thr Ala Gly Lys Gly Gly Ala Ile Tyr Ala Gly Thr Ser Asn Ser
    210                 215                 220

Phe Glu Ser Asn Asn Cys Asp Leu Phe Phe Ile Asn Asn Ala Cys Cys
225                 230                 235                 240

Ala Gly Gly Ala Ile Phe Ser Pro Ile Cys Ser Leu Thr Gly Asn Arg
                245                 250                 255

Gly Asn Ile Val Phe Tyr Asn Asn Arg Cys Phe Lys Asn Val Glu Thr
            260                 265                 270

Ala Ser Ser Glu Ala Ser Asp Gly Gly Ala Ile Lys Val Thr Thr Arg
        275                 280                 285

Leu Asp Val Thr Gly Asn Arg Gly Arg Ile Phe Phe Ser Asp Asn Ile
    290                 295                 300

Thr Lys Asn Tyr Gly Gly Ala Ile Tyr Ala Pro Val Val Thr Leu Val
305                 310                 315                 320

Asp Asn Gly Pro Thr Tyr Phe Ile Asn Asn Ile Ala Asn Asn Lys Gly
                325                 330                 335

Gly Ala Ile Tyr Ile Asp Gly Thr Ser Asn Ser Lys Ile Ser Ala Asp
            340                 345                 350

Arg His Ala Ile Ile Phe Asn Glu Asn Ile Val Thr Asn Val Thr Asn
        355                 360                 365

Ala Asn Gly Thr Ser Thr Ser Ala Asn Pro Pro Arg Arg Asn Ala Ile
    370                 375                 380

Thr Val Ala Ser Ser Ser Gly Glu Ile Leu Leu Gly Ala Gly Ser Ser
385                 390                 395                 400

Gln Asn Leu Ile Phe Tyr Asp Pro Ile Glu Val Ser Asn Ala Gly Val
                405                 410                 415

Ser Val Ser Phe Asn Lys Glu Ala Asp Gln Thr Gly Ser Val Val Phe
            420                 425                 430
```

```
Ser Gly Ala Thr Val Asn Ser Ala Asp Phe His Gln Arg Asn Leu Gln
        435                 440                 445

Thr Lys Thr Pro Ala Pro Leu Thr Leu Ser Asn Gly Phe Leu Cys Ile
    450                 455                 460

Glu Asp His Ala Gln Leu Thr Val Asn Arg Phe Thr Gln Thr Gly Gly
465                 470                 475                 480

Val Val Ser Leu Gly Asn Gly Ala Val Leu Ser Cys Tyr Lys Asn Gly
                485                 490                 495

Thr Gly Asp Ser Ala Ser Asn Ala Ser Ile Thr Leu Lys His Ile Gly
            500                 505                 510

Leu Asn Leu Ser Ser Ile Leu Lys Ser Gly Ala Glu Ile Pro Leu Leu
        515                 520                 525

Trp Val Glu Pro Thr Asn Asn Ser Asn Asn Tyr Thr Ala Asp Thr Ala
    530                 535                 540

Ala Thr Phe Ser Leu Ser Asp Val Lys Leu Ser Leu Ile Asp Asp Tyr
545                 550                 555                 560

Gly Asn Ser Pro Tyr Glu Ser Thr Asp Leu Thr His Ala Leu Ser Ser
                565                 570                 575

Gln Pro Met Leu Ser Ile Ser Glu Ala Ser Asp Asn Gln Leu Gln Ser
            580                 585                 590

Glu Asn Ile Asp Phe Ser Gly Leu Asn Val Pro His Tyr Gly Trp Gln
        595                 600                 605

Gly Leu Trp Thr Trp Gly Trp Ala Lys Thr Gln Asp Pro Glu Pro Ala
    610                 615                 620

Ser Ser Ala Thr Ile Thr Asp Pro Gln Lys Ala Asn Arg Phe His Arg
625                 630                 635                 640

Thr Leu Leu Leu Thr Trp Leu Pro Ala Gly Tyr Val Pro Ser Pro Lys
                645                 650                 655

His Arg Ser Pro Leu Ile Ala Asn Thr Leu Trp Gly Asn Met Leu Leu
            660                 665                 670

Ala Thr Glu Ser Leu Lys Asn Ser Ala Glu Leu Thr Pro Ser Gly His
        675                 680                 685

Pro Phe Trp Gly Ile Thr Gly Gly Gly Leu Gly Met Met Val Tyr Gln
    690                 695                 700

Asp Pro Arg Glu Asn His Pro Gly Phe His Met Arg Ser Ser Gly Tyr
705                 710                 715                 720

Ser Ala Gly Met Ile Ala Gly Gln Thr His Thr Phe Ser Leu Lys Phe
                725                 730                 735

Ser Gln Thr Tyr Thr Lys Leu Asn Glu Arg Tyr Ala Lys Asn Asn Val
            740                 745                 750

Ser Ser Lys Asn Tyr Ser Cys Gln Gly Glu Met Leu Phe Ser Leu Gln
        755                 760                 765

Glu Gly Phe Leu Leu Thr Lys Leu Val Gly Leu Tyr Ser Tyr Gly Asp
    770                 775                 780

His Asn Cys His His Phe Tyr Thr Gln Gly Glu Asn Leu Thr Ser Gln
785                 790                 795                 800

Gly Thr Phe Arg Ser Gln Thr Met Gly Gly Ala Val Phe Phe Asp Leu
                805                 810                 815

Pro Met Lys Pro Phe Gly Ser Thr His Ile Leu Thr Ala Pro Phe Leu
            820                 825                 830

Gly Ala Leu Gly Ile Tyr Ser Ser Leu Ser His Phe Thr Glu Val Gly
        835                 840                 845

Ala Tyr Pro Arg Ser Phe Ser Thr Lys Thr Pro Leu Ile Asn Val Leu
    850                 855                 860
```

Val Pro Ile Gly Val Lys Gly Ser Phe Met Asn Ala Thr His Arg Pro
865 870 875 880

Gln Ala Trp Thr Val Glu Leu Ala Tyr Gln Pro Val Leu Tyr Arg Gln
885 890 895

Glu Pro Gly Ile Ala Ala Gln Leu Leu Ala Ser Lys Gly Ile Trp Phe
900 905 910

Gly Ser Gly Ser Pro Ser Ser Arg His Ala Met Ser Tyr Lys Ile Ser
915 920 925

Gln Gln Thr Gln Pro Leu Ser Trp Leu Thr Leu His Phe Gln Tyr His
930 935 940

Gly Phe Tyr Ser Ser Ser Thr Phe Cys Asn Tyr Leu Asn Gly Glu Ile
945 950 955 960

Ala Leu Arg Phe

<210> SEQ ID NO 53
<211> LENGTH: 1920
<212> TYPE: DNA
<213> ORGANISM: Chlamydia trachomatis

<400> SEQUENCE: 53
gtgaacgttc gtacgtactc tgttcagagg ggggggggtaa aaacgatttc tgctagtgca 60
gttcctccta cagcagctgt tttatcgaga aaaaagcgtg ctatagaaga gaagaaggag 120
gaagcttctt ctggaaagat agaaaatctt gatgctagca aatacgatct tactcccaag 180
aacatagaag aaaaactagg aattactcct gaacagaaat ctactgttaa agacctatta 240
aataaactga aaaaggtcat tagtgcttac aactctatgc cagataaaaa ttcggaagcg 300
ggacagaatt ccttgattca acaaggaaaa tacgtcgatg ccattcagaa gaagcttcca 360
gcatcatcgc aggctcagcc taaacaggca aaagctaagg aacagaaagc cgaagaaaaa 420
cctaagacga ctccgattga aggtgttctt gaaaccatca aaacagaatt taaaggccat 480
cgtgtacctg ttgagaaaat catccatgga atatggatcg caggagcgcc tccggatggt 540
atcgaagatt atatgcgagt ctttttagat acttatgaag gttttgactt ctacttctgg 600
gtagatgaga atgcttatgc agcagctaaa ttttctagca ttttgaagaa ggtcgctttc 660
gatgcggcta ttcaagatct acgatctgcc acagatgagt ctacgaaggc ctttgttaaa 720
gactacgatg aattaaaaca gaaatatgaa aagaaagttg cggagacgac ttctcaagca 780
gaaaaagacc aatatctcaa agatctaaag gatcttttag agaaatttac aaaaatcagt 840
gatgagattc gtggaaaatt tgatcggctg tttcttaaga atgtgattgt tgctcagaac 900
ggattcttta atttctgctt gctgaaaggc ctcggcaata tcaatgacga aacgcgtgca 960
gagtatttag agaaagaact caaacttcct actgaggaga tcgaacagta taaaaagctt 1020
aaagagacga acaaagagaa gatagccgct attgtaaaac aactaaacga gaaacttgga 1080
tcggatcggg taaaaatcaa agacattaaa gagctgcaat ctatgaagca agctcgaaat 1140
gtctacaatt atgaacagga aatgtttctg cgctggaact atgcagccgc aacagatcag 1200
attcgtatgt atatgttgga ggaacttgga ggtctttata ctgatctgga tatgatgcct 1260
tcatactctc aggaagtatt ggagcttatc aaaaagcaca gtgatggaaa ccgaatgttt 1320
gaggatatga gctctagacg ggcgatttct gatgcggttt taaagatggc tgtaggtaag 1380
gcgacaacag tttccatgga agaggtagca aaggatatcg atgtttctcg cttaacagaa 1440
gaggataaga caaaattaaa tgctctattt aaggatctag agccatttgc aaaaccggat 1500
tctaaaggag ctgaagcaga agggggtgaa ggagcaaaag gtatgaaaaa gagcttttttc 1560

-continued

```
cagcccatag atctgaatat tgtcagaaat accatgccta tcttgagacg ctatcatcac   1620

tatcctgagt taggatggtt tattcgagga ttgaacggat tgatggtctc tcataaggga   1680

agcactgcgg tttctgctgt cattgtaggg caacaggctg cctaccagga actagcagca   1740

cttagacaag atgtcctttc aggggagttt ttccattctt tagaaaattt gacacataga   1800

aaccataagg agcgtattgg aaatcatctc gtcgctaatt atttggctaa aagtctcttt   1860

tttgattact gccaagattc agtgatgccg gaggctgtaa gtaccttagg tattagatga   1920
```

<210> SEQ ID NO 54
<211> LENGTH: 639
<212> TYPE: PRT
<213> ORGANISM: Chlamydia trachomatis

<400> SEQUENCE: 54

```
Met Asn Val Arg Thr Tyr Ser Val Gln Arg Gly Gly Val Lys Thr Ile
1               5                   10                  15

Ser Ala Ser Ala Val Pro Pro Thr Ala Ala Val Leu Ser Arg Lys Lys
            20                  25                  30

Arg Ala Ile Glu Glu Lys Lys Glu Glu Ala Ser Ser Gly Lys Ile Glu
        35                  40                  45

Asn Leu Asp Ala Ser Lys Tyr Asp Leu Thr Pro Lys Asn Ile Glu Glu
    50                  55                  60

Lys Leu Gly Ile Thr Pro Glu Gln Lys Ser Thr Val Lys Asp Leu Leu
65                  70                  75                  80

Asn Lys Leu Lys Lys Val Ile Ser Ala Tyr Asn Ser Met Pro Asp Lys
                85                  90                  95

Asn Ser Glu Ala Gly Gln Asn Ser Leu Ile Gln Gln Gly Lys Tyr Val
            100                 105                 110

Asp Ala Ile Gln Lys Lys Leu Pro Ala Ser Ser Gln Ala Gln Pro Lys
        115                 120                 125

Gln Ala Lys Ala Lys Glu Gln Lys Ala Glu Glu Lys Pro Lys Thr Thr
    130                 135                 140

Pro Ile Glu Gly Val Leu Glu Thr Ile Lys Thr Glu Phe Lys Gly His
145                 150                 155                 160

Arg Val Pro Val Glu Lys Ile Ile His Gly Ile Trp Ile Ala Gly Ala
                165                 170                 175

Pro Pro Asp Gly Ile Glu Asp Tyr Met Arg Val Phe Leu Asp Thr Tyr
            180                 185                 190

Glu Gly Phe Asp Phe Tyr Phe Trp Val Asp Glu Asn Ala Tyr Ala Ala
        195                 200                 205

Ala Lys Phe Ser Ser Ile Leu Lys Lys Val Ala Phe Asp Ala Ala Ile
    210                 215                 220

Gln Asp Leu Arg Ser Ala Thr Asp Glu Ser Thr Lys Ala Phe Val Lys
225                 230                 235                 240

Asp Tyr Asp Glu Leu Lys Gln Lys Tyr Glu Lys Lys Val Ala Glu Thr
                245                 250                 255

Thr Ser Gln Ala Glu Lys Asp Gln Tyr Leu Lys Asp Leu Lys Asp Leu
            260                 265                 270

Leu Glu Lys Phe Thr Lys Ile Ser Asp Glu Ile Arg Gly Lys Phe Asp
        275                 280                 285

Arg Leu Phe Leu Lys Asn Val Ile Val Ala Gln Asn Gly Phe Phe Asn
    290                 295                 300

Phe Cys Leu Leu Lys Gly Leu Gly Asn Ile Asn Asp Glu Thr Arg Ala
305                 310                 315                 320
```

-continued

```
Glu Tyr Leu Glu Lys Glu Leu Lys Leu Pro Thr Glu Glu Ile Glu Gln
                325                 330                 335

Tyr Lys Lys Leu Lys Glu Thr Asn Lys Glu Lys Ile Ala Ala Ile Val
            340                 345                 350

Lys Gln Leu Asn Glu Lys Leu Gly Ser Asp Arg Val Lys Ile Lys Asp
        355                 360                 365

Ile Lys Glu Leu Gln Ser Met Lys Gln Ala Arg Asn Val Tyr Asn Tyr
    370                 375                 380

Glu Gln Glu Met Phe Leu Arg Trp Asn Tyr Ala Ala Ala Thr Asp Gln
385                 390                 395                 400

Ile Arg Met Tyr Met Leu Glu Glu Leu Gly Gly Leu Tyr Thr Asp Leu
                405                 410                 415

Asp Met Met Pro Ser Tyr Ser Gln Glu Val Leu Glu Leu Ile Lys Lys
            420                 425                 430

His Ser Asp Gly Asn Arg Met Phe Glu Asp Met Ser Ser Arg Arg Ala
        435                 440                 445

Ile Ser Asp Ala Val Leu Lys Met Ala Val Gly Lys Ala Thr Thr Val
    450                 455                 460

Ser Met Glu Glu Val Ala Lys Asp Ile Asp Val Ser Arg Leu Thr Glu
465                 470                 475                 480

Glu Asp Lys Thr Lys Leu Asn Ala Leu Phe Lys Asp Leu Glu Pro Phe
                485                 490                 495

Ala Lys Pro Asp Ser Lys Gly Ala Glu Ala Glu Gly Gly Glu Gly Ala
            500                 505                 510

Lys Gly Met Lys Lys Ser Phe Phe Gln Pro Ile Asp Leu Asn Ile Val
        515                 520                 525

Arg Asn Thr Met Pro Ile Leu Arg Arg Tyr His His Tyr Pro Glu Leu
    530                 535                 540

Gly Trp Phe Ile Arg Gly Leu Asn Gly Leu Met Val Ser His Lys Gly
545                 550                 555                 560

Ser Thr Ala Val Ser Ala Val Ile Val Gly Gln Gln Ala Ala Tyr Gln
                565                 570                 575

Glu Leu Ala Ala Leu Arg Gln Asp Val Leu Ser Gly Glu Phe Phe His
            580                 585                 590

Ser Leu Glu Asn Leu Thr His Arg Asn His Lys Glu Arg Ile Gly Asn
        595                 600                 605

His Leu Val Ala Asn Tyr Leu Ala Lys Ser Leu Phe Phe Asp Tyr Cys
    610                 615                 620

Gln Asp Ser Val Met Pro Glu Ala Val Ser Thr Leu Gly Ile Arg
625                 630                 635
```

<210> SEQ ID NO 55
<211> LENGTH: 1590
<212> TYPE: DNA
<213> ORGANISM: Chlamydia trachomatis

<400> SEQUENCE: 55

```
atgcatcaca ggaagttttt agcagtttcc attgctttcg taagtttagc ttttgggcta      60

acatcttgtt atcataaaaa agaagaacca aaagatgttt tgcggattgc gatctgtcat     120

gatccaatgt ctttagatcc gcgtcaggtt tttttaagca aagatgtttc tattgtaaaa     180

gctctctatg aagggttagt ccgggaaaaa gaagctgcgt tccagctagc tttggcagaa     240

agatatcatc aatctgatga tggttgtgtt tatacttttt ttctaaaaaa tacattctgg     300

agcaacggag atgttgtaac agcatatgat tttgaagagt ctattaaaca aatttatttc     360
```

```
cgagaaattg ataacccttc gttacgctct cttgcattaa ttaaaaattc tcatgctgtt    420

ttaacaggag ctctccctgt tgaagattta ggtgttagag ctttgaatgc gaaaactcta    480

gaaattgttt tagaaaaccc gtttccttat tttctagaga tattggcgca cccggttttt    540

tatccggtgc acacctcttt acgagaatat tacaaagata agcgtaacaa acgcgttttc    600

ccgataattt ctaatggtcc ttttgcgatt caatgttatg agccgcaaag atatttacta    660

atcaacaaaa accctctgta tcatgccaag cacgatgttc tgttaaattc ggtatgtttg    720

cagatagttc ctgatatcca tacagctatg cagttattcc aaaaaaatca tatcgattta    780

gttgggttac cctggagctc ctccttttct ttagaagaac aaagaaatct ccctagagaa    840

aaattatttg attatcctgt attgagttgc tctgttttat tctgtaacat tcatcaaaca    900

cctttaaata atccctcgct gagaacagcc ctctctttag caatcaatcg agaaacttta    960

ttaaaactag caggtaaagg ctgtagcgct acgagctttg ttcacccaca attatctcag   1020

atacctgcta ctactttgtc tcaagatgag cggattgctt tagcaaaagg ctacttgacc   1080

gaagctttaa agactttatc tcaagaagat ttagaaaaaa ttacattaat ttatcctata   1140

gaatctgttt gcttacgagc cgttgttcaa gaaattcgcc aacaattatt tgatgtactg   1200

ggatttaaaa tttctacatt aggattagaa tatcattgtt ttttagacaa acgttccaga   1260

ggagaattct ccttagcaac tggtaattgg attgcagact atcatcaagc tagtgctttc   1320

ctgtctgtcc taggtaatgg gacaagatat aaagactttc aattgattaa ctggcagaac   1380

caaaagtaca caaatatagt tgctcaactt ctgattcaag aatcaagcga cctacagctt   1440

atggcagagc agttgttgct taaagaaagt cctcttattc ctctatacca cctcgattat   1500

gtgtatgcga aacagcctcg ggtgtctgat ctccaaacct cttctcgtgg agaaattgat   1560

ttaaaaagag tttcattagc tgaaggatag                                    1590
```

<210> SEQ ID NO 56
<211> LENGTH: 529
<212> TYPE: PRT
<213> ORGANISM: Chlamydia trachomatis

<400> SEQUENCE: 56

```
Met His His Arg Lys Phe Leu Ala Val Ser Ile Ala Phe Val Ser Leu
1               5                   10                  15

Ala Phe Gly Leu Thr Ser Cys Tyr His Lys Lys Glu Glu Pro Lys Asp
            20                  25                  30

Val Leu Arg Ile Ala Ile Cys His Asp Pro Met Ser Leu Asp Pro Arg
        35                  40                  45

Gln Val Phe Leu Ser Lys Asp Val Ser Ile Val Lys Ala Leu Tyr Glu
    50                  55                  60

Gly Leu Val Arg Glu Lys Glu Ala Ala Phe Gln Leu Ala Leu Ala Glu
65                  70                  75                  80

Arg Tyr His Gln Ser Asp Asp Gly Cys Val Tyr Thr Phe Phe Leu Lys
                85                  90                  95

Asn Thr Phe Trp Ser Asn Gly Asp Val Val Thr Ala Tyr Asp Phe Glu
            100                 105                 110

Glu Ser Ile Lys Gln Ile Tyr Phe Arg Glu Ile Asp Asn Pro Ser Leu
        115                 120                 125

Arg Ser Leu Ala Leu Ile Lys Asn Ser His Ala Val Leu Thr Gly Ala
    130                 135                 140

Leu Pro Val Glu Asp Leu Gly Val Arg Ala Leu Asn Ala Lys Thr Leu
145                 150                 155                 160
```

```
Glu Ile Val Leu Glu Asn Pro Phe Pro Tyr Phe Leu Glu Ile Leu Ala
                165                 170                 175

His Pro Val Phe Tyr Pro Val His Thr Ser Leu Arg Glu Tyr Tyr Lys
            180                 185                 190

Asp Lys Arg Asn Lys Arg Val Phe Pro Ile Ile Ser Asn Gly Pro Phe
        195                 200                 205

Ala Ile Gln Cys Tyr Glu Pro Gln Arg Tyr Leu Leu Ile Asn Lys Asn
    210                 215                 220

Pro Leu Tyr His Ala Lys His Asp Val Leu Leu Asn Ser Val Cys Leu
225                 230                 235                 240

Gln Ile Val Pro Asp Ile His Thr Ala Met Gln Leu Phe Gln Lys Asn
                245                 250                 255

His Ile Asp Leu Val Gly Leu Pro Trp Ser Ser Ser Phe Ser Leu Glu
            260                 265                 270

Glu Gln Arg Asn Leu Pro Arg Glu Lys Leu Phe Asp Tyr Pro Val Leu
        275                 280                 285

Ser Cys Ser Val Leu Phe Cys Asn Ile His Gln Thr Pro Leu Asn Asn
    290                 295                 300

Pro Ser Leu Arg Thr Ala Leu Ser Leu Ala Ile Asn Arg Glu Thr Leu
305                 310                 315                 320

Leu Lys Leu Ala Gly Lys Gly Cys Ser Ala Thr Ser Phe Val His Pro
                325                 330                 335

Gln Leu Ser Gln Ile Pro Ala Thr Thr Leu Ser Gln Asp Glu Arg Ile
            340                 345                 350

Ala Leu Ala Lys Gly Tyr Leu Thr Glu Ala Leu Lys Thr Leu Ser Gln
        355                 360                 365

Glu Asp Leu Glu Lys Ile Thr Leu Ile Tyr Pro Ile Glu Ser Val Cys
    370                 375                 380

Leu Arg Ala Val Val Gln Glu Ile Arg Gln Gln Leu Phe Asp Val Leu
385                 390                 395                 400

Gly Phe Lys Ile Ser Thr Leu Gly Leu Glu Tyr His Cys Phe Leu Asp
                405                 410                 415

Lys Arg Ser Arg Gly Glu Phe Ser Leu Ala Thr Gly Asn Trp Ile Ala
            420                 425                 430

Asp Tyr His Gln Ala Ser Ala Phe Leu Ser Val Leu Gly Asn Gly Thr
        435                 440                 445

Arg Tyr Lys Asp Phe Gln Leu Ile Asn Trp Gln Asn Gln Lys Tyr Thr
    450                 455                 460

Asn Ile Val Ala Gln Leu Leu Ile Gln Glu Ser Ser Asp Leu Gln Leu
465                 470                 475                 480

Met Ala Glu Gln Leu Leu Leu Lys Glu Ser Pro Leu Ile Pro Leu Tyr
                485                 490                 495

His Leu Asp Tyr Val Tyr Ala Lys Gln Pro Arg Val Ser Asp Leu Gln
            500                 505                 510

Thr Ser Ser Arg Gly Glu Ile Asp Leu Lys Arg Val Ser Leu Ala Glu
        515                 520                 525

Gly
```

<210> SEQ ID NO 57
<211> LENGTH: 2091
<212> TYPE: DNA
<213> ORGANISM: Chlamydia muridarum

<400> SEQUENCE: 57

-continued

```
atgaggattc caatgacact ctttcacact catcacgatg ccgtctctcc ggacggctac     60

ttatgttctt cccttcagtt agttggctct ggcacatatg aaggagaaat cgaaatccaa    120

aatattcctt cttatttcct tggattccga ttacccaccc attgcgttca tcttaatttg    180

aagagttctc tagcccagtt aggagtagat gcatctcttc ttcactgcga actaagcaaa    240

aatcaacaac gtgcacatat gcacgtgcag ttcaccggct atggccctat cgctgagtcc    300

atgctatctc ttctcaaacc cggagatcga gtagccaaac tgtttgctgc agatgatcgt    360

agactagtcc gctcccctga ttatcttgaa agcatgctaa aaaatactga taagacagga    420

catcctctgc tccgatttgg aaaaaaactc gagcatctta tctcttttga tgtggtggac    480

gatcgcctcg ttgtatcact ccccaccttg ccaggcatag tcaattatga cccagacatc    540

tatggacttc ttcccttaat tcaaaaatca ctaagcaatc ctaaattgag tattcgccac    600

ttcttgtctc tctatcagaa gatcgtagaa ggaccacaca tcccttatga aggaaacatt    660

ttgttaatca aaacagagcc tcttcatatc cgcacagtat ttgctcgcgt ggtcgatcaa    720

atgctccctc aaggtctatt tcacacttct gccaacattt tagaacccac aacgcgagag    780

tctggagata tttttgaatt ttttggaaat ccctccactc ttgtagaaag aatccctcta    840

gaattcttca ctatcgaacc ctacaaagaa cactcttact tctgtaatcg agatctattg    900

caaactacct tgcaatcgga aagtgaaatc aaaaaaatat tcgatacagc tcctcaagag    960

cctgtaaaag ccgccactta tttatcaaaa ggaagtgaaa tttcttctct tgatgcagat   1020

tcttggctta cgggatccgc agctgcatac caatgtagcg aaaaacaggc agctaaagac   1080

gaatacatcc acgctcaacc ctgttatcca tttttggaag caatggaaac gggactcatc   1140

aatagcgaag gagctttact cactcggttt ttcccctctt ccagcttaaa agggatgttg   1200

atctcctatc atgtacgcca ctatcttaag caaatttact ttcaagttcc ttcttataca   1260

tatggagact acttctctca taatgaccga ggattactgt tagatctata tcaggcgaac   1320

attgatgtgt tctgggctga tgaagagagc ggccgtgtat tgcaatatac aaaacggcgc   1380

gacaaaaata gtggaatgtt cgtcgttaaa aatcgagtag aagagttcca atcagcatat   1440

ttcgtagcga tttatggatc acgtctcctg gaaaataatt tctcggccca actaaacacg   1500

cttcttgcag ggttacaaaa agctgcacac actctaggca ttccaggctt ctcaaaaccc   1560

actcctcttg ccgtaatcac aggaggaggg actggcgtta tggctacagg aaatcgtgtt   1620

gcaaaagagt tgggaattct ttcttgcggg accgttctcg atttggaagc ttcacctgca   1680

caaatagatc agcctgcaaa cgaattttta gatgccaaaa tgacataccg tctaccgcaa   1740

cttatagaaa gacaagaaca tttttattca gaccttgcca ttttagttgt tggtggtgtt   1800

ggaacagatt tcgaacttta cctagaactc gtctacttga aaacaggcgc caaacctcct   1860

actccaattt tccttattgg gcctgttgaa tactggaaag agaaagttgc tcatgcctat   1920

gagattaatc ttaaagcagg aactattcgt ggttctgagt ggatcagcaa ctgcttattc   1980

tgcattacat ctcctgaagc aggaattgct gtattcgaac agttcctcgc tggagaactt   2040

cccataggat atgattatcc tccagctcca gacggattag ttatcgtcta a            2091
```

<210> SEQ ID NO 58
<211> LENGTH: 696
<212> TYPE: PRT
<213> ORGANISM: Chlamydia muridarum

<400> SEQUENCE: 58

```
Met Arg Ile Pro Met Thr Leu Phe His Thr His His Asp Ala Val Ser
1               5                   10                  15
```

```
Pro Asp Gly Tyr Leu Cys Ser Ser Leu Gln Leu Val Gly Ser Gly Thr
            20                  25                  30

Tyr Glu Gly Glu Ile Glu Ile Gln Asn Ile Pro Ser Tyr Phe Leu Gly
        35                  40                  45

Phe Arg Leu Pro Thr His Cys Val His Leu Asn Leu Lys Ser Ser Leu
    50                  55                  60

Ala Gln Leu Gly Val Asp Ala Ser Leu Leu His Cys Glu Leu Ser Lys
65                  70                  75                  80

Asn Gln Gln Arg Ala His Met His Val Gln Phe Thr Gly Tyr Gly Pro
                85                  90                  95

Ile Ala Glu Ser Met Leu Ser Leu Leu Lys Pro Gly Asp Arg Val Ala
            100                 105                 110

Lys Leu Phe Ala Ala Asp Asp Arg Arg Leu Val Arg Ser Pro Asp Tyr
        115                 120                 125

Leu Glu Ser Met Leu Lys Asn Thr Asp Lys Thr Gly His Pro Leu Leu
    130                 135                 140

Arg Phe Gly Lys Lys Leu Glu His Leu Ile Ser Phe Asp Val Val Asp
145                 150                 155                 160

Asp Arg Leu Val Val Ser Leu Pro Thr Leu Pro Gly Ile Val Asn Tyr
                165                 170                 175

Asp Pro Asp Ile Tyr Gly Leu Leu Pro Leu Ile Gln Lys Ser Leu Ser
            180                 185                 190

Asn Pro Lys Leu Ser Ile Arg His Phe Leu Ser Leu Tyr Gln Lys Ile
        195                 200                 205

Val Glu Gly Pro His Ile Pro Tyr Glu Gly Asn Ile Leu Leu Ile Lys
    210                 215                 220

Thr Glu Pro Leu His Ile Arg Thr Val Phe Ala Arg Val Val Asp Gln
225                 230                 235                 240

Met Leu Pro Gln Gly Leu Phe His Thr Ser Ala Asn Ile Leu Glu Pro
                245                 250                 255

Thr Thr Arg Glu Ser Gly Asp Ile Phe Glu Phe Phe Gly Asn Pro Ser
            260                 265                 270

Thr Leu Val Glu Arg Ile Pro Leu Glu Phe Phe Thr Ile Glu Pro Tyr
        275                 280                 285

Lys Glu His Ser Tyr Phe Cys Asn Arg Asp Leu Leu Gln Thr Thr Leu
    290                 295                 300

Gln Ser Glu Ser Glu Ile Lys Lys Ile Phe Asp Thr Ala Pro Gln Glu
305                 310                 315                 320

Pro Val Lys Ala Ala Thr Tyr Leu Ser Lys Gly Ser Glu Ile Ser Ser
                325                 330                 335

Leu Asp Ala Asp Ser Trp Leu Thr Gly Ser Ala Ala Ala Tyr Gln Cys
            340                 345                 350

Ser Glu Lys Gln Ala Ala Lys Asp Glu Tyr Ile His Ala Gln Pro Cys
        355                 360                 365

Tyr Pro Phe Leu Glu Ala Met Glu Thr Gly Leu Ile Asn Ser Glu Gly
    370                 375                 380

Ala Leu Leu Thr Arg Phe Phe Pro Ser Ser Ser Leu Lys Gly Met Leu
385                 390                 395                 400

Ile Ser Tyr His Val Arg His Tyr Leu Lys Gln Ile Tyr Phe Gln Val
                405                 410                 415

Pro Ser Tyr Thr Tyr Gly Asp Tyr Phe Ser His Asn Asp Arg Gly Leu
            420                 425                 430

Leu Leu Asp Leu Tyr Gln Ala Asn Ile Asp Val Phe Trp Ala Asp Glu
```

```
        435                 440                 445

Glu Ser Gly Arg Val Leu Gln Tyr Thr Lys Arg Arg Asp Lys Asn Ser
    450                 455                 460

Gly Met Phe Val Val Lys Asn Arg Val Glu Glu Phe Gln Ser Ala Tyr
465                 470                 475                 480

Phe Val Ala Ile Tyr Gly Ser Arg Leu Leu Glu Asn Asn Phe Ser Ala
                485                 490                 495

Gln Leu Asn Thr Leu Leu Ala Gly Leu Gln Lys Ala Ala His Thr Leu
            500                 505                 510

Gly Ile Pro Gly Phe Ser Lys Pro Thr Pro Leu Ala Val Ile Thr Gly
        515                 520                 525

Gly Gly Thr Gly Val Met Ala Thr Gly Asn Arg Val Ala Lys Glu Leu
    530                 535                 540

Gly Ile Leu Ser Cys Gly Thr Val Leu Asp Leu Glu Ala Ser Pro Ala
545                 550                 555                 560

Gln Ile Asp Gln Pro Ala Asn Glu Phe Leu Asp Ala Lys Met Thr Tyr
                565                 570                 575

Arg Leu Pro Gln Leu Ile Glu Arg Gln Glu His Phe Tyr Ser Asp Leu
            580                 585                 590

Ala Ile Leu Val Val Gly Gly Val Gly Thr Asp Phe Glu Leu Tyr Leu
        595                 600                 605

Glu Leu Val Tyr Leu Lys Thr Gly Ala Lys Pro Pro Thr Pro Ile Phe
    610                 615                 620

Leu Ile Gly Pro Val Glu Tyr Trp Lys Glu Lys Val Ala His Ala Tyr
625                 630                 635                 640

Glu Ile Asn Leu Lys Ala Gly Thr Ile Arg Gly Ser Glu Trp Ile Ser
                645                 650                 655

Asn Cys Leu Phe Cys Ile Thr Ser Pro Glu Ala Gly Ile Ala Val Phe
            660                 665                 670

Glu Gln Phe Leu Ala Gly Glu Leu Pro Ile Gly Tyr Asp Tyr Pro Pro
        675                 680                 685

Ala Pro Asp Gly Leu Val Ile Val
    690                 695
```

<210> SEQ ID NO 59
<211> LENGTH: 4563
<212> TYPE: DNA
<213> ORGANISM: Chlamydia muridarum

<400> SEQUENCE: 59

```
atgagttccg agaaagataa aaaaaactcc tgttctaagt tttccttatc ggtagtagca      60

gctattctcg cttctatgag tggtttatcg aattgttccg atctttatgc cgtaggaagt     120

tctgcagacc atcctgccta cttgattcct caagcggggt tattattgga tcatattaag     180

gatatattca ttggccctaa agatagtcag gataaggggc agtataagtt gattattggt     240

gaggctggct ctttccaaga tagtaatgca gagactcttc ctcaaaaggt agagcacagc     300

actttgtttt cagttacaac acctataatt gtgcaaggaa tagatcaaca agatcaggtc     360

tcttcgcagg gattggtctg taatttttca ggagatcatt cagaggagat ttttgagaga     420

gaatcctttt tagggatcgc tttcctaggg aatggtagca aggatggaat cacgttaaca     480

gatataaaat cttcgttatc tggtgctgcc ttgtattctt cagatgatct tatttttgaa     540

agaattaagg gagatataga gctttcttct tgttcatctt tagaaagagg aggagcttgt     600

tcagctcaaa gtattttaat tcatgattgt caaggattaa cggtaaaaca ttgtgccgca     660
```

-continued

```
ggggtgaatg ttgaaggagt tagtgctagc gaccatctcg gatttggggg cggggccttc    720
tctactacaa gttctctttc tggagagaag agtttgtata tgcctgcagg cgatattgtg    780
gtggctacct gcgatggtcc tgtgtgtttc gaaggaaata gtgctcagtt agcaaatggt    840
ggcgctattg ccgcttctgg taaagttctt tttgtagcta acgaaaaaaa gatttccttt    900
acagacaacc aagctttgtc tggaggagct atttctgcat cttctagtat ttctttccaa    960
aattgtgctg agcttgtgtt caagagtaat cttgcaaaag gagttaaaga taaatgttct   1020
ttgggaggag gtgctttagc ctctttagaa tccgtagttt tgaaagataa tctcggtatt   1080
acttatgaaa aaaatcagtc ctattcggaa ggaggggcta tttttgggaa ggattgtgag   1140
atttttgaaa acagggggcc tgttgtattc agagataaata cagctgcttt aggaggcgga   1200
gctattttgg cgcaacaaac tgtggcgatt tgtggtaata agtctggaat atcttttgaa   1260
ggaagtaagt ctagttttgg aggggccatt gcttgtggaa atttctcttc tgagaataat   1320
tcttcagctt tgggatcaat tgatatctct aacaatctag gagatatctc ttttcttcgg   1380
actctgtgta ctacttcgga tttagggcaa acggattacc aagggggagg ggccttattc   1440
gctgaaaata tttctctttc tgagaatgct ggtgcaatta ctttcaaaga caatattgtg   1500
aagacatttg cctcaaatgg aaaaatgttg ggtggagggg caattttagc ttcaggaaat   1560
gttttgatta gcaaaaactc tggagagatt tcttttgtag ggaatgctcg agctcctcag   1620
gctattccga ctcgttcatc tgacgaattg tcttttggcg cacaattaac tcaaactact   1680
tcaggatgtt ctggaggagg agctcttttt ggtaaagagg ttgccattgt tcaaaatgcc   1740
actgttgtat tcgagcaaaa tcgcttacag tgtggcgagc aggaaacaca tggtggaggc   1800
ggtgctgttt atggtatgga gagtgcctct attattggaa actcttttgt gagattcgga   1860
aataattacg ctgtagggaa tcagatttct ggaggagctc ttttatccaa gaaggtccgt   1920
ttagctgaaa atacaagggt agatttttct cgaaatatcg ctactttctg cggcggggct   1980
gttcaagttt ctgatggaag ttgcgaattg atcaacaatg ggtatgtgct attcagagat   2040
aaccgagggc agacatttgg tggggctatt tcttgcttga aaggagatgt gatcatttcc   2100
ggaaataaag atagggttga gtttagagat aacattgtga cgcggcctta ttttgaagaa   2160
aatgaagaaa aagttgagac agcagatatt aattcagata agcaagaagc agaagagcgc   2220
tctttattag agaacattga gcagagcttt attactgcaa ctaatcagac ctttttctta   2280
gaggaagaga aactcccatc agaagctttt atctctgctg aagaactttc aaagagaaga   2340
gaatgtgctg gtggggcgat tttgcaaaa cgggtctaca ttacggataa taaagaacct   2400
atcttgtttt cgcataattt ttctgatgtt tatgggggag ctatttttac gggttctcta   2460
caggaaactg ataaacaaga tgttgtaact cctgaagttg tgatatcagg caacgatggg   2520
gatgtcattt tttctggaaa tgcagctaaa catgataagc atttacctga tacaggtggt   2580
ggagccattt gtacacagaa tttgacgatt tcccaaaaca atgggaatgt cttgttcttg   2640
aacaattttg cttgttctgg tggagcagtt cgcatagagg atcatggaga agttctttta   2700
gaggcttttg gggagatat tattttcaat ggaaactctt ctttcagagc tcaaggatcg   2760
gatgcgatct attttgctgg taaggactct agaattaaag ctttaaatgc tactgaagga   2820
catgcgattg tgttccaaga tgcattggtg tttgaaaata tagaagaaag aaagtcttcg   2880
ggactattgg tgattaactc tcaggaaaat gagggttata cgggatccgt ccgattttta   2940
ggatctgaaa gtaaggttcc tcaatggatt catgtgcaac agggaggtct tgagttgcta   3000
catggagcta ttttatgtag ttatggggtt aaacaagatc ctagagctaa aatagtatta   3060
```

```
tctgctggat ctaaattgaa gattctagat tcagagcaag aaaataacgc agaaattgga   3120

gatcttgaag attctgttaa ttcagaaaaa acaccatctc tttggattgg gaagaacgct   3180

caagcaaaag tccctctggt tgatatccat actatttcta ttgatttagc atcattttct   3240

tctaaagctc aggaaacccc tgaggaagct ccacaagtca tcgtccctaa gggaagttgt   3300

gtccactcgg gagagttaag tttggagttg gttaatacaa caggaaaagg ttatgagaat   3360

catgcgttgt taaaaaatga tactcaggtt tctctcatgt ctttcaaaga ggaaaatgat   3420

ggatctttag aagatttgag taagttgtct gtttcggatt tacgcattaa agtttctact   3480

ccagatattg tagaagaaac ttatggccat atgggggatt ggtctgaagc tacaattcaa   3540

gatggggctc ttgtcattaa ttggcatcct actggatata aattagatcc gcaaaaagct   3600

ggttctttgg tattcaatgc attatgggag gaagaggctg tattgtctac tctaaaaaat   3660

gctcggattg cccataacct taccattcag agaatggaat ttgattattc tacaaatgct   3720

tggggattag cttttagtag ctttagagag ctatcttcag agaagcttgt ttctgttgat   3780

ggatatagag gctcttatat aggggcttct gcaggcattg atactcagtt gatggaagat   3840

tttgttttgg gaatcagcac ggcttccttc ttcgggaaaa tgcatagtca gaattttgat   3900

gcagagattt ctcgacatgg ttttgttggt tcggtctata caggcttcct agctggggcc   3960

tggttcttca aggggcagta cagtcttggc gaaacacata acgatatgac aactcgttac   4020

ggggttttgg gagaatctaa tgctacttgg aagtctcgag gagtactagc agatgcttta   4080

gttgaatatc gtagtttagt cggtccagca cgacctaaat tttatgcttt gcattttaat   4140

ccttatgtcg aggtatctta tgcatctgcg aagttcccta gttttgtaga acaaggagga   4200

gaagctcgtg cttttgaaga aacctcttta acaaacatta ccgttccctt tggtatgaaa   4260

tttgaactat cttttacaaa aggacagttt tcagagacta attctcttgg aataggttgt   4320

gcatgggaaa tgtatcggaa agtcgaagga agatctgtag agctactaga agctggtttt   4380

gattgggaag gatctcctat agatctccct aaacaagagc tgagagtggc tttagaaaac   4440

aatacggaat ggagttcgta ttttagtaca gctctaggag taacagcatt ttgtggagga   4500

ttttcttcta tggataataa actaggatac gaagcgaatg ctggaatgcg tttgattttc   4560

tag                                                                 4563
```

<210> SEQ ID NO 60
<211> LENGTH: 1520
<212> TYPE: PRT
<213> ORGANISM: Chlamydia muridarum

<400> SEQUENCE: 60

```
Met Ser Ser Glu Lys Asp Lys Lys Asn Ser Cys Ser Lys Phe Ser Leu
1               5                   10                  15

Ser Val Val Ala Ala Ile Leu Ala Ser Met Ser Gly Leu Ser Asn Cys
            20                  25                  30

Ser Asp Leu Tyr Ala Val Gly Ser Ser Ala Asp His Pro Ala Tyr Leu
        35                  40                  45

Ile Pro Gln Ala Gly Leu Leu Leu Asp His Ile Lys Asp Ile Phe Ile
    50                  55                  60

Gly Pro Lys Asp Ser Gln Asp Lys Gly Gln Tyr Lys Leu Ile Ile Gly
65                  70                  75                  80

Glu Ala Gly Ser Phe Gln Asp Ser Asn Ala Glu Thr Leu Pro Gln Lys
                85                  90                  95

Val Glu His Ser Thr Leu Phe Ser Val Thr Thr Pro Ile Ile Val Gln
            100                 105                 110
```

```
Gly Ile Asp Gln Gln Asp Gln Val Ser Ser Gln Gly Leu Val Cys Asn
        115                 120                 125

Phe Ser Gly Asp His Ser Glu Glu Ile Phe Glu Arg Glu Ser Phe Leu
    130                 135                 140

Gly Ile Ala Phe Leu Gly Asn Gly Ser Lys Asp Gly Ile Thr Leu Thr
145                 150                 155                 160

Asp Ile Lys Ser Ser Leu Ser Gly Ala Ala Leu Tyr Ser Ser Asp Asp
                165                 170                 175

Leu Ile Phe Glu Arg Ile Lys Gly Asp Ile Glu Leu Ser Ser Cys Ser
            180                 185                 190

Ser Leu Glu Arg Gly Gly Ala Cys Ser Ala Gln Ser Ile Leu Ile His
        195                 200                 205

Asp Cys Gln Gly Leu Thr Val Lys His Cys Ala Ala Gly Val Asn Val
    210                 215                 220

Glu Gly Val Ser Ala Ser Asp His Leu Gly Phe Gly Gly Gly Ala Phe
225                 230                 235                 240

Ser Thr Thr Ser Ser Leu Ser Gly Glu Lys Ser Leu Tyr Met Pro Ala
                245                 250                 255

Gly Asp Ile Val Val Ala Thr Cys Asp Gly Pro Val Cys Phe Glu Gly
            260                 265                 270

Asn Ser Ala Gln Leu Ala Asn Gly Gly Ala Ile Ala Ala Ser Gly Lys
        275                 280                 285

Val Leu Phe Val Ala Asn Glu Lys Lys Ile Ser Phe Thr Asp Asn Gln
    290                 295                 300

Ala Leu Ser Gly Gly Ala Ile Ser Ala Ser Ser Ser Ile Ser Phe Gln
305                 310                 315                 320

Asn Cys Ala Glu Leu Val Phe Lys Ser Asn Leu Ala Lys Gly Val Lys
                325                 330                 335

Asp Lys Cys Ser Leu Gly Gly Gly Ala Leu Ala Ser Leu Glu Ser Val
            340                 345                 350

Val Leu Lys Asp Asn Leu Gly Ile Thr Tyr Glu Lys Asn Gln Ser Tyr
        355                 360                 365

Ser Glu Gly Gly Ala Ile Phe Gly Lys Asp Cys Glu Ile Phe Glu Asn
    370                 375                 380

Arg Gly Pro Val Val Phe Arg Asp Asn Thr Ala Ala Leu Gly Gly Gly
385                 390                 395                 400

Ala Ile Leu Ala Gln Gln Thr Val Ala Ile Cys Gly Asn Lys Ser Gly
                405                 410                 415

Ile Ser Phe Glu Gly Ser Lys Ser Ser Phe Gly Gly Ala Ile Ala Cys
            420                 425                 430

Gly Asn Phe Ser Ser Glu Asn Asn Ser Ser Ala Leu Gly Ser Ile Asp
        435                 440                 445

Ile Ser Asn Asn Leu Gly Asp Ile Ser Phe Leu Arg Thr Leu Cys Thr
    450                 455                 460

Thr Ser Asp Leu Gly Gln Thr Asp Tyr Gln Gly Gly Gly Ala Leu Phe
465                 470                 475                 480

Ala Glu Asn Ile Ser Leu Ser Glu Asn Ala Gly Ala Ile Thr Phe Lys
                485                 490                 495

Asp Asn Ile Val Lys Thr Phe Ala Ser Asn Gly Lys Met Leu Gly Gly
            500                 505                 510

Gly Ala Ile Leu Ala Ser Gly Asn Val Leu Ile Ser Lys Asn Ser Gly
        515                 520                 525

Glu Ile Ser Phe Val Gly Asn Ala Arg Ala Pro Gln Ala Ile Pro Thr
```

```
    530                 535                 540

Arg Ser Ser Asp Glu Leu Ser Phe Gly Ala Gln Leu Thr Gln Thr Thr
545                 550                 555                 560

Ser Gly Cys Ser Gly Gly Gly Ala Leu Phe Gly Lys Glu Val Ala Ile
                565                 570                 575

Val Gln Asn Ala Thr Val Val Phe Glu Gln Asn Arg Leu Gln Cys Gly
            580                 585                 590

Glu Gln Glu Thr His Gly Gly Gly Gly Ala Val Tyr Gly Met Glu Ser
        595                 600                 605

Ala Ser Ile Ile Gly Asn Ser Phe Val Arg Phe Gly Asn Asn Tyr Ala
    610                 615                 620

Val Gly Asn Gln Ile Ser Gly Gly Ala Leu Leu Ser Lys Lys Val Arg
625                 630                 635                 640

Leu Ala Glu Asn Thr Arg Val Asp Phe Ser Arg Asn Ile Ala Thr Phe
                645                 650                 655

Cys Gly Gly Ala Val Gln Val Ser Asp Gly Ser Cys Glu Leu Ile Asn
            660                 665                 670

Asn Gly Tyr Val Leu Phe Arg Asp Asn Arg Gly Gln Thr Phe Gly Gly
        675                 680                 685

Ala Ile Ser Cys Leu Lys Gly Asp Val Ile Ile Ser Gly Asn Lys Asp
    690                 695                 700

Arg Val Glu Phe Arg Asp Asn Ile Val Thr Arg Pro Tyr Phe Glu Glu
705                 710                 715                 720

Asn Glu Glu Lys Val Glu Thr Ala Asp Ile Asn Ser Asp Lys Gln Glu
                725                 730                 735

Ala Glu Glu Arg Ser Leu Leu Glu Asn Ile Glu Gln Ser Phe Ile Thr
            740                 745                 750

Ala Thr Asn Gln Thr Phe Phe Leu Glu Glu Glu Lys Leu Pro Ser Glu
        755                 760                 765

Ala Phe Ile Ser Ala Glu Glu Leu Ser Lys Arg Arg Glu Cys Ala Gly
    770                 775                 780

Gly Ala Ile Phe Ala Lys Arg Val Tyr Ile Thr Asp Asn Lys Glu Pro
785                 790                 795                 800

Ile Leu Phe Ser His Asn Phe Ser Asp Val Tyr Gly Gly Ala Ile Phe
                805                 810                 815

Thr Gly Ser Leu Gln Glu Thr Asp Lys Gln Asp Val Val Thr Pro Glu
            820                 825                 830

Val Val Ile Ser Gly Asn Asp Gly Asp Val Ile Phe Ser Gly Asn Ala
        835                 840                 845

Ala Lys His Asp Lys His Leu Pro Asp Thr Gly Gly Gly Ala Ile Cys
    850                 855                 860

Thr Gln Asn Leu Thr Ile Ser Gln Asn Asn Gly Asn Val Leu Phe Leu
865                 870                 875                 880

Asn Asn Phe Ala Cys Ser Gly Gly Ala Val Arg Ile Glu Asp His Gly
                885                 890                 895

Glu Val Leu Leu Glu Ala Phe Gly Gly Asp Ile Ile Phe Asn Gly Asn
            900                 905                 910

Ser Ser Phe Arg Ala Gln Gly Ser Asp Ala Ile Tyr Phe Ala Gly Lys
        915                 920                 925

Asp Ser Arg Ile Lys Ala Leu Asn Ala Thr Glu Gly His Ala Ile Val
    930                 935                 940

Phe Gln Asp Ala Leu Val Phe Glu Asn Ile Glu Glu Arg Lys Ser Ser
945                 950                 955                 960
```

```
Gly Leu Leu Val Ile Asn Ser Gln Glu Asn Glu Gly Tyr Thr Gly Ser
                965                 970                 975

Val Arg Phe Leu Gly Ser Glu Ser Lys Val Pro Gln Trp Ile His Val
            980                 985                 990

Gln Gln Gly Gly Leu Glu Leu Leu  His Gly Ala Ile Leu  Cys Ser Tyr
        995                 1000                1005

Gly Val  Lys Gln Asp Pro Arg  Ala Lys Ile Val Leu  Ser Ala Gly
    1010                 1015                 1020

Ser Lys  Leu Lys Ile Leu Asp  Ser Glu Gln Glu Asn  Asn Ala Glu
    1025                 1030                 1035

Ile Gly  Asp Leu Glu Asp Ser  Val Asn Ser Glu Lys  Thr Pro Ser
    1040                 1045                 1050

Leu Trp  Ile Gly Lys Asn Ala  Gln Ala Lys Val Pro  Leu Val Asp
    1055                 1060                 1065

Ile His  Thr Ile Ser Ile Asp  Leu Ala Ser Phe Ser  Ser Lys Ala
    1070                 1075                 1080

Gln Glu  Thr Pro Glu Glu Ala  Pro Gln Val Ile Val  Pro Lys Gly
    1085                 1090                 1095

Ser Cys  Val His Ser Gly Glu  Leu Ser Leu Glu Leu  Val Asn Thr
    1100                 1105                 1110

Thr Gly  Lys Gly Tyr Glu Asn  His Ala Leu Leu Lys  Asn Asp Thr
    1115                 1120                 1125

Gln Val  Ser Leu Met Ser Phe  Lys Glu Glu Asn Asp  Gly Ser Leu
    1130                 1135                 1140

Glu Asp  Leu Ser Lys Leu Ser  Val Ser Asp Leu Arg  Ile Lys Val
    1145                 1150                 1155

Ser Thr  Pro Asp Ile Val Glu  Glu Thr Tyr Gly His  Met Gly Asp
    1160                 1165                 1170

Trp Ser  Glu Ala Thr Ile Gln  Asp Gly Ala Leu Val  Ile Asn Trp
    1175                 1180                 1185

His Pro  Thr Gly Tyr Lys Leu  Asp Pro Gln Lys Ala  Gly Ser Leu
    1190                 1195                 1200

Val Phe  Asn Ala Leu Trp Glu  Glu Glu Ala Val Leu  Ser Thr Leu
    1205                 1210                 1215

Lys Asn  Ala Arg Ile Ala His  Asn Leu Thr Ile Gln  Arg Met Glu
    1220                 1225                 1230

Phe Asp  Tyr Ser Thr Asn Ala  Trp Gly Leu Ala Phe  Ser Ser Phe
    1235                 1240                 1245

Arg Glu  Leu Ser Ser Glu Lys  Leu Val Ser Val Asp  Gly Tyr Arg
    1250                 1255                 1260

Gly Ser  Tyr Ile Gly Ala Ser  Ala Gly Ile Asp Thr  Gln Leu Met
    1265                 1270                 1275

Glu Asp  Phe Val Leu Gly Ile  Ser Thr Ala Ser Phe  Phe Gly Lys
    1280                 1285                 1290

Met His  Ser Gln Asn Phe Asp  Ala Glu Ile Ser Arg  His Gly Phe
    1295                 1300                 1305

Val Gly  Ser Val Tyr Thr Gly  Phe Leu Ala Gly Ala  Trp Phe Phe
    1310                 1315                 1320

Lys Gly  Gln Tyr Ser Leu Gly  Glu Thr His Asn Asp  Met Thr Thr
    1325                 1330                 1335

Arg Tyr  Gly Val Leu Gly Glu  Ser Asn Ala Thr Trp  Lys Ser Arg
    1340                 1345                 1350

Gly Val  Leu Ala Asp Ala Leu  Val Glu Tyr Arg Ser  Leu Val Gly
    1355                 1360                 1365
```

```
Pro Ala  Arg Pro Lys Phe Tyr  Ala Leu His Phe Asn  Pro Tyr Val
    1370                 1375                 1380

Glu Val  Ser Tyr Ala Ser Ala  Lys Phe Pro Ser Phe  Val Glu Gln
    1385                 1390                 1395

Gly Gly  Glu Ala Arg Ala Phe  Glu Glu Thr Ser Leu  Thr Asn Ile
    1400                 1405                 1410

Thr Val  Pro Phe Gly Met Lys  Phe Glu Leu Ser Phe  Thr Lys Gly
    1415                 1420                 1425

Gln Phe  Ser Glu Thr Asn Ser  Leu Gly Ile Gly Cys  Ala Trp Glu
    1430                 1435                 1440

Met Tyr  Arg Lys Val Glu Gly  Arg Ser Val Glu Leu  Leu Glu Ala
    1445                 1450                 1455

Gly Phe  Asp Trp Glu Gly Ser  Pro Ile Asp Leu Pro  Lys Gln Glu
    1460                 1465                 1470

Leu Arg  Val Ala Leu Glu Asn  Asn Thr Glu Trp Ser  Ser Tyr Phe
    1475                 1480                 1485

Ser Thr  Ala Leu Gly Val Thr  Ala Phe Cys Gly Gly  Phe Ser Ser
    1490                 1495                 1500

Met Asp  Asn Lys Leu Gly Tyr  Glu Ala Asn Ala Gly  Met Arg Leu
    1505                 1510                 1515

Ile Phe
    1520
```

<210> SEQ ID NO 61
<211> LENGTH: 2931
<212> TYPE: DNA
<213> ORGANISM: Chlamydia muridarum

<400> SEQUENCE: 61

```
atgaaaaaac tgttcttttt tgtccttatt ggaagctcta tactgggatt tactcgagaa     60
gtccctcctt cgattctttt aaagcctata ctaaatccat accatatgac cgggttattt    120
tttcccaagg ttaatttgct tggagacaca cataatctca ctgattacca tttggataat    180
ctaaaatgca ttctggcttg cctacaaaga actccttatg aaggagctgc tttcacagta    240
accgattact taggtttttc agatacacaa aaggatggta ttttttgttt taaaaatctt    300
actccagaga gtggaggggt tattggttcc ccaactcaaa acactcctac tataaaaatt    360
cataatacaa tcggccccgt tcttttcgaa aataatacct gtcatagact gtggacacag    420
accgatcccg aaaatgaagg aaacaaagca cgcgaaggcg gggcaattca tgctggggac    480
gtttacataa gcaataacca gaaccttgtc ggattcataa agaactttgc ttatgttcaa    540
ggtggagcta ttagtgctaa tacttttgcc tataaagaaa ataaatcgag ctttctttgc    600
ctaaataact cttgtataca aactaagacg ggagggaaag gtggtgctat ttacgttagt    660
acgagctgct ctttcgagaa caataacaag gatctgcttt tcatccaaaa ctccggctgt    720
gcaggaggag ctatcttctc tccaacctgt tctctaatag gaaaccaagg agatattgtt    780
ttttacagca accacggttt taaaaatgtt gataatgcaa ctaacgaatc tggggatgga    840
ggagctatta aagtaactac ccgcttggac atcaccaata atggtagtca aatctttttt    900
tctgataata tctcaagaaa ttttggagga gctattcatg ctccttgtct tcatcttgtt    960
ggtaatgggc caacctattt tacaaacaat atagctaatc acacaggtgg ggctatttat   1020
ataacaggaa cagaaacctc aaagatttct gcagatcacc atgctattat ttttgataat   1080
aacatttctg caaacgccac caatgcggac ggatctagca gcaacactaa tcctcctcac   1140
```

```
agaaatgcga tcactatgga caattccgct ggaggaatag aacttggtgc agggaagagc   1200

cagaatctta ttttctatga tcctattcaa gtgacgaatg ctggagttac cgtagacttc   1260

aataaggatg cctcccaaac cggatgtgta gttttctctg gagcgactgt cctttctgca   1320

gatatttctc aggctaattt gcaaactaaa acacctgcaa cgcttactct cagtcacggt   1380

cttctgtgta tcgaagatcg tgctcagctc acagtgaaca attttacaca aacaggaggg   1440

attgtagcct taggaaatgg agcagtttta agcagctacc aacacagcac tacagacgcc   1500

actcaaactc cccctacaac caccactaca gatgcttccg taactcttaa tcacattgga   1560

ttaaatctcc cctctattct taaggatgga gcagagatgc ctctattatg ggtagaacct   1620

ataagcacaa ctcaaggtaa cactacaaca tatacgtcag ataccgcggc ttccttctca   1680

ttaaatggag ccacactctc tctcattgat gaagatggaa attctcccta tgaaaacacg   1740

gacctctctc gtgcattgta cgctcaacct atgctagcaa tttctgaggc cagtgataac   1800

caattgcaat ccgaaagcat ggacttttct aaagttaatg ttcctcacta tggatggcaa   1860

ggactttgga cctgggggtg ggcaaaaact gaaaatccaa caacaactcc tccagcaaca   1920

attactgatc cgaaaaaagc taatcagttt catagaactt tattattaac gtggctccct   1980

gctggttata tccccagccc taaacataaa agccctttaa tagctaatac cttgtggggg   2040

aatatacttt ttgcaacgga aaacttaaaa aatagctcag ggcaagaact tcttgatcgt   2100

cctttctggg gaattacagg agggggcttg ggatgatgg tctatcaaga acctagaaaa   2160

gaccatcctg gattccacat gcatacctcc ggatattcag caggaatgat tacaggaaac   2220

acacatacct tctcattacg attcagccag tcctatacaa aactcaatga acgttatgcc   2280

aagaactatg tgtcttctaa aaattactct tgccaagggg aaatgctttt gtccttacaa   2340

gaaggactca tgctgactaa actaattggt ctctatagtt atgggaatca caacagccac   2400

catttctata cccaaggaga agacctatcg tctcaagggg agttccatag tcagactttt   2460

ggaggggctg tctttttga tctacctctg aaaccttttg gaagaacaca catacttaca   2520

gctcctttct taggtgccat tggtatgtat tctaagctgt ctagctttac agaagtagga   2580

gcctatccaa gaacctttat tacagaaacg cctttaatca atgtcctgat tcctatcgga   2640

gtaaaaggta gcttcatgaa tgccacccat agacctcagg cctggactgt agagcttgct   2700

taccaacctg ttctttacag acaagaacct agtatctcta cccaattact cgctggtaaa   2760

ggtatgtggt ttgggcatgg aagtcctgca tctcgccacg ctctagctta taaaatttca   2820

cagaaaacac agcttttgcg atttgcaaca cttcaactcc agtatcacgg atactattcg   2880

tcttccactt tctgtaatta tctgaatgga gaggtatctt tacgtttcta a            2931
```

<210> SEQ ID NO 62
<211> LENGTH: 976
<212> TYPE: PRT
<213> ORGANISM: Chlamydia muridarum

<400> SEQUENCE: 62

```
Met Lys Lys Leu Phe Phe Phe Val Leu Ile Gly Ser Ser Ile Leu Gly
1               5                   10                  15

Phe Thr Arg Glu Val Pro Pro Ser Ile Leu Leu Lys Pro Ile Leu Asn
            20                  25                  30

Pro Tyr His Met Thr Gly Leu Phe Phe Pro Lys Val Asn Leu Leu Gly
        35                  40                  45

Asp Thr His Asn Leu Thr Asp Tyr His Leu Asp Asn Leu Lys Cys Ile
    50                  55                  60
```

```
Leu Ala Cys Leu Gln Arg Thr Pro Tyr Glu Gly Ala Ala Phe Thr Val
65                  70                  75                  80

Thr Asp Tyr Leu Gly Phe Ser Asp Thr Gln Lys Asp Gly Ile Phe Cys
                85                  90                  95

Phe Lys Asn Leu Thr Pro Glu Ser Gly Gly Val Ile Gly Ser Pro Thr
            100                 105                 110

Gln Asn Thr Pro Thr Ile Lys Ile His Asn Thr Ile Gly Pro Val Leu
        115                 120                 125

Phe Glu Asn Asn Thr Cys His Arg Leu Trp Thr Gln Thr Asp Pro Glu
    130                 135                 140

Asn Glu Gly Asn Lys Ala Arg Glu Gly Gly Ala Ile His Ala Gly Asp
145                 150                 155                 160

Val Tyr Ile Ser Asn Asn Gln Asn Leu Val Gly Phe Ile Lys Asn Phe
                165                 170                 175

Ala Tyr Val Gln Gly Gly Ala Ile Ser Ala Asn Thr Phe Ala Tyr Lys
            180                 185                 190

Glu Asn Lys Ser Ser Phe Leu Cys Leu Asn Asn Ser Cys Ile Gln Thr
        195                 200                 205

Lys Thr Gly Gly Lys Gly Gly Ala Ile Tyr Val Ser Thr Ser Cys Ser
    210                 215                 220

Phe Glu Asn Asn Asn Lys Asp Leu Leu Phe Ile Gln Asn Ser Gly Cys
225                 230                 235                 240

Ala Gly Gly Ala Ile Phe Ser Pro Thr Cys Ser Leu Ile Gly Asn Gln
                245                 250                 255

Gly Asp Ile Val Phe Tyr Ser Asn His Gly Phe Lys Asn Val Asp Asn
            260                 265                 270

Ala Thr Asn Glu Ser Gly Asp Gly Gly Ala Ile Lys Val Thr Thr Arg
        275                 280                 285

Leu Asp Ile Thr Asn Asn Gly Ser Gln Ile Phe Phe Ser Asp Asn Ile
    290                 295                 300

Ser Arg Asn Phe Gly Gly Ala Ile His Ala Pro Cys Leu His Leu Val
305                 310                 315                 320

Gly Asn Gly Pro Thr Tyr Phe Thr Asn Asn Ile Ala Asn His Thr Gly
                325                 330                 335

Gly Ala Ile Tyr Ile Thr Gly Thr Glu Thr Ser Lys Ile Ser Ala Asp
            340                 345                 350

His His Ala Ile Ile Phe Asp Asn Asn Ile Ser Ala Asn Ala Thr Asn
        355                 360                 365

Ala Asp Gly Ser Ser Ser Asn Thr Asn Pro Pro His Arg Asn Ala Ile
    370                 375                 380

Thr Met Asp Asn Ser Ala Gly Gly Ile Glu Leu Gly Ala Gly Lys Ser
385                 390                 395                 400

Gln Asn Leu Ile Phe Tyr Asp Pro Ile Gln Val Thr Asn Ala Gly Val
                405                 410                 415

Thr Val Asp Phe Asn Lys Asp Ala Ser Gln Thr Gly Cys Val Val Phe
            420                 425                 430

Ser Gly Ala Thr Val Leu Ser Ala Asp Ile Ser Gln Ala Asn Leu Gln
        435                 440                 445

Thr Lys Thr Pro Ala Thr Leu Thr Leu Ser His Gly Leu Leu Cys Ile
    450                 455                 460

Glu Asp Arg Ala Gln Leu Thr Val Asn Asn Phe Thr Gln Thr Gly Gly
465                 470                 475                 480

Ile Val Ala Leu Gly Asn Gly Ala Val Leu Ser Ser Tyr Gln His Ser
                485                 490                 495
```

```
Thr Thr Asp Ala Thr Gln Thr Pro Pro Thr Thr Thr Thr Thr Asp Ala
            500                 505                 510

Ser Val Thr Leu Asn His Ile Gly Leu Asn Leu Pro Ser Ile Leu Lys
        515                 520                 525

Asp Gly Ala Glu Met Pro Leu Leu Trp Val Glu Pro Ile Ser Thr Thr
    530                 535                 540

Gln Gly Asn Thr Thr Thr Tyr Thr Ser Asp Thr Ala Ala Ser Phe Ser
545                 550                 555                 560

Leu Asn Gly Ala Thr Leu Ser Leu Ile Asp Glu Asp Gly Asn Ser Pro
                565                 570                 575

Tyr Glu Asn Thr Asp Leu Ser Arg Ala Leu Tyr Ala Gln Pro Met Leu
            580                 585                 590

Ala Ile Ser Glu Ala Ser Asp Asn Gln Leu Gln Ser Glu Ser Met Asp
        595                 600                 605

Phe Ser Lys Val Asn Val Pro His Tyr Gly Trp Gln Gly Leu Trp Thr
    610                 615                 620

Trp Gly Trp Ala Lys Thr Glu Asn Pro Thr Thr Thr Pro Pro Ala Thr
625                 630                 635                 640

Ile Thr Asp Pro Lys Lys Ala Asn Gln Phe His Arg Thr Leu Leu Leu
                645                 650                 655

Thr Trp Leu Pro Ala Gly Tyr Ile Pro Ser Pro Lys His Lys Ser Pro
            660                 665                 670

Leu Ile Ala Asn Thr Leu Trp Gly Asn Ile Leu Phe Ala Thr Glu Asn
        675                 680                 685

Leu Lys Asn Ser Ser Gly Gln Glu Leu Leu Asp Arg Pro Phe Trp Gly
    690                 695                 700

Ile Thr Gly Gly Gly Leu Gly Met Met Val Tyr Gln Glu Pro Arg Lys
705                 710                 715                 720

Asp His Pro Gly Phe His Met His Thr Ser Gly Tyr Ser Ala Gly Met
                725                 730                 735

Ile Thr Gly Asn Thr His Thr Phe Ser Leu Arg Phe Ser Gln Ser Tyr
            740                 745                 750

Thr Lys Leu Asn Glu Arg Tyr Ala Lys Asn Tyr Val Ser Ser Lys Asn
        755                 760                 765

Tyr Ser Cys Gln Gly Glu Met Leu Leu Ser Leu Gln Glu Gly Leu Met
    770                 775                 780

Leu Thr Lys Leu Ile Gly Leu Tyr Ser Tyr Gly Asn His Asn Ser His
785                 790                 795                 800

His Phe Tyr Thr Gln Gly Glu Asp Leu Ser Ser Gln Gly Glu Phe His
                805                 810                 815

Ser Gln Thr Phe Gly Gly Ala Val Phe Phe Asp Leu Pro Leu Lys Pro
            820                 825                 830

Phe Gly Arg Thr His Ile Leu Thr Ala Pro Phe Leu Gly Ala Ile Gly
        835                 840                 845

Met Tyr Ser Lys Leu Ser Ser Phe Thr Glu Val Gly Ala Tyr Pro Arg
    850                 855                 860

Thr Phe Ile Thr Glu Thr Pro Leu Ile Asn Val Leu Ile Pro Ile Gly
865                 870                 875                 880

Val Lys Gly Ser Phe Met Asn Ala Thr His Arg Pro Gln Ala Trp Thr
                885                 890                 895

Val Glu Leu Ala Tyr Gln Pro Val Leu Tyr Arg Gln Glu Pro Ser Ile
            900                 905                 910

Ser Thr Gln Leu Leu Ala Gly Lys Gly Met Trp Phe Gly His Gly Ser
```

-continued

```
        915                 920                 925

Pro Ala Ser Arg His Ala Leu Ala Tyr Lys Ile Ser Gln Lys Thr Gln
    930                 935                 940

Leu Leu Arg Phe Ala Thr Leu Gln Leu Gln Tyr His Gly Tyr Tyr Ser
945                 950                 955                 960

Ser Ser Thr Phe Cys Asn Tyr Leu Asn Gly Glu Val Ser Leu Arg Phe
                965                 970                 975
```

```
<210> SEQ ID NO 63
<211> LENGTH: 1272
<212> TYPE: DNA
<213> ORGANISM: Chlamydia trachomatis

<400> SEQUENCE: 63

gcacctcaac ctcgcggaac gcttcctagc tcgaccacaa aaattggatc agaagtttgg      60

attgaacaaa aagtccgcca atatccagag cttttatggt tagtagagcc gtcctctacg     120

ggagcctctt taaaatctcc ttcaggagcc atcttttctc caacattatt ccaaaaaaag     180

gtccctgctt tcgatatcgc agtgcgcagt ttgattcact tacatttatt aatccagggt     240

tcccgccaag cctatgctca actgatccaa ctacagacca gcgaatcccc tctaacattt     300

aagcaattcc ttgcattgca taagcaatta actctatttt taaattcccc taaggaattt     360

tatgactctg ttaaagtgtt agagacagct atcgtcttac gtcacttagg ctgttcaact     420

aaggctgttg ctgcgtttaa accttatttc tcagaaatgc aaagagaggc tttttacact     480

aaggctctgc atgtactaca caccttccca gagctaagcc catcatttgc tcgcctctct     540

ccggagcaga aaactctctt cttctccttg agaaaattgg cgaattacga tgagttactc     600

tcgctgacga acaccccaag ttttcagctt ctgtctgctg ggcgctcgca acgagctctt     660

ttagctctgg acttgtacct ctatgctttg gattcctgtg gagaacaggg gatgtcctct     720

caattccaca caaacttcgc acctctacag tccatgttgc aacaatacgc tactgtagaa     780

gaggcctttt ctcgttattt tacttaccga gctaatcgat taggatttga tggctcttct     840

cgatccgaga tggctttagt aagaatggcc accttgatga acttgtctcc ttccgaagct     900

gcgattttaa ccacaagctt caaaaccctt cctacagaag aagcggatac tttgatcaat     960

agtttctata ccaataaggg cgattcgttg gctctttctc tgcgagggtt gcctacactt    1020

gtatccgaac tgacgcgaac tgcccatggc aataccaatg cagaagctcg atctcagcaa    1080

atttatgcaa ctaccctatc gctagtagta aagagtctga aagcgcacaa agaaatgcta    1140

aacaagcaaa ttctttctaa ggaaattgtt ttagatttct cagaaactgc agcttcttgc    1200

caaggattgg atatcttttc cgagaatgtc gctgttcaaa ttcacttaaa tggaaccgtt    1260

agtatccatt ta                                                        1272
```

```
<210> SEQ ID NO 64
<211> LENGTH: 424
<212> TYPE: PRT
<213> ORGANISM: Chlamydia trachomatis

<400> SEQUENCE: 64

Ala Pro Gln Pro Arg Gly Thr Leu Pro Ser Ser Thr Thr Lys Ile Gly
1               5                   10                  15

Ser Glu Val Trp Ile Glu Gln Lys Val Arg Gln Tyr Pro Glu Leu Leu
            20                  25                  30

Trp Leu Val Glu Pro Ser Ser Thr Gly Ala Ser Leu Lys Ser Pro Ser
        35                  40                  45
```

-continued

```
Gly Ala Ile Phe Ser Pro Thr Leu Phe Gln Lys Lys Val Pro Ala Phe
    50                  55                  60

Asp Ile Ala Val Arg Ser Leu Ile His Leu His Leu Leu Ile Gln Gly
65                  70                  75                  80

Ser Arg Gln Ala Tyr Ala Gln Leu Ile Gln Leu Gln Thr Ser Glu Ser
                85                  90                  95

Pro Leu Thr Phe Lys Gln Phe Leu Ala Leu His Lys Gln Leu Thr Leu
            100                 105                 110

Phe Leu Asn Ser Pro Lys Glu Phe Tyr Asp Ser Val Lys Val Leu Glu
        115                 120                 125

Thr Ala Ile Val Leu Arg His Leu Gly Cys Ser Thr Lys Ala Val Ala
    130                 135                 140

Ala Phe Lys Pro Tyr Phe Ser Glu Met Gln Arg Glu Ala Phe Tyr Thr
145                 150                 155                 160

Lys Ala Leu His Val Leu His Thr Phe Pro Glu Leu Ser Pro Ser Phe
                165                 170                 175

Ala Arg Leu Ser Pro Glu Gln Lys Thr Leu Phe Phe Ser Leu Arg Lys
            180                 185                 190

Leu Ala Asn Tyr Asp Glu Leu Leu Ser Leu Thr Asn Thr Pro Ser Phe
        195                 200                 205

Gln Leu Leu Ser Ala Gly Arg Ser Gln Arg Ala Leu Leu Ala Leu Asp
    210                 215                 220

Leu Tyr Leu Tyr Ala Leu Asp Ser Cys Gly Glu Gln Gly Met Ser Ser
225                 230                 235                 240

Gln Phe His Thr Asn Phe Ala Pro Leu Gln Ser Met Leu Gln Gln Tyr
                245                 250                 255

Ala Thr Val Glu Glu Ala Phe Ser Arg Tyr Phe Thr Tyr Arg Ala Asn
            260                 265                 270

Arg Leu Gly Phe Asp Gly Ser Ser Arg Ser Glu Met Ala Leu Val Arg
        275                 280                 285

Met Ala Thr Leu Met Asn Leu Ser Pro Ser Glu Ala Ala Ile Leu Thr
    290                 295                 300

Thr Ser Phe Lys Thr Leu Pro Thr Glu Glu Ala Asp Thr Leu Ile Asn
305                 310                 315                 320

Ser Phe Tyr Thr Asn Lys Gly Asp Ser Leu Ala Leu Ser Leu Arg Gly
                325                 330                 335

Leu Pro Thr Leu Val Ser Glu Leu Thr Arg Thr Ala His Gly Asn Thr
            340                 345                 350

Asn Ala Glu Ala Arg Ser Gln Gln Ile Tyr Ala Thr Thr Leu Ser Leu
        355                 360                 365

Val Val Lys Ser Leu Lys Ala His Lys Glu Met Leu Asn Lys Gln Ile
    370                 375                 380

Leu Ser Lys Glu Ile Val Leu Asp Phe Ser Glu Thr Ala Ala Ser Cys
385                 390                 395                 400

Gln Gly Leu Asp Ile Phe Ser Glu Asn Val Ala Val Gln Ile His Leu
                405                 410                 415

Asn Gly Thr Val Ser Ile His Leu
            420
```

<210> SEQ ID NO 65
<211> LENGTH: 2427
<212> TYPE: DNA
<213> ORGANISM: Chlamydia trachomatis

<400> SEQUENCE: 65

-continued

```
actaagcctt ctttcttata cgttattcaa cctttttccg tatttaatcc acgattagga     60
cgtttctcta cagactcaga tacttatatc gaagaagaaa accgcctagc atcgttcatt    120
gagagtttgc cactggagat cttcgatata ccttctttca tggaaaccgc gatttccaat    180
agcccctata ttttatcttg ggagacaact aaagacggcg ctctgttcac tattcttgaa    240
cccaaactct cagcttgcgc agccacttgc ctggtagccc cttctataca aatgaaatcc    300
gatgcggagc tcctagaaga aattaagcaa gcgttattac gcagctctca tgacggtgtg    360
aaatatcgca tcaccagaga atccttctct ccagaaaaga aaactcctaa ggttgctcta    420
gtcgatgacg atattgaatt gattcgcaat gtcgactttt tgggtagagc tgttgacatt    480
gtcaaattag accctattaa tattctgaat accgtaagcg aagagaatat tctagattac    540
tcttttacaa gagaaacggc tcagctgagc gcggatggtc gttttggtat tcctccaggg    600
actaagctat tccctaaacc ttcttttgat gtagaaatca gtacctccat tttcgaagaa    660
acaacttcat ttactcgaag tttttctgca tcggttactt ttagtgtacc agacctcgcg    720
gcgactatgc ctcttcaaag ccctcccatg gtagaaaatg gtcaaaaaga aatttgtgtc    780
attcaaaaac acttattccc aagctactct cctaaactag tcgatattgt taaacgatac    840
aaaagagagg ctaagatctt gattaacaag cttgcctttg gaatgttatg gcgacatcgg    900
gctaaaagcc aaatcctcac cgagggaagc gtacgtctag acttacaagg attcacagaa    960
tcgaagtaca attaccagat tcaagtagga tcccatacga ttgcagctgt attaatcgat   1020
atggatattt ccaagattca atccaaatca gaacaagctt atgcaattag gaaaatcaaa   1080
tcaggctttc aacgtagctt ggatgactat catatttatc aaattgaaag aaaacaaacc   1140
ttttcttttt ctccgaagca tcgcagcctc tcatccacat cccattccga agattctgat   1200
ttggatcttt ctgaagcagc cgccttttca ggaagtctta cctgcgagtt tgtaaaaaaa   1260
agcactcaac atgccaagaa taccgtcaca tgttccacag ccgctcattc cctatacaca   1320
ctcaaagaag atgacagctc gaacccctct gaaaaacgat tagatagttg tttccgcaat   1380
tggattgaaa acaaactaag cgccaattct ccagattcct ggtcagcgtt tattcaaaaa   1440
ttcggaacac actatattgc atcagcaact tttggaggga taggtttcca agtgctcaaa   1500
ctatcttttg aacaggtgga ggatctacat agcaaaaaga tctccttaga aaccgcagca   1560
gccaactctc tattaaaagg ttctgtatcc agcagcacag aatctggata ctccagctat   1620
agctccacgt cttcttctca tacggtattt ttaggaggaa cggtcttacc ttcggttcat   1680
gatgaacgtt tagactttaa agattggtcg gaaagtgtgc acctggaacc tgttcctatc   1740
caggtttctt tacaacctat aacgaattta ctagttcctc tccattttcc taatatcggt   1800
gctgcagagc tctctaataa acgagaatct cttcaacaag cgattcgagt ctatctcaaa   1860
gaacataaag tagatgagca aggagaacgt actacattta catcaggaat cgataatcct   1920
tcttcctggt ttaccttaga agctgcccac tctcctctta tagtcagtac tccttacatt   1980
gcttcgtggt ctacgcttcc ttatttgttc ccaacattaa gagaacgttc ttcggcaacc   2040
cctatcgttt tctatttttg tgtagataat aatgaacatg cttcgcaaaa aatattaaac   2100
caatcgtatt gcttcctcgg gtccttgcct attcgacaaa aaatttttgg tagcgaattt   2160
gctagtttcc cctatctatc tttctatgga aatgcaaaag aggcgtactt tgataacacg   2220
tactacccaa cgcgttgtgg gtggattgtt gaaaagttaa atactacaca agatcaattc   2280
ctccgggatg gagacgaggt gcgactaaaa catgtttcca gcggaaagta tctagcaaca   2340
actcctctta aggataccca tggtacactc acgcgtacaa cgaactgtga agatgctatc   2400
```

tttattatta aaaaatcttc aggttat 2427

<210> SEQ ID NO 66
<211> LENGTH: 809
<212> TYPE: PRT
<213> ORGANISM: Chlamydia trachomatis

<400> SEQUENCE: 66

Thr Lys Pro Ser Phe Leu Tyr Val Ile Gln Pro Phe Ser Val Phe Asn
1 5 10 15

Pro Arg Leu Gly Arg Phe Ser Thr Asp Ser Asp Thr Tyr Ile Glu Glu
20 25 30

Glu Asn Arg Leu Ala Ser Phe Ile Glu Ser Leu Pro Leu Glu Ile Phe
35 40 45

Asp Ile Pro Ser Phe Met Glu Thr Ala Ile Ser Asn Ser Pro Tyr Ile
50 55 60

Leu Ser Trp Glu Thr Thr Lys Asp Gly Ala Leu Phe Thr Ile Leu Glu
65 70 75 80

Pro Lys Leu Ser Ala Cys Ala Ala Thr Cys Leu Val Ala Pro Ser Ile
85 90 95

Gln Met Lys Ser Asp Ala Glu Leu Leu Glu Glu Ile Lys Gln Ala Leu
100 105 110

Leu Arg Ser Ser His Asp Gly Val Lys Tyr Arg Ile Thr Arg Glu Ser
115 120 125

Phe Ser Pro Glu Lys Lys Thr Pro Lys Val Ala Leu Val Asp Asp Asp
130 135 140

Ile Glu Leu Ile Arg Asn Val Asp Phe Leu Gly Arg Ala Val Asp Ile
145 150 155 160

Val Lys Leu Asp Pro Ile Asn Ile Leu Asn Thr Val Ser Glu Glu Asn
165 170 175

Ile Leu Asp Tyr Ser Phe Thr Arg Glu Thr Ala Gln Leu Ser Ala Asp
180 185 190

Gly Arg Phe Gly Ile Pro Pro Gly Thr Lys Leu Phe Pro Lys Pro Ser
195 200 205

Phe Asp Val Glu Ile Ser Thr Ser Ile Phe Glu Glu Thr Thr Ser Phe
210 215 220

Thr Arg Ser Phe Ser Ala Ser Val Thr Phe Ser Val Pro Asp Leu Ala
225 230 235 240

Ala Thr Met Pro Leu Gln Ser Pro Pro Met Val Glu Asn Gly Gln Lys
245 250 255

Glu Ile Cys Val Ile Gln Lys His Leu Phe Pro Ser Tyr Ser Pro Lys
260 265 270

Leu Val Asp Ile Val Lys Arg Tyr Lys Arg Glu Ala Lys Ile Leu Ile
275 280 285

Asn Lys Leu Ala Phe Gly Met Leu Trp Arg His Arg Ala Lys Ser Gln
290 295 300

Ile Leu Thr Glu Gly Ser Val Arg Leu Asp Leu Gln Gly Phe Thr Glu
305 310 315 320

Ser Lys Tyr Asn Tyr Gln Ile Gln Val Gly Ser His Thr Ile Ala Ala
325 330 335

Val Leu Ile Asp Met Asp Ile Ser Lys Ile Gln Ser Lys Ser Glu Gln
340 345 350

Ala Tyr Ala Ile Arg Lys Ile Lys Ser Gly Phe Gln Arg Ser Leu Asp
355 360 365

Asp Tyr His Ile Tyr Gln Ile Glu Arg Lys Gln Thr Phe Ser Phe Ser

```
    370                 375                 380

Pro Lys His Arg Ser Leu Ser Ser Thr Ser His Ser Glu Asp Ser Asp
385                 390                 395                 400

Leu Asp Leu Ser Glu Ala Ala Ala Phe Ser Gly Ser Leu Thr Cys Glu
                405                 410                 415

Phe Val Lys Lys Ser Thr Gln His Ala Lys Asn Thr Val Thr Cys Ser
            420                 425                 430

Thr Ala Ala His Ser Leu Tyr Thr Leu Lys Glu Asp Asp Ser Ser Asn
        435                 440                 445

Pro Ser Glu Lys Arg Leu Asp Ser Cys Phe Arg Asn Trp Ile Glu Asn
    450                 455                 460

Lys Leu Ser Ala Asn Ser Pro Asp Ser Trp Ser Ala Phe Ile Gln Lys
465                 470                 475                 480

Phe Gly Thr His Tyr Ile Ala Ser Ala Thr Phe Gly Gly Ile Gly Phe
                485                 490                 495

Gln Val Leu Lys Leu Ser Phe Glu Gln Val Glu Asp Leu His Ser Lys
            500                 505                 510

Lys Ile Ser Leu Glu Thr Ala Ala Ala Asn Ser Leu Leu Lys Gly Ser
        515                 520                 525

Val Ser Ser Ser Thr Glu Ser Gly Tyr Ser Ser Tyr Ser Ser Thr Ser
    530                 535                 540

Ser Ser His Thr Val Phe Leu Gly Gly Thr Val Leu Pro Ser Val His
545                 550                 555                 560

Asp Glu Arg Leu Asp Phe Lys Asp Trp Ser Glu Ser Val His Leu Glu
                565                 570                 575

Pro Val Pro Ile Gln Val Ser Leu Gln Pro Ile Thr Asn Leu Leu Val
            580                 585                 590

Pro Leu His Phe Pro Asn Ile Gly Ala Ala Glu Leu Ser Asn Lys Arg
        595                 600                 605

Glu Ser Leu Gln Gln Ala Ile Arg Val Tyr Leu Lys Glu His Lys Val
    610                 615                 620

Asp Glu Gln Gly Glu Arg Thr Thr Phe Thr Ser Gly Ile Asp Asn Pro
625                 630                 635                 640

Ser Ser Trp Phe Thr Leu Glu Ala Ala His Ser Pro Leu Ile Val Ser
                645                 650                 655

Thr Pro Tyr Ile Ala Ser Trp Ser Thr Leu Pro Tyr Leu Phe Pro Thr
            660                 665                 670

Leu Arg Glu Arg Ser Ser Ala Thr Pro Ile Val Phe Tyr Phe Cys Val
        675                 680                 685

Asp Asn Asn Glu His Ala Ser Gln Lys Ile Leu Asn Gln Ser Tyr Cys
    690                 695                 700

Phe Leu Gly Ser Leu Pro Ile Arg Gln Lys Ile Phe Gly Ser Glu Phe
705                 710                 715                 720

Ala Ser Phe Pro Tyr Leu Ser Phe Tyr Gly Asn Ala Lys Glu Ala Tyr
                725                 730                 735

Phe Asp Asn Thr Tyr Tyr Pro Thr Arg Cys Gly Trp Ile Val Glu Lys
            740                 745                 750

Leu Asn Thr Thr Gln Asp Gln Phe Leu Arg Asp Gly Asp Glu Val Arg
        755                 760                 765

Leu Lys His Val Ser Ser Gly Lys Tyr Leu Ala Thr Thr Pro Leu Lys
    770                 775                 780

Asp Thr His Gly Thr Leu Thr Arg Thr Thr Asn Cys Glu Asp Ala Ile
785                 790                 795                 800
```

Phe Ile Ile Lys Lys Ser Ser Gly Tyr
805

<210> SEQ ID NO 67
<211> LENGTH: 537
<212> TYPE: DNA
<213> ORGANISM: Chlamydia trachomatis

<400> SEQUENCE: 67
ggtaaagcac cgtctttgca ggctattcta gccgaagtcg aagacacctc ctctcgtcta 60
cacgctcatc acaatgagct tgctatgatc tctgaacgcc tcgatgagca agacacgaaa 120
ctacagcaac tttcgtcaac acaagatcat aacctacctc gacaagttca gcgactagaa 180
acggaccaaa aagctttggc aaaaacactg gcgattcttt cgcaatccgt ccaagatatt 240
cggtcttctg tacaaaataa attacaagaa atccaacaag aacaaaaaaa attagcacaa 300
aatttgcgag cgcttcgtaa ctctttacaa gctctcgttg atggctcttc tccagaaaat 360
tatattgatt tcctaactgg tgaaaccccg gaacatattc atattgttaa acaaggagag 420
accctgagca agatcgcgag taaatataac atccccgtcg tagaattaaa aaaacttaat 480
aaactaaatt cggatactat ttttacagat caaagaattc gccttccgaa aaagaaa 537

<210> SEQ ID NO 68
<211> LENGTH: 179
<212> TYPE: PRT
<213> ORGANISM: Chlamydia trachomatis

<400> SEQUENCE: 68

Gly Lys Ala Pro Ser Leu Gln Ala Ile Leu Ala Glu Val Glu Asp Thr
1 5 10 15

Ser Ser Arg Leu His Ala His His Asn Glu Leu Ala Met Ile Ser Glu
20 25 30

Arg Leu Asp Glu Gln Asp Thr Lys Leu Gln Gln Leu Ser Ser Thr Gln
35 40 45

Asp His Asn Leu Pro Arg Gln Val Gln Arg Leu Glu Thr Asp Gln Lys
50 55 60

Ala Leu Ala Lys Thr Leu Ala Ile Leu Ser Gln Ser Val Gln Asp Ile
65 70 75 80

Arg Ser Ser Val Gln Asn Lys Leu Gln Glu Ile Gln Gln Glu Gln Lys
85 90 95

Lys Leu Ala Gln Asn Leu Arg Ala Leu Arg Asn Ser Leu Gln Ala Leu
100 105 110

Val Asp Gly Ser Ser Pro Glu Asn Tyr Ile Asp Phe Leu Thr Gly Glu
115 120 125

Thr Pro Glu His Ile His Ile Val Lys Gln Gly Glu Thr Leu Ser Lys
130 135 140

Ile Ala Ser Lys Tyr Asn Ile Pro Val Val Glu Leu Lys Lys Leu Asn
145 150 155 160

Lys Leu Asn Ser Asp Thr Ile Phe Thr Asp Gln Arg Ile Arg Leu Pro
165 170 175

Lys Lys Lys

<210> SEQ ID NO 69
<211> LENGTH: 780
<212> TYPE: DNA
<213> ORGANISM: Chlamydia trachomatis

<400> SEQUENCE: 69

```
gcacaagtaa tttcttccga taacacattc caagtctatg aaaagggaga ttggcaccca     60

gccctatata atactaaaaa gcagttgcta gagatctcct ctactcctcc taaagtaacc    120

gtgacaactt taagctcata ttttcaaaac tttgttagag tcttgcttac agatacacaa    180

ggaaatcttt cttcattcga agaccataat ctcaatctag aagaattttt atctcaacca    240

actcctgtaa tacatggtct tgccctttat gtggtctacg ctatcctaca caacgatgca    300

gcttcctcta aattatctgc ttcccaagta gcgaaaaatc caacagctat agaatctata    360

gttcttccta tagaaggttt tggtttgtgg ggacctatct atggattcct tgctctagaa    420

aaagacggga atactgttct tggtacttct tggtatcaac atggcgagac tcctggatta    480

ggagcaaata tcgctaaccc tcaatggcaa aaaaatttca gaggcaaaaa agtatttcta    540

gtctcagctt ctggagaaac agattttgct aagacaaccc taggactgga agttataaaa    600

ggatctgtat ctgcagcatt aggagactca cctaaagctg cttcttccat cgacggaatt    660

tcaggagcta ctttgacttg taatggtgtt accgaatcct tctctcattc tctagctccc    720

taccgcgctt tgttgacttt cttcgccaac tctaaaccta gtggagagtc tcatgaccac    780
```

```
<210> SEQ ID NO 70
<211> LENGTH: 260
<212> TYPE: PRT
<213> ORGANISM: Chlamydia trachomatis

<400> SEQUENCE: 70

Ala Gln Val Ile Ser Ser Asp Asn Thr Phe Gln Val Tyr Glu Lys Gly
1               5                   10                  15

Asp Trp His Pro Ala Leu Tyr Asn Thr Lys Lys Gln Leu Leu Glu Ile
            20                  25                  30

Ser Ser Thr Pro Pro Lys Val Thr Val Thr Thr Leu Ser Ser Tyr Phe
        35                  40                  45

Gln Asn Phe Val Arg Val Leu Leu Thr Asp Thr Gln Gly Asn Leu Ser
    50                  55                  60

Ser Phe Glu Asp His Asn Leu Asn Leu Glu Glu Phe Leu Ser Gln Pro
65                  70                  75                  80

Thr Pro Val Ile His Gly Leu Ala Leu Tyr Val Val Tyr Ala Ile Leu
                85                  90                  95

His Asn Asp Ala Ala Ser Ser Lys Leu Ser Ala Ser Gln Val Ala Lys
            100                 105                 110

Asn Pro Thr Ala Ile Glu Ser Ile Val Leu Pro Ile Glu Gly Phe Gly
        115                 120                 125

Leu Trp Gly Pro Ile Tyr Gly Phe Leu Ala Leu Glu Lys Asp Gly Asn
    130                 135                 140

Thr Val Leu Gly Thr Ser Trp Tyr Gln His Gly Glu Thr Pro Gly Leu
145                 150                 155                 160

Gly Ala Asn Ile Ala Asn Pro Gln Trp Gln Lys Asn Phe Arg Gly Lys
                165                 170                 175

Lys Val Phe Leu Val Ser Ala Ser Gly Glu Thr Asp Phe Ala Lys Thr
            180                 185                 190

Thr Leu Gly Leu Glu Val Ile Lys Gly Ser Val Ser Ala Ala Leu Gly
        195                 200                 205

Asp Ser Pro Lys Ala Ala Ser Ser Ile Asp Gly Ile Ser Gly Ala Thr
    210                 215                 220

Leu Thr Cys Asn Gly Val Thr Glu Ser Phe Ser His Ser Leu Ala Pro
225                 230                 235                 240

Tyr Arg Ala Leu Leu Thr Phe Phe Ala Asn Ser Lys Pro Ser Gly Glu
```

-continued 245 250 255

Ser His Asp His
260

<210> SEQ ID NO 71
<211> LENGTH: 1572
<212> TYPE: DNA
<213> ORGANISM: Chlamydia trachomatis

<400> SEQUENCE: 71
ggggtgttag agacctctat ggcagagtct ctctctacaa acgttattag cttagctgac 60
accaaagcga aagacaacac ttctcataaa agcaaaaaag caagaaaaaa ccacagcaaa 120
gagactcccg tagaccgtaa agaggttgct ccggttcatg agtctaaagc tacaggacct 180
aaacaggatt cttgctttgg cagaatgtat acagtcaaag ttaatgatga tcgcaatgtt 240
gaaatcacac aagctgttcc tgaatatgct acggtaggat ctccctatcc tattgaaatt 300
actgctacag gtaaaaggga ttgtgttgat gttatcatta ctcagcaatt accatgtgaa 360
gcagagttcg tacgcagtga tccagcgaca actcctactg ctgatggtaa gctagtttgg 420
aaaattgacc gcttaggaca aggcgaaaag agtaaaatta ctgtatgggt aaaacctctt 480
aaagaaggtt gctgctttac agctgcaaca gtatgcgctt gtccagagat ccgttcggtt 540
acaaaatgtg gacaacctgc tatctgtgtt aaacaagaag gcccagagaa tgcttgtttg 600
cgttgcccag tagtttacaa aattaatata gtgaaccaag gaacagcaac agctcgtaac 660
gttgttgttg aaaatcctgt tccagatggt tacgctcatt cttctggaca gcgtgtactg 720
acgtttactc ttggagatat gcaacctgga gagcacagaa caattactgt agagttttgt 780
ccgcttaaac gtggtcgtgc taccaatata gcaacggttt cttactgtgg aggacataaa 840
aatacagcaa gcgtaacaac tgtgatcaac gagccttgcg tacaagtaag tattgcagga 900
gcagattggt cttatgtttg taagcctgta gaatatgtga tctccgtttc caatcctgga 960
gatcttgtgt tgcgagatgt cgtcgttgaa gacactcttt ctcccggagt cacagttctt 1020
gaagctgcag gagctcaaat ttcttgtaat aaagtagttt ggactgtgaa agaactgaat 1080
cctggagagt ctctacagta taaagttcta gtaagagcac aaactcctgg acaattcaca 1140
aataatgttg ttgtgaagag ctgctctgac tgtggtactt gtacttcttg cgcagaagcg 1200
acaacttact ggaaaggagt tgctgctact catatgtgcg tagtagatac ttgtgaccct 1260
gtttgtgtag gagaaaatac tgtttaccgt atttgtgtca ccaacagagg ttctgcagaa 1320
gatacaaatg tttctttaat gcttaaattc tctaaagaac tgcaacctgt atccttctct 1380
ggaccaacta aaggaacgat tacaggcaat acagtagtat tcgattcgtt acctagatta 1440
ggttctaaag aaactgtaga gtttctgta acattgaaag cagtatcagc tggagatgct 1500
cgtggggaag cgattctttc ttccgataca ttgactgttc cagtttctga tacagagaat 1560
acacacatct at 1572

<210> SEQ ID NO 72
<211> LENGTH: 524
<212> TYPE: PRT
<213> ORGANISM: Chlamydia trachomatis

<400> SEQUENCE: 72

Gly Val Leu Glu Thr Ser Met Ala Glu Ser Leu Ser Thr Asn Val Ile
1 5 10 15

Ser Leu Ala Asp Thr Lys Ala Lys Asp Asn Thr Ser His Lys Ser Lys
20 25 30

```
Lys Ala Arg Lys Asn His Ser Lys Glu Thr Pro Val Asp Arg Lys Glu
        35                  40                  45

Val Ala Pro Val His Glu Ser Lys Ala Thr Gly Pro Lys Gln Asp Ser
    50                  55                  60

Cys Phe Gly Arg Met Tyr Thr Val Lys Val Asn Asp Asp Arg Asn Val
65                  70                  75                  80

Glu Ile Thr Gln Ala Val Pro Glu Tyr Ala Thr Val Gly Ser Pro Tyr
                85                  90                  95

Pro Ile Glu Ile Thr Ala Thr Gly Lys Arg Asp Cys Val Asp Val Ile
            100                 105                 110

Ile Thr Gln Gln Leu Pro Cys Glu Ala Glu Phe Val Arg Ser Asp Pro
        115                 120                 125

Ala Thr Thr Pro Thr Ala Asp Gly Lys Leu Val Trp Lys Ile Asp Arg
    130                 135                 140

Leu Gly Gln Gly Glu Lys Ser Lys Ile Thr Val Trp Val Lys Pro Leu
145                 150                 155                 160

Lys Glu Gly Cys Cys Phe Thr Ala Ala Thr Val Cys Ala Cys Pro Glu
                165                 170                 175

Ile Arg Ser Val Thr Lys Cys Gly Gln Pro Ala Ile Cys Val Lys Gln
            180                 185                 190

Glu Gly Pro Glu Asn Ala Cys Leu Arg Cys Pro Val Val Tyr Lys Ile
        195                 200                 205

Asn Ile Val Asn Gln Gly Thr Ala Thr Ala Arg Asn Val Val Val Glu
    210                 215                 220

Asn Pro Val Pro Asp Gly Tyr Ala His Ser Ser Gly Gln Arg Val Leu
225                 230                 235                 240

Thr Phe Thr Leu Gly Asp Met Gln Pro Gly Glu His Arg Thr Ile Thr
                245                 250                 255

Val Glu Phe Cys Pro Leu Lys Arg Gly Arg Ala Thr Asn Ile Ala Thr
            260                 265                 270

Val Ser Tyr Cys Gly Gly His Lys Asn Thr Ala Ser Val Thr Thr Val
        275                 280                 285

Ile Asn Glu Pro Cys Val Gln Val Ser Ile Ala Gly Ala Asp Trp Ser
    290                 295                 300

Tyr Val Cys Lys Pro Val Glu Tyr Val Ile Ser Val Ser Asn Pro Gly
305                 310                 315                 320

Asp Leu Val Leu Arg Asp Val Val Val Glu Asp Thr Leu Ser Pro Gly
                325                 330                 335

Val Thr Val Leu Glu Ala Ala Gly Ala Gln Ile Ser Cys Asn Lys Val
            340                 345                 350

Val Trp Thr Val Lys Glu Leu Asn Pro Gly Glu Ser Leu Gln Tyr Lys
        355                 360                 365

Val Leu Val Arg Ala Gln Thr Pro Gly Gln Phe Thr Asn Asn Val Val
    370                 375                 380

Val Lys Ser Cys Ser Asp Cys Gly Thr Cys Thr Ser Cys Ala Glu Ala
385                 390                 395                 400

Thr Thr Tyr Trp Lys Gly Val Ala Ala Thr His Met Cys Val Val Asp
                405                 410                 415

Thr Cys Asp Pro Val Cys Val Gly Glu Asn Thr Val Tyr Arg Ile Cys
            420                 425                 430

Val Thr Asn Arg Gly Ser Ala Glu Asp Thr Asn Val Ser Leu Met Leu
        435                 440                 445

Lys Phe Ser Lys Glu Leu Gln Pro Val Ser Phe Ser Gly Pro Thr Lys
```

-continued

```
    450                 455                 460

Gly Thr Ile Thr Gly Asn Thr Val Val Phe Asp Ser Leu Pro Arg Leu
465                 470                 475                 480

Gly Ser Lys Glu Thr Val Glu Phe Ser Val Thr Leu Lys Ala Val Ser
                485                 490                 495

Ala Gly Asp Ala Arg Gly Glu Ala Ile Leu Ser Ser Asp Thr Leu Thr
            500                 505                 510

Val Pro Val Ser Asp Thr Glu Asn Thr His Ile Tyr
        515                 520


<210> SEQ ID NO 73
<211> LENGTH: 1323
<212> TYPE: DNA
<213> ORGANISM: Chlamydia trachomatis

<400> SEQUENCE: 73

caggctgcac accatcacta tcaccgctac acagataaac tgcacagaca aaaccataaa     60

aaagatctca tctctcccaa acctaccgaa caagaggcgt gcaatacttc ttcccttagt    120

aaggaattaa tccctctatc agaacaaaga ggccttttat cccccatctg tgactttatt    180

tcggaacgcc cttgcttaca cggagtttct gttagaaatc tcaagcaagc gctaaaaaat    240

tctgcaggaa cccaaattgc actggattgg tctattctcc ctcaatggtt caatcctcgg    300

gtctctcatg cccctaagct ttctatccga gactttgggt atagcgcaca ccaaactgtt    360

accgaagcca ctcctccttg ctggcaaaac tgctttaatc catctgcggc cgttactatc    420

tatgattcct catatgggaa aggggtcttt caaatatcct atacccttgt ccgctattgg    480

agagagaatg ctgcgactgc tggcgatgct atgatgctcg cagggagtat caatgattat    540

ccctctcgtc agaacatttt ctctcagttt actttctccc aaaacttccc aaatgaacgg    600

gtgagtctga caattggtca gtactcactc tatgcaatag acggaacatt atacaataac    660

gatcaacaac ttggattcat tagttacgca ttatcacaaa atccaacagc aacttattcc    720

tctggaagtc ttggagctta cctacaagtc gctcctaccg caagcacaag tcttcaaata    780

ggatttcaag acgcttataa tatctccgga tcctctatca aatggagtaa ccttacaaaa    840

aatagataca attttcacgg ttttgcttcc tgggctcccc gctgttgctt aggatctggc    900

cagtactccg tgcttcttta tgtgactaga caagttccag aacagatgga acaaacaatg    960

ggatggtcag tcaatgcgag tcaacacata tcttctaaac tgtatgtgtt tggaagatac   1020

agcggtgtta caggacatgt gttcccgatt aaccgcacgt attcattcgg tatggcctct   1080

gcaaatttat ttaaccgtaa cccacaagat ttatttggaa ttgcttgcgc attcaataat   1140

gtacacctct ctgcttctcc aaatactaaa agaaaatacg aaactgtaat cgaagggttt   1200

gcaactatcg gttgcggccc ctatctttct ttcgctccag acttccaact ctacctctac   1260

ccagctcttc gtccaaacaa acaatctgcc cgtgtttata gcgtgcgagc taatttagct   1320

atc                                                                  1323


<210> SEQ ID NO 74
<211> LENGTH: 441
<212> TYPE: PRT
<213> ORGANISM: Chlamydia trachomatis

<400> SEQUENCE: 74

Gln Ala Ala His His His Tyr His Arg Tyr Thr Asp Lys Leu His Arg
1               5                   10                  15

Gln Asn His Lys Lys Asp Leu Ile Ser Pro Lys Pro Thr Glu Gln Glu
```

```
            20                  25                  30

Ala Cys Asn Thr Ser Ser Leu Ser Lys Glu Leu Ile Pro Leu Ser Glu
        35                  40                  45

Gln Arg Gly Leu Leu Ser Pro Ile Cys Asp Phe Ile Ser Glu Arg Pro
    50                  55                  60

Cys Leu His Gly Val Ser Val Arg Asn Leu Lys Gln Ala Leu Lys Asn
65                  70                  75                  80

Ser Ala Gly Thr Gln Ile Ala Leu Asp Trp Ser Ile Leu Pro Gln Trp
                85                  90                  95

Phe Asn Pro Arg Val Ser His Ala Pro Lys Leu Ser Ile Arg Asp Phe
            100                 105                 110

Gly Tyr Ser Ala His Gln Thr Val Thr Glu Ala Thr Pro Pro Cys Trp
        115                 120                 125

Gln Asn Cys Phe Asn Pro Ser Ala Ala Val Thr Ile Tyr Asp Ser Ser
    130                 135                 140

Tyr Gly Lys Gly Val Phe Gln Ile Ser Tyr Thr Leu Val Arg Tyr Trp
145                 150                 155                 160

Arg Glu Asn Ala Ala Thr Ala Gly Asp Ala Met Met Leu Ala Gly Ser
                165                 170                 175

Ile Asn Asp Tyr Pro Ser Arg Gln Asn Ile Phe Ser Gln Phe Thr Phe
            180                 185                 190

Ser Gln Asn Phe Pro Asn Glu Arg Val Ser Leu Thr Ile Gly Gln Tyr
        195                 200                 205

Ser Leu Tyr Ala Ile Asp Gly Thr Leu Tyr Asn Asn Asp Gln Gln Leu
    210                 215                 220

Gly Phe Ile Ser Tyr Ala Leu Ser Gln Asn Pro Thr Ala Thr Tyr Ser
225                 230                 235                 240

Ser Gly Ser Leu Gly Ala Tyr Leu Gln Val Ala Pro Thr Ala Ser Thr
                245                 250                 255

Ser Leu Gln Ile Gly Phe Gln Asp Ala Tyr Asn Ile Ser Gly Ser Ser
            260                 265                 270

Ile Lys Trp Ser Asn Leu Thr Lys Asn Arg Tyr Asn Phe His Gly Phe
        275                 280                 285

Ala Ser Trp Ala Pro Arg Cys Cys Leu Gly Ser Gly Gln Tyr Ser Val
    290                 295                 300

Leu Leu Tyr Val Thr Arg Gln Val Pro Glu Gln Met Glu Gln Thr Met
305                 310                 315                 320

Gly Trp Ser Val Asn Ala Ser Gln His Ile Ser Ser Lys Leu Tyr Val
                325                 330                 335

Phe Gly Arg Tyr Ser Gly Val Thr Gly His Val Phe Pro Ile Asn Arg
            340                 345                 350

Thr Tyr Ser Phe Gly Met Ala Ser Ala Asn Leu Phe Asn Arg Asn Pro
        355                 360                 365

Gln Asp Leu Phe Gly Ile Ala Cys Ala Phe Asn Asn Val His Leu Ser
    370                 375                 380

Ala Ser Pro Asn Thr Lys Arg Lys Tyr Glu Thr Val Ile Glu Gly Phe
385                 390                 395                 400

Ala Thr Ile Gly Cys Gly Pro Tyr Leu Ser Phe Ala Pro Asp Phe Gln
                405                 410                 415

Leu Tyr Leu Tyr Pro Ala Leu Arg Pro Asn Lys Gln Ser Ala Arg Val
            420                 425                 430

Tyr Ser Val Arg Ala Asn Leu Ala Ile
        435                 440
```

<210> SEQ ID NO 75
<211> LENGTH: 2871
<212> TYPE: DNA
<213> ORGANISM: Chlamydia trachomatis

<400> SEQUENCE: 75

```
acaaattcag cggctacatc ttctatccaa acgactggag agactgtagt aaactatacg     60
aattcagcct ccgcccccaa tgtaactgta tcgacctcct cttcttccac acaagccaca    120
gccacttcga ataaaacttc ccaagccgtt gctggaaaaa tcacttctcc agatacttca    180
gaaagctcag aaactagctc tacctcatca agcgatcata tccctagcga ttacgatgac    240
gttggtagca atagtggaga tattagcaac aactacgatg acgtaggtag taacaacgga    300
gatatcagta gcaattatga cgatgctgct gctgattacg agccgataag aactactgaa    360
aatatttatg agagtattgg tggctctaga acaagtggcc cagaaaatac aagtggtggt    420
gcagcagcag cactcaattc tctaagaggc tcctcctaca gcaattatga cgatgctgct    480
gctgattacg agccgataag aactactgaa aatatttatg agagtattgg tggctctaga    540
acaagtggcc cagaaaatac gagtggtggt gcagcagcag cactcaattc tctaagaggc    600
tcctcctaca gcaattatga cgatgctgct gctgattacg agccgataag aactactgaa    660
aatatttatg agagtattgg tggctctaga acaagtggcc cagaaaatac gagtgatggt    720
gcagcagcag cagcactcaa ttctctaaga ggctcctcct acacaacagg gcctcgtaac    780
gagggtgtat tcggccctgg accggaagga ctaccagaca tgtctcttcc ttcatacgat    840
cctacaaata aaacctcgtt attgactttc ctctccaacc ctcatgtaaa gtcgaaaatg    900
cttgaaaact cggggcattt cgtcttcatt gatacagata gaagtagttt cattcttgtt    960
cctaacggaa attgggacca agtctgttca attaaagttc aaaatggaaa gaccaaagaa   1020
gatctcgaca tcaaagactt ggaaaacatg tgtgcaaaat tctgtacagg gtttagcaaa   1080
ttctctggtg actgggacag tcttgtagaa cctatggtgt cagccaaagc tggagtggcc   1140
agcggaggca atcttcccaa tacagtgatt atcaataata aattcaaaac ttgcgttgct   1200
tatggtcctt ggaatagcca ggaagcaagt tctggttata caccttctgc ttggagacgt   1260
ggtcatcgag tagattttgg aggaattttt gagaaagcca acgactttaa taaaatcaac   1320
tggggaactc aagccgggcc tagtagcgaa gacgatggca tttccttctc caatgaaact   1380
cctggagctg gtcctgcagc tgctccatca ccaacgccat cctctattcc tatcatcaat   1440
gtcaatgtca atgttggcgg aactaatgtg aatattggag atacgaatgt caacacgact   1500
aacaccacac caacaactca atctacagac gcctctacag atacaagcga tatcgatgac   1560
ataaatacca acaaccaaac tgatgatatc aatacgacag acaaagactc tgacggagct   1620
ggtggagtca atggcgatat atccgaaaca gaatcctctt ctggagatga ttcaggaagt   1680
gtctcttcct cagaatcaga caagaatgcc tctgtcggaa atgacggacc tgctatgaaa   1740
gatatccttt ctgccgtgcg taaacaccta gacgtcgttt accctggcga aaatggcggt   1800
tctacagaag ggcctctccc agctaaccaa actctcggag acgtaatctc tgatgtagag   1860
aataaaggct ccgctcagga tacaaaattg tcaggaaata caggagctgg ggatgacgat   1920
ccaacaacca cagctgctgt aggtaatgga gcggaagaga tcactctttc cgacacagat   1980
tctggtatcg gagatgatgt atccgataca gcgtcttcat ctggggatga atccggagga   2040
gtctcctctc cctcttcaga atccaataaa aatactgccg ttggaaatga cggaccttct   2100
ggactagata tcctcgctgc cgtacgtaaa catttagata aggtttaccc tggcgacaat   2160
```

```
ggtggttcta cagaagggcc tctccaagct aaccaaactc ttggagatat cgtccaggat   2220

atggaaacaa cagggacatc ccaagaaacc gttgtatccc catggaaagg aagcacttct   2280

tcaacggaat cagcaggagg aagtggtagc gtacaaacac tactgccttc accacctcca   2340

accccgtcaa ctacaacatt aagaacgggc acaggagcta ccaccacatc cttgatgatg   2400

ggaggaccaa tcaaagctga cataataaca actggtggcg gaggacgaat tcctggagga   2460

ggaacgttag aaaagctgct ccctcgtata cgtgcgcact tagacatatc ctttgatgcg   2520

caaggcgatc tcgtaagtac tgaagagcct cagcttggct cgattgtaaa caaattccgc   2580

caagaaactg gttcaagagg aatcttagct ttcgttgaga gtgctccagg caagccggga   2640

tctgcacagg tcttaacggg tacaggggga gataaaggca acctattcca agcagctgcc   2700

gcagtcaccc aagccttagg aaatgttgca gggaaagtca accttgcgat acaaggccaa   2760

aaactatcat ccctagtcaa tgacgacggg aaggggtctg ttggaagaga tttattccaa   2820

gcagcagccc aaacaactca agtgctaagc gcactgattg ataccgtagg a            2871
```

<210> SEQ ID NO 76
<211> LENGTH: 957
<212> TYPE: PRT
<213> ORGANISM: Chlamydia trachomatis

<400> SEQUENCE: 76

```
Thr Asn Ser Ala Ala Thr Ser Ser Ile Gln Thr Thr Gly Glu Thr Val
1               5                   10                  15

Val Asn Tyr Thr Asn Ser Ala Ser Ala Pro Asn Val Thr Val Ser Thr
            20                  25                  30

Ser Ser Ser Ser Thr Gln Ala Thr Ala Thr Ser Asn Lys Thr Ser Gln
        35                  40                  45

Ala Val Ala Gly Lys Ile Thr Ser Pro Asp Thr Ser Glu Ser Ser Glu
    50                  55                  60

Thr Ser Ser Thr Ser Ser Ser Asp His Ile Pro Ser Asp Tyr Asp Asp
65                  70                  75                  80

Val Gly Ser Asn Ser Gly Asp Ile Ser Asn Asn Tyr Asp Asp Val Gly
                85                  90                  95

Ser Asn Asn Gly Asp Ile Ser Ser Asn Tyr Asp Asp Ala Ala Ala Asp
            100                 105                 110

Tyr Glu Pro Ile Arg Thr Thr Glu Asn Ile Tyr Glu Ser Ile Gly Gly
        115                 120                 125

Ser Arg Thr Ser Gly Pro Glu Asn Thr Ser Gly Gly Ala Ala Ala Ala
    130                 135                 140

Leu Asn Ser Leu Arg Gly Ser Ser Tyr Ser Asn Tyr Asp Asp Ala Ala
145                 150                 155                 160

Ala Asp Tyr Glu Pro Ile Arg Thr Thr Glu Asn Ile Tyr Glu Ser Ile
                165                 170                 175

Gly Gly Ser Arg Thr Ser Gly Pro Glu Asn Thr Ser Gly Gly Ala Ala
            180                 185                 190

Ala Ala Leu Asn Ser Leu Arg Gly Ser Ser Tyr Ser Asn Tyr Asp Asp
        195                 200                 205

Ala Ala Ala Asp Tyr Glu Pro Ile Arg Thr Thr Glu Asn Ile Tyr Glu
    210                 215                 220

Ser Ile Gly Gly Ser Arg Thr Ser Gly Pro Glu Asn Thr Ser Asp Gly
225                 230                 235                 240

Ala Ala Ala Ala Ala Leu Asn Ser Leu Arg Gly Ser Ser Tyr Thr Thr
                245                 250                 255
```

-continued

```
Gly Pro Arg Asn Glu Gly Val Phe Gly Pro Gly Pro Glu Gly Leu Pro
            260                 265                 270

Asp Met Ser Leu Pro Ser Tyr Asp Pro Thr Asn Lys Thr Ser Leu Leu
        275                 280                 285

Thr Phe Leu Ser Asn Pro His Val Lys Ser Lys Met Leu Glu Asn Ser
    290                 295                 300

Gly His Phe Val Phe Ile Asp Thr Asp Arg Ser Ser Phe Ile Leu Val
305                 310                 315                 320

Pro Asn Gly Asn Trp Asp Gln Val Cys Ser Ile Lys Val Gln Asn Gly
                325                 330                 335

Lys Thr Lys Glu Asp Leu Asp Ile Lys Asp Leu Glu Asn Met Cys Ala
            340                 345                 350

Lys Phe Cys Thr Gly Phe Ser Lys Phe Ser Gly Asp Trp Asp Ser Leu
        355                 360                 365

Val Glu Pro Met Val Ser Ala Lys Ala Gly Val Ala Ser Gly Gly Asn
    370                 375                 380

Leu Pro Asn Thr Val Ile Ile Asn Asn Lys Phe Lys Thr Cys Val Ala
385                 390                 395                 400

Tyr Gly Pro Trp Asn Ser Gln Glu Ala Ser Ser Gly Tyr Thr Pro Ser
                405                 410                 415

Ala Trp Arg Arg Gly His Arg Val Asp Phe Gly Gly Ile Phe Glu Lys
            420                 425                 430

Ala Asn Asp Phe Asn Lys Ile Asn Trp Gly Thr Gln Ala Gly Pro Ser
        435                 440                 445

Ser Glu Asp Asp Gly Ile Ser Phe Ser Asn Glu Thr Pro Gly Ala Gly
    450                 455                 460

Pro Ala Ala Ala Pro Ser Pro Thr Pro Ser Ser Ile Pro Ile Ile Asn
465                 470                 475                 480

Val Asn Val Asn Val Gly Gly Thr Asn Val Asn Ile Gly Asp Thr Asn
                485                 490                 495

Val Asn Thr Thr Asn Thr Thr Pro Thr Thr Gln Ser Thr Asp Ala Ser
            500                 505                 510

Thr Asp Thr Ser Asp Ile Asp Asp Ile Asn Thr Asn Asn Gln Thr Asp
        515                 520                 525

Asp Ile Asn Thr Thr Asp Lys Asp Ser Asp Gly Ala Gly Gly Val Asn
    530                 535                 540

Gly Asp Ile Ser Glu Thr Glu Ser Ser Ser Gly Asp Asp Ser Gly Ser
545                 550                 555                 560

Val Ser Ser Ser Glu Ser Asp Lys Asn Ala Ser Val Gly Asn Asp Gly
                565                 570                 575

Pro Ala Met Lys Asp Ile Leu Ser Ala Val Arg Lys His Leu Asp Val
            580                 585                 590

Val Tyr Pro Gly Glu Asn Gly Gly Ser Thr Glu Gly Pro Leu Pro Ala
        595                 600                 605

Asn Gln Thr Leu Gly Asp Val Ile Ser Asp Val Glu Asn Lys Gly Ser
    610                 615                 620

Ala Gln Asp Thr Lys Leu Ser Gly Asn Thr Gly Ala Gly Asp Asp Asp
625                 630                 635                 640

Pro Thr Thr Thr Ala Ala Val Gly Asn Gly Ala Glu Glu Ile Thr Leu
                645                 650                 655

Ser Asp Thr Asp Ser Gly Ile Gly Asp Asp Val Ser Asp Thr Ala Ser
            660                 665                 670

Ser Ser Gly Asp Glu Ser Gly Gly Val Ser Ser Pro Ser Ser Glu Ser
        675                 680                 685
```

```
Asn Lys Asn Thr Ala Val Gly Asn Asp Gly Pro Ser Gly Leu Asp Ile
    690                 695                 700

Leu Ala Ala Val Arg Lys His Leu Asp Lys Val Tyr Pro Gly Asp Asn
705                 710                 715                 720

Gly Gly Ser Thr Glu Gly Pro Leu Gln Ala Asn Gln Thr Leu Gly Asp
                725                 730                 735

Ile Val Gln Asp Met Glu Thr Thr Gly Thr Ser Gln Glu Thr Val Val
            740                 745                 750

Ser Pro Trp Lys Gly Ser Thr Ser Ser Thr Glu Ser Ala Gly Gly Ser
        755                 760                 765

Gly Ser Val Gln Thr Leu Leu Pro Ser Pro Pro Pro Thr Pro Ser Thr
    770                 775                 780

Thr Thr Leu Arg Thr Gly Thr Gly Ala Thr Thr Thr Ser Leu Met Met
785                 790                 795                 800

Gly Gly Pro Ile Lys Ala Asp Ile Ile Thr Thr Gly Gly Gly Gly Arg
                805                 810                 815

Ile Pro Gly Gly Gly Thr Leu Glu Lys Leu Leu Pro Arg Ile Arg Ala
            820                 825                 830

His Leu Asp Ile Ser Phe Asp Ala Gln Gly Asp Leu Val Ser Thr Glu
        835                 840                 845

Glu Pro Gln Leu Gly Ser Ile Val Asn Lys Phe Arg Gln Glu Thr Gly
    850                 855                 860

Ser Arg Gly Ile Leu Ala Phe Val Glu Ser Ala Pro Gly Lys Pro Gly
865                 870                 875                 880

Ser Ala Gln Val Leu Thr Gly Thr Gly Gly Asp Lys Gly Asn Leu Phe
                885                 890                 895

Gln Ala Ala Ala Ala Val Thr Gln Ala Leu Gly Asn Val Ala Gly Lys
            900                 905                 910

Val Asn Leu Ala Ile Gln Gly Gln Lys Leu Ser Ser Leu Val Asn Asp
        915                 920                 925

Asp Gly Lys Gly Ser Val Gly Arg Asp Leu Phe Gln Ala Ala Ala Gln
    930                 935                 940

Thr Thr Gln Val Leu Ser Ala Leu Ile Asp Thr Val Gly
945                 950                 955
```

<210> SEQ ID NO 77
<211> LENGTH: 702
<212> TYPE: DNA
<213> ORGANISM: Chlamydia trachomatis

<400> SEQUENCE: 77

```
tgtttaaaag aagggggaga ctccaatagt gaaaaattta ttgtagggac taatgcaacc      60

taccctcctt ttgagtttgt tgataagcga ggagaggttg taggcttcga tatagacttg     120

gctagagaga ttagtaacaa gctggggaaa acgctggacg ttcgggagtt ttcctttgat     180

gcactcattc taaacctaaa acagcatcgg attgatgcgg ttataacagg gatgtccatt     240

actccttcta gattgaagga aattcttatg attccctatt atggggagga aataaaacac     300

ttggttttag tgtttaaagg agagaataag catccattgc cactcactca atatcgttct     360

gtagctgttc aaacaggaac ctatcaagag gcctatttac agtctctttc tgaagttcat     420

attcgctctt ttgatagcac tctagaagta ctcatggaag tcatgcatgg taaatctccc     480

gtcgctgttt tagagccatc tatcgctcaa gttgtcttga aagatttccc ggctctttct     540

acagcaacca tagatctccc tgaagatcag tgggttttag gatacgggat tggcgttgct     600
```

```
tcagatcgcc cagctttagc cttgaaaatc gaggcagctg tgcaagagat ccgaaaagaa    660

ggagtgctag cagagttgga acagaagtgg ggtttgaaca ac                       702


<210> SEQ ID NO 78
<211> LENGTH: 234
<212> TYPE: PRT
<213> ORGANISM: Chlamydia trachomatis

<400> SEQUENCE: 78

Cys Leu Lys Glu Gly Gly Asp Ser Asn Ser Glu Lys Phe Ile Val Gly
1               5                   10                  15

Thr Asn Ala Thr Tyr Pro Pro Phe Glu Phe Val Asp Lys Arg Gly Glu
            20                  25                  30

Val Val Gly Phe Asp Ile Asp Leu Ala Arg Glu Ile Ser Asn Lys Leu
        35                  40                  45

Gly Lys Thr Leu Asp Val Arg Glu Phe Ser Phe Asp Ala Leu Ile Leu
    50                  55                  60

Asn Leu Lys Gln His Arg Ile Asp Ala Val Ile Thr Gly Met Ser Ile
65                  70                  75                  80

Thr Pro Ser Arg Leu Lys Glu Ile Leu Met Ile Pro Tyr Tyr Gly Glu
                85                  90                  95

Glu Ile Lys His Leu Val Leu Val Phe Lys Gly Glu Asn Lys His Pro
            100                 105                 110

Leu Pro Leu Thr Gln Tyr Arg Ser Val Ala Val Gln Thr Gly Thr Tyr
        115                 120                 125

Gln Glu Ala Tyr Leu Gln Ser Leu Ser Glu Val His Ile Arg Ser Phe
    130                 135                 140

Asp Ser Thr Leu Glu Val Leu Met Glu Val Met His Gly Lys Ser Pro
145                 150                 155                 160

Val Ala Val Leu Glu Pro Ser Ile Ala Gln Val Val Leu Lys Asp Phe
                165                 170                 175

Pro Ala Leu Ser Thr Ala Thr Ile Asp Leu Pro Glu Asp Gln Trp Val
            180                 185                 190

Leu Gly Tyr Gly Ile Gly Val Ala Ser Asp Arg Pro Ala Leu Ala Leu
        195                 200                 205

Lys Ile Glu Ala Ala Val Gln Glu Ile Arg Lys Glu Gly Val Leu Ala
    210                 215                 220

Glu Leu Glu Gln Lys Trp Gly Leu Asn Asn
225                 230


<210> SEQ ID NO 79
<211> LENGTH: 498
<212> TYPE: DNA
<213> ORGANISM: Chlamydia trachomatis

<400> SEQUENCE: 79

tccaggcaga atgctgagga aaatctaaaa aattttgcta aagagcttaa actccccgac     60

gtggccttcg atcagaataa tacgtgcatt ttgtttgttg atggagagtt ttctcttcac    120

ctgacctacg aagaacactc tgatcgcctt tatgtttacg cacctcttct tgacggactg    180

ccagacaatc cgcaaagaag gttagctcta tatgagaagt tgttagaagg ctctatgctc    240

ggaggccaaa tggctggtgg aggggtagga gtcgctacta aggaacagtt gatcttaatg    300

cactgcgtgt tagacatgaa gtatgcagag accaacctac tcaaagcttt tgcacagctt    360

tttattgaaa ccgttgtgaa atggcgaact gtttgttctg atatcagcgc tggacgagaa    420

cccactgttg ataccatgcc acaaatgcct caagggggtg gcggaggaat tcaacctcct    480
```

```
ccagcaggaa tccgtgca                                                    498


<210> SEQ ID NO 80
<211> LENGTH: 166
<212> TYPE: PRT
<213> ORGANISM: Chlamydia trachomatis

<400> SEQUENCE: 80

Ser Arg Gln Asn Ala Glu Glu Asn Leu Lys Asn Phe Ala Lys Glu Leu
1               5                   10                  15

Lys Leu Pro Asp Val Ala Phe Asp Gln Asn Asn Thr Cys Ile Leu Phe
            20                  25                  30

Val Asp Gly Glu Phe Ser Leu His Leu Thr Tyr Glu Glu His Ser Asp
        35                  40                  45

Arg Leu Tyr Val Tyr Ala Pro Leu Leu Asp Gly Leu Pro Asp Asn Pro
    50                  55                  60

Gln Arg Arg Leu Ala Leu Tyr Glu Lys Leu Leu Glu Gly Ser Met Leu
65                  70                  75                  80

Gly Gly Gln Met Ala Gly Gly Gly Val Gly Val Ala Thr Lys Glu Gln
                85                  90                  95

Leu Ile Leu Met His Cys Val Leu Asp Met Lys Tyr Ala Glu Thr Asn
            100                 105                 110

Leu Leu Lys Ala Phe Ala Gln Leu Phe Ile Glu Thr Val Val Lys Trp
        115                 120                 125

Arg Thr Val Cys Ser Asp Ile Ser Ala Gly Arg Glu Pro Thr Val Asp
    130                 135                 140

Thr Met Pro Gln Met Pro Gln Gly Gly Gly Gly Gly Ile Gln Pro Pro
145                 150                 155                 160

Pro Ala Gly Ile Arg Ala
                165


<210> SEQ ID NO 81
<211> LENGTH: 2298
<212> TYPE: DNA
<213> ORGANISM: Chlamydia trachomatis

<400> SEQUENCE: 81

tcaatacaac ctacatccat ttctttaact aagaatataa cggcagcttt agccggagag      60

caggtcgatg ctgctgcagt gtatatgccg caggctgttt ttttctttca gcaactggat     120

gaaaaaagca aggggctgaa acaggcttta ggattgctcg aagaggttga tctagaaaaa     180

tttataccgt ctttagaaaa atcacctaca cctatcacta cgggaacaac gagtaaaatt     240

tccgctgatg ggattgagat tgttggagag ctttcttcag aaacaatttt ggcagatcct     300

aataaagctg cagctcaggt tttggagag gggcttgcag atagttttga tgattggctc     360

agattatctg aaaatggggg gattcaagat cctacagcaa tagaagaaga gattgttact     420

aagtatcaaa cagaactcaa tactctgcgc aataaactca agcaacaatc tttaacagac     480

gatgagtata cgaagcttta tgctattcct caaaactttg ttaaagagat agaaagctta     540

aagaatgaaa ataatgtgag gttaattccc aaaagtaaag tcactaactt ttggcagaat     600

atcatgctca cttacaactc ggtaacctcg ttatcagaac ctgttaccga tgcgatgaat     660

acgactatgg cggagtactc tctttatatt gagagagcta cagaggctgc caagttgata     720

cgggagataa ccaacacgat caaagacatt ttcaatccag tttgggatgt gcgtgaacaa     780

acaggaattt ttgggttaaa aggagctgag tataacgctt tagaaggcaa tatgattcaa     840
```

```
agcttgctta gctttgcggg tctattccgg cagttaatga gtcgtactgc aacagttgat    900

gagataggcg cactttatcc taaaaatgat aaaaacgaag acgtcattca tactgctatt    960

gatgattatg tgaattcttt agctgatttg aaagccaatg aacaggtcaa actcaacggt   1020

ctgttgagtt tagtatatgc ttattatgct agtactttag gttttgctaa gaaggatgta   1080

ttcaataatg cacaagcttc ttttacagat tatactaatt ttctaaacca agagatccaa   1140

tattggacgc ctagagagac ttcaagtttt aatatctcca atcaagcatt gcaaaccttt   1200

aaaaataagc cttcggctga ttataacggc gtatatcttt ttgataataa aggattagag   1260

actaatctct ttaatcctac gttcttcttt gatgttgtga gtctcatgac agctgatcct   1320

acgaagacta tgtctcgaca ggattacaat aaggtgatta cagcctcgga atccagtatt   1380

cagaagatta atcaggctat taccgcttgg gaactagcta ttgcagaatg tgggactaaa   1440

aaagcgaagc tcgaaccatc cagtttaaat tattttaatg ctatggtcga agcgaagaag   1500

accttcgtag agacctctcc aatacagatg gtctattcat ctttgatgtt ggataagtat   1560

cttccgaatc agcagtacat attagagaca ttaggaagtc agatgacttt ctctaacaag   1620

gctgctcggt atttaaatga tatcattgcg tatgcagtta gcttccaaac agctgacgtc   1680

tattattctt tagggatgta tcttcgacaa atgaaccagc aggaatttcc tgaggtgatt   1740

tctcgtgcta acgatactgt gaaaaaagag atagatcgga gtcgtgcgga tctctttcac   1800

tgtaaaaaag ctatcgaaaa gattaaagaa ttagtgactt ctgtaaatgc ggatactgaa   1860

ttgacctcat ctcagcgtgc agagttatta gagacgttag ctagttatgc ttttgaattt   1920

gagaatctct atcacaacct ctctaatgtt tacgtcatgg tttctaaggt acagatttct   1980

ggcgtaagca agcctgatga agtggatgag gcttttactg ctaagattgg atcgaaggaa   2040

ttcgatactt ggattcagca gcttacaaca tttgaaagtg ctgtgattga aggtgggcgt   2100

aatggtgtga tgcctggggg agagcagcag gttttacaga gtttagagag caagcagcaa   2160

gattacacgt cgttcaacca gaatcagcaa ttagctctac aaatggagtc cgcagcgatt   2220

caacaagagt ggactatggt agcagcagcc ttagcattaa tgaatcagat tttgctaag    2280

ttgatccgta gatttaaa                                                 2298
```

<210> SEQ ID NO 82
<211> LENGTH: 766
<212> TYPE: PRT
<213> ORGANISM: Chlamydia trachomatis

<400> SEQUENCE: 82

```
Ser Ile Gln Pro Thr Ser Ile Ser Leu Thr Lys Asn Ile Thr Ala Ala
1               5                   10                  15

Leu Ala Gly Glu Gln Val Asp Ala Ala Ala Val Tyr Met Pro Gln Ala
            20                  25                  30

Val Phe Phe Phe Gln Gln Leu Asp Glu Lys Ser Lys Gly Leu Lys Gln
        35                  40                  45

Ala Leu Gly Leu Leu Glu Glu Val Asp Leu Glu Lys Phe Ile Pro Ser
    50                  55                  60

Leu Glu Lys Ser Pro Thr Pro Ile Thr Thr Gly Thr Thr Ser Lys Ile
65                  70                  75                  80

Ser Ala Asp Gly Ile Glu Ile Val Gly Glu Leu Ser Ser Glu Thr Ile
                85                  90                  95

Leu Ala Asp Pro Asn Lys Ala Ala Ala Gln Val Phe Gly Glu Gly Leu
            100                 105                 110

Ala Asp Ser Phe Asp Asp Trp Leu Arg Leu Ser Glu Asn Gly Gly Ile
```

```
        115                 120                 125

Gln Asp Pro Thr Ala Ile Glu Glu Glu Ile Val Thr Lys Tyr Gln Thr
    130                 135                 140

Glu Leu Asn Thr Leu Arg Asn Lys Leu Lys Gln Gln Ser Leu Thr Asp
145                 150                 155                 160

Asp Glu Tyr Thr Lys Leu Tyr Ala Ile Pro Gln Asn Phe Val Lys Glu
                165                 170                 175

Ile Glu Ser Leu Lys Asn Glu Asn Asn Val Arg Leu Ile Pro Lys Ser
            180                 185                 190

Lys Val Thr Asn Phe Trp Gln Asn Ile Met Leu Thr Tyr Asn Ser Val
        195                 200                 205

Thr Ser Leu Ser Glu Pro Val Thr Asp Ala Met Asn Thr Thr Met Ala
    210                 215                 220

Glu Tyr Ser Leu Tyr Ile Glu Arg Ala Thr Glu Ala Ala Lys Leu Ile
225                 230                 235                 240

Arg Glu Ile Thr Asn Thr Ile Lys Asp Ile Phe Asn Pro Val Trp Asp
                245                 250                 255

Val Arg Glu Gln Thr Gly Ile Phe Gly Leu Lys Gly Ala Glu Tyr Asn
            260                 265                 270

Ala Leu Glu Gly Asn Met Ile Gln Ser Leu Leu Ser Phe Ala Gly Leu
        275                 280                 285

Phe Arg Gln Leu Met Ser Arg Thr Ala Thr Val Asp Glu Ile Gly Ala
    290                 295                 300

Leu Tyr Pro Lys Asn Asp Lys Asn Glu Asp Val Ile His Thr Ala Ile
305                 310                 315                 320

Asp Asp Tyr Val Asn Ser Leu Ala Asp Leu Lys Ala Asn Glu Gln Val
                325                 330                 335

Lys Leu Asn Gly Leu Leu Ser Leu Val Tyr Ala Tyr Tyr Ala Ser Thr
            340                 345                 350

Leu Gly Phe Ala Lys Lys Asp Val Phe Asn Asn Ala Gln Ala Ser Phe
        355                 360                 365

Thr Asp Tyr Thr Asn Phe Leu Asn Gln Glu Ile Gln Tyr Trp Thr Pro
    370                 375                 380

Arg Glu Thr Ser Ser Phe Asn Ile Ser Asn Gln Ala Leu Gln Thr Phe
385                 390                 395                 400

Lys Asn Lys Pro Ser Ala Asp Tyr Asn Gly Val Tyr Leu Phe Asp Asn
                405                 410                 415

Lys Gly Leu Glu Thr Asn Leu Phe Asn Pro Thr Phe Phe Phe Asp Val
            420                 425                 430

Val Ser Leu Met Thr Ala Asp Pro Thr Lys Thr Met Ser Arg Gln Asp
        435                 440                 445

Tyr Asn Lys Val Ile Thr Ala Ser Glu Ser Ser Ile Gln Lys Ile Asn
    450                 455                 460

Gln Ala Ile Thr Ala Trp Glu Leu Ala Ile Ala Glu Cys Gly Thr Lys
465                 470                 475                 480

Lys Ala Lys Leu Glu Pro Ser Ser Leu Asn Tyr Phe Asn Ala Met Val
                485                 490                 495

Glu Ala Lys Lys Thr Phe Val Glu Thr Ser Pro Ile Gln Met Val Tyr
            500                 505                 510

Ser Ser Leu Met Leu Asp Lys Tyr Leu Pro Asn Gln Gln Tyr Ile Leu
        515                 520                 525

Glu Thr Leu Gly Ser Gln Met Thr Phe Ser Asn Lys Ala Ala Arg Tyr
    530                 535                 540
```

```
Leu Asn Asp Ile Ile Ala Tyr Ala Val Ser Phe Gln Thr Ala Asp Val
545                 550                 555                 560

Tyr Tyr Ser Leu Gly Met Tyr Leu Arg Gln Met Asn Gln Gln Glu Phe
                565                 570                 575

Pro Glu Val Ile Ser Arg Ala Asn Asp Thr Val Lys Lys Glu Ile Asp
            580                 585                 590

Arg Ser Arg Ala Asp Leu Phe His Cys Lys Lys Ala Ile Glu Lys Ile
        595                 600                 605

Lys Glu Leu Val Thr Ser Val Asn Ala Asp Thr Glu Leu Thr Ser Ser
    610                 615                 620

Gln Arg Ala Glu Leu Leu Glu Thr Leu Ala Ser Tyr Ala Phe Glu Phe
625                 630                 635                 640

Glu Asn Leu Tyr His Asn Leu Ser Asn Val Tyr Val Met Val Ser Lys
                645                 650                 655

Val Gln Ile Ser Gly Val Ser Lys Pro Asp Glu Val Asp Glu Ala Phe
            660                 665                 670

Thr Ala Lys Ile Gly Ser Lys Glu Phe Asp Thr Trp Ile Gln Gln Leu
        675                 680                 685

Thr Thr Phe Glu Ser Ala Val Ile Glu Gly Gly Arg Asn Gly Val Met
    690                 695                 700

Pro Gly Gly Glu Gln Gln Val Leu Gln Ser Leu Glu Ser Lys Gln Gln
705                 710                 715                 720

Asp Tyr Thr Ser Phe Asn Gln Asn Gln Gln Leu Ala Leu Gln Met Glu
                725                 730                 735

Ser Ala Ala Ile Gln Gln Glu Trp Thr Met Val Ala Ala Ala Leu Ala
            740                 745                 750

Leu Met Asn Gln Ile Phe Ala Lys Leu Ile Arg Arg Phe Lys
        755                 760                 765


<210> SEQ ID NO 83
<211> LENGTH: 1296
<212> TYPE: DNA
<213> ORGANISM: Chlamydia trachomatis

<400> SEQUENCE: 83

gatcctttga gtgcaaaaca gttaatgtat ctgtttcctc agctctcaga agaggatgta     60

tctgtttttg ctcgatgcat tttgtcttca aagcgtccag aatacctctt ttcaaaatcg    120

gaggaagagc tctttgcaaa attgattttg ccaagggttt ctctaggtgt tcatcgggac    180

gatgatttag cgagagtgtt ggtgttagcg gagccttctg cagaagagca gaaggctcga    240

tactattcat tgtatctgga tgttttagct ttgcgtgcat acgttgaaag agagcgtttg    300

gcgagtgctg cacacggaga tcctgagcgg atagatttgg caaccataga agctattaat    360

accatccttt ttcaggaaga aggatggagg tatccttcaa aacaagagat gtttgaaaac    420

aggttttctg agttagctgc tgttacagat agtaagtttg gagtttgctt gggaactgta    480

gtgctttatc aagctgtcgc ccagcggctt gatttgtctc tggaccctgt cacccctcct    540

ggacatattt acttacgcta taaggacaag gtgaatattg aaaccacttc tggaggaagg    600

catcttccta ctgaaaggta ttgtgaatgc ataaaaagagt cgcagttaaa ggtgcgttcg    660

cagatggagc ttatagggtt aacttttatg aatagaggag ctttcttttt gcaaaaagga    720

gagtttcttc aggcgtcctt agcttatgag caagctcaat catatttatc agacgagcag    780

atttctgatt tgttagggat tacttatgtt cttttaggaa agaaggcggc gggagaggct    840

cttttaaaga aatctgcaga aaagactcgg cgagggtcat ctatctatga ctatttccaa    900
```

```
ggatatattt cccccgaaat cctaggggtg ttgtttgccg attcaggggt gacctatcaa    960

gaaactttgg agtatcgaaa aaaactagtg atgctttcca agaagtatcc aaaaagtgga   1020

tctcttaggt tgaggttggc gacaacagca ttggagctag ggctggtcaa ggagggggtg   1080

cagttgttag aagagagtgt taaggatgcc ccagaggacc tctctttacg tctgcagttt   1140

tgtaaaattc tttgcaatcg acatgattat gtccgagcaa aatatcattt tgatcaagcg   1200

caagctcttc tcattaaaga agggttgttt tccgaaaaaa cttcctatac tctcttaaaa   1260

actatcggga aaaagctatc tctttttgct ccgagt                             1296


<210> SEQ ID NO 84
<211> LENGTH: 432
<212> TYPE: PRT
<213> ORGANISM: Chlamydia trachomatis

<400> SEQUENCE: 84

Asp Pro Leu Ser Ala Lys Gln Leu Met Tyr Leu Phe Pro Gln Leu Ser
1               5                   10                  15

Glu Glu Asp Val Ser Val Phe Ala Arg Cys Ile Leu Ser Ser Lys Arg
            20                  25                  30

Pro Glu Tyr Leu Phe Ser Lys Ser Glu Glu Glu Leu Phe Ala Lys Leu
        35                  40                  45

Ile Leu Pro Arg Val Ser Leu Gly Val His Arg Asp Asp Asp Leu Ala
    50                  55                  60

Arg Val Leu Val Leu Ala Glu Pro Ser Ala Glu Glu Gln Lys Ala Arg
65                  70                  75                  80

Tyr Tyr Ser Leu Tyr Leu Asp Val Leu Ala Leu Arg Ala Tyr Val Glu
                85                  90                  95

Arg Glu Arg Leu Ala Ser Ala Ala His Gly Asp Pro Glu Arg Ile Asp
            100                 105                 110

Leu Ala Thr Ile Glu Ala Ile Asn Thr Ile Leu Phe Gln Glu Glu Gly
        115                 120                 125

Trp Arg Tyr Pro Ser Lys Gln Glu Met Phe Glu Asn Arg Phe Ser Glu
    130                 135                 140

Leu Ala Ala Val Thr Asp Ser Lys Phe Gly Val Cys Leu Gly Thr Val
145                 150                 155                 160

Val Leu Tyr Gln Ala Val Ala Gln Arg Leu Asp Leu Ser Leu Asp Pro
                165                 170                 175

Val Thr Pro Pro Gly His Ile Tyr Leu Arg Tyr Lys Asp Lys Val Asn
            180                 185                 190

Ile Glu Thr Thr Ser Gly Gly Arg His Leu Pro Thr Glu Arg Tyr Cys
        195                 200                 205

Glu Cys Ile Lys Glu Ser Gln Leu Lys Val Arg Ser Gln Met Glu Leu
    210                 215                 220

Ile Gly Leu Thr Phe Met Asn Arg Gly Ala Phe Phe Leu Gln Lys Gly
225                 230                 235                 240

Glu Phe Leu Gln Ala Ser Leu Ala Tyr Glu Gln Ala Gln Ser Tyr Leu
                245                 250                 255

Ser Asp Glu Gln Ile Ser Asp Leu Leu Gly Ile Thr Tyr Val Leu Leu
            260                 265                 270

Gly Lys Lys Ala Ala Gly Glu Ala Leu Leu Lys Lys Ser Ala Glu Lys
        275                 280                 285

Thr Arg Arg Gly Ser Ser Ile Tyr Asp Tyr Phe Gln Gly Tyr Ile Ser
    290                 295                 300

Pro Glu Ile Leu Gly Val Leu Phe Ala Asp Ser Gly Val Thr Tyr Gln
```

```
305                 310                 315                 320

Glu Thr Leu Glu Tyr Arg Lys Lys Leu Val Met Leu Ser Lys Lys Tyr
                325                 330                 335

Pro Lys Ser Gly Ser Leu Arg Leu Arg Leu Ala Thr Thr Ala Leu Glu
            340                 345                 350

Leu Gly Leu Val Lys Glu Gly Val Gln Leu Leu Glu Glu Ser Val Lys
        355                 360                 365

Asp Ala Pro Glu Asp Leu Ser Leu Arg Leu Gln Phe Cys Lys Ile Leu
    370                 375                 380

Cys Asn Arg His Asp Tyr Val Arg Ala Lys Tyr His Phe Asp Gln Ala
385                 390                 395                 400

Gln Ala Leu Leu Ile Lys Glu Gly Leu Phe Ser Glu Lys Thr Ser Tyr
        405                 410                 415

Thr Leu Leu Lys Thr Ile Gly Lys Lys Leu Ser Leu Phe Ala Pro Ser
    420                 425                 430


<210> SEQ ID NO 85
<211> LENGTH: 2031
<212> TYPE: DNA
<213> ORGANISM: Chlamydia trachomatis

<400> SEQUENCE: 85

tcttcagatc tacttgaaaa agatgtgaaa tcgatcaaaa gagaactcaa ggctttacat      60

gaagatgttc ttgagttagt ccggatctcg catcagcaaa aaaattgggt ccagtctaca     120

gatttttctg tttctccaga gatcagtgta ttgaaggatt gcggagatcc tgcgttccct     180

aatttattat gcgaagaccc ttatgttgaa aaagtggtcc cttcgttgtt aaaggaaggt     240

tttgttccga aaggtatttt gcgtacagct caagtaggaa ggcctgataa cctaagtccg     300

tttaatggct ttgttaatat cgttcgattt tatgaattgt gcgttcctaa tttggctgtt     360

gagcatgttg gtaaatacga ggagtttgcg cctagtttag ccttaaagat agaagagcat     420

tatgtagagg atgggtctgg ggataaagaa tttcatattt atttgcgtcc taatatgttt     480

tgggagccga tagatcctac gctgttccct aaaaatataa ctttagcaga cagcttctta     540

agaccacatc ctgtcaccgc tcatgatgtg aagttctatt acgatgtagt catgaatccc     600

tatgttgcag aaatgcgtgc agtggctatg agatcttatt ttgaggatat ggtttcggtt     660

cgggtagaaa acgatttgaa attaatcgtt cgttggagag ctcatactgt acgtaatgaa     720

cagggagagg aagagaaaaa agtgctctat tctgctttcg cgaatacatt ggcactccaa     780

ccgttacctt gtttcgtgta tcagcatttc gcaaatggag agaagatcgt tccagaagat     840

tctgatcccg atacgtatcg caaagattcg gtatgggcgc aaaacttttc ttcacattgg     900

gcgtataatt acatagtgag ctgtggagca ttccgatttg cagggatgga tgatgagaaa     960

attactttag ttcgtaatcc taattatcat aatccgtttg cggctcttgt ggagaagcgc    1020

tatatctata tgaaagatag tacagattct ctcttccaag atttcaaagc tgggaaggtg    1080

gatattgcgt atttccctcc taaccatgtc gataatctag cgagcttcat gcaaacctct    1140

gcttataagg aacaagctgc tagaggagag gcaattttag aaaaaaattc atcagaccgg    1200

tcctattctt acatcggatg gaattgtctt tctcttttct ttaacaatcg ttcggtacga    1260

caagccatga atatgttgat cgatcgggat cgcattattg agcagtgctt ggatggtcgt    1320

ggagtctctg tgagtgggcc tttttctctc tgctctccat catacaacag agatgtagag    1380

ggatggcaat actctccgga agaggccgca cgtaaattag aggaagaggg ctggatcgat    1440

gctgatggag atggtattcg tgagaaagta atcgatggag ttgtagtgcc tttccgtttc    1500
```

-continued

```
cggttatgct actatgtgaa aagtgtaaca gcacgaacga ttgccgaata tgtagctacg   1560

gtatgtaaag aggtgggtat cgagtgttgc ttactcgggt tagatatggc ggattattca   1620

caagccctcg aggagaaaaa tttcgatgct attctttccg gatggtgttt aggaacccct   1680

ccagaagatc ctcgtgctct atggcattcg gaaggagctt tggagaaagg atctgccaat   1740

gctgttggat tttgtaatga ggaagcagac cgtatcatcg aacagctcag ttacgagtat   1800

gattctaata agcgccaagc cttgtatcac cgttttcacg aggtgattca tgaggaatct   1860

ccttacgcgt ttctctattc aagacagtac tcccttgtct ataaggagtt tgtaaaaaat   1920

atttttgtgc caacagaaca tcaggatttg attcctggag ctcaagatga gacagtgaat   1980

ttatccatgt tgtgggtaga taaagaggag ggtcgatgct ccgctatatc t            2031
```

```
<210> SEQ ID NO 86
<211> LENGTH: 677
<212> TYPE: PRT
<213> ORGANISM: Chlamydia trachomatis

<400> SEQUENCE: 86

Ser Ser Asp Leu Leu Glu Lys Asp Val Lys Ser Ile Lys Arg Glu Leu
1               5                   10                  15

Lys Ala Leu His Glu Asp Val Leu Glu Leu Val Arg Ile Ser His Gln
            20                  25                  30

Gln Lys Asn Trp Val Gln Ser Thr Asp Phe Ser Val Ser Pro Glu Ile
        35                  40                  45

Ser Val Leu Lys Asp Cys Gly Asp Pro Ala Phe Pro Asn Leu Leu Cys
    50                  55                  60

Glu Asp Pro Tyr Val Glu Lys Val Val Pro Ser Leu Leu Lys Glu Gly
65                  70                  75                  80

Phe Val Pro Lys Gly Ile Leu Arg Thr Ala Gln Val Gly Arg Pro Asp
                85                  90                  95

Asn Leu Ser Pro Phe Asn Gly Phe Val Asn Ile Val Arg Phe Tyr Glu
            100                 105                 110

Leu Cys Val Pro Asn Leu Ala Val Glu His Val Gly Lys Tyr Glu Glu
        115                 120                 125

Phe Ala Pro Ser Leu Ala Leu Lys Ile Glu Glu His Tyr Val Glu Asp
    130                 135                 140

Gly Ser Gly Asp Lys Glu Phe His Ile Tyr Leu Arg Pro Asn Met Phe
145                 150                 155                 160

Trp Glu Pro Ile Asp Pro Thr Leu Phe Pro Lys Asn Ile Thr Leu Ala
                165                 170                 175

Asp Ser Phe Leu Arg Pro His Pro Val Thr Ala His Asp Val Lys Phe
            180                 185                 190

Tyr Tyr Asp Val Val Met Asn Pro Tyr Val Ala Glu Met Arg Ala Val
        195                 200                 205

Ala Met Arg Ser Tyr Phe Glu Asp Met Val Ser Val Arg Val Glu Asn
    210                 215                 220

Asp Leu Lys Leu Ile Val Arg Trp Arg Ala His Thr Val Arg Asn Glu
225                 230                 235                 240

Gln Gly Glu Glu Glu Lys Lys Val Leu Tyr Ser Ala Phe Ala Asn Thr
                245                 250                 255

Leu Ala Leu Gln Pro Leu Pro Cys Phe Val Tyr Gln His Phe Ala Asn
            260                 265                 270

Gly Glu Lys Ile Val Pro Glu Asp Ser Asp Pro Asp Thr Tyr Arg Lys
        275                 280                 285
```

```
Asp Ser Val Trp Ala Gln Asn Phe Ser Ser His Trp Ala Tyr Asn Tyr
    290                 295                 300

Ile Val Ser Cys Gly Ala Phe Arg Phe Ala Gly Met Asp Asp Glu Lys
305                 310                 315                 320

Ile Thr Leu Val Arg Asn Pro Asn Tyr His Asn Pro Phe Ala Ala Leu
                325                 330                 335

Val Glu Lys Arg Tyr Ile Tyr Met Lys Asp Ser Thr Asp Ser Leu Phe
            340                 345                 350

Gln Asp Phe Lys Ala Gly Lys Val Asp Ile Ala Tyr Phe Pro Pro Asn
        355                 360                 365

His Val Asp Asn Leu Ala Ser Phe Met Gln Thr Ser Ala Tyr Lys Glu
    370                 375                 380

Gln Ala Ala Arg Gly Glu Ala Ile Leu Glu Lys Asn Ser Ser Asp Arg
385                 390                 395                 400

Ser Tyr Ser Tyr Ile Gly Trp Asn Cys Leu Ser Leu Phe Phe Asn Asn
                405                 410                 415

Arg Ser Val Arg Gln Ala Met Asn Met Leu Ile Asp Arg Asp Arg Ile
            420                 425                 430

Ile Glu Gln Cys Leu Asp Gly Arg Gly Val Ser Val Ser Gly Pro Phe
        435                 440                 445

Ser Leu Cys Ser Pro Ser Tyr Asn Arg Asp Val Glu Gly Trp Gln Tyr
    450                 455                 460

Ser Pro Glu Glu Ala Ala Arg Lys Leu Glu Glu Glu Gly Trp Ile Asp
465                 470                 475                 480

Ala Asp Gly Asp Gly Ile Arg Glu Lys Val Ile Asp Gly Val Val Val
                485                 490                 495

Pro Phe Arg Phe Arg Leu Cys Tyr Tyr Val Lys Ser Val Thr Ala Arg
            500                 505                 510

Thr Ile Ala Glu Tyr Val Ala Thr Val Cys Lys Glu Val Gly Ile Glu
        515                 520                 525

Cys Cys Leu Leu Gly Leu Asp Met Ala Asp Tyr Ser Gln Ala Leu Glu
    530                 535                 540

Glu Lys Asn Phe Asp Ala Ile Leu Ser Gly Trp Cys Leu Gly Thr Pro
545                 550                 555                 560

Pro Glu Asp Pro Arg Ala Leu Trp His Ser Glu Gly Ala Leu Glu Lys
                565                 570                 575

Gly Ser Ala Asn Ala Val Gly Phe Cys Asn Glu Glu Ala Asp Arg Ile
            580                 585                 590

Ile Glu Gln Leu Ser Tyr Glu Tyr Asp Ser Asn Lys Arg Gln Ala Leu
        595                 600                 605

Tyr His Arg Phe His Glu Val Ile His Glu Glu Ser Pro Tyr Ala Phe
    610                 615                 620

Leu Tyr Ser Arg Gln Tyr Ser Leu Val Tyr Lys Glu Phe Val Lys Asn
625                 630                 635                 640

Ile Phe Val Pro Thr Glu His Gln Asp Leu Ile Pro Gly Ala Gln Asp
                645                 650                 655

Glu Thr Val Asn Leu Ser Met Leu Trp Val Asp Lys Glu Glu Gly Arg
            660                 665                 670

Cys Ser Ala Ile Ser
        675
```

<210> SEQ ID NO 87
<211> LENGTH: 1194
<212> TYPE: DNA

<213> ORGANISM: Chlamydia trachomatis

<400> SEQUENCE: 87

```
gctgcagcta ctcaagatgc acaagaggtt atcggctctc aggaagcttc tgaggcaagt      60
atgctcaaag gatgtgagga tctcataaat cctgcagctg caacccgaat caaaaaaaaa     120
ggagagaagt ttgaatcatt agaagctcgt cgcaaaccaa cagcggataa agcagaaaag     180
aaatccgaga gcacagagga aaaaggcgat actcctcttg aagatcgttt cacagaagat     240
ctttccgaag tctccggaga agattttcga ggattgaaaa attcgttcga tgatgattct     300
tctcctgacg aaattctcga tgcgctcaca agtaaatttt ctgatcccac aataaaggat     360
ctagctcttg attatctaat tcaaacagct ccctctgatg ggaaacttaa gtccactctc     420
attcaggcaa agcatcaact gatgagccag aatcctcagg cgattgttgg aggacgcaat     480
gttctgttag cttcagaaac ctttgcttcc agagcaaata catctccttc atcgcttcgc     540
tccttatatt tccaagtaac ctcatccccc tctaattgcg ctaatttaca tcaaatgctt     600
gcttcttact tgccatcaga gaaaaccgct gttatggagt ttctagtaaa tggcatggta     660
gcagatttaa aatcggaggg cccttccatt cctcctgcaa aattgcaagt atatatgacg     720
gaactaagca atctccaagc cttacactct gtaaatagct tttttgatag aaatattggg     780
aacttggaaa atagcttaaa gcatgaagga catgccccta ttccatcctt aacgacagga     840
aatttaacta aaaccttctt acaattagta gaagataaat tcccttcctc ttccaaagct     900
caaaaggcat taaatgaact ggtaggccca gatactggtc ctcaaactga agttttaaac     960
ttattcttcc gcgctcttaa tggctgttcg cctagaatat tctctggagc tgaaaaaaaa    1020
cagcagctgg catcggttat cacaaatacg ctagatgcga taaatgcgga taatgaggat    1080
tatcctaaac caggtgactt cccacgatct tccttctcta gtacgcctcc tcatgctcca    1140
gtacctcaat ctgagattcc aacgtcacct acctcaacac agcctccatc accc          1194
```

<210> SEQ ID NO 88
<211> LENGTH: 398
<212> TYPE: PRT
<213> ORGANISM: Chlamydia trachomatis

<400> SEQUENCE: 88

```
Ala Ala Ala Thr Gln Asp Ala Gln Glu Val Ile Gly Ser Gln Glu Ala
1               5                   10                  15

Ser Glu Ala Ser Met Leu Lys Gly Cys Glu Asp Leu Ile Asn Pro Ala
            20                  25                  30

Ala Ala Thr Arg Ile Lys Lys Lys Gly Glu Lys Phe Glu Ser Leu Glu
        35                  40                  45

Ala Arg Arg Lys Pro Thr Ala Asp Lys Ala Glu Lys Lys Ser Glu Ser
    50                  55                  60

Thr Glu Glu Lys Gly Asp Thr Pro Leu Glu Asp Arg Phe Thr Glu Asp
65                  70                  75                  80

Leu Ser Glu Val Ser Gly Glu Asp Phe Arg Gly Leu Lys Asn Ser Phe
                85                  90                  95

Asp Asp Asp Ser Ser Pro Asp Glu Ile Leu Asp Ala Leu Thr Ser Lys
            100                 105                 110

Phe Ser Asp Pro Thr Ile Lys Asp Leu Ala Leu Asp Tyr Leu Ile Gln
        115                 120                 125

Thr Ala Pro Ser Asp Gly Lys Leu Lys Ser Thr Leu Ile Gln Ala Lys
    130                 135                 140

His Gln Leu Met Ser Gln Asn Pro Gln Ala Ile Val Gly Gly Arg Asn
```

```
145                 150                 155                 160

Val Leu Leu Ala Ser Glu Thr Phe Ala Ser Arg Ala Asn Thr Ser Pro
                165                 170                 175

Ser Ser Leu Arg Ser Leu Tyr Phe Gln Val Thr Ser Ser Pro Ser Asn
            180                 185                 190

Cys Ala Asn Leu His Gln Met Leu Ala Ser Tyr Leu Pro Ser Glu Lys
        195                 200                 205

Thr Ala Val Met Glu Phe Leu Val Asn Gly Met Val Ala Asp Leu Lys
    210                 215                 220

Ser Glu Gly Pro Ser Ile Pro Pro Ala Lys Leu Gln Val Tyr Met Thr
225                 230                 235                 240

Glu Leu Ser Asn Leu Gln Ala Leu His Ser Val Asn Ser Phe Phe Asp
                245                 250                 255

Arg Asn Ile Gly Asn Leu Glu Asn Ser Leu Lys His Glu Gly His Ala
            260                 265                 270

Pro Ile Pro Ser Leu Thr Thr Gly Asn Leu Thr Lys Thr Phe Leu Gln
        275                 280                 285

Leu Val Glu Asp Lys Phe Pro Ser Ser Ser Lys Ala Gln Lys Ala Leu
    290                 295                 300

Asn Glu Leu Val Gly Pro Asp Thr Gly Pro Gln Thr Glu Val Leu Asn
305                 310                 315                 320

Leu Phe Phe Arg Ala Leu Asn Gly Cys Ser Pro Arg Ile Phe Ser Gly
                325                 330                 335

Ala Glu Lys Lys Gln Gln Leu Ala Ser Val Ile Thr Asn Thr Leu Asp
            340                 345                 350

Ala Ile Asn Ala Asp Asn Glu Asp Tyr Pro Lys Pro Gly Asp Phe Pro
        355                 360                 365

Arg Ser Ser Phe Ser Ser Thr Pro Pro His Ala Pro Val Pro Gln Ser
    370                 375                 380

Glu Ile Pro Thr Ser Pro Thr Ser Thr Gln Pro Pro Ser Pro
385                 390                 395


<210> SEQ ID NO 89
<211> LENGTH: 591
<212> TYPE: DNA
<213> ORGANISM: Chlamydia trachomatis

<400> SEQUENCE: 89

tgttgcgcca actcttatgg atcgactctt gcaaaaaata cagccgagat aaaagaagaa      60

tctgttacac ttcgcgagaa gccggatgcc ggctgtaaaa agaaatcttc ttgttacttg     120

agaaaatttt tctcgcgcaa gaaacctaaa gagaagacag agcctgtgtt gccgaacttt     180

aagtcttacg cagatccaat gacagattcc gaaagaaaag acctttcttt cgtagtatct     240

gctgctgctg ataagtcttc tattgctttg gctatggctc aggggaaat taaaggcgca      300

ttatcgcgta ttagagagat ccatcctctt gcattgttac aagctcttgc agaagatcct     360

gctttaattg ctggaatgaa aaagatgcaa ggacgggatt gggtctggaa tatctttatc     420

acagaattaa gcaaagtttt ttctcaagca gcatctttag ggctttcag cgttgcagac      480

gttgccgcgt tcgcgtcgac cttaggatta gactcgggga ccgttacctc aattgttgat     540

ggggaaaggt gggctgagct gatcgatgtc gtgattcaga accctgctat a              591


<210> SEQ ID NO 90
<211> LENGTH: 197
<212> TYPE: PRT
<213> ORGANISM: Chlamydia trachomatis
```

<400> SEQUENCE: 90

```
Cys Cys Ala Asn Ser Tyr Gly Ser Thr Leu Ala Lys Asn Thr Ala Glu
1               5                   10                  15

Ile Lys Glu Glu Ser Val Thr Leu Arg Glu Lys Pro Asp Ala Gly Cys
            20                  25                  30

Lys Lys Lys Ser Ser Cys Tyr Leu Arg Lys Phe Phe Ser Arg Lys Lys
        35                  40                  45

Pro Lys Glu Lys Thr Glu Pro Val Leu Pro Asn Phe Lys Ser Tyr Ala
    50                  55                  60

Asp Pro Met Thr Asp Ser Glu Arg Lys Asp Leu Ser Phe Val Val Ser
65                  70                  75                  80

Ala Ala Ala Asp Lys Ser Ser Ile Ala Leu Ala Met Ala Gln Gly Glu
                85                  90                  95

Ile Lys Gly Ala Leu Ser Arg Ile Arg Glu Ile His Pro Leu Ala Leu
            100                 105                 110

Leu Gln Ala Leu Ala Glu Asp Pro Ala Leu Ile Ala Gly Met Lys Lys
        115                 120                 125

Met Gln Gly Arg Asp Trp Val Trp Asn Ile Phe Ile Thr Glu Leu Ser
    130                 135                 140

Lys Val Phe Ser Gln Ala Ala Ser Leu Gly Ala Phe Ser Val Ala Asp
145                 150                 155                 160

Val Ala Ala Phe Ala Ser Thr Leu Gly Leu Asp Ser Gly Thr Val Thr
                165                 170                 175

Ser Ile Val Asp Gly Glu Arg Trp Ala Glu Leu Ile Asp Val Val Ile
            180                 185                 190

Gln Asn Pro Ala Ile
        195
```

<210> SEQ ID NO 91
<211> LENGTH: 723
<212> TYPE: DNA
<213> ORGANISM: Chlamydia trachomatis

<400> SEQUENCE: 91

```
aaagttaaaa ttaatgatca gttcatttgt atttccccat acatttctgc tcgatggaat      60

cagatagctt tcatagagtc ttgtgatgga gggacggaag ggggtattac tttgaaactc     120

catttaattg atggagagac agtctctata cctaatctag gacaagcgat tgttgatgag     180

gtgttccaag agcacttgct atatttagag tccacagctc ctcagaaaaa caaggaagag     240

gaaaaaatta gctctttgtt aggagctgtt caacaaatgg ctaaaggatg cgaagtacag     300

gttttttctc aaaagggctt ggtttctatg ttactaggag gagctggttc gattaatgtg     360

ttgttgcaac attctccaga acataaggat catcctgatc ttcctaccga tttactggag     420

aggatagcgc aaatgatgcg ttcattatct ataggaccaa cttctatttt agctaagcca     480

gagcctcatt gcaactgttt gcattgtcaa attggacgag ctacagtgga agaagaggat     540

gccggagtat cggatgagga tcttactttt cgttcatggg atatctctca aagtggagaa     600

aagatgtaca ctgttacaga tcctttgaat ccagaagagc agtttaatgt gtatttagga     660

acgccgattg gatgcacatg tgggcagcca tactgtgaac acgtgaaagc tgttctttat     720

act                                                                   723
```

<210> SEQ ID NO 92
<211> LENGTH: 241
<212> TYPE: PRT

<213> ORGANISM: Chlamydia trachomatis

<400> SEQUENCE: 92

```
Lys Val Lys Ile Asn Asp Gln Phe Ile Cys Ile Ser Pro Tyr Ile Ser
1               5                   10                  15

Ala Arg Trp Asn Gln Ile Ala Phe Ile Glu Ser Cys Asp Gly Gly Thr
            20                  25                  30

Glu Gly Gly Ile Thr Leu Lys Leu His Leu Ile Asp Gly Glu Thr Val
        35                  40                  45

Ser Ile Pro Asn Leu Gly Gln Ala Ile Val Asp Glu Val Phe Gln Glu
    50                  55                  60

His Leu Leu Tyr Leu Glu Ser Thr Ala Pro Gln Lys Asn Lys Glu Glu
65                  70                  75                  80

Glu Lys Ile Ser Ser Leu Leu Gly Ala Val Gln Gln Met Ala Lys Gly
                85                  90                  95

Cys Glu Val Gln Val Phe Ser Gln Lys Gly Leu Val Ser Met Leu Leu
            100                 105                 110

Gly Gly Ala Gly Ser Ile Asn Val Leu Leu Gln His Ser Pro Glu His
        115                 120                 125

Lys Asp His Pro Asp Leu Pro Thr Asp Leu Leu Glu Arg Ile Ala Gln
    130                 135                 140

Met Met Arg Ser Leu Ser Ile Gly Pro Thr Ser Ile Leu Ala Lys Pro
145                 150                 155                 160

Glu Pro His Cys Asn Cys Leu His Cys Gln Ile Gly Arg Ala Thr Val
                165                 170                 175

Glu Glu Glu Asp Ala Gly Val Ser Asp Glu Asp Leu Thr Phe Arg Ser
            180                 185                 190

Trp Asp Ile Ser Gln Ser Gly Glu Lys Met Tyr Thr Val Thr Asp Pro
        195                 200                 205

Leu Asn Pro Glu Glu Gln Phe Asn Val Tyr Leu Gly Thr Pro Ile Gly
    210                 215                 220

Cys Thr Cys Gly Gln Pro Tyr Cys Glu His Val Lys Ala Val Leu Tyr
225                 230                 235                 240

Thr
```

<210> SEQ ID NO 93
<211> LENGTH: 951
<212> TYPE: DNA
<213> ORGANISM: Chlamydia muridarum

<400> SEQUENCE: 93

```
gcatccaagt ctcgtcatta tcttaaccag ccttggtaca ttatcttatt catctttgtt      60

cttagtctgg ttgctggtac ccttctttct tcagtttcct atgttctatc tccaatccaa     120

aaacaagctg cagaatttga tcgtaatcag caaatgttga tggccgcaca aattatttcc     180

tatgacaata aattccaaat atatgctgaa ggggattggc aacctgctgt ctataataca     240

aaaaaacaga tactagaaaa aagctcttcc actccaccac aagtgactgt ggcgactcta     300

tgctcttatt ttcaaaattt tgttagagtt ttgcttacag actcccaagg gaatctttct     360

tcttttgaag atcacaatct taacctagaa gagttcttat cccaccccac atcttcagta     420

caagatcact ctctgcatgt aatttatgct attctagcaa acgatgaatc ctctaaaaag     480

ttatcatcct cccaagtagc aaaaaatccg gtatccatag agtctattat tcttcctata     540

aaaggatttg gtttatgggg accaatctat ggatttcttg ctttagaaaa ggacggtaat     600

acggttctag ggacatgctg gtatcaacat ggtgagactc caggattagg agcaaatata     660
```

-continued actaatcccc aatggcaaca aaatttcaga ggaaaaaaag tatttctcgc ttcctcttcc 720
ggagaaaccg attttgctaa aacaactcta ggactagaag ttataaaagg atctgtttct 780
gcattattag ggactctcc caaagctaat tccgctgttg atggaatttc aggagctaca 840
ctgacctgta atggagttac tgaagctttt gctaattcgc tagctcctta ccgcccctta 900
ttgactttct tcgccaatct taactctagt ggagaatctc atgacaacca a 951

<210> SEQ ID NO 94
<211> LENGTH: 317
<212> TYPE: PRT
<213> ORGANISM: Chlamydia muridarum

<400> SEQUENCE: 94

Ala Ser Lys Ser Arg His Tyr Leu Asn Gln Pro Trp Tyr Ile Ile Leu
1 5 10 15

Phe Ile Phe Val Leu Ser Leu Val Ala Gly Thr Leu Leu Ser Ser Val
20 25 30

Ser Tyr Val Leu Ser Pro Ile Gln Lys Gln Ala Ala Glu Phe Asp Arg
35 40 45

Asn Gln Gln Met Leu Met Ala Ala Gln Ile Ile Ser Tyr Asp Asn Lys
50 55 60

Phe Gln Ile Tyr Ala Glu Gly Asp Trp Gln Pro Ala Val Tyr Asn Thr
65 70 75 80

Lys Lys Gln Ile Leu Glu Lys Ser Ser Ser Thr Pro Pro Gln Val Thr
85 90 95

Val Ala Thr Leu Cys Ser Tyr Phe Gln Asn Phe Val Arg Val Leu Leu
100 105 110

Thr Asp Ser Gln Gly Asn Leu Ser Ser Phe Glu Asp His Asn Leu Asn
115 120 125

Leu Glu Glu Phe Leu Ser His Pro Thr Ser Ser Val Gln Asp His Ser
130 135 140

Leu His Val Ile Tyr Ala Ile Leu Ala Asn Asp Glu Ser Ser Lys Lys
145 150 155 160

Leu Ser Ser Ser Gln Val Ala Lys Asn Pro Val Ser Ile Glu Ser Ile
165 170 175

Ile Leu Pro Ile Lys Gly Phe Gly Leu Trp Gly Pro Ile Tyr Gly Phe
180 185 190

Leu Ala Leu Glu Lys Asp Gly Asn Thr Val Leu Gly Thr Cys Trp Tyr
195 200 205

Gln His Gly Glu Thr Pro Gly Leu Gly Ala Asn Ile Thr Asn Pro Gln
210 215 220

Trp Gln Gln Asn Phe Arg Gly Lys Lys Val Phe Leu Ala Ser Ser Ser
225 230 235 240

Gly Glu Thr Asp Phe Ala Lys Thr Thr Leu Gly Leu Glu Val Ile Lys
245 250 255

Gly Ser Val Ser Ala Leu Leu Gly Asp Ser Pro Lys Ala Asn Ser Ala
260 265 270

Val Asp Gly Ile Ser Gly Ala Thr Leu Thr Cys Asn Gly Val Thr Glu
275 280 285

Ala Phe Ala Asn Ser Leu Ala Pro Tyr Arg Pro Leu Leu Thr Phe Phe
290 295 300

Ala Asn Leu Asn Ser Ser Gly Glu Ser His Asp Asn Gln
305 310 315

<210> SEQ ID NO 95
<211> LENGTH: 1410
<212> TYPE: DNA
<213> ORGANISM: Chlamydia muridarum

<400> SEQUENCE: 95

```
aatggaaaag ttctgtgtga ggtttctgtg tccttccgtt cgattctgct gacggctctg     60

ctttcacttt cttttacaaa cactatgcag gctgcacacc atcattatca ccgttatgat    120

gataaactac gcagacaata ccataaaaag gacttgccca ctcaagagaa tgttcggaaa    180

gagttttgta atccctactc tcatagtagt gatcctatcc ctttgtcaca acaacgagga    240

gtcctatctc ctatctgtga tttagtctca gagtgctcgt tttgaacgg gatttccgtt     300

aggagtctta aacaaacact gaaaaattct gctgggactc aagttgcttt agactggtct    360

atccttcctc aatggttcaa tcctagatcc tcttgggctc ctaagctctc tattcgagat    420

cttggatatg gtaaacccca gtcccttatt gaagcagatt ccccttgttg tcaaacctgc    480

ttcaacccat ctgctgctat tacgatttac gattcttcat gtgggaaggg tgttgtccaa    540

gtgtcataca cccttgttcg ttattggaga gaaacggctg cacttgcagg gcaaactatg    600

atgcttgcag gaagtattaa tgattatcct gctcgccaaa acatattctc tcaacttaca    660

ttttcccaaa ctttccctaa tgagagagta aatctaactg ttggtcaata ctctctttac    720

tcgatagacg gaacgctgta caacaatgat cagcagctag gatttattag ttatgcgttg    780

tcgcaaaatc caacagcgac ttattcctct ggaagccttg gcgcctatct acaagtcgct    840

ccaacagaaa gcacctgtct tcaagttggg ttccaagatg cctataatat ttcaggttcc    900

tcgatcaaat ggaataatct tacaaaaaat aagtataact tccatggcta tgcatcttgg    960

gctccacact gttgcttagg acctggacaa tactctgttc ttctttatgt aaccagaaag   1020

gttcctgagc aaatgatgca gacaatgggc tggtctgtga atgcaagtca atacatctct   1080

tctaaacttt atgtatttgg aagatacagc ggagtcacag gccaattgtc tcctattaac   1140

cgaacctatt catttggctt agtctctcct aatttattga accgtaaccc acaagactta   1200

tttggagtag cttgcgcatt caataatata cacgcctccg cctttcaaaa tgctcaaaga   1260

aaatatgaaa ctgtgatcga gggatttgca actattggtt gcggacctta catctccttt   1320

gctccagatt tccaacttta cctctatcct gctctgcgtc caaataaaca aagcgcccga   1380

gtctatagcg ttcgcgcaaa cctagctatt                                    1410
```

<210> SEQ ID NO 96
<211> LENGTH: 470
<212> TYPE: PRT
<213> ORGANISM: Chlamydia muridarum

<400> SEQUENCE: 96

```
Asn Gly Lys Val Leu Cys Glu Val Ser Val Ser Phe Arg Ser Ile Leu
1               5                   10                  15

Leu Thr Ala Leu Leu Ser Leu Ser Phe Thr Asn Thr Met Gln Ala Ala
            20                  25                  30

His His His Tyr His Arg Tyr Asp Asp Lys Leu Arg Arg Gln Tyr His
        35                  40                  45

Lys Lys Asp Leu Pro Thr Gln Glu Asn Val Arg Lys Glu Phe Cys Asn
    50                  55                  60

Pro Tyr Ser His Ser Ser Asp Pro Ile Pro Leu Ser Gln Gln Arg Gly
65                  70                  75                  80

Val Leu Ser Pro Ile Cys Asp Leu Val Ser Glu Cys Ser Phe Leu Asn
                85                  90                  95
```

```
Gly Ile Ser Val Arg Ser Leu Lys Gln Thr Leu Lys Asn Ser Ala Gly
            100                 105                 110

Thr Gln Val Ala Leu Asp Trp Ser Ile Leu Pro Gln Trp Phe Asn Pro
        115                 120                 125

Arg Ser Ser Trp Ala Pro Lys Leu Ser Ile Arg Asp Leu Gly Tyr Gly
    130                 135                 140

Lys Pro Gln Ser Leu Ile Glu Ala Asp Ser Pro Cys Cys Gln Thr Cys
145                 150                 155                 160

Phe Asn Pro Ser Ala Ala Ile Thr Ile Tyr Asp Ser Ser Cys Gly Lys
                165                 170                 175

Gly Val Val Gln Val Ser Tyr Thr Leu Val Arg Tyr Trp Arg Glu Thr
            180                 185                 190

Ala Ala Leu Ala Gly Gln Thr Met Met Leu Ala Gly Ser Ile Asn Asp
        195                 200                 205

Tyr Pro Ala Arg Gln Asn Ile Phe Ser Gln Leu Thr Phe Ser Gln Thr
    210                 215                 220

Phe Pro Asn Glu Arg Val Asn Leu Thr Val Gly Gln Tyr Ser Leu Tyr
225                 230                 235                 240

Ser Ile Asp Gly Thr Leu Tyr Asn Asn Asp Gln Gln Leu Gly Phe Ile
                245                 250                 255

Ser Tyr Ala Leu Ser Gln Asn Pro Thr Ala Thr Tyr Ser Ser Gly Ser
            260                 265                 270

Leu Gly Ala Tyr Leu Gln Val Ala Pro Thr Glu Ser Thr Cys Leu Gln
        275                 280                 285

Val Gly Phe Gln Asp Ala Tyr Asn Ile Ser Gly Ser Ser Ile Lys Trp
    290                 295                 300

Asn Asn Leu Thr Lys Asn Lys Tyr Asn Phe His Gly Tyr Ala Ser Trp
305                 310                 315                 320

Ala Pro His Cys Cys Leu Gly Pro Gly Gln Tyr Ser Val Leu Leu Tyr
                325                 330                 335

Val Thr Arg Lys Val Pro Glu Gln Met Met Gln Thr Met Gly Trp Ser
            340                 345                 350

Val Asn Ala Ser Gln Tyr Ile Ser Ser Lys Leu Tyr Val Phe Gly Arg
        355                 360                 365

Tyr Ser Gly Val Thr Gly Gln Leu Ser Pro Ile Asn Arg Thr Tyr Ser
    370                 375                 380

Phe Gly Leu Val Ser Pro Asn Leu Leu Asn Arg Asn Pro Gln Asp Leu
385                 390                 395                 400

Phe Gly Val Ala Cys Ala Phe Asn Asn Ile His Ala Ser Ala Phe Gln
                405                 410                 415

Asn Ala Gln Arg Lys Tyr Glu Thr Val Ile Glu Gly Phe Ala Thr Ile
            420                 425                 430

Gly Cys Gly Pro Tyr Ile Ser Phe Ala Pro Asp Phe Gln Leu Tyr Leu
        435                 440                 445

Tyr Pro Ala Leu Arg Pro Asn Lys Gln Ser Ala Arg Val Tyr Ser Val
    450                 455                 460

Arg Ala Asn Leu Ala Ile
465                 470
```

<210> SEQ ID NO 97
<211> LENGTH: 1578
<212> TYPE: DNA
<213> ORGANISM: Chlamydia muridarum

<400> SEQUENCE: 97

```
agcggggtgt tagagacctc tatggcagag tctctctcta ccaacgttat tagcttagct     60
gacaccaaag cgaaagagac cacttctcat caaaaagaca gaaaagcaag aaaaaatcat    120
caaaatagga cttccgtagt ccgtaaagag gttactgcag ttcgtgatac taaagctgta    180
gagcctagac aggattcttg ctttggcaaa atgtatacag tcaaagttaa tgatgatcgt    240
aatgtagaaa tcgtgcagtc cgttcctgaa tatgctacgg taggatctcc atatcctatt    300
gagattactg ctatagggaa aagagactgt gttgatgtaa tcattacaca gcaattacca    360
tgcgaagcag agtttgttag cagtgatcca gctactactc ctactgctga tggtaagcta    420
gtttggaaaa ttgatcggtt aggacagggc gaaaagagta aaattactgt atgggtaaaa    480
cctcttaaag aaggttgctg ctttacagct gcaacggttt gtgcttgtcc agagatccgt    540
tcggttacga aatgtggcca gcctgctatc tgtgttaaac aggaaggtcc agaaagcgca    600
tgtttgcgtt gcccagtaac ttatagaatt aatgtagtca accaaggaac agcaacagca    660
cgtaatgttg ttgtggaaaa tcctgttcca gatggctatg ctcatgcatc cggacagcgt    720
gtattgacat atactcttgg ggatatgcaa cctggagaac agagaacaat caccgtggag    780
ttttgtccgc ttaaacgtgg tcgagtcaca aatattgcta cagtttctta ctgtggtgga    840
cacaaaaata ctgctagcgt aacaacagtg atcaatgagc cttgcgtgca agttaacatc    900
gagggagcag attggtctta tgtttgtaag cctgtagaat atgttatctc tgtttctaac    960
cctggtgact tagttttacg agacgttgta attgaagata cgctttctcc tggaataact   1020
gttgttgaag cagctggagc tcagatttct tgtaataaat tggtttggac tttgaaggaa   1080
ctcaatcctg gagagtcttt acaatataag gttctagtaa gagctcaaac tccagggcaa   1140
ttcacaaaca acgttgttgt gaaaagttgc tctgattgcg gtatttgtac ttcttgcgca   1200
gaagcaacaa cttactggaa aggagttgct gctactcata tgtgcgtagt agatacttgt   1260
gatcctattt gcgtaggaga gaacactgtt tatcgtatct gtgtgacaaa cagaggttct   1320
gctgaagata caaatgtgtc cttaattttg aaattctcta aagaattaca acctatatct   1380
ttctctggac caactaaagg aaccattaca ggaaacacgg tagtgtttga ttcgttacct   1440
agattaggtt ctaaagaaac tgtagagttt tctgtaacgt tgaaagcagt atccgctgga   1500
gatgctcgtg gggaagctat tctttcttcc gatacattga cagttcctgt atctgatacg   1560
gagaatacac atatctat                                                 1578
```

<210> SEQ ID NO 98
<211> LENGTH: 526
<212> TYPE: PRT
<213> ORGANISM: Chlamydia muridarum

<400> SEQUENCE: 98

```
Ser Gly Val Leu Glu Thr Ser Met Ala Glu Ser Leu Ser Thr Asn Val
1               5                   10                  15

Ile Ser Leu Ala Asp Thr Lys Ala Lys Glu Thr Thr Ser His Gln Lys
            20                  25                  30

Asp Arg Lys Ala Arg Lys Asn His Gln Asn Arg Thr Ser Val Val Arg
        35                  40                  45

Lys Glu Val Thr Ala Val Arg Asp Thr Lys Ala Val Glu Pro Arg Gln
    50                  55                  60

Asp Ser Cys Phe Gly Lys Met Tyr Thr Val Lys Val Asn Asp Asp Arg
65                  70                  75                  80

Asn Val Glu Ile Val Gln Ser Val Pro Glu Tyr Ala Thr Val Gly Ser
                85                  90                  95
```

-continued

```
Pro Tyr Pro Ile Glu Ile Thr Ala Ile Gly Lys Arg Asp Cys Val Asp
            100                 105                 110

Val Ile Ile Thr Gln Gln Leu Pro Cys Glu Ala Glu Phe Val Ser Ser
        115                 120                 125

Asp Pro Ala Thr Thr Pro Thr Ala Asp Gly Lys Leu Val Trp Lys Ile
    130                 135                 140

Asp Arg Leu Gly Gln Gly Glu Lys Ser Lys Ile Thr Val Trp Val Lys
145                 150                 155                 160

Pro Leu Lys Glu Gly Cys Cys Phe Thr Ala Ala Thr Val Cys Ala Cys
                165                 170                 175

Pro Glu Ile Arg Ser Val Thr Lys Cys Gly Gln Pro Ala Ile Cys Val
            180                 185                 190

Lys Gln Glu Gly Pro Glu Ser Ala Cys Leu Arg Cys Pro Val Thr Tyr
        195                 200                 205

Arg Ile Asn Val Val Asn Gln Gly Thr Ala Thr Ala Arg Asn Val Val
    210                 215                 220

Val Glu Asn Pro Val Pro Asp Gly Tyr Ala His Ala Ser Gly Gln Arg
225                 230                 235                 240

Val Leu Thr Tyr Thr Leu Gly Asp Met Gln Pro Gly Glu Gln Arg Thr
                245                 250                 255

Ile Thr Val Glu Phe Cys Pro Leu Lys Arg Gly Arg Val Thr Asn Ile
            260                 265                 270

Ala Thr Val Ser Tyr Cys Gly Gly His Lys Asn Thr Ala Ser Val Thr
        275                 280                 285

Thr Val Ile Asn Glu Pro Cys Val Gln Val Asn Ile Glu Gly Ala Asp
    290                 295                 300

Trp Ser Tyr Val Cys Lys Pro Val Glu Tyr Val Ile Ser Val Ser Asn
305                 310                 315                 320

Pro Gly Asp Leu Val Leu Arg Asp Val Val Ile Glu Asp Thr Leu Ser
                325                 330                 335

Pro Gly Ile Thr Val Val Glu Ala Ala Gly Ala Gln Ile Ser Cys Asn
            340                 345                 350

Lys Leu Val Trp Thr Leu Lys Glu Leu Asn Pro Gly Glu Ser Leu Gln
        355                 360                 365

Tyr Lys Val Leu Val Arg Ala Gln Thr Pro Gly Gln Phe Thr Asn Asn
    370                 375                 380

Val Val Val Lys Ser Cys Ser Asp Cys Gly Ile Cys Thr Ser Cys Ala
385                 390                 395                 400

Glu Ala Thr Thr Tyr Trp Lys Gly Val Ala Ala Thr His Met Cys Val
                405                 410                 415

Val Asp Thr Cys Asp Pro Ile Cys Val Gly Glu Asn Thr Val Tyr Arg
            420                 425                 430

Ile Cys Val Thr Asn Arg Gly Ser Ala Glu Asp Thr Asn Val Ser Leu
        435                 440                 445

Ile Leu Lys Phe Ser Lys Glu Leu Gln Pro Ile Ser Phe Ser Gly Pro
    450                 455                 460

Thr Lys Gly Thr Ile Thr Gly Asn Thr Val Val Phe Asp Ser Leu Pro
465                 470                 475                 480

Arg Leu Gly Ser Lys Glu Thr Val Glu Phe Ser Val Thr Leu Lys Ala
                485                 490                 495

Val Ser Ala Gly Asp Ala Arg Gly Glu Ala Ile Leu Ser Ser Asp Thr
            500                 505                 510

Leu Thr Val Pro Val Ser Asp Thr Glu Asn Thr His Ile Tyr
```

515 520 525

<210> SEQ ID NO 99
<211> LENGTH: 498
<212> TYPE: DNA
<213> ORGANISM: Chlamydia muridarum

<400> SEQUENCE: 99
tccagacaga atgctgagga aaatctaaaa aattttgcta aagagctcaa gctccccgac 60
gtggccttcg atcagaataa tacgtgcatt ttgtttgttg atggagagtt ttctcttcac 120
ctgacctacg aagagcactc tgatcgcctt tatgtttacg cacctctcct tgacggactc 180
ccagataatc cgcaaagaaa gttggctctg tatgagaaat tgttggaagg ctctatgctc 240
ggaggccaaa tggctggtgg aggagtagga gttgctacta aagaacagtt gatcctaatg 300
cattgcgtgt tagatatgaa atatgcagag actaatctat tgaaagcttt tgcacagctt 360
ttcattgaaa ctgttgtgaa atggcgaacg gtctgttctg atatcagcgc tggacgagaa 420
ccttccgttg acactatgcc tcaaatgcct caaggaggca gcggaggaat tcaacctcct 480
ccaacaggaa ttcgtgcg 498

<210> SEQ ID NO 100
<211> LENGTH: 166
<212> TYPE: PRT
<213> ORGANISM: Chlamydia muridarum

<400> SEQUENCE: 100

Ser Arg Gln Asn Ala Glu Glu Asn Leu Lys Asn Phe Ala Lys Glu Leu
1 5 10 15

Lys Leu Pro Asp Val Ala Phe Asp Gln Asn Asn Thr Cys Ile Leu Phe
20 25 30

Val Asp Gly Glu Phe Ser Leu His Leu Thr Tyr Glu Glu His Ser Asp
35 40 45

Arg Leu Tyr Val Tyr Ala Pro Leu Leu Asp Gly Leu Pro Asp Asn Pro
50 55 60

Gln Arg Lys Leu Ala Leu Tyr Glu Lys Leu Leu Glu Gly Ser Met Leu
65 70 75 80

Gly Gly Gln Met Ala Gly Gly Gly Val Gly Val Ala Thr Lys Glu Gln
85 90 95

Leu Ile Leu Met His Cys Val Leu Asp Met Lys Tyr Ala Glu Thr Asn
100 105 110

Leu Leu Lys Ala Phe Ala Gln Leu Phe Ile Glu Thr Val Val Lys Trp
115 120 125

Arg Thr Val Cys Ser Asp Ile Ser Ala Gly Arg Glu Pro Ser Val Asp
130 135 140

Thr Met Pro Gln Met Pro Gln Gly Gly Ser Gly Gly Ile Gln Pro Pro
145 150 155 160

Pro Thr Gly Ile Arg Ala
165

<210> SEQ ID NO 101
<211> LENGTH: 603
<212> TYPE: DNA
<213> ORGANISM: Chlamydia muridarum

<400> SEQUENCE: 101
ctcgctaatc ggttatttct aatcaccctt ataggttttg gctattctgc ttacggtgcc 60
agcacaggga aatcaccttc tttacaggtt attttagctg aagtcgagga tacatcttcg 120

```
cgcttacaag ctcatcagaa tgagcttgtt atgctctcgg aacgtttaga tgagcaagac    180

acaaaacttc aacaactctc gtcaactcag gcccgtaatc ttcctcaaca agttcaacgg    240

cttgagattg atctgagagc tctggctaaa acagctgctg tgctctcgca atctgttcag    300

gatatccgat catccgtgca aaataaatta caagaaatcc aacaagaaca aaaaaattta    360

gctcaaaatt tacgagcgct tcgcaactcc ttacaagcac tagttgatgg ctcttcccca    420

gaaaattata ttgatttttt ggccggggag acacctgaac atattcacgt tgttaaacaa    480

ggagaaaccc tgagtaaaat cgctagtaag tacaatatcc ctgtcgcaga attgaaaaaa    540

cttaataaat taaattccga tactattttt actgatcaaa gaatccgact tccaaaaaag    600

aaa                                                                   603
```

<210> SEQ ID NO 102
<211> LENGTH: 201
<212> TYPE: PRT
<213> ORGANISM: Chlamydia muridarum

<400> SEQUENCE: 102

```
Leu Ala Asn Arg Leu Phe Leu Ile Thr Leu Ile Gly Phe Gly Tyr Ser
1               5                   10                  15

Ala Tyr Gly Ala Ser Thr Gly Lys Ser Pro Ser Leu Gln Val Ile Leu
            20                  25                  30

Ala Glu Val Glu Asp Thr Ser Ser Arg Leu Gln Ala His Gln Asn Glu
        35                  40                  45

Leu Val Met Leu Ser Glu Arg Leu Asp Glu Gln Asp Thr Lys Leu Gln
    50                  55                  60

Gln Leu Ser Ser Thr Gln Ala Arg Asn Leu Pro Gln Gln Val Gln Arg
65                  70                  75                  80

Leu Glu Ile Asp Leu Arg Ala Leu Ala Lys Thr Ala Ala Val Leu Ser
                85                  90                  95

Gln Ser Val Gln Asp Ile Arg Ser Ser Val Gln Asn Lys Leu Gln Glu
            100                 105                 110

Ile Gln Gln Glu Gln Lys Asn Leu Ala Gln Asn Leu Arg Ala Leu Arg
        115                 120                 125

Asn Ser Leu Gln Ala Leu Val Asp Gly Ser Ser Pro Glu Asn Tyr Ile
    130                 135                 140

Asp Phe Leu Ala Gly Glu Thr Pro Glu His Ile His Val Val Lys Gln
145                 150                 155                 160

Gly Glu Thr Leu Ser Lys Ile Ala Ser Lys Tyr Asn Ile Pro Val Ala
                165                 170                 175

Glu Leu Lys Lys Leu Asn Lys Leu Asn Ser Asp Thr Ile Phe Thr Asp
            180                 185                 190

Gln Arg Ile Arg Leu Pro Lys Lys Lys
        195                 200
```

<210> SEQ ID NO 103
<211> LENGTH: 3018
<212> TYPE: DNA
<213> ORGANISM: Chlamydia muridarum

<400> SEQUENCE: 103

```
acgactccaa taagtaattc tccatcttct attccaactg ttacagtatc aactactaca     60

gcatcttctg gatctctcgg aacttctact gtatcatcaa cgactacaag tacttcagtc    120

gcacaaacag caacaacaac atcttctgct tctacatcta taattcagtc tagtggagaa    180
```

-continued

```
aacatccaat ccactacagg taccccttct cctattacgt ctagtgtttc aacatccgct    240
ccatctccta aagcctccgc cactgcaaac aaaacttcaa gcgctgtttc tgggaaaatt    300
acctcacaag aaacttctga ggaatccgaa acccaagcca ctacatctga tggagaagtt    360
agtagtaatt acgatgatgt tgataccccg accaattcgt ccgattcgac agttgatagt    420
gattaccaag atgttgagac tcagtacaaa acaattagca acaatggtga aaacacttat    480
gaaacaatcg gaagtcatgg tgagaaaaac acacacgtcc aggaaagcca tgcatccgga    540
acaggaaatc ccataaataa tcagcaagaa gctattagac agctccgatc atctacctat    600
acaaccagcc ctcgtaatga gaatatattt agtccaggac cggaaggtct acctaatatg    660
tctcttccta gttacagccc tacagataaa agttctctac tagctttcct atctaatccc    720
aatacaaaag caaaaatgct cgaacactcc gggcatttag tctttataga cacaactaga    780
agtagcttta tctttgttcc gaatggaaat tgggatcaag tctgttccat gaaggttcag    840
aatgggaaaa ctaaagaaga ccttggctta aaggacttag aagatatgtg tgcaaagttt    900
tgcacaggat acaataaatt ctcctctgat tggggaaatc gagttgaccc cttggtctct    960
tctaaggccg ggatagaaag tggggggcac ctcccaagct cagttatcat caacaacaaa   1020
tttagaacct gtgttgccta tggccgtgg aaccccaaag aaaacggccc caattatact   1080
ccttcagcct ggagacgtgg gcatcgagta gattttggaa agatctttga tggaacagcg   1140
ccgtttaata aaatcaactg gggctcttcc cctacccctg gtgatgacgg catctccttc   1200
tctaatgaaa ctattgggtc tgaaccattc gcgacacctc cctcatcccc atcgcaaacc   1260
cccgttatca acgtcaatgt taatgtcggt ggaaccaatg ttaatattgg ggatacaaac   1320
gtatctaaag gatccggcac accaacatct tctcaatctg tggacatgtc tacagatact   1380
agcgatttag ataccagtga tattgataca aacaaccaaa ctaacggcga tatcaacacg   1440
aatgacaact ccaataatgt cgatggaagt ttatctgacg ttgattcaag ggtggaagac   1500
gatgacggtg tatcggatac agagtccact aatggcaatg actctggtaa aactacttcc   1560
acagaagaaa atggtgaccc aagcggacca gacatcctgg ctgctgtacg taaacaccta   1620
gacactgtct atccaggaga aaatggcgga tctacagaag gacctctccc tgctaatcaa   1680
aatctgggga acgttatcca tgatgtggag cagaatggat ctgctaaaga aactattatc   1740
actccaggag atacagggcc tacagactca agctcctctg tagatgctga tgcagacgtt   1800
gaagatactt ctgatactga ctctggaatc ggagacgacg acggtgtatc ggatacagag   1860
tccactaatg gtaataactc tggtaaaact acttccacag aagaaaatgg tgacccaagc   1920
ggaccagaca tcctggctgc tgtacgtaaa cacctagaca ctgtctatcc aggagaaaat   1980
ggcggatcta cagaaggacc tctccctgct aatcaaaatc tggggaacgt tatccatgat   2040
gtagaacaaa acggagccgc tcaagaaact attatcactc caggagatac ggaatctaca   2100
gacacaagct ctagtgtaaa tgctaatgca gacttagaag atgtttctga tgctgattca   2160
ggattcgggg atgatgacgg tatatcggat acagagtcca ctaatggtaa cgactctgga   2220
aaaaatactc ctgtagggga tggtggtaca ccaagcggac cagatatcct agctgctgta   2280
cgcaaacatc tagacactgt ctatccagga gaaaatggtg gatctacaga gagaccttta   2340
cccgctaatc aaaatttagg agatatcatt catgatgtag aacaaaacgg aagcgctaaa   2400
gaaactgtag tatcgcctta tcgaggagga ggaggaaata catcttcccc aattggatta   2460
gcctccctgc ttccagcaac accatccaca cctttgatga caacacctag aacaaatggg   2520
aaagctgcag cttcttcttt gatgataaaa ggaggagaaa ctcaagccaa gctagttaag   2580
```

```
aatggcggca atatccctgg agaaaccaca ttagcagaat tactccctcg tttaagagga   2640

caccttgaca aagtctttac ttcagacggg aagtttacaa atcttaatgg acctcaactt   2700

ggagccatca tagaccaatt ccgcaaagaa acgggttccg gaggaatcat agctcataca   2760

gatagtgttc caggagagaa cggaacagcc tctcctctca caggaagttc aggggaaaaa   2820

gtctctctct atgatgcagc gaaaaacgtc actcaagctt taacaagtgt tacgaacaaa   2880

gtaaccctag caatgcaagg acaaaaactg gaaggaatta taaacaacaa caataccccc   2940

tcttctattg gacaaaatct tttcgcagca gcgagggcaa cgacacaatc cctcagttca   3000

ttaattggaa ccgtacaa                                                  3018
```

<210> SEQ ID NO 104
<211> LENGTH: 1006
<212> TYPE: PRT
<213> ORGANISM: Chlamydia muridarum

<400> SEQUENCE: 104

```
Thr Thr Pro Ile Ser Asn Ser Pro Ser Ser Ile Pro Thr Val Thr Val
1               5                   10                  15

Ser Thr Thr Thr Ala Ser Ser Gly Ser Leu Gly Thr Ser Thr Val Ser
            20                  25                  30

Ser Thr Thr Thr Ser Thr Ser Val Ala Gln Thr Ala Thr Thr Thr Ser
        35                  40                  45

Ser Ala Ser Thr Ser Ile Ile Gln Ser Ser Gly Glu Asn Ile Gln Ser
    50                  55                  60

Thr Thr Gly Thr Pro Ser Pro Ile Thr Ser Ser Val Ser Thr Ser Ala
65                  70                  75                  80

Pro Ser Pro Lys Ala Ser Ala Thr Ala Asn Lys Thr Ser Ser Ala Val
                85                  90                  95

Ser Gly Lys Ile Thr Ser Gln Glu Thr Ser Glu Glu Ser Glu Thr Gln
            100                 105                 110

Ala Thr Thr Ser Asp Gly Glu Val Ser Ser Asn Tyr Asp Asp Val Asp
        115                 120                 125

Thr Pro Thr Asn Ser Ser Asp Ser Thr Val Asp Ser Asp Tyr Gln Asp
    130                 135                 140

Val Glu Thr Gln Tyr Lys Thr Ile Ser Asn Asn Gly Glu Asn Thr Tyr
145                 150                 155                 160

Glu Thr Ile Gly Ser His Gly Glu Lys Asn Thr His Val Gln Glu Ser
                165                 170                 175

His Ala Ser Gly Thr Gly Asn Pro Ile Asn Asn Gln Gln Glu Ala Ile
            180                 185                 190

Arg Gln Leu Arg Ser Ser Thr Tyr Thr Thr Ser Pro Arg Asn Glu Asn
        195                 200                 205

Ile Phe Ser Pro Gly Pro Glu Gly Leu Pro Asn Met Ser Leu Pro Ser
    210                 215                 220

Tyr Ser Pro Thr Asp Lys Ser Ser Leu Leu Ala Phe Leu Ser Asn Pro
225                 230                 235                 240

Asn Thr Lys Ala Lys Met Leu Glu His Ser Gly His Leu Val Phe Ile
                245                 250                 255

Asp Thr Thr Arg Ser Ser Phe Ile Phe Val Pro Asn Gly Asn Trp Asp
            260                 265                 270

Gln Val Cys Ser Met Lys Val Gln Asn Gly Lys Thr Lys Glu Asp Leu
        275                 280                 285

Gly Leu Lys Asp Leu Glu Asp Met Cys Ala Lys Phe Cys Thr Gly Tyr
    290                 295                 300
```

```
Asn Lys Phe Ser Ser Asp Trp Gly Asn Arg Val Asp Pro Leu Val Ser
305                 310                 315                 320

Ser Lys Ala Gly Ile Glu Ser Gly Gly His Leu Pro Ser Ser Val Ile
                325                 330                 335

Ile Asn Asn Lys Phe Arg Thr Cys Val Ala Tyr Gly Pro Trp Asn Pro
            340                 345                 350

Lys Glu Asn Gly Pro Asn Tyr Thr Pro Ser Ala Trp Arg Arg Gly His
        355                 360                 365

Arg Val Asp Phe Gly Lys Ile Phe Asp Gly Thr Ala Pro Phe Asn Lys
    370                 375                 380

Ile Asn Trp Gly Ser Ser Pro Thr Pro Gly Asp Asp Gly Ile Ser Phe
385                 390                 395                 400

Ser Asn Glu Thr Ile Gly Ser Glu Pro Phe Ala Thr Pro Pro Ser Ser
                405                 410                 415

Pro Ser Gln Thr Pro Val Ile Asn Val Asn Val Asn Val Gly Gly Thr
            420                 425                 430

Asn Val Asn Ile Gly Asp Thr Asn Val Ser Lys Gly Ser Gly Thr Pro
        435                 440                 445

Thr Ser Ser Gln Ser Val Asp Met Ser Thr Asp Thr Ser Asp Leu Asp
    450                 455                 460

Thr Ser Asp Ile Asp Thr Asn Asn Gln Thr Asn Gly Asp Ile Asn Thr
465                 470                 475                 480

Asn Asp Asn Ser Asn Asn Val Asp Gly Ser Leu Ser Asp Val Asp Ser
                485                 490                 495

Arg Val Glu Asp Asp Asp Gly Val Ser Asp Thr Glu Ser Thr Asn Gly
            500                 505                 510

Asn Asp Ser Gly Lys Thr Thr Ser Thr Glu Glu Asn Gly Asp Pro Ser
        515                 520                 525

Gly Pro Asp Ile Leu Ala Ala Val Arg Lys His Leu Asp Thr Val Tyr
    530                 535                 540

Pro Gly Glu Asn Gly Gly Ser Thr Glu Gly Pro Leu Pro Ala Asn Gln
545                 550                 555                 560

Asn Leu Gly Asn Val Ile His Asp Val Glu Gln Asn Gly Ser Ala Lys
                565                 570                 575

Glu Thr Ile Ile Thr Pro Gly Asp Thr Gly Pro Thr Asp Ser Ser Ser
            580                 585                 590

Ser Val Asp Ala Asp Ala Asp Val Glu Asp Thr Ser Asp Thr Asp Ser
        595                 600                 605

Gly Ile Gly Asp Asp Asp Gly Val Ser Asp Thr Glu Ser Thr Asn Gly
    610                 615                 620

Asn Asn Ser Gly Lys Thr Thr Ser Thr Glu Glu Asn Gly Asp Pro Ser
625                 630                 635                 640

Gly Pro Asp Ile Leu Ala Ala Val Arg Lys His Leu Asp Thr Val Tyr
                645                 650                 655

Pro Gly Glu Asn Gly Gly Ser Thr Glu Gly Pro Leu Pro Ala Asn Gln
            660                 665                 670

Asn Leu Gly Asn Val Ile His Asp Val Glu Gln Asn Gly Ala Ala Gln
        675                 680                 685

Glu Thr Ile Ile Thr Pro Gly Asp Thr Glu Ser Thr Asp Thr Ser Ser
    690                 695                 700

Ser Val Asn Ala Asn Ala Asp Leu Glu Asp Val Ser Asp Ala Asp Ser
705                 710                 715                 720

Gly Phe Gly Asp Asp Asp Gly Ile Ser Asp Thr Glu Ser Thr Asn Gly
```

```
                725                 730                 735

Asn Asp Ser Gly Lys Asn Thr Pro Val Gly Asp Gly Gly Thr Pro Ser
            740                 745                 750

Gly Pro Asp Ile Leu Ala Ala Val Arg Lys His Leu Asp Thr Val Tyr
        755                 760                 765

Pro Gly Glu Asn Gly Gly Ser Thr Glu Arg Pro Leu Pro Ala Asn Gln
    770                 775                 780

Asn Leu Gly Asp Ile Ile His Asp Val Glu Gln Asn Gly Ser Ala Lys
785                 790                 795                 800

Glu Thr Val Val Ser Pro Tyr Arg Gly Gly Gly Gly Asn Thr Ser Ser
                805                 810                 815

Pro Ile Gly Leu Ala Ser Leu Leu Pro Ala Thr Pro Ser Thr Pro Leu
            820                 825                 830

Met Thr Thr Pro Arg Thr Asn Gly Lys Ala Ala Ala Ser Ser Leu Met
        835                 840                 845

Ile Lys Gly Gly Glu Thr Gln Ala Lys Leu Val Lys Asn Gly Gly Asn
    850                 855                 860

Ile Pro Gly Glu Thr Thr Leu Ala Glu Leu Leu Pro Arg Leu Arg Gly
865                 870                 875                 880

His Leu Asp Lys Val Phe Thr Ser Asp Gly Lys Phe Thr Asn Leu Asn
                885                 890                 895

Gly Pro Gln Leu Gly Ala Ile Ile Asp Gln Phe Arg Lys Glu Thr Gly
            900                 905                 910

Ser Gly Gly Ile Ile Ala His Thr Asp Ser Val Pro Gly Glu Asn Gly
        915                 920                 925

Thr Ala Ser Pro Leu Thr Gly Ser Ser Gly Glu Lys Val Ser Leu Tyr
    930                 935                 940

Asp Ala Ala Lys Asn Val Thr Gln Ala Leu Thr Ser Val Thr Asn Lys
945                 950                 955                 960

Val Thr Leu Ala Met Gln Gly Gln Lys Leu Glu Gly Ile Ile Asn Asn
                965                 970                 975

Asn Asn Thr Pro Ser Ser Ile Gly Gln Asn Leu Phe Ala Ala Ala Arg
            980                 985                 990

Ala Thr Thr Gln Ser Leu Ser Ser  Leu Ile Gly Thr Val  Gln
        995                 1000                1005
```

<210> SEQ ID NO 105
<211> LENGTH: 702
<212> TYPE: DNA
<213> ORGANISM: Chlamydia muridarum

<400> SEQUENCE: 105

```
tgttcaaaag agagcaaaga ctctgttagt gaaaaattta ttgtaggaac taacgcaacg      60

tatcctcctt ttgagtttgt tgatgaaaga ggtgagacgg ttggctttga tattgattta     120

gctagggaga ttagtaaaaa gctagggaaa aaattagaag tccgagaatt tgcttttgat     180

gcactcgttc tcaatttaaa acagcatcgt attgatgcaa ttatggcagg ggtgtccatt     240

acgtcttctc gattgaaaga aattttgatg attccctact atggcgaaga aataaagagt     300

ttggttttag tgtttaagga tggagactca aagtctttac cactagatca gtataattct     360

gttgctgttc aaactggcac gtaccaagag gaatatttac agtctcttcc aggggtgcgt     420

attcgctctt ttgatagtac tttagaagtg cttatggaag ttttgcatag caagtctcct     480

atagctgttt tagaaccgtc tattgcgcag gtcgttttaa aagattttcc gacgctcact     540

actgaaacga tagatcttcc tgaagataaa tgggttttag ggtatggaat tggagttgct     600
```

-continued tctgatcgac catctctagc ttctgatata gaagctgctg tacaagagat caagaaagaa 660
ggagtgttag cagagttaga gcaaaaatgg ggtttgaacg gc 702

<210> SEQ ID NO 106
<211> LENGTH: 234
<212> TYPE: PRT
<213> ORGANISM: Chlamydia muridarum

<400> SEQUENCE: 106

Cys Ser Lys Glu Ser Lys Asp Ser Val Ser Glu Lys Phe Ile Val Gly
1 5 10 15

Thr Asn Ala Thr Tyr Pro Pro Phe Glu Phe Val Asp Glu Arg Gly Glu
20 25 30

Thr Val Gly Phe Asp Ile Asp Leu Ala Arg Glu Ile Ser Lys Lys Leu
35 40 45

Gly Lys Lys Leu Glu Val Arg Glu Phe Ala Phe Asp Ala Leu Val Leu
50 55 60

Asn Leu Lys Gln His Arg Ile Asp Ala Ile Met Ala Gly Val Ser Ile
65 70 75 80

Thr Ser Ser Arg Leu Lys Glu Ile Leu Met Ile Pro Tyr Tyr Gly Glu
85 90 95

Glu Ile Lys Ser Leu Val Leu Val Phe Lys Asp Gly Asp Ser Lys Ser
100 105 110

Leu Pro Leu Asp Gln Tyr Asn Ser Val Ala Val Gln Thr Gly Thr Tyr
115 120 125

Gln Glu Glu Tyr Leu Gln Ser Leu Pro Gly Val Arg Ile Arg Ser Phe
130 135 140

Asp Ser Thr Leu Glu Val Leu Met Glu Val Leu His Ser Lys Ser Pro
145 150 155 160

Ile Ala Val Leu Glu Pro Ser Ile Ala Gln Val Val Leu Lys Asp Phe
165 170 175

Pro Thr Leu Thr Thr Glu Thr Ile Asp Leu Pro Glu Asp Lys Trp Val
180 185 190

Leu Gly Tyr Gly Ile Gly Val Ala Ser Asp Arg Pro Ser Leu Ala Ser
195 200 205

Asp Ile Glu Ala Ala Val Gln Glu Ile Lys Lys Glu Gly Val Leu Ala
210 215 220

Glu Leu Glu Gln Lys Trp Gly Leu Asn Gly
225 230

<210> SEQ ID NO 107
<211> LENGTH: 378
<212> TYPE: DNA
<213> ORGANISM: Chlamydia trachomatis

<400> SEQUENCE: 107
gaagaaaaag gcatcttaca attggttgaa atttcgcgag caatggcttt acagggagtt 60
tgtccttgga ctaatttaca gagtgtggag tctatgttgc agtatatagc aggggagtgt 120
caggagttgg ctgatgctgt acaagaaaat aaagcttcgt tggaaatcgc ttcggaagcc 180
ggagacgtac ttactttagt attgaccttg tgtttcttgc tagaaagaga aggaaagctt 240
aaagctgaag aagtatttgt agaagctttg gctaagttgc gtcgtcgatc tcctcatgtt 300
tttgatcctc ataatcaaat ttctttagaa caggctgaag aatactgggc tcgtatgaaa 360
cagcaagaaa aaatttct 378

<210> SEQ ID NO 108
<211> LENGTH: 126
<212> TYPE: PRT
<213> ORGANISM: Chlamydia trachomatis

<400> SEQUENCE: 108

```
Glu Glu Lys Gly Ile Leu Gln Leu Val Glu Ile Ser Arg Ala Met Ala
1               5                   10                  15

Leu Gln Gly Val Cys Pro Trp Thr Asn Leu Gln Ser Val Glu Ser Met
            20                  25                  30

Leu Gln Tyr Ile Ala Gly Glu Cys Gln Glu Leu Ala Asp Ala Val Gln
        35                  40                  45

Glu Asn Lys Ala Ser Leu Glu Ile Ala Ser Glu Ala Gly Asp Val Leu
    50                  55                  60

Thr Leu Val Leu Thr Leu Cys Phe Leu Leu Glu Arg Glu Gly Lys Leu
65                  70                  75                  80

Lys Ala Glu Glu Val Phe Val Glu Ala Leu Ala Lys Leu Arg Arg Arg
                85                  90                  95

Ser Pro His Val Phe Asp Pro His Asn Gln Ile Ser Leu Glu Gln Ala
            100                 105                 110

Glu Glu Tyr Trp Ala Arg Met Lys Gln Gln Glu Lys Ile Ser
        115                 120                 125
```

<210> SEQ ID NO 109
<211> LENGTH: 1173
<212> TYPE: DNA
<213> ORGANISM: Chlamydia trachomatis

<400> SEQUENCE: 109

```
gattactaca cgatattggg tgtagcgaag actgctactc ctgaagaaat aaagaaagct      60

taccgtaagc tcgctgtaaa gtaccatcca gataagaatc ctggggatgc tgaagcggag     120

cgacgcttta aagaagtttc tgaagcctat gaagtattag gtgatgcgca gaagcgggag     180

tcatatgatc gttacggcaa agacggtcca tttgctggtg ctggaggatt cggtggcgct     240

ggcatgggga atatggaaga cgctttgcga acatttatgg gagcttttgg cggcgatttc     300

ggtggtaatg gaggcggttt ctttgaaggg ctttttggag gacttggaga agctttcgga     360

atgcgtggag gctcagaaag ttctcgacaa ggagctagta agaaggtgca tattacgctg     420

tccttcgagg aggcggcaaa aggtgttgaa aaagaacttc ttgtttcagg ctataaatct     480

tgtgatgctt gttctggtag tggagccaat actgctaaag gtgtaaaagt ttgtgatcga     540

tgcaagggct ctggtcaggt agtgcaaagc cgaggctttt tctccatggc ttctacttgc     600

cctgattgta gtggtgaagg tcgggttatc acagatcctt gttcagtttg tcgtgggcag     660

ggacgtatca aggataaacg tagcgtccat gttaatatcc cagctggagt cgattctggg     720

atgagattaa agatggaagg ctatggagat gctggccaaa atggagcgcc tgcaggggat     780

ctgtatgttt ttattgatgt agagcctcat cctgttttcg agcgccatgg ggatgattta     840

gttttagagc ttcctattgg atttgttgat gcggctttag ggatcaagaa ggaaatccct     900

acactcttaa aagaaggtac ttgccgtttg agtatcccag aagggattca gagcggaaca     960

gttcttaaag ttagagggca gggattccct aatgtgcatg ggaaatccag aggagatctt    1020

ttagtaagag tatctgtgga gactccccag cacctatcta atgaacaaaa agatttattg    1080

agacagtttg ctgctacgga gaaggctgaa aatttcccta agaaacggag tttcttagac    1140

aaaatcaaag gtttttttc tgactttgct gta                                 1173
```

<210> SEQ ID NO 110
<211> LENGTH: 391
<212> TYPE: PRT
<213> ORGANISM: Chlamydia trachomatis

<400> SEQUENCE: 110

```
Asp Tyr Tyr Thr Ile Leu Gly Val Ala Lys Thr Ala Thr Pro Glu Glu
1               5                   10                  15

Ile Lys Lys Ala Tyr Arg Lys Leu Ala Val Lys Tyr His Pro Asp Lys
            20                  25                  30

Asn Pro Gly Asp Ala Glu Ala Glu Arg Arg Phe Lys Glu Val Ser Glu
        35                  40                  45

Ala Tyr Glu Val Leu Gly Asp Ala Gln Lys Arg Glu Ser Tyr Asp Arg
    50                  55                  60

Tyr Gly Lys Asp Gly Pro Phe Ala Gly Ala Gly Gly Phe Gly Gly Ala
65                  70                  75                  80

Gly Met Gly Asn Met Glu Asp Ala Leu Arg Thr Phe Met Gly Ala Phe
                85                  90                  95

Gly Gly Asp Phe Gly Gly Asn Gly Gly Gly Phe Phe Glu Gly Leu Phe
            100                 105                 110

Gly Gly Leu Gly Glu Ala Phe Gly Met Arg Gly Gly Ser Glu Ser Ser
        115                 120                 125

Arg Gln Gly Ala Ser Lys Lys Val His Ile Thr Leu Ser Phe Glu Glu
    130                 135                 140

Ala Ala Lys Gly Val Glu Lys Glu Leu Leu Val Ser Gly Tyr Lys Ser
145                 150                 155                 160

Cys Asp Ala Cys Ser Gly Ser Gly Ala Asn Thr Ala Lys Gly Val Lys
                165                 170                 175

Val Cys Asp Arg Cys Lys Gly Ser Gly Gln Val Val Gln Ser Arg Gly
            180                 185                 190

Phe Phe Ser Met Ala Ser Thr Cys Pro Asp Cys Ser Gly Glu Gly Arg
        195                 200                 205

Val Ile Thr Asp Pro Cys Ser Val Cys Arg Gly Gln Gly Arg Ile Lys
    210                 215                 220

Asp Lys Arg Ser Val His Val Asn Ile Pro Ala Gly Val Asp Ser Gly
225                 230                 235                 240

Met Arg Leu Lys Met Glu Gly Tyr Gly Asp Ala Gly Gln Asn Gly Ala
                245                 250                 255

Pro Ala Gly Asp Leu Tyr Val Phe Ile Asp Val Glu Pro His Pro Val
            260                 265                 270

Phe Glu Arg His Gly Asp Asp Leu Val Leu Glu Leu Pro Ile Gly Phe
        275                 280                 285

Val Asp Ala Ala Leu Gly Ile Lys Lys Glu Ile Pro Thr Leu Leu Lys
    290                 295                 300

Glu Gly Thr Cys Arg Leu Ser Ile Pro Glu Gly Ile Gln Ser Gly Thr
305                 310                 315                 320

Val Leu Lys Val Arg Gly Gln Gly Phe Pro Asn Val His Gly Lys Ser
                325                 330                 335

Arg Gly Asp Leu Leu Val Arg Val Ser Val Glu Thr Pro Gln His Leu
            340                 345                 350

Ser Asn Glu Gln Lys Asp Leu Leu Arg Gln Phe Ala Ala Thr Glu Lys
        355                 360                 365

Ala Glu Asn Phe Pro Lys Lys Arg Ser Phe Leu Asp Lys Ile Lys Gly
    370                 375                 380
```

-continued

```
Phe Phe Ser Asp Phe Ala Val
385                 390


<210> SEQ ID NO 111
<211> LENGTH: 360
<212> TYPE: DNA
<213> ORGANISM: Chlamydia trachomatis

<400> SEQUENCE: 111

aataaaaaac tccaagatct gtctaaactg ctcactattg agcttttcaa gaaacgtaca     60

cggttggaaa cagtaaaaaa agcgctctcc acaatagaac atcgcttaca acaaatacag    120

gagcacatcg cgaaaatttc cttaacaagg cacaaacaat tcctatgtcg gtcatatacc    180

catgaatatg accaacattt agaacattta caaagagagc aaacttctct atataaacag    240

catcagaccc tgaaaacgtc tttgaaagat gcttatggcg acatacaaaa acaactagac    300

caaagaaaaa ttatcgaaaa gatccatgac agtaaatatc ctataaagag cgcgaataac    360


<210> SEQ ID NO 112
<211> LENGTH: 120
<212> TYPE: PRT
<213> ORGANISM: Chlamydia trachomatis

<400> SEQUENCE: 112

Asn Lys Lys Leu Gln Asp Leu Ser Lys Leu Leu Thr Ile Glu Leu Phe
1               5                   10                  15

Lys Lys Arg Thr Arg Leu Glu Thr Val Lys Lys Ala Leu Ser Thr Ile
            20                  25                  30

Glu His Arg Leu Gln Gln Ile Gln Glu His Ile Ala Lys Ile Ser Leu
        35                  40                  45

Thr Arg His Lys Gln Phe Leu Cys Arg Ser Tyr Thr His Glu Tyr Asp
    50                  55                  60

Gln His Leu Glu His Leu Gln Arg Glu Gln Thr Ser Leu Tyr Lys Gln
65                  70                  75                  80

His Gln Thr Leu Lys Thr Ser Leu Lys Asp Ala Tyr Gly Asp Ile Gln
                85                  90                  95

Lys Gln Leu Asp Gln Arg Lys Ile Ile Glu Lys Ile His Asp Ser Lys
            100                 105                 110

Tyr Pro Ile Lys Ser Ala Asn Asn
        115                 120


<210> SEQ ID NO 113
<211> LENGTH: 1224
<212> TYPE: DNA
<213> ORGANISM: Chlamydia trachomatis

<400> SEQUENCE: 113

gcgtggtggc tacacaaacg attccctcat gtgcagctgt ctattctaga aaaagagtct     60

cgatctggag ggctaattgt cacagagaaa caacaagggt tttccctcaa tatgggccct    120

aaaggttttg ttttagctca tgatgggcaa cacacccttc acctcattca gtctttaggc    180

ctagcagacg agctattata tagctctcca gaggctaaaa accgctttat ccactataat    240

aataaaaccc gaaaagtctc gccttggact attttcaaac aaaatctccc tctctctttt    300

gctaaggatt tctttgcgcg tccttacaaa caagacagct ccgtggaagc cttctttaaa    360

agacacagtt cttccaagct tagaagaaat cttttaaatc ccattagcat tgctattcgt    420

gcaggacata gtcatatatt gtctgcacag atggcttacc cagaattaac acgaagagaa    480

gctcaaacag gatcgttgtt acgtagttat ctcaaagatt ttcctaaaga gaaacgcaca    540
```

-continued

```
ggcccttatt tagctacctt gcggtctggg atgggaatgc taacccaggc tttgcatgat    600

aaattgcctg ctacctggta tttttctgca cccgtcagca aaatccgtca gttggcgaat    660

gggaaaattt ctctttcatc tcctcaagga gaaataacgg gagatatgct catttatgct    720

gggtccgtgc acgatctccc ttcctgtcta gaagggatcc ctgaaaccaa gcttatcaag    780

caaacgactt catcttggga tctctcttgt gtatctttag gatggcatgc atccttccct    840

atccctcatg gatatggcat gcttttcgct gatacgcctc ccttattagg gatcgtgttt    900

aatacggaag tgttccctca acccgagcgg cctaatacaa tagtctctct tcttttagaa    960

ggtcgatggc accaagaaga agcgtatgct ttctcactag cagctatttc tgagtacctg   1020

caaatttaca ctcctcccca agctttctca ctattctctc ctcgagaggg acttccccaa   1080

caccatgttg gatttatcca atcccgccaa cgccttctat ctaaacttcc tcacaatata   1140

aaaattgtag ggcagaattt tgcaggtcca ggtctcaacc gcgctacagc gtctgcttat   1200

aaagctatag cttctttact atca                                          1224
```

<210> SEQ ID NO 114
<211> LENGTH: 408
<212> TYPE: PRT
<213> ORGANISM: Chlamydia trachomatis

<400> SEQUENCE: 114

```
Ala Trp Trp Leu His Lys Arg Phe Pro His Val Gln Leu Ser Ile Leu
1               5                   10                  15

Glu Lys Glu Ser Arg Ser Gly Gly Leu Ile Val Thr Glu Lys Gln Gln
            20                  25                  30

Gly Phe Ser Leu Asn Met Gly Pro Lys Gly Phe Val Leu Ala His Asp
        35                  40                  45

Gly Gln His Thr Leu His Leu Ile Gln Ser Leu Gly Leu Ala Asp Glu
    50                  55                  60

Leu Leu Tyr Ser Ser Pro Glu Ala Lys Asn Arg Phe Ile His Tyr Asn
65                  70                  75                  80

Asn Lys Thr Arg Lys Val Ser Pro Trp Thr Ile Phe Lys Gln Asn Leu
                85                  90                  95

Pro Leu Ser Phe Ala Lys Asp Phe Phe Ala Arg Pro Tyr Lys Gln Asp
            100                 105                 110

Ser Ser Val Glu Ala Phe Phe Lys Arg His Ser Ser Ser Lys Leu Arg
        115                 120                 125

Arg Asn Leu Leu Asn Pro Ile Ser Ile Ala Ile Arg Ala Gly His Ser
    130                 135                 140

His Ile Leu Ser Ala Gln Met Ala Tyr Pro Glu Leu Thr Arg Arg Glu
145                 150                 155                 160

Ala Gln Thr Gly Ser Leu Leu Arg Ser Tyr Leu Lys Asp Phe Pro Lys
                165                 170                 175

Glu Lys Arg Thr Gly Pro Tyr Leu Ala Thr Leu Arg Ser Gly Met Gly
            180                 185                 190

Met Leu Thr Gln Ala Leu His Asp Lys Leu Pro Ala Thr Trp Tyr Phe
        195                 200                 205

Ser Ala Pro Val Ser Lys Ile Arg Gln Leu Ala Asn Gly Lys Ile Ser
    210                 215                 220

Leu Ser Ser Pro Gln Gly Glu Ile Thr Gly Asp Met Leu Ile Tyr Ala
225                 230                 235                 240

Gly Ser Val His Asp Leu Pro Ser Cys Leu Glu Gly Ile Pro Glu Thr
                245                 250                 255
```

```
Lys Leu Ile Lys Gln Thr Thr Ser Ser Trp Asp Leu Ser Cys Val Ser
            260                 265                 270

Leu Gly Trp His Ala Ser Phe Pro Ile Pro His Gly Tyr Gly Met Leu
        275                 280                 285

Phe Ala Asp Thr Pro Pro Leu Leu Gly Ile Val Phe Asn Thr Glu Val
    290                 295                 300

Phe Pro Gln Pro Glu Arg Pro Asn Thr Ile Val Ser Leu Leu Leu Glu
305                 310                 315                 320

Gly Arg Trp His Gln Glu Glu Ala Tyr Ala Phe Ser Leu Ala Ala Ile
                325                 330                 335

Ser Glu Tyr Leu Gln Ile Tyr Thr Pro Pro Gln Ala Phe Ser Leu Phe
            340                 345                 350

Ser Pro Arg Glu Gly Leu Pro Gln His His Val Gly Phe Ile Gln Ser
        355                 360                 365

Arg Gln Arg Leu Leu Ser Lys Leu Pro His Asn Ile Lys Ile Val Gly
    370                 375                 380

Gln Asn Phe Ala Gly Pro Gly Leu Asn Arg Ala Thr Ala Ser Ala Tyr
385                 390                 395                 400

Lys Ala Ile Ala Ser Leu Leu Ser
                405
```

<210> SEQ ID NO 115
<211> LENGTH: 2070
<212> TYPE: DNA
<213> ORGANISM: Chlamydia trachomatis

<400> SEQUENCE: 115

```
acgctctttc attctcatca tgatgccgtc tctccagaca gctacctatg ttcttccctt      60

cagttagttg gtactggcgt atacgaagga gaaatcgaga ttcaaaatat cccctcttat     120

ttccttggat tccaattacc ctctcattgc atacacctta atttaaagag ctctctagct     180

caattaggaa tagatgcctc ccttcttcac tgcgaattga gcaaaaatca acatcgagca     240

catatacatg ctcaatttac cggtcatggc cccattgctg aatctatgct agcccttctc     300

caaccaggag atcgtgtagc aaaactattt gctgcagacg atcgcagact ggtccgatct     360

ccagattacc tcgaaagcat gctgaaaaat acagataaag ctggccatcc tttgctctgt     420

tttgggaaaa aattagaaca cttgatttct tttgatgtgg tagatgatcg ccttgtcgtc     480

tcccttccta ccctgccggg agttgttcgt tatgattcgg atatttatgg actccttcct     540

cttattcaaa aatcactcag taatcccaaa ctcagcattc gtcacttttt agctctgtac     600

caacagattg tggaagggca acatgtctct tgcggaaacc atattcttct gatcaaaaca     660

gaaccgctgc acatccgcac tgtatttgct cgcgtggtaa atcaactcct ccctcaaggt     720

ctctcccaca cttctgccaa tattttggaa ccaaccactc gagaatccgg ggatatcttt     780

gaattttttg ggaacccttc tgcacagata gaaagaattc ctttagaatt tttcactatc     840

gaaccctata aagaacattc ttacttctgt aatcgggatt tattacaaac catcttacaa     900

tcagaaagcg aaatcaaaaa aatattcgaa acagcgccca aagaacctgt caaagctgcc     960

acctatttat caaaaggcag tgaaatctct tccctgcaca cagactcttg gctcacagga    1020

tccgcagctg cctatcaata tagtgagcaa gcagataaaa acgagtacac tcatgctcaa    1080

ccttgctatc ctttcttaga agcaatggaa atgggcctga tcaatagcga aggagcctta    1140

ctcactcgtt atttcccttc agctagctta aaaggaatgt tgatttccta ccatgtgcgc    1200

cactatctca aacaaatcta ctttcaagtt ccctcttata cacatggaaa ctatttctct    1260
```

```
cataatgaca gaggtttgct attagatctg cagcaagcag atattgatgt tttctgggca   1320

gatgaagaaa gcggccgtgt gttgcaatat acaaaacgac gcgataagaa tagcggtatg   1380

ttcgtgatca aaaatcgtgt tgaagagttt cgatcagctt attttattgc tatttatggc   1440

tctcgtctcc ttgagaataa tttctctgct cagctccata ccctcctagc gggcttacag   1500

caagcagcac atactctcgg cattcctgga ttctcaaagc ctaccccact tgcagtcatc   1560

accggaggcg gcactggagt tatggccaca ggaaatcgtg tagctaaaga actaggaatc   1620

ctatcttgtg gaaccgttct tgatttagaa gcttctccag cacaaatcga ccaacctacc   1680

aatgaattct tagatgctaa aatgacatac cgcctacctc aacttataga aaggcaagaa   1740

cacttttatg cagaccttcc tatccttgta gttggcggtg taggaaccga tttcgaactc   1800

tacctagaac ttgtctatct caaaacagga gctaaaccac cgactcccat tttcctaatt   1860

ggacctattg aatactggaa agaaaaagtg gcccacgcct acgagatcaa cctcaaagca   1920

ggaaccatcc gtggatccga atggatcagc aactgcctat attgtatcac ttctccggaa   1980

gctggaattg ccgtattcga acaattccta gctggagaac tccctatagg atacgactat   2040

cctccagctc cagatggatt agtgatcgtc                                     2070
```

<210> SEQ ID NO 116
<211> LENGTH: 690
<212> TYPE: PRT
<213> ORGANISM: Chlamydia trachomatis

<400> SEQUENCE: 116

```
Thr Leu Phe His Ser His His Asp Ala Val Ser Pro Asp Ser Tyr Leu
1               5                   10                  15

Cys Ser Ser Leu Gln Leu Val Gly Thr Gly Val Tyr Glu Gly Glu Ile
            20                  25                  30

Glu Ile Gln Asn Ile Pro Ser Tyr Phe Leu Gly Phe Gln Leu Pro Ser
        35                  40                  45

His Cys Ile His Leu Asn Leu Lys Ser Ser Leu Ala Gln Leu Gly Ile
    50                  55                  60

Asp Ala Ser Leu Leu His Cys Glu Leu Ser Lys Asn Gln His Arg Ala
65                  70                  75                  80

His Ile His Ala Gln Phe Thr Gly His Gly Pro Ile Ala Glu Ser Met
                85                  90                  95

Leu Ala Leu Leu Gln Pro Gly Asp Arg Val Ala Lys Leu Phe Ala Ala
            100                 105                 110

Asp Asp Arg Arg Leu Val Arg Ser Pro Asp Tyr Leu Glu Ser Met Leu
        115                 120                 125

Lys Asn Thr Asp Lys Ala Gly His Pro Leu Leu Cys Phe Gly Lys Lys
    130                 135                 140

Leu Glu His Leu Ile Ser Phe Asp Val Val Asp Asp Arg Leu Val Val
145                 150                 155                 160

Ser Leu Pro Thr Leu Pro Gly Val Val Arg Tyr Asp Ser Asp Ile Tyr
                165                 170                 175

Gly Leu Leu Pro Leu Ile Gln Lys Ser Leu Ser Asn Pro Lys Leu Ser
            180                 185                 190

Ile Arg His Phe Leu Ala Leu Tyr Gln Gln Ile Val Glu Gly Gln His
        195                 200                 205

Val Ser Cys Gly Asn His Ile Leu Leu Ile Lys Thr Glu Pro Leu His
    210                 215                 220

Ile Arg Thr Val Phe Ala Arg Val Val Asn Gln Leu Leu Pro Gln Gly
```

```
225                 230                 235                 240

Leu Ser His Thr Ser Ala Asn Ile Leu Glu Pro Thr Thr Arg Glu Ser
                245                 250                 255

Gly Asp Ile Phe Glu Phe Phe Gly Asn Pro Ser Ala Gln Ile Glu Arg
            260                 265                 270

Ile Pro Leu Glu Phe Phe Thr Ile Glu Pro Tyr Lys Glu His Ser Tyr
        275                 280                 285

Phe Cys Asn Arg Asp Leu Leu Gln Thr Ile Leu Gln Ser Glu Ser Glu
    290                 295                 300

Ile Lys Lys Ile Phe Glu Thr Ala Pro Lys Glu Pro Val Lys Ala Ala
305                 310                 315                 320

Thr Tyr Leu Ser Lys Gly Ser Glu Ile Ser Ser Leu His Thr Asp Ser
                325                 330                 335

Trp Leu Thr Gly Ser Ala Ala Ala Tyr Gln Tyr Ser Glu Gln Ala Asp
            340                 345                 350

Lys Asn Glu Tyr Thr His Ala Gln Pro Cys Tyr Pro Phe Leu Glu Ala
        355                 360                 365

Met Glu Met Gly Leu Ile Asn Ser Glu Gly Ala Leu Leu Thr Arg Tyr
    370                 375                 380

Phe Pro Ser Ala Ser Leu Lys Gly Met Leu Ile Ser Tyr His Val Arg
385                 390                 395                 400

His Tyr Leu Lys Gln Ile Tyr Phe Gln Val Pro Ser Tyr Thr His Gly
                405                 410                 415

Asn Tyr Phe Ser His Asn Asp Arg Gly Leu Leu Leu Asp Leu Gln Gln
            420                 425                 430

Ala Asp Ile Asp Val Phe Trp Ala Asp Glu Glu Ser Gly Arg Val Leu
        435                 440                 445

Gln Tyr Thr Lys Arg Arg Asp Lys Asn Ser Gly Met Phe Val Ile Lys
    450                 455                 460

Asn Arg Val Glu Glu Phe Arg Ser Ala Tyr Phe Ile Ala Ile Tyr Gly
465                 470                 475                 480

Ser Arg Leu Leu Glu Asn Asn Phe Ser Ala Gln Leu His Thr Leu Leu
                485                 490                 495

Ala Gly Leu Gln Gln Ala Ala His Thr Leu Gly Ile Pro Gly Phe Ser
            500                 505                 510

Lys Pro Thr Pro Leu Ala Val Ile Thr Gly Gly Gly Thr Gly Val Met
        515                 520                 525

Ala Thr Gly Asn Arg Val Ala Lys Glu Leu Gly Ile Leu Ser Cys Gly
    530                 535                 540

Thr Val Leu Asp Leu Glu Ala Ser Pro Ala Gln Ile Asp Gln Pro Thr
545                 550                 555                 560

Asn Glu Phe Leu Asp Ala Lys Met Thr Tyr Arg Leu Pro Gln Leu Ile
                565                 570                 575

Glu Arg Gln Glu His Phe Tyr Ala Asp Leu Pro Ile Leu Val Val Gly
            580                 585                 590

Gly Val Gly Thr Asp Phe Glu Leu Tyr Leu Glu Leu Val Tyr Leu Lys
        595                 600                 605

Thr Gly Ala Lys Pro Pro Thr Pro Ile Phe Leu Ile Gly Pro Ile Glu
    610                 615                 620

Tyr Trp Lys Glu Lys Val Ala His Ala Tyr Glu Ile Asn Leu Lys Ala
625                 630                 635                 640

Gly Thr Ile Arg Gly Ser Glu Trp Ile Ser Asn Cys Leu Tyr Cys Ile
                645                 650                 655
```

```
Thr Ser Pro Glu Ala Gly Ile Ala Val Phe Glu Gln Phe Leu Ala Gly
            660                 665                 670

Glu Leu Pro Ile Gly Tyr Asp Tyr Pro Pro Ala Pro Asp Gly Leu Val
        675                 680                 685

Ile Val
    690
```

<210> SEQ ID NO 117
<211> LENGTH: 4500
<212> TYPE: DNA
<213> ORGANISM: Chlamydia trachomatis

<400> SEQUENCE: 117

```
tgcgtagatc ttcatgctgg aggacagtct gtaaatgagc tggtatatgt aggccctcaa     60
gcggttttat tgttagacca aattcgagat ctattcgttg ggtctaaaga tagtcaggct    120
gaaggacagt ataggttaat tgtaggagat ccaagttctt tccaagagaa agatgcggat    180
actcttcccg ggaaggtaga gcaaagtact ttgttctcag taaccaatcc cgtggttttc    240
caaggtgtgg accaacagga tcaagtctct tcccaagggt taatttgtag ttttacgagc    300
agcaaccttg attctcctcg tgacggagaa tctttttttag gtattgcttt tgttggggat    360
agtagtaagg ctggaatcac attaactgac gtgaaagctt ctttgtctgg agcggcttta    420
tattctacag aagatcttat ctttgaaaag attaagggtg gattggaatt tgcatcatgt    480
tcttctctag aacagggggg agcttgtgca gctcaaagta ttttgattca tgattgtcaa    540
ggattgcagg ttaaacactg tactacagcc gtgaatgctg aggggtctag tgcgaatgat    600
catcttggat ttggaggagg cgctttcttt gttacgggtt ctctttctgg agagaaaagt    660
ctctatatgc ctgcaggaga tatggtagtt gcgaattgtg atggggctat atcttttgaa    720
ggaaacagcg cgaactttgc taatggagga gcgattgctg cctctgggaa agtgcttttt    780
gtcgctaatg ataaaaagac ttcttttata gagaaccgag ctttgtctgg aggagcgatt    840
gcagcctctt ctgatattgc ctttcaaaac tgcgcagaac tagttttcaa aggcaattgt    900
gcaattggaa cagaggataa aggttcttta ggtggagggg ctatatcttc tctaggcacc    960
gttcttttgc aagggaatca cgggataact tgtgataaga atgagtctgc ttcgcaagga   1020
ggcgccattt ttggcaaaaa ttgtcagatt tctgacaacg aggggccagt ggttttcaga   1080
gatagtacag cttgcttagg aggaggcgct attgcagctc aagaaattgt ttctattcag   1140
aacaatcagg ctgggatttc cttcgaggga ggtaaggcta gtttcggagg aggtattgcg   1200
tgtggatctt tttcttccgc aggtggtgct tctgttttag ggaccattga tatttcgaag   1260
aatttaggcg cgatttcgtt ctctcgtact ttatgtacga cctcagattt aggacaaatg   1320
gagtaccagg gaggaggagc tctatttggt gaaaatattt ctctttctga gaatgctggt   1380
gtgctcacct ttaaagacaa cattgtgaag acttttgctt cgaatgggaa aattctggga   1440
ggaggagcga ttttagctac tggtaaggtg gaaattacta ataattccga aggaatttct   1500
tttacaggaa atgcgagagc tccacaagct cttccaactc aagaggagtt tcctttattc   1560
agcaaaaaag aagggcgacc actctcttca ggatattctg gggaggagc gattttagga   1620
agagaagtag ctattctcca caacgctgca gtagtatttg agcaaaatcg tttgcagtgc   1680
agcgaagaag aagcgacatt attaggttgt tgtggaggag gcgctgttca tgggatggat   1740
agcacttcga ttgttggcaa ctcttcagta agatttggta ataattacgc aatgggacaa   1800
ggagtctcag gaggagctct tttatctaaa acagtgcagt tagctgggaa tggaagcgtc   1860
gatttttctc gaaatattgc tagtttggga ggaggagctc ttcaagcttc tgaaggaaat   1920
```

tgtgagctag ttgataacgg ctatgtgcta ttcagagata atcgagggag ggtttatggg 1980
ggtgctattt cttgcttacg tggagatgta gtcatttctg gaaacaaggg tagagttgaa 2040
tttaaagaca acatagcaac acgtctttat gtggaagaaa ctgtagaaaa ggttgaagag 2100
gtagagccag ctcctgagca aaaagacaat aatgagcttt ctttcttagg gagagcagaa 2160
cagagtttta ttactgcagc taatcaagct cttttcgcat ctgaagatgg ggatttatca 2220
cctgagtcat ccatttcttc tgaagaactt gcgaaaagaa gagagtgtgc tggaggagct 2280
atttttgcaa aacgggttcg tattgtagat aaccaagagg ccgttgtatt ctcgaataac 2340
ttctctgata tttatggcgg cgccattttt acaggttctc ttcgagaaga ggataagtta 2400
gatgggcaaa tccctgaagt cttgatctca ggcaatgcag gggatgttgt tttttccgga 2460
aattcctcga agcgtgatga gcatcttcct catacaggtg ggggagccat ttgtactcaa 2520
aatttgacga tttctcagaa tacagggaat gttctgtttt ataacaacgt ggcctgttcg 2580
ggaggagctg ttcgtataga ggatcatggt aatgttcttt tagaagcttt tggaggagat 2640
attgttttta aaggaaattc ttctttcaga gcacaaggat ccgatgctat ctattttgca 2700
ggtaaagaat cgcatattac agccctgaat gctacggaag gacatgctat tgttttccac 2760
gacgcattag tttttgaaaa tctagaagaa aggaaatctg ctgaagtatt gttaatcaat 2820
agtcgagaaa atccaggtta cactggatct attcgatttt tagaagcaga aagtaaagtt 2880
cctcaatgta ttcatgtaca acaaggaagc cttgagttgc taaatggagc cacattatgt 2940
agttatggtt ttaaacaaga tgctggagct aagttggtat tggctgctgg agctaaactg 3000
aagattttag attcaggaac tcctgtacaa caagggcatg ctatcagtaa acctgaagca 3060
gaaatcgagt catcttctga accagagggt gcacattctc tttggattgc gaagaatgct 3120
caaacaacag ttcctatggt tgatatccat actatttctg tagatttagc ctccttctct 3180
tctagtcaac aggaggggac agtagaagct cctcaggtta ttgttcctgg aggaagttat 3240
gttcgatctg gagagcttaa tttggagtta gttaacacaa caggtactgg ttatgaaaat 3300
catgctttat tgaagaatga ggctaaagtt ccattgatgt ctttcgttgc ttctggtgat 3360
gaagcttcag ccgaaatcag taacttgtcg gtttctgatt tacagattca tgtagtaact 3420
ccagagattg aagaagacac atacggccat atgggagatt ggtctgaggc taaaattcaa 3480
gatggaactc ttgtcattag ttggaatcct actggatatc gattagatcc tcaaaaagca 3540
ggggctttag tatttaatgc attatgggaa gaaggggctg tcttgtctgc tctgaaaaat 3600
gcacgctttg ctcataatct cactgctcag cgtatggaat tcgattattc tacaaatgtg 3660
tggggattcg cctttggtgg tttccgaact ctatctgcag agaatctggt tgctattgat 3720
ggatacaaag gagcttatgg tggtgcttct gctggagtcg atattcaatt gatggaagat 3780
tttgttctag gagttagtgg agctgctttc ctaggtaaaa tggatagtca gaagtttgat 3840
gcggaggttt ctcggaaggg agttgttggt tctgtatata caggattttt agctggatcc 3900
tggttcttca aaggacaata tagccttgga gaaacacaga acgatatgaa aacgcgttat 3960
ggagtactag gagagtcgag tgcttcttgg acatctcgag gagtactggc agatgcttta 4020
gttgaatacc gaagtttagt tggtcctgtg agacctactt tttatgcttt gcatttcaat 4080
ccttatgtcg aagtatctta tgcttctatg aaattccctg gctttacaga acaaggaaga 4140
gaagcgcgtt cttttgaaga cgcttccctt accaatatca ccattccttt agggatgaag 4200
tttgaattgg cgttcataaa aggacagttt tcagaggtga actctttggg aataagttat 4260
gcatgggaag cttatcgaaa agtagaagga ggcgcggtgc agcttttaga agctgggttt 4320
gattgggagg gagctccaat ggatcttcct agacaggagc tgcgtgtcgc tctggaaaat 4380
aatacggaat ggagttctta cttcagcaca gtcttaggat taacagcttt ttgtggagga 4440
tttacttcta cagatagtaa actaggatat gaggcgaata ctggattgcg attgatcttt 4500

<210> SEQ ID NO 118
<211> LENGTH: 1500
<212> TYPE: PRT
<213> ORGANISM: Chlamydia trachomatis

<400> SEQUENCE: 118

Cys Val Asp Leu His Ala Gly Gly Gln Ser Val Asn Glu Leu Val Tyr
1 5 10 15

Val Gly Pro Gln Ala Val Leu Leu Leu Asp Gln Ile Arg Asp Leu Phe
20 25 30

Val Gly Ser Lys Asp Ser Gln Ala Glu Gly Gln Tyr Arg Leu Ile Val
35 40 45

Gly Asp Pro Ser Ser Phe Gln Glu Lys Asp Ala Asp Thr Leu Pro Gly
50 55 60

Lys Val Glu Gln Ser Thr Leu Phe Ser Val Thr Asn Pro Val Val Phe
65 70 75 80

Gln Gly Val Asp Gln Gln Asp Gln Val Ser Ser Gln Gly Leu Ile Cys
85 90 95

Ser Phe Thr Ser Ser Asn Leu Asp Ser Pro Arg Asp Gly Glu Ser Phe
100 105 110

Leu Gly Ile Ala Phe Val Gly Asp Ser Ser Lys Ala Gly Ile Thr Leu
115 120 125

Thr Asp Val Lys Ala Ser Leu Ser Gly Ala Ala Leu Tyr Ser Thr Glu
130 135 140

Asp Leu Ile Phe Glu Lys Ile Lys Gly Gly Leu Glu Phe Ala Ser Cys
145 150 155 160

Ser Ser Leu Glu Gln Gly Gly Ala Cys Ala Ala Gln Ser Ile Leu Ile
165 170 175

His Asp Cys Gln Gly Leu Gln Val Lys His Cys Thr Thr Ala Val Asn
180 185 190

Ala Glu Gly Ser Ser Ala Asn Asp His Leu Gly Phe Gly Gly Gly Ala
195 200 205

Phe Phe Val Thr Gly Ser Leu Ser Gly Glu Lys Ser Leu Tyr Met Pro
210 215 220

Ala Gly Asp Met Val Val Ala Asn Cys Asp Gly Ala Ile Ser Phe Glu
225 230 235 240

Gly Asn Ser Ala Asn Phe Ala Asn Gly Gly Ala Ile Ala Ala Ser Gly
245 250 255

Lys Val Leu Phe Val Ala Asn Asp Lys Lys Thr Ser Phe Ile Glu Asn
260 265 270

Arg Ala Leu Ser Gly Gly Ala Ile Ala Ala Ser Ser Asp Ile Ala Phe
275 280 285

Gln Asn Cys Ala Glu Leu Val Phe Lys Gly Asn Cys Ala Ile Gly Thr
290 295 300

Glu Asp Lys Gly Ser Leu Gly Gly Gly Ala Ile Ser Ser Leu Gly Thr
305 310 315 320

Val Leu Leu Gln Gly Asn His Gly Ile Thr Cys Asp Lys Asn Glu Ser
325 330 335

Ala Ser Gln Gly Gly Ala Ile Phe Gly Lys Asn Cys Gln Ile Ser Asp
340 345 350

```
Asn Glu Gly Pro Val Val Phe Arg Asp Ser Thr Ala Cys Leu Gly Gly
        355                 360                 365

Gly Ala Ile Ala Ala Gln Glu Ile Val Ser Ile Gln Asn Asn Gln Ala
    370                 375                 380

Gly Ile Ser Phe Glu Gly Gly Lys Ala Ser Phe Gly Gly Gly Ile Ala
385                 390                 395                 400

Cys Gly Ser Phe Ser Ser Ala Gly Gly Ala Ser Val Leu Gly Thr Ile
                405                 410                 415

Asp Ile Ser Lys Asn Leu Gly Ala Ile Ser Phe Ser Arg Thr Leu Cys
            420                 425                 430

Thr Thr Ser Asp Leu Gly Gln Met Glu Tyr Gln Gly Gly Gly Ala Leu
        435                 440                 445

Phe Gly Glu Asn Ile Ser Leu Ser Glu Asn Ala Gly Val Leu Thr Phe
    450                 455                 460

Lys Asp Asn Ile Val Lys Thr Phe Ala Ser Asn Gly Lys Ile Leu Gly
465                 470                 475                 480

Gly Gly Ala Ile Leu Ala Thr Gly Lys Val Glu Ile Thr Asn Asn Ser
                485                 490                 495

Glu Gly Ile Ser Phe Thr Gly Asn Ala Arg Ala Pro Gln Ala Leu Pro
            500                 505                 510

Thr Gln Glu Glu Phe Pro Leu Phe Ser Lys Lys Glu Gly Arg Pro Leu
        515                 520                 525

Ser Ser Gly Tyr Ser Gly Gly Gly Ala Ile Leu Gly Arg Glu Val Ala
    530                 535                 540

Ile Leu His Asn Ala Ala Val Val Phe Glu Gln Asn Arg Leu Gln Cys
545                 550                 555                 560

Ser Glu Glu Glu Ala Thr Leu Leu Gly Cys Cys Gly Gly Gly Ala Val
                565                 570                 575

His Gly Met Asp Ser Thr Ser Ile Val Gly Asn Ser Ser Val Arg Phe
            580                 585                 590

Gly Asn Asn Tyr Ala Met Gly Gln Gly Val Ser Gly Gly Ala Leu Leu
        595                 600                 605

Ser Lys Thr Val Gln Leu Ala Gly Asn Gly Ser Val Asp Phe Ser Arg
    610                 615                 620

Asn Ile Ala Ser Leu Gly Gly Gly Ala Leu Gln Ala Ser Glu Gly Asn
625                 630                 635                 640

Cys Glu Leu Val Asp Asn Gly Tyr Val Leu Phe Arg Asp Asn Arg Gly
                645                 650                 655

Arg Val Tyr Gly Gly Ala Ile Ser Cys Leu Arg Gly Asp Val Val Ile
            660                 665                 670

Ser Gly Asn Lys Gly Arg Val Glu Phe Lys Asp Asn Ile Ala Thr Arg
        675                 680                 685

Leu Tyr Val Glu Glu Thr Val Glu Lys Val Glu Glu Val Glu Pro Ala
    690                 695                 700

Pro Glu Gln Lys Asp Asn Asn Glu Leu Ser Phe Leu Gly Arg Ala Glu
705                 710                 715                 720

Gln Ser Phe Ile Thr Ala Ala Asn Gln Ala Leu Phe Ala Ser Glu Asp
                725                 730                 735

Gly Asp Leu Ser Pro Glu Ser Ser Ile Ser Ser Glu Glu Leu Ala Lys
            740                 745                 750

Arg Arg Glu Cys Ala Gly Gly Ala Ile Phe Ala Lys Arg Val Arg Ile
        755                 760                 765

Val Asp Asn Gln Glu Ala Val Val Phe Ser Asn Asn Phe Ser Asp Ile
```

-continued

```
    770                 775                 780

Tyr Gly Gly Ala Ile Phe Thr Gly Ser Leu Arg Glu Glu Asp Lys Leu
785                 790                 795                 800

Asp Gly Gln Ile Pro Glu Val Leu Ile Ser Gly Asn Ala Gly Asp Val
                805                 810                 815

Val Phe Ser Gly Asn Ser Ser Lys Arg Asp Glu His Leu Pro His Thr
            820                 825                 830

Gly Gly Gly Ala Ile Cys Thr Gln Asn Leu Thr Ile Ser Gln Asn Thr
        835                 840                 845

Gly Asn Val Leu Phe Tyr Asn Asn Val Ala Cys Ser Gly Gly Ala Val
    850                 855                 860

Arg Ile Glu Asp His Gly Asn Val Leu Leu Glu Ala Phe Gly Gly Asp
865                 870                 875                 880

Ile Val Phe Lys Gly Asn Ser Ser Phe Arg Ala Gln Gly Ser Asp Ala
                885                 890                 895

Ile Tyr Phe Ala Gly Lys Glu Ser His Ile Thr Ala Leu Asn Ala Thr
            900                 905                 910

Glu Gly His Ala Ile Val Phe His Asp Ala Leu Val Phe Glu Asn Leu
        915                 920                 925

Glu Glu Arg Lys Ser Ala Glu Val Leu Leu Ile Asn Ser Arg Glu Asn
    930                 935                 940

Pro Gly Tyr Thr Gly Ser Ile Arg Phe Leu Glu Ala Glu Ser Lys Val
945                 950                 955                 960

Pro Gln Cys Ile His Val Gln Gln Gly Ser Leu Glu Leu Leu Asn Gly
                965                 970                 975

Ala Thr Leu Cys Ser Tyr Gly Phe Lys Gln Asp Ala Gly Ala Lys Leu
            980                 985                 990

Val Leu Ala Ala Gly Ala Lys Leu  Lys Ile Leu Asp Ser  Gly Thr Pro
        995                 1000                1005

Val Gln  Gln Gly His Ala Ile  Ser Lys Pro Glu Ala  Glu Ile Glu
    1010                1015                1020

Ser Ser  Ser Glu Pro Glu Gly  Ala His Ser Leu Trp  Ile Ala Lys
    1025                1030                1035

Asn Ala  Gln Thr Thr Val Pro  Met Val Asp Ile His  Thr Ile Ser
    1040                1045                1050

Val Asp  Leu Ala Ser Phe Ser  Ser Ser Gln Gln Glu  Gly Thr Val
    1055                1060                1065

Glu Ala  Pro Gln Val Ile Val  Pro Gly Gly Ser Tyr  Val Arg Ser
    1070                1075                1080

Gly Glu  Leu Asn Leu Glu Leu  Val Asn Thr Thr Gly  Thr Gly Tyr
    1085                1090                1095

Glu Asn  His Ala Leu Leu Lys  Asn Glu Ala Lys Val  Pro Leu Met
    1100                1105                1110

Ser Phe  Val Ala Ser Gly Asp  Glu Ala Ser Ala Glu  Ile Ser Asn
    1115                1120                1125

Leu Ser  Val Ser Asp Leu Gln  Ile His Val Val Thr  Pro Glu Ile
    1130                1135                1140

Glu Glu  Asp Thr Tyr Gly His  Met Gly Asp Trp Ser  Glu Ala Lys
    1145                1150                1155

Ile Gln  Asp Gly Thr Leu Val  Ile Ser Trp Asn Pro  Thr Gly Tyr
    1160                1165                1170

Arg Leu  Asp Pro Gln Lys Ala  Gly Ala Leu Val Phe  Asn Ala Leu
    1175                1180                1185
```

-continued

```
Trp Glu  Glu Gly Ala Val Leu  Ser Ala Leu Lys Asn  Ala Arg Phe
    1190                 1195                 1200

Ala His  Asn Leu Thr Ala Gln  Arg Met Glu Phe Asp  Tyr Ser Thr
    1205                 1210                 1215

Asn Val  Trp Gly Phe Ala Phe  Gly Gly Phe Arg Thr  Leu Ser Ala
    1220                 1225                 1230

Glu Asn  Leu Val Ala Ile Asp  Gly Tyr Lys Gly Ala  Tyr Gly Gly
    1235                 1240                 1245

Ala Ser  Ala Gly Val Asp Ile  Gln Leu Met Glu Asp  Phe Val Leu
    1250                 1255                 1260

Gly Val  Ser Gly Ala Ala Phe  Leu Gly Lys Met Asp  Ser Gln Lys
    1265                 1270                 1275

Phe Asp  Ala Glu Val Ser Arg  Lys Gly Val Val Gly  Ser Val Tyr
    1280                 1285                 1290

Thr Gly  Phe Leu Ala Gly Ser  Trp Phe Phe Lys Gly  Gln Tyr Ser
    1295                 1300                 1305

Leu Gly  Glu Thr Gln Asn Asp  Met Lys Thr Arg Tyr  Gly Val Leu
    1310                 1315                 1320

Gly Glu  Ser Ser Ala Ser Trp  Thr Ser Arg Gly Val  Leu Ala Asp
    1325                 1330                 1335

Ala Leu  Val Glu Tyr Arg Ser  Leu Val Gly Pro Val  Arg Pro Thr
    1340                 1345                 1350

Phe Tyr  Ala Leu His Phe Asn  Pro Tyr Val Glu Val  Ser Tyr Ala
    1355                 1360                 1365

Ser Met  Lys Phe Pro Gly Phe  Thr Glu Gln Gly Arg  Glu Ala Arg
    1370                 1375                 1380

Ser Phe  Glu Asp Ala Ser Leu  Thr Asn Ile Thr Ile  Pro Leu Gly
    1385                 1390                 1395

Met Lys  Phe Glu Leu Ala Phe  Ile Lys Gly Gln Phe  Ser Glu Val
    1400                 1405                 1410

Asn Ser  Leu Gly Ile Ser Tyr  Ala Trp Glu Ala Tyr  Arg Lys Val
    1415                 1420                 1425

Glu Gly  Gly Ala Val Gln Leu  Leu Glu Ala Gly Phe  Asp Trp Glu
    1430                 1435                 1440

Gly Ala  Pro Met Asp Leu Pro  Arg Gln Glu Leu Arg  Val Ala Leu
    1445                 1450                 1455

Glu Asn  Asn Thr Glu Trp Ser  Ser Tyr Phe Ser Thr  Val Leu Gly
    1460                 1465                 1470

Leu Thr  Ala Phe Cys Gly Gly  Phe Thr Ser Thr Asp  Ser Lys Leu
    1475                 1480                 1485

Gly Tyr  Glu Ala Asn Thr Gly  Leu Arg Leu Ile Phe
    1490                 1495                 1500
```

<210> SEQ ID NO 119
<211> LENGTH: 2247
<212> TYPE: DNA
<213> ORGANISM: Chlamydia trachomatis

<400> SEQUENCE: 119

```
tgcgtagatc ttcatgctgg aggacagtct gtaaatgagc tggtatatgt aggccctcaa     60

gcggttttat tgttagacca aattcgagat ctattcgttg ggtctaaaga tagtcaggct    120

gaaggacagt ataggttaat tgtaggagat ccaagttctt tccaagagaa agatgcggat    180

actcttcccg ggaaggtaga gcaaagtact ttgttctcag taaccaatcc cgtggttttc    240

caaggtgtgg accaacagga tcaagtctct tcccaagggt taatttgtag ttttacgagc    300
```

-continued

```
agcaaccttg attctcctcg tgacggagaa tctttttttag gtattgcttt tgttggggat    360
agtagtaagg ctggaatcac attaactgac gtgaaagctt ctttgtctgg agcggcttta    420
tattctacag aagatcttat ctttgaaaag attaagggtg gattggaatt tgcatcatgt    480
tcttctctag aacagggggg agcttgtgca gctcaaagta ttttgattca tgattgtcaa    540
ggattgcagg ttaaacactg tactacagcc gtgaatgctg aggggtctag tgcgaatgat    600
catcttggat ttggaggagg cgctttcttt gttacgggtt ctctttctgg agagaaaagt    660
ctctatatgc ctgcaggaga tatggtagtt gcgaattgtg atggggctat atcttttgaa    720
ggaaacagcg cgaactttgc taatggagga gcgattgctg cctctgggaa agtgcttttt    780
gtcgctaatg ataaaaagac ttcttttata gagaaccgag ctttgtctgg aggagcgatt    840
gcagcctctt ctgatattgc ctttcaaaac tgcgcagaac tagttttcaa aggcaattgt    900
gcaattggaa cagaggataa aggttcttta ggtggagggg ctatatcttc tctaggcacc    960
gttcttttgc aagggaatca cgggataact tgtgataaga atgagtctgc ttcgcaagga   1020
ggcgccattt ttggcaaaaa ttgtcagatt tctgacaacg aggggccagt ggttttcaga   1080
gatagtacag cttgcttagg aggaggcgct attgcagctc aagaaattgt ttctattcag   1140
aacaatcagg ctgggatttc cttcgaggga ggtaaggcta gtttcggagg aggtattgcg   1200
tgtggatctt tttcttccgc aggtggtgct tctgttttag ggaccattga tatttcgaag   1260
aatttaggcg cgatttcgtt ctctcgtact ttatgtacga cctcagattt aggacaaatg   1320
gagtaccagg gaggaggagc tctatttggt gaaaatattt ctctttctga gaatgctggt   1380
gtgctcacct ttaaagacaa cattgtgaag actttttgctt cgaatgggaa aattctggga   1440
ggaggagcga ttttagctac tggtaaggtg gaaattacta ataattccga aggaatttct   1500
tttacaggaa atgcgagagc tccacaagct cttccaactc aagaggagtt tcctttattc   1560
agcaaaaaag aagggcgacc actctcttca ggatattctg gggaggagc gattttagga   1620
agagaagtag ctattctcca caacgctgca gtagtatttg agcaaaatcg tttgcagtgc   1680
agcgaagaag aagcgacatt attaggttgt tgtggaggag gcgctgttca tgggatggat   1740
agcacttcga ttgttggcaa ctcttcagta agatttggta ataattacgc aatgggacaa   1800
ggagtctcag gaggagctct tttatctaaa acagtgcagt tagctgggaa tggaagcgtc   1860
gatttttctc gaaatattgc tagtttggga ggaggagctc ttcaagcttc tgaaggaaat   1920
tgtgagctag ttgataacgg ctatgtgcta ttcagagata atcgagggag ggtttatggg   1980
ggtgctattt cttgcttacg tggagatgta gtcatttctg gaaacaaggg tagagttgaa   2040
tttaaagaca acatagcaac acgtctttat gtggaagaaa ctgtagaaaa ggttgaagag   2100
gtagagccag ctcctgagca aaaagacaat aatgagcttt ctttcttagg gagagcagaa   2160
cagagtttta ttactgcagc taatcaagct cttttcgcat ctgaagatgg ggatttatca   2220
cctgagtcat ccatttcttc tgaagaa                                       2247
```

<210> SEQ ID NO 120
<211> LENGTH: 749
<212> TYPE: PRT
<213> ORGANISM: Chlamydia trachomatis

<400> SEQUENCE: 120

```
Cys Val Asp Leu His Ala Gly Gly Gln Ser Val Asn Glu Leu Val Tyr
1               5                   10                  15

Val Gly Pro Gln Ala Val Leu Leu Leu Asp Gln Ile Arg Asp Leu Phe
            20                  25                  30
```

```
Val Gly Ser Lys Asp Ser Gln Ala Glu Gly Gln Tyr Arg Leu Ile Val
        35                  40                  45

Gly Asp Pro Ser Ser Phe Gln Glu Lys Asp Ala Asp Thr Leu Pro Gly
    50                  55                  60

Lys Val Glu Gln Ser Thr Leu Phe Ser Val Thr Asn Pro Val Val Phe
65                  70                  75                  80

Gln Gly Val Asp Gln Gln Asp Gln Val Ser Ser Gln Gly Leu Ile Cys
                85                  90                  95

Ser Phe Thr Ser Ser Asn Leu Asp Ser Pro Arg Asp Gly Glu Ser Phe
            100                 105                 110

Leu Gly Ile Ala Phe Val Gly Asp Ser Ser Lys Ala Gly Ile Thr Leu
        115                 120                 125

Thr Asp Val Lys Ala Ser Leu Ser Gly Ala Ala Leu Tyr Ser Thr Glu
    130                 135                 140

Asp Leu Ile Phe Glu Lys Ile Lys Gly Gly Leu Glu Phe Ala Ser Cys
145                 150                 155                 160

Ser Ser Leu Glu Gln Gly Gly Ala Cys Ala Ala Gln Ser Ile Leu Ile
                165                 170                 175

His Asp Cys Gln Gly Leu Gln Val Lys His Cys Thr Thr Ala Val Asn
            180                 185                 190

Ala Glu Gly Ser Ser Ala Asn Asp His Leu Gly Phe Gly Gly Gly Ala
        195                 200                 205

Phe Phe Val Thr Gly Ser Leu Ser Gly Glu Lys Ser Leu Tyr Met Pro
    210                 215                 220

Ala Gly Asp Met Val Val Ala Asn Cys Asp Gly Ala Ile Ser Phe Glu
225                 230                 235                 240

Gly Asn Ser Ala Asn Phe Ala Asn Gly Gly Ala Ile Ala Ala Ser Gly
                245                 250                 255

Lys Val Leu Phe Val Ala Asn Asp Lys Lys Thr Ser Phe Ile Glu Asn
            260                 265                 270

Arg Ala Leu Ser Gly Gly Ala Ile Ala Ala Ser Ser Asp Ile Ala Phe
        275                 280                 285

Gln Asn Cys Ala Glu Leu Val Phe Lys Gly Asn Cys Ala Ile Gly Thr
    290                 295                 300

Glu Asp Lys Gly Ser Leu Gly Gly Gly Ala Ile Ser Ser Leu Gly Thr
305                 310                 315                 320

Val Leu Leu Gln Gly Asn His Gly Ile Thr Cys Asp Lys Asn Glu Ser
                325                 330                 335

Ala Ser Gln Gly Gly Ala Ile Phe Gly Lys Asn Cys Gln Ile Ser Asp
            340                 345                 350

Asn Glu Gly Pro Val Val Phe Arg Asp Ser Thr Ala Cys Leu Gly Gly
        355                 360                 365

Gly Ala Ile Ala Ala Gln Glu Ile Val Ser Ile Gln Asn Asn Gln Ala
    370                 375                 380

Gly Ile Ser Phe Glu Gly Gly Lys Ala Ser Phe Gly Gly Gly Ile Ala
385                 390                 395                 400

Cys Gly Ser Phe Ser Ser Ala Gly Gly Ala Ser Val Leu Gly Thr Ile
                405                 410                 415

Asp Ile Ser Lys Asn Leu Gly Ala Ile Ser Phe Ser Arg Thr Leu Cys
            420                 425                 430

Thr Thr Ser Asp Leu Gly Gln Met Glu Tyr Gln Gly Gly Gly Ala Leu
        435                 440                 445

Phe Gly Glu Asn Ile Ser Leu Ser Glu Asn Ala Gly Val Leu Thr Phe
```

-continued

```
    450                 455                 460

Lys Asp Asn Ile Val Lys Thr Phe Ala Ser Asn Gly Lys Ile Leu Gly
465                 470                 475                 480

Gly Gly Ala Ile Leu Ala Thr Gly Lys Val Glu Ile Thr Asn Asn Ser
                485                 490                 495

Glu Gly Ile Ser Phe Thr Gly Asn Ala Arg Ala Pro Gln Ala Leu Pro
            500                 505                 510

Thr Gln Glu Glu Phe Pro Leu Phe Ser Lys Lys Glu Gly Arg Pro Leu
        515                 520                 525

Ser Ser Gly Tyr Ser Gly Gly Gly Ala Ile Leu Gly Arg Glu Val Ala
    530                 535                 540

Ile Leu His Asn Ala Ala Val Val Phe Glu Gln Asn Arg Leu Gln Cys
545                 550                 555                 560

Ser Glu Glu Glu Ala Thr Leu Leu Gly Cys Cys Gly Gly Gly Ala Val
                565                 570                 575

His Gly Met Asp Ser Thr Ser Ile Val Gly Asn Ser Ser Val Arg Phe
            580                 585                 590

Gly Asn Asn Tyr Ala Met Gly Gln Gly Val Ser Gly Gly Ala Leu Leu
        595                 600                 605

Ser Lys Thr Val Gln Leu Ala Gly Asn Gly Ser Val Asp Phe Ser Arg
    610                 615                 620

Asn Ile Ala Ser Leu Gly Gly Gly Ala Leu Gln Ala Ser Glu Gly Asn
625                 630                 635                 640

Cys Glu Leu Val Asp Asn Gly Tyr Val Leu Phe Arg Asp Asn Arg Gly
                645                 650                 655

Arg Val Tyr Gly Gly Ala Ile Ser Cys Leu Arg Gly Asp Val Val Ile
            660                 665                 670

Ser Gly Asn Lys Gly Arg Val Glu Phe Lys Asp Asn Ile Ala Thr Arg
        675                 680                 685

Leu Tyr Val Glu Glu Thr Val Glu Lys Val Glu Glu Val Glu Pro Ala
    690                 695                 700

Pro Glu Gln Lys Asp Asn Asn Glu Leu Ser Phe Leu Gly Arg Ala Glu
705                 710                 715                 720

Gln Ser Phe Ile Thr Ala Ala Asn Gln Ala Leu Phe Ala Ser Glu Asp
                725                 730                 735

Gly Asp Leu Ser Pro Glu Ser Ser Ile Ser Ser Glu Glu
            740                 745


<210> SEQ ID NO 121
<211> LENGTH: 2259
<212> TYPE: DNA
<213> ORGANISM: Chlamydia trachomatis

<400> SEQUENCE: 121

gaagaacttg cgaaaagaag agagtgtgct ggaggagcta tttttgcaaa acgggttcgt      60

attgtagata accaagaggc cgttgtattc tcgaataact tctctgatat ttatggcggc     120

gccattttta caggttctct tcgagaagag gataagttag atgggcaaat ccctgaagtc     180

ttgatctcag gcaatgcagg ggatgttgtt ttttccggaa attcctcgaa gcgtgatgag     240

catcttcctc atacaggtgg gggagccatt tgtactcaaa atttgacgat ttctcagaat     300

acagggaatg ttctgtttta taacaacgtg gcctgttcgg gaggagctgt tcgtatagag     360

gatcatggta atgttctttt agaagctttt ggaggagata ttgtttttaa aggaaattct     420

tctttcagag cacaaggatc cgatgctatc tattttgcag gtaaagaatc gcatattaca     480
```

```
gccctgaatg ctacggaagg acatgctatt gttttccacg acgcattagt ttttgaaaat    540
ctagaagaaa ggaaatctgc tgaagtattg ttaatcaata gtcgagaaaa tccaggttac    600
actggatcta ttcgattttt agaagcagaa agtaaagttc ctcaatgtat tcatgtacaa    660
caaggaagcc ttgagttgct aaatggagcc acattatgta gttatggttt taaacaagat    720
gctggagcta agttggtatt ggctgctgga gctaaactga agattttaga ttcaggaact    780
cctgtacaac aagggcatgc tatcagtaaa cctgaagcag aaatcgagtc atcttctgaa    840
ccagagggtg cacattctct ttggattgcg aagaatgctc aaacaacagt tcctatggtt    900
gatatccata ctatttctgt agatttagcc tccttctctt ctagtcaaca ggaggggaca    960
gtagaagctc ctcaggttat tgttcctgga ggaagttatg ttcgatctgg agagcttaat   1020
ttggagttag ttaacacaac aggtactggt tatgaaaatc atgctttatt gaagaatgag   1080
gctaaagttc cattgatgtc tttcgttgct tctggtgatg aagcttcagc cgaaatcagt   1140
aacttgtcgg tttctgattt acagattcat gtagtaactc cagagattga agaagacaca   1200
tacggccata tgggagattg gtctgaggct aaaattcaag atggaactct tgtcattagt   1260
tggaatccta ctggatatcg attagatcct caaaaagcag gggctttagt atttaatgca   1320
ttatgggaag aaggggctgt cttgtctgct ctgaaaaatg cacgctttgc tcataatctc   1380
actgctcagc gtatggaatt cgattattct acaaatgtgt ggggattcgc ctttggtggt   1440
ttccgaactc tatctgcaga gaatctggtt gctattgatg gatacaaagg agcttatggt   1500
ggtgcttctg ctggagtcga tattcaattg atggaagatt ttgttctagg agttagtgga   1560
gctgctttcc taggtaaaat ggatagtcag aagtttgatg cggaggtttc tcggaaggga   1620
gttgttggtt ctgtatatac aggattttta gctggatcct ggttcttcaa aggacaatat   1680
agccttggag aaacacagaa cgatatgaaa acgcgttatg gagtactagg agagtcgagt   1740
gcttcttgga catctcgagg agtactggca gatgctttag ttgaataccg aagtttagtt   1800
ggtcctgtga gacctacttt ttatgctttg catttcaatc cttatgtcga agtatcttat   1860
gcttctatga aattccctgg ctttacagaa caaggaagag aagcgcgttc ttttgaagac   1920
gcttccctta ccaatatcac cattccttta gggatgaagt ttgaattggc gttcataaaa   1980
ggacagtttt cagaggtgaa ctctttggga ataagttatg catgggaagc ttatcgaaaa   2040
gtagaaggag gcgcggtgca gcttttagaa gctgggtttg attgggaggg agctccaatg   2100
gatcttccta gacaggagct gcgtgtcgct ctggaaaata atacggaatg gagttcttac   2160
ttcagcacag tcttaggatt aacagctttt tgtggaggat ttacttctac agatagtaaa   2220
ctaggatatg aggcgaatac tggattgcga ttgatcttt                          2259
```

<210> SEQ ID NO 122
<211> LENGTH: 753
<212> TYPE: PRT
<213> ORGANISM: Chlamydia trachomatis

<400> SEQUENCE: 122

```
Glu Glu Leu Ala Lys Arg Arg Glu Cys Ala Gly Gly Ala Ile Phe Ala
1               5                   10                  15

Lys Arg Val Arg Ile Val Asp Asn Gln Glu Ala Val Val Phe Ser Asn
            20                  25                  30

Asn Phe Ser Asp Ile Tyr Gly Gly Ala Ile Phe Thr Gly Ser Leu Arg
        35                  40                  45

Glu Glu Asp Lys Leu Asp Gly Gln Ile Pro Glu Val Leu Ile Ser Gly
    50                  55                  60
```

```
Asn Ala Gly Asp Val Val Phe Ser Gly Asn Ser Ser Lys Arg Asp Glu
65                  70                  75                  80

His Leu Pro His Thr Gly Gly Gly Ala Ile Cys Thr Gln Asn Leu Thr
                85                  90                  95

Ile Ser Gln Asn Thr Gly Asn Val Leu Phe Tyr Asn Asn Val Ala Cys
            100                 105                 110

Ser Gly Gly Ala Val Arg Ile Glu Asp His Gly Asn Val Leu Leu Glu
        115                 120                 125

Ala Phe Gly Gly Asp Ile Val Phe Lys Gly Asn Ser Ser Phe Arg Ala
    130                 135                 140

Gln Gly Ser Asp Ala Ile Tyr Phe Ala Gly Lys Glu Ser His Ile Thr
145                 150                 155                 160

Ala Leu Asn Ala Thr Glu Gly His Ala Ile Val Phe His Asp Ala Leu
                165                 170                 175

Val Phe Glu Asn Leu Glu Glu Arg Lys Ser Ala Glu Val Leu Leu Ile
            180                 185                 190

Asn Ser Arg Glu Asn Pro Gly Tyr Thr Gly Ser Ile Arg Phe Leu Glu
        195                 200                 205

Ala Glu Ser Lys Val Pro Gln Cys Ile His Val Gln Gln Gly Ser Leu
    210                 215                 220

Glu Leu Leu Asn Gly Ala Thr Leu Cys Ser Tyr Gly Phe Lys Gln Asp
225                 230                 235                 240

Ala Gly Ala Lys Leu Val Leu Ala Ala Gly Ala Lys Leu Lys Ile Leu
                245                 250                 255

Asp Ser Gly Thr Pro Val Gln Gln Gly His Ala Ile Ser Lys Pro Glu
            260                 265                 270

Ala Glu Ile Glu Ser Ser Ser Glu Pro Glu Gly Ala His Ser Leu Trp
        275                 280                 285

Ile Ala Lys Asn Ala Gln Thr Thr Val Pro Met Val Asp Ile His Thr
    290                 295                 300

Ile Ser Val Asp Leu Ala Ser Phe Ser Ser Ser Gln Gln Glu Gly Thr
305                 310                 315                 320

Val Glu Ala Pro Gln Val Ile Val Pro Gly Gly Ser Tyr Val Arg Ser
                325                 330                 335

Gly Glu Leu Asn Leu Glu Leu Val Asn Thr Thr Gly Thr Gly Tyr Glu
            340                 345                 350

Asn His Ala Leu Leu Lys Asn Glu Ala Lys Val Pro Leu Met Ser Phe
        355                 360                 365

Val Ala Ser Gly Asp Glu Ala Ser Ala Glu Ile Ser Asn Leu Ser Val
    370                 375                 380

Ser Asp Leu Gln Ile His Val Val Thr Pro Glu Ile Glu Glu Asp Thr
385                 390                 395                 400

Tyr Gly His Met Gly Asp Trp Ser Glu Ala Lys Ile Gln Asp Gly Thr
                405                 410                 415

Leu Val Ile Ser Trp Asn Pro Thr Gly Tyr Arg Leu Asp Pro Gln Lys
            420                 425                 430

Ala Gly Ala Leu Val Phe Asn Ala Leu Trp Glu Glu Gly Ala Val Leu
        435                 440                 445

Ser Ala Leu Lys Asn Ala Arg Phe Ala His Asn Leu Thr Ala Gln Arg
    450                 455                 460

Met Glu Phe Asp Tyr Ser Thr Asn Val Trp Gly Phe Ala Phe Gly Gly
465                 470                 475                 480

Phe Arg Thr Leu Ser Ala Glu Asn Leu Val Ala Ile Asp Gly Tyr Lys
                485                 490                 495
```

```
Gly Ala Tyr Gly Gly Ala Ser Ala Gly Val Asp Ile Gln Leu Met Glu
            500                 505                 510

Asp Phe Val Leu Gly Val Ser Gly Ala Ala Phe Leu Gly Lys Met Asp
        515                 520                 525

Ser Gln Lys Phe Asp Ala Glu Val Ser Arg Lys Gly Val Val Gly Ser
    530                 535                 540

Val Tyr Thr Gly Phe Leu Ala Gly Ser Trp Phe Phe Lys Gly Gln Tyr
545                 550                 555                 560

Ser Leu Gly Glu Thr Gln Asn Asp Met Lys Thr Arg Tyr Gly Val Leu
                565                 570                 575

Gly Glu Ser Ser Ala Ser Trp Thr Ser Arg Gly Val Leu Ala Asp Ala
            580                 585                 590

Leu Val Glu Tyr Arg Ser Leu Val Gly Pro Val Arg Pro Thr Phe Tyr
        595                 600                 605

Ala Leu His Phe Asn Pro Tyr Val Glu Val Ser Tyr Ala Ser Met Lys
    610                 615                 620

Phe Pro Gly Phe Thr Glu Gln Gly Arg Glu Ala Arg Ser Phe Glu Asp
625                 630                 635                 640

Ala Ser Leu Thr Asn Ile Thr Ile Pro Leu Gly Met Lys Phe Glu Leu
                645                 650                 655

Ala Phe Ile Lys Gly Gln Phe Ser Glu Val Asn Ser Leu Gly Ile Ser
            660                 665                 670

Tyr Ala Trp Glu Ala Tyr Arg Lys Val Glu Gly Gly Ala Val Gln Leu
        675                 680                 685

Leu Glu Ala Gly Phe Asp Trp Glu Gly Ala Pro Met Asp Leu Pro Arg
    690                 695                 700

Gln Glu Leu Arg Val Ala Leu Glu Asn Asn Thr Glu Trp Ser Ser Tyr
705                 710                 715                 720

Phe Ser Thr Val Leu Gly Leu Thr Ala Phe Cys Gly Gly Phe Thr Ser
                725                 730                 735

Thr Asp Ser Lys Leu Gly Tyr Glu Ala Asn Thr Gly Leu Arg Leu Ile
            740                 745                 750

Phe
```

<210> SEQ ID NO 123
<211> LENGTH: 2838
<212> TYPE: DNA
<213> ORGANISM: Chlamydia trachomatis

<400> SEQUENCE: 123

```
agagaggttc cttctagaat ctttcttatg cccaactcag ttccagatcc tacgaaagag      60

tcgctatcaa ataaaattag tttgacagga gacactcaca atctcactaa ctgctatctc     120

gataacctac gctacatact ggctattcta caaaaaactc ccaatgaagg agctgctgtc     180

acaataacag attacctaag cttttttgat acacaaaaag aaggtattta ttttgcaaaa     240

aatctcaccc ctgaaagtgg tggtgcgatt ggttatgcga gtcccaattc tcctaccgtg     300

gagattcgtg atacaatagg tcctgtaatc tttgaaaata atacttgttg cagactattt     360

acatggagaa atccttatgc tgctgataaa ataagagaag gcggagccat tcatgctcaa     420

aatctttaca taaatcataa tcatgatgtg gtcggattta tgaagaactt ttcttatgtc     480

caaggaggag ccattagtac cgctaatacc tttgttgtga gcgagaatca gtcttgtttt     540

ctctttatgg acaacatctg tattcaaact aatacagcag gaaaaggtgg cgctatctat     600

gctggaacga gcaattcttt tgagagtaat aactgcgatc tcttcttcat caataacgcc     660
```

```
tgttgtgcag gaggagcgat cttctcccct atctgttctc taacaggaaa tcgtggtaac    720
atcgttttct ataacaatcg ctgctttaaa aatgtagaaa cagcttcttc agaagcttct    780
gatggaggag caattaaagt aactactcgc ctagatgtta caggcaatcg tggtaggatc    840
tttttagtg acaatatcac aaaaaattat ggcggagcta tttacgctcc tgtagttacc     900
ctagtggata atggccctac ctactttata aacaatatcg ccaataataa gggggggcgct    960
atctatatag acggaaccag taactccaaa atttctgccg accgccatgc tattattttt   1020
aatgaaaata ttgtgactaa tgtaactaat gcaaatggta ccagtacgtc agctaatcct   1080
cctagaagaa atgcaataac agtagcaagc tcctctggtg aaattctatt aggagcaggg   1140
agtagccaaa atttaatttt ttatgatcct attgaagtta gcaatgcagg ggtctctgtg   1200
tccttcaata aggaagctga tcaaacaggc tctgtagtat tttcaggagc tactgttaat   1260
tctgcagatt ttcatcaacg caatttacaa acaaaaacac ctgcacccct tactctcagt   1320
aatggttttc tatgtatcga agatcatgct cagcttacag tgaatcgatt cacacaaact   1380
gggggtgttg tttctcttgg gaatggagca gttctgagtt gctataaaaa tggtacagga   1440
gattctgcta gcaatgcctc tataacactg aagcatattg gattgaatct ttcttccatt   1500
ctgaaaagtg gtgctgagat tcctttattg tgggtagagc ctacaaataa cagcaataac   1560
tatacagcag atactgcagc taccttttca ttaagtgatg taaaactctc actcattgat   1620
gactacggga actctcctta tgaatccaca gatctgaccc atgctctgtc atcacagcct   1680
atgctatcta tttctgaagc tagcgataac cagctacaat cagaaaatat agatttttcg   1740
ggactaaatg tccctcatta tggatggcaa ggactttgga cttggggctg ggcaaaaact   1800
caagatccag aaccagcatc ttcagcaaca atcactgatc cacaaaaagc caatagattt   1860
catagaacct tactactaac atggcttcct gccgggtatg ttcctagccc aaaacacaga   1920
agtcccctca tagctaacac cttatggggg aatatgctgc ttgcaacaga aagcttaaaa   1980
aatagtgcag agctgacacc tagtggtcat cctttctggg gaattacagg aggaggacta   2040
ggcatgatgg tttaccaaga tcctcgagaa aatcatcctg gattccatat gcgctcttcc   2100
ggatactctg cggggatgat agcagggcag acacacacct tctcattgaa attcagtcag   2160
acctacacca aactcaatga gcgttacgca aaaaacaacg tatcttctaa aaattactca   2220
tgccaaggag aaatgctctt ctcattgcaa gaaggtttct tgctgactaa attagttggg   2280
ctttacagct atggagacca taactgtcac catttctata ctcaaggaga aaatctaaca   2340
tctcaaggga cgttccgcag tcaaacgatg ggaggtgctg tctttttga tctccctatg    2400
aaaccctttg gatcaacgca tatactgaca gctccctttt taggtgctct tggtatttat   2460
tctagcctgt ctcactttac tgaggtggga gcctatccgc gaagcttttc tacaaagact   2520
cctttgatca atgtcctagt ccctattgga gttaaaggta gctttatgaa tgctacccac   2580
agacctcaag cctggactgt agaattggca taccaacccg ttctgtatag acaagaacca   2640
gggatcgcag cccagctcct agccagtaag ggtatttggt tcggtagtgg aagcccctca   2700
tcgcgtcatg ccatgtccta taaaatctca cagcaaacac aacctttgag ttggttaact   2760
ctccatttcc agtatcatgg attctactcc tcttcaacct tctgtaatta tctcaatggg   2820
gaaattgctc tgcgattc                                                 2838
```

<210> SEQ ID NO 124
<211> LENGTH: 946
<212> TYPE: PRT
<213> ORGANISM: Chlamydia trachomatis

<400> SEQUENCE: 124

Arg Glu Val Pro Ser Arg Ile Phe Leu Met Pro Asn Ser Val Pro Asp
1               5                   10                  15

Pro Thr Lys Glu Ser Leu Ser Asn Lys Ile Ser Leu Thr Gly Asp Thr
            20                  25                  30

His Asn Leu Thr Asn Cys Tyr Leu Asp Asn Leu Arg Tyr Ile Leu Ala
        35                  40                  45

Ile Leu Gln Lys Thr Pro Asn Glu Gly Ala Ala Val Thr Ile Thr Asp
    50                  55                  60

Tyr Leu Ser Phe Phe Asp Thr Gln Lys Glu Gly Ile Tyr Phe Ala Lys
65                  70                  75                  80

Asn Leu Thr Pro Glu Ser Gly Gly Ala Ile Gly Tyr Ala Ser Pro Asn
                85                  90                  95

Ser Pro Thr Val Glu Ile Arg Asp Thr Ile Gly Pro Val Ile Phe Glu
            100                 105                 110

Asn Asn Thr Cys Cys Arg Leu Phe Thr Trp Arg Asn Pro Tyr Ala Ala
        115                 120                 125

Asp Lys Ile Arg Glu Gly Gly Ala Ile His Ala Gln Asn Leu Tyr Ile
    130                 135                 140

Asn His Asn His Asp Val Val Gly Phe Met Lys Asn Phe Ser Tyr Val
145                 150                 155                 160

Gln Gly Gly Ala Ile Ser Thr Ala Asn Thr Phe Val Val Ser Glu Asn
                165                 170                 175

Gln Ser Cys Phe Leu Phe Met Asp Asn Ile Cys Ile Gln Thr Asn Thr
            180                 185                 190

Ala Gly Lys Gly Gly Ala Ile Tyr Ala Gly Thr Ser Asn Ser Phe Glu
        195                 200                 205

Ser Asn Asn Cys Asp Leu Phe Phe Ile Asn Asn Ala Cys Cys Ala Gly
    210                 215                 220

Gly Ala Ile Phe Ser Pro Ile Cys Ser Leu Thr Gly Asn Arg Gly Asn
225                 230                 235                 240

Ile Val Phe Tyr Asn Asn Arg Cys Phe Lys Asn Val Glu Thr Ala Ser
                245                 250                 255

Ser Glu Ala Ser Asp Gly Gly Ala Ile Lys Val Thr Thr Arg Leu Asp
            260                 265                 270

Val Thr Gly Asn Arg Gly Arg Ile Phe Phe Ser Asp Asn Ile Thr Lys
        275                 280                 285

Asn Tyr Gly Gly Ala Ile Tyr Ala Pro Val Val Thr Leu Val Asp Asn
    290                 295                 300

Gly Pro Thr Tyr Phe Ile Asn Asn Ile Ala Asn Asn Lys Gly Gly Ala
305                 310                 315                 320

Ile Tyr Ile Asp Gly Thr Ser Asn Ser Lys Ile Ser Ala Asp Arg His
                325                 330                 335

Ala Ile Ile Phe Asn Glu Asn Ile Val Thr Asn Val Thr Asn Ala Asn
            340                 345                 350

Gly Thr Ser Thr Ser Ala Asn Pro Pro Arg Arg Asn Ala Ile Thr Val
        355                 360                 365

Ala Ser Ser Ser Gly Glu Ile Leu Leu Gly Ala Gly Ser Ser Gln Asn
    370                 375                 380

Leu Ile Phe Tyr Asp Pro Ile Glu Val Ser Asn Ala Gly Val Ser Val
385                 390                 395                 400

Ser Phe Asn Lys Glu Ala Asp Gln Thr Gly Ser Val Val Phe Ser Gly
                405                 410                 415

```
Ala Thr Val Asn Ser Ala Asp Phe His Gln Arg Asn Leu Gln Thr Lys
            420                 425                 430

Thr Pro Ala Pro Leu Thr Leu Ser Asn Gly Phe Leu Cys Ile Glu Asp
        435                 440                 445

His Ala Gln Leu Thr Val Asn Arg Phe Thr Gln Thr Gly Gly Val Val
    450                 455                 460

Ser Leu Gly Asn Gly Ala Val Leu Ser Cys Tyr Lys Asn Gly Thr Gly
465                 470                 475                 480

Asp Ser Ala Ser Asn Ala Ser Ile Thr Leu Lys His Ile Gly Leu Asn
                485                 490                 495

Leu Ser Ser Ile Leu Lys Ser Gly Ala Glu Ile Pro Leu Leu Trp Val
            500                 505                 510

Glu Pro Thr Asn Asn Ser Asn Asn Tyr Thr Ala Asp Thr Ala Ala Thr
        515                 520                 525

Phe Ser Leu Ser Asp Val Lys Leu Ser Leu Ile Asp Asp Tyr Gly Asn
    530                 535                 540

Ser Pro Tyr Glu Ser Thr Asp Leu Thr His Ala Leu Ser Ser Gln Pro
545                 550                 555                 560

Met Leu Ser Ile Ser Glu Ala Ser Asp Asn Gln Leu Gln Ser Glu Asn
                565                 570                 575

Ile Asp Phe Ser Gly Leu Asn Val Pro His Tyr Gly Trp Gln Gly Leu
            580                 585                 590

Trp Thr Trp Gly Trp Ala Lys Thr Gln Asp Pro Glu Pro Ala Ser Ser
        595                 600                 605

Ala Thr Ile Thr Asp Pro Gln Lys Ala Asn Arg Phe His Arg Thr Leu
    610                 615                 620

Leu Leu Thr Trp Leu Pro Ala Gly Tyr Val Pro Ser Pro Lys His Arg
625                 630                 635                 640

Ser Pro Leu Ile Ala Asn Thr Leu Trp Gly Asn Met Leu Leu Ala Thr
                645                 650                 655

Glu Ser Leu Lys Asn Ser Ala Glu Leu Thr Pro Ser Gly His Pro Phe
            660                 665                 670

Trp Gly Ile Thr Gly Gly Gly Leu Gly Met Met Val Tyr Gln Asp Pro
        675                 680                 685

Arg Glu Asn His Pro Gly Phe His Met Arg Ser Ser Gly Tyr Ser Ala
    690                 695                 700

Gly Met Ile Ala Gly Gln Thr His Thr Phe Ser Leu Lys Phe Ser Gln
705                 710                 715                 720

Thr Tyr Thr Lys Leu Asn Glu Arg Tyr Ala Lys Asn Asn Val Ser Ser
                725                 730                 735

Lys Asn Tyr Ser Cys Gln Gly Glu Met Leu Phe Ser Leu Gln Glu Gly
            740                 745                 750

Phe Leu Leu Thr Lys Leu Val Gly Leu Tyr Ser Tyr Gly Asp His Asn
        755                 760                 765

Cys His His Phe Tyr Thr Gln Gly Glu Asn Leu Thr Ser Gln Gly Thr
    770                 775                 780

Phe Arg Ser Gln Thr Met Gly Gly Ala Val Phe Phe Asp Leu Pro Met
785                 790                 795                 800

Lys Pro Phe Gly Ser Thr His Ile Leu Thr Ala Pro Phe Leu Gly Ala
                805                 810                 815

Leu Gly Ile Tyr Ser Ser Leu Ser His Phe Thr Glu Val Gly Ala Tyr
            820                 825                 830

Pro Arg Ser Phe Ser Thr Lys Thr Pro Leu Ile Asn Val Leu Val Pro
```

-continued

```
        835                 840                 845

Ile Gly Val Lys Gly Ser Phe Met Asn Ala Thr His Arg Pro Gln Ala
    850                 855                 860

Trp Thr Val Glu Leu Ala Tyr Gln Pro Val Leu Tyr Arg Gln Glu Pro
865                 870                 875                 880

Gly Ile Ala Ala Gln Leu Leu Ala Ser Lys Gly Ile Trp Phe Gly Ser
                885                 890                 895

Gly Ser Pro Ser Ser Arg His Ala Met Ser Tyr Lys Ile Ser Gln Gln
            900                 905                 910

Thr Gln Pro Leu Ser Trp Leu Thr Leu His Phe Gln Tyr His Gly Phe
        915                 920                 925

Tyr Ser Ser Ser Thr Phe Cys Asn Tyr Leu Asn Gly Glu Ile Ala Leu
    930                 935                 940

Arg Phe
945


<210> SEQ ID NO 125
<211> LENGTH: 1914
<212> TYPE: DNA
<213> ORGANISM: Chlamydia trachomatis

<400> SEQUENCE: 125

aacgttcgta cgtactctgt tcagaggggg ggggtaaaaa cgatttctgc tagtgcagtt      60

cctcctacag cagctgtttt atcgagaaaa aagcgtgcta tagaagagaa gaaggaggaa     120

gcttcttctg gaaagataga aatcttgat gctagcaaat acgatcttac tcccaagaac     180

atagaagaaa aactaggaat tactcctgaa cagaaatcta ctgttaaaga cctattaaat     240

aaactgaaaa aggtcattag tgcttacaac tctatgccag ataaaaattc ggaagcggga     300

cagaattcct tgattcaaca aggaaaatac gtcgatgcca ttcagaagaa gcttccagca     360

tcatcgcagg ctcagcctaa acaggcaaaa gctaaggaac agaaagccga agaaaaacct     420

aagacgactc cgattgaagg tgttcttgaa accatcaaaa cagaatttaa aggccatcgt     480

gtacctgttg agaaaatcat ccatggaata tggatcgcag gagcgcctcc ggatggtatc     540

gaagattata tgcgagtctt tttagatact tatgaaggtt ttgacttcta cttctgggta     600

gatgagaatg cttatgcagc agctaaattt tctagcattt tgaagaaggt cgctttcgat     660

gcggctattc aagatctacg atctgccaca gatgagtcta cgaaggcctt tgttaaagac     720

tacgatgaat taaaacagaa atatgaaaag aaagttgcgg agacgacttc tcaagcagaa     780

aaagaccaat atctcaaaga tctaaaggat cttttagaga aatttacaaa aatcagtgat     840

gagattcgtg gaaaatttga tcggctgttt cttaagaatg tgattgttgc tcagaacgga     900

ttctttaatt tctgcttgct gaaaggcctc ggcaatatca atgacgaaac gcgtgcagag     960

tatttagaga aagaactcaa acttcctact gaggagatcg aacagtataa aaagcttaaa    1020

gagacgaaca aagagaagat agccgctatt gtaaaacaac taaacgagaa acttggatcg    1080

gatcgggtaa aaatcaaaga cattaaagag ctgcaatcta tgaagcaagc tcgaaatgtc    1140

tacaattatg aacaggaaat gtttctgcgc tggaactatg cagccgcaac agatcagatt    1200

cgtatgtata tgttggagga acttggaggt ctttatactg atctggatat gatgccttca    1260

tactctcagg aagtattgga gcttatcaaa aagcacagtg atggaaaccg aatgtttgag    1320

gatatgagct ctagacgggc gatttctgat gcggttttaa agatggctgt aggtaaggcg    1380

acaacagttt ccatggaaga ggtagcaaag gatatcgatg tttctcgctt aacagaagag    1440

gataagacaa aattaaatgc tctatttaag gatctagagc catttgcaaa accggattct    1500
```

aaaggagctg aagcagaagg gggtgaagga gcaaaaggta tgaaaaagag ctttttccag 1560
cccatagatc tgaatattgt cagaaatacc atgcctatct tgagacgcta tcatcactat 1620
cctgagttag gatggtttat tcgaggattg aacggattga tggtctctca taagggaagc 1680
actgcggttt ctgctgtcat tgtagggcaa caggctgcct accaggaact agcagcactt 1740
agacaagatg tcctttcagg ggagtttttc cattctttag aaaatttgac acatagaaac 1800
cataaggagc gtattggaaa tcatctcgtc gctaattatt tggctaaaag tctctttttt 1860
gattactgcc aagattcagt gatgccggag gctgtaagta ccttaggtat taga 1914

<210> SEQ ID NO 126
<211> LENGTH: 638
<212> TYPE: PRT
<213> ORGANISM: Chlamydia trachomatis

<400> SEQUENCE: 126

Asn Val Arg Thr Tyr Ser Val Gln Arg Gly Gly Val Lys Thr Ile Ser
1 5 10 15

Ala Ser Ala Val Pro Pro Thr Ala Ala Val Leu Ser Arg Lys Lys Arg
20 25 30

Ala Ile Glu Glu Lys Lys Glu Glu Ala Ser Ser Gly Lys Ile Glu Asn
35 40 45

Leu Asp Ala Ser Lys Tyr Asp Leu Thr Pro Lys Asn Ile Glu Glu Lys
50 55 60

Leu Gly Ile Thr Pro Glu Gln Lys Ser Thr Val Lys Asp Leu Leu Asn
65 70 75 80

Lys Leu Lys Lys Val Ile Ser Ala Tyr Asn Ser Met Pro Asp Lys Asn
85 90 95

Ser Glu Ala Gly Gln Asn Ser Leu Ile Gln Gln Gly Lys Tyr Val Asp
100 105 110

Ala Ile Gln Lys Lys Leu Pro Ala Ser Ser Gln Ala Gln Pro Lys Gln
115 120 125

Ala Lys Ala Lys Glu Gln Lys Ala Glu Glu Lys Pro Lys Thr Thr Pro
130 135 140

Ile Glu Gly Val Leu Glu Thr Ile Lys Thr Glu Phe Lys Gly His Arg
145 150 155 160

Val Pro Val Glu Lys Ile Ile His Gly Ile Trp Ile Ala Gly Ala Pro
165 170 175

Pro Asp Gly Ile Glu Asp Tyr Met Arg Val Phe Leu Asp Thr Tyr Glu
180 185 190

Gly Phe Asp Phe Tyr Phe Trp Val Asp Glu Asn Ala Tyr Ala Ala Ala
195 200 205

Lys Phe Ser Ser Ile Leu Lys Lys Val Ala Phe Asp Ala Ala Ile Gln
210 215 220

Asp Leu Arg Ser Ala Thr Asp Glu Ser Thr Lys Ala Phe Val Lys Asp
225 230 235 240

Tyr Asp Glu Leu Lys Gln Lys Tyr Glu Lys Lys Val Ala Glu Thr Thr
245 250 255

Ser Gln Ala Glu Lys Asp Gln Tyr Leu Lys Asp Leu Lys Asp Leu Leu
260 265 270

Glu Lys Phe Thr Lys Ile Ser Asp Glu Ile Arg Gly Lys Phe Asp Arg
275 280 285

Leu Phe Leu Lys Asn Val Ile Val Ala Gln Asn Gly Phe Phe Asn Phe
290 295 300

-continued

```
Cys Leu Leu Lys Gly Leu Gly Asn Ile Asn Asp Glu Thr Arg Ala Glu
305                 310                 315                 320

Tyr Leu Glu Lys Glu Leu Lys Leu Pro Thr Glu Glu Ile Glu Gln Tyr
                325                 330                 335

Lys Lys Leu Lys Glu Thr Asn Lys Glu Lys Ile Ala Ala Ile Val Lys
            340                 345                 350

Gln Leu Asn Glu Lys Leu Gly Ser Asp Arg Val Lys Ile Lys Asp Ile
        355                 360                 365

Lys Glu Leu Gln Ser Met Lys Gln Ala Arg Asn Val Tyr Asn Tyr Glu
    370                 375                 380

Gln Glu Met Phe Leu Arg Trp Asn Tyr Ala Ala Ala Thr Asp Gln Ile
385                 390                 395                 400

Arg Met Tyr Met Leu Glu Glu Leu Gly Gly Leu Tyr Thr Asp Leu Asp
                405                 410                 415

Met Met Pro Ser Tyr Ser Gln Glu Val Leu Glu Leu Ile Lys Lys His
            420                 425                 430

Ser Asp Gly Asn Arg Met Phe Glu Asp Met Ser Ser Arg Arg Ala Ile
        435                 440                 445

Ser Asp Ala Val Leu Lys Met Ala Val Gly Lys Ala Thr Thr Val Ser
    450                 455                 460

Met Glu Glu Val Ala Lys Asp Ile Asp Val Ser Arg Leu Thr Glu Glu
465                 470                 475                 480

Asp Lys Thr Lys Leu Asn Ala Leu Phe Lys Asp Leu Glu Pro Phe Ala
                485                 490                 495

Lys Pro Asp Ser Lys Gly Ala Glu Ala Glu Gly Gly Glu Gly Ala Lys
            500                 505                 510

Gly Met Lys Lys Ser Phe Phe Gln Pro Ile Asp Leu Asn Ile Val Arg
        515                 520                 525

Asn Thr Met Pro Ile Leu Arg Arg Tyr His His Tyr Pro Glu Leu Gly
    530                 535                 540

Trp Phe Ile Arg Gly Leu Asn Gly Leu Met Val Ser His Lys Gly Ser
545                 550                 555                 560

Thr Ala Val Ser Ala Val Ile Val Gly Gln Gln Ala Ala Tyr Gln Glu
                565                 570                 575

Leu Ala Ala Leu Arg Gln Asp Val Leu Ser Gly Glu Phe Phe His Ser
            580                 585                 590

Leu Glu Asn Leu Thr His Arg Asn His Lys Glu Arg Ile Gly Asn His
        595                 600                 605

Leu Val Ala Asn Tyr Leu Ala Lys Ser Leu Phe Phe Asp Tyr Cys Gln
    610                 615                 620

Asp Ser Val Met Pro Glu Ala Val Ser Thr Leu Gly Ile Arg
625                 630                 635
```

<210> SEQ ID NO 127
<211> LENGTH: 1523
<212> TYPE: DNA
<213> ORGANISM: Chlamydia trachomatis

<400> SEQUENCE: 127

```
gttatcataa aaaagaagaa ccaaaagatg ttttgcggat tgcgatctgt catgatccaa      60

tgtctttaga tccgcgtcag gtttttttaa gcaaagatgt ttctattgta aaagctctct     120

atgaagggtt agtccgggaa aaagaagctg cgttccagct agctttggca gaaagatatc     180

atcaatctga tgatggttgt gtttatactt tttttctaaa aaatacattc tggagcaacg     240

gagatgttgt aacagcatat gattttgaag agtctattaa acaaatttat ttccgagaaa     300
```

```
ttgataaccc ttcgttacgc tctcttgcat taattaaaaa ttctcatgct gttttaacag    360

gagctctccc tgttgaagat ttaggtgtta gagctttgaa tgcgaaaact ctagaaattg    420

ttttagaaaa cccgtttcct tattttctag agatattggc gcacccggtt ttttatccgg    480

tgcacacctc tttacgagaa tattacaaag ataagcgtaa caaacgcgtt ttcccgataa    540

tttctaatgg tccttttgcg attcaatgtt atgagccgca aagatattta ctaatcaaca    600

aaaaccctct gtatcatgcc aagcacgatg ttctgttaaa ttcggtatgt ttgcagatag    660

ttcctgatat ccatacagct atgcagttat tccaaaaaaa tcatatcgat ttagttgggt    720

taccctggag ctcctccttt tctttagaag aacaaagaaa tctccctaga gaaaaattat    780

ttgattatcc tgtattgagt tgctctgttt tattctgtaa cattcatcaa acacctttaa    840

ataatccctc gctgagaaca gccctctctt tagcaatcaa tcgagaaact ttattaaaac    900

tagcaggtaa aggctgtagc gctacgagct ttgttcaccc acaattatct cagatacctg    960

ctactacttt gtctcaagat gagcggattg ctttagcaaa aggctacttg accgaagctt   1020

taaagacttt atctcaagaa gatttagaaa aaattacatt aatttatcct atagaatctg   1080

tttgcttacg agccgttgtt caagaaattc gccaacaatt atttgatgta ctgggattta   1140

aaatttctac attaggatta gaatatcatt gtttttaga caaacgttcc agaggagaat   1200

tctccttagc aactggtaat tggattgcag actatcatca agctagtgct ttcctgtctg   1260

tcctaggtaa tgggacaaga tataaagact ttcaattgat taactggcag aaccaaaagt   1320

acacaaatat agttgctcaa cttctgattc aagaatcaag cgacctacag cttatggcag   1380

agcagttgtt gcttaaagaa agtcctctta ttcctctata ccacctcgat tatgtgtatg   1440

cgaaacagcc tcgggtgtct gatctccaaa cctcttctcg tggagaaatt gatttaaaaa   1500

gagtttcatt agctgaagga tag                                           1523
```

<210> SEQ ID NO 128
<211> LENGTH: 507
<212> TYPE: PRT
<213> ORGANISM: Chlamydia trachomatis

<400> SEQUENCE: 128

```
Cys Tyr His Lys Lys Glu Glu Pro Lys Asp Val Leu Arg Ile Ala Ile
1               5                   10                  15

Cys His Asp Pro Met Ser Leu Asp Pro Arg Gln Val Phe Leu Ser Lys
            20                  25                  30

Asp Val Ser Ile Val Lys Ala Leu Tyr Glu Gly Leu Val Arg Glu Lys
        35                  40                  45

Glu Ala Ala Phe Gln Leu Ala Leu Ala Glu Arg Tyr His Gln Ser Asp
    50                  55                  60

Asp Gly Cys Val Tyr Thr Phe Phe Leu Lys Asn Thr Phe Trp Ser Asn
65                  70                  75                  80

Gly Asp Val Val Thr Ala Tyr Asp Phe Glu Glu Ser Ile Lys Gln Ile
                85                  90                  95

Tyr Phe Arg Glu Ile Asp Asn Pro Ser Leu Arg Ser Leu Ala Leu Ile
            100                 105                 110

Lys Asn Ser His Ala Val Leu Thr Gly Ala Leu Pro Val Glu Asp Leu
        115                 120                 125

Gly Val Arg Ala Leu Asn Ala Lys Thr Leu Glu Ile Val Leu Glu Asn
    130                 135                 140

Pro Phe Pro Tyr Phe Leu Glu Ile Leu Ala His Pro Val Phe Tyr Pro
145                 150                 155                 160
```

```
Val His Thr Ser Leu Arg Glu Tyr Tyr Lys Asp Lys Arg Asn Lys Arg
                165                 170                 175

Val Phe Pro Ile Ile Ser Asn Gly Pro Phe Ala Ile Gln Cys Tyr Glu
            180                 185                 190

Pro Gln Arg Tyr Leu Leu Ile Asn Lys Asn Pro Leu Tyr His Ala Lys
        195                 200                 205

His Asp Val Leu Leu Asn Ser Val Cys Leu Gln Ile Val Pro Asp Ile
    210                 215                 220

His Thr Ala Met Gln Leu Phe Gln Lys Asn His Ile Asp Leu Val Gly
225                 230                 235                 240

Leu Pro Trp Ser Ser Ser Phe Ser Leu Glu Glu Gln Arg Asn Leu Pro
                245                 250                 255

Arg Glu Lys Leu Phe Asp Tyr Pro Val Leu Ser Cys Ser Val Leu Phe
            260                 265                 270

Cys Asn Ile His Gln Thr Pro Leu Asn Asn Pro Ser Leu Arg Thr Ala
        275                 280                 285

Leu Ser Leu Ala Ile Asn Arg Glu Thr Leu Leu Lys Leu Ala Gly Lys
    290                 295                 300

Gly Cys Ser Ala Thr Ser Phe Val His Pro Gln Leu Ser Gln Ile Pro
305                 310                 315                 320

Ala Thr Thr Leu Ser Gln Asp Glu Arg Ile Ala Leu Ala Lys Gly Tyr
                325                 330                 335

Leu Thr Glu Ala Leu Lys Thr Leu Ser Gln Glu Asp Leu Glu Lys Ile
            340                 345                 350

Thr Leu Ile Tyr Pro Ile Glu Ser Val Cys Leu Arg Ala Val Val Gln
        355                 360                 365

Glu Ile Arg Gln Gln Leu Phe Asp Val Leu Gly Phe Lys Ile Ser Thr
    370                 375                 380

Leu Gly Leu Glu Tyr His Cys Phe Leu Asp Lys Arg Ser Arg Gly Glu
385                 390                 395                 400

Phe Ser Leu Ala Thr Gly Asn Trp Ile Ala Asp Tyr His Gln Ala Ser
                405                 410                 415

Ala Phe Leu Ser Val Leu Gly Asn Gly Thr Arg Tyr Lys Asp Phe Gln
            420                 425                 430

Leu Ile Asn Trp Gln Asn Gln Lys Tyr Thr Asn Ile Val Ala Gln Leu
        435                 440                 445

Leu Ile Gln Glu Ser Ser Asp Leu Gln Leu Met Ala Glu Gln Leu Leu
    450                 455                 460

Leu Lys Glu Ser Pro Leu Ile Pro Leu Tyr His Leu Asp Tyr Val Tyr
465                 470                 475                 480

Ala Lys Gln Pro Arg Val Ser Asp Leu Gln Thr Ser Ser Arg Gly Glu
                485                 490                 495

Ile Asp Leu Lys Arg Val Ser Leu Ala Glu Gly
            500                 505
```

<210> SEQ ID NO 129
<211> LENGTH: 2076
<212> TYPE: DNA
<213> ORGANISM: Chlamydia muridarum

<400> SEQUENCE: 129

```
atgacactct ttcacactca tcacgatgcc gtctctccgg acggctactt atgttcttcc      60

cttcagttag ttggctctgg cacatatgaa ggagaaatcg aaatccaaaa tattccttct     120

tatttccttg gattccgatt acccacccat tgcgttcatc ttaatttgaa gagttctcta     180
```

```
gcccagttag gagtagatgc atctcttctt cactgcgaac taagcaaaaa tcaacaacgt    240

gcacatatgc acgtgcagtt caccggctat ggccctatcg ctgagtccat gctatctctt    300

ctcaaacccg gagatcgagt agccaaactg tttgctgcag atgatcgtag actagtccgc    360

tcccctgatt atcttgaaag catgctaaaa aatactgata agacaggaca tcctctgctc    420

cgatttggaa aaaaactcga gcatcttatc tcttttgatg tggtggacga tcgcctcgtt    480

gtatcactcc ccaccttgcc aggcatagtc aattatgacc cagacatcta tggacttctt    540

cccttaattc aaaaatcact aagcaatcct aaattgagta ttcgccactt cttgtctctc    600

tatcagaaga tcgtagaagg accacacatc ccttatgaag gaaacatttt gttaatcaaa    660

acagagcctc ttcatatccg cacagtattt gctcgcgtgg tcgatcaaat gctccctcaa    720

ggtctatttc acacttctgc caacatttta gaacccacaa cgcgagagtc tggagatatt    780

tttgaatttt ttggaaatcc ctccactctt gtagaaagaa tccctctaga attcttcact    840

atcgaaccct acaaagaaca ctcttacttc tgtaatcgag atctattgca aactaccttg    900

caatcggaaa gtgaaatcaa aaaaatattc gatacagctc ctcaagagcc tgtaaaagcc    960

gccacttatt tatcaaaagg aagtgaaatt tcttctcttg atgcagattc ttggcttacg   1020

ggatccgcag ctgcatacca atgtagcgaa aaacaggcag ctaaagacga atacatccac   1080

gctcaaccct gttatccatt tttggaagca atggaaacgg gactcatcaa tagcgaagga   1140

gctttactca ctcggttttt cccctcttcc agcttaaaag ggatgttgat ctcctatcat   1200

gtacgccact atcttaagca aatttacttt caagttcctt cttatacata tggagactac   1260

ttctctcata atgaccgagg attactgtta gatctatatc aggcgaacat tgatgtgttc   1320

tgggctgatg aagagagcgg ccgtgtattg caatatacaa aacggcgcga caaaaaatagt  1380

ggaatgttcg tcgttaaaaa tcgagtagaa gagttccaat cagcatattt cgtagcgatt   1440

tatggatcac gtctcctgga aaataatttc tcggcccaac taaacacgct tcttgcaggg   1500

ttacaaaaag ctgcacacac tctaggcatt ccaggcttct caaaacccac tcctcttgcc   1560

gtaatcacag gaggagggac tggcgttatg gctacaggaa atcgtgttgc aaaagagttg   1620

ggaattcttt cttgcgggac cgttctcgat ttggaagctt cacctgcaca aatagatcag   1680

cctgcaaacg aatttttaga tgccaaaatg acataccgtc taccgcaact tatagaaaga   1740

caagaacatt tttattcaga ccttgccatt ttagttgttg gtggtgttgg aacagatttc   1800

gaactttacc tagaactcgt ctacttgaaa acaggcgcca aacctcctac tccaattttc   1860

cttattgggc ctgttgaata ctggaaagag aaagttgctc atgcctatga gattaatctt   1920

aaagcaggaa ctattcgtgg ttctgagtgg atcagcaact gcttattctg cattacatct   1980

cctgaagcag gaattgctgt attcgaacag ttcctcgctg gagaacttcc cataggatat   2040

gattatcctc cagctccaga cggattagtt atcgtc                             2076
```

<210> SEQ ID NO 130
<211> LENGTH: 692
<212> TYPE: PRT
<213> ORGANISM: Chlamydia muridarum

<400> SEQUENCE: 130

```
Met Thr Leu Phe His Thr His His Asp Ala Val Ser Pro Asp Gly Tyr
1               5                   10                  15

Leu Cys Ser Ser Leu Gln Leu Val Gly Ser Gly Thr Tyr Glu Gly Glu
            20                  25                  30

Ile Glu Ile Gln Asn Ile Pro Ser Tyr Phe Leu Gly Phe Arg Leu Pro
```

-continued

```
        35                  40                  45

Thr His Cys Val His Leu Asn Leu Lys Ser Ser Leu Ala Gln Leu Gly
    50                  55                  60

Val Asp Ala Ser Leu Leu His Cys Glu Leu Ser Lys Asn Gln Gln Arg
65                  70                  75                  80

Ala His Met His Val Gln Phe Thr Gly Tyr Gly Pro Ile Ala Glu Ser
                85                  90                  95

Met Leu Ser Leu Leu Lys Pro Gly Asp Arg Val Ala Lys Leu Phe Ala
            100                 105                 110

Ala Asp Asp Arg Arg Leu Val Arg Ser Pro Asp Tyr Leu Glu Ser Met
        115                 120                 125

Leu Lys Asn Thr Asp Lys Thr Gly His Pro Leu Leu Arg Phe Gly Lys
    130                 135                 140

Lys Leu Glu His Leu Ile Ser Phe Asp Val Val Asp Asp Arg Leu Val
145                 150                 155                 160

Val Ser Leu Pro Thr Leu Pro Gly Ile Val Asn Tyr Asp Pro Asp Ile
                165                 170                 175

Tyr Gly Leu Leu Pro Leu Ile Gln Lys Ser Leu Ser Asn Pro Lys Leu
            180                 185                 190

Ser Ile Arg His Phe Leu Ser Leu Tyr Gln Lys Ile Val Glu Gly Pro
        195                 200                 205

His Ile Pro Tyr Glu Gly Asn Ile Leu Leu Ile Lys Thr Glu Pro Leu
    210                 215                 220

His Ile Arg Thr Val Phe Ala Arg Val Val Asp Gln Met Leu Pro Gln
225                 230                 235                 240

Gly Leu Phe His Thr Ser Ala Asn Ile Leu Glu Pro Thr Thr Arg Glu
                245                 250                 255

Ser Gly Asp Ile Phe Glu Phe Phe Gly Asn Pro Ser Thr Leu Val Glu
            260                 265                 270

Arg Ile Pro Leu Glu Phe Phe Thr Ile Glu Pro Tyr Lys Glu His Ser
        275                 280                 285

Tyr Phe Cys Asn Arg Asp Leu Leu Gln Thr Thr Leu Gln Ser Glu Ser
    290                 295                 300

Glu Ile Lys Lys Ile Phe Asp Thr Ala Pro Gln Glu Pro Val Lys Ala
305                 310                 315                 320

Ala Thr Tyr Leu Ser Lys Gly Ser Glu Ile Ser Ser Leu Asp Ala Asp
                325                 330                 335

Ser Trp Leu Thr Gly Ser Ala Ala Ala Tyr Gln Cys Ser Glu Lys Gln
            340                 345                 350

Ala Ala Lys Asp Glu Tyr Ile His Ala Gln Pro Cys Tyr Pro Phe Leu
        355                 360                 365

Glu Ala Met Glu Thr Gly Leu Ile Asn Ser Glu Gly Ala Leu Leu Thr
    370                 375                 380

Arg Phe Phe Pro Ser Ser Ser Leu Lys Gly Met Leu Ile Ser Tyr His
385                 390                 395                 400

Val Arg His Tyr Leu Lys Gln Ile Tyr Phe Gln Val Pro Ser Tyr Thr
                405                 410                 415

Tyr Gly Asp Tyr Phe Ser His Asn Asp Arg Gly Leu Leu Leu Asp Leu
            420                 425                 430

Tyr Gln Ala Asn Ile Asp Val Phe Trp Ala Asp Glu Glu Ser Gly Arg
        435                 440                 445

Val Leu Gln Tyr Thr Lys Arg Arg Asp Lys Asn Ser Gly Met Phe Val
    450                 455                 460
```

```
Val Lys Asn Arg Val Glu Glu Phe Gln Ser Ala Tyr Phe Val Ala Ile
465                 470                 475                 480

Tyr Gly Ser Arg Leu Leu Glu Asn Asn Phe Ser Ala Gln Leu Asn Thr
                485                 490                 495

Leu Leu Ala Gly Leu Gln Lys Ala Ala His Thr Leu Gly Ile Pro Gly
            500                 505                 510

Phe Ser Lys Pro Thr Pro Leu Ala Val Ile Thr Gly Gly Gly Thr Gly
        515                 520                 525

Val Met Ala Thr Gly Asn Arg Val Ala Lys Glu Leu Gly Ile Leu Ser
    530                 535                 540

Cys Gly Thr Val Leu Asp Leu Glu Ala Ser Pro Ala Gln Ile Asp Gln
545                 550                 555                 560

Pro Ala Asn Glu Phe Leu Asp Ala Lys Met Thr Tyr Arg Leu Pro Gln
                565                 570                 575

Leu Ile Glu Arg Gln Glu His Phe Tyr Ser Asp Leu Ala Ile Leu Val
            580                 585                 590

Val Gly Gly Val Gly Thr Asp Phe Glu Leu Tyr Leu Glu Leu Val Tyr
        595                 600                 605

Leu Lys Thr Gly Ala Lys Pro Pro Thr Pro Ile Phe Leu Ile Gly Pro
    610                 615                 620

Val Glu Tyr Trp Lys Glu Lys Val Ala His Ala Tyr Glu Ile Asn Leu
625                 630                 635                 640

Lys Ala Gly Thr Ile Arg Gly Ser Glu Trp Ile Ser Asn Cys Leu Phe
                645                 650                 655

Cys Ile Thr Ser Pro Glu Ala Gly Ile Ala Val Phe Glu Gln Phe Leu
            660                 665                 670

Ala Gly Glu Leu Pro Ile Gly Tyr Asp Tyr Pro Pro Ala Pro Asp Gly
        675                 680                 685

Leu Val Ile Val
    690
```

<210> SEQ ID NO 131
<211> LENGTH: 4473
<212> TYPE: DNA
<213> ORGANISM: Chlamydia muridarum

<400> SEQUENCE: 131

```
aattgttccg atctttatgc cgtaggaagt tctgcagacc atcctgccta cttgattcct      60

caagcggggt tattattgga tcatattaag gatatattca ttggccctaa agatagtcag     120

gataaggggc agtataagtt gattattggt gaggctggct ctttccaaga tagtaatgca     180

gagactcttc ctcaaaaggt agagcacagc actttgtttt cagttacaac acctataatt     240

gtgcaaggaa tagatcaaca agatcaggtc tcttcgcagg gattggtctg taatttttca     300

ggagatcatt cagaggagat ttttgagaga gaatcctttt tagggatcgc tttcctaggg     360

aatggtagca aggatggaat cacgttaaca gatataaaat cttcgttatc tggtgctgcc     420

ttgtattctt cagatgatct tatttttgaa agaattaagg gagatataga gctttcttct     480

tgttcatctt tagaaagagg aggagcttgt tcagctcaaa gtattttaat tcatgattgt     540

caaggattaa cggtaaaaca ttgtgccgca ggggtgaatg ttgaaggagt tagtgctagc     600

gaccatctcg gatttggggg cggggccttc tctactacaa gttctctttc tggagagaag     660

agtttgtata tgcctgcagg cgatattgtg gtggctacct gcgatggtcc tgtgtgtttc     720

gaaggaaata gtgctcagtt agcaaatggt ggcgctattg ccgcttctgg taaagttctt     780

tttgtagcta acgaaaaaaa gatttccttt acagacaacc aagctttgtc tggaggagct     840
```

-continued

```
atttctgcat cttctagtat ttctttccaa aattgtgctg agcttgtgtt caagagtaat    900
cttgcaaaag gagttaaaga taaatgttct ttgggaggag gtgctttagc ctctttagaa    960
tccgtagttt tgaaagataa tctcggtatt acttatgaaa aaaatcagtc ctattcggaa   1020
ggaggggcta tttttgggaa ggattgtgag atttttgaaa acaggggggcc tgttgtattc   1080
agagataata cagctgcttt aggaggcgga gctattttgg cgcaacaaac tgtggcgatt   1140
tgtggtaata agtctggaat atcttttgaa ggaagtaagt ctagttttgg aggggccatt   1200
gcttgtggaa atttctcttc tgagaataat tcttcagctt tgggatcaat tgatatctct   1260
aacaatctag gagatatctc ttttcttcgg actctgtgta ctacttcgga tttagggcaa   1320
acggattacc aagggggagg ggccttattc gctgaaaata tttctctttc tgagaatgct   1380
ggtgcaatta ctttcaaaga caatattgtg aagacatttg cctcaaatgg aaaaatgttg   1440
ggtggagggg caattttagc ttcaggaaat gttttgatta gcaaaaactc tggagagatt   1500
tcttttgtag ggaatgctcg agctcctcag gctattccga ctcgttcatc tgacgaattg   1560
tcttttggcg cacaattaac tcaaactact tcaggatgtt ctggaggagg agctcttttt   1620
ggtaaagagg ttgccattgt tcaaaatgcc actgttgtat tcgagcaaaa tcgcttacag   1680
tgtggcgagc aggaaacaca tggtggaggc ggtgctgttt atggtatgga gagtgcctct   1740
attattggaa actcttttgt gagattcgga aataattacg ctgtagggaa tcagatttct   1800
ggaggagctc ttttatccaa gaaggtccgt ttagctgaaa atacaagggt agatttttct   1860
cgaaatatcg ctactttctg cggcggggct gttcaagttt ctgatggaag ttgcgaattg   1920
atcaacaatg ggtatgtgct attcagagat aaccgagggc agacatttgg tggggctatt   1980
tcttgcttga aaggagatgt gatcatttcc ggaaataaag atagggttga gtttagagat   2040
aacattgtga cgcggcctta ttttgaagaa aatgaagaaa aagttgagac agcagatatt   2100
aattcagata agcaagaagc agaagagcgc tctttattag agaacattga gcagagcttt   2160
attactgcaa ctaatcagac ctttttctta gaggaagaga aactcccatc agaagctttt   2220
atctctgctg aagaactttc aaagagaaga gaatgtgctg gtggggcgat tttgcaaaa   2280
cgggtctaca ttacggataa taaagaacct atcttgtttt cgcataattt ttctgatgtt   2340
tatgggggag ctatttttac gggttctcta caggaaactg ataaacaaga tgttgtaact   2400
cctgaagttg tgatatcagg caacgatggg gatgtcattt tttctggaaa tgcagctaaa   2460
catgataagc atttacctga tacaggtggt ggagccattt gtacacagaa tttgacgatt   2520
tcccaaaaca atgggaatgt cttgttcttg aacaattttg cttgttctgg tggagcagtt   2580
cgcatagagg atcatggaga agttctttta gaggcttttg gggagatat tattttcaat   2640
ggaaactctt ctttcagagc tcaaggatcg gatgcgatct attttgctgg taaggactct   2700
agaattaaag ctttaaatgc tactgaagga catgcgattg tgttccaaga tgcattggtg   2760
tttgaaaata tagaagaaag aaagtcttcg ggactattgg tgattaactc tcaggaaaat   2820
gagggttata cgggatccgt ccgattttta ggatctgaaa gtaaggttcc tcaatggatt   2880
catgtgcaac agggaggtct tgagttgcta catggagcta ttttatgtag ttatggggtt   2940
aaacaagatc ctagagctaa aatagtatta tctgctggat ctaaattgaa gattctagat   3000
tcagagcaag aaaataacgc agaaattgga gatcttgaag attctgttaa ttcagaaaaa   3060
acaccatctc tttggattgg gaagaacgct caagcaaaag tccctctggt tgatatccat   3120
actatttcta ttgatttagc atcattttct tctaaagctc aggaaacccc tgaggaagct   3180
ccacaagtca tcgtccctaa gggaagttgt gtccactcgg gagagttaag tttggagttg   3240
```

gttaatacaa caggaaaagg ttatgagaat catgcgttgt taaaaaatga tactcaggtt 3300
tctctcatgt ctttcaaaga ggaaaatgat ggatctttag aagatttgag taagttgtct 3360
gtttcggatt tacgcattaa agtttctact ccagatattg tagaagaaac ttatggccat 3420
atgggggatt ggtctgaagc tacaattcaa gatggggctc ttgtcattaa ttggcatcct 3480
actggatata aattagatcc gcaaaaagct ggttctttgg tattcaatgc attatgggag 3540
gaagaggctg tattgtctac tctaaaaaat gctcggattg cccataacct taccattcag 3600
agaatggaat ttgattattc tacaaatgct tggggattag cttttagtag ctttagagag 3660
ctatcttcag agaagcttgt ttctgttgat ggatatagag gctcttatat aggggcttct 3720
gcaggcattg atactcagtt gatggaagat tttgttttgg gaatcagcac ggcttccttc 3780
ttcgggaaaa tgcatagtca gaattttgat gcagagattt ctcgacatgg ttttgttggt 3840
tcggtctata caggcttcct agctggggcc tggttcttca aggggcagta cagtcttggc 3900
gaaacacata acgatatgac aactcgttac ggggttttgg gagaatctaa tgctacttgg 3960
aagtctcgag gagtactagc agatgcttta gttgaatatc gtagtttagt cggtccagca 4020
cgacctaaat tttatgcttt gcattttaat ccttatgtcg aggtatctta tgcatctgcg 4080
aagttcccta gttttgtaga acaaggagga gaagctcgtg cttttgaaga aacctcttta 4140
acaaacatta ccgttccctt tggtatgaaa tttgaactat cttttacaaa aggacagttt 4200
tcagagacta attctcttgg aataggttgt gcatgggaaa tgtatcggaa agtcgaagga 4260
agatctgtag agctactaga agctggtttt gattgggaag gatctcctat agatctccct 4320
aaacaagagc tgagagtggc tttagaaaac aatacggaat ggagttcgta ttttagtaca 4380
gctctaggag taacagcatt ttgtggagga ttttcttcta tggataataa actaggatac 4440
gaagcgaatg ctggaatgcg tttgattttc tag 4473

<210> SEQ ID NO 132
<211> LENGTH: 1490
<212> TYPE: PRT
<213> ORGANISM: Chlamydia muridarum

<400> SEQUENCE: 132

Asn Cys Ser Asp Leu Tyr Ala Val Gly Ser Ser Ala Asp His Pro Ala
1 5 10 15

Tyr Leu Ile Pro Gln Ala Gly Leu Leu Leu Asp His Ile Lys Asp Ile
20 25 30

Phe Ile Gly Pro Lys Asp Ser Gln Asp Lys Gly Gln Tyr Lys Leu Ile
35 40 45

Ile Gly Glu Ala Gly Ser Phe Gln Asp Ser Asn Ala Glu Thr Leu Pro
50 55 60

Gln Lys Val Glu His Ser Thr Leu Phe Ser Val Thr Thr Pro Ile Ile
65 70 75 80

Val Gln Gly Ile Asp Gln Gln Asp Gln Val Ser Ser Gln Gly Leu Val
85 90 95

Cys Asn Phe Ser Gly Asp His Ser Glu Glu Ile Phe Glu Arg Glu Ser
100 105 110

Phe Leu Gly Ile Ala Phe Leu Gly Asn Gly Ser Lys Asp Gly Ile Thr
115 120 125

Leu Thr Asp Ile Lys Ser Ser Leu Ser Gly Ala Ala Leu Tyr Ser Ser
130 135 140

Asp Asp Leu Ile Phe Glu Arg Ile Lys Gly Asp Ile Glu Leu Ser Ser
145 150 155 160

-continued

```
Cys Ser Ser Leu Glu Arg Gly Gly Ala Cys Ser Ala Gln Ser Ile Leu
                165                 170                 175

Ile His Asp Cys Gln Gly Leu Thr Val Lys His Cys Ala Ala Gly Val
            180                 185                 190

Asn Val Glu Gly Val Ser Ala Ser Asp His Leu Gly Phe Gly Gly Gly
        195                 200                 205

Ala Phe Ser Thr Thr Ser Ser Leu Ser Gly Glu Lys Ser Leu Tyr Met
    210                 215                 220

Pro Ala Gly Asp Ile Val Val Ala Thr Cys Asp Gly Pro Val Cys Phe
225                 230                 235                 240

Glu Gly Asn Ser Ala Gln Leu Ala Asn Gly Gly Ala Ile Ala Ala Ser
                245                 250                 255

Gly Lys Val Leu Phe Val Ala Asn Glu Lys Lys Ile Ser Phe Thr Asp
            260                 265                 270

Asn Gln Ala Leu Ser Gly Gly Ala Ile Ser Ala Ser Ser Ser Ile Ser
        275                 280                 285

Phe Gln Asn Cys Ala Glu Leu Val Phe Lys Ser Asn Leu Ala Lys Gly
    290                 295                 300

Val Lys Asp Lys Cys Ser Leu Gly Gly Gly Ala Leu Ala Ser Leu Glu
305                 310                 315                 320

Ser Val Val Leu Lys Asp Asn Leu Gly Ile Thr Tyr Glu Lys Asn Gln
                325                 330                 335

Ser Tyr Ser Glu Gly Gly Ala Ile Phe Gly Lys Asp Cys Glu Ile Phe
            340                 345                 350

Glu Asn Arg Gly Pro Val Val Phe Arg Asp Asn Thr Ala Ala Leu Gly
        355                 360                 365

Gly Gly Ala Ile Leu Ala Gln Gln Thr Val Ala Ile Cys Gly Asn Lys
    370                 375                 380

Ser Gly Ile Ser Phe Glu Gly Ser Lys Ser Ser Phe Gly Gly Ala Ile
385                 390                 395                 400

Ala Cys Gly Asn Phe Ser Ser Glu Asn Asn Ser Ser Ala Leu Gly Ser
                405                 410                 415

Ile Asp Ile Ser Asn Asn Leu Gly Asp Ile Ser Phe Leu Arg Thr Leu
            420                 425                 430

Cys Thr Thr Ser Asp Leu Gly Gln Thr Asp Tyr Gln Gly Gly Gly Ala
        435                 440                 445

Leu Phe Ala Glu Asn Ile Ser Leu Ser Glu Asn Ala Gly Ala Ile Thr
    450                 455                 460

Phe Lys Asp Asn Ile Val Lys Thr Phe Ala Ser Asn Gly Lys Met Leu
465                 470                 475                 480

Gly Gly Gly Ala Ile Leu Ala Ser Gly Asn Val Leu Ile Ser Lys Asn
                485                 490                 495

Ser Gly Glu Ile Ser Phe Val Gly Asn Ala Arg Ala Pro Gln Ala Ile
            500                 505                 510

Pro Thr Arg Ser Ser Asp Glu Leu Ser Phe Gly Ala Gln Leu Thr Gln
        515                 520                 525

Thr Thr Ser Gly Cys Ser Gly Gly Gly Ala Leu Phe Gly Lys Glu Val
    530                 535                 540

Ala Ile Val Gln Asn Ala Thr Val Val Phe Glu Gln Asn Arg Leu Gln
545                 550                 555                 560

Cys Gly Glu Gln Glu Thr His Gly Gly Gly Gly Ala Val Tyr Gly Met
                565                 570                 575

Glu Ser Ala Ser Ile Ile Gly Asn Ser Phe Val Arg Phe Gly Asn Asn
```

-continued

```
            580                 585                 590

Tyr Ala Val Gly Asn Gln Ile Ser Gly Gly Ala Leu Leu Ser Lys Lys
        595                 600                 605

Val Arg Leu Ala Glu Asn Thr Arg Val Asp Phe Ser Arg Asn Ile Ala
    610                 615                 620

Thr Phe Cys Gly Gly Ala Val Gln Val Ser Asp Gly Ser Cys Glu Leu
625                 630                 635                 640

Ile Asn Asn Gly Tyr Val Leu Phe Arg Asp Asn Arg Gly Gln Thr Phe
                645                 650                 655

Gly Gly Ala Ile Ser Cys Leu Lys Gly Asp Val Ile Ile Ser Gly Asn
            660                 665                 670

Lys Asp Arg Val Glu Phe Arg Asp Asn Ile Val Thr Arg Pro Tyr Phe
        675                 680                 685

Glu Glu Asn Glu Glu Lys Val Glu Thr Ala Asp Ile Asn Ser Asp Lys
    690                 695                 700

Gln Glu Ala Glu Glu Arg Ser Leu Leu Glu Asn Ile Glu Gln Ser Phe
705                 710                 715                 720

Ile Thr Ala Thr Asn Gln Thr Phe Phe Leu Glu Glu Glu Lys Leu Pro
                725                 730                 735

Ser Glu Ala Phe Ile Ser Ala Glu Glu Leu Ser Lys Arg Arg Glu Cys
            740                 745                 750

Ala Gly Gly Ala Ile Phe Ala Lys Arg Val Tyr Ile Thr Asp Asn Lys
        755                 760                 765

Glu Pro Ile Leu Phe Ser His Asn Phe Ser Asp Val Tyr Gly Gly Ala
    770                 775                 780

Ile Phe Thr Gly Ser Leu Gln Glu Thr Asp Lys Gln Asp Val Val Thr
785                 790                 795                 800

Pro Glu Val Val Ile Ser Gly Asn Asp Gly Asp Val Ile Phe Ser Gly
                805                 810                 815

Asn Ala Ala Lys His Asp Lys His Leu Pro Asp Thr Gly Gly Gly Ala
            820                 825                 830

Ile Cys Thr Gln Asn Leu Thr Ile Ser Gln Asn Asn Gly Asn Val Leu
        835                 840                 845

Phe Leu Asn Asn Phe Ala Cys Ser Gly Gly Ala Val Arg Ile Glu Asp
    850                 855                 860

His Gly Glu Val Leu Leu Glu Ala Phe Gly Gly Asp Ile Ile Phe Asn
865                 870                 875                 880

Gly Asn Ser Ser Phe Arg Ala Gln Gly Ser Asp Ala Ile Tyr Phe Ala
                885                 890                 895

Gly Lys Asp Ser Arg Ile Lys Ala Leu Asn Ala Thr Glu Gly His Ala
            900                 905                 910

Ile Val Phe Gln Asp Ala Leu Val Phe Glu Asn Ile Glu Glu Arg Lys
        915                 920                 925

Ser Ser Gly Leu Leu Val Ile Asn Ser Gln Glu Asn Glu Gly Tyr Thr
    930                 935                 940

Gly Ser Val Arg Phe Leu Gly Ser Glu Ser Lys Val Pro Gln Trp Ile
945                 950                 955                 960

His Val Gln Gln Gly Gly Leu Glu Leu Leu His Gly Ala Ile Leu Cys
                965                 970                 975

Ser Tyr Gly Val Lys Gln Asp Pro Arg Ala Lys Ile Val Leu Ser Ala
            980                 985                 990

Gly Ser Lys Leu Lys Ile Leu Asp  Ser Glu Gln Glu Asn  Asn Ala Glu
        995                 1000                1005
```

```
Ile Gly Asp Leu Glu Asp Ser Val Asn Ser Glu Lys Thr Pro Ser
    1010                1015                1020

Leu Trp Ile Gly Lys Asn Ala Gln Ala Lys Val Pro Leu Val Asp
    1025                1030                1035

Ile His Thr Ile Ser Ile Asp Leu Ala Ser Phe Ser Ser Lys Ala
    1040                1045                1050

Gln Glu Thr Pro Glu Glu Ala Pro Gln Val Ile Val Pro Lys Gly
    1055                1060                1065

Ser Cys Val His Ser Gly Glu Leu Ser Leu Glu Leu Val Asn Thr
    1070                1075                1080

Thr Gly Lys Gly Tyr Glu Asn His Ala Leu Leu Lys Asn Asp Thr
    1085                1090                1095

Gln Val Ser Leu Met Ser Phe Lys Glu Glu Asn Asp Gly Ser Leu
    1100                1105                1110

Glu Asp Leu Ser Lys Leu Ser Val Ser Asp Leu Arg Ile Lys Val
    1115                1120                1125

Ser Thr Pro Asp Ile Val Glu Glu Thr Tyr Gly His Met Gly Asp
    1130                1135                1140

Trp Ser Glu Ala Thr Ile Gln Asp Gly Ala Leu Val Ile Asn Trp
    1145                1150                1155

His Pro Thr Gly Tyr Lys Leu Asp Pro Gln Lys Ala Gly Ser Leu
    1160                1165                1170

Val Phe Asn Ala Leu Trp Glu Glu Glu Ala Val Leu Ser Thr Leu
    1175                1180                1185

Lys Asn Ala Arg Ile Ala His Asn Leu Thr Ile Gln Arg Met Glu
    1190                1195                1200

Phe Asp Tyr Ser Thr Asn Ala Trp Gly Leu Ala Phe Ser Ser Phe
    1205                1210                1215

Arg Glu Leu Ser Ser Glu Lys Leu Val Ser Val Asp Gly Tyr Arg
    1220                1225                1230

Gly Ser Tyr Ile Gly Ala Ser Ala Gly Ile Asp Thr Gln Leu Met
    1235                1240                1245

Glu Asp Phe Val Leu Gly Ile Ser Thr Ala Ser Phe Phe Gly Lys
    1250                1255                1260

Met His Ser Gln Asn Phe Asp Ala Glu Ile Ser Arg His Gly Phe
    1265                1270                1275

Val Gly Ser Val Tyr Thr Gly Phe Leu Ala Gly Ala Trp Phe Phe
    1280                1285                1290

Lys Gly Gln Tyr Ser Leu Gly Glu Thr His Asn Asp Met Thr Thr
    1295                1300                1305

Arg Tyr Gly Val Leu Gly Glu Ser Asn Ala Thr Trp Lys Ser Arg
    1310                1315                1320

Gly Val Leu Ala Asp Ala Leu Val Glu Tyr Arg Ser Leu Val Gly
    1325                1330                1335

Pro Ala Arg Pro Lys Phe Tyr Ala Leu His Phe Asn Pro Tyr Val
    1340                1345                1350

Glu Val Ser Tyr Ala Ser Ala Lys Phe Pro Ser Phe Val Glu Gln
    1355                1360                1365

Gly Gly Glu Ala Arg Ala Phe Glu Glu Thr Ser Leu Thr Asn Ile
    1370                1375                1380

Thr Val Pro Phe Gly Met Lys Phe Glu Leu Ser Phe Thr Lys Gly
    1385                1390                1395

Gln Phe Ser Glu Thr Asn Ser Leu Gly Ile Gly Cys Ala Trp Glu
    1400                1405                1410
```

```
Met Tyr  Arg Lys Val Glu Gly  Arg Ser Val Glu Leu  Leu Glu Ala
    1415                 1420                 1425

Gly Phe  Asp Trp Glu Gly Ser  Pro Ile Asp Leu Pro  Lys Gln Glu
    1430                 1435                 1440

Leu Arg  Val Ala Leu Glu Asn  Asn Thr Glu Trp Ser  Ser Tyr Phe
    1445                 1450                 1455

Ser Thr  Ala Leu Gly Val Thr  Ala Phe Cys Gly Gly  Phe Ser Ser
    1460                 1465                 1470

Met Asp  Asn Lys Leu Gly Tyr  Glu Ala Asn Ala Gly  Met Arg Leu
    1475                 1480                 1485

Ile Phe
    1490

<210> SEQ ID NO 133
<211> LENGTH: 2877
<212> TYPE: DNA
<213> ORGANISM: Chlamydia muridarum

<400> SEQUENCE: 133
actcgagaag tccctccttc gattctttta aagcctatac taaatccata ccatatgacc     60
gggttatttt ttcccaaggt taatttgctt ggagacacac ataatctcac tgattaccat    120
ttggataatc taaaatgcat tctggcttgc ctacaaagaa ctccttatga aggagctgct    180
ttcacagtaa ccgattactt aggtttttca gatacacaaa aggatggtat tttttgtttt    240
aaaaatctta ctccagagag tggaggggtt attggttccc caactcaaaa cactcctact    300
ataaaaattc ataatacaat cggccccgtt cttttcgaaa ataatacctg tcatagactg    360
tggacacaga ccgatcccga aaatgaagga aacaaagcac gcgaaggcgg ggcaattcat    420
gctggggacg tttacataag caataaccag aaccttgtcg gattcataaa gaactttgct    480
tatgttcaag gtggagctat tagtgctaat acttttgcct ataaagaaaa taaatcgagc    540
tttctttgcc taaataactc ttgtatacaa actaagacgg gagggaaagg tggtgctatt    600
tacgttagta cgagctgctc tttcgagaac aataacaagg atctgctttt catccaaaac    660
tccggctgtg caggaggagc tatcttctct ccaacctgtt ctctaatagg aaaccaagga    720
gatattgttt tttacagcaa ccacggtttt aaaaatgttg ataatgcaac taacgaatct    780
ggggatggag gagctattaa agtaactacc cgcttggaca tcaccaataa tggtagtcaa    840
atcttttttt ctgataatat ctcaagaaat tttggaggag ctattcatgc tccttgtctt    900
catcttgttg gtaatgggcc aacctatttt acaaacaata tagctaatca cacaggtggg    960
gctatttata taacaggaac agaaacctca aagatttctg cagatcacca tgctattatt   1020
tttgataata acatttctgc aaacgccacc aatgcggacg gatctagcag caacactaat   1080
cctcctcaca gaaatgcgat cactatggac aattccgctg gaggaataga acttggtgca   1140
gggaagagcc agaatcttat tttctatgat cctattcaag tgacgaatgc tggagttacc   1200
gtagacttca ataaggatgc ctcccaaacc ggatgtgtag ttttctctgg agcgactgtc   1260
ctttctgcag atatttctca ggctaatttg caaactaaaa cacctgcaac gcttactctc   1320
agtcacggtc ttctgtgtat cgaagatcgt gctcagctca cagtgaacaa ttttacacaa   1380
acaggaggga ttgtagcctt aggaaatgga gcagttttaa gcagctacca acacagcact   1440
acagacgcca ctcaaactcc ccctacaacc accactacag atgcttccgt aactcttaat   1500
cacattggat taaatctccc ctctattctt aaggatggag cagagatgcc tctattatgg   1560
gtagaaccta taagcacaac tcaaggtaac actacaacat atacgtcaga taccgcggct   1620
```

tccttctcat taaatggagc cacactctct ctcattgatg aagatggaaa ttctccctat 1680
gaaaacacgg acctctctcg tgcattgtac gctcaaccta tgctagcaat ttctgaggcc 1740
agtgataacc aattgcaatc cgaaagcatg gacttttcta aagttaatgt tcctcactat 1800
ggatggcaag gactttggac ctgggggtgg gcaaaaactg aaaatccaac aacaactcct 1860
ccagcaacaa ttactgatcc gaaaaaagct aatcagtttc atagaacttt attattaacg 1920
tggctccctg ctggttatat ccccagccct aaacataaaa gccctttaat agctaatacc 1980
ttgtggggga atatactttt tgcaacggaa aacttaaaaa atagctcagg gcaagaactt 2040
cttgatcgtc ctttctgggg aattacagga gggggcttgg ggatgatggt ctatcaagaa 2100
cctagaaaag accatcctgg attccacatg catacctccg gatattcagc aggaatgatt 2160
acaggaaaca cacatacctt ctcattacga ttcagccagt cctatacaaa actcaatgaa 2220
cgttatgcca agaactatgt gtcttctaaa aattactctt gccaaggggga aatgcttttg 2280 tccttacaag aaggactcat gctgactaaa ctaattggtc tctatagtta tgggaatcac 2340
aacagccacc atttctatac ccaaggagaa gacctatcgt ctcaaggggga gttccatagt 2400 cagacttttg gaggggctgt ctttttgat ctacctctga aacctttttgg aagaacacac 2460 atacttacag ctcctttctt aggtgccatt ggtatgtatt ctaagctgtc tagctttaca 2520
gaagtaggag cctatccaag aacctttatt acagaaacgc ctttaatcaa tgtcctgatt 2580
cctatcggag taaaaggtag cttcatgaat gccacccata gacctcaggc ctggactgta 2640
gagcttgctt accaacctgt tctttacaga caagaaccta gtatctctac ccaattactc 2700
gctggtaaag gtatgtggtt tggcatgga agtcctgcat ctcgccacgc tctagcttat 2760
aaaatttcac agaaaacaca gcttttgcga tttgcaacac ttcaactcca gtatcacgga 2820
tactattcgt cttccacttt ctgtaattat ctgaatggag aggtatcttt acgtttc 2877

<210> SEQ ID NO 134
<211> LENGTH: 959
<212> TYPE: PRT
<213> ORGANISM: Chlamydia muridarum

<400> SEQUENCE: 134

Thr Arg Glu Val Pro Pro Ser Ile Leu Leu Lys Pro Ile Leu Asn Pro
1 5 10 15

Tyr His Met Thr Gly Leu Phe Phe Pro Lys Val Asn Leu Leu Gly Asp
20 25 30

Thr His Asn Leu Thr Asp Tyr His Leu Asp Asn Leu Lys Cys Ile Leu
35 40 45

Ala Cys Leu Gln Arg Thr Pro Tyr Glu Gly Ala Ala Phe Thr Val Thr
50 55 60

Asp Tyr Leu Gly Phe Ser Asp Thr Gln Lys Asp Gly Ile Phe Cys Phe
65 70 75 80

Lys Asn Leu Thr Pro Glu Ser Gly Gly Val Ile Gly Ser Pro Thr Gln
85 90 95

Asn Thr Pro Thr Ile Lys Ile His Asn Thr Ile Gly Pro Val Leu Phe
100 105 110

Glu Asn Asn Thr Cys His Arg Leu Trp Thr Gln Thr Asp Pro Glu Asn
115 120 125

Glu Gly Asn Lys Ala Arg Glu Gly Gly Ala Ile His Ala Gly Asp Val
130 135 140

Tyr Ile Ser Asn Asn Gln Asn Leu Val Gly Phe Ile Lys Asn Phe Ala
145 150 155 160

```
Tyr Val Gln Gly Gly Ala Ile Ser Ala Asn Thr Phe Ala Tyr Lys Glu
                165                 170                 175

Asn Lys Ser Ser Phe Leu Cys Leu Asn Asn Ser Cys Ile Gln Thr Lys
            180                 185                 190

Thr Gly Gly Lys Gly Gly Ala Ile Tyr Val Ser Thr Ser Cys Ser Phe
        195                 200                 205

Glu Asn Asn Asn Lys Asp Leu Leu Phe Ile Gln Asn Ser Gly Cys Ala
    210                 215                 220

Gly Gly Ala Ile Phe Ser Pro Thr Cys Ser Leu Ile Gly Asn Gln Gly
225                 230                 235                 240

Asp Ile Val Phe Tyr Ser Asn His Gly Phe Lys Asn Val Asp Asn Ala
                245                 250                 255

Thr Asn Glu Ser Gly Asp Gly Gly Ala Ile Lys Val Thr Thr Arg Leu
            260                 265                 270

Asp Ile Thr Asn Asn Gly Ser Gln Ile Phe Phe Ser Asp Asn Ile Ser
        275                 280                 285

Arg Asn Phe Gly Gly Ala Ile His Ala Pro Cys Leu His Leu Val Gly
    290                 295                 300

Asn Gly Pro Thr Tyr Phe Thr Asn Asn Ile Ala Asn His Thr Gly Gly
305                 310                 315                 320

Ala Ile Tyr Ile Thr Gly Thr Glu Thr Ser Lys Ile Ser Ala Asp His
                325                 330                 335

His Ala Ile Ile Phe Asp Asn Asn Ile Ser Ala Asn Ala Thr Asn Ala
            340                 345                 350

Asp Gly Ser Ser Ser Asn Thr Asn Pro Pro His Arg Asn Ala Ile Thr
        355                 360                 365

Met Asp Asn Ser Ala Gly Gly Ile Glu Leu Gly Ala Gly Lys Ser Gln
    370                 375                 380

Asn Leu Ile Phe Tyr Asp Pro Ile Gln Val Thr Asn Ala Gly Val Thr
385                 390                 395                 400

Val Asp Phe Asn Lys Asp Ala Ser Gln Thr Gly Cys Val Val Phe Ser
                405                 410                 415

Gly Ala Thr Val Leu Ser Ala Asp Ile Ser Gln Ala Asn Leu Gln Thr
            420                 425                 430

Lys Thr Pro Ala Thr Leu Thr Leu Ser His Gly Leu Leu Cys Ile Glu
        435                 440                 445

Asp Arg Ala Gln Leu Thr Val Asn Asn Phe Thr Gln Thr Gly Gly Ile
    450                 455                 460

Val Ala Leu Gly Asn Gly Ala Val Leu Ser Ser Tyr Gln His Ser Thr
465                 470                 475                 480

Thr Asp Ala Thr Gln Thr Pro Pro Thr Thr Thr Thr Thr Asp Ala Ser
                485                 490                 495

Val Thr Leu Asn His Ile Gly Leu Asn Leu Pro Ser Ile Leu Lys Asp
            500                 505                 510

Gly Ala Glu Met Pro Leu Leu Trp Val Glu Pro Ile Ser Thr Thr Gln
        515                 520                 525

Gly Asn Thr Thr Thr Tyr Thr Ser Asp Thr Ala Ala Ser Phe Ser Leu
    530                 535                 540

Asn Gly Ala Thr Leu Ser Leu Ile Asp Glu Asp Gly Asn Ser Pro Tyr
545                 550                 555                 560

Glu Asn Thr Asp Leu Ser Arg Ala Leu Tyr Ala Gln Pro Met Leu Ala
                565                 570                 575

Ile Ser Glu Ala Ser Asp Asn Gln Leu Gln Ser Glu Ser Met Asp Phe
```

```
            580                 585                 590

Ser Lys Val Asn Val Pro His Tyr Gly Trp Gln Gly Leu Trp Thr Trp
        595                 600                 605

Gly Trp Ala Lys Thr Glu Asn Pro Thr Thr Thr Pro Pro Ala Thr Ile
    610                 615                 620

Thr Asp Pro Lys Lys Ala Asn Gln Phe His Arg Thr Leu Leu Leu Thr
625                 630                 635                 640

Trp Leu Pro Ala Gly Tyr Ile Pro Ser Pro Lys His Lys Ser Pro Leu
                645                 650                 655

Ile Ala Asn Thr Leu Trp Gly Asn Ile Leu Phe Ala Thr Glu Asn Leu
            660                 665                 670

Lys Asn Ser Ser Gly Gln Glu Leu Leu Asp Arg Pro Phe Trp Gly Ile
        675                 680                 685

Thr Gly Gly Gly Leu Gly Met Met Val Tyr Gln Glu Pro Arg Lys Asp
    690                 695                 700

His Pro Gly Phe His Met His Thr Ser Gly Tyr Ser Ala Gly Met Ile
705                 710                 715                 720

Thr Gly Asn Thr His Thr Phe Ser Leu Arg Phe Ser Gln Ser Tyr Thr
                725                 730                 735

Lys Leu Asn Glu Arg Tyr Ala Lys Asn Tyr Val Ser Ser Lys Asn Tyr
            740                 745                 750

Ser Cys Gln Gly Glu Met Leu Leu Ser Leu Gln Glu Gly Leu Met Leu
        755                 760                 765

Thr Lys Leu Ile Gly Leu Tyr Ser Tyr Gly Asn His Asn Ser His His
    770                 775                 780

Phe Tyr Thr Gln Gly Glu Asp Leu Ser Ser Gln Gly Glu Phe His Ser
785                 790                 795                 800

Gln Thr Phe Gly Gly Ala Val Phe Phe Asp Leu Pro Leu Lys Pro Phe
                805                 810                 815

Gly Arg Thr His Ile Leu Thr Ala Pro Phe Leu Gly Ala Ile Gly Met
            820                 825                 830

Tyr Ser Lys Leu Ser Ser Phe Thr Glu Val Gly Ala Tyr Pro Arg Thr
        835                 840                 845

Phe Ile Thr Glu Thr Pro Leu Ile Asn Val Leu Ile Pro Ile Gly Val
    850                 855                 860

Lys Gly Ser Phe Met Asn Ala Thr His Arg Pro Gln Ala Trp Thr Val
865                 870                 875                 880

Glu Leu Ala Tyr Gln Pro Val Leu Tyr Arg Gln Glu Pro Ser Ile Ser
                885                 890                 895

Thr Gln Leu Leu Ala Gly Lys Gly Met Trp Phe Gly His Gly Ser Pro
            900                 905                 910

Ala Ser Arg His Ala Leu Ala Tyr Lys Ile Ser Gln Lys Thr Gln Leu
        915                 920                 925

Leu Arg Phe Ala Thr Leu Gln Leu Gln Tyr His Gly Tyr Tyr Ser Ser
    930                 935                 940

Ser Thr Phe Cys Asn Tyr Leu Asn Gly Glu Val Ser Leu Arg Phe
945                 950                 955
```

<210> SEQ ID NO 135
<211> LENGTH: 567
<212> TYPE: DNA
<213> ORGANISM: Chlamydia trachomatis

<400> SEQUENCE: 135

```
atgagaaaga ctatttttaa agcgtttaat ttattattct cccttctttt tctttcttca      60
```

```
tgctcttatc cttgcagaga ttgggaatgc catggttgcg actccgcaag acctcgtaaa    120

tcctcttttg gattcgtacc tttctactcc gatgaagaaa ttcaacaagc ttttgttgaa    180

gattttgatt ccaaagaaga gcagctgtac aaaacgagcg cacagagtac ctctttccga    240

aatatcactt tcgctacaga tagttattct attaaaggag aggataacct cacgattctt    300

gcaagcttag ttcgtcattt gcataaatct cctaaagcta cgctatatat agagggccat    360

acagatgaac gtggagctgc agcttataac ctagctttag gagctcgtcg tgcgaatgct    420

gtaaaacaat acctcatcaa acagggaatc gctgcagacc gcttattcac tatttcttac    480

ggaaaagaac atcctgttca tccaggccat aatgaattag cttggcaaca aaatcgtcgt    540

actgaattta agatccatgc tcgctaa                                        567
```

<210> SEQ ID NO 136
<211> LENGTH: 188
<212> TYPE: PRT
<213> ORGANISM: Chlamydia trachomatis

<400> SEQUENCE: 136

```
Met Arg Lys Thr Ile Phe Lys Ala Phe Asn Leu Leu Phe Ser Leu Leu
1               5                   10                  15

Phe Leu Ser Ser Cys Ser Tyr Pro Cys Arg Asp Trp Glu Cys His Gly
            20                  25                  30

Cys Asp Ser Ala Arg Pro Arg Lys Ser Ser Phe Gly Phe Val Pro Phe
        35                  40                  45

Tyr Ser Asp Glu Glu Ile Gln Gln Ala Phe Val Glu Asp Phe Asp Ser
    50                  55                  60

Lys Glu Glu Gln Leu Tyr Lys Thr Ser Ala Gln Ser Thr Ser Phe Arg
65                  70                  75                  80

Asn Ile Thr Phe Ala Thr Asp Ser Tyr Ser Ile Lys Gly Glu Asp Asn
                85                  90                  95

Leu Thr Ile Leu Ala Ser Leu Val Arg His Leu His Lys Ser Pro Lys
            100                 105                 110

Ala Thr Leu Tyr Ile Glu Gly His Thr Asp Glu Arg Gly Ala Ala Ala
        115                 120                 125

Tyr Asn Leu Ala Leu Gly Ala Arg Arg Ala Asn Ala Val Lys Gln Tyr
    130                 135                 140

Leu Ile Lys Gln Gly Ile Ala Ala Asp Arg Leu Phe Thr Ile Ser Tyr
145                 150                 155                 160

Gly Lys Glu His Pro Val His Pro Gly His Asn Glu Leu Ala Trp Gln
                165                 170                 175

Gln Asn Arg Arg Thr Glu Phe Lys Ile His Ala Arg
            180                 185
```

<210> SEQ ID NO 137
<211> LENGTH: 504
<212> TYPE: DNA
<213> ORGANISM: Chlamydia trachomatis

<400> SEQUENCE: 137

```
tgctcttatc cttgcagaga ttgggaatgc catggttgcg actccgcaag acctcgtaaa     60

tcctcttttg gattcgtacc tttctactcc gatgaagaaa ttcaacaagc ttttgttgaa    120

gattttgatt ccaaagaaga gcagctgtac aaaacgagcg cacagagtac ctctttccga    180

aatatcactt tcgctacaga tagttattct attaaaggag aggataacct cacgattctt    240

gcaagcttag ttcgtcattt gcataaatct cctaaagcta cgctatatat agagggccat    300
```

acagatgaac gtggagctgc agcttataac ctagctttag gagctcgtcg tgcgaatgct 360
gtaaaacaat acctcatcaa acagggaatc gctgcagacc gcttattcac tatttcttac 420
ggaaaagaac atcctgttca tccaggccat aatgaattag cttggcaaca aaatcgtcgt 480
actgaattta agatccatgc tcgc 504

<210> SEQ ID NO 138
<211> LENGTH: 168
<212> TYPE: PRT
<213> ORGANISM: Chlamydia trachomatis

<400> SEQUENCE: 138

Cys Ser Tyr Pro Cys Arg Asp Trp Glu Cys His Gly Cys Asp Ser Ala
1 5 10 15

Arg Pro Arg Lys Ser Ser Phe Gly Phe Val Pro Phe Tyr Ser Asp Glu
20 25 30

Glu Ile Gln Gln Ala Phe Val Glu Asp Phe Asp Ser Lys Glu Glu Gln
35 40 45

Leu Tyr Lys Thr Ser Ala Gln Ser Thr Ser Phe Arg Asn Ile Thr Phe
50 55 60

Ala Thr Asp Ser Tyr Ser Ile Lys Gly Glu Asp Asn Leu Thr Ile Leu
65 70 75 80

Ala Ser Leu Val Arg His Leu His Lys Ser Pro Lys Ala Thr Leu Tyr
85 90 95

Ile Glu Gly His Thr Asp Glu Arg Gly Ala Ala Ala Tyr Asn Leu Ala
100 105 110

Leu Gly Ala Arg Arg Ala Asn Ala Val Lys Gln Tyr Leu Ile Lys Gln
115 120 125

Gly Ile Ala Ala Asp Arg Leu Phe Thr Ile Ser Tyr Gly Lys Glu His
130 135 140

Pro Val His Pro Gly His Asn Glu Leu Ala Trp Gln Gln Asn Arg Arg
145 150 155 160

Thr Glu Phe Lys Ile His Ala Arg
165

<210> SEQ ID NO 139
<211> LENGTH: 1494
<212> TYPE: DNA
<213> ORGANISM: Chlamydia trachomatis

<400> SEQUENCE: 139
atgatgaaaa gattattatg tgtgttgcta tcgacatcag ttttctcttc gccaatgcta 60
ggctatagtg cgtcaaagaa agattctaag gctgatattt gtcttgcagt atcctcagga 120
gatcaagagg tttcacaaga agatctgctc aaagaagtat cccgaggatt ttctcgggtc 180
gctgctaagg caacgcctgg agttgtatat atagaaaatt ttcctaaaac agggaaccag 240
gctattgctt ctccaggaaa caaaagaggc tttcaagaga acccttttga ttattttaat 300
gacgaatttt ttaatcgatt ttttggattg ccttcgcata gagagcagca gcgtccgcag 360
cagcgtgatg ctgtaagagg aactgggttc attgtttctg aagatggtta tgttgttact 420
aaccatcatg tagtcgagga tgcaggaaaa attcatgtta ctctccacga cggacaaaaa 480
tacacagcta agatcgtggg gttagatcca aaaacagatc ttgctgtgat caaaattcaa 540
gcggagaaat taccattttt gacttttggg aattctgatc agctgcagat aggtgactgg 600
gctattgcta ttggaaatcc ttttggattg caagcaacgg tcactgtcgg ggtcattagt 660

-continued

```
gctaaaggaa gaaatcagct acatattgta gatttcgaag actttattca aacagatgct    720

gccattaatc ctgggaattc aggcggtcca ttgttaaaca tcaatggtca agttatcggg    780

gttaatactg ccattgtcag tggtagcggg ggatatattg gaatagggtt tgctattcct    840

agcttgatgg ctaaacgagt cattgatcaa ttgattagtg atgggcaggt aacaagaggc    900

tttttgggag ttaccttgca accgatagat tctgaattgg ctacttgtta caaattggaa    960

aaagtgtacg gagctttggt gacggatgtt gttaaaggtt ctccagcaga aaaagcaggg   1020

ctgcgccaag aagatgtcat tgtggcttac aatggaaaag aagtagagtc tttgagtgcg   1080

ttgcgtaatg ccatttccct aatgatgcca gggactcgtg ttgttttaaa aatcgttcgt   1140

gaagggaaaa caatcgagat acctgtgacg gttacacaga tcccaacaga ggatggcgtt   1200

tcagcgttgc agaagatggg agtccgtgtt cagaacatta ctccagaaat ttgtaagaaa   1260

ctcggattgg cagcagatac ccgagggatt ctggtagttg ctgtggaggc aggctcgcct   1320

gcagcttctg caggcgtcgc tcctggacag cttatcttag cggtgaatag gcagcgagtc   1380

gcttccgttg aagagttaaa tcaggttttg aaaaactcga aaggagagaa tgttctcctt   1440

atggtttctc aaggagatgt ggtgcgattc atcgtcttga aatcagacga gtag         1494
```

<210> SEQ ID NO 140
<211> LENGTH: 497
<212> TYPE: PRT
<213> ORGANISM: Chlamydia trachomatis

<400> SEQUENCE: 140

```
Met Met Lys Arg Leu Leu Cys Val Leu Leu Ser Thr Ser Val Phe Ser
1               5                   10                  15

Ser Pro Met Leu Gly Tyr Ser Ala Ser Lys Lys Asp Ser Lys Ala Asp
            20                  25                  30

Ile Cys Leu Ala Val Ser Ser Gly Asp Gln Glu Val Ser Gln Glu Asp
        35                  40                  45

Leu Leu Lys Glu Val Ser Arg Gly Phe Ser Arg Val Ala Ala Lys Ala
    50                  55                  60

Thr Pro Gly Val Val Tyr Ile Glu Asn Phe Pro Lys Thr Gly Asn Gln
65                  70                  75                  80

Ala Ile Ala Ser Pro Gly Asn Lys Arg Gly Phe Gln Glu Asn Pro Phe
                85                  90                  95

Asp Tyr Phe Asn Asp Glu Phe Phe Asn Arg Phe Phe Gly Leu Pro Ser
            100                 105                 110

His Arg Glu Gln Gln Arg Pro Gln Gln Arg Asp Ala Val Arg Gly Thr
        115                 120                 125

Gly Phe Ile Val Ser Glu Asp Gly Tyr Val Val Thr Asn His His Val
    130                 135                 140

Val Glu Asp Ala Gly Lys Ile His Val Thr Leu His Asp Gly Gln Lys
145                 150                 155                 160

Tyr Thr Ala Lys Ile Val Gly Leu Asp Pro Lys Thr Asp Leu Ala Val
                165                 170                 175

Ile Lys Ile Gln Ala Glu Lys Leu Pro Phe Leu Thr Phe Gly Asn Ser
            180                 185                 190

Asp Gln Leu Gln Ile Gly Asp Trp Ala Ile Ala Ile Gly Asn Pro Phe
        195                 200                 205

Gly Leu Gln Ala Thr Val Thr Val Gly Val Ile Ser Ala Lys Gly Arg
    210                 215                 220

Asn Gln Leu His Ile Val Asp Phe Glu Asp Phe Ile Gln Thr Asp Ala
225                 230                 235                 240
```

```
Ala Ile Asn Pro Gly Asn Ser Gly Gly Pro Leu Leu Asn Ile Asn Gly
                245                 250                 255

Gln Val Ile Gly Val Asn Thr Ala Ile Val Ser Gly Ser Gly Gly Tyr
            260                 265                 270

Ile Gly Ile Gly Phe Ala Ile Pro Ser Leu Met Ala Lys Arg Val Ile
        275                 280                 285

Asp Gln Leu Ile Ser Asp Gly Gln Val Thr Arg Gly Phe Leu Gly Val
    290                 295                 300

Thr Leu Gln Pro Ile Asp Ser Glu Leu Ala Thr Cys Tyr Lys Leu Glu
305                 310                 315                 320

Lys Val Tyr Gly Ala Leu Val Thr Asp Val Val Lys Gly Ser Pro Ala
                325                 330                 335

Glu Lys Ala Gly Leu Arg Gln Glu Asp Val Ile Val Ala Tyr Asn Gly
            340                 345                 350

Lys Glu Val Glu Ser Leu Ser Ala Leu Arg Asn Ala Ile Ser Leu Met
        355                 360                 365

Met Pro Gly Thr Arg Val Val Leu Lys Ile Val Arg Glu Gly Lys Thr
    370                 375                 380

Ile Glu Ile Pro Val Thr Val Thr Gln Ile Pro Thr Glu Asp Gly Val
385                 390                 395                 400

Ser Ala Leu Gln Lys Met Gly Val Arg Val Gln Asn Ile Thr Pro Glu
                405                 410                 415

Ile Cys Lys Lys Leu Gly Leu Ala Ala Asp Thr Arg Gly Ile Leu Val
            420                 425                 430

Val Ala Val Glu Ala Gly Ser Pro Ala Ala Ser Ala Gly Val Ala Pro
        435                 440                 445

Gly Gln Leu Ile Leu Ala Val Asn Arg Gln Arg Val Ala Ser Val Glu
    450                 455                 460

Glu Leu Asn Gln Val Leu Lys Asn Ser Lys Gly Glu Asn Val Leu Leu
465                 470                 475                 480

Met Val Ser Gln Gly Asp Val Val Arg Phe Ile Val Leu Lys Ser Asp
                485                 490                 495

Glu
```

<210> SEQ ID NO 141
<211> LENGTH: 1443
<212> TYPE: DNA
<213> ORGANISM: Chlamydia trachomatis

<400> SEQUENCE: 141

```
tcgccaatgc taggctatag tgcgtcaaag aaagattcta aggctgatat ttgtcttgca     60

gtatcctcag gagatcaaga ggtttcacaa gaagatctgc tcaaagaagt atcccgagga    120

ttttctcggg tcgctgctaa ggcaacgcct ggagttgtat atatagaaaa ttttcctaaa    180

acagggaacc aggctattgc ttctccagga aacaaaagag gctttcaaga gaacccttt t   240

gattatttta atgacgaatt ttttaatcga ttttttggat tgccttcgca tagagagcag    300

cagcgtccgc agcagcgtga tgctgtaaga ggaactgggt tcattgtttc tgaagatggt    360

tatgttgtta ctaaccatca tgtagtcgag gatgcaggaa aaattcatgt tactctccac    420

gacggacaaa aatacacagc taagatcgtg gggttagatc caaaaacaga tcttgctgtg    480

atcaaaattc aagcggagaa attaccattt ttgacttttg ggaattctga tcagctgcag    540

ataggtgact gggctattgc tattggaaat ccttttggat tgcaagcaac ggtcactgtc    600

ggggtcatta gtgctaaagg aagaaatcag ctacatattg tagatttcga agactttatt    660
```

```
caaacagatg ctgccattaa tcctgggaat tcaggcggtc cattgttaaa catcaatggt    720

caagttatcg ggttaatac tgccattgtc agtggtagcg gggatatat tggaataggg    780

tttgctattc ctagcttgat ggctaaacga gtcattgatc aattgattag tgatgggcag    840

gtaacaagag gcttttggg agttaccttg caaccgatag attctgaatt ggctacttgt    900

tacaaattgg aaaaagtgta cggagctttg gtgacggatg ttgttaaagg ttctccagca    960

gaaaaagcag ggctgcgcca agaagatgtc attgtggctt acaatggaaa agaagtagag   1020

tctttgagtg cgttgcgtaa tgccatttcc ctaatgatgc cagggactcg tgttgtttta   1080

aaaatcgttc gtgaagggaa aacaatcgag atacctgtga cggttacaca gatcccaaca   1140

gaggatggcg tttcagcgtt gcagaagatg ggagtccgtg ttcagaacat tactccagaa   1200

atttgtaaga aactcggatt ggcagcagat acccgaggga ttctggtagt tgctgtggag   1260

gcaggctcgc ctgcagcttc tgcaggcgtc gctcctggac agcttatctt agcggtgaat   1320

aggcagcgag tcgcttccgt tgaagagtta aatcaggttt tgaaaaactc gaaaggagag   1380

aatgttctcc ttatggtttc tcaaggagat gtggtgcgat tcatcgtctt gaaatcagac   1440

gag                                                                 1443
```

<210> SEQ ID NO 142
<211> LENGTH: 481
<212> TYPE: PRT
<213> ORGANISM: Chlamydia trachomatis

<400> SEQUENCE: 142

```
Ser Pro Met Leu Gly Tyr Ser Ala Ser Lys Lys Asp Ser Lys Ala Asp
1               5                   10                  15

Ile Cys Leu Ala Val Ser Ser Gly Asp Gln Glu Val Ser Gln Glu Asp
            20                  25                  30

Leu Leu Lys Glu Val Ser Arg Gly Phe Ser Arg Val Ala Ala Lys Ala
        35                  40                  45

Thr Pro Gly Val Val Tyr Ile Glu Asn Phe Pro Lys Thr Gly Asn Gln
    50                  55                  60

Ala Ile Ala Ser Pro Gly Asn Lys Arg Gly Phe Gln Glu Asn Pro Phe
65                  70                  75                  80

Asp Tyr Phe Asn Asp Glu Phe Phe Asn Arg Phe Phe Gly Leu Pro Ser
                85                  90                  95

His Arg Glu Gln Gln Arg Pro Gln Gln Arg Asp Ala Val Arg Gly Thr
            100                 105                 110

Gly Phe Ile Val Ser Glu Asp Gly Tyr Val Val Thr Asn His His Val
        115                 120                 125

Val Glu Asp Ala Gly Lys Ile His Val Thr Leu His Asp Gly Gln Lys
    130                 135                 140

Tyr Thr Ala Lys Ile Val Gly Leu Asp Pro Lys Thr Asp Leu Ala Val
145                 150                 155                 160

Ile Lys Ile Gln Ala Glu Lys Leu Pro Phe Leu Thr Phe Gly Asn Ser
                165                 170                 175

Asp Gln Leu Gln Ile Gly Asp Trp Ala Ile Ala Ile Gly Asn Pro Phe
            180                 185                 190

Gly Leu Gln Ala Thr Val Thr Val Gly Val Ile Ser Ala Lys Gly Arg
        195                 200                 205

Asn Gln Leu His Ile Val Asp Phe Glu Asp Phe Ile Gln Thr Asp Ala
    210                 215                 220

Ala Ile Asn Pro Gly Asn Ser Gly Gly Pro Leu Leu Asn Ile Asn Gly
```

```
225                 230                 235                 240

Gln Val Ile Gly Val Asn Thr Ala Ile Val Ser Gly Ser Gly Gly Tyr
                245                 250                 255

Ile Gly Ile Gly Phe Ala Ile Pro Ser Leu Met Ala Lys Arg Val Ile
            260                 265                 270

Asp Gln Leu Ile Ser Asp Gly Gln Val Thr Arg Gly Phe Leu Gly Val
        275                 280                 285

Thr Leu Gln Pro Ile Asp Ser Glu Leu Ala Thr Cys Tyr Lys Leu Glu
    290                 295                 300

Lys Val Tyr Gly Ala Leu Val Thr Asp Val Val Lys Gly Ser Pro Ala
305                 310                 315                 320

Glu Lys Ala Gly Leu Arg Gln Glu Asp Val Ile Val Ala Tyr Asn Gly
                325                 330                 335

Lys Glu Val Glu Ser Leu Ser Ala Leu Arg Asn Ala Ile Ser Leu Met
            340                 345                 350

Met Pro Gly Thr Arg Val Val Leu Lys Ile Val Arg Glu Gly Lys Thr
        355                 360                 365

Ile Glu Ile Pro Val Thr Val Thr Gln Ile Pro Thr Glu Asp Gly Val
    370                 375                 380

Ser Ala Leu Gln Lys Met Gly Val Arg Val Gln Asn Ile Thr Pro Glu
385                 390                 395                 400

Ile Cys Lys Lys Leu Gly Leu Ala Ala Asp Thr Arg Gly Ile Leu Val
                405                 410                 415

Val Ala Val Glu Ala Gly Ser Pro Ala Ala Ser Ala Gly Val Ala Pro
            420                 425                 430

Gly Gln Leu Ile Leu Ala Val Asn Arg Gln Arg Val Ala Ser Val Glu
        435                 440                 445

Glu Leu Asn Gln Val Leu Lys Asn Ser Lys Gly Glu Asn Val Leu Leu
    450                 455                 460

Met Val Ser Gln Gly Asp Val Val Arg Phe Ile Val Leu Lys Ser Asp
465                 470                 475                 480

Glu
```

<210> SEQ ID NO 143
<211> LENGTH: 1347
<212> TYPE: DNA
<213> ORGANISM: Chlamydia muridarum

<400> SEQUENCE: 143

```
atgctaacta actttacctt tcgcaactgt cttttgtttt tcgtcacatt gtccagtgtc     60

cctgttttct cggcacccca acctcgcgta acgcttccta gtggagccaa taaaatcgga    120

tcagaagctt ggatagagca aaaagtccgt caatatccag aacttttgtg gttagttgaa    180

ccttctcctg caggaacttc tttaaacgct ccttcgggga tgatcttttc tcccctattg    240

ttccaaaaga aagtccctgc ttttgatatc gcagtacgca gtctgattca cctacacctg    300

cttatccagg gctcccgcca agcttatgct cagcttgtcc agctgcaggc taatgaatcc    360

cctatgacat ttaaacagtt ccttacccta cataagcagc tctccttatt cctaaattct    420

cctaaagagt tttatgattc cgtcaaaatt ttagaaactg ctatcatcct acgccactta    480

ggatgttcaa caaaagctgt tgccacattt aagccttatt tttcagaaac gcaaaaagag    540

gtcttctata caaaagcttt gcatgttctg catactttcc cagaattgag cccttcgttt    600

gctagactct ctccagaaca aaaaacgctc ttcttctcat tgagaaagct cgctaattat    660

gatgagttac tttccctgac aaatgcccct agtttacaac tactatctgc tgtacgctcg    720
```

```
cgacgcgcgc ttttggctct agacttgtat ctctatgctt tagatttttg tggagaacag    780

gggatatcct ctcagtttca tatggacttt tctcctttac agtccatgtt gcaacaatat    840

gctacggttg aagaagcctt ctcccgctac tttacttacc gagctaatcg cctaggattt    900

gcgggttctt ctcgaactga aatggcctta gttagaatag ctactttaat gaacctatcc    960

ccttcagaag ctgctatttt aacaacaagc tttaagtctc tttccttgga agatgctgaa   1020

agcttagtga atagctttta tacaaataag ggagactctt tagctctttc tttacgagga   1080

ctaccaactc ttatatctga actaacacgc gctgcgcatg gaaatacgaa tgcggaagct   1140

cgagctcagc aaatttacgc cacaacgtta tcattggtag caaaaagctt gaaagctcac   1200

aaagagatgc aaaacaaaca aattcttccc gaagaagtcg ttttagattt ctctgaaact   1260

gcttcttcct gtcaaggatt ggacatcttc tctgagaacg ttgctgttca aatccacttg   1320

aatggatctg tcagcatcca tctataa                                       1347
```

<210> SEQ ID NO 144
<211> LENGTH: 448
<212> TYPE: PRT
<213> ORGANISM: Chlamydia muridarum

<400> SEQUENCE: 144

```
Met Leu Thr Asn Phe Thr Phe Arg Asn Cys Leu Leu Phe Phe Val Thr
1               5                   10                  15

Leu Ser Ser Val Pro Val Phe Ser Ala Pro Gln Pro Arg Val Thr Leu
            20                  25                  30

Pro Ser Gly Ala Asn Lys Ile Gly Ser Glu Ala Trp Ile Glu Gln Lys
        35                  40                  45

Val Arg Gln Tyr Pro Glu Leu Leu Trp Leu Val Glu Pro Ser Pro Ala
    50                  55                  60

Gly Thr Ser Leu Asn Ala Pro Ser Gly Met Ile Phe Ser Pro Leu Leu
65                  70                  75                  80

Phe Gln Lys Lys Val Pro Ala Phe Asp Ile Ala Val Arg Ser Leu Ile
                85                  90                  95

His Leu His Leu Leu Ile Gln Gly Ser Arg Gln Ala Tyr Ala Gln Leu
            100                 105                 110

Val Gln Leu Gln Ala Asn Glu Ser Pro Met Thr Phe Lys Gln Phe Leu
        115                 120                 125

Thr Leu His Lys Gln Leu Ser Leu Phe Leu Asn Ser Pro Lys Glu Phe
    130                 135                 140

Tyr Asp Ser Val Lys Ile Leu Glu Thr Ala Ile Ile Leu Arg His Leu
145                 150                 155                 160

Gly Cys Ser Thr Lys Ala Val Ala Thr Phe Lys Pro Tyr Phe Ser Glu
                165                 170                 175

Thr Gln Lys Glu Val Phe Tyr Thr Lys Ala Leu His Val Leu His Thr
            180                 185                 190

Phe Pro Glu Leu Ser Pro Ser Phe Ala Arg Leu Ser Pro Glu Gln Lys
        195                 200                 205

Thr Leu Phe Phe Ser Leu Arg Lys Leu Ala Asn Tyr Asp Glu Leu Leu
    210                 215                 220

Ser Leu Thr Asn Ala Pro Ser Leu Gln Leu Leu Ser Ala Val Arg Ser
225                 230                 235                 240

Arg Arg Ala Leu Leu Ala Leu Asp Leu Tyr Leu Tyr Ala Leu Asp Phe
                245                 250                 255

Cys Gly Glu Gln Gly Ile Ser Ser Gln Phe His Met Asp Phe Ser Pro
```

```
            260                 265                 270

Leu Gln Ser Met Leu Gln Gln Tyr Ala Thr Val Glu Glu Ala Phe Ser
        275                 280                 285

Arg Tyr Phe Thr Tyr Arg Ala Asn Arg Leu Gly Phe Ala Gly Ser Ser
    290                 295                 300

Arg Thr Glu Met Ala Leu Val Arg Ile Ala Thr Leu Met Asn Leu Ser
305                 310                 315                 320

Pro Ser Glu Ala Ala Ile Leu Thr Thr Ser Phe Lys Ser Leu Ser Leu
                325                 330                 335

Glu Asp Ala Glu Ser Leu Val Asn Ser Phe Tyr Thr Asn Lys Gly Asp
            340                 345                 350

Ser Leu Ala Leu Ser Leu Arg Gly Leu Pro Thr Leu Ile Ser Glu Leu
        355                 360                 365

Thr Arg Ala Ala His Gly Asn Thr Asn Ala Glu Ala Arg Ala Gln Gln
    370                 375                 380

Ile Tyr Ala Thr Thr Leu Ser Leu Val Ala Lys Ser Leu Lys Ala His
385                 390                 395                 400

Lys Glu Met Gln Asn Lys Gln Ile Leu Pro Glu Glu Val Val Leu Asp
                405                 410                 415

Phe Ser Glu Thr Ala Ser Ser Cys Gln Gly Leu Asp Ile Phe Ser Glu
            420                 425                 430

Asn Val Ala Val Gln Ile His Leu Asn Gly Ser Val Ser Ile His Leu
        435                 440                 445
```

<210> SEQ ID NO 145
<211> LENGTH: 1224
<212> TYPE: DNA
<213> ORGANISM: Chlamydia muridarum

<400> SEQUENCE: 145

```
tcagaagctt ggatagagca aaaagtccgt caatatccag aacttttgtg gttagttgaa      60
ccttctcctg caggaacttc tttaaacgct ccttcgggga tgatcttttc tcccctattg     120
ttccaaaaga aagtccctgc ttttgatatc gcagtacgca gtctgattca cctacacctg     180
cttatccagg gctcccgcca agcttatgct cagcttgtcc agctgcaggc taatgaatcc     240
cctatgacat ttaaacagtt ccttacccta cataagcagc tctccttatt cctaaattct     300
cctaaagagt tttatgattc cgtcaaaatt ttagaaactg ctatcatcct acgccactta     360
ggatgttcaa caaaagctgt tgccacattt aagccttatt tttcagaaac gcaaaaagag     420
gtcttctata caaaagcttt gcatgttctg catactttcc cagaattgag cccttcgttt     480
gctagactct ctccagaaca aaaaacgctc ttcttctcat tgagaaagct cgctaattat     540
gatgagttac tttccctgac aaatgcccct agtttacaac tactatctgc tgtacgctcg     600
cgacgcgcgc ttttggctct agacttgtat ctctatgctt tagatttttg tggagaacag     660
gggatatcct ctcagtttca tatggacttt tctcctttac agtccatgtt gcaacaatat     720
gctacggttg aagaagcctt ctcccgctac tttacttacc gagctaatcg cctaggattt     780
gcgggttctt ctcgaactga aatggcctta gttagaatag ctactttaat gaacctatcc     840
ccttcagaag ctgctatttt aacaacaagc tttaagtctc tttccttgga agatgctgaa     900
agcttagtga atagctttta tacaaataag ggagactctt tagctctttc tttacgagga     960
ctaccaactc ttatatctga actaacacgc gctgcgcatg gaaatacgaa tgcggaagct    1020
cgagctcagc aaatttacgc cacaacgtta tcattggtag caaaaagctt gaaagctcac    1080
aaagagatgc aaaacaaaca aattcttccc gaagaagtcg ttttagattt ctctgaaact    1140
```

gcttcttcct gtcaaggatt ggacatcttc tctgagaacg ttgctgttca aatccacttg 1200
aatggatctg tcagcatcca tcta 1224

<210> SEQ ID NO 146
<211> LENGTH: 408
<212> TYPE: PRT
<213> ORGANISM: Chlamydia muridarum

<400> SEQUENCE: 146

```
Ser Glu Ala Trp Ile Glu Gln Lys Val Arg Gln Tyr Pro Glu Leu Leu
1               5                   10                  15

Trp Leu Val Glu Pro Ser Pro Ala Gly Thr Ser Leu Asn Ala Pro Ser
            20                  25                  30

Gly Met Ile Phe Ser Pro Leu Leu Phe Gln Lys Lys Val Pro Ala Phe
        35                  40                  45

Asp Ile Ala Val Arg Ser Leu Ile His Leu His Leu Leu Ile Gln Gly
    50                  55                  60

Ser Arg Gln Ala Tyr Ala Gln Leu Val Gln Leu Gln Ala Asn Glu Ser
65                  70                  75                  80

Pro Met Thr Phe Lys Gln Phe Leu Thr Leu His Lys Gln Leu Ser Leu
                85                  90                  95

Phe Leu Asn Ser Pro Lys Glu Phe Tyr Asp Ser Val Lys Ile Leu Glu
            100                 105                 110

Thr Ala Ile Ile Leu Arg His Leu Gly Cys Ser Thr Lys Ala Val Ala
        115                 120                 125

Thr Phe Lys Pro Tyr Phe Ser Glu Thr Gln Lys Glu Val Phe Tyr Thr
    130                 135                 140

Lys Ala Leu His Val Leu His Thr Phe Pro Glu Leu Ser Pro Ser Phe
145                 150                 155                 160

Ala Arg Leu Ser Pro Glu Gln Lys Thr Leu Phe Phe Ser Leu Arg Lys
                165                 170                 175

Leu Ala Asn Tyr Asp Glu Leu Leu Ser Leu Thr Asn Ala Pro Ser Leu
            180                 185                 190

Gln Leu Leu Ser Ala Val Arg Ser Arg Arg Ala Leu Leu Ala Leu Asp
        195                 200                 205

Leu Tyr Leu Tyr Ala Leu Asp Phe Cys Gly Glu Gln Gly Ile Ser Ser
    210                 215                 220

Gln Phe His Met Asp Phe Ser Pro Leu Gln Ser Met Leu Gln Gln Tyr
225                 230                 235                 240

Ala Thr Val Glu Glu Ala Phe Ser Arg Tyr Phe Thr Tyr Arg Ala Asn
                245                 250                 255

Arg Leu Gly Phe Ala Gly Ser Ser Arg Thr Glu Met Ala Leu Val Arg
            260                 265                 270

Ile Ala Thr Leu Met Asn Leu Ser Pro Ser Glu Ala Ala Ile Leu Thr
        275                 280                 285

Thr Ser Phe Lys Ser Leu Ser Leu Glu Asp Ala Glu Ser Leu Val Asn
    290                 295                 300

Ser Phe Tyr Thr Asn Lys Gly Asp Ser Leu Ala Leu Ser Leu Arg Gly
305                 310                 315                 320

Leu Pro Thr Leu Ile Ser Glu Leu Thr Arg Ala Ala His Gly Asn Thr
                325                 330                 335

Asn Ala Glu Ala Arg Ala Gln Gln Ile Tyr Ala Thr Thr Leu Ser Leu
            340                 345                 350

Val Ala Lys Ser Leu Lys Ala His Lys Glu Met Gln Asn Lys Gln Ile
```

-continued

```
        355                 360                 365

Leu Pro Glu Glu Val Val Leu Asp Phe Ser Glu Thr Ala Ser Ser Cys
    370                 375                 380

Gln Gly Leu Asp Ile Phe Ser Glu Asn Val Ala Val Gln Ile His Leu
385                 390                 395                 400

Asn Gly Ser Val Ser Ile His Leu
                405


<210> SEQ ID NO 147
<211> LENGTH: 2430
<212> TYPE: DNA
<213> ORGANISM: Chlamydia muridarum

<400> SEQUENCE: 147

atgccccact ctcctttttt atatgttgtt caaccgcatt ctgtttttaa tcctagattg     60

ggagagcggc accctattac tttagatttc atcaaagaaa agaatcgatt agctgatttt    120

attgaaaacc tacctttaga aatttttgga gccccttctt tcttggaaaa tgcttcttta    180

gaagcctctt atgtcttgtc tagggaatcc acaaaagatg gcactctttt taccgttcta    240

gaacccaaac tatctgcctg cgtagctact tgccttgtgg attcttctat tcctatggag    300

cccgataacg agctcttaga agaaattaaa cacactttgt tgaaaagctc ttgtgatggc    360

gtacaatatc gtgtaacccg agagactctc caaaacaaag atgaagcccc cagagtctct    420

ttagttgctg atgatatcga acttatccgc aatgtagatt ttttaggacg ttccgttgat    480

attgtaaaat tggatccctt gaatattcct aataccgtaa gcgaggagaa tgctctcgat    540

tactctttca caagggaaac cgccaaactt agccctgacg gacgagttgg catccctcaa    600

gggacaaaaa ttttgccagc tccctctctt gaagttgaaa ttagcacctc tatttttgag    660

gaaacctctt cttttgaaca aaacttttct tcctctatta ctttttgtgt accacctctt    720

acctcttttt ctcctttgca agaacctcct ctagtgggag ctggacagca ggaaattctt    780

gtgactaaaa agcacttatt ccctagctat accccctaaac ttattgatat tgtcaaacga    840

cacaaaagag acgcaaagat tctagtaaac aagatccagt tcgagaaact atggagaagt    900

catgccaaaa gtcaaatctt aaaagaaggc tctgttcgct tggatttaca aggatttaca    960

ggggagctgt ttaactacca acttcaagta ggatctcata caattgcagc cgtgttaatt   1020

gatccggaaa ttgctaacgt caaatccctc cccgaacaaa cttacgctgt aagaaaaatt   1080

aaatcagggt tccaatgtag tttggatgac caacacattt atcaagtcgc agtaaaaaaa   1140

catctttctc tgtcttcaca acctccgaag atatctccgt tatctcaatc cgaaagctcc   1200

gatttaagtc tctttgaagc agcagcgttt tcagcaagcc taacttacga gttcgtaaag   1260

aaaaatacat atcatgctaa gaatactgta acttgctcca cggtatcgca ctctctgtat   1320

attctcaaag aagatgacgg ggctaatgct gcagaaaaac gcttagacaa cagtttccga   1380

aactgggtcg aaaataagtt gaacgcaaat tctccagatt cttgtactgc atttattcaa   1440

aaattcggca cacattacat cacatcggca acttttggag gatctgggtt ccaagttctt   1500

aaattatcct ttgaacaggt agaaggcctc cgtagtaaga agatctccct agaagcagca   1560

gcagcaaatt ccttattaaa aagctctgtg tcaaacagca cggaatctgg ctactctact   1620

tacgattcct cttcttcttc tcatacagta ttcctagggg gcactgtatt accctctgtt   1680

catgatggac agttagattt taaagattgg tctgaaagtg tctgtttaga acctgttccc   1740

attcacattt ctttactccc cttaacagac ttgctcaccc ctctttattt tcctgaaacg   1800

gatacaaccg aactatctaa taaacgtaat gctctccaac aagcggttcg agtttacctt   1860
```

```
aaagaccatc gttcagctaa acaaagcgaa cgctccgtat tcacagcggg gatcaatagt   1920

ccttcttcct ggttcacatt agaatctgct aattcacctc ttgttgtgag ttctccttac   1980

atgacgtatt ggtctactct cccctatctc ttccccacat taaaagagcg ttcttcagca   2040

gctcccatcg tttttttattt ttgtgtggat aataatgaac acgcctccca aaaaatttta   2100

aaccaaacat attgcttcat aggttcttta cctattcgac aaaagatttt tggcagagaa   2160

tttgctgaga atccttattt atctttctat ggaaggtttg gagaagctta ttttgatggc   2220

ggttatccag aacgttgtgg atggattgtt gaaaagttaa atactactaa agatcaaatt   2280

ctccgcgatg aggatgaagt gcaactaaag catgtttata gcggagagta tctgtctaca   2340

attcctatta aggattccca ttgcacactc tcgcgtacat gcaccgaatc gaatgctgtt   2400

tttattatca aaaaaccttc gagctattga                                    2430
```

<210> SEQ ID NO 148
<211> LENGTH: 809
<212> TYPE: PRT
<213> ORGANISM: Chlamydia muridarum

<400> SEQUENCE: 148

```
Met Pro His Ser Pro Phe Leu Tyr Val Val Gln Pro His Ser Val Phe
1               5                   10                  15

Asn Pro Arg Leu Gly Glu Arg His Pro Ile Thr Leu Asp Phe Ile Lys
            20                  25                  30

Glu Lys Asn Arg Leu Ala Asp Phe Ile Glu Asn Leu Pro Leu Glu Ile
        35                  40                  45

Phe Gly Ala Pro Ser Phe Leu Glu Asn Ala Ser Leu Glu Ala Ser Tyr
    50                  55                  60

Val Leu Ser Arg Glu Ser Thr Lys Asp Gly Thr Leu Phe Thr Val Leu
65                  70                  75                  80

Glu Pro Lys Leu Ser Ala Cys Val Ala Thr Cys Leu Val Asp Ser Ser
                85                  90                  95

Ile Pro Met Glu Pro Asp Asn Glu Leu Leu Glu Glu Ile Lys His Thr
            100                 105                 110

Leu Leu Lys Ser Ser Cys Asp Gly Val Gln Tyr Arg Val Thr Arg Glu
        115                 120                 125

Thr Leu Gln Asn Lys Asp Glu Ala Pro Arg Val Ser Leu Val Ala Asp
    130                 135                 140

Asp Ile Glu Leu Ile Arg Asn Val Asp Phe Leu Gly Arg Ser Val Asp
145                 150                 155                 160

Ile Val Lys Leu Asp Pro Leu Asn Ile Pro Asn Thr Val Ser Glu Glu
                165                 170                 175

Asn Ala Leu Asp Tyr Ser Phe Thr Arg Glu Thr Ala Lys Leu Ser Pro
            180                 185                 190

Asp Gly Arg Val Gly Ile Pro Gln Gly Thr Lys Ile Leu Pro Ala Pro
        195                 200                 205

Ser Leu Glu Val Glu Ile Ser Thr Ser Ile Phe Glu Glu Thr Ser Ser
    210                 215                 220

Phe Glu Gln Asn Phe Ser Ser Ser Ile Thr Phe Cys Val Pro Pro Leu
225                 230                 235                 240

Thr Ser Phe Ser Pro Leu Gln Glu Pro Pro Leu Val Gly Ala Gly Gln
                245                 250                 255

Gln Glu Ile Leu Val Thr Lys Lys His Leu Phe Pro Ser Tyr Thr Pro
            260                 265                 270
```

```
Lys Leu Ile Asp Ile Val Lys Arg His Lys Arg Asp Ala Lys Ile Leu
        275                 280                 285

Val Asn Lys Ile Gln Phe Glu Lys Leu Trp Arg Ser His Ala Lys Ser
    290                 295                 300

Gln Ile Leu Lys Glu Gly Ser Val Arg Leu Asp Leu Gln Gly Phe Thr
305                 310                 315                 320

Gly Glu Leu Phe Asn Tyr Gln Leu Gln Val Gly Ser His Thr Ile Ala
                325                 330                 335

Ala Val Leu Ile Asp Pro Glu Ile Ala Asn Val Lys Ser Leu Pro Glu
            340                 345                 350

Gln Thr Tyr Ala Val Arg Lys Ile Lys Ser Gly Phe Gln Cys Ser Leu
        355                 360                 365

Asp Asp Gln His Ile Tyr Gln Val Ala Val Lys Lys His Leu Ser Leu
    370                 375                 380

Ser Ser Gln Pro Pro Lys Ile Ser Pro Leu Ser Gln Ser Glu Ser Ser
385                 390                 395                 400

Asp Leu Ser Leu Phe Glu Ala Ala Ala Phe Ser Ala Ser Leu Thr Tyr
                405                 410                 415

Glu Phe Val Lys Lys Asn Thr Tyr His Ala Lys Asn Thr Val Thr Cys
            420                 425                 430

Ser Thr Val Ser His Ser Leu Tyr Ile Leu Lys Glu Asp Asp Gly Ala
        435                 440                 445

Asn Ala Ala Glu Lys Arg Leu Asp Asn Ser Phe Arg Asn Trp Val Glu
    450                 455                 460

Asn Lys Leu Asn Ala Asn Ser Pro Asp Ser Cys Thr Ala Phe Ile Gln
465                 470                 475                 480

Lys Phe Gly Thr His Tyr Ile Thr Ser Ala Thr Phe Gly Gly Ser Gly
                485                 490                 495

Phe Gln Val Leu Lys Leu Ser Phe Glu Gln Val Glu Gly Leu Arg Ser
            500                 505                 510

Lys Lys Ile Ser Leu Glu Ala Ala Ala Ala Asn Ser Leu Leu Lys Ser
        515                 520                 525

Ser Val Ser Asn Ser Thr Glu Ser Gly Tyr Ser Thr Tyr Asp Ser Ser
    530                 535                 540

Ser Ser Ser His Thr Val Phe Leu Gly Gly Thr Val Leu Pro Ser Val
545                 550                 555                 560

His Asp Gly Gln Leu Asp Phe Lys Asp Trp Ser Glu Ser Val Cys Leu
                565                 570                 575

Glu Pro Val Pro Ile His Ile Ser Leu Leu Pro Leu Thr Asp Leu Leu
            580                 585                 590

Thr Pro Leu Tyr Phe Pro Glu Thr Asp Thr Thr Glu Leu Ser Asn Lys
        595                 600                 605

Arg Asn Ala Leu Gln Gln Ala Val Arg Val Tyr Leu Lys Asp His Arg
    610                 615                 620

Ser Ala Lys Gln Ser Glu Arg Ser Val Phe Thr Ala Gly Ile Asn Ser
625                 630                 635                 640

Pro Ser Ser Trp Phe Thr Leu Glu Ser Ala Asn Ser Pro Leu Val Val
                645                 650                 655

Ser Ser Pro Tyr Met Thr Tyr Trp Ser Thr Leu Pro Tyr Leu Phe Pro
            660                 665                 670

Thr Leu Lys Glu Arg Ser Ser Ala Ala Pro Ile Val Phe Tyr Phe Cys
        675                 680                 685

Val Asp Asn Asn Glu His Ala Ser Gln Lys Ile Leu Asn Gln Thr Tyr
    690                 695                 700
```

Cys Phe Ile Gly Ser Leu Pro Ile Arg Gln Lys Ile Phe Gly Arg Glu
705 710 715 720

Phe Ala Glu Asn Pro Tyr Leu Ser Phe Tyr Gly Arg Phe Gly Glu Ala
725 730 735

Tyr Phe Asp Gly Gly Tyr Pro Glu Arg Cys Gly Trp Ile Val Glu Lys
740 745 750

Leu Asn Thr Thr Lys Asp Gln Ile Leu Arg Asp Glu Asp Glu Val Gln
755 760 765

Leu Lys His Val Tyr Ser Gly Glu Tyr Leu Ser Thr Ile Pro Ile Lys
770 775 780

Asp Ser His Cys Thr Leu Ser Arg Thr Cys Thr Glu Ser Asn Ala Val
785 790 795 800

Phe Ile Ile Lys Lys Pro Ser Ser Tyr
805

<210> SEQ ID NO 149
<211> LENGTH: 2424
<212> TYPE: DNA
<213> ORGANISM: Chlamydia muridarum

<400> SEQUENCE: 149
ccccactctc cttttttata tgttgttcaa ccgcattctg tttttaatcc tagattggga 60
gagcggcacc ctattacttt agatttcatc aaagaaaaga atcgattagc tgattttatt 120
gaaaacctac ctttagaaat ttttggagcc ccttctttct tggaaaatgc ttctttagaa 180
gcctcttatg tcttgtctag ggaatccaca aaagatggca ctctttttac cgttctagaa 240
cccaaactat ctgcctgcgt agctacttgc cttgtggatt cttctattcc tatggagccc 300
gataacgagc tcttagaaga aattaaacac actttgttga aaagctcttg tgatggcgta 360
caatatcgtg taacccgaga gactctccaa aacaaagatg aagcccccag agtctcttta 420
gttgctgatg atatcgaact tatccgcaat gtagattttt taggacgttc cgttgatatt 480
gtaaaattgg atcccttgaa tattcctaat accgtaagcg aggagaatgc tctcgattac 540
tctttcacaa gggaaaccgc caaacttagc cctgacggac gagttggcat ccctcaaggg 600
acaaaaattt tgccagctcc ctctcttgaa gttgaaatta gcacctctat ttttgaggaa 660
acctcttctt ttgaacaaaa cttttcttcc tctattactt tttgtgtacc acctcttacc 720
tctttttctc ctttgcaaga acctcctcta gtgggagctg gacagcagga aattcttgtg 780
actaaaaagc acttattccc tagctatacc cctaaactta ttgatattgt caaacgacac 840
aaaagagacg caaagattct agtaaacaag atccagttcg agaaactatg gagaagtcat 900
gccaaaagtc aaatcttaaa agaaggctct gttcgcttgg atttacaagg atttacaggg 960
gagctgttta actaccaact tcaagtagga tctcatacaa ttgcagccgt gttaattgat 1020
ccggaaattg ctaacgtcaa atccctcccc gaacaaactt acgctgtaag aaaaattaaa 1080
tcagggttcc aatgtagttt ggatgaccaa cacatttatc aagtcgcagt aaaaaaacat 1140
ctttctctgt cttcacaacc tccgaagata tctccgttat ctcaatccga aagctccgat 1200
ttaagtctct ttgaagcagc agcgttttca gcaagcctaa cttacgagtt cgtaaagaaa 1260
aatacatatc atgctaagaa tactgtaact tgctccacgg tatcgcactc tctgtatatt 1320
ctcaaagaag atgacggggc taatgctgca gaaaaacgct tagacaacag tttccgaaac 1380
tgggtcgaaa ataagttgaa cgcaaattct ccagattctt gtactgcatt tattcaaaaa 1440
ttcggcacac attacatcac atcggcaact tttggaggat ctgggttcca agttcttaaa 1500

```
ttatcctttg aacaggtaga aggcctccgt agtaagaaga tctccctaga agcagcagca   1560
gcaaattcct tattaaaaag ctctgtgtca aacagcacgg aatctggcta ctctacttac   1620
gattcctctt cttcttctca tacagtattc ctagggggca ctgtattacc ctctgttcat   1680
gatggacagt tagattttaa agattggtct gaaagtgtct gtttagaacc tgttcccatt   1740
cacatttctt tactcccctt aacagacttg ctcacccctc tttattttcc tgaaacggat   1800
acaaccgaac tatctaataa acgtaatgct ctccaacaag cggttcgagt ttaccttaaa   1860
gaccatcgtt cagctaaaca aagcgaacgc tccgtattca cagcggggat caatagtcct   1920
tcttcctggt tcacattaga atctgctaat tcacctcttg ttgtgagttc tccttacatg   1980
acgtattggt ctactctccc ctatctcttc cccacattaa aagagcgttc ttcagcagct   2040
cccatcgttt tttatttttg tgtggataat aatgaacacg cctcccaaaa aattttaaac   2100
caaacatatt gcttcatagg ttctttacct attcgacaaa agatttttgg cagagaattt   2160
gctgagaatc cttatttatc tttctatgga aggtttggag aagcttattt tgatggcggt   2220
tatccagaac gttgtggatg gattgttgaa aagttaaata ctactaaaga tcaaattctc   2280
cgcgatgagg atgaagtgca actaaagcat gtttatagcg gagagtatct gtctacaatt   2340
cctattaagg attcccattg cacactctcg cgtacatgca ccgaatcgaa tgctgttttt   2400
attatcaaaa aaccttcgag ctat                                          2424
```

<210> SEQ ID NO 150
<211> LENGTH: 808
<212> TYPE: PRT
<213> ORGANISM: Chlamydia muridarum

<400> SEQUENCE: 150

```
Pro His Ser Pro Phe Leu Tyr Val Val Gln Pro His Ser Val Phe Asn
1               5                   10                  15

Pro Arg Leu Gly Glu Arg His Pro Ile Thr Leu Asp Phe Ile Lys Glu
            20                  25                  30

Lys Asn Arg Leu Ala Asp Phe Ile Glu Asn Leu Pro Leu Glu Ile Phe
        35                  40                  45

Gly Ala Pro Ser Phe Leu Glu Asn Ala Ser Leu Glu Ala Ser Tyr Val
    50                  55                  60

Leu Ser Arg Glu Ser Thr Lys Asp Gly Thr Leu Phe Thr Val Leu Glu
65                  70                  75                  80

Pro Lys Leu Ser Ala Cys Val Ala Thr Cys Leu Val Asp Ser Ser Ile
                85                  90                  95

Pro Met Glu Pro Asp Asn Glu Leu Leu Glu Glu Ile Lys His Thr Leu
            100                 105                 110

Leu Lys Ser Ser Cys Asp Gly Val Gln Tyr Arg Val Thr Arg Glu Thr
        115                 120                 125

Leu Gln Asn Lys Asp Glu Ala Pro Arg Val Ser Leu Val Ala Asp Asp
    130                 135                 140

Ile Glu Leu Ile Arg Asn Val Asp Phe Leu Gly Arg Ser Val Asp Ile
145                 150                 155                 160

Val Lys Leu Asp Pro Leu Asn Ile Pro Asn Thr Val Ser Glu Glu Asn
                165                 170                 175

Ala Leu Asp Tyr Ser Phe Thr Arg Glu Thr Ala Lys Leu Ser Pro Asp
            180                 185                 190

Gly Arg Val Gly Ile Pro Gln Gly Thr Lys Ile Leu Pro Ala Pro Ser
        195                 200                 205

Leu Glu Val Glu Ile Ser Thr Ser Ile Phe Glu Glu Thr Ser Ser Phe
```

-continued

```
    210                 215                 220

Glu Gln Asn Phe Ser Ser Ser Ile Thr Phe Cys Val Pro Pro Leu Thr
225                 230                 235                 240

Ser Phe Ser Pro Leu Gln Glu Pro Pro Leu Val Gly Ala Gly Gln Gln
                245                 250                 255

Glu Ile Leu Val Thr Lys Lys His Leu Phe Pro Ser Tyr Thr Pro Lys
            260                 265                 270

Leu Ile Asp Ile Val Lys Arg His Lys Arg Asp Ala Lys Ile Leu Val
        275                 280                 285

Asn Lys Ile Gln Phe Glu Lys Leu Trp Arg Ser His Ala Lys Ser Gln
    290                 295                 300

Ile Leu Lys Glu Gly Ser Val Arg Leu Asp Leu Gln Gly Phe Thr Gly
305                 310                 315                 320

Glu Leu Phe Asn Tyr Gln Leu Gln Val Gly Ser His Thr Ile Ala Ala
                325                 330                 335

Val Leu Ile Asp Pro Glu Ile Ala Asn Val Lys Ser Leu Pro Glu Gln
            340                 345                 350

Thr Tyr Ala Val Arg Lys Ile Lys Ser Gly Phe Gln Cys Ser Leu Asp
        355                 360                 365

Asp Gln His Ile Tyr Gln Val Ala Val Lys Lys His Leu Ser Leu Ser
    370                 375                 380

Ser Gln Pro Pro Lys Ile Ser Pro Leu Ser Gln Ser Glu Ser Ser Asp
385                 390                 395                 400

Leu Ser Leu Phe Glu Ala Ala Ala Phe Ser Ala Ser Leu Thr Tyr Glu
                405                 410                 415

Phe Val Lys Lys Asn Thr Tyr His Ala Lys Asn Thr Val Thr Cys Ser
            420                 425                 430

Thr Val Ser His Ser Leu Tyr Ile Leu Lys Glu Asp Asp Gly Ala Asn
        435                 440                 445

Ala Ala Glu Lys Arg Leu Asp Asn Ser Phe Arg Asn Trp Val Glu Asn
    450                 455                 460

Lys Leu Asn Ala Asn Ser Pro Asp Ser Cys Thr Ala Phe Ile Gln Lys
465                 470                 475                 480

Phe Gly Thr His Tyr Ile Thr Ser Ala Thr Phe Gly Gly Ser Gly Phe
                485                 490                 495

Gln Val Leu Lys Leu Ser Phe Glu Gln Val Glu Gly Leu Arg Ser Lys
            500                 505                 510

Lys Ile Ser Leu Glu Ala Ala Ala Ala Asn Ser Leu Leu Lys Ser Ser
        515                 520                 525

Val Ser Asn Ser Thr Glu Ser Gly Tyr Ser Thr Tyr Asp Ser Ser Ser
    530                 535                 540

Ser Ser His Thr Val Phe Leu Gly Gly Thr Val Leu Pro Ser Val His
545                 550                 555                 560

Asp Gly Gln Leu Asp Phe Lys Asp Trp Ser Glu Ser Val Cys Leu Glu
                565                 570                 575

Pro Val Pro Ile His Ile Ser Leu Leu Pro Leu Thr Asp Leu Leu Thr
            580                 585                 590

Pro Leu Tyr Phe Pro Glu Thr Asp Thr Thr Glu Leu Ser Asn Lys Arg
        595                 600                 605

Asn Ala Leu Gln Gln Ala Val Arg Val Tyr Leu Lys Asp His Arg Ser
    610                 615                 620

Ala Lys Gln Ser Glu Arg Ser Val Phe Thr Ala Gly Ile Asn Ser Pro
625                 630                 635                 640
```

```
Ser Ser Trp Phe Thr Leu Glu Ser Ala Asn Ser Pro Leu Val Val Ser
                645                 650                 655

Ser Pro Tyr Met Thr Tyr Trp Ser Thr Leu Pro Tyr Leu Phe Pro Thr
            660                 665                 670

Leu Lys Glu Arg Ser Ser Ala Ala Pro Ile Val Phe Tyr Phe Cys Val
        675                 680                 685

Asp Asn Asn Glu His Ala Ser Gln Lys Ile Leu Asn Gln Thr Tyr Cys
    690                 695                 700

Phe Ile Gly Ser Leu Pro Ile Arg Gln Lys Ile Phe Gly Arg Glu Phe
705                 710                 715                 720

Ala Glu Asn Pro Tyr Leu Ser Phe Tyr Gly Arg Phe Gly Glu Ala Tyr
                725                 730                 735

Phe Asp Gly Gly Tyr Pro Glu Arg Cys Gly Trp Ile Val Glu Lys Leu
            740                 745                 750

Asn Thr Thr Lys Asp Gln Ile Leu Arg Asp Glu Asp Glu Val Gln Leu
        755                 760                 765

Lys His Val Tyr Ser Gly Glu Tyr Leu Ser Thr Ile Pro Ile Lys Asp
    770                 775                 780

Ser His Cys Thr Leu Ser Arg Thr Cys Thr Glu Ser Asn Ala Val Phe
785                 790                 795                 800

Ile Ile Lys Lys Pro Ser Ser Tyr
                805
```

<210> SEQ ID NO 151
<211> LENGTH: 1494
<212> TYPE: DNA
<213> ORGANISM: Chlamydia muridarum

<400> SEQUENCE: 151

```
atgatgaaaa gattattatg tgtgttgcta tcgacatcag ttttctcttc gcccatgttg     60
ggctatagtg cgccaaagaa agattccagt actggcattt gtcttgcagc atctcaaagt    120
gatcgggaac tttcccaaga agatttgcta aaagaagtgt ctagaggatt ttccaaagtc    180
gctgctcagg caactccagg agttgtgtat atagaaaatt ttcctaaaac tgggagtcaa    240
gctattgctt ctcctgggaa taaaaggggt tttcaagaga atccctttga ttatttcaat    300
gatgagtttt tcaatcgatt ttttggttta ccctcgcata gagagcagcc tcgtccccaa    360
cagcgtgatg ctgtaagagg aacaggtttt attgtgtcag aagatgggta cgttgtgacc    420
aaccatcacg tagtggaaga tgcggggaaa attcatgtta ctttacacga tggacaaaaa    480
tacaccgcaa aaatcatagg attagatcct aaaacggatc tcgctgtgat taagatccaa    540
gcaaaaaatc tccctttttt aacttttgga aactctgatc agcttcagat aggggattgg    600
tcaatagcca ttggaaatcc tttcggatta caagccacag taaccgttgg cgtgattagt    660
gctaagggaa gaaaccaatt acatattgtt gattttgaag attttattca gacggatgca    720
gcaattaatc ccgggaattc aggtggtcca ttattgaaca ttgatggaca ggttattgga    780
gtgaatacag caatcgttag cggtagcggg ggatacattg gaataggatt tgccattcct    840
agcttaatgg ctaaacgagt tattgaccaa ctcattagcg atggacaggt gacgagagga    900
tttttaggag taaccttaca gcctattgat tcggagcttg ccgcttgtta caaattagaa    960
aaggtgtacg gagccttgat tacggatgtt gttaagggat ctcctgcaga aaaagcaggt   1020
ttgcgccagg aagatgtcat tgttgcttac aatgggaaag aagtggagtc tttgagtgct   1080
ttacgtaatg cgatttcttt gatgatgcca gggactcgtg ttgtcttaaa agttgtgcgt   1140
gaagggaaat tcattgaaat acctgtcact gttacacaaa ttcctgcgga ggatggggta   1200
```

```
tctgctcttc aaaaaatggg agttcgggta cagaatctta ctccagagat atgcaagaaa   1260

ctaggattag cgtctgatac tcgagggatt tttgtagtgt ccgtagaagc tggttctcct   1320

gcagcttctg caggagtggt tccaggacaa cttattctgg ctgtaaacag acagagagtt   1380

tcttctgttg aagaattgaa tcaggtcttg aagaatgcaa aaggagagaa tgttctcctt   1440

atggtttctc aaggagaagt cattcgattc gttgttttaa agtctgatga atag         1494


<210> SEQ ID NO 152
<211> LENGTH: 497
<212> TYPE: PRT
<213> ORGANISM: Chlamydia muridarum

<400> SEQUENCE: 152

Met Met Lys Arg Leu Leu Cys Val Leu Leu Ser Thr Ser Val Phe Ser
1               5                   10                  15

Ser Pro Met Leu Gly Tyr Ser Ala Pro Lys Lys Asp Ser Ser Thr Gly
            20                  25                  30

Ile Cys Leu Ala Ala Ser Gln Ser Asp Arg Glu Leu Ser Gln Glu Asp
        35                  40                  45

Leu Leu Lys Glu Val Ser Arg Gly Phe Ser Lys Val Ala Ala Gln Ala
    50                  55                  60

Thr Pro Gly Val Val Tyr Ile Glu Asn Phe Pro Lys Thr Gly Ser Gln
65                  70                  75                  80

Ala Ile Ala Ser Pro Gly Asn Lys Arg Gly Phe Gln Glu Asn Pro Phe
                85                  90                  95

Asp Tyr Phe Asn Asp Glu Phe Phe Asn Arg Phe Phe Gly Leu Pro Ser
            100                 105                 110

His Arg Glu Gln Pro Arg Pro Gln Gln Arg Asp Ala Val Arg Gly Thr
        115                 120                 125

Gly Phe Ile Val Ser Glu Asp Gly Tyr Val Val Thr Asn His His Val
    130                 135                 140

Val Glu Asp Ala Gly Lys Ile His Val Thr Leu His Asp Gly Gln Lys
145                 150                 155                 160

Tyr Thr Ala Lys Ile Ile Gly Leu Asp Pro Lys Thr Asp Leu Ala Val
                165                 170                 175

Ile Lys Ile Gln Ala Lys Asn Leu Pro Phe Leu Thr Phe Gly Asn Ser
            180                 185                 190

Asp Gln Leu Gln Ile Gly Asp Trp Ser Ile Ala Ile Gly Asn Pro Phe
        195                 200                 205

Gly Leu Gln Ala Thr Val Thr Val Gly Val Ile Ser Ala Lys Gly Arg
    210                 215                 220

Asn Gln Leu His Ile Val Asp Phe Glu Asp Phe Ile Gln Thr Asp Ala
225                 230                 235                 240

Ala Ile Asn Pro Gly Asn Ser Gly Gly Pro Leu Leu Asn Ile Asp Gly
                245                 250                 255

Gln Val Ile Gly Val Asn Thr Ala Ile Val Ser Gly Ser Gly Gly Tyr
            260                 265                 270

Ile Gly Ile Gly Phe Ala Ile Pro Ser Leu Met Ala Lys Arg Val Ile
        275                 280                 285

Asp Gln Leu Ile Ser Asp Gly Gln Val Thr Arg Gly Phe Leu Gly Val
    290                 295                 300

Thr Leu Gln Pro Ile Asp Ser Glu Leu Ala Ala Cys Tyr Lys Leu Glu
305                 310                 315                 320

Lys Val Tyr Gly Ala Leu Ile Thr Asp Val Val Lys Gly Ser Pro Ala
```

-continued

```
                325                 330                 335

Glu Lys Ala Gly Leu Arg Gln Glu Asp Val Ile Val Ala Tyr Asn Gly
            340                 345                 350

Lys Glu Val Glu Ser Leu Ser Ala Leu Arg Asn Ala Ile Ser Leu Met
        355                 360                 365

Met Pro Gly Thr Arg Val Val Leu Lys Val Val Arg Glu Gly Lys Phe
    370                 375                 380

Ile Glu Ile Pro Val Thr Val Thr Gln Ile Pro Ala Glu Asp Gly Val
385                 390                 395                 400

Ser Ala Leu Gln Lys Met Gly Val Arg Val Gln Asn Leu Thr Pro Glu
                405                 410                 415

Ile Cys Lys Lys Leu Gly Leu Ala Ser Asp Thr Arg Gly Ile Phe Val
            420                 425                 430

Val Ser Val Glu Ala Gly Ser Pro Ala Ala Ser Ala Gly Val Val Pro
        435                 440                 445

Gly Gln Leu Ile Leu Ala Val Asn Arg Gln Arg Val Ser Ser Val Glu
    450                 455                 460

Glu Leu Asn Gln Val Leu Lys Asn Ala Lys Gly Glu Asn Val Leu Leu
465                 470                 475                 480

Met Val Ser Gln Gly Glu Val Ile Arg Phe Val Val Leu Lys Ser Asp
                485                 490                 495

Glu
```

<210> SEQ ID NO 153
<211> LENGTH: 1443
<212> TYPE: DNA
<213> ORGANISM: Chlamydia muridarum

<400> SEQUENCE: 153

```
tcgcccatgt tgggctatag tgcgccaaag aaagattcca gtactggcat ttgtcttgca     60

gcatctcaaa gtgatcggga actttcccaa gaagatttgc taaaagaagt gtctagagga    120

ttttccaaag tcgctgctca ggcaactcca ggagttgtgt atatagaaaa ttttcctaaa    180

actgggagtc aagctattgc ttctcctggg aataaaaggg gttttcaaga gaatcccttt    240

gattatttca atgatgagtt tttcaatcga ttttttggtt taccctcgca tagagagcag    300

cctcgtcccc aacagcgtga tgctgtaaga ggaacaggtt ttattgtgtc agaagatggg    360

tacgttgtga ccaaccatca cgtagtggaa gatgcgggga aaattcatgt tactttacac    420

gatggacaaa aatacaccgc aaaaaatcata ggattagatc ctaaaacgga tctcgctgtg    480

attaagatcc aagcaaaaaa tctccctttt ttaacttttg gaaactctga tcagcttcag    540

atagggggatt ggtcaatagc cattggaaat cctttcggat tacaagccac agtaaccgtt    600

ggcgtgatta gtgctaaggg aagaaaccaa ttacatattg ttgattttga agattttatt    660

cagacggatg cagcaattaa tcccgggaat tcaggtggtc cattattgaa cattgatgga    720

caggttattg gagtgaatac agcaatcgtt agcggtagcg gggatacat tggaatagga    780

tttgccattc ctagcttaat ggctaaacga gttattgacc aactcattag cgatggacag    840

gtgacgagag gattttttagg agtaacctta cagcctattg attcggagct tgccgcttgt    900

tacaaattag aaaaggtgta cggagccttg attacggatg ttgttaaggg atctcctgca    960

gaaaaagcag gtttgcgcca ggaagatgtc attgttgctt acaatgggaa agaagtggag   1020

tctttgagtg ctttacgtaa tgcgatttct ttgatgatgc cagggactcg tgttgtctta   1080

aaagttgtgc gtgaagggaa attcattgaa atacctgtca ctgttacaca aattcctgcg   1140
```

```
gaggatgggg tatctgctct tcaaaaaatg ggagttcggg tacagaatct tactccagag   1200

atatgcaaga aactaggatt agcgtctgat actcgaggga tttttgtagt gtccgtagaa   1260

gctggttctc ctgcagcttc tgcaggagtg gttccaggac aacttattct ggctgtaaac   1320

agacagagag tttcttctgt tgaagaattg aatcaggtct tgaagaatgc aaaaggagag   1380

aatgttctcc ttatggtttc tcaaggagaa gtcattcgat tcgttgtttt aaagtctgat   1440

gaa                                                                 1443
```

```
<210> SEQ ID NO 154
<211> LENGTH: 481
<212> TYPE: PRT
<213> ORGANISM: Chlamydia muridarum

<400> SEQUENCE: 154

Ser Pro Met Leu Gly Tyr Ser Ala Pro Lys Lys Asp Ser Ser Thr Gly
1               5                   10                  15

Ile Cys Leu Ala Ala Ser Gln Ser Asp Arg Glu Leu Ser Gln Glu Asp
            20                  25                  30

Leu Leu Lys Glu Val Ser Arg Gly Phe Ser Lys Val Ala Ala Gln Ala
        35                  40                  45

Thr Pro Gly Val Val Tyr Ile Glu Asn Phe Pro Lys Thr Gly Ser Gln
    50                  55                  60

Ala Ile Ala Ser Pro Gly Asn Lys Arg Gly Phe Gln Glu Asn Pro Phe
65                  70                  75                  80

Asp Tyr Phe Asn Asp Glu Phe Phe Asn Arg Phe Phe Gly Leu Pro Ser
                85                  90                  95

His Arg Glu Gln Pro Arg Pro Gln Gln Arg Asp Ala Val Arg Gly Thr
            100                 105                 110

Gly Phe Ile Val Ser Glu Asp Gly Tyr Val Val Thr Asn His His Val
        115                 120                 125

Val Glu Asp Ala Gly Lys Ile His Val Thr Leu His Asp Gly Gln Lys
    130                 135                 140

Tyr Thr Ala Lys Ile Ile Gly Leu Asp Pro Lys Thr Asp Leu Ala Val
145                 150                 155                 160

Ile Lys Ile Gln Ala Lys Asn Leu Pro Phe Leu Thr Phe Gly Asn Ser
                165                 170                 175

Asp Gln Leu Gln Ile Gly Asp Trp Ser Ile Ala Ile Gly Asn Pro Phe
            180                 185                 190

Gly Leu Gln Ala Thr Val Thr Val Gly Val Ile Ser Ala Lys Gly Arg
        195                 200                 205

Asn Gln Leu His Ile Val Asp Phe Glu Asp Phe Ile Gln Thr Asp Ala
    210                 215                 220

Ala Ile Asn Pro Gly Asn Ser Gly Gly Pro Leu Leu Asn Ile Asp Gly
225                 230                 235                 240

Gln Val Ile Gly Val Asn Thr Ala Ile Val Ser Gly Ser Gly Gly Tyr
                245                 250                 255

Ile Gly Ile Gly Phe Ala Ile Pro Ser Leu Met Ala Lys Arg Val Ile
            260                 265                 270

Asp Gln Leu Ile Ser Asp Gly Gln Val Thr Arg Gly Phe Leu Gly Val
        275                 280                 285

Thr Leu Gln Pro Ile Asp Ser Glu Leu Ala Ala Cys Tyr Lys Leu Glu
    290                 295                 300

Lys Val Tyr Gly Ala Leu Ile Thr Asp Val Val Lys Gly Ser Pro Ala
305                 310                 315                 320
```

-continued

```
Glu Lys Ala Gly Leu Arg Gln Glu Asp Val Ile Val Ala Tyr Asn Gly
                325                 330                 335

Lys Glu Val Glu Ser Leu Ser Ala Leu Arg Asn Ala Ile Ser Leu Met
            340                 345                 350

Met Pro Gly Thr Arg Val Val Leu Lys Val Val Arg Glu Gly Lys Phe
        355                 360                 365

Ile Glu Ile Pro Val Thr Val Thr Gln Ile Pro Ala Glu Asp Gly Val
    370                 375                 380

Ser Ala Leu Gln Lys Met Gly Val Arg Val Gln Asn Leu Thr Pro Glu
385                 390                 395                 400

Ile Cys Lys Lys Leu Gly Leu Ala Ser Asp Thr Arg Gly Ile Phe Val
                405                 410                 415

Val Ser Val Glu Ala Gly Ser Pro Ala Ala Ser Ala Gly Val Val Pro
            420                 425                 430

Gly Gln Leu Ile Leu Ala Val Asn Arg Gln Arg Val Ser Ser Val Glu
        435                 440                 445

Glu Leu Asn Gln Val Leu Lys Asn Ala Lys Gly Glu Asn Val Leu Leu
    450                 455                 460

Met Val Ser Gln Gly Glu Val Ile Arg Phe Val Val Leu Lys Ser Asp
465                 470                 475                 480

Glu
```

<210> SEQ ID NO 155
<211> LENGTH: 1647
<212> TYPE: DNA
<213> ORGANISM: Chlamydia trachomatis

<400> SEQUENCE: 155

```
atgtttgtgt cgttcgataa atcccgttgc agagcggatg tccccgattt ttttgaaagg      60

acaggaaact ttcttctcca ttgtgtggca agagggatca atgttttata tcgtgtgaaa     120

caaatctcta actatccttc atgctatttc tcacataaag agatttcgtg ttgtcgtcgt     180

attgcaaaca ttgtgatctg tattctcaca gggcctctga tgttattggc cactgtgtta     240

ggattattag cgtataggtt ttcttctact taccagactt ctttacaaga acgctttcgt     300

tataaatatg aacaaaagca agctttagat gaataccgtg atagggaaga aaaagtcatt     360

acgcttcaga agttttgtag aggatttcta gttagaaatc atttgctcaa ccaagaaact     420

ttaacaacgt gtaagcaatg gggggcaaaaa ctattagaag gagaaaaatt cccaagggtc     480

ccagaaggac ggtctcttgt atatatttca aaacagtttc cttctttagt agcaaaacac     540

gttggggctc aagatgccag gtctcgttgg catcatattt tttctatgcg caaagcgctt     600

gcttatttag atattaagcg catacgagca ccacgcgcta gagtttatca aaactttata     660

ttcgaagaaa aacttcctgt ttcacgaatt tctgtagatt caatgtgtct ctataaagaa     720

aatccacaag ctttcgatga ggcgatcaaa gaactcttat ttctatttaa agaagtgcat     780

ttcagggatt ttgttgtaga aacagagtct ccaacagacg atttcccctt agccgtgaaa     840

gtacacaact attgggtatg cccacgatac gataatttac ctttatttat tcaagaagga     900

aaagatggct ctccagaagg gcgtatagga ctggtcgatc tagaaacttt ttcttggtct     960

ccacatccat accccgtaga agaactagct gtgatgtttc ctatgcataa agagcttctt    1020

atgacagagg cgaaaaaact acaaatccct ttctctacaa aggaggtcga gcgctctgta    1080

gagaaagggc ttgctttttt tgaacatatg ctagggcatc aagatttttg ttcccaaaaa    1140

agcgtaacgc cattgcgtaa ttgtgcccct tatattcatc tagaagtatg gagattctca    1200
```

-continued ctgaaaattt ttgatatttt aaaagctgct attcaactaa atggagcact caatgttctg 1260
ttatctccag atattcgaga gcggttgagt gctatttcgg ataagcaatg gttggctatt 1320
agctcccagg ttacgtcatc gttactcgag caagtttcta caaacatcta tcagtctcat 1380
actgaagagg ctaaacgagt aaattcttca gggactttta tcatgtgtcg atctcctatc 1440
ttccggaaaa gcatcttcat taaaaatctc ccacaattct taaacaagaa attgcagttg 1500
cttccagagg agaaagcaat cagcgaggcg cttgcttctc tatgtttacg tgcagtaatg 1560
gaagagctag tagcaacagg aaatatttat tcttatgatt ctatggatga ttttttgaa 1620 gggcagtatt gtcgcattcg ttattag 1647

<210> SEQ ID NO 156
<211> LENGTH: 548
<212> TYPE: PRT
<213> ORGANISM: Chlamydia trachomatis

<400> SEQUENCE: 156

Met Phe Val Ser Phe Asp Lys Ser Arg Cys Arg Ala Asp Val Pro Asp
1 5 10 15

Phe Phe Glu Arg Thr Gly Asn Phe Leu Leu His Cys Val Ala Arg Gly
20 25 30

Ile Asn Val Leu Tyr Arg Val Lys Gln Ile Ser Asn Tyr Pro Ser Cys
35 40 45

Tyr Phe Ser His Lys Glu Ile Ser Cys Cys Arg Arg Ile Ala Asn Ile
50 55 60

Val Ile Cys Ile Leu Thr Gly Pro Leu Met Leu Leu Ala Thr Val Leu
65 70 75 80

Gly Leu Leu Ala Tyr Arg Phe Ser Ser Thr Tyr Gln Thr Ser Leu Gln
85 90 95

Glu Arg Phe Arg Tyr Lys Tyr Glu Gln Lys Gln Ala Leu Asp Glu Tyr
100 105 110

Arg Asp Arg Glu Glu Lys Val Ile Thr Leu Gln Lys Phe Cys Arg Gly
115 120 125

Phe Leu Val Arg Asn His Leu Leu Asn Gln Glu Thr Leu Thr Thr Cys
130 135 140

Lys Gln Trp Gly Gln Lys Leu Leu Glu Gly Glu Lys Phe Pro Arg Val
145 150 155 160

Pro Glu Gly Arg Ser Leu Val Tyr Ile Ser Lys Gln Phe Pro Ser Leu
165 170 175

Val Ala Lys His Val Gly Ala Gln Asp Ala Arg Ser Arg Trp His His
180 185 190

Ile Phe Ser Met Arg Lys Ala Leu Ala Tyr Leu Asp Ile Lys Arg Ile
195 200 205

Arg Ala Pro Arg Ala Arg Val Tyr Gln Asn Phe Ile Phe Glu Glu Lys
210 215 220

Leu Pro Val Ser Arg Ile Ser Val Asp Ser Met Cys Leu Tyr Lys Glu
225 230 235 240

Asn Pro Gln Ala Phe Asp Glu Ala Ile Lys Glu Leu Leu Phe Leu Phe
245 250 255

Lys Glu Val His Phe Arg Asp Phe Val Val Glu Thr Glu Ser Pro Thr
260 265 270

Asp Asp Phe Pro Leu Ala Val Lys Val His Asn Tyr Trp Val Cys Pro
275 280 285

Arg Tyr Asp Asn Leu Pro Leu Phe Ile Gln Glu Gly Lys Asp Gly Ser
290 295 300

```
Pro Glu Gly Arg Ile Gly Leu Val Asp Leu Glu Thr Phe Ser Trp Ser
305                 310                 315                 320

Pro His Pro Tyr Pro Val Glu Glu Leu Ala Val Met Phe Pro Met His
                325                 330                 335

Lys Glu Leu Leu Met Thr Glu Ala Lys Lys Leu Gln Ile Pro Phe Ser
            340                 345                 350

Thr Lys Glu Val Glu Arg Ser Val Glu Lys Gly Leu Ala Phe Phe Glu
        355                 360                 365

His Met Leu Gly His Gln Asp Phe Cys Ser Gln Lys Ser Val Thr Pro
    370                 375                 380

Leu Arg Asn Cys Ala Pro Tyr Ile His Leu Glu Val Trp Arg Phe Ser
385                 390                 395                 400

Leu Lys Ile Phe Asp Ile Leu Lys Ala Ala Ile Gln Leu Asn Gly Ala
                405                 410                 415

Leu Asn Val Leu Leu Ser Pro Asp Ile Arg Glu Arg Leu Ser Ala Ile
            420                 425                 430

Ser Asp Lys Gln Trp Leu Ala Ile Ser Ser Gln Val Thr Ser Ser Leu
        435                 440                 445

Leu Glu Gln Val Ser Thr Asn Ile Tyr Gln Ser His Thr Glu Glu Ala
    450                 455                 460

Lys Arg Val Asn Ser Ser Gly Thr Phe Ile Met Cys Arg Ser Pro Ile
465                 470                 475                 480

Phe Arg Lys Ser Ile Phe Ile Lys Asn Leu Pro Gln Phe Leu Asn Lys
                485                 490                 495

Lys Leu Gln Leu Leu Pro Glu Glu Lys Ala Ile Ser Glu Ala Leu Ala
            500                 505                 510

Ser Leu Cys Leu Arg Ala Val Met Glu Glu Leu Val Ala Thr Gly Asn
        515                 520                 525

Ile Tyr Ser Tyr Asp Ser Met Asp Asp Phe Phe Glu Gly Gln Tyr Cys
    530                 535                 540

Arg Ile Arg Tyr
545
```

<210> SEQ ID NO 157
<211> LENGTH: 1641
<212> TYPE: DNA
<213> ORGANISM: Chlamydia trachomatis

<400> SEQUENCE: 157

```
tttgtgtcgt tcgataaatc ccgttgcaga gcggatgtcc ccgatttttt tgaaaggaca     60

ggaaactttc ttctccattg tgtggcaaga gggatcaatg ttttatatcg tgtgaaacaa    120

atctctaact atccttcatg ctatttctca cataaagaga tttcgtgttg tcgtcgtatt    180

gcaaacattg tgatctgtat tctcacaggg cctctgatgt tattggccac tgtgttagga    240

ttattagcgt ataggttttc ttctacttac cagacttctt tacaagaacg ctttcgttat    300

aaatatgaac aaaagcaagc tttagatgaa taccgtgata gggaagaaaa agtcattacg    360

cttcagaagt tttgtagagg atttctagtt agaaatcatt tgctcaacca agaaacttta    420

acaacgtgta agcaatgggg gcaaaaacta ttagaaggag aaaaattccc aagggtccca    480

gaaggacggt ctcttgtata tatttcaaaa cagtttcctt ctttagtagc aaaacacgtt    540

ggggctcaag atgccaggtc tcgttggcat catatttttt ctatgcgcaa agcgcttgct    600

tatttagata ttaagcgcat acgagcacca cgcgctagag tttatcaaaa ctttatattc    660

gaagaaaaac ttcctgtttc acgaatttct gtagattcaa tgtgtctcta taaagaaaat    720
```

```
ccacaagctt tcgatgaggc gatcaaagaa ctcttatttc tatttaaaga agtgcatttc    780

agggattttg ttgtagaaac agagtctcca acagacgatt tccccttagc cgtgaaagta    840

cacaactatt gggtatgccc acgatacgat aatttacctt tatttattca agaaggaaaa    900

gatggctctc cagaagggcg tataggactg gtcgatctag aaactttttc ttggtctcca    960

catccatacc ccgtagaaga actagctgtg atgtttccta tgcataaaga gcttcttatg   1020

acagaggcga aaaaactaca aatccctttc tctacaaagg aggtcgagcg ctctgtagag   1080

aaagggcttg ctttttttga acatatgcta gggcatcaag atttttgttc ccaaaaaagc   1140

gtaacgccat tgcgtaattg tgccccttat attcatctag aagtatggag attctcactg   1200

aaaatttttg atattttaaa agctgctatt caactaaatg gagcactcaa tgttctgtta   1260

tctccagata ttcgagagcg gttgagtgct atttcggata agcaatggtt ggctattagc   1320

tcccaggtta cgtcatcgtt actcgagcaa gtttctacaa acatctatca gtctcatact   1380

gaagaggcta aacgagtaaa ttcttcaggg acttttatca tgtgtcgatc tcctatcttc   1440

cggaaaagca tcttcattaa aaatctccca caattcttaa acaagaaatt gcagttgctt   1500

ccagaggaga aagcaatcag cgaggcgctt gcttctctat gtttacgtgc agtaatggaa   1560

gagctagtag caacaggaaa tatttattct tatgattcta tggatgattt ttttgaaggg   1620

cagtattgtc gcattcgtta t                                             1641
```

<210> SEQ ID NO 158
<211> LENGTH: 547
<212> TYPE: PRT
<213> ORGANISM: Chlamydia trachomatis

<400> SEQUENCE: 158

```
Phe Val Ser Phe Asp Lys Ser Arg Cys Arg Ala Asp Val Pro Asp Phe
1               5                   10                  15

Phe Glu Arg Thr Gly Asn Phe Leu Leu His Cys Val Ala Arg Gly Ile
            20                  25                  30

Asn Val Leu Tyr Arg Val Lys Gln Ile Ser Asn Tyr Pro Ser Cys Tyr
        35                  40                  45

Phe Ser His Lys Glu Ile Ser Cys Cys Arg Arg Ile Ala Asn Ile Val
    50                  55                  60

Ile Cys Ile Leu Thr Gly Pro Leu Met Leu Leu Ala Thr Val Leu Gly
65                  70                  75                  80

Leu Leu Ala Tyr Arg Phe Ser Ser Thr Tyr Gln Thr Ser Leu Gln Glu
                85                  90                  95

Arg Phe Arg Tyr Lys Tyr Glu Gln Lys Gln Ala Leu Asp Glu Tyr Arg
            100                 105                 110

Asp Arg Glu Glu Lys Val Ile Thr Leu Gln Lys Phe Cys Arg Gly Phe
        115                 120                 125

Leu Val Arg Asn His Leu Leu Asn Gln Glu Thr Leu Thr Thr Cys Lys
    130                 135                 140

Gln Trp Gly Gln Lys Leu Leu Glu Gly Glu Lys Phe Pro Arg Val Pro
145                 150                 155                 160

Glu Gly Arg Ser Leu Val Tyr Ile Ser Lys Gln Phe Pro Ser Leu Val
                165                 170                 175

Ala Lys His Val Gly Ala Gln Asp Ala Arg Ser Arg Trp His His Ile
            180                 185                 190

Phe Ser Met Arg Lys Ala Leu Ala Tyr Leu Asp Ile Lys Arg Ile Arg
        195                 200                 205
```

-continued

```
Ala Pro Arg Ala Arg Val Tyr Gln Asn Phe Ile Phe Glu Glu Lys Leu
    210                 215                 220

Pro Val Ser Arg Ile Ser Val Asp Ser Met Cys Leu Tyr Lys Glu Asn
225                 230                 235                 240

Pro Gln Ala Phe Asp Glu Ala Ile Lys Glu Leu Leu Phe Leu Phe Lys
                245                 250                 255

Glu Val His Phe Arg Asp Phe Val Val Glu Thr Glu Ser Pro Thr Asp
            260                 265                 270

Asp Phe Pro Leu Ala Val Lys Val His Asn Tyr Trp Val Cys Pro Arg
        275                 280                 285

Tyr Asp Asn Leu Pro Leu Phe Ile Gln Glu Gly Lys Asp Gly Ser Pro
    290                 295                 300

Glu Gly Arg Ile Gly Leu Val Asp Leu Glu Thr Phe Ser Trp Ser Pro
305                 310                 315                 320

His Pro Tyr Pro Val Glu Glu Leu Ala Val Met Phe Pro Met His Lys
                325                 330                 335

Glu Leu Leu Met Thr Glu Ala Lys Lys Leu Gln Ile Pro Phe Ser Thr
            340                 345                 350

Lys Glu Val Glu Arg Ser Val Glu Lys Gly Leu Ala Phe Phe Glu His
        355                 360                 365

Met Leu Gly His Gln Asp Phe Cys Ser Gln Lys Ser Val Thr Pro Leu
    370                 375                 380

Arg Asn Cys Ala Pro Tyr Ile His Leu Glu Val Trp Arg Phe Ser Leu
385                 390                 395                 400

Lys Ile Phe Asp Ile Leu Lys Ala Ala Ile Gln Leu Asn Gly Ala Leu
                405                 410                 415

Asn Val Leu Leu Ser Pro Asp Ile Arg Glu Arg Leu Ser Ala Ile Ser
            420                 425                 430

Asp Lys Gln Trp Leu Ala Ile Ser Ser Gln Val Thr Ser Ser Leu Leu
        435                 440                 445

Glu Gln Val Ser Thr Asn Ile Tyr Gln Ser His Thr Glu Glu Ala Lys
    450                 455                 460

Arg Val Asn Ser Ser Gly Thr Phe Ile Met Cys Arg Ser Pro Ile Phe
465                 470                 475                 480

Arg Lys Ser Ile Phe Ile Lys Asn Leu Pro Gln Phe Leu Asn Lys Lys
                485                 490                 495

Leu Gln Leu Leu Pro Glu Glu Lys Ala Ile Ser Glu Ala Leu Ala Ser
            500                 505                 510

Leu Cys Leu Arg Ala Val Met Glu Glu Leu Val Ala Thr Gly Asn Ile
        515                 520                 525

Tyr Ser Tyr Asp Ser Met Asp Asp Phe Phe Glu Gly Gln Tyr Cys Arg
    530                 535                 540

Ile Arg Tyr
545
```

<210> SEQ ID NO 159
<211> LENGTH: 1644
<212> TYPE: DNA
<213> ORGANISM: Chlamydia trachomatis

<400> SEQUENCE: 159

```
atgcgaacag actctctttt caatcctccc gactctacta gaggagtttt tcagttttta      60

gagactcagt gtgatcgagc cgtggctcgg tccagacaaa gccaatttat agggttagtc     120

tctgctgtag cagctgcagc attattattg ttgcttgtgg tcgctctatc tgttccagga     180
```

-continued

```
ttcccagttg cagcttcaat tgttgtaggg gttctctttg ctttatcgat cgtagcatta    240

acagcttcgt ttttggtata tatagctaat gctaagcttg ttgcaataag aattaaattc    300

ttgagtagtg gtctgcaaga tcacttttcg gagtcatcta ttttagggac tctccgtaaa    360

ggacgtggtg ctagtattcc gcttatttcc ggacaagcag atgatcctct ccctaatcgg    420

attgggatca aaaaaagcac tgaaatgcgt gttcttcaaa aaggaattgg gacagattat    480

aaaaaatata agcagcatct tgatagagtg aataatgatt tcacttttgt ctgtgagggg    540

attagcgctt taattcctac agaaaaagat gctccattcc ctatagaacc ttctcattta    600

gcaggtgttt ttttagtatc attttcacca gacaagaatc cgattctaaa gattacgcgt    660

catgctgaga agatgttaca gcctcctcaa ggcggattcc ctaacgggct ggtttggttg    720

tgtggagctc tttctgatcc taagaaattt gcagctccct ttctatcttt gattgagaag    780

actcaccaag ggattttggt gagtaaagac ttgaaagaca ataaggaaag aaagctagct    840

ttagaggctt cccttctttc attgaatatt ttcttttccg gttggtgttt ggggaatccg    900

gagtacaatc agtatatcac aactgctgta gctgagaaat atagggatgt ctctgtaaga    960

aattgtattt atgatttcct ggatacaggg aatgtgattt cagctcttgc tttagcaagt   1020

agttattcac aagattccgc ttgggctgca gggttgcaga aagttttacg tgaagaagat   1080

aaaaagacta agaaaaagtc acgtgaagaa gtctcttgtt tgtatcgtga tatagatcca   1140

ggctgttgtt taagagccct tcctaagcga tttgaatcca agtcttcagg tagtcaaggt   1200

agtcctaaag agcagttaag ctctttgttg aaagctttag accagaaaat tccttcaggg   1260

attttaggat tgattgcaaa agcttcttct gcagatctca aggctgattt tgcaggtatg   1320

cttgaagtta ttaagcaatt acaagcttta ttcgattctt acccaccttt atgcgaagac   1380

aatattctct tgtggttaag cgcttcttta gaacaagtag gcttgcagaa gaaattgaga   1440

acctttttac cttcatcaga aaaaaaactc ttagaaagag ttctctctac atttttatta   1500

ggtttgtata ctcgaggagt cttttctgta gggcaagtga atcagctagc tactatttgt   1560

aatactcagg actctacaga attctgccag agagtaagtg acctttcgtt aattaaacga   1620

gctctacctg cattatttgg ttaa                                           1644
```

```
<210> SEQ ID NO 160
<211> LENGTH: 547
<212> TYPE: PRT
<213> ORGANISM: Chlamydia trachomatis

<400> SEQUENCE: 160

Met Arg Thr Asp Ser Leu Phe Asn Pro Pro Asp Ser Thr Arg Gly Val
1               5                   10                  15

Phe Gln Phe Leu Glu Thr Gln Cys Asp Arg Ala Val Ala Arg Ser Arg
            20                  25                  30

Gln Ser Gln Phe Ile Gly Leu Val Ser Ala Val Ala Ala Ala Ala Leu
        35                  40                  45

Leu Leu Leu Leu Val Val Ala Leu Ser Val Pro Gly Phe Pro Val Ala
    50                  55                  60

Ala Ser Ile Val Val Gly Val Leu Phe Ala Leu Ser Ile Val Ala Leu
65                  70                  75                  80

Thr Ala Ser Phe Leu Val Tyr Ile Ala Asn Ala Lys Leu Val Ala Ile
                85                  90                  95

Arg Ile Lys Phe Leu Ser Ser Gly Leu Gln Asp His Phe Ser Glu Ser
            100                 105                 110

Ser Ile Leu Gly Thr Leu Arg Lys Gly Arg Gly Ala Ser Ile Pro Leu
```

-continued

```
        115                 120                 125

Ile Ser Gly Gln Ala Asp Asp Pro Leu Pro Asn Arg Ile Gly Ile Lys
    130                 135                 140

Lys Ser Thr Glu Met Arg Val Leu Gln Lys Gly Ile Gly Thr Asp Tyr
145                 150                 155                 160

Lys Lys Tyr Lys Gln His Leu Asp Arg Val Asn Asn Asp Phe Thr Phe
                165                 170                 175

Val Cys Glu Gly Ile Ser Ala Leu Ile Pro Thr Glu Lys Asp Ala Pro
            180                 185                 190

Phe Pro Ile Glu Pro Ser His Leu Ala Gly Val Phe Leu Val Ser Phe
        195                 200                 205

Ser Pro Asp Lys Asn Pro Ile Leu Lys Ile Thr Arg His Ala Glu Lys
    210                 215                 220

Met Leu Gln Pro Pro Gln Gly Gly Phe Pro Asn Gly Leu Val Trp Leu
225                 230                 235                 240

Cys Gly Ala Leu Ser Asp Pro Lys Lys Phe Ala Ala Pro Phe Leu Ser
                245                 250                 255

Leu Ile Glu Lys Thr His Gln Gly Ile Leu Val Ser Lys Asp Leu Lys
            260                 265                 270

Asp Asn Lys Glu Arg Lys Leu Ala Leu Glu Ala Ser Leu Leu Ser Leu
        275                 280                 285

Asn Ile Phe Phe Ser Gly Trp Cys Leu Gly Asn Pro Glu Tyr Asn Gln
    290                 295                 300

Tyr Ile Thr Thr Ala Val Ala Glu Lys Tyr Arg Asp Val Ser Val Arg
305                 310                 315                 320

Asn Cys Ile Tyr Asp Phe Leu Asp Thr Gly Asn Val Ile Ser Ala Leu
                325                 330                 335

Ala Leu Ala Ser Ser Tyr Ser Gln Asp Ser Ala Trp Ala Ala Gly Leu
            340                 345                 350

Gln Lys Val Leu Arg Glu Glu Asp Lys Lys Thr Lys Lys Lys Ser Arg
        355                 360                 365

Glu Glu Val Ser Cys Leu Tyr Arg Asp Ile Asp Pro Gly Cys Cys Leu
    370                 375                 380

Arg Ala Leu Pro Lys Arg Phe Glu Ser Lys Ser Ser Gly Ser Gln Gly
385                 390                 395                 400

Ser Pro Lys Glu Gln Leu Ser Ser Leu Leu Lys Ala Leu Asp Gln Lys
                405                 410                 415

Ile Pro Ser Gly Ile Leu Gly Leu Ile Ala Lys Ala Ser Ser Ala Asp
            420                 425                 430

Leu Lys Ala Asp Phe Ala Gly Met Leu Glu Val Ile Lys Gln Leu Gln
        435                 440                 445

Ala Leu Phe Asp Ser Tyr Pro Pro Leu Cys Glu Asp Asn Ile Leu Leu
    450                 455                 460

Trp Leu Ser Ala Ser Leu Glu Gln Val Gly Leu Gln Lys Lys Leu Arg
465                 470                 475                 480

Thr Phe Leu Pro Ser Ser Glu Lys Lys Leu Leu Glu Arg Val Leu Ser
                485                 490                 495

Thr Phe Leu Leu Gly Leu Tyr Thr Arg Gly Val Phe Ser Val Gly Gln
            500                 505                 510

Val Asn Gln Leu Ala Thr Ile Cys Asn Thr Gln Asp Ser Thr Glu Phe
        515                 520                 525

Cys Gln Arg Val Ser Asp Leu Ser Leu Ile Lys Arg Ala Leu Pro Ala
    530                 535                 540
```

Leu Phe Gly
545

<210> SEQ ID NO 161
<211> LENGTH: 1638
<212> TYPE: DNA
<213> ORGANISM: Chlamydia trachomatis

<400> SEQUENCE: 161
cgaacagact ctcttttcaa tcctcccgac tctactagag gagtttttca gtttttagag 60
actcagtgtg atcgagccgt ggctcggtcc agacaaagcc aatttatagg gttagtctct 120
gctgtagcag ctgcagcatt attattgttg cttgtggtcg ctctatctgt tccaggattc 180
ccagttgcag cttcaattgt tgtaggggtt ctctttgctt tatcgatcgt agcattaaca 240
gcttcgtttt tggtatatat agctaatgct aagcttgttg caataagaat taaattcttg 300
agtagtggtc tgcaagatca cttttcggag tcatctattt tagggactct ccgtaaagga 360
cgtggtgcta gtattccgct tatttccgga caagcagatg atcctctccc taatcggatt 420
gggatcaaaa aaagcactga aatgcgtgtt cttcaaaaag gaattgggac agattataaa 480
aaatataagc agcatcttga tagagtgaat aatgatttca cttttgtctg tgaggggatt 540
agcgctttaa ttcctacaga aaaagatgct ccattcccta tagaaccttc tcatttagca 600
ggtgtttttt tagtatcatt ttcaccagac aagaatccga ttctaaagat tacgcgtcat 660
gctgagaaga tgttacagcc tcctcaaggc ggattcccta acgggctggt ttggttgtgt 720
ggagctcttt ctgatcctaa gaaatttgca gctccctttc tatctttgat tgagaagact 780
caccaaggga ttttggtgag taaagacttg aaagacaata aggaaagaaa gctagcttta 840
gaggcttccc ttctttcatt gaatattttc ttttccggtt ggtgtttggg gaatccggag 900
tacaatcagt atatcacaac tgctgtagct gagaaatata gggatgtctc tgtaagaaat 960
tgtatttatg atttcctgga tacagggaat gtgatttcag ctcttgcttt agcaagtagt 1020
tattcacaag attccgcttg ggctgcaggg ttgcagaaag ttttacgtga agaagataaa 1080
aagactaaga aaaagtcacg tgaagaagtc tcttgtttgt atcgtgatat agatccaggc 1140
tgttgtttaa gagcccttcc taagcgattt gaatccaagt cttcaggtag tcaaggtagt 1200
cctaaagagc agttaagctc tttgttgaaa gctttagacc agaaaattcc ttcagggatt 1260
ttaggattga ttgcaaaagc ttcttctgca gatctcaagg ctgattttgc aggtatgctt 1320
gaagttatta agcaattaca agctttattc gattcttacc cacctttatg cgaagacaat 1380
attctcttgt ggttaagcgc ttctttagaa caagtaggct tgcagaagaa attgagaacc 1440
tttttacctt catcagaaaa aaaactctta gaaagagttc tctctacatt tttattaggt 1500
ttgtatactc gaggagtctt ttctgtaggg caagtgaatc agctagctac tatttgtaat 1560
actcaggact ctacagaatt ctgccagaga gtaagtgacc tttcgttaat taaacgagct 1620
ctacctgcat tatttggt 1638

<210> SEQ ID NO 162
<211> LENGTH: 546
<212> TYPE: PRT
<213> ORGANISM: Chlamydia trachomatis

<400> SEQUENCE: 162

Arg Thr Asp Ser Leu Phe Asn Pro Pro Asp Ser Thr Arg Gly Val Phe
1 5 10 15

Gln Phe Leu Glu Thr Gln Cys Asp Arg Ala Val Ala Arg Ser Arg Gln
20 25 30

```
Ser Gln Phe Ile Gly Leu Val Ser Ala Val Ala Ala Ala Ala Leu Leu
        35                  40                  45

Leu Leu Leu Val Val Ala Leu Ser Val Pro Gly Phe Pro Val Ala Ala
    50                  55                  60

Ser Ile Val Val Gly Val Leu Phe Ala Leu Ser Ile Val Ala Leu Thr
65                  70                  75                  80

Ala Ser Phe Leu Val Tyr Ile Ala Asn Ala Lys Leu Val Ala Ile Arg
                85                  90                  95

Ile Lys Phe Leu Ser Ser Gly Leu Gln Asp His Phe Ser Glu Ser Ser
            100                 105                 110

Ile Leu Gly Thr Leu Arg Lys Gly Arg Gly Ala Ser Ile Pro Leu Ile
        115                 120                 125

Ser Gly Gln Ala Asp Asp Pro Leu Pro Asn Arg Ile Gly Ile Lys Lys
    130                 135                 140

Ser Thr Glu Met Arg Val Leu Gln Lys Gly Ile Gly Thr Asp Tyr Lys
145                 150                 155                 160

Lys Tyr Lys Gln His Leu Asp Arg Val Asn Asn Asp Phe Thr Phe Val
                165                 170                 175

Cys Glu Gly Ile Ser Ala Leu Ile Pro Thr Glu Lys Asp Ala Pro Phe
            180                 185                 190

Pro Ile Glu Pro Ser His Leu Ala Gly Val Phe Leu Val Ser Phe Ser
        195                 200                 205

Pro Asp Lys Asn Pro Ile Leu Lys Ile Thr Arg His Ala Glu Lys Met
    210                 215                 220

Leu Gln Pro Pro Gln Gly Gly Phe Pro Asn Gly Leu Val Trp Leu Cys
225                 230                 235                 240

Gly Ala Leu Ser Asp Pro Lys Lys Phe Ala Ala Pro Phe Leu Ser Leu
                245                 250                 255

Ile Glu Lys Thr His Gln Gly Ile Leu Val Ser Lys Asp Leu Lys Asp
            260                 265                 270

Asn Lys Glu Arg Lys Leu Ala Leu Glu Ala Ser Leu Leu Ser Leu Asn
        275                 280                 285

Ile Phe Phe Ser Gly Trp Cys Leu Gly Asn Pro Glu Tyr Asn Gln Tyr
    290                 295                 300

Ile Thr Thr Ala Val Ala Glu Lys Tyr Arg Asp Val Ser Val Arg Asn
305                 310                 315                 320

Cys Ile Tyr Asp Phe Leu Asp Thr Gly Asn Val Ile Ser Ala Leu Ala
                325                 330                 335

Leu Ala Ser Ser Tyr Ser Gln Asp Ser Ala Trp Ala Ala Gly Leu Gln
            340                 345                 350

Lys Val Leu Arg Glu Glu Asp Lys Lys Thr Lys Lys Lys Ser Arg Glu
        355                 360                 365

Glu Val Ser Cys Leu Tyr Arg Asp Ile Asp Pro Gly Cys Cys Leu Arg
    370                 375                 380

Ala Leu Pro Lys Arg Phe Glu Ser Lys Ser Ser Gly Ser Gln Gly Ser
385                 390                 395                 400

Pro Lys Glu Gln Leu Ser Ser Leu Leu Lys Ala Leu Asp Gln Lys Ile
                405                 410                 415

Pro Ser Gly Ile Leu Gly Leu Ile Ala Lys Ala Ser Ser Ala Asp Leu
            420                 425                 430

Lys Ala Asp Phe Ala Gly Met Leu Glu Val Ile Lys Gln Leu Gln Ala
        435                 440                 445

Leu Phe Asp Ser Tyr Pro Pro Leu Cys Glu Asp Asn Ile Leu Leu Trp
```

-continued

```
    450                 455                 460

Leu Ser Ala Ser Leu Glu Gln Val Gly Leu Gln Lys Lys Leu Arg Thr
465                 470                 475                 480

Phe Leu Pro Ser Ser Glu Lys Lys Leu Leu Glu Arg Val Leu Ser Thr
                485                 490                 495

Phe Leu Leu Gly Leu Tyr Thr Arg Gly Val Phe Ser Val Gly Gln Val
            500                 505                 510

Asn Gln Leu Ala Thr Ile Cys Asn Thr Gln Asp Ser Thr Glu Phe Cys
        515                 520                 525

Gln Arg Val Ser Asp Leu Ser Leu Ile Lys Arg Ala Leu Pro Ala Leu
    530                 535                 540

Phe Gly
545


<210> SEQ ID NO 163
<211> LENGTH: 1155
<212> TYPE: DNA
<213> ORGANISM: Chlamydia trachomatis

<400> SEQUENCE: 163

atggacggga caaaaattca cgaaacacgc tccttctctt ggttaaacaa ccaacaagcc      60

atccctcctt ccgaaatggt gaaggaggct tttcaacgtt acgcagacgt attttcgtac     120

agcgcaaata cctccattct gactttacaa gcagaagctg aagcttctgc ccgcaaactc     180

acagggtgtc aggagaaggc ttttaccttt cattttattc ttcattaccc gaatgtcacg     240

gccattatcg tggccgctct tctggaaaac caaaatgcct tccaggggcg taatcacctt     300

cttgttcctt cttgcgagca acaatttatc attaatgctc tctgccgtcg gcaaaactta     360

gggacaacct atgattgggt aaccagcaaa aacggccgcg taaaagaatc cgatctagca     420

gaagctcttt ccccgcggac cttgctgttt tccatatctg ctgcgaatgg tatgacagga     480

tttctggaag cgatccctga gcttgctgcg ttatgtaaag aacgcggggt aattttccac     540

atagacctga gtgatatctt aggaagatgc gcgctacccg cagaactcta tcaagcagat     600

atccttactt tttcttcaca gtctcttggt gggattggtc cctcaggagc gatgtttatt     660

tctcccgctt taacaaaata tttttcctta tggcttccta gtaatccaca agtccctacc     720

tgcctgagtt ctcttgcagc tttttctctt gcctgtcagg aacgtacaac cgctttctcc     780

tctcttgtgc tttctgctat ttcttctcga gcagctctta aacaggctct ttccgctatt     840

cctcaagtcg aattcctttt ggaagacagt gcccctcgtc tccctaatgt cgctgtcttt     900

gctattcctg gtatccctgc agagtcctta ggatttttcc tttcccagaa aaatattttt     960

gtagggttag gctatgaacg cttccagcct ctatcgcaga ttttacaaag ttcgggcatc    1020

tctcccttct tatgccacag cgctttacac gtatctttta ctgaacgtac tcctactaca    1080

cacttctctg cattagcaac cgccttacaa gaagggatct ctcacctaca accactggtt    1140

actcaatcct tatga                                                     1155


<210> SEQ ID NO 164
<211> LENGTH: 384
<212> TYPE: PRT
<213> ORGANISM: Chlamydia trachomatis

<400> SEQUENCE: 164

Met Asp Gly Thr Lys Ile His Glu Thr Arg Ser Phe Ser Trp Leu Asn
1               5                   10                  15

Asn Gln Gln Ala Ile Pro Pro Ser Glu Met Val Lys Glu Ala Phe Gln
```

-continued

```
                20                  25                  30

Arg Tyr Ala Asp Val Phe Ser Tyr Ser Ala Asn Thr Ser Ile Leu Thr
        35                  40                  45

Leu Gln Ala Glu Ala Glu Ala Ser Ala Arg Lys Leu Thr Gly Cys Gln
    50                  55                  60

Glu Lys Ala Phe Thr Phe His Phe Ile Leu His Tyr Pro Asn Val Thr
65                  70                  75                  80

Ala Ile Ile Val Ala Ala Leu Leu Glu Asn Gln Asn Ala Phe Gln Gly
                85                  90                  95

Arg Asn His Leu Leu Val Pro Ser Cys Glu Gln Gln Phe Ile Ile Asn
            100                 105                 110

Ala Leu Cys Arg Arg Gln Asn Leu Gly Thr Thr Tyr Asp Trp Val Thr
        115                 120                 125

Ser Lys Asn Gly Arg Val Lys Glu Ser Asp Leu Ala Glu Ala Leu Ser
    130                 135                 140

Pro Arg Thr Leu Leu Phe Ser Ile Ser Ala Ala Asn Gly Met Thr Gly
145                 150                 155                 160

Phe Leu Glu Ala Ile Pro Glu Leu Ala Ala Leu Cys Lys Glu Arg Gly
                165                 170                 175

Val Ile Phe His Ile Asp Leu Ser Asp Ile Leu Gly Arg Cys Ala Leu
            180                 185                 190

Pro Ala Glu Leu Tyr Gln Ala Asp Ile Leu Thr Phe Ser Ser Gln Ser
        195                 200                 205

Leu Gly Gly Ile Gly Pro Ser Gly Ala Met Phe Ile Ser Pro Ala Leu
    210                 215                 220

Thr Lys Tyr Phe Ser Leu Trp Leu Pro Ser Asn Pro Gln Val Pro Thr
225                 230                 235                 240

Cys Leu Ser Ser Leu Ala Ala Phe Ser Leu Ala Cys Gln Glu Arg Thr
                245                 250                 255

Thr Ala Phe Ser Ser Leu Val Leu Ser Ala Ile Ser Ser Arg Ala Ala
            260                 265                 270

Leu Lys Gln Ala Leu Ser Ala Ile Pro Gln Val Glu Phe Leu Leu Glu
        275                 280                 285

Asp Ser Ala Pro Arg Leu Pro Asn Val Ala Val Phe Ala Ile Pro Gly
    290                 295                 300

Ile Pro Ala Glu Ser Leu Gly Phe Phe Leu Ser Gln Lys Asn Ile Phe
305                 310                 315                 320

Val Gly Leu Gly Tyr Glu Arg Phe Gln Pro Leu Ser Gln Ile Leu Gln
                325                 330                 335

Ser Ser Gly Ile Ser Pro Phe Leu Cys His Ser Ala Leu His Val Ser
            340                 345                 350

Phe Thr Glu Arg Thr Pro Thr Thr His Phe Ser Ala Leu Ala Thr Ala
        355                 360                 365

Leu Gln Glu Gly Ile Ser His Leu Gln Pro Leu Val Thr Gln Ser Leu
    370                 375                 380
```

<210> SEQ ID NO 165
<211> LENGTH: 1149
<212> TYPE: DNA
<213> ORGANISM: Chlamydia trachomatis

<400> SEQUENCE: 165

```
gacgggacaa aaattcacga aacacgctcc ttctcttggt taaacaacca acaagccatc      60

cctccttccg aaatggtgaa ggaggctttt caacgttacg cagacgtatt ttcgtacagc     120
```

-continued

```
gcaaatacct ccattctgac tttacaagca gaagctgaag cttctgcccg caaactcaca    180

gggtgtcagg agaaggcttt tacctttcat tttattcttc attacccgaa tgtcacggcc    240

attatcgtgg ccgctcttct ggaaaaccaa aatgccttcc aggggcgtaa tcaccttctt    300

gttccttctt gcgagcaaca atttatcatt aatgctctct gccgtcggca aaacttaggg    360

acaacctatg attgggtaac cagcaaaaac ggccgcgtaa aagaatccga tctagcagaa    420

gctctttccc cgcggacctt gctgttttcc atatctgctg cgaatggtat gacaggattt    480

ctggaagcga tccctgagct tgctgcgtta tgtaaagaac gcggggtaat tttccacata    540

gacctgagtg atatcttagg aagatgcgcg ctacccgcag aactctatca agcagatatc    600

cttacttttt cttcacagtc tcttggtggg attggtccct caggagcgat gtttatttct    660

cccgctttaa caaaatattt ttccttatgg cttcctagta atccacaagt ccctacctgc    720

ctgagttctc ttgcagcttt ttctcttgcc tgtcaggaac gtacaaccgc tttctcctct    780

cttgtgcttt ctgctatttc ttctcgagca gctcttaaac aggctctttc cgctattcct    840

caagtcgaat tccttttgga agacagtgcc cctcgtctcc ctaatgtcgc tgtctttgct    900

attcctggta tccctgcaga gtccttagga tttttccttt cccagaaaaa tatttttgta    960

gggttaggct atgaacgctt ccagcctcta tcgcagattt tacaaagttc gggcatctct   1020

cccttcttat gccacagcgc tttacacgta tcttttactg aacgtactcc tactacacac   1080

ttctctgcat tagcaaccgc cttacaagaa gggatctctc acctacaacc actggttact   1140

caatcctta                                                           1149
```

<210> SEQ ID NO 166
<211> LENGTH: 383
<212> TYPE: PRT
<213> ORGANISM: Chlamydia trachomatis

<400> SEQUENCE: 166

```
Asp Gly Thr Lys Ile His Glu Thr Arg Ser Phe Ser Trp Leu Asn Asn
1               5                   10                  15

Gln Gln Ala Ile Pro Pro Ser Glu Met Val Lys Glu Ala Phe Gln Arg
            20                  25                  30

Tyr Ala Asp Val Phe Ser Tyr Ser Ala Asn Thr Ser Ile Leu Thr Leu
        35                  40                  45

Gln Ala Glu Ala Glu Ala Ser Ala Arg Lys Leu Thr Gly Cys Gln Glu
    50                  55                  60

Lys Ala Phe Thr Phe His Phe Ile Leu His Tyr Pro Asn Val Thr Ala
65                  70                  75                  80

Ile Ile Val Ala Ala Leu Leu Glu Asn Gln Asn Ala Phe Gln Gly Arg
                85                  90                  95

Asn His Leu Leu Val Pro Ser Cys Glu Gln Gln Phe Ile Ile Asn Ala
            100                 105                 110

Leu Cys Arg Arg Gln Asn Leu Gly Thr Thr Tyr Asp Trp Val Thr Ser
        115                 120                 125

Lys Asn Gly Arg Val Lys Glu Ser Asp Leu Ala Glu Ala Leu Ser Pro
    130                 135                 140

Arg Thr Leu Leu Phe Ser Ile Ser Ala Ala Asn Gly Met Thr Gly Phe
145                 150                 155                 160

Leu Glu Ala Ile Pro Glu Leu Ala Ala Leu Cys Lys Glu Arg Gly Val
                165                 170                 175

Ile Phe His Ile Asp Leu Ser Asp Ile Leu Gly Arg Cys Ala Leu Pro
            180                 185                 190
```

```
Ala Glu Leu Tyr Gln Ala Asp Ile Leu Thr Phe Ser Ser Gln Ser Leu
        195                 200                 205

Gly Gly Ile Gly Pro Ser Gly Ala Met Phe Ile Ser Pro Ala Leu Thr
    210                 215                 220

Lys Tyr Phe Ser Leu Trp Leu Pro Ser Asn Pro Gln Val Pro Thr Cys
225                 230                 235                 240

Leu Ser Ser Leu Ala Ala Phe Ser Leu Ala Cys Gln Glu Arg Thr Thr
                245                 250                 255

Ala Phe Ser Ser Leu Val Leu Ser Ala Ile Ser Ser Arg Ala Ala Leu
            260                 265                 270

Lys Gln Ala Leu Ser Ala Ile Pro Gln Val Glu Phe Leu Leu Glu Asp
        275                 280                 285

Ser Ala Pro Arg Leu Pro Asn Val Ala Val Phe Ala Ile Pro Gly Ile
    290                 295                 300

Pro Ala Glu Ser Leu Gly Phe Phe Leu Ser Gln Lys Asn Ile Phe Val
305                 310                 315                 320

Gly Leu Gly Tyr Glu Arg Phe Gln Pro Leu Ser Gln Ile Leu Gln Ser
                325                 330                 335

Ser Gly Ile Ser Pro Phe Leu Cys His Ser Ala Leu His Val Ser Phe
            340                 345                 350

Thr Glu Arg Thr Pro Thr Thr His Phe Ser Ala Leu Ala Thr Ala Leu
        355                 360                 365

Gln Glu Gly Ile Ser His Leu Gln Pro Leu Val Thr Gln Ser Leu
    370                 375                 380
```

<210> SEQ ID NO 167
<211> LENGTH: 852
<212> TYPE: DNA
<213> ORGANISM: Chlamydia trachomatis

<400> SEQUENCE: 167

```
atgccgcacc aagtcttatt gtctcctgtt tgcgatcttt tatcgaatgc tgaaggtata     60

gagacgcaag tactgtttgg agaaaggata tgcaaccata accatcgaca ctatgcctat    120

tctcaactag tcttttcttc tatatggaag ccataccctg gcgactctct acagaatatt    180

cctctattct cttcccaact gcagcctcct aatgctgttg tctgctctca agaagctttt    240

ttagatcctt ggcatatccc cttacctttt gccgctccgc tccacataga taaccaaaat    300

caagtgtccc tatctcctgc tagcatagca ttattaaatt ccaattccag aagtaactat    360

gcaaaagctt tctgctctac caaagagatt cgttttttaa attcttcatt ctctccaaga    420

gatttagttt ctttcgcaga acaattgata gatactccgt acgtttgggg tggccggtgc    480

attcataaac agcttcctcg taatggtgta gattgttcgg ggtatattca actactttac    540

caagtcacag gaagaaatat ccctcgcaat gctagagatc aatacagaga ctgttctcca    600

gtaaaagatt tctcgtctct acctatagga ggacttatct tcctcaagaa agcaagcacg    660

ggacaaatca accatgttat gatgaaaatc tcggagcatg aattcattca tgctgcggaa    720

aaaataggga aagtagaaaa agtaatccta ggaaataggg ctttctttaa agggaatcta    780

ttctgctcat taggtgaacc gcctatagaa gctgtttttg gcgttcctaa aaatagaaaa    840

gccttctttt ga                                                        852
```

<210> SEQ ID NO 168
<211> LENGTH: 283
<212> TYPE: PRT
<213> ORGANISM: Chlamydia trachomatis

<400> SEQUENCE: 168

```
Met Pro His Gln Val Leu Leu Ser Pro Val Cys Asp Leu Leu Ser Asn
1               5                   10                  15

Ala Glu Gly Ile Glu Thr Gln Val Leu Phe Gly Glu Arg Ile Cys Asn
            20                  25                  30

His Asn His Arg His Tyr Ala Tyr Ser Gln Leu Val Phe Ser Ser Ile
        35                  40                  45

Trp Lys Pro Tyr Pro Gly Asp Ser Leu Gln Asn Ile Pro Leu Phe Ser
    50                  55                  60

Ser Gln Leu Gln Pro Pro Asn Ala Val Val Cys Ser Gln Glu Ala Phe
65                  70                  75                  80

Leu Asp Pro Trp His Ile Pro Leu Pro Phe Ala Ala Pro Leu His Ile
                85                  90                  95

Asp Asn Gln Asn Gln Val Ser Leu Ser Pro Ala Ser Ile Ala Leu Leu
            100                 105                 110

Asn Ser Asn Ser Arg Ser Asn Tyr Ala Lys Ala Phe Cys Ser Thr Lys
        115                 120                 125

Glu Ile Arg Phe Leu Asn Ser Ser Phe Ser Pro Arg Asp Leu Val Ser
    130                 135                 140

Phe Ala Glu Gln Leu Ile Asp Thr Pro Tyr Val Trp Gly Gly Arg Cys
145                 150                 155                 160

Ile His Lys Gln Leu Pro Arg Asn Gly Val Asp Cys Ser Gly Tyr Ile
                165                 170                 175

Gln Leu Leu Tyr Gln Val Thr Gly Arg Asn Ile Pro Arg Asn Ala Arg
            180                 185                 190

Asp Gln Tyr Arg Asp Cys Ser Pro Val Lys Asp Phe Ser Ser Leu Pro
        195                 200                 205

Ile Gly Gly Leu Ile Phe Leu Lys Lys Ala Ser Thr Gly Gln Ile Asn
    210                 215                 220

His Val Met Met Lys Ile Ser Glu His Glu Phe Ile His Ala Ala Glu
225                 230                 235                 240

Lys Ile Gly Lys Val Glu Lys Val Ile Leu Gly Asn Arg Ala Phe Phe
                245                 250                 255

Lys Gly Asn Leu Phe Cys Ser Leu Gly Glu Pro Pro Ile Glu Ala Val
            260                 265                 270

Phe Gly Val Pro Lys Asn Arg Lys Ala Phe Phe
        275                 280
```

<210> SEQ ID NO 169
<211> LENGTH: 846
<212> TYPE: DNA
<213> ORGANISM: Chlamydia trachomatis

<400> SEQUENCE: 169

```
ccgcaccaag tcttattgtc tcctgtttgc gatcttttat cgaatgctga aggtatagag     60

acgcaagtac tgtttggaga aaggatatgc aaccataacc atcgacacta tgcctattct    120

caactagtct tttcttctat atggaagcca taccctggcg actctctaca gaatattcct    180

ctattctctt cccaactgca gcctcctaat gctgttgtct gctctcaaga agctttttta    240

gatccttggc atatcccctt accttttgcc gctccgctcc acatagataa ccaaaatcaa    300

gtgtccctat ctcctgctag catagcatta ttaaattcca attccagaag taactatgca    360

aaagctttct gctctaccaa agagattcgt tttttaaatt cttcattctc tccaagagat    420

ttagtttctt tcgcagaaca attgatagat actccgtacg tttggggtgg ccggtgcatt    480
```

```
cataaacagc ttcctcgtaa tggtgtagat tgttcggggt atattcaact actttaccaa    540

gtcacaggaa gaaatatccc tcgcaatgct agagatcaat acagagactg ttctccagta    600

aaagatttct cgtctctacc tataggagga cttatcttcc tcaagaaagc aagcacggga    660

caaatcaacc atgttatgat gaaaatctcg gagcatgaat tcattcatgc tgcggaaaaa    720

atagggaaag tagaaaaagt aatcctagga aataggcctt tctttaaagg gaatctattc    780

tgctcattag gtgaaccgcc tatagaagct gtttttggcg ttcctaaaaa tagaaaagcc    840

ttcttt                                                               846


<210> SEQ ID NO 170
<211> LENGTH: 282
<212> TYPE: PRT
<213> ORGANISM: Chlamydia trachomatis

<400> SEQUENCE: 170

Pro His Gln Val Leu Leu Ser Pro Val Cys Asp Leu Leu Ser Asn Ala
1               5                   10                  15

Glu Gly Ile Glu Thr Gln Val Leu Phe Gly Glu Arg Ile Cys Asn His
            20                  25                  30

Asn His Arg His Tyr Ala Tyr Ser Gln Leu Val Phe Ser Ser Ile Trp
        35                  40                  45

Lys Pro Tyr Pro Gly Asp Ser Leu Gln Asn Ile Pro Leu Phe Ser Ser
    50                  55                  60

Gln Leu Gln Pro Pro Asn Ala Val Val Cys Ser Gln Glu Ala Phe Leu
65                  70                  75                  80

Asp Pro Trp His Ile Pro Leu Pro Phe Ala Ala Pro Leu His Ile Asp
                85                  90                  95

Asn Gln Asn Gln Val Ser Leu Ser Pro Ala Ser Ile Ala Leu Leu Asn
            100                 105                 110

Ser Asn Ser Arg Ser Asn Tyr Ala Lys Ala Phe Cys Ser Thr Lys Glu
        115                 120                 125

Ile Arg Phe Leu Asn Ser Ser Phe Ser Pro Arg Asp Leu Val Ser Phe
    130                 135                 140

Ala Glu Gln Leu Ile Asp Thr Pro Tyr Val Trp Gly Gly Arg Cys Ile
145                 150                 155                 160

His Lys Gln Leu Pro Arg Asn Gly Val Asp Cys Ser Gly Tyr Ile Gln
                165                 170                 175

Leu Leu Tyr Gln Val Thr Gly Arg Asn Ile Pro Arg Asn Ala Arg Asp
            180                 185                 190

Gln Tyr Arg Asp Cys Ser Pro Val Lys Asp Phe Ser Ser Leu Pro Ile
        195                 200                 205

Gly Gly Leu Ile Phe Leu Lys Lys Ala Ser Thr Gly Gln Ile Asn His
    210                 215                 220

Val Met Met Lys Ile Ser Glu His Glu Phe Ile His Ala Ala Glu Lys
225                 230                 235                 240

Ile Gly Lys Val Glu Lys Val Ile Leu Gly Asn Arg Ala Phe Phe Lys
                245                 250                 255

Gly Asn Leu Phe Cys Ser Leu Gly Glu Pro Pro Ile Glu Ala Val Phe
            260                 265                 270

Gly Val Pro Lys Asn Arg Lys Ala Phe Phe
        275                 280


<210> SEQ ID NO 171
<211> LENGTH: 11
<212> TYPE: PRT
```

-continued

```
<213> ORGANISM: Artificial Sequence
<220> FEATURE:
<223> OTHER INFORMATION: Synthetic peptide

<400> SEQUENCE: 171

Lys Leu Lys Leu Leu Leu Leu Leu Lys Leu Lys
1               5                   10
```